(12) United States Patent
Ohki et al.

(10) Patent No.: US 6,232,290 B1
(45) Date of Patent: May 15, 2001

(54) CYCLIC HEXAPEPTIDES WITH ANTIMICROBIAL ACTIVITY

(75) Inventors: Hidenori Ohki, Takarazuka; Kenji Murano; Takashi Tojo, both of Osaka; Nobuyuki Shiraishi; Takahiro Matsuya, both of Ikeda; Hiroshi Matsuda, Kyoto; Hiroaki Mizuno, Osaka; David Barrett, Nara; Keiji Matsuda, Takatsuki; Kohji Kawabata, Kawanishi, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/446,101

(22) PCT Filed: Feb. 5, 1999

(86) PCT No.: PCT/JP99/00538
§ 371 Date: Dec. 22, 1999
§ 102(e) Date: Dec. 22, 1999

(87) PCT Pub. No.: WO99/40108
PCT Pub. Date: Aug. 12, 1999

(30) Foreign Application Priority Data

Feb. 9, 1998 (AU) .................................................... PP1728
Apr. 23, 1998 (AU) .................................................... PP3138

(51) Int. Cl.[7] .............................. A61K 38/12; C07K 7/56
(52) U.S. Cl. ............................................. 514/11; 530/317
(58) Field of Search .......................... 514/9, 11; 530/317, 530/321

(56) References Cited

U.S. PATENT DOCUMENTS

| | | | |
|---|---|---|---|
| 5,376,634 | 12/1994 | Iwamoto et al. | 514/9 |
| 5,569,646 | 10/1996 | Ohki et al. | 514/11 |
| 5,629,289 | * 5/1997 | Rodriguez | 514/11 |
| 5,693,750 | 12/1997 | Ohki et al. | 530/317 |
| 5,932,543 | * 8/1999 | Burkhardt et al. | 514/11 |

FOREIGN PATENT DOCUMENTS

644199 * 3/1995 (EP) .
96/11210 * 4/1996 (WO) .

* cited by examiner

Primary Examiner—Jeffrey E. Russel
(74) Attorney, Agent, or Firm—Oblon, Spivak, McClelland, Maier & Neustadt, P.C.

(57) ABSTRACT

This invention relates to new polypeptide compounds represented by general formula (I), wherein $R^1$, $R^2$, $R^3$ and $R^4$ are as defined in the description or a salt thereof which has antimicrobial activities (especially, antifungal activities), inhibitory activity on β-1,3-glucan synthase, to process for preparation thereof, to a pharmaceutical composition comprising the same, and to a method for prophylactic and/or therapeutic treatment of infectious diseases including *Pneumocystis carinii* infection (e.g. *Pneumocystis carinii* pneumonia) in a human being or an animal.

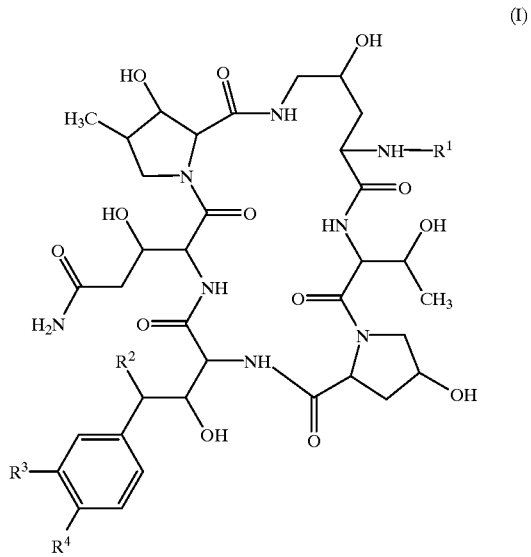

9 Claims, No Drawings

CYCLIC HEXAPEPTIDES WITH ANTIMICROBIAL ACTIVITY

TECHNICAL FIELD

The present invention relates to new polypeptide compound and a salt thereof which are useful as a medicament.

BACKGROUND ART

In U.S. Pat. No. 5,376,634 and WO 96/11210, there are disclosed the polypeptide compound and a pharmaceutically acceptable salt thereof, which have antimicrobial activities (especially antifungal activity).

DISCLOSURE OF INVENTION

The present invention relates to new polypeptide compound and a salt thereof.

More particularly, it relates to new polypeptide compound and a salt thereof, which have antimicrobial activities [especially Aspergillus, Cryptococcus, Candida, Mucor, Actinonyces, Histoplasma, Dermatophyte, Malassezia, Fusarium and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, to a process for preparation thereof, to a pharmaceutical composition comprising the same, and to a methods for the prophylactic and/or therapeutic treatment of infectious disease including *Pneumocystis carinii* infection (e.g. *Pneumocystis carinii* pneumonia) in a human being or an animal.

The object polypeptide compounds of the present invention are new and can be represented by the following general formula [I]:

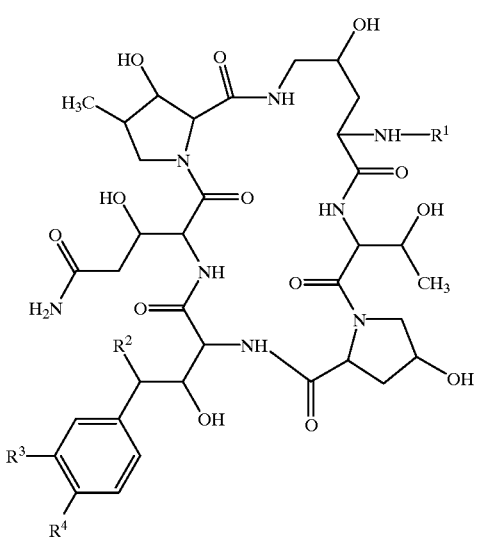

Wherein
$R^1$ is hydrogen;
  arylamino(lower)alkanoyl which may have one or more suitable substituent(s);
  aroyl substituted with heterocyclic group which may have one or more suitable substituent(s);
  aroyl substituted with aryl having higher alkyl;
  aroyl substituted with aryl having lower alkyl;
  aryl($C_2$–$C_6$)alkanoyl substituted with aryl having lower alkyl;
  lower alkanoyl substituted with unsaturated condensed heterocyclic group which may have one or more suitable substituent(s);
  lower alkanoyl substituted with pyridyl which may have one or more suitable substituent(s);
  amino protective group;
  heptylnaphthoyl;
  hexylnaphthoyl;
  aroyl substituted with heterocyclic carbamoyl which may have one or more suitable substituent(s);
  lower alkanoyl substituted with cyclo(lower)alkyl which may have one or more suitable substituent(s);
  lower alkanoyl substituted with thienyl having heterocyclic group which may have one or more suitable substituent(s); or
  lower alkenoyl substituted with heterocyclic group which may have one or more suitable substituent(s),
$R^2$ is hydrogen or hydroxy,
$R^3$ is hydroxy, hydroxysulfonyloxy or lower alkoxy, and
$R^4$ is hydroxy or lower alkoxy,
or a salt thereof.

The new polypeptide compound [I] and a salt thereof can be prepared by the process as illustrated in the following reaction schemes.

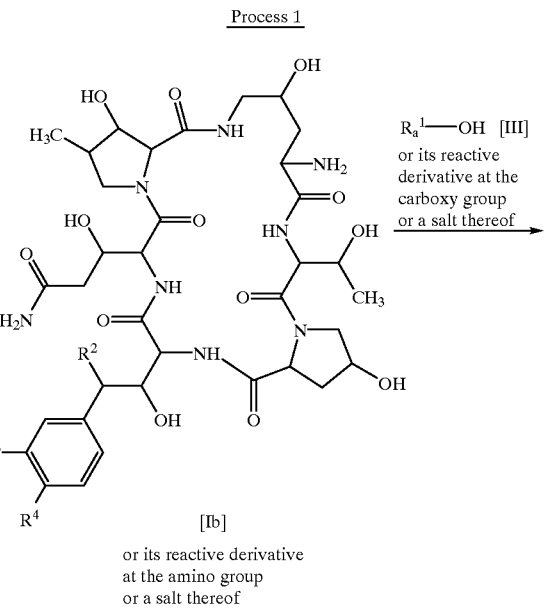

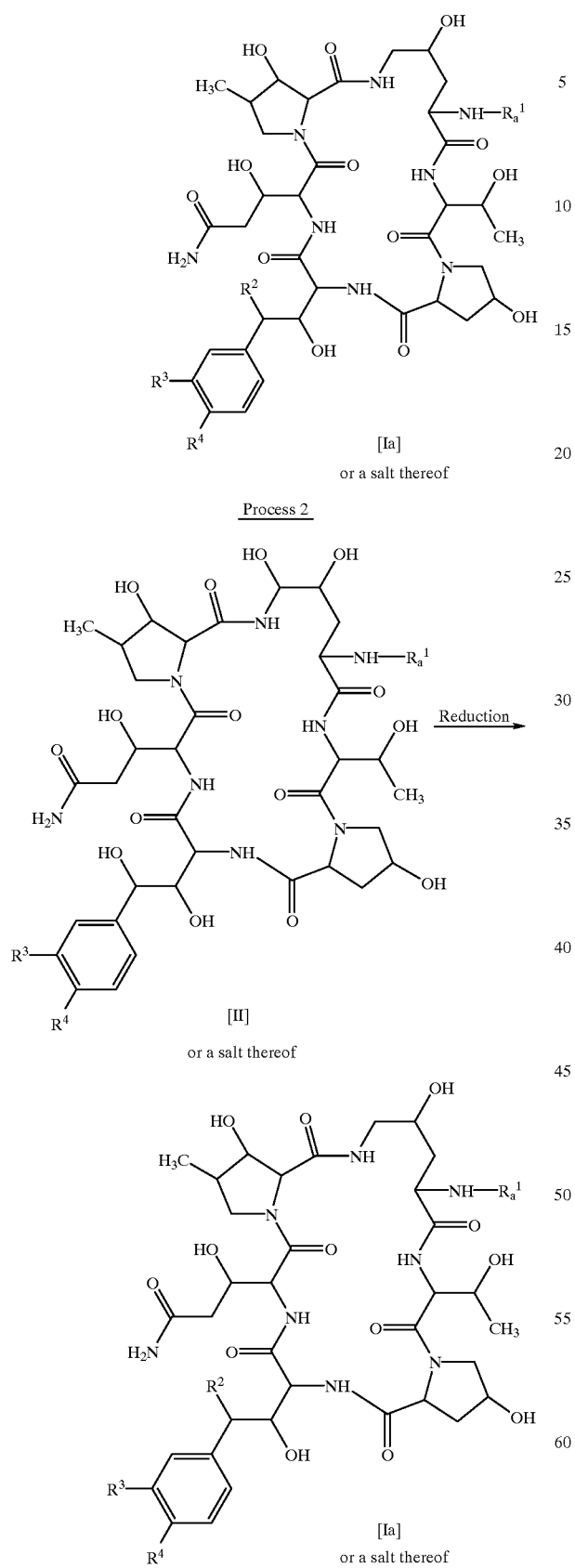
[Ia] or a salt thereof
Process 2
[II] or a salt thereof
[Ia] or a salt thereof
Process 3
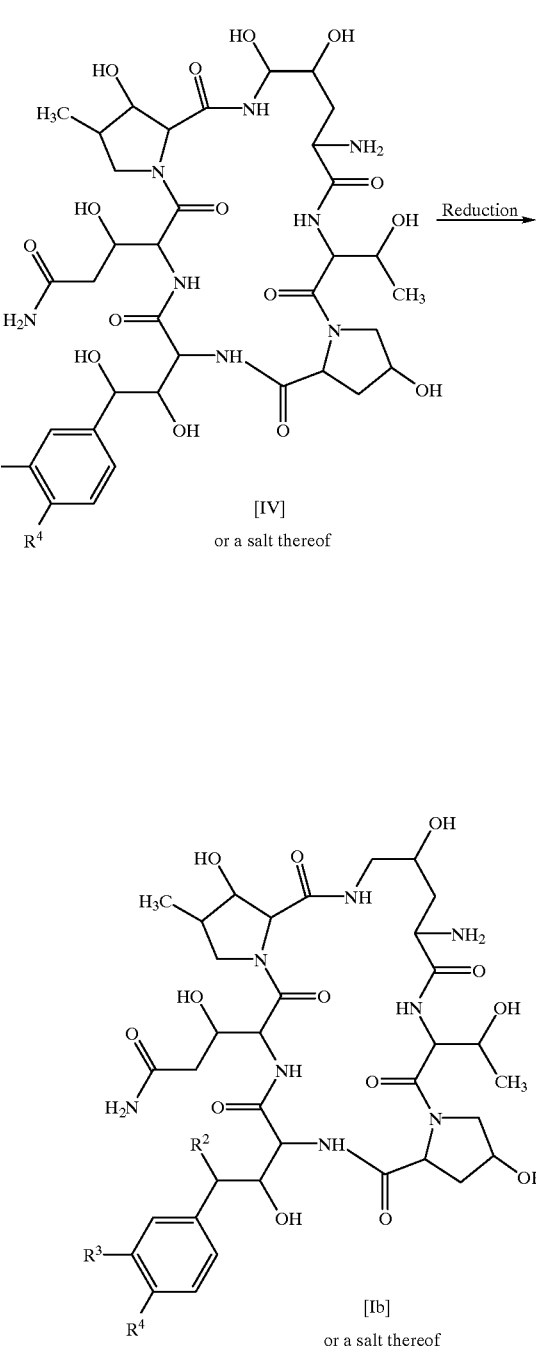
[IV] or a salt thereof
[Ib] or a salt thereof
The starting compound [II] and [IV], or a salt thereof can be prepared by the process as illustrated in the following reaction schemes.

Process A
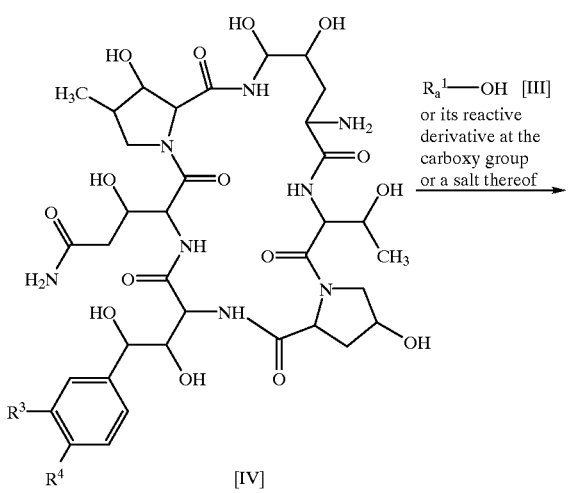
[IV]
or its reactive derivative
at the amino group
or a salt thereof
$R_a^1$—OH [III]
or its reactive
derivative at the
carboxy group
or a salt thereof
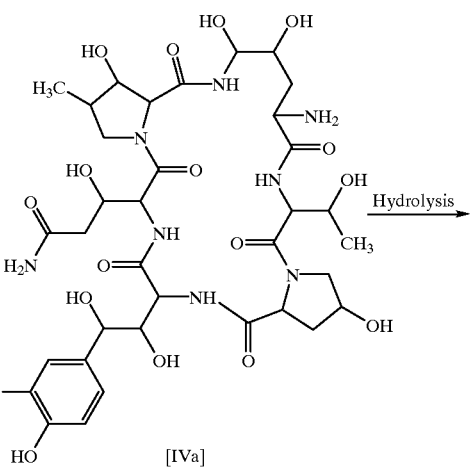
[IVa]
or its reactive derivative
at the sulfonic acid group
or a salt thereof
Hydrolysis
-continued
Process B
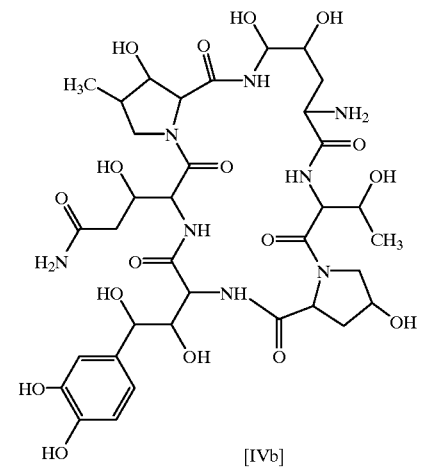
[IVb]
or a salt thereof -continued
Process C

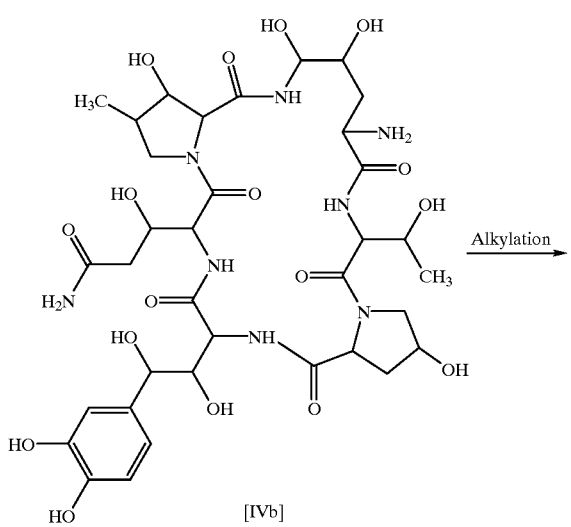

[IVb]
or its reactive derivative
at the hydroxy group
or a salt thereof

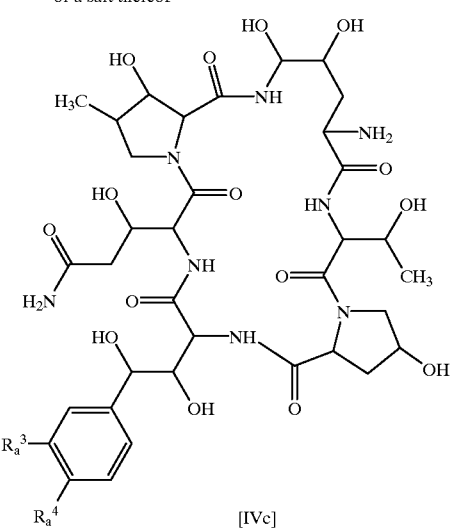

[IVc]
or a salt thereof wherein
R², R³ and R⁴ are as defined above,
$R_a^1$ is arylamino(lower)alkanoyl which may have one or more suitable substituent(s);
  aroyl substituted with heterocyclic group which may have one or more suitable substituent(s);
  aroyl substituted with aryl having higher alkyl;
  aroyl substituted with aryl having lower alkyl;
  aryl($C_2$–$C_6$)alkanoyl substituted with aryl having lower alkyl;
  lower alkanoyl substituted with unsaturated condensed heterocyclic group which may have one or more suitable substituent(s);
  lower alkanoyl substituted with pyridyl which may have one or more suitable substituent(s);
  amino protective group;
  heptylnaphthoyl;
  hexylnaphthoyl;
  aroyl substituted with heterocyclic carbamoyl which may have one or more suitable substituent(s);
  lower alkanoyl substituted with cyclo(lower)alkyl which may have one or more suitable substituent(s);
  lower alkanoyl substituted with thienyl having heterocyclic group which may have one or more suitable substituent(s); or
  lower alkenoyl substituted with heterocyclic group which may have one or more suitable substituent(s),
$R_a^3$ is lower alkoxy, and
$R_a^4$ is hydroxy or lower alkoxy.

Suitable salt of the new polypeptide compound [I] is a pharmaceutically acceptable and conventional non-toxic salt, and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;
  a salt with an organic base, for example, an organic amine salt (e.g., triethylamine salt, diisopropylethylamine salt pyridine salt, picoline salt, ethanolamine salt, triethanolamine salt, dicyclohexylamine salt, N,N'-dibenzylethylenediame salt, etc.);
  an inorganic acid addition salt (e.g., hydrochloride, hydrobromide, sulfate, phosphate, etc.);
  an organic carboxylic sulfonic acid addition salt (e.g., formate, acetate, trifluoroacetate, maleate, tartrate, fumarate, methanesulfonate, benzenesulfonate, toluenesulfonate, etc.);
  a salt with a basic or acidic amino acid (e.g., arginine, aspartic acid, glutamic acid, etc.).

Suitable examples and illustration of the various definitions in the above and subsequent descriptions of the present specification, which the present invention intends to include within the scope thereof, are explained in detail as follows:

The term "lower" is used to intend a group having 1 to 6 carbon atom(s), unless otherwise provided.

The term "higher" is used to intend a group having 7 to 20 carbon atoms, unless otherwise provided.

Suitable example of "one or more" may be the number of 1 to 6, in which the preferred one may be the number of 1 to 3.

Suitable example of "lower alkanoyl" may include straight or branched one such as formyl, acetyl, 2-methylacetyl, 2,2-dimethylacetyl, propionyl, butyryl, isobutyryl, pentanoyl, 2,2-dimethylpropionyl, hexanoyl, and the like.

Suitable example of "suitable substituent(s)" in the R¹ and $R_a^1$ may include higher alkoxy, aryl which have one or more higher alkoxy, higher alkyl, lower alkyl, aryl which has one or more lower alkoxy, heterocyclic group which may have one or more higher alkoxy, aryl which has one or more cyclo(lower)alkyl, aryl which has one or more lower alkoxy (higher)alkoxy, aryl which has one or more heterocyclic groups, cyclo(lower)alkyl which has one or more cyclo (lower)alkyl, aryl substituted with aryl which may have one or more lower alkoxy, aryl substituted with aryl which may have one more higher alkoxy, aryl substituted with aryl which may have one or more lower alkoxy having heterocyclic group, aryl which has one or more lower alkoxy (lower)alkoxy, heterocyclic group which may have one or more higher alkyl, aryl substituted with aryl which may have one or more aryloxy(lower)alkoxy, aryl substituted with aryl which may have one or more lower alkenyloxy, aryl substituted with aryl which may have one or more lower alkoxy(higher)alkoxy, aryl substituted with aryl which may have one or more heterocyclic(lower)alkoxy, aryl which has one or more aryloxy(lower)alkoxy, heterocyclic group which may have one or more heterocyclic groups, aryl which has one or more cyclo(lower)alkyloxy, aryl which has one or more heterocyclic groups having lower alkoxy, aryl which has one or more heterocyclic groups having cyclo(lower)alkyloxy, aryl which has one or more heterocyclic groups having aryl(lower)alkyloxy, aryl which has one or more heterocyclic groups having cyclo(lower)alkyl, aryl which has one or more heterocyclic groups having aryl, heterocyclic group which may have one or more aryl having lower alkoxy, heterocyclic group which may have one or more aryl having higher alkoxy(lower)alkyl, heterocyclic group which may have one or more aryl having lower alkoxy(lower)alkoxy, heterocyclic group which may have one or more aryl having cyclo(lower)alkyl, heterocyclic group which may have one or more aryl having heterocyclic group, heterocyclic group which may have one or more aryl substituted with heterocyclic(lower)alkyl having aryl, heterocyclic group which may have one or more heterocyclic groups having aryl, aryl substituted with aryl which may have one or more cyclo(lower)alkyloxy, aryl substituted with aryl which may have one or more lower alkoxy(lower)alkyl, aryl substituted with aryl which may have one or more lower alkoxy(lower)alkoxy, aryl substituted with aryl which may have one or more lower alkoxy(lower)alkoxy(lower)alkyl, aryl substituted with aryl which may have one or more lower alkoxy(lower)alkoxy(lower)alkoxy, aryl substituted with aryl which may have one or more heterocyclic groups, aryl which has one or more cyclo(lower)alkyloxy, aryl which has one or more lower alkoxy(higher)alkylthio, aryl which has one or more lower alkoxy having heterocyclic group, cyclo(lower)alkyl which may have one or more lower alkyl, cyclo(lower)alkyl-which may have one or more aryl, aryl, and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy and the like,
    in which the preferred one may be methoxy, ethoxy, propoxy, butoxy, pentyloxy, hexyloxy and isohexyloxy.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like,
    in which the preferred one may be ($C_7$–$C_{14}$)alkoxy, and the more preferred one may be heptyloxy and octyloxy.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl and the like,
    in which the preferred one may be methyl, pentyl, hexyl and isohexyl.

Suitable example of "higher alkyl" may include straight or branched one having 7 to 20 carbon atoms, such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, icosyl, and the like, in which the preferred one may be ($C_7$–$C_{14}$)alkyl, and the more preferred one may be heptyl, octyl, nonyl and decyl.

Suitable example of "aryl" and "ar" moiety may include phenyl which may have lower alkyl (e.g., phenyl, mesityl, xylyl, tolyl, etc.), naphthyl, anthryl, indanyl, and the like, in which the preferred one may be phenyl and naphthyl, and this "aryl" and "ar" moiety may have halogen or lower alkoxy.

Suitable example of "aroyl" may include benzoyl, toluoyl, naphthyl, anthrylcarbonyl, and the like, in which the preferred one may be benzoyl and naphthoyl, and this "aroyl" may have lower alkyl.

Suitable example of "heterocyclic group " and "heterocyclic" moiety may include unsaturated 3 to 8-membered (more preferably 5 or 6-membered) heteromonocylic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 to 6-membered) heteromonocylic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocylic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated b 3to 8-membered (more preferably 5 or 6-membered) heteromonocylic group containing 1 to 2 oxygen atom(s) and 1 to 3 nitrogen atom(s), for example, morpholinyl, sydnonyl, morpholino, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 to 6-membered) heteromonocylic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.); dihydrothiazinyl, etc.;

saturated 3 to 8-membered (more preferably 5 to 6-membered) heteromonocylic group containing 1 to 2 sulfur atom(s) and 1 to 3 nitrogen atom(s), for example thiazolidinyl, thiomorpholinyl, thiomorpholino, etc.;

unsaturated 3 to 8-membered (more preferably 5 to 6-membered) heteromonocylic group containing 1 to 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 to 6-membered) heteromonocylic group containing an oxygen atom, for example, furyl, etc.;

saturated 3 to 8-membered (more preferably 5 to 6-membered) heteromonocylic group containing an oxygen atom, for example, tetrahydrofuran, tetrahydropyran, etc.;

unsaturated 3 to 8-membered (more preferably 5 to 6-membered) heteromonocylic group containing an oxygen atom and 1 to 2 sulfur atom(s), for example, dihydrooxathiinyl, etc.;

unsaturated condensed heterocyclic group containing 1 or 2 sulfur atom(s), for example benzothienyl, benzodithiinyl, etc.;

unsaturated condensed heterocyclic group containing an oxygen atom and 1 or 2 sulfur atom(s), for example, benzoxathiinyl, etc.; and the like and this "heterocyclic group" and "heterocyclic" moiety may have lower alkyl or cyclo(lower)alkyl.

Suitable example of "lower alkenyloxy" may include vinyloxy, 1-(or 2-)propenyloxy, 1-(or 2- or 3-)butenyloxy, 1-(or 2- or 3- or 4-)pentenyloxy, 1-(or 2- or 3- or 4- or 5-)hexenyloxy, and the like, in which the preferred one may be ($C_2$–$C_6$)alkenyloxy, and the most preferred one may be 2-propenyloxy.

Suitable example of "cyclo(lower)alkyl" may include cyclopropyl, cyclobutyl, cyclopentyl, cyclohexyl, and the like, in which the preferred one may be cyclo($C_4$–$C_6$)alkyl, and the most preferred one may be cyclohexyl and this "cyclo(lower)alkyl" may have lower alkyl.

Suitable "amino protective group" may include acyl group as explained below, a conventional protective group such as ar(lower)alkyl which may have 1 to 3 suitable substituent(s) (e.g. benzyl, phenethyl, 1-phenylethyl, benzhydryl, trityl, etc.), [5-(lower)alkyl-2-oxo-1,3-dioxol-4-yl](lower)alkyl [e.g. (5-methyl-2-oxo-1,3-dioxol-4-yl)methyl, etc.] or the like; and the like.

Suitable "acyl group" and "acyl" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows.

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

Aromatic acyl such as aroyl (e.g., benzoyl, toluoyl, naphthoyl, etc.);

ar(lower)alkanoyl [e.g., phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthyloropanoyl, naphthylbutanoyl, etc.), etc.];

ar(lower)alkenoyl [e.g., phenyl($C_3$–$C_6$)alkenoyl (e.g., phenylpropenoyl, phenylbutenoyl, phenylmethacryloyl, phenylpentenoyl, phenylhexenoyl, etc.), naphthyl($C_3$–$C_6$)alkenoyl (e.g., naphthylpropenoyl, naphthylbutenoyl, etc.), etc.];

ar(lower)alkoxycarbonyl [e.g., phenyl ($C_1$–$C_6$) alkoxycarbonyl (e.g., benzyloxycarbonyl, etc.), fluorenyl($C_1$–$C_6$)alkoxycarbonyl (e.g., fluorenylmethyloxycarbonyl, etc.), etc.]; aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like;

in which suitable "heterocyclic" moiety in the terms "heterocycliccarbonyl", "heterocyclic(lower)alkanoyl", heterocyclic(lower)alkenoyl" and "heterocyclicglyoxyloyl" can be referred to aforementioned "heterocyclic" moiety, in which the preferred one may be ar(lower)alkoxycarbonyl, and the more preferred one may be phenyl($C_1$–$C_4$)alkoxycarbonyl and fluorenyl($C_1$–$C_4$)alkoxycarbonyl, and the most preferred one may be benzyloxycarbonyl and fluorenylmethyloxycarbonyl.

Suitable example of "arylamino" moiety in the term of "arylamino(lower)alkanoyl which may have one or more suitable substituent(s)" may be phenylamino, mesitylamino, tolylamino, naphthylamino, anthrylamino, and the like, in which the preferred one may be naphthylamino.

Suitable example of "lower alkanoyl" moiety in the term of "arylamino(lower)alkanoyl which may have one or more suitable substituent(s)" can be referred to aforementioned "lower alkanoyl", in which the preferred one may be formyl.

Suitable example of "suitable substituent(s)" moiety in the term of "arylamino(lower)alkanoyl which may have one or more suitable substituent(s)" can be referred to aforementioned "suitable substituent(s)", in which the preferred one may be higher alkoxy, and the most preferred one may be heptyloxy.

Suitable example of "arylamino(lower)alkanoyl which may have one or more suitable substituent(s)" may be naphthylaminocarbonyl having higher alkoxy, in which the preferred one may be naphthylaminocarbonyl having heptyloxy.

Suitable example of "aroyl" moiety in the term of "aroyl substituted with heterocyclic group which may have one or more suitable substituent(s)" can be referred to aforementioned "aroyl", in which the preferred one may be benzoyl.

Suitable example of "heterocyclic group" moiety in the term of "aroyl substituted with heterocyclic group which may have one or more suitable substituent(s)" can be referred to aforementioned "heterocyclic group", in which the preferred one may be saturated 3 or 8-membered heteromonocylic group containing 1 to 4 nitrogen atom(s), unsaturated 3 to 8-membered heteromonocyclic group containing 1 to 2 sulfur atom(s) and 1 to 3 nitrogen atom(s), unsaturated 3 to 8-membered heteromonocyclic group containing 1 to 2 oxygen atom(s) and 1 to 3 nitrogen atom(s) and unsaturated condensed heterocyclic group containing 1 to 2 sulfur atom(s) and 1 to 3 nitrogen atom(s) and the more preferred one may be piperazinyl, thiadiazolyl, oxadiazolyl, imidazothiadiazolyl and isoxazolyl.

Suitable example of "suitable substituent(s)" moiety in the term of "aroyl substituted with heterocyclic group which may have one or more suitable substituent(s)" can be referred to aforementioned "suitable substituent(s)", in which the preferred one may be aryl which has one or more higher alkoxy, aryl which has one or more lower alkoxy, aryl which has one or more cyclo(lower)alkyl, aryl which has one or more lower alkoxy(higher)alkoxy, aryl which has one or more heterocyclic groups, cyclo(lower)alkyl which may have one or more cyclo(lower)alkyl, aryl substituted with aryl which may have one or more lower alkoxy, aryl substituted with aryl which may have one or more higher alkoxy, aryl substituted with aryl which may have one or more lower alkoxy having heterocyclic group, aryl which has one or more lower alkoxy(lower)alkoxy, heterocyclic group which may have one or more higher alkyl, aryl substituted with aryl which may have one or more aryloxy(lower)alkoxy, aryl substituted with aryl which may have one or more lower alkenyloxy, aryl substituted with aryl which may have one or more lower alkoxy(higher)alkoxy, aryl substituted with aryl which has one or more heterocyclic(lower)alkoxy, in which heterocyclic group may have one or more lower alkyl, aryl which has one or more aryloxy(lower)alkoxy, heterocyclic group which may have one or more heterocyclic groups, aryl which has one or more cylco(lower)alkyloxy, aryl which has one or more heterocyclic groups having lower alkoxy, aryl which has one or more heterocyclic groups having cyclo(lower)alkyloxy, aryl which has one or more heterocyclic groups having aryl(lower)alkyloxy, aryl which has one or more heterocyclic groups having cyclo(lower)alkyl, aryl which has one or more heterocyclic groups having aryl, heterocyclic group which may have one or more aryl having lower alkoxy, heterocyclic group which may have one or more aryl having higher alkoxy(lower)alkyl, heterocyclic group which may have one or more aryl having lower alkoxy(lower)alkoxy, heterocyclic group which may have one or more aryl having cyclo(lower)alkyl, heterocyclic group which may have one or more aryl having heterocyclic group, heterocyclic group which may have one or more aryl substituted with heterocyclic(lower)alkyl having aryl, heterocyclic group which may have one or more heterocyclic groups having aryl, aryl substituted with aryl which may have one or more cyclo(lower)alkyloxy, aryl substituted with aryl which may have one or more lower alkoxy(lower)alkyl, aryl substituted with aryl which may have one or more lower alkoxy(lower)alkoxy, aryl substituted with aryl which may have one or more lower alkoxy(lower)alkoxy(lower)alkyl, aryl substituted with aryl which may have one or more lower alkoxy(lower)alkoxy(lower)alkoxy, aryl substituted with aryl which may have one or more heterocyclic groups, aryl which has one or more cyclo(lower)alkyloxy, aryl which has one or more lower alkoxy(higher)alkylthio, aryl which has one or more lower alkoxy having heterocyclic group, cyclo(lower)alkyl which may have one or more lower alkyl, cyclo(lower)alkyl which may have one or more aryl, aryl, in which the preferred one may be phenyl having $(C_7–C_{14})$ alkyl, phenyl having $(C_4–C_6)$alkoxy, phenyl having cyclo $(C_4–C_6)$alkyl, phenyl having $(C_1–C_4)$alkoxy$(C_7–C_{14})$ alkoxy, phenyl having saturated 3 to 8-membered heteromonocyclic group containing 1 to 4 nitrogen atom(s), cyclo$(C_4–C_6)$alkyl having cyclo$(C_4–C_6)$alkyl, phenyl substituted with phenyl having $(C_1–C_6)$alkoxy, phenyl substituted with phenyl having $(C_7–C_{14})$alkoxy, phenyl substituted with phenyl which has $(C_1–C_4)$alkoxy having saturated 3 to 8-membered heteromonocyclic group containing 1 to 4 nitrogen atom(s), phenyl having $(C_1–C_4)$alkoxy$(C_4–C_6)$ alkoxy, unsaturated 3 to 8-membered heteromonocyclic group containing 1 to 4 nitrogen atom(s) having $(C_7–C_{14})$ alkyl, phenyl substituted with phenyl having phenyloxy$(C_1–C_4)$alkoxy, phenyl substituted with phenyl having $(C_3–C_6)$alkenyloxy, phenyl substituted with phenyl having $(C_2–C_4)$alkoxy$(C_7–C_{14})$alkoxy, phenyl substituted with phenyl which has $(C_1–C_4)$alkoxy having saturated 3 to 8-membered heteromonocyclic group containing 1 or 2 oxygen atom(s) and 1 to 3 nitrogen atom(s) having 1 to 4 $(C_1–C_4)$alkyl, phenyl having phenyloxy$(C_1–C_4)$alkoxy, phenyl having $(C_1–C_4)$alkoxy$(C_7–C_{14})$alkoxy, unsaturated 3 to 8-membered heteromonocyclic group containing 1 to 4 nitrogen atom(s) having saturated 3 to 8-membered heteromonocyclic group containing 1 to 4 nitrogen atom(s), phenyl having cyclo$(C_4–C_6)$alkyloxy, phenyl which has saturated 3 to 8-membered heteromonocyclic group containing 1 to 4 nitrogen atom(s) having $(C_1–C_4)$alkoxy, phenyl which has saturated 3 to 8-membered heteromonocyclic group containing 1 to 4 nitrogen atom(s) having phenyl$(C_1–C_4)$alkoxy, phenyl which has saturated 3 to 8-membered heteromonocyclic group containing 1 to 4 nitrogen atom(s) having cyclo$(c_4–C_6)$alkyl, phenyl which has saturated 3 to 8-membered heteromonocyclic group containing 1 to 4 nitrogen atom(s) substituted with cyclo$(C_4–C_6)$alkyl having di$(C_1–C_4)$alkyl, phenyl which has saturated 3 to 8-membered heteromonocyclic group containing 1 to 4 nitrogen atom(s) substituted with cyclo$(C_4–C_6)$alkyl having $(C_1–C_4)$alkyl, phenyl which has saturated 3 to 8-membered heteromonocyclic group containing 1 to 4 nitrogen atom(s) substituted with $(C_1–C_4)$alkoxy and phenyl having halogen, phenyl which ha s saturated 3 to 8-membered heteromonocyclic group containing 1 to 4 nitrogen atom(s) substituted with phenyl, phenyl which has unsaturated 3 to 8-membered heteromonocyclic group containing 1 or 2 sulfur atom(s) and 1 to 3 nitrogen atom(s) substituted with phenyl having $(C_1–C_6)$alkoxy, unsaturated 3 to 8-membered heteromonocyclic group containing 1 to 4 nitrogen atom(s) which has phenyl having $(C_1–C_6)$alkoxy, unsaturated 3 to 8-membered heteromonocyclic group containing 1 to 4 nitrogen atom(s) which has phenyl having $(C_7–C_{14})$alkoxy$(C_1–C_6)$alkyl, saturated 3 to 8-membered heteromonocyclic group containing 1 to 4 nitrogen atom(s) which has phenyl having $(C_4–C_6)$alkyl, unsaturated 3 to 8-membered heteromonocyclic group containing 1 to 4 nitrogen atom(s) which has phenyl having saturated 3 to 8-membered heteromonocyclic group containing 1 to 4 nitrogen atom(s), unsaturated 3 to 8-membered heteromonocyclic group containing 1 to 4 nitrogen atom(s) which has phenyl substituted with $(C_1–C_6)$alkyl having saturated 3 to 8-membered heteromonocyclic group containing 1 to 4 nitrogen atom(s) having phenyl, unsaturated 3 to 8-membered heteromonocyclic group containing 1 to 4 nitrogen atom(s) which has saturated 3 to 8-membered heteromonocyclic group containing 1 to 4 nitrogen atom(s) having phenyl, phenyl substituted with phenyl which has cyclo$(C_4–C_6)$alkyloxy, phenyl substituted with phenyl which has $(C_1–C_6)$alkoxy$(C_1–C_6)$alkyl, phenyl substituted with phenyl which has $(C_1–C_6)$alkoxy$(c_1–C_6)$ alkoxy, phenyl substituted with phenyl which has $(C_1–C_6)$ alkoxy$(C_1–C_6)$alkoxy$(C_1–C_6)$alkyl, phenyl substituted with phenyl which has $(C_1–C_6)$alkoxy$(C_1–C_6)$alkoxy$(C_1–C_6)$ alkoxy, phenyl substituted with phenyl which has saturated 3 to 8-membered heteromonocyclic group containing 1 to 4 nitrogen atom(s) having cyclo$(C_4–C_6)$alkyl, phenyl substituted with phenyl which has saturated 3 to 8-member heteromonocyclic group containing 1 to 4 nitrogen atom(s) substituted with cyclo$(C_4–C_6)$alkyl having di$(C_1–C_4)$alkyl, phenyl which has cyclo$(c_4–C_6)$alkyloxy, phenyl which has $(C_1–C_6)$alkoxy$(C_7–C_{14})$alkylthio, phenyl which has $(C_1–C_6)$alkoxy having saturated 3 to 8-membered heteromonocyclic group containing 1 to 4 nitrogen atom(s), phenyl which has $(C_1–C_6)$alkoxy having saturated 3 to 8-membered heteromonocyclic group containing 1 or 2 oxygen atom(s) and 1 to 3 nitrogen atom(s), phenyl which has $(C_1–C_6)$ alkoxy having saturated 3 to 8-membered heteromonocyclic group containing 1 or 2 oxygen atom(s) and 1 to 3 nitrogen atom(s) having di($C_1$–$C_4$)alkyl, phenyl which has ($C_1$–$C_6$) alkoxy having saturated 3 to 8-membered heteromonocyclic group containing 1 or 2 sulfur atom(s) and 1 to 3 nitrogen atom(s), cyclo($C_4$–$C_6$)alkyl which has ($C_1$–$C_6$)alkyl, cyclo ($C_4$–$C_6$)alkyl which has phenyl, indanyl, phenyl substituted with saturated 3 to 8-membered heteromonocyclic group containing 1 or 2 oxygen atom(s) and 1 to 3 nitrogen atom(s), phenyl substituted with saturated 3 to 8-membered heteromonocyclic group containing 1 to 4 nitrogen atom(s) having ($C_1$–$C_6$)alkyl, phenyl substituted with saturated 3 to 8-membered heteromonocyclic group containing 1 or 2 oxygen atom(s) and 1 to 3 nitrogen atom(s) having di($C_1$–$C_4$)alkyl, and phenyl substituted with saturated 3 to 8-membered heteromonocyclic group containing 1 or 2 sulfur atom(s) and 1 to 3 nitrogen atom(s), and the most preferred one may be phenyl having octyloxy, phenyl having hexyloxy, phenyl having cyclohexyl, phenyl having piperidyl, cyclohexyl having cyclohexyl, phenyl having methoxyoctyloxy, phenyl having methoxyheptyloxy, phenyl having butoxy, phenyl having pentyloxy, phenyl substituted with phenyl having methoxy, phenyl substituted with phenyl having propyloxy, phenyl substituted with phenyl having butoxy, phenyl substituted with phenyl having pentyloxy, phenyl substituted with phenyl having hexyloxy, phenyl substituted with phenyl having heptyloxy, phenyl substituted with phenyl which has propyloxy having piperidyl, phenyl having methoxyhexyloxy, isoxazolyl having decyloxy, phenyl substituted with phenyl having phenyloxypropyloxy, phenyl substituted with phenyl having propenyloxy, phenyl substituted with phenyl having phenyloxybutoxy, phenyl substituted with phenyl having methoxyoctyloxy, phenyl substituted with phenyl which has propoxy having dimethyl, phenyl having phenyloxypropoxy, phenyl having phenyloxybutoxy, phenyl having phenyloxypentyloxy, phenyl having methoxypentyloxy, phenyl having methoxyheptyloxy, pyridyl having piperidyl, phenyl having cyclohexyloxy, phenyl which has piperidyl having propoxy, phenyl which has piperidyl having cyclohexyl, phenyl which has piperidyl having phenymethoxy, phenyl which has piperazinyl having cyclohexyl, phenyl which has piperazinyl substituted with cyclohexyl having dimethyl, phenyl which has piperazinyl substituted with cyclohexyl having methyl, phenyl which has piperidyl substituted with methoxy and chlorophenyl, phenyl which has piperidyl substituted with phenyl, phenyl which has piperazinyl substituted with phenyl, phenyl which has thiadiazolyl substituted with pentyloxyphenyl, pyrazolyl which has hexyloxyphenyl, pyrazolyl which has heptyloxymethylphenyl, piperazinyl which has phenyl having cyclohexyl, pyrazolyl which has phenyl having piperidyl, pyrazolyl which has phenyl having pyrrolidinyl, pyrazolyl which has phenyl substituted with piperazinylmethyl having phenyl, pyridyl which has piperidyl having phenyl, phenyl substituted with phenyl which has cyclohexyloxy, phenyl substituted with phenyl which has ethoxymethyl, phenyl substituted with phenyl which has ethoxypropoxy, phenyl substituted with phenyl which has ethoxyethoxy, phenyl substituted with phenyl which has methoxypropoxy, phenyl substituted with phenyl which has methoxyethoxy, phenyl substituted with phenyl which has methoxypentyloxy, phenyl substituted with phenyl which has methoxyethoxymethyl, phenyl substituted with phenyl which has methoxyethoxyethoxy, phenyl substituted with phenyl which has piperazinyl having cyclohexyl, phenyl substituted with phenyl which has morpholinyl having dimethyl, phenyl which has cyclohexyloxy, phenyl which has methoxyheptylthio, phenyl which has piperidinobutoxy, phenyl which has piperidinopentyloxy, phenyl which has piperidinohexyloxy, phenyl which has morpholinopentyloxy, phenyl which has morpholinopentyloxy having dimethyl, phenyl which has morpholinohexyloxy having dimethyl, phenyl which has thiomorpholinopentyloxy, cyclohexyl which has pentyl, cyclohexyl which has phenyl, indanyl, phenyl having piperidyl, phenyl having morpholinyl, phenyl having thiomorpholino, phenyl substituted with phenyl having methoxybutoxy, phenyl substituted with piperazinyl having ethyl, and phenyl substituted with morpholinyl having dimethyl.

Suitable example of "aroyl substituted wit heterocyclic group which may have one or more suitable substituent(s)" may be benzoyl substituted with piperazinyl which has phenyl having octyloxy, benzoyl substituted with piperazinyl which has phenyl having hexyloxy, benzoyl substituted with thiadiazolyl which has phenyl having hexyloxy, benzoyl substituted with oxadiazolyl which has phenyl having hexyloxy, benzoyl substituted with piperazinyl which has phenyl having cyclohexyl, benzoyl substituted with thiadiazolyl which has phenyl having methoxyoctyloxy, benzoyl substituted with thiadiazolyl which has phenyl having piperidyl, benzoyl substituted with piperazinyl which has cyclohexyl having cyclohexyl, benzoyl substituted with piperazinyl which has phenyl having methoxyoctyloxy, benzoyl substituted with piperazinyl which has phenyl having methoxyheptyloxy, benzoyl substituted with imidazothiadiazolyl which has phenyl having butyloxy, benzoyl substituted with imidazothiadiazolyl which has phenyl having pentyloxy, benzoyl substituted with oxadiazolyl which has phenyl substituted with phenyl having methoxy, benzoyl substituted with oxadiazolyl which has phenyl substituted with phenyl having propyloxy, benzoyl substituted with oxadiazolyl which has phenyl substituted with phenyl having butyloxy, benzoyl substituted with oxadiazolyl which has phenyl substituted with phenyl having pentyloxy, benzoyl substituted with oxadiazolyl which has phenyl substituted with phenyl having hexyloxy, benzoyl substituted with oxadiazolyl which has phenyl substituted with phenyl having heptyloxy, benzoyl substituted with oxadiazolyl which has phenyl substituted with phenyl which has propyloxy having piperidyl, benzoyl substituted with thiadiazolyl which has phenyl having methoxyhexyloxy, benzoyl substituted with oxadiazolyl which has pyrazolyl having decyl, benzoyl substituted with thiadiazolyl which has pyrazolyl having decyl, benzoyl substituted with oxadiazolyl which has phenyl substituted with phenyl having phenyloxypropyloxy, benzoyl substituted with oxadiazolyl which has phenyl substituted with phenyl having propenyloxy, benzoyl substituted with thiadiazolyl which has phenyl having methoxyhexyloxy, benzoyl substituted with oxadiazolyl which has phenyl substituted with phenyl having phenyloxybutyloxy, benzoyl substituted with oxadiazolyl which has phenyl substituted with phenyl having methoxyoctyloxy, benzoyl substituted with oxadiazolyl which has phenyl substituted with phenyl which has propyloxy having dimethylmorpholinyl, benzoyl substituted with thiadiazolyl which has phenyl having phenyloxybutyloxy, benzoyl substituted with thiadiazolyl which has phenyl having phenyloxypentyloxy, benzoyl substituted with thiadiazolyl which has phenyl having phenyloxypropyloxy, benzoyl substituted with thiadiazolyl which has phenyl having methoxypentyloxy, benzoyl substituted with thiadiazolyl which has phenyl having methoxyheptyloxy, benzoyl substituted with thiadiazolyl which has pyridyl having piperidyl, benzoyl substituted with imidazothiadiazolyl which has phenyl having pentyloxy, benzoyl substituted with imidazothiadiazolyl which has phenyl having cyclohexyloxy, benzoyl substituted with isoxazolyl which has phenyl having pentyloxy, benzoyl substituted with thiadiazolyl having phenyl which has piperidyl having propoxy, benzoyl substituted with thiadiazolyl having phenyl which has piperidyl having cyclohexyloxy, benzoyl substituted with thiadiazolyl having phenyl which has piperidyl having phenylmethoxy, benzoyl substituted with imidazothiadiazolyl having phenyl which has piperazinyl having cyclohexyl, benzoyl substituted with thiadiazolyl having phenyl which has piperazinyl substituted with cyclohexyl having dimethyl, benzoyl substituted with thiadiazolyl having phenyl which has piperazinyl having cyclohexyl, benzoyl substituted with thiadiazolyl having phenyl which has piperazinyl substituted with cyclohexyl having methyl, benzoyl substituted with thiadiazolyl having phenyl which has piperidyl substituted with methoxy and chlorophenyl, benzoyl substituted with thiadiazolyl having phenyl which has piperidyl substituted with phenyl, benzoyl substituted with thiadiazolyl having phenyl which has piperazinyl substituted with phenyl, benzoyl substituted with thiadiazolyl having phenyl which has thiazolyl substituted with pentyloxyphenyl, benzoyl substituted with thiadiazolyl having pyrazolyl which has hexyloxyphenyl, benzoyl substituted with thiadiazolyl having pyrazolyl which has heptyloxymethylphenyl, benzoyl substituted with piperidyl having piperazinyl which has phenyl having cyclohexyl, benzoyl substituted with thiadiazolyl having pyrazolyl which has phenyl having piperidyl, benzoyl substituted with thiadiazolyl having pyrazolyl which has phenyl having pyrrolidinyl, benzoyl substituted with thiadiazolyl having pyrazolyl which has phenyl substituted with piperazinylmethyl having phenyl, benzoyl substituted with thiadiazolyl having pyridyl which has piperidyl having phenyl, benzoyl substituted with thiadiazolyl having phenyl substituted with phenyl which has cyclohexyloxy, benzoyl substituted with thiadiazolyl having phenyl substituted with phenyl which has ethoxymethyl, benzoyl substituted with thiadiazolyl having phenyl substituted with phenyl which has ethoxypropoxy, benzoyl substituted with thiadiazolyl having phenyl substituted with phenyl which has ethoxyethoxy, benzoyl substituted with thiadiazolyl having phenyl substituted with phenyl which has methoxypropoxy, benzoyl substituted with thiadiazolyl having phenyl substituted with phenyl which has methoxyethoxy, benzoyl substituted with piperazinyl having phenyl substituted with phenyl which has methoxypentyloxy, benzoyl substituted with thiadiazolyl having phenyl substituted with phenyl which has methoxyethoxymethyl, benzoyl substituted with thiadiazolyl having phenyl substituted with phenyl which has methoxyethoxyethoxy, benzoyl substituted with thiadiazolyl having phenyl substituted with phenyl which has piperazinyl having cyclohexyl, benzoyl substituted with thiadiazolyl having phenyl substituted with phenyl which has morpholinyl having dimethyl, benzoyl substituted with oxadiazolyl which has phenyl having cyclohexyloxy, benzoyl substituted with thiadiazolyl which has phenyl having cyclohexyloxy, benzoyl substituted with piperazinyl which has phenyl having cyclohexyloxy, benzoyl substituted with piperazinyl which has phenyl having methoxyheptylthio, benzoyl substituted with imidazothiadiazolyl which has phenyl having piperidinobutoxy, benzoyl substituted with imidazothiadiazolyl which has phenyl having piperidinopentyloxy, benzoyl substituted with imidazothiadiazolyl which has phenyl having piperidinohexyloxy, benzoyl substituted with imidazothiadiazolyl which has phenyl having morpholinopentyloxy, benzoyl substituted with imidazothiadiazolyl having phenyl which has morpholinopentyloxy having dimethyl, benzoyl substituted with imidazothiadiazolyl having phenyl which has morpholinohexyloxy having dimethyl, benzoyl substituted with imidazothiadiazolyl having phenyl which has thiomorpholinopentyloxy, benzoyl substituted with piperazinyl which has cyclohexyl having pentyl, benzoyl substituted with piperazinyl which has cyclohexyl having phenyl, benzoyl substituted with piperazinyl which has indanyl, benzoyl substituted with imidazothiadiazolyl having phenyl which has piperazinyl having ethyl, benzoyl substituted with imidazothiadiazolyl which has phenyl having butoxy, benzoyl substituted with imidazothiadiazolyl which has phenyl having methoxypentyloxy, benzoyl substituted with piperazinyl which has phenyl having cyclohexyl, dimethylbenzoyl substituted with thiadiazolyl which has phenyl having methoxyhexyloxy, naphthoyl substituted with oxadiazolyl having phenyl substituted with phenyl having butoxy, naphthoyl substituted with thiadiazolyl which has phenyl having methoxyhexyloxy, benzoyl substituted with thiazolyl which has phenyl having pentyloxy, benzoyl substituted with thiazolyl which has phenyl having hexyloxy, benzoyl substituted with thiazolyl which has phenyl having heptyloxy, benzoyl substituted with thiazolyl having phenyl substituted with phenyl having propoxy, benzoyl substituted with imidazothiadiazolyl which has phenyl having methoxyhexyloxy, benzoyl substituted with imidazothiadiazolyl which has phenyl having methoxyheptyloxy, benzoyl substituted with imidazothiadiazolyl which has phenyl having methoxyoctyloxy, benzoyl substituted with imidazothiadiazolyl which has phenyl having morpholino, benzoyl substituted with imidazothiadiazolyl which has phenyl having dimethylmorpholino, benzoyl substituted with imidazothiadiazolyl which has phenyl having thiomorpholino, benzoyl substituted with imidazothiadiazolyl which has phenyl having pentyloxy, benzoyl substituted with imidazothiadiazolyl which has phenyl having hexyloxy, benzoyl substituted with thiadiazolyl which has phenyl having cyclohexyl, benzoyl substituted with oxadiazolyl which has phenyl having cyclohexyl, benzoyl substituted with thiadiazolyl which has phenyl substituted with phenyl having propoxy, benzoyl substituted with thiadiazolyl which has phenyl substituted with phenyl having ethoxy, benzoyl substituted with thiadiazolyl which has phenyl substituted with phenyl having methoxybutoxy, and benzoyl substituted with thiadiazolyl which has phenyl substituted with phenyl having butoxy.

Suitable example of "aroyl" moiety in the term of "aroyl substituted with aryl having higher alkyl" can be referred to aforementioned "aroyl", in which the preferred one may be benzoyl.

Suitable example of "aryl" moiety in the term of "aroyl substituted with aryl having higher alkyl" can be referred to aforementioned "aryl", in which the preferred one may be phenyl.

Suitable example of "higher alkyl" moiety in the term of "aroyl substituted with aryl having higher alkyl" can be referred to aforementioned "higher alkyl", in which the preferred one may be ($C_7$–$C_{14}$)alkyl, and the more preferred one may be heptyl.

Suitable example of "aroyl substituted with aryl having higher alkyl" may be benzoyl substituted with phenyl having ($C_7$–$C_{14}$)alkyl, in which the preferred one may be benzoyl substituted with phenyl having heptyl.

Suitable example of "aroyl" moiety in the term of "aroyl substituted with aryl having lower alkyl" can be referred to aforementioned "aroyl", in which the preferred one may be benzoyl.

Suitable example of "aryl" moiety in the term of "aroyl substituted with aryl having lower alkyl" can be referred to aforementioned "aryl", in which the preferred one may be phenyl.

Suitable example of "lower alkyl" moiety in the term of "aroyl substituted with aryl having lower alkyl" can be referred to aforementioned "lower alkyl", in which the preferred one may be ($C_4$–$C_6$)alkyl, and the more preferred one may be hexyl.

Suitable example of "aroyl substituted with aryl having lower alkyl" may be benzoyl substituted with phenyl having ($C_4$–$C_6$)alkyl, in which the preferred one may be benzoyl substituted with phenyl having hexyl.

Suitable example of "aryl" moiety in the term of "aryl ($C_2$–$C_6$)alkanoyl substituted with aryl having lower alkyl"

can be referred to aforementioned "aryl", in which the preferred one may be phenyl.

Suitable example of "($C_2$–$C_6$)alkanoyl" moiety in the term of "aryl($C_2$–$C_6$)alkanoyl substituted with aryl having lower alkyl" may be acetyl, propionyl, butyryl, etc., in which the preferred one may be ($C_2$–$C_4$)alkanoyl, and the more preferred one may be propionyl.

Suitable example of "lower alkyl" moiety in the term of "aryl($C_2$–$C_6$)alkanoyl substituted with aryl having lower alkyl" can be referred to aforementioned "lower alkyl", in which the preferred one may be ($C_4$–$C_6$)alkyl, and the more preferred one may be pentyl.

Suitable example of "aryl($C_2$–$C_6$)alkanoyl substituted with aryl having lower alkyl" may be phenylpropionyl substituted with phenyl having pentyl.

Suitable example of "lower alkanoyl" moiety in the term of "lower alkanoyl substituted with unsaturated condensed heterocyclic group which may have one or more suitable substituent(s)" can be referred to aforementioned "lower alkanoyl", in which the preferred one may be ($C_1$–$C_3$)alkanoyl, and the more preferred one may be formyl.

Suitable example of "unsaturated condensed heterocyclic group" moiety in the term of "lower alkanoyl substituted with unsaturated condensed heterocyclic group which may have one or more suitable substituent(s)" can be referred to aforementioned "heterocyclic group", in which the preferred one may be unsaturated condensed heterocyclic group containing 1 or 2 oxygen atom(s) and 1 to 3 nitrogen atom(s), and the more preferred one may be benzoxazolyl.

Suitable example of "suitable substituent(s)" moiety in the term of "lower alkanoyl substituted with unsaturated condensed heterocyclic group which may have one or more suitable substituent(s)" may be heterocyclic group which may have one or more higher alkoxy and aryl which may have one or more lower alkoxy, in which the preferred one may be unsaturated 3 to 8-membered heteromonocyclic group containing 1 to 4 nitrogen atom(s) having ($C_7$–$C_{14}$)alkoxy and phenyl having ($C_4$–$C_6$)alkoxy, and the more preferred one may be pyridyl having octyloxy and phenyl having hexyloxy.

Suitable example of "lower alkanoyl substituted with unsaturated condensed heterocyclic group which may have one or more suitable substituent(s)" may be benzoxazolylcarbonyl which has pyridyl having ($C_7$–$C_{14}$)alkoxy and benzoxazolylcarbonyl which has phenyl having ($C_4$–$C_6$)alkoxy, in which the preferred one may be benzoxazolylcarbonyl which has pyridyl having octyloxy and benzoxazolylcarbonyl which has phenyl having hexyloxy.

Suitable example of "lower alkanoyl" moiety in the term of "lower alkanoyl substituted with pyridyl which may have one or more suitable substituted(s)" can be referred to aforementioned "lower alkanoyl", in which the preferred one may be ($C_1$–$C_3$)alkanoyl, and the more preferred one may be formyl.

Suitable example of "suitable substituent(s)" moiety in the term of "lower alkanoyl substituted with pyridyl which may have one or more suitable substituent(s)" can be referred to aforementioned "suitable substituent(s)", in which the preferred one may be higher alkoxy, and the more preferred one may be ($C_7$–$C_{14}$)alkoxy, and the most preferred one may be heptyloxy and octyloxy.

Suitable example of "lower alkanoyl substituted with pyridyl which may have one or more suitable substituent(s)" may be pyridylcarbonyl having ($C_7$–$C_{14}$)alkoxy, in which the preferred one may be pyridylcarbonyl having octyloxy and pyridylcarbonyl having heptyloxy.

Suitable example of "aroyl" moiety in the term of "aroyl substituted with heterocyclic carbamoyl which may have one or more suitable substituent(s)" can be referred to aforementioned "aroyl", in which the preferred one may be benzoyl.

Suitable example of "heterocyclic" moiety in the term of "aroyl substituted with heterocyclic carbamoyl which may have one or more suitable substituent(s)" can be referred to aforementioned "heterocyclic" moiety, in which the preferred one may be unsaturated 3 to 8-membered heteromonocyclic group containing 1 or 2 sulfur atom(s) and 1 to 3 nitrogen atom(s), and the more preferred one may be thiadiazolyl.

Suitable example of "suitable substituent(s)" moiety in the term of "aroyl substituted with heterocyclic carbamoyl which may have one or more suitable substituent(s)" can be referred to aforementioned "suitable substituent(s)", in which the preferred one may be phenyl having ($C_1$–$C_6$)alkoxy, and the more preferred one may be phenyl having pentyloxy.

Suitable example of "aroyl substituted with heterocyclic carbamoyl which may have one or more suitable substituent(s)" may be benzoyl substituted with thiadiazolyl carbamoyl which has phenyl having pentyloxy.

Suitable example of "lower alkanoyl" moiety in the term of "lower alkanoyl substituted with cyclo(lower)alkyl which may have one or more suitable substituent(s)" can be referred to aforementioned "lower alkanoyl", in which the preferred one may be formyl.

Suitable example of "cycle(lower)alkyl" moiety in the term of "lower alkanoyl substituted with cyclo(lower)alkyl which may have one or more suitable substituent(s)" can be referred to aforementioned "cyclo(lower)alkyl", in which the preferred one may be cyclohexyl.

Suitable example of "suitable substituent(s)" moiety in the term of "lower alkanoyl substituted with cyclo(lower)alkyl which may have one or more suitable substituent(s)" can be referred to aforementioned "suitable substituent(s)", in which the preferred one may be heterocyclic group which may have one or more aryl having lower alkoxy(lower)alkoxy, and the more preferred one may be thiadiazolyl which has phenyl having methoxyhexyloxy.

Suitable example of "lower alkanoyl" moiety in the term of "lower alkanoyl substituted with thienyl having heterocyclic group which may have one or more suitable substituent(s)" can be referred to aforementioned "lower alkanoyl", in which the preferred one may be formyl.

Suitable example of "heterocyclic group" moiety in the term of "lower alkanoyl substituted with thienyl having heterocyclic group which may one or more suitable substituent(s)" can be referred to aforementioned "heterocyclic group", in which the preferred one may be unsaturated 3 to 8-membered heteromonocyclic group containing 1 or 2 oxygen atom(s) and 1 to 3 nitrogen atom(s), and the more preferred one may be oxadiazolyl.

Suitable example of "suitable substituent(s)" moiety in the term of "lower alkanoyl substituted with thienyl having heterocyclic group which may have one or more suitable substituent(s)" can be referred to aforementioned "suitable substituent(s)", in which the preferred one may be aryl substituted with aryl which may have one or more lower alkoxy, and the more preferred one may be phenyl substituted with phenyl having pentyloxy.

Suitable example of "lower alkenoyl" moiety in the term of "lower alkenoyl substituted with heterocyclic group which may have one or more suitable substituent(s)" may be acryloyl, butenoyl, pentenoyl, hexenoyl, 2,4-hexendienoyl, and the like, in which the preferred one may be 2,4-hexenedienoyl.

Suitable example of "heterocyclic group" moiety in the term of "lower alkenoyl substituted with heterocyclic group which may have one or more suitable substituent(s)" can be referred to aforementioned "heterocyclic group" moiety, in which the preferred one may be unsaturated 3 to 8-membered heteromonocyclic group containing 1 or 2 sulfur atom(s) and 1 to 3 nitrogen atom(s), and the more preferred one may be thiadiazolyl.

Suitable example of "suitable substituent(s)" moiety in the term of "lower alkenoyl substituted with heterocyclic group which may have one or more suitable substituent(s)" can be referred to aforementioned "suitable substituent(s)", in which the preferred one may be aryl having lower alkoxy(lower)alkoxy, and the more preferred one may be phenyl having methoxyhexyloxy.

The processes for preparing the object polypeptide compound [I] and the starting compound [II] or a salt thereof the present invention are explained in detail in the following Process 1

The object polypeptide compound [Ia] or a salt thereof can be prepared by reacting the compound [Ib] or its reactive derivative at the amino group or a salt thereof with the compound [III] or its reactive derivative at the carboxy group or a salt thereof.

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g., benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachloropentyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H-pyridone, N-hydroxysuccinimide, N-hydroxyphthalmide, 1-hydroxy-1H-benzotriazole, etc.], and the like. These reactive derivatives can optionally be selected from them according to the mind of the compound [III] to be used.

Suitable salts of the compound [III] and its reactive derivative can be referred to the ones as exemplified for the object polypeptide compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-n'-(4-diethylaminocyclohexyl)carbodiimide; N,N'-diethylcarbodiimide; N,N'-diisopropylcarbodiimide; N-ethyl-N'-(3-dimethylaminopropy)carbodiimide; N,N-carbonylbis-(2-methylimidazole); pentamethyleneketene-N-cyclohexylimine; diphenylketene-N-cyclohexylimine, ethoxyacetylene; 1-alkoxy-2-chloroethylene; trialkyl phosphite; ethyl polyphosphate; isopropyl polyphosphate; phosphorus oxychloride (phosphoryl chloride); phosphorous trichloride; thionyl chloride; oxalyl chloride; lower alkyl haloformate [e.g., ethyl chloroformate, ispopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

Process 2

The object compound [$I_a$] or a salt thereof can be prepared by reducing a compound [II] or a salt thereof.

Suitable salts of the compounds [$I_a$] and [II] may be the same as those exemplified for the compound [I].

The reaction can be carried out in a conventional manner, namely, chemical reduction or catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, hydride transfer reagent such as aluminum hydride compound (e.g. lithium aluminum hydride, lithium hydridotri-t-butoxyaluminate, etc.), borohydride compound (e.g. sodium borohydride, sodium cyanoborohydride, etc.) or the like etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g., spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.]or the like.

The reaction of this process is usually carried out in a solvent such as water, alcohol [e.g. methanol, ethanol, propanol, etc.], acetic acid, diethyl ether, dioxane, tetrahydrofuran, methylene chloride, etc. or a mixture thereof.

The reaction is preferably carried out under somewhat milder conditions such as under cooling to warming.

It is included within the scope of the present invention that "hydroxy" in $R^2$ may be reduced to "hydrogen" during the reaction.

Process 3

The object compound [Ib] or a salt thereof can be prepared by reducing the starting compound [IV] or a salt thereof to reduction reaction.

This reaction can be carried out in substantially the same manner as Process 2, and therefore the reaction mode and reaction conditions [e.g. solvent, reaction temperature, etc.] of this reaction are to be referred to those as explained in Process 2.

Process A

The object compound [II] or a salt thereof can be prepared by reacting the starting compound [IV] or its reactive derivative at the amino group or a salt thereof with the compound [III] or its reactive derivative at the carboxy group or a salt thereof.

This reaction can be carried out in substantially the same manner as Process 1, and therefore the reaction mode and reaction conditions [e.g. solvent, reaction temperature, etc.] of this reaction are to be referred to those as explained in Process 1.

Process B

The compound [IVb] or a salt thereof can be prepared by subjecting the compound [IVa] or its reactive derivative at the sulfonic acid group or a salt thereof to hydrolysis reaction of the sulfonic acid group.

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g. trimethylamine, triethylamine, etc.], picoline, 1,5-diazabicyclo[4.3.0]-non-5-ene, or the like.

Suitable acid may include an organic acid [e.g., formic acid, acetic acid, propionoc acid, trichloroacetic acid, trifluoroacetic acid, etc], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like preferably carried out in the presence of cation trapping agent [e.g., anisole, phenol, etc.].

The reaction is usually carried out in a conventional solvent such as water, alcohol [e.g. methanol, ethanol, isopropyl alcohol, etc.], tetrahydrofuran, dioxane, toluene, methylene chloride, ethylene dichloride, chloroform, N,N-dimethylformamide, N,N-dimethylacetamide or any other organic solvent which do not adversely affect the reaction, or the mixture thereof.

The reaction temperature is not critical and the reaction is usually carried out under cooling to warming.

The starting compound [IVa] is known compound. It can be prepared by fermentation and synthetic processes disclosed in EP 0462531 A2.

Process C

The compound [IVc] or a salt thereof can be prepared by subjecting the compound [IVb] or its reactive derivative at the hydroxy group or a salt thereof with the diazo compound [e.g., diazomethane, phenyldiazomethane, diphenyldiazomethane, trimethylsilyldiazomethane, β-diazopropionic acid etc.] or a salt thereof to alkylation reaction of the hydroxy group.

This reaction is usually carried out in the solvent such as water, alcohol [e.g. methanol, ethanol, etc.], benzene, N,N-dimethylformamide, tetrahydrofuran, toluene, methylene chloride, ethylene dichloride, chloroform, dioxane, diethyl ether, acetonitrile or any other solvents which do not adversely affect the reaction, or the mixture thereof.

The reaction temperature is not critical and the reaction is usually carried out under cooling to heating.

The reaction may be usually carried out in the presence of an acid including Lewis acid.

Suitable acid may include an organic acid [e.g., formic acid, acetic acid, propionic acid, trichloroacetic acid, trifluoroacetic acid, etc], and an inorganic acid [e.g., hydrochloric acid, hydrobromic acid, sulfuric acid, hydrogen chloride, hydrogen bromide, zinc halide (e.g., zinc chloride, zince bromide, etc.), etc.] and the like.

The reaction may be also carried out in the presence of an inorganic or an organic base such as an alkali metal [e.g., sodium, potassium, etc.], an alkali metal hydroxide [e.g., sodium hydroxide, potassium hydroxide, etc.], an alkali metal hydrogencarbonate [e.g., sodium hydrogencarbonate, potassium hydrogencarbonate, etc.], alkaline metal carbonate [e.g., sodium carbonate, potassium carbonate, etc.], tri(lower)alkylamine [e.g. trimethylamine, triethylamine, diisopropylethylamine, etc.], alkali metal hydride [e.g., sodium hydride, etc.], alkali metal (lower)alkoxide [e.g., sodium methoxide, sodium ethoxide, etc.], pyridine, lutidine, picoline, dimethylaminopyridine, N-(lower)alkylmorpholine, N,N-di(lower)alkylbenzylamine, N,N-di(lower)alkylaniline or the like.

When the base, the acid and/or the starting compound are in liquid, they can be used also as a solvent.

The compounds obtained by the above Processes 1 to 3 and Processes A to C can be isolated and purified by a conventional method such as pulverization, recrystallization, column-chromatography, high-performance liquid chromatography (HPLC), reprecipitation, desalting resin column chromatography, or the like.

The compounds obtained by the above Processes 1 to 3 and Processes A to C may be obtained as its hydrate, and its hydrate is included within the scope of present invention.

It is to be noted that each of the object compound (I) may include one or more stereoisomer such as optical isomer(s) and geometrical isomer(s) due to asymmetric carbon atom(s) and double bond(s) and all such isomers and the mixture thereof are included within the scope of the present invention.

The object compound (I) or a salt thereof includes solvated compound [e.g., enclosure compound (e.g., hydrate, etc.)].

The object compound (I) or a salt thereof includes both its crystal form and non-crystal form.

It should be understood that the compounds in the present invention may include the prodrug form.

The patent applications and publications cited herein are incorporated by reference.

This application is based on application No. PP1728/98 and application No. PP3138/98 filed in Australia, the content of which is incorporated hereinto by reference.

Biological Property of the Polypeptide Compound [I] of the Present Invention

In order to show the usefulness of the polypeptide compound [I] of the present invention, the biological data of the representative compound is explained in the following.

Test (Antimicrobial activity):

In vitro antimicrobial activity of the object compound of Example 12 disclosed later was determined by microdilution method as described below.

Test Method:

The antifungal susceptibility assays were performed by the microdilution method according to M27-A guidelines recommended by the National Committee for Clinical Laboratory Standards (NCCLS) to determine the MICs of the compounds. RPMI1640 medium with L-glutamine, without sodium bicarbonate, and buffered with 165 mM morpholinepropanesulfonic acid buffer (pH 7.0) was used as a test medium. Inoculum suspension of $10^6$ CFU/ml were prepared by a hemocytometric procedure, and diluted to obtain an inoculum size of approximately $0.5 \times 10^3$ to $2.5 \times 10^3$ CFU/ml. Microplates were incubated at 35° C. and readings were taken when good growth in the growth control. The MICs were defined as the lower concentrations at which no visible growth was observed.

| | Test Result : MIC ($\mu$g/ml) |
|---|---|
| Test compound Test organism | The object compound of Example 12 |
| *candida albicans* FP-633 | 0.0625 | polypeptide compound [I] of the present invention has an antimicrobial activity (especially, antifungal activity).

The pharmaceutical composition of the present invention can be used in the form of a pharmaceutical preparation, for example, in solid, semisolid or liquid form, which contains the object polypeptide compound [I] or a pharmaceutically acceptable salt thereof, as an active ingredient in admixture with an organic or inorganic carrier or excipient which is suitable for rectal; pulmonary (nasal or buccal inhalation); ocular; external (topical); oral adminstration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object polypeptide compound [I] or a pharmaceutically acceptable salt thereof is/are included in the pharmaceutical composition in an amount sufficient to produce the desired antimicrobial effect upon the process or condition of diseases.

For applying the composition to human, it is preferable to apply it by intravenous, intramuscular, ulmonary, oral adminstration, or insufflation. While the dosage of therapeutically effective amount of the object polypeptide compound [I] varies from and also depends upon the age and condition of each individual patient to be treated, in the case of intravenous administration, a daily dose of 0.01–20 mg of the object polypeptide compound [I] per kg weight of human being in the case of intramuscular administration, a daily dose of 0.1–20 mg of the object polypeptide compound [I] per kg weight of human being, in case of oral administration, a daily dose of 0.5–50 mg of the object polypeptide compound [I] per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol adminstration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

Preparation 1

A solution of 4-hydroxybenzoic acid methyl ester (100 g) and 1,6-dibromohexane (481 g) in N,N-dimethylformamide (500 ml) was treated with potassium carbonate (109 g) then heated at 60° C. for 2 hours. After cooling, the mixture was diluted with ethyl acetate (3 L) and washed with water (7×1 L). The organic layer was dried over magnesium sulfate, filtered, and evaporated to give a crude oil. Hexane (~100 ml) was added and the resulting precipitate removed by filtration and discarded and the filtrate loaded onto a silica gel column (2 kg). Elution with hexane, followed by 9:1 hexane-ethyl acetate and 8:1 hexane-ethyl acetate afforded methyl 4-(6-bromo-n-hexyloxy)benzoate (186 g) as a white solid.

NMR (CDCl$_3$, $\delta$): 1.46–1.55 (4H, m), 1.78–1.97 (4H, m), 3.38–3.46 (2H, m), 3.88 (3H, s), 4.01 (2H, t, J=6.3 Hz), 6.90 (2H, d, J=8.9 Hz), 7.98 (2H, d, J–8.9 Hz)

MASS (m/z): 315, 317 (M$^+$)

The following compound was obtained in a manner similar to that of Preparation 1.

Preparation 2

Methyl 4-(7-bromo-n-heptyloxy)benzoate

NMR (DMSO-d$_6$, $\delta$): 1.2–1.6 (6H, m), 1.6–2.0 (4H, m), 3.53 (2H, t, J=6.7 Hz), 3.81 (3H, s), 4.04 (2H, t, J=6.4 Hz), 7.03 (2H, d, J=8.9 Hz), 7.90 (2H, d, J=8.9 Hz)

MASS (m/z): 329 (M+1), 331 (M+3)

Preparation 3

A solution of methyl 4-(6-bromo-n-hexyloxy)benzoate (186 g) in methanol (1 L) was treated with 28% sodium methoxide in methanol (340 ml) and the solution refluxed for 2 hours. After cooling, the stirred solution was adjusted to pH 2 with 1M-hydrochloric acid then extracted with ethyl acetate. The organic layer was washed with water, dried over magnesium sulfate, filtered and evaporated to give a crude oil. This oil was purified on a silica gel column (2 kg, 9:1 hexane-ethyl acetate elution) to give methyl 4-(6-methoxy-n-hexyloxy)benzoate (127 g) as an oil.

NMR (CDCl$_3$, $\delta$): 1.37–1.68 (6H, m), 1.74–1.88 (2H, m), 3.33 (3H, s), 3.39 (2H, t, J=6.3 Hz), 3.88 (3H, s), 4.01 (2H, t, J=6.4 Hz), 6.90 (2H, d, J=8.9 Hz), 7.97 (2H, d, J=8.9 Hz)

The following compound was obtained in a manner similar to that of Preparation 3.

Preparation 4

Methyl 4-(7-methoxy-n-heptyloxy)benzoate

NMR (DMSO-d$_6$, $\delta$): 1.2–1.6 (8H, m), 1.6–1.9 (2H, m), 3.21 (3H, s), 3.29 (2H, t, J=6.4 Hz), 3.81 (3H, s), 4.04 (2H, t, J=6.5 Hz), 7.03 (2H, d, J=8.9 Hz), 7.90 (2H, d, J=8.9 Hz)

MASS (m/z): 281 (M+1)

Preparation 5

A solution of methyl 4-(6-methoxy-n-hexyloxy)benzoate (17.05 g) in 1:1 tetrahydrofuran-methanol (300 ml) was treated with hydrazine monohydrate (66 ml) and refluxed for 15 hours then cooled to room temperature. The reaction mixture was poured into water and the resulting precipitate collected by filtration, washed thoroughly with water then dried under hi-vacuum at 50° C. to give 4-(6-methoxy-n-hexyloxy)benzohydrazide (15.63 g) as a white solid.

NMR (DMSO-$d_6$, δ): 1.29–1.58 (6H, m), 1.65–1.78 (2H, m), 3.21 (3H, s), 3.30 (2H, t, J=6.4 Hz), 4.00 (2H, t, J=6.4 Hz), 4.40 (2H, s), 6.96 (2H, d, J=8.8 Hz), 7.78 (2H, d, J=8.8 Hz), 9.59 (1H, s)

MASS (m/z): 267 (M+1)

The following compound was obtained in a manner similar to that of Preparation 5.

Preparation 6

4-(7-Methoxy-n-heptyloxy)benzohydrazide

NMR (DMSO-$d_6$, δ): 1.2–1.6 (8H, m), 1.6–1.9 (2H, m), 3.21 (3H, s), 3.30 (2H, t, J=6.4 Hz), 4.00 (2H, t, J=6.4 Hz), 4.40 (2H, s), 6.96 (2H, d, J=8.7 Hz), 7.78 (2H, d, J=8.9 Hz), 9.59 (1H, s)

MASS (m/z): 281 (M+1)

Preparation 7

A mixture of 4-(6-methoxy-n-hexyloxy)benzohydrazide (106.82 g) and pyridine (162 ml) in tetrahydrofuran (1 L) at 0°.5° C. was treated portionwise with 4-methoxycarbonylbenzoyl chloride 83.75 g) over 30 minutes. After a further 1 hour at 0°–5° C., and 2 hours at room temperature, tlc indicated completed reaction and the reaction mixture was poured into water (7 L). The resulting precipitate was collected by filtration, washed thoroughly with water, and dried under hi-vacuum at 50° C. to give N-[4-(6-methoxy-n-hexyloxy)benzoyl]-N'-(4-methoxycarbonylbenzoyl)hydrazine (171.0 g) as a white solid.

NMR (DMSO-$d_6$, δ): 1.40–1.80 (8H, m), 3.22 (3H, s), 3.31 (2H, t, J=6.4 Hz), 3.90 (3H, s), 4.05 (2H, t, J=6.3 Hz), 7.04 (2H, d, J=8.8 Hz), 7.90 (2H, d, J=8.8 Hz), 8.03 (2H, d, J=8.6 Hz), 8.10 (2H, d, J=8.6 Hz), 10.41 (1H, s), 10.64 (1H, s)

The following compound was obtained in a manner similar to that of Preparation 7.

Preparation 8

N-[4-(7-Methoxy-n-heptyloxy)benzoyl]-N'-(4-methoxycarbonylbenzoyl)hydrazine

NMR (DMSO-$d_6$, δ): 1.2–1.6 (8H, m), 1.6–1.9 (2H, m), 3.21 (3H, s), 3.30 (2H, t, J=6.4 Hz), 3.90 (3H, s), 4.05 (2H, t, J=6.4 Hz), 7.04 (2H, d, J=8.8 Hz), 7.90 (2H, d, J=8.8 Hz), 8.03 (2H, d, J=8.6 Hz), 8.10 (2H, d, J=8.6 Hz), 10.42 (1H, s), 10.63 (1H, s)

MASS (m/z): 443 (M+1)

Preparation 9

A mixture of N-[4-(6-methoxy-n-hexyloxy)benzoyl]-N'-(4-methoxycarbonylbenzoyl)hydrazine (193.4 g) and phosphorus pentasulfide (113.34 g) in tetrahydrofuran (2.5 L) was heated to reflux for 1 hour then cooled to room temperature and poured into water (7 L). The resulting precipitate was collected by filtration, washed thoroughly with water then partially dried. The solid was added to 1:1 $CH_3CN$—$H_2O$ (200 ml), sitrred then filtered. This procedure was repeated a further 2 times, and the resulting yellow powder washed thoroughly with acetonitrile (500 ml×5) then dried under hi-vacuum at 50° C. to give methyl 4-[5-[4-(6-methoxy-n-hexyloxy)phenyl]-1,3,4-thiadiazol-2-yl]benzoate (179.6 g) as a yellow powder.

NMR (CDCl$_3$, δ):1.40–1.87 (8H, m), 3.34 (3H, s), 3.40 (2H, t, J=6.2 Hz), 3.96 (3H, s), 4.03 (2H, t, J=6.5 Hz), 6.99 (2H, d, J=8.8 Hz), 7.95 (2H, d, J=8.8 Hz), 8.07 (2H, d, J=8.5 Hz), 8.16 (2H, d, J=8.5 Hz)

The following compound was obtained in a manner similar to that of Preparation 9.

Preparation 10

Methyl 4-[5-[4-(7-methoxy-n-heptyloxy)phenyl]-1,3,4-thiadiazol-2-yl]benzoate

NMR (CDCl$_3$, δ):1.3–2.0 (10H, m), 3.34 (3H, s), 3.38 (2H, t, J=6.42 Hz), 3.96 (3H, s), 4.03 (2H, t, J=6.5 Hz), 6.99 (2H, d, J=8.8 Hz), 7.95 (2H, d, J=8.8 Hz), 8.07 (2H, d, J=8.4 Hz), 8.43 (2H, d, J=8.4 Hz)

MASS (m/z):441 (M+1)

Preparation 11

A mixture of methyl 4-[5-[4-(6-methoxy-n-hexyloxy)-phenyl]-1,3,4-thiadiazol-2-yl]benzoate (179.6 g), sodium hydroxide (25.3 g), water (250 ml), methanol (1 L), and tetrahydrofuran (750 ml) was heated under refluxing for 1 hour then cooled to room temperature and poured into water (7 L). The pH of the stirred mixture was adjusted to 2.0 with 6N-hydrochloric acid and the precipitate collected by filtration, washed thoroughly with water, followed by acetonitrile, then dried under hi-vacuum at 50° C. to give 4-[5-[4-(6-methoxy-n-hexyloxy)phenyl]-1,3,4-thiadiazol-2-yl]benzoic acid (167 g) as a yellow powder.

NMR (DMSO-$d_6$, δ):1.27–1.85 (8H, m), 3.22 (3H, s), 3.22 (2H, t, J=6.4 Hz), 4.06 (2H, t, J=6.3 Hz), 7.12 (2H, d, J=8.83 Hz), 7.97 (2H, d, J=8.7 Hz), 8.12 (4H, s), 13.28 (1H, br s)

The following compound was obtained in a manner similar to that of Preparation 11.

Preparation 12

4-[5-[4-(7-Methoxy-n-heptyloxy)phenyl]-1,3,4-thiadiazol-2-yl]benzoic acid

IR (KBr):2939.0, 2867.6, 2642.0, 1712.5, 1604.5, 1440.6, 1402.0, 1253.5 cm$^{-1}$

MASS (m/z):427 (M+1)

Preparation 13

A mixture of 4-[5-[4-(6-methoxy-n-hexyloxy)phenyl]-1,3,4-thiadiazole-2-yl]benzoic acid (50 g), 1-hydroxybenzotriazole (18 g) and 1-ethyl-3-(3'-dimethylaminopropyl)carbodiimide, hydrochloride (34.86 g) in methylene chloride (1 L) was stirred for 16 hours at room temperature then evaporated under reduced pressure and dried for 1 hour under hi-vacuum. Water (1 L) was added to the residue and the resulting precipitate collected by filtration, washed with water (1 L×5), acetonitrile (1L×5), isopropyl ether (250 ml×2), then dried under hi-vacuum to give 4-[5-[4-(6-methoxy-n-hexyloxy)phenyl]-1,3,4-thiadiazol-2-yl]benzoic acid benzotriazol-1-yl ester (56.92 g) as a yellow powder.

IR (KBr):1778 cm$^{-1}$

NMR (CDCl$_3$, δ):1.44–1.89 (8H, m), 3.35 (3H, s), 3.40 (2H, t, J=6.2 Hz), 4.05 (2H, t, J=6.4 Hz), 7.01 (2H, d, J=8.8 Hz), 7.43–7.63 (3H, m), 7.98 (2H, d, J=8.8 Hz), 8.13 (1H, d, J=8.2 Hz), 8.24 (2H, d, J=8.5 Hz), 8.41 (2H, d, J=8.5 Hz)

The following compounds [Preparations 14 and 15] were obtained in a manner similar to that of Preparation 13.

Preparation 14

4-[5-[4-(7-Methoxy-n-heptyloxy)phenyl]-1,3,4-thiadiazol-2-yl]benzoic acid benzotriazol-1-yl ester IR (KBr):3446.2, 2937.1, 2865.7, 1778.0, 1602.6, 1253.5 cm$^{-1}$ NMR (CDCl$_3$, δ):1.3–2.0 (10H, m), 3.34 (3H, s) 3.39 (2H, t, J=6.4 Hz), 4.03 (2H, t, J=6.5 Hz), 7.01 (2H, d, J=8.8 Hz), 7.4–7.7 (3H, m), 7.98 (2H, d, J=8.8 Hz), 8.13 (1H, d, J=8.2 Hz), 8.24 (2H, d, J=8.7 Hz), 8.41 (2H, d, J=8.7 Hz)

MASS (m/z):544 (M+1)

Preparation 15

4-[5-(4-Pentyloxyphenyl)isoxazol-3-yl]benzoic acid benzotriazol-1-yl ester

Preparation 16

To 3-hydroxybenzoic acid methyl ester (25 g) and potassium carbonate (25 g) in N,N-dimethylformamide (300 ml) were added 1-bromopentane (25 ml) and the mixture was stirred for 7 hours at 80° C. the reaction mixture was added to a mixture of water and ethyl acetate. The organic layer was taken and dried over magnesium sulfate. The magnesium sulfate was filtered off and the filtrate was evaporated under reduced pressure to give 3-amyloxybenzoic acid methyl ester (35 g).

IR (KBr): 2954, 2870, 1724, 1587 cm$^{-1}$

NMR (CDCl$_3$, δ)): 0.94 (3H, t, J=7.0 Hz), 1.43 (4H, m), 1.80 (2H, m), 3.91 (3H, s), 3.99 (2H, t, J=6.6 Hz), 7.09 (1H, ddd, J=7.8, 1.7 and 1.7 Hz), 7.32 (1H, t, J=7.8 Hz), 7.55 (1H, dd, J=1.7 and 1.1 Hz), 7.61 (1H, ddd, J=7.8, 1.7 and 1.1 Hz)

MASS (m/z):223 (M+1)

Preparation 17

To 3-amyloxybenzoic acid methyl ester (35 g) in methanol (200 ml) was added 1N-sodium hydroxide aqueous solution (200 ml) and the mixture was stirred for 2 days at room temperature. Hydroxy chloride (20 ml) was added to the raction mixture. The precipitate was filtered and washed with water, acetonitrile and diisopropyl ether to give 3-amyloxybenzoic acid (30 mg).

IR (KBr):2954, 2848, 2570, 1691, 1600, 1591 cm$^{-1}$

NMR (DMSO-d$_6$, δ):0.9 (3H, t, J=7.0 Hz), 1.40 (4H, m), 1.73 (2H, m), 4.00 (2H, t, J=6.6 Hz), 7.17 (1H, ddd, J=7.7, 2.6 and 1.2 Hz), 7.39 (1H, t, J=7.7 Hz), 7.42 (1H, dd, J=1.5 and 1.2 Hz), 7.52 (1H, ddd, J=7.7, 1.5 and 1.2 Hz)

MASS (m/z:209 (M+1)

Preparation 18

To a solution of 1-bydroxybenzotriazole (24 g) and 3-amyloxybenzoic acid (29.5 g) in dichloromethane (500 ml) was added 1-ethyl-3-(3'-dimethylaminopropyl) carbodiimide hydrochloride (WSCD.HCl) (41 g) and the mixture was stirred for 5 hours at ambient temperature. The reacrtion mixture was added to water. The organic layer was taken and dried over magnesium sulfate. Magnesium sulfate was filtered off, and the filtrate was evaporated under reduced pressure to give 3-amyloxybenzoic acid benzotriazol-1-yl ester (42 g).

IR (KBr):2956, 2935, 2869, 1788 1600 cm$^{-1}$

NMR (CDCl$_3$, δ):0.95 (3H, t, J=7.0 Hz), 1.45 (4H, m), 1.84 (2H, m), 4.05 (2H, t, J=6.5 Hz), 7.30 (1H, d, J=9.4 Hz), 7.43–7.56 (4H, m), 7.74 (1H, t, J=2.0 Hz), 8.10 (1H, d, J=8.5 Hz), 8.53 (1H, d, J=8.5 Hz)

MASS (m/z):326 (M+1)

Preparation 19

To a solution of 4-n-butyloxybenzoic acid benzotriazol-1-yl ester (15 g) in N,N-dimethylformamide (100 ml) was added thiosemicarbazide (5.27 g) and the mixture was stirred for 12 hours at ambient temperature. The reaction mixture was pulverized with diisopropyl ether. The precipitate was collected by filtration to give 1-(4-n-butyloxybenzoyl)thiosemicarbazide (11.51 g).

NMR (DMSO-d$_6$, δ):0.93 (3H, t, J=7.0 Hz), 1.2–1.5 (2H, m), 1.6–1.8 (2H, m), 4.02 (2H, t, J=6.5 Hz), 6.98 (2H, d, J=8.8 Hz), 7,56 (1H, s), 7.83 (1H, s), 7.84 (2H, d, J=8.8 Hz), 9.26 (1H, s), 10.21 (1H, s)

The following compound was obtained in a manner similar to that of Preparation 19.

Preparation 20

1-(3-Amyloxybenzoyl)thiosemicarbazide

NMR (DMSO-d$_6$, δ):0.90 (3H, t, J=6.8 Hz), 1.39 (4H, m), 1.73 (2H, m), 4.01 (2H, t, J=6.4 Hz), 7.10 (1H, d, J=8.0 Hz), 7.30–8.00 (5H, m), 9.33 (1H, s), 10.34 (1H, s), 8.53 (1H, d, J=8.5 Hz)

MASS (m/z):182 (M+1)

Preparation 21

To a slurry of 1-(4-n-butyloxybenzoyl)thiosemicarbazide (20 g) in toluene (213.3 ml) at 40° C., was added dropwise over 30 minutes, methanesulfonic acid (6.92 ml). The mixture was stirred under refluxing for 12 hours. After cooling to 10° C., the sulfonate salt was filtered and dried. The salt was placed in water, the solution was adjusted to pH 9 with 1N sodium hydroxide and extracted with ethyl acetate. The organic layer was separated, washed with brine, dried over magnesium sulfate and evaporated under reduced pressure to give 2-amino-5-(4-n-butyloxyphenyl)-1,3,4-thiadiazole (4.314 g).

NMR (CDCl$_3$, δ):0.94 (3H, t, J=7.0 Hz), 1.2–1.6 (2H, m), 1.6–1.9 (2H, m), 4.01 (2H, t, J=6.5 Hz), 7.00 (2H, d, J=8.8 Hz), 7.28 (2H, s), 7.66 (2H, d, J=8.8 Hz)

The following compound was obtained in a manner similar to that of Preparation 21.

Preparation 22

2-Amino-5-(3-amyloxyphenyl)-1,3,4-thiadiazole

IR (KBr):3291.9, 3114.5, 2952.5, 1610.3 cm$^{-1}$

NMR (DMSO-d$_6$, δ):0.90 (3H, t, J=7.0 Hz), 1.39 (4H, m), 1.73 (2H, m), 4.01 (2H, t, J=6.5 Hz), 7.00 (1H, d, J=8.5 Hz), 7.25–7.42 (5H, m)

MASS (m/z):264 (M+1)

Preparation 23

To a suspension of 2-amino-5-(4-n-butyloxyphenyl)-1,3,4-thiadiazole (1.5 g) in ethanol (30 ml) was added ethyl 4-bromoacetylbenzoate (1.86 g) and the mixture was stirred under refluxing for 1.5 hours. The reaction mixture was pulverized with ethyl acetate. The precipitate was filtered and dried. To a suspension of the powder in xylene (15 ml) was added trifluoroacetic acid (3 ml) and the mixture was stirred under refluxing for 3 hours. The reaction mixture was pulverized with diisopropyl ether. The precipitate was filtered and dried to give 4-[2-(4-butyloxyphenyl)imidazo-[2,1-b ][1,3,4]thiadiazol-6-yl]benzoic acid ethyl ester trifluoroacetic acid salt (2.15 g).

IR (KBr):1714.4, 1602.6, 1278.6, 1255.4, 1178.3 cm$^{-1}$

The following compound was obtained in amanner similar to that of Preparation 23

Preparation 24

4-[2-(3-Amyloxyphenyl)imidazo[2,1-b][1,3,4]thiadiazol-6-yl]benzoic acid ethyl ester trifluoroacetic acid salt IR (KBr):2869.6, 1704.8, 1573.6, 1278.6 cm$^{-1}$
MASS (m/z):436 (M+1)

Preparation 25

To a solution of 4-[2-(4-butyloxyphenyl)imidazo[2,1-b]-[1,3,4]thiadiazol-6-yl]benzoic acid ethyl ester trifluoroacetic acid salt (2.05 g) in the mixture of methanol (41 ml) and tetrahydrofuran (20.5 ml) was added 2N NaOH aq. (19.1 ml) and refluxed for 17 hours. The reaction mixture was adjusted to pH 1–2 with 1N HCl and the resulting precipitate was collected by filtration to give 4-[2-(4-butyloxyphenyl)imidazo[2,1-b][1,3,4]thiadiazol-6-yl]benzoic acid (1.544 g).

The following compound was obtained in a manner similar to that of Preparation 25.

Preparation 26

4-[2-(3-Amyloxyphenyl)imidazo[2,1-b][1,3,4]-thiadiazol-6-yl]benzoic acid

IR (KBr):2935.1, 2867.6, 1685.5, 1608.3 1484.9, 1288.2 cm$^{-1}$

NMR (DMSO-d$_6$, δ):0.91 (3H, t, J=7.0 Hz), 1.39 (4H, m), 1.75 (2H, m), 4.07 (2H, t, J=6.5 Hz), 7.19 (1H, m), 7.42–7.49 (3H, m), 8.00 (4H, s), 8.89 (1H, s)

MASS (m/z):408 (M+1)

The Starting compound used and the Object Compounds (27) to (30) obtained the following Preparations 27 to 30 are given in the table as below, in which the formula of the starting compound is in the upper column and the formula of the object compounds (27) to (30) are in the lower column, respectively.

| Preparation No. | Formula |
|---|---|
| 27 |  |

-continued
| Preparation No. | Formula |
|---|---|
| | 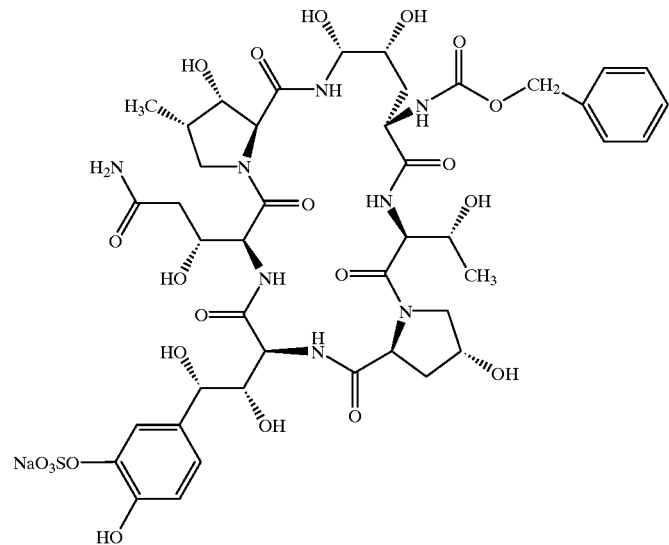 |
| 28 | 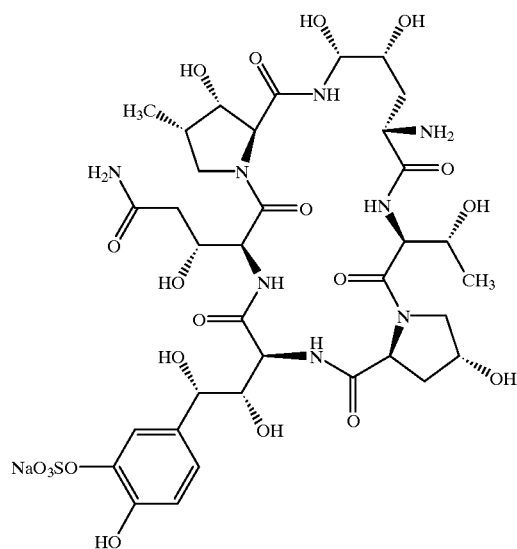 |

-continued
| Preparation No. | Formula |
|---|---|
| | 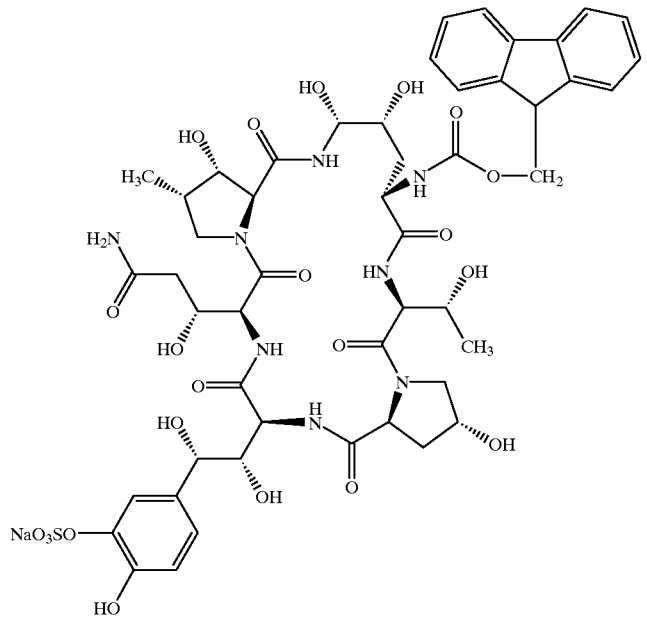 |
| 29 | 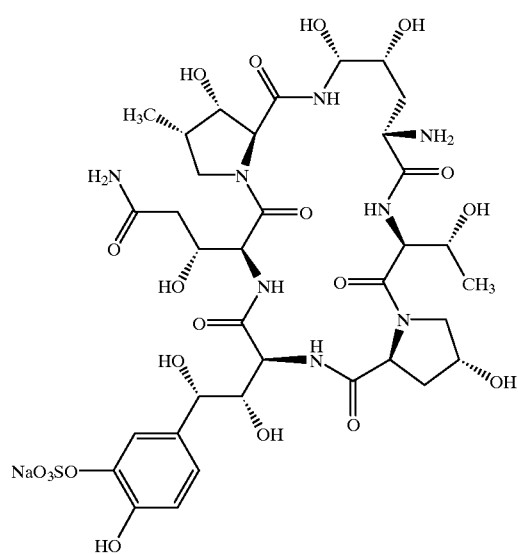 |

-continued
| Preparation No. | Formula |
|---|---|
|  | 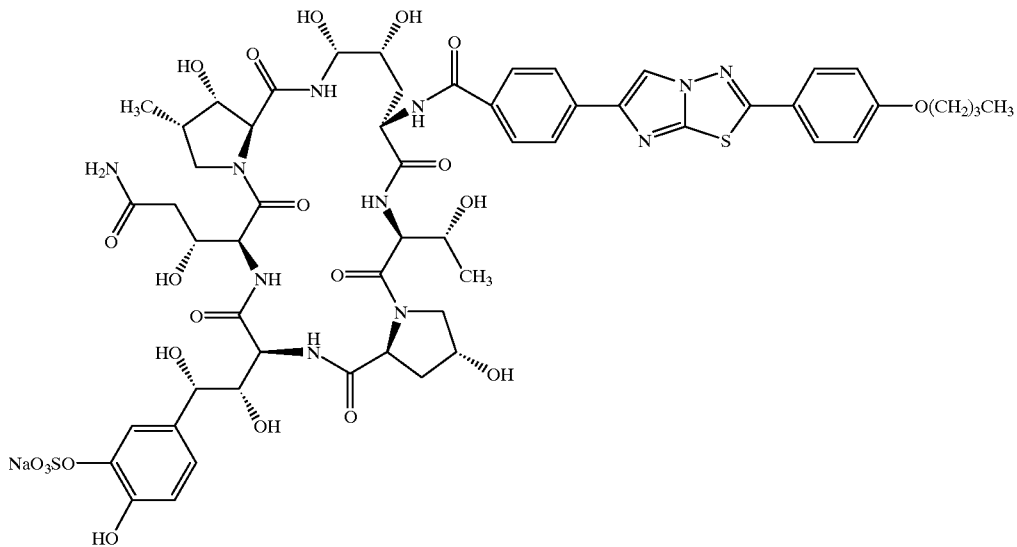 |
| 30 | 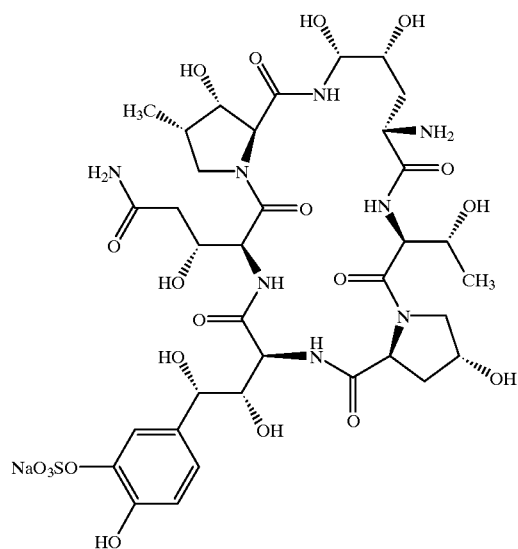 |

| Preparation No. | Formula |
|---|---|
| | 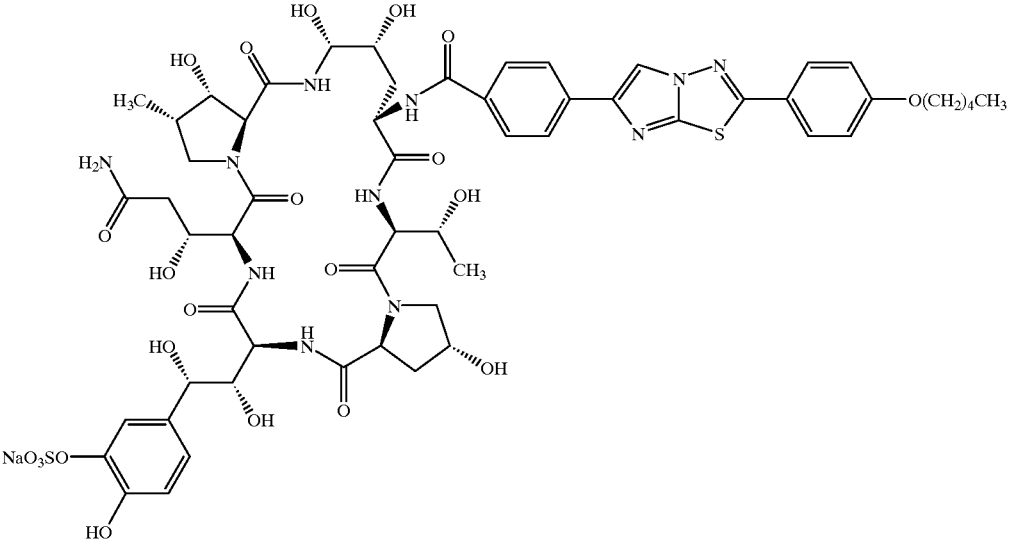 |

Preparatin 27

To a solution of Starting Compound (1 g) in tetrahydrofuran (10 ml) and pH 6.86 standard buffer soltuion (prepared by Nacalai Tesque, Inc.) (10 ml) was added dropwise with stirring to benzyloxycarbonyl chloride (0.15 ml) in an icebath. The solution was then stirred for 2 hours. the reaction mixture was acidified with dilute hydrogen chloride, and evaporated under reduced pressure. The residue was dissolved in water, and subjected to column chromatography on ion exchange resin (DOWEX-50WX4 (Trademark: prepared by Dow Chemical)) eluting with water. The fractions containing the object compound were combined, and subjected to column chromatography on ODS (YMC-gel ODS-AM-S-50 (Trademark: prepared by Yamamura Chemical Lab.)) eluting with 5% acetonitrile aqueous solution. The fractions containing the object compound were combined, and evaporated under reduced pressure to remove acetonitrile. The residue was lyophilized to give Object Compound (27) (0.78 g).

IR (KBr):3462, 3336, 1668, 1539, 1265 cm$^{-1}$

NMR (DMSO-$d_6$, δ):0.96 (3H, d, J=6.6 Hz), 1.05 (3H, d, J=5.8 Hz), 1.78–5.53 (35H, m), 6.71–8.84 (16H, m)

MASS (m/z):1068.90 (M—Na$^+$)

Preparation 28

To a solution of Starting Compound (54.4 g) and ethyldiisopropylamine (35 ml) in N,N-dimethylformamide (230 ml) was added 9-fluorenylmethyl chloroformate (15.8 g) at room temperature. The soltuion was stirred for 5 hours at the same temperature. Ethyl acetate (1.5 L) was added to the reaction mixture and the mixture was stirred for 30 minutes. The powder was collected by filtration to give crude material (94.3 g). The crude material was purified by column chromatography on DOWEX and on ODS to give Object Compound (28) (52.6 g).

NMR (DMSO-$_6$, δ):0.96 (3H, d, J=6.8 Hz), 1.03 (3H, d, J=5.6 Hz), 1.60–2.00 (3H, m), 2.05–2.49 (4H, m), 3.18 (1H, t, J=11.1 Hz), 3.60–4.48 (17H, m), 4.68–5.36 (10H, m), 5.35 (1H, d, J=5.9 Hz), 6.73 (1H, d, J=8.2 Hz), 6.82 (1H, dd, J=8.2 and 1.6 Hz), 6.84 (1H, m), 6.97 (1H, m), 7.04 (1H, d, J=1.6 Hz), 7.27–7.46 (6H, m), 7.74–7.78 (3H, m), 7.89 (2H, d, J=7.2 Hz), 8.06 (2H, t, J=7.2 Hz), 8.77 (1H, s)

Preparation 29

To a solution of 1-hydroxybenzotriazole (216 mg) and 4-[2-(4-butyloxyphenyl)imidazo[2,1-b][1,3,4]thiadiazol-6-yl]benzoic acid (420 mg) in N,N-dimethylformamide (20 ml) was added 1-ethyl-3-(3'-dimethylaminopropyl) carbodiimide hydrochloride (245 mg) and the mixture was stirred for 2 hours at ambient temperature. Then to the reaction mixture was added Starting Compound (1 g) and diisopropylethylamine (0.279 ml) and the mixture was stirred for 5 hours at ambient temperature. The reaction mixture was pulverized with ethyl acetate. The precipitate was collected by filtration and dried over under reduced pressure. The powder was added to water and subjected to ion-exchange column chromatography on DOWEX-50WX4 and eluted with water. The fractions containing the Object Compound were combined and subjected to column chromatography on ODS (YMC-gel ODS-AM S-50) and eluted with 25–30% acetonitrile aq. The fractions containing the Object Compound were combined and evaporated under reduced pressure to remove acetonitrile. The residue was lyophilized to give Object Compound (29) (891 mg).

NMR (DMSO-$d_6$, δ):0.94 (3H, t, J=7.2 Hz), 0.96 (3H, d, J=7.1 Hz), 1.11 (3H, d, J=5.5 Hz), 1.3–1.6 (2H, m), 1.6–2.1 (5H, m), 2.1–2.7 (4H, m), 3.25 (1H, m), 3.6–4.5 (16H, m), 4.7–5.3 (10H, m), 5.53 (1H, d, J=5.8 Hz), 6.73 (1H, d, J=8.2 Hz), 6.82 (1H, d,=8,2 Hz), 6.86 (1H, s), 7.05 (1H, s), 7.14 (2H, d, J=8.9 Hz), 7.2–7.5 (3H, m), 7.90 (2H, d, J=8.9 Hz), 7.9–8.0 (4H, m), 8.10 (1H, d, J=7.7 Hz), 8.30 (1H, d, J=6.8 Hz), 8.70 (1H, d, J=6.8 Hz), 8.86 (1H, s)

MASS (m/z): 1356 (M+Na$^+$)

The following compound was obtained in a manner similar to that of Preparation 29.

Preparation 30

IR (KBr): 3359, 1673.9, 1648.8, 1257.4 cm$^{-1}$

NMR DMSO-$d_6$, δ) 0.91 (3H, t, J=7.1 Hz), 0.96 (3H, d, J=6.7 Hz), 1.09 (3H, d, J=5.9 Hz), 1.3–1.5 (4H, m), 1.6–2.7 (9H, m), 3.19 (1H, m), 3.6–4.6 (15H, m), 4.7–5.3 (11H, m), 5.53 (1H, d, J=5.9 Hz), 6.73 (1H, d, J=8.3 Hz), 6.83 (1H, d, J=8.3 Hz), 6.88 (1H, s), 7.06 (1H, s), 7.14 (2H, d, J=8.9 Hz), 7.2–7.4 (3H, m), 7.90 (2H, d, J=8.9 Hz), 7.97 (4H, m), 8.08 (1H, d, J=6 Hz), 8.31 (1H, d, J=5 Hz), 8.76 (1H, d, J=5 Hz), 8.85 (1H, s), 8.86 (1H, s)

MASS (m/z): 1325 (M+Na$^+$)

Elemental Analysis Calcd. for $C_{57}H_{70}N_{11}O_{22}S_2Na.8H_2O$: C 45.87, H 5.81, N 10.32 Found: C 46.04, H 5.77, N 10.28

Preparation 31

A solution of 4-(4'-hydroxyphenyl)benzoic acid (25.6 g) in 10% hydrochloric acid-methanol was stirred for 3 days at room temperature. Then the solvent was evaporated in vacuo and the residue was triturated with toluene-ethyl acetate (20:1) to afford methyl 4-(4'-hydroxyphenyl)benzoate (26.5 g).

NMR (CDCl$_3$, δ): 3.94 (3H, s), 6.93 (2H, d, J=8.4 Hz), 7.27 (1H, s), 7.53 (2H, d, J=8.6 Hz), 7.60 (2H, d, J=8.4 Hz), 8.08 (2H, d, J=8.4 Hz)

MASS (m/z): 229 (M$^+$+1)

Preparation 32

A solution of 4-(4'-hydroxyphenyl)benzoic acid (4.98 g), methyliodide (5 ml), and sodium carbonate (7.19 g) in N,N-dimethylformamide (50 ml) was stirred for 17 hours at room temperature. The reaction mixture was partitioned between ethyl acetate and water. The aqueous layer was extracted with ethyl acetate. The combined organic layer was washed with water and brine. After dried over magnesium sulfate, the solution was evaporated in vacuo. The residue was triturated with n-hexane to afford methyl 4-(4'-methoxyphenyl)benzoate (5.45 g).

IR (KBr): 1718 cm$^{-1}$

NMR (CDCl$_3$, δ): 3.86 (3H, s), 3.93 (3H, s), 7.00 (2H, d, J=8.8 Hz), 7.57 (2H, d, J=8.8 Hz), 7.61 (2H, d, J=8.6 Hz), 8.07 (2H, d, J=8.6 Hz)

MASS (m/z): 243 (M$^+$+1)

Preparation 33

A mixture of methyl 4-[5-[4'-[4"-[3-(piperizin-1-yl)-propyloxy]phenyl]phenyl]-1,3,4-oxadiazol-2-yl]benzoate (1.13 g), 1N sodium hydroxide aqueous solution (3.5 ml), methanol (5 ml) and tetrahydrofuran (5 ml) was refluxed for 17 hours. The mixture was cooled down to room temperature and evaporated in vacuo. To the residue was added 1N hydrochloric acid aqueous solution. The powder was obtained by filtration to give 4-[5-[4'-[4"-[3-(piperizin-1-yl)-propyloxy]phenyl]phenyl]-1,3,4-oxadiazol-2-yl]benzoic acid hydrochloric acid salt (1.01 g).

IR (KBr): 3431, 2943, 2877, 2694, 2640, 2571, 2543, 1699 cm$^{-1}$

NMR (DMSO-$d_6$, δ): 1.56 (2H, m), 1.78 (4H, m), 2.19 (2H, m), 3.17 (6H, m), 4.14 (2H, t, J=7.0 Hz), 7.09 (2H, d, J=8.8 Hz), 7.77 (2H, d, J=8.8 Hz), 7.92 (2H, d, J=8.6 Hz), 8.17 (2H, d, J=8.6 Hz), 8.20 (2H, d, J=8.5 Hz), 8.27 (2H, d, J=8.5 Hz)

MASS (m/z): 484 (M$^+$+1) free

Preparation 34

A solution of methyl pyrazole-4-carboxylate (10 g) in N,N-dimethylformamide (100 ml) was treated with potassium carbonate (10.95 g) and 1-bromodecane (19.31 g) and the mixture was stirred for 16 hours at room temperature. Ethyl acetate was added and the solution was washed with water (6x), dried over magnesium sulfate and the evaporated residue was purified by silica gel chromatography (5:1 hexane-ethyl acetate elution) to give methyl 1-decylpyrazole-4-carboxylate (19.4 g) as a white solid.

NMR (CDCl$_3$, δ): 0.84–0.90 (3H, m), 1.25 (14H, br s), 1.83–1.90 (2H, m), 3.82 (3H, s), 4.15 (2H, t, J=7 Hz), 7.87 (1H, s), 7.90 (1H, s)

MASS (m/z): 267 (M$^+$)

Preparation 35

A solution of methyl 4-(4'-hydroxyphenyl)benzoate (2 g) in N,N-dimethylformamide (20 ml) was treated with potassium carbonate (1.21 g) and 3-phenoxypropylbromide (2.07 g) was stirred for 15 hours at room temperature and 4 hours at 85° C. After cooling, the reaction was quenched with water and the precipitate was collected, washed thoroughly with water and dried to give methyl 4-[4'-(3-phenoxypropyloxy)phenyl]-benzoate (2.6 g).

NMR (DMSO-$d_6$, δ): 2.14–2.26 (2H, m), 3.87 (3H, s), 4.12–4.29 (4H, m), 6.89–6.98 (3H, m), 7.08 (2H, d, J=8.8 Hz), 7.25–7.33 (2H, m), 7.70 (2H, d, J=8.8 Hz), 7.78 (2H, d, J=8.5 Hz), 8.00 (2H, d, J=8.4 Hz)

MASS (m/z): 363 (M$^+$)

Preparation 36

A solution of methyl 4-(4'-hydroxyphenyl)benzoate (5 g) in N,N-dimethylformamide (50 ml) was treated with potassium carbonate (6.06 g) and allyl bromide (2.46 ml), then heated at 60° C. for 3 hours. After cooling, the reaction mixture was poured into ice-water (~200 ml) and the resulting precipitate was collected by filtration, washed with water, then isopropyl ether, then dried to give methyl 4-[4'-(allyloxy) phenyl]benzoate (5.55 g) as a solid.

mp: 148–149° C.

NMR (CDCl$_3$, δ): 3.93 (3H, s), 4.29–4.61 (2H, m), 5.28–5.49 (2H, m), 5.99–6.18 (1H, m), 7.00 (2H, d, J=8.8 Hz), 7.56 (2H, d, J=8.8 Hz), 7.61 (2H, d, J=8.5 Hz), 8.07 (2H, d, J=8.5 Hz)

MASS (m/z): 269 (M$^+$)

Preparation 37

A solution of 4-(4'-hydroxyphenyl)benzoic acid (4 g) and 1N sodium hydroxide (41 ml) in dimethyl sulfoxide (40 ml) was heated for 30 minutes at 85° C., then treated with 4-phenoxybutyl bromide (6.42 g) and heating continued for 8 hours. After cooling, the reaction was poured into water and adjusted to pH 2 and the resulting precipitate was collected, washed with water, and dried to give 4-[4'-(4-phenoxybutyloxy) phenyl]benzoic acid (6.7 g).

IR (KBr): 1683.6, 1594.8, 1535.1 cm$^{-1}$

NMR (DMSO-$d_6$, δ): 1.89 (4H, br s), 3.34 (1H, br s), 4.04–4.10 (4H, m), 6.91–6.95 (3H, m), 7.05 (2H, d, J=7.9 Hz), 7.24–7.30 (2H, m), 7.66–7.76 (4H, m), 7.98 (2H, d, J=7.8 Hz)

Preparation 38

A mixture of 4-[4'-(4-phenoxybutyloxy)phenyl]benzoic acid (5 g), 1-hydroxybenzotriazole (2.24 g) and 1-ethyl-3-(3'-dimethylaminopropyl) carbodiimide hydrochloride (3.97 g) in N,N-dimethylformamide (70 ml) was stirred for 18 hours at room temperature, then treated with tert-butylcarbazate (2.19 g) and the mixture was stirred for further 4 hours at ambient temperature. Water was added and the precipitate was collected, washed with water, and dried to give N-(tert-butoxycarbonyl)-N'-[4-[4'-(4-phenoxybutyloxy) phenyl]benzoyl]hydrazine (6 g) as a solid.

IR (KBr): 1650.8, 1492.6, 1290.1, 1249.6 cm$^{-1}$

NMR (DMSO-d$_6$, δ): 1.44 (9H, br s), 1.90 (4H, br s), 4.04–4.10 (4H, m), 6.88–6.96 (3H, m), 7.05 (2H, d, J=8.7 Hz), 7.24–7.32 (2H, m), 7.69 (2H, d, J=8.8 Hz), 7.75 (2H, d, J=8.5 Hz), 7.92 (2H, d, J=8.2 Hz), 8.91 (1H, s), 10.21 (1H, s)

Preparation 39

A solution of N-(tert-butoxycarbonyl)-N'-[4-[4'-(4-phenoxybutyloxy) phenyl]benzoyl]hydrazine (6 g) in trifluoroacetic acid (40 ml) was stirred for 2 hours at room temperature, then evaporated under reduced pressure, dissolved in water, then adjusted to pH 8 with saturated sodium hydrogen carbonate solution. The precipitate was collected, washed with water, and dried to give 4-[4'-(4-phenoxybutyloxy) phenyl]benzoylhydrazine (5 g).

IR (KBr): 3282.3, 1604.5 cm$^{-1}$

NMR (DMSO-d$_6$, δ): 1.89 (4H, br s), 4.04–4.09 (4H, m), 4.55 (2H, br), 6.83–6.96 (3H, m), 7.04 (2H, d, J=8.6 Hz), 7.24–7.28 (2H, m), 7.64–7.72 (4H, m), 7.88 (2H, d, J=8.3 Hz), 9.79 (1H, s)

MASS (m/z): 377 (M$^+$)

Preparation 40

A solution of 4-methoxycarbonylbenzoylhydrazine (432 mg) in tetrahydrofuran (15 ml)-pyridine (5 ml) was treated with 4-[4'-(8-methoxy-n-octyloxy)phenyl]benzoic acid benzotriazol-1-yl ester (1.054 g) and the mixture was stirred for 72 hours at room temperature, then water (~100 ml) was added to the reaction mixture and the precipitate was collected, washed with water and dried to give N-[4-[4'-(8-methoxy-n-octyloxy) phenyl]benzoyl]-N'-(4-methoxycarbonyl-benzoyl) hydrazine (1.10 g).

IR (KBr): 3220.5, 2933.2, 2856.1, 1724.0, 1679.7, 1654.6 cm$^{-1}$

NMR (DMSO-d$_6$, δ): 1.20–1.60 (10H, m), 1.60–1.80 (2H, m), 3.21 (3H, s), 3.21–3.33 (2H, m), 3.90 (3H, s), 4.02 (2H, t, J=6.9 Hz), 7.05 (2H, d, J=8.7 Hz), 7.70 (2H, d, J=8.6 Hz), 7.79 (2H, d, J=8.3 Hz), 7.99 (2H, d, J=8.3 Hz), 8.04 (2H, d, J=8.5 Hz), 8.11 (2H, d, J=8.5 Hz), 10.60 (1H, s), 10.70 (1H, s)

MASS (m/z): 533 (M$^+$)

Preparation 41

A suspension of N-(4-methoxybenzoyl)-N'-(4-methoxycarbonylbenzoyl) hydrazine (10 g) and di-phosphorus pentasulfide (6.77 g) in tetrahydrofuran (100 ml) was refluxed for 3 hours. The reaction mixture was cooled, poured into water (300 ml), stirred for 30 minutes and extracted with dichloromethane (1500 ml) and methanol (300 ml). The organic layer was washed with water and brine, dried over magnesium sulfate and evaporated under reduced pressure. The residue was triturated with acetonitrile. The solid was collected by filtration and dried under reduced pressure to give methyl 4-[5-(4-methoxyphenyl)-1,3,4-thiadiazol-2-yl]benzoate (8.15 g).

IR (KBr): 2952.5, 2840.6, 1714.4, 1606.4, 1278.6, 1251.6 cm$^{-1}$

NMR (CDCl$_3$, δ): 3.89 (3H, s), 3.96 (3H, s), 7.01 (2H, d, J=8.9 Hz), 7.97 (2H , d, J=8.9 Hz), 8.07 (2H, d, J=8.7 Hz), 8.16 (2H, d, J=8.7 Hz)

MASS (m/z): 327 (M$^+$+1)

Preparation 42

To a solution of borontribormide (2.0M in dichloromethane, 103 ml) was added dropwise methyl 4-[5-(4-methoxyphenyl)-1,3,4-thiadiazol-2-yl]benzoate (6.75 g) and dichloromethane (100 ml) at −78° C. The reaction mixture was allowed to warm to room temperature, and the mixture was stirred overnight. The reaction mixture was poured into ice-water (100 ml). The precipitate was collected by filtration, washed with water and dried under reduced pressure at 60° C. to give a mixture of methyl 4-[5-(4-hydroxyphenyl)-1,3,4-thiadiazol-2-yl]benzoate and 4-[5-(4-hydroxyphenyl)-1,3,4-thiadiazol-2-yl]benzoic acid (6.56 g), that was used crude in the next reaction.

Preparation 43

To a suspension of a mixture of methyl 4-[5-(4-hydroxyphenyl)-1,3,4-thiadiazol-2-yl]benzoate and 4-[5-(4-hydroxyphenyl)-1,3,4-thiadiazol-2-yl]benzoic acid (600 mg), potassium carbonate (531 mg) and N,N-dimethylformamide (3 ml) was added 4-phenoxybutylbromide (880 mg) and the mixture was stirred at 100° C. (bath temperature) for 2 hours. After cooling, the mixture was added to 0.1N hydrochloric acid (100 ml). The resulting precipitate was collected by filtration and washed with water. To this material was added tetrahydrofuran (20 ml), ethanol (20 ml) and 10% sodium hydroxide aqueous solution (1.39 ml). The mixture was refluxed for 2 hours. After cooling, the reaction mixture was diluted with water (100 ml), adjusted to pH 1.8 with 1N hydrochloric acid, then extracted with a mixture of dichloromethane (1000 ml), tetrahydrofuran (200 ml) and methanol (200 ml). The organic layer was washed with brine and dried over magnesium sulfate. The solvents were removed under reduced pressure and the residue was triturated with acetonitrile. The solid was collected by filtration and dried to give 4-[5-[4-(4-phenoxybutyloxy)phenyl]-1,3,4-thiadiazol-2-yl] benzoic acid (685 mg).

IR (KBr): 3371.0, 2674.8, 2547.5, 1685.5, 1604.5, 1249.6 cm$^{-1}$

Preparation 44

To a suspension of a mixture of methyl 4-[5-(4-hydroxyphenyl)-1,3,4-thiadiazol-2-yl]benzoate and 4-[5-(4-hydroxyphenyl)-1,3,4-thiadiazol-2-yl]benzoic acid (2.0 g), potassium carbonate (14.6 g) and N,N-dimethylformamide (15 ml) was added 1,5-dibromopentane (10 ml) and the mixture was stirred at 100° C. (bath temperature) for 1.5 hours. The resulting mixture was neutralized by 0.1N hydrochloric acid and extracted with dichloromethane. The organic layer was washed with brine and dried over magnesium sulfate. The solvents were removed under reduced pressure and the residue was triturated with n-hexane. The solid was collected by filtration and dried. To this compound was added phenol (1.43 g), potassium carbonate (2.10 g) and N,N-dimethylformamide (30 ml), and the mixture was stirred at 100° C. (bath temperature) for 20 hours. After cooling, the reaction mixture was poured into saturated sodium hydrogen carbonate aqueous solution. The resulting precipitate was collected by filtration, washed with water. To this compound was added tetrahydrofuran (20 ml), ethanol (20 ml) and 10% sodium hydroxide aqueous solution (2.6 ml). The mixture was refluxed for 1.5 hours. The reactor mixture was diluted with water, acidified with 1N hydrochloric acid (10 ml). The resulting precipitate was collected by filtration, washed with water, dried under reduced pressure to give 4-[5-[4-(5-phenoxy-n-pentyloxy) phenyl]-1,3, 4-thiadiazol-2-yl]benzoic acid (2.47 g), that was used crude in the next reaction.

MASS (m/z): 461 (M$^+$+1)

Preparation 45

To a suspension of a mixture of methyl 4-[5-(4-hydroxyphenyl)-1,3,4-thiadiazol-2-yl]benzoate and 4-[5-(4- hydroxyphenyl)-1,3,4-thiadiazol-2-yl]benzoic acid (3.12 g), potassium carbonate (22.07 g) and N,N-dimethylformamide (15 ml) was added 1,5-dibromopentane (15 ml) and the mixture was stirred at 100° C. (bath temperature) for 5 hours. The resulting mixture was neutralized by 0.1N hydrochloric acid and extracted with dichloromethane. The organic layer was washed with brine and dried over magnesium sulfate. The solvents were removed under reduced pressure and the residue was triturated with n-hexane. The solid was collected by filtration and dried to give a crude powder (3.71 g). To the crude powder (2.11 g) was added methanol (100 ml) and sodium methoxide (28% in methanol) (10 ml), and refluxed for 2 hours. Then to the reaction mixture was added sodium methoxide (28% in methanol) (5 ml) and refluxed for 1.5 hours. After cooling, the reaction mixture was added to water and tetrahydrofuran, stirred overnight and adjusted to pH 2 with 4N hydrochloric acid. The resulting precipitate was collected by filtration, washed with acetonitrile and dried under reduced pressure to give 4-[5-[4-(5-methoxy-n-pentyloxy) phenyl]-1,3,4-thiadiazol-2-yl]benzoic acid (1.34 g).

IR (KBr): 2940.9, 2865.7, 2663.2, 2549.4, 1685.5, 1604.5, 1432.9, 1413.6, 1292.1, 1253.5 cm$^{-1}$

NMR (DMSO-d$_6$, δ): 1.3–1.7 (4H, m), 1.7–2.0 (2H, m), 3.23 (3H, s), 3.36 (2H, m), 4.07 (2H, t, J=6.4 Hz), 7.13 (2H, d, J=8.8 Hz), 7.97 (2H, d, J=8.8 Hz), 8.12 (4H, s)

MASS (m/z): 399 (M$^+$+1)

Preparation 46

To a solution of piperidine (2.98 g) and methyl 6-chloronicotinate (5.00 g) in N,N-dimethylformamide (75 ml) was added potassium carbonate (12.08 g). The mixture was stirred at 100° C. for 3 hours. After cooling to ambient temperature, to the reaction mixture was added water (100 ml) and then the mixture was stirred for 15 minutes at ambient temperature. The resulting precipitates were filtered, washed with water, and dried to give methyl 6-(1-piperidyl)nicotinate (5.55 g), as a white solid.

IR (KBr): 2941, 2850, 1701, 1608, 1552, 1508, 1435, 1415 cm$^{-1}$

NMR (CDCl$_3$, δ): 1.5–1.8 (6H, m), 3.6–3.7 (4H, m), 3.86 (3H, s), 6.57 (1H, d, J=9.1 Hz), 7.98 (1H, dd, J=9.1 and 2.4 Hz), 8.78 (1H, d, J=2.0 Hz)

MASS (m/z): 221 (M$^+$+1)

Preparation 47

To a solution of methyl 6-(1-piperidyl)nicotinate (5.00 g) in a mixed solvent of ethanol (25 ml) and tetrahydrofuran (10 ml) was added hydrazine monohydrate (11.0 ml). The solution was refluxed for 6 hours, during which period additional hydrazine monohydrate (11.0 ml) was added to the mixture. After cooling to ambient temperature, the reaction mixture was added to water (100 ml) and then stirred for 20 minutes at ambient temperature. The resulting precipitates were filtered, washed with water, and dried to give 6-(1-piperidyl)nicotinoylhydrazine (3.44 g), as a white solid.

IR (KBr): 3300, 2931, 2846, 1649, 1608, 1554, 1502, 1417, 1348, 1242 cm$^{-1}$

NMR (CDCl$_3$, δ): 1.5–1.8 (6H, m), 3.4–3.8 (6H, m), 6.61 (1H, d, J=8.9 Hz), 7.51 (1H, br s), 7.85 (1H, dd, J=9.0 and 2.5 Hz), 8.54 (1H, d, J=2.0 Hz)

MASS (m/z): 221 (M$^+$+1)

Preparation 48

To a solution of N-[6-(1-piperidyl)nicotinoyl]-N'-(4-methoxycarbonylbenzoyl) hydrazine (2.00 g) in pyridine (40 ml) was added phosphorus pentasulfide (1.74 g). The mixture was refluxed for 4 hours. After cooling to ambient temperature, the reaction mixture was poured into cold water (150 ml) and the mixture was adjusted to pH 11 with 1N sodium hydroxide aqueous solution and the mixture was stirred for 30 minutes at ambient temperature. The resulting precipitates were filtered, washed with water and dried to give methyl 4-[5-[6-(1-piperidyl)pyridin-3-yl]-1,3,4-thiadiazol-2-yl]benzoate (1.59 g), as a yellow solid.

IR (KBr): 2933, 2848, 1720, 1604, 1433, 1279, 1109 cm$^{-1}$

NMR (CDCl$_3$, δ): 1.6–1.8 (6H, m), 3.6–3.8 (4H, m), 3.96 (3H, s), 6.73 (1H, d, J=9.1 Hz), 8.06 (2H, d, J=8.7 Hz), 8.14 (1H, dd, J=9.2 and 2.9 Hz), 8.16 (2H, d, J=8.6 Hz), 8.70 (1H, d, J=2.2 Hz)

MASS (m/z): 381 (M$^+$+1)

Preparation 49

To a refluxing suspension of methyl 4-[5-[2-(1-piperidyl)pyridin-5-yl]-1,3,4-thiadiazol-2-yl]benzoate (1.50 g) in a mixed solvent of tetrahydrofuran (75 ml) and ethanol (15 ml) was added dropwise 10% sodium hydroxide aqueous solution (3.15 ml). The mixture was refluxed for 1.5 hours and cooled to ambient temperature. To the reaction mixture was added water (100 ml) and the pH was adjusted to 1 with 1N hydrochloric acid (15 ml). The mixture was stirred for 30 minutes at ambient temperature and the resulting precipitates were filtered, washed with water and dried to give 4-[5-[6-(1-piperidyl) pyridin-3-yl]-1,3,4-thiadiazol-2-yl] benzoic acid hydrochloride (1.36 g), as a yellow solid.

IR (KRr): 3479, 2935, 2854, 1695, 1605, 1431, 1281, 1250 cm$^{-1}$

NMR (DMSO-d$_6$, δ): 1.5–1.7 (6H, m), 3.6–3.7 (4H, m), 6.99 (1H, d, J=9.1 Hz), 8.08 (1H, dd, J=9.1 and 2.5 Hz), 8.11 (4H, s), 8.71 (1H, d, J=2.4 Hz)

MASS (m/z): 367 (M$^+$+1) (free)

Preparation 50

To a suspension of 4-[5-[6-(1-piperidyl)pyridin-3-yl]-1,3,4-thiadiazol-2-yl]benzoic acid hydrochloride (1.20 g) in methylene chloride (60 ml) was added triethylamine (0.57 ml) and 1-(3-dimethylaminopropyl)-3-ethylcarbodiimide hydrochloride (1.43 g). The mixture was stirred for 6 hours at ambient temperature. To the reaction mixture was added water and the organic layer was separated, washed with aqueous sodium hydrogen carbonate solution and saturated sodium chloride solution, and dried over magnesium sulfate, and concentrated in vacuo. Diisopropyl ether was added to the residue and the precipitates were filtered, washed with the same solvent, and dried to give 4-[5-[6-(1-piperidyl) pyridin-3-yl]-1,3,4-thiadiazol-2-yl]benzoic acid benzotriazol-1-yl ester (1.18 g), as a yellow solid.

IR (KRr): 2931, 2854, 1778, 1600, 1547, 1512, 1431, 1358, 1242, 993 cm$^{-1}$

NMR (CDCl$_3$, δ): 1.6–1.8 (6H, m), 3.6–3.8 (4H, m), 6.75 (1H, d, J=9.1 Hz), 7.4–7.7 (3H, m), 8.13 (1H, d, J=8.2 Hz, 8.16 (1H, dd, J=9.1 and 2.5 Hz), 8.24 (2H, d, J=8.6 Hz), 8.40 (2H, d, J=8.6 Hz), 8.72 (1H, d, J=2.3 Hz)

MASS (m/z: 484 (M$^{3O}$+1)

Preparation 51

A solution of methyl 4-(4'-hydroxyphenyl)benzoate (2.02 g), n-butylbromide (3 ml) and sodium carbonate (3.6 g) in N,N-dimethylformamide was stirred for 17 hours at 80° C. The reaction mixture was cooled to room temperature and partitioned between ethyl acetate and water. The aqueous layer was extracted with ethyl acetate. The combined organic layer was washed with water and brine. After dried over magnesium sulfate, the solution was evaporated in vacuo. The residue was triturated with n-hexane to afford methyl 4-(4'-butyloxyphenyl)benzoate (2.45 g).

IR (KBr): 2956, 2935, 2873, 1722 cm$^{-1}$

NMR (DMSO-d$_6$, δ): 0.94 (3H, d, J=7.3 Hz), 1.45 (2H, qt, J=7.3 and 6.9 Hz), 1.70 (2H, tt, J=6.9 and 6.9 Hz), 4.03 (2H, t, J=6.9 Hz), 7.04 (2H, d, J=8.8 Hz), 7.68 (2H, d, J=8.8 Hz), 7.78 (2H, d, J=8.5 Hz), 8.00 (2H, d, J=8.5 Hz)

MASS (m/z): 285 (M$^+$+1)

The following compounds [Preparations 52 to 54] were obtained in a manner similar to that of Preparation 51.

Preparation 52

Methyl 4-(4'-n-pentyloxyphenyl)benzoate

IR (KBr): 2958, 2935, 2866, 1722 cm$^{-1}$

NMR (DMSO-d$_6$, δ): 0.91 (3H, t, J=7.0 Hz), 1.39 (4H, m), 1.74 (2H, m), 3.87 (3H, s), 4.02 (2H, t, J=6.4 Hz), 7.04 (2H, t, J=8.8 Hz), 7.69 (2H, d, J=8.8 Hz), 7.78 (2H, d, J=8.5 Hz), 8.00 (2H, d, J=8.5 Hz)

MASS (m/z): 299 (M$^+$+1)

Preparation 53

Methyl 4-(4'-n-hexyloxyphenyl)benzoate

IR (KBr): 2954, 2933, 2866, 1725 cm$^{-1}$

NMR (DMSO-d$_6$, δ): 0.87 (3H, m), 1.20–1.87 (8H, m), 3.87 (3H, s), 4.02 (2H, m), 7.04 (2H, d, J=8.7 Hz), 7.68 (2H, d, J=8.7 Hz), 7.78 (2H, d, J=8.4 Hz), 8.00 (2H, d, J=8.4 Hz)

MASS (m/z): 313 (M$^+$+1)

Preparation 54

Methyl 4-(4'-n-heptyloxyphenyl)benzoate

IR (KBr): 2956, 2931, 2856, 1724 cm$^{-1}$

NMR (DMSO-d$_6$--67 ): 0.86 (3H, m), 1.20–1.80 (10H, m), 3.87 (3H, s), 4.05 (2H, m), 7.04 (2H, d, J=8.7 Hz), 7.69 (2H, d, J=8.7 Hz), 7.78 (2H, d, J=8.5 Hz), 8.00 (2H, d, J=8.5 Hz)

MASS (m/z): 327 (M$^+$+1)

Preparation 55

A solution of methyl 4-[4'-(3-bromopropyoxy)phenyl]benzoate (1.5 g), potassium carbonate (1.2 g) and cis-2,6-dimethylmorpholine (990.6 mg) in N,N-dimethyformamide was stirred for 15 hours at room temperature, then diluted with ethyl acetate and washed with water (5x), dried over magnesium sulfate, evaporated, then purified by silica gel chromatography (20:1 dichloromethane-ethanol elution) to give methyl 4-[4'-[3-(2,6-dimethylmorpholino)propoxy]phenyl]benzoate (755 mg).

NMR (CDCl$_3$, δ): 1.18 (6H, d, J=6.3 Hz), 1.70–1.90 (2H, m), 2.00–2.14 (2H, m), 2.50–2.65 (2H, m), 2.82 (2H, d, J=11 Hz), 3.74 (2H, br s), 3.93 (3H, s), 4.08 (2H, t, J=6.2 Hz), 6.98 (2H, d, J=8.7 Hz), 7.56 (2H, d, J=8.7 Hz), 7.61 (2H, d, J=8.3 Hz), 8.08 (2H, d, J=8.3 Hz)

MASS (m/z): 384 (M$^+$)

The following compound was obtained in a manner similar to that of Preparation 55.

Preparation 56

Methyl 4-[4'-[3-(piperizin-1-yl)propyloxy]phenyl]benzoate

IR (KBr): 2933, 2852, 2771, 1718 cm$^{-1}$

NMR (CDCl$_3$, δ): 1.47 (2H, m), 1.64 (4H, m), 2.04 (2H, tt, J=6.3 and 6.3 Hz), 2.51 (6H, m), 3.93 (3H, s), 4.07 (2H, t, J=6.3 Hz), 6.98 (2H, d, J=8.8 Hz), 7.56 (2H, d, J=8.8 Hz), 7.61 (2H, d, J=8.6 Hz), 8.07 (2H, d, J=8.6 Hz)

MASS (m/z): 354 (M$^+$1)

Preparation 57

A mixture of N-[4-(4'-allyloxyphenyl)benzoyl]-N'-(4-methoxycarbonylbenzoyl)hydrazine (1.5 g) and phosphorus oxychloride (15 ml) was heated to reflux for 6 hours, then cooled to room temperature and poured into ice-water, stirred for ~2 hours then filtered. The resulting solid was washed thoroughly with water and dried at 50° C. under vacuum to give methyl 4-[5-[4'-[4"-allyloxyphenyl]phenyl]-1,3,4-oxadiazol-2-yl]benzoate as a solid.

IR (KBr): 1720.2, 1650.8, 1284.4, 1255.4 cm$^{-1}$

NMR (DMSO-d$_6$, δ): 3.98 (3H, s), 4.61 (2H, d, J=5.3 Hz), 5.30–5.50 (2H, m), 6.03–6.17 (1H, m), 7.04 (2H, d, J=8.8 Hz), 7.61 (2H, d, J=8.8 Hz), 7.74 (2H, d, J=8.5 Hz), 8.20 (2H, d, J=8.5 Hz), 8.23 (4H, s)

MASS (m/z): 413 (M$^+$)

The following compounds [Preparations 58 to 68] were obtained in a manner similar to that of Preparation 56.

Preparation 58

Methyl 4-[5-[4'-(4"-methoxyphenyl)phenyl]-1,3,4-oxadiazol-2-yl]benzoate

IR (KBr): 1716 cm$^{-1}$

NMR (CDCl$_3$, δ): 3.88 (3H, s), 3.98 (3H, s), 7.02 (2H, d, J=8.8 Hz), 7.61 (2H, d, J=8.8 Hz)

MASS (m/z): 387 (M$^+$+1)

Preparation 59

Methyl 4-[5-[4'-(4"-butyloxyphenyl)phenyl]-1,3,4-oxadiazol-2-yl]benzoate

IR (KBr: 2956, 2933, 2871, 1720 cm$^{-1}$

NMR (CDCl$_3$, δ): 1.00 (3H, t, J=7.3 Hz), 1.54 (2H, qt, J=7.3 and 7.0 Hz), 1.82 (2H, tt, J=7.0 and 7.0 Hz), 3.98 (3H, s), 4.03 (2H, t, J=7.0 Hz), 7.00 (2H, d, J=8.7 Hz), 7.60 (2H, d, J=8.7 Hz), 7.73 (2H, d, J=8.4 Hz), 8.22 (6H, m)

MASS (m/z): 429 (M$^+$30 1)

Preparation 60

Methyl 4-[5-[4'-(4"-n-pentyloxyphenyl)phenyl]-1,3,4-oxadiazol-2-yl]benzoate

IR (KBr): 2956, 2931, 2870, 1720 cm$^{-1}$

NMR (CDCl$_3$, δ): 0.995 (3H, t, J=7.0 Hz), 1.43 (4H, m), 1.83 (2H, tt, J=7.0 Hz), 3.98 (3H, s), 4.02 (2H, t, J=7.0 Hz), 7.00 (2H, d, J=8.7 Hz), 7.60 (2H, d, J=8.7 Hz), 7.73 (2H, d, J=8.4 Hz), 8.23 (2H, m)

MASS (m/z): 443 (M$^+$+1)

Preparation 61

Methyl 4-[5-[4'-(4"-n-hexyloxyphenyl)phenyl]-1,3,4-oxadiazol-2-yl]benzoate

IR (KBr): 2954, 2933, 2870, 1722 cm$^{-1}$

NMR (CDCl$_3$, δ): 0.92 (3H, t, J=6.7 Hz), 1.39 (6H, m), 1.82 (2H, tt, J=6.9 Hz), 3.98 (3H, s), 4.02 (2H, t, J=6.5 Hz), 7.00 (2H, d, J=8.6 Hz), 7.60 (2H, d, J=8.6 Hz), 7.73 (2H, d, J=8.3 Hz), 8.22 (6H, m)

MASS (m/z): 457 (M$^+$+1)

Preparation 62

Methyl 4-[5-[4'-(4"-n-heptyloxyphenyl)phenyl]-1,3,4-oxadiazol-2-yl]benzoate

IR (KBr): 2954, 2931, 2856, 1722 cm$^{-1}$

NMR (CDCl$_3$, δ): 0.90 (3H, br), 1.20–2.00 (10H, br), 3.98 (3H, s), 4.02 (2H, br), 7.00 (2H, d, J=7.6 Hz), 7.59 (2H, d, J=7.6 Hz), 7.73 (2H, d, J=6.8 Hz), 8.20 (6H, m)

MASS (m/z): 471 (M$^+$+1)

Preparation 63

Methyl 4-[5-[4'-[4"-[3-(piperizin-1-yl)propyloxy]phenyl]phenyl]-1,3,4-oxadiazol-2-yl]benzoate IR (KBr): 2931, 2852, 2804, 2679, 1720 cm$^{-1}$ NMR (CDCl$_3$, δ): 1.51 (2H, m), 1.74 (4H, m), 2.14 (2H, m), 2.64 (6H, m), 3.98 (3H, s), 4.10 (2H, t, J=6.2 Hz), 7.00 (2H, d, J=8.8 Hz), 7.60 (2H, d, J=8.7 Hz), 7.73 (2H, d, J=8.20 Hz), 8.20 (2H, d, J=8.5 Hz), 8.23 (4H, s)

MASS (m/z): 498 (M$^+$+1)

Preparation 64

Methyl 4-[5-(1-n-decylpyrazol-4-yl)-1,3,4-oxadiazol-2-yl]benzoate

NMR (CDCl$_3$, δ): 0.84–0.91 (3H, m), 1.26–1.32 (14H, m), 1.80–2.00 (2H, m), 3.97 (3H, s), 4.21 (2H, t, J=7.1 Hz), 7.26 (1H, s), 8.09 (1H, s), 8.26 (4H, s)

MASS (m/z): 411 (M$^+$)

Preparation 65

Methyl 4-[5-[4'-[4"-(3-phenoxypropyloxy)-phenyl]phenyl]-1,3,4-oxadiazol-2-yl]benzoate IR (KBr): 1718.3, 1600.6, 1490.7, 1280.5, 1245.8 cm$^{-1}$ NMR (CDCl$_3$, δ): 2.26–2.35 (2H, m), 3.98 (3H, s), 4.16–4.27 (4H, m), 6.91–7.05 (5H, m), 7.26–7.33 (2H, m), 7.60 (2H, d, J=8.7 Hz), 7.73 (2H, d, J=8.4 Hz), 8.20 (2H, d, J=8.4 Hz), 8.23 (4H, s)

MASS (m/z): 507 (M$^+$)

Preparation 66

Methyl 4-[5-[4'-[4"-(4-phenoxybutyloxy)-phenyl]phenyl]-1,3,4-oxadiazol-2-yl]benzoate IR (KBr: 1720.2, 1602.6 cm$^{-1}$ NMR (CDCl$_3$, δ): 2.02 (4H, br s), 3.93 (3H, s), 3.97–4.06 (4H, m), 6.83–7.04 (6H, m), 7.26–7.33 (1H, m), 7.60 (2H, d, J=8.7 Hz), 7.89 (2H, d, J=8.7 Hz), 8.18–8.23 (6H, m)

MASS (m/z): 521 (M$^+$)

Preparation 67

Methyl 4-[5-[4'-[4"-(8-methoxy-n-octyloxy)phenyl]-phenyl]-1,3,4-oxadiazol-2-yl]benzoate IR (KBr): 1720.2 cm$^{-1}$ NMR (CDCl$_3$, δ): 1.20–1.95 (12H, m), 3.34 (3H, s), 3.38 (2H, t, J=7 Hz), 3.98 (3H, s), 4.02 (2H, t, J=6.5 Hz), 7.00 (2H, d, J=8.7 Hz), 7.59 (2H, d J=8.7 Hz), 7.73 (2H, d, J=8.5 Hz), 8.19 (2H, d J=8.5 Hz), 8.22 (4H, s)

MASS (m/z): 515 (M$^+$)

Preparation 68

Methyl 4-[5-[4'-[4"-[3-(2,6-dimethylmorphinopropyloxy]phenyl]phenyl]-1,3,4-oxadiazol-2-yl]benzoate NMR (CDCl$_3$, δ): 1.26 (6H, d, J=6.3 Hz), 2.32–2.60 (4H, m), 3.15–3.30 (2H, m), 3.43 (2H, d, J=11.1 Hz), 3.98 (3H, s), 4.10–4.20 (2H, m), 4.30–4.50 (2H, m), 6.98 (2H, d, J=8.7 Hz), 7.61 (2H, d, J=8.8 Hz), 7.73 (2H, d, J=8.5 Hz), 8.20 (2H, d, J=8.5 Hz), 8.23 (4H, s)

MASS (m/z): 528 (M$^+$)

The following compound was obtained in a manner similar to that of Preparation 9.

Preparation 69

Methyl 4-[5-(1-n-decylpyrazol-4-yl)-1,3,4-thiadiazol-2-yl]benzoate

NMR (DMSO-d$_6$, δ): 0.84 (3H, br s), 1.23 (14H, br s), 1.70–1.90 (2H, m), 3.90 (3H, s), 4.15–4.23 (2H, m), 8.09 (1H, s), 8.13 (4H, s), 8.58 (1H, s)

MASS (m/z): 427 (M$^+$)

The following compound was obtained in a manner similar to that of Preparation 1.

Preparation 70

Methyl 4-[4'-(3-bromopropyloxy)phenyl]benzoate

NMR (DMSO-d$_6$, δ): 2.22–2.32 (2H, m), 3.69 (2H, t, J=6.6 Hz), 3.87 (3H, s), 4.15 (2H, t, J=6 Hz), 7.08 (2H, d, J=8.8 Hz), 7.71 (2H, d, J=8.7 Hz), 7.79 (2H, d, J=8.5 Hz), 8.01 (2H, d, J=8.4 Hz)

The following compound was obtained in a manner similar to that of Preparation 19.

Preparation 71

1-(4-Cyclohexyloxybenzoyl)-3-thiosemicarbazide

NMR (DMSO-d$_6$, δ): 1.32 (6H, m), 1.71 (2H, m), 1.91 (2H, m), 4.45 (1H, m), 7.00 (2H, d, J=8.8 Hz), 7.57 (2H, s), 7.84 (2H, d, J=8.7 Hz), 9.27 (1H, s), 10.21 (1H, s)

MASS (m/z): 294 (M$^+$+1)

The following compound was obtained in a manner similar to that of Preparation 21.

Preparation 72

2-Amino-5-(4-cyclohexyloxyphenyl)-1,3,4-thiadiazole

IR KBr): 3272.6, 3114.5, 2937.1, 2856.1, 1604.5, 1519.6, 1465.6 cm$^{-1}$

NMR (DMSO-d$_6$, δ): 1.17–1.48 (6H, m), 1.73 (2H, m), 1.92 (2H, m), 4.40 (1H, m), 7.00 (2H, d, J=8.8 Hz), 7.27 (2H, s), 7.64 (2H, d, J=8.8 Hz)

MASS (m/z): 276 (M$^+$+1)

The following compound was obtained in a manner similar to that of Preparation 23.

Preparation 73

4-[2-(4-Cyclohexyloxyphenyl)imidazo[2,1-b][1,3,4]-thiadiazol-6-yl]benzoic acid ethyl ester trifluoroacetate IR (KBr): 2931.3, 2861.8, 1714.4, 1702.8, 1502.3, 1280.5, 1257.4 cm$^{-1}$ MASS (m/z): 448 (M$^+$+1)

The following compound was obtained in a manner similar to that of Preparation 25.

Preparation 74

4-[2-(4-Cyclohexyloxyphenyl)imidazo[2,1-b][1,3,4]-thiadiazol-6-yl]benzoic acid

IR (KBr): 2931.3, 1679.7, 1606.4, 1473.3, 1421.3, 1290.1, 1249.6 cm$^{-1}$

NMR (DMSO-d$_6$, δ): 1.43 (6H, m), 1.74 (2H, m), 1.94 (2H, m), 4.50 (1H, m), 7.14 (2H, d, J=8.8 Hz), 7.88 (2H, d, J=8.8 Hz), 8.00 (4H, s), 8.86 (1H, s)

MASS (m/z): 420 (M$^+$+1)

The following compounds [Preparations 75 to 84] were obtained in a manner similar to that of Preparation 5.

Preparation 75

4-(4'-Methoxyphenyl)benzoylhydrazine

IR (KBr): 3292, 3205, 1655, 1622 cm$^{-1}$

NMR (CDCl$_3$, δ): 1.59 (2H, br), 3.86 (3H, s), 6.99 (2H, d, J=7.9 Hz), 7.38 (1H, br), 7.55 (2H, d, J=7.9 Hz), 7.62 (2H, d, J=7.3 Hz), 7.79 (2H, d, J=7.3 Hz)

MASS (m/z): 243 (M$^+$+1)

Preparation 76

4-(4'-Butyloxyphenyl)benzoylhydrazine

IR (KBr): 3340, 3277, 3194, 2956, 2918, 2870, 1655, 1610 cm$^{-1}$

NMR (CDCl$_3$, δ): 0.99 (3H, t, J=7.3 Hz), 1.53 (4H, m), 1.80 (2H, tt, J=6.4 and 6.4 Hz), 4.02 (2H, t, J=6.4 Hz), 6.98 (2H, d, J=8.8 Hz), 7.38 (1H, s), 7.54 (2H, d, J=8.8 Hz), 7.62 (2H, d, J=8.4 Hz), 7.79 (2H, d, J=8.4 Hz)

MASS (m/z): 285 (M$^+$+1)

Preparation 77

4-(4'-n-Pentyloxyphenyl)benzoylhydrazine

IR (KBr): 3288, 3205, 3059, 2958, 2937, 2868, 1655, 1622, 1601 cm$^{-1}$

NMR (CDCl$_3$, δ): 0.94 (3H, t, J=6.8 Hz), 1.44 (4H, m), 1.60 (2H, br), 1.82 (2H, m), 4.00 (2H, t, J=6.8 Hz), 6.98 (2H, t, J=8.5 Hz), 7.38 (1H, br), 7.54 (2H, d, J=8.5 Hz), 7.62 (2H, d, J=8.1 Hz), 7.79 (2H, d, J=8.1 Hz)

MASS (m/z): 299 (M$^+$+1)

Preparation 78

4-(4'-n-Hexyloxyphenyl)benzoylhydrazine

IR (KBr): 3288, 3207, 3057, 2954, 2935, 2868, 1655, 1626, 1606 cm$^{-1}$

NMR (CDCl$_3$, δ): 0.91 (3H, m), 1.36 (6H, m), 1.81 (2H, m), 4.01 (2H, m), 6.98 (2H, d, J=8.0 Hz), 7.20 (1H, br), 7.54 (2H, d, J=8.0 Hz), 7.62 (2H, d, J=7.9 Hz), 7.78 (2H, d, J=7.9 Hz)

MASS (m/z): 313 (M$^+$+1)

Preparation 79

4-(4'-n-Heptyloxyphenyl)benzoylhydrazine

IR (KBr): 3286, 3205, 3061, 2956, 2931, 2856, 1654, 1623, 1608 cm$^{-1}$

NMR (CDCl$_3$, δ): 0.90 (3H, m), 1.32 (8H, m), 1.81 (2H, m), 4.00 (2H, m), 6.98 (2H, d, J=8.4 Hz), 7.40 (1H, br), 7.52 (2H, d, J=8.4 Hz), 7.64 (2H, d, J=8.4 Hz), 7.77 (2H, d, J=8.4 Hz)

MASS (m/z): 327 (M$^+$+1)

Preparation 80

4-[4'-[3-(Piperazin-1-yl)propyloxy]phenyl]-benzoylhydrazine

IR (KBr): 3275, 3105, 3041, 2956, 2933, 2870, 2852, 2814, 2767, 1643 cm$^{-1}$

NMR (CDCl$_3$, δ): 1.47 (2H, m), 1.63 (4H, m), 2.03 (2H, tt, J=6.3 Hz), 2.50 (6H, m), 4.06 (2H, t, J=6.3 Hz), 6.98 (2H, d, J=8.8 Hz), 7.41 (1H, s), 7.54 (2H, d, J=8.8 Hz), 7.62 (2H, d, J=8.5 Hz), 7.79 (2H, d, J=8.5 Hz)

MASS (m/z): 354 (M$^+$+1)

Preparation 81

1-n-Decyl-4-pyrazolylcarbonylhydrazine

NMR (DMSO-d$_6$, δ): 0.82–0.95 (3H, m), 1.22 (14H, br s), 1.62–1.81 (2H, m), 4.08 (2H, t, J=6.9 Hz), 4.29 (2H, d, J=4 Hz), 7.82 (1H, s), 8.12 (1H, s), 9.28 (1H, br s)

MASS (m/z): 267 (M$^+$)

Preparation 82

4-[4'-(3-Phenoxypropyloxy)phenyl]benzoylhydrazine

NMR (DMSO-d$_6$, δ): 2.16–2.26 (2H, m), 4.11–4.23 (4H, m), 4.54 (2H, s), 6.89–6.98 (3H, m), 7.06 (2H, d, J=8.8 Hz), 7.25–7.33 (2H, m), 7.67 (2H, d, J=8.7 Hz), 7.70 (2H, d, J=8.4 Hz), 7.89 (2H, d, J=8.4 Hz), 9.79 (1H, s)

MASS (m/z): 363 (M$^+$)

Preparation 83

4-[4'-Allyloxyphenyl]benzoylhydrazine

NMR (DMSO-d$_6$, δ): 4.51 (2H, s), 4.60–4.65 (2H, m), 5.25–5.47 (2H, m), 5.98–6.17 (1H, m), 7.06 (2H, d, J=8.8 Hz), 7.67 (2H, d, J=8.8 Hz), 7.70 (2H, d, J=8.4 Hz), 7.89 (2H, d, J=8.4 Hz), 9.80 (1H, s)

MASS (m/z): 269 (M$^+$)

Preparation 84

4-[4'-[3-(2,6-Dimethylmorpholino)propyloxy]phenyl]-benzoylhydrazine

NMR (DMSO-d$_6$, δ): 1.04 (6H, d, J=6.3 Hz), 1.58 (2H, t, J=10.6 Hz), 1.86–1.92 (2H, m), 2.40 (2H, t, J=7 Hz), 2.75 (2H, d, J=10.2 Hz), 3.51–3.58 (2H, m), 4.05 (2H, t, J=6.2 Hz), 4.50 (2H, s), 7.02 (2H, d, J=8.8 Hz), 7.64–7.71 (4H, m), 7.88 (2H, d, J=8.4 Hz), 9.79 (1H, s)

MASS (m/z): 384 (M$^+$)

The following compounds [Preparations 85 to 96] were obtained in a manner similar to that of Preparation 7.

Preparation 85

1-[4-(4'-Methoxyphenyl)benzoyl]-2-(4-methoxycarbonyl-benzoyl)hydrazine

IR (KBr): 3228, 2956, 2840, 1720, 1680, 1655 cm$^{-1}$

NMR (DMSO-d$_6$, δ): 3.82 (3H, s), 3.90 (3H, s), 7.06 (2H, d, J=8.8 Hz), 7.72 (2H, d, J=8.8 Hz), 7.79 (2H, d, J=8.5 Hz), 8.00 (2H, d, J=8.5 Hz), 8.05 (2H, d, J=8.7 Hz), 8.11 (2H, d, J=8.7 Hz), 10.60 (1H, s), 10.72 (1H, s)

MASS (m/z): 405 (M$^+$+1)

Preparation 86

1-[4-(4'-Butyloxyphenyl)benzoyl]-2-(4-methoxycarbonylbenzoyl)hydrazine

IR (KBr): 3242, 3088, 3028, 2956, 2933, 2872, 1724, 1682, 1655, 1605 cm$^{-1}$

NMR (DMSO-d$_6$, δ): 0.95 (3H, t, J=7.3 Hz), 1.45 (2H, qt, J=7.3 and 6.4 Hz), 1.73 (2H, tt, J=6.4 and 6.4 Hz), 3.91 (3H, s), 4.03 (2H, t, J=6.4 Hz), 7.05 (2H, d, J=8.8 Hz), 7.70 (2H, d, J=8.8 Hz), 7.90 (2H, d, J=8.4 Hz), 8.00 (2H, d, J=8.4 Hz), 8.05 (2H, d, J=8.4 Hz), 8.05 (2H, d, J=8.7 Hz), 8.11 (2H, d, J=8.7 Hz), 10.60 (1H, s), 10.72 (1H, s)

MASS (m/z): 447 (M$^+$+1)

Preparation 87

1-[4-(4'-Pentyloxyphenyl)benzoyl]-2-(4-methoxycarbonylbenzoyl)hydrazine

IR (KBr): 3226, 3030, 2958, 2931, 2870, 1724, 1680, 1655, 1605 cm$^{-1}$

NMR (DMSO-d$_6$, δ): 0.91 (3H, t, J=6.7 Hz), 1.40 (4H, m), 1.74 (2H, m), 3.90 (3H, s), 4.03 (2H, t, J=6.5 Hz), 7.05 (2H, d, J=8.6 Hz), 7.70 (2H, d, J=8.6 Hz), 7.78 (2H, d, J=8.3 Hz), 8.00 (2H, d, J=8.3 Hz), 8.07 (2H, d, J=8.6 Hz), 8.09 (2H, d, J=8.6 Hz), 10.60 (1H, s), 10.72 (1H, s)

MASS (m/z): 461 (M$^+$+1)

Preparation 88

1-[4-(4'-n-Hexyloxyphenyl)benzoyl]-2-(4-methoxycarbonylbenzoyl)hydrazine

IR (KBr): 3242, 3219, 3091, 3028, 2956, 2933, 2866, 1724, 1680, 1655, 1605 cm$^{-1}$

NMR (DMSO-d$_6$, δ): 0.89 (3H, t, J=6.2 Hz), 1.35 (6H, m), 1.74 (2H, m), 3.90 (3H, s), 4.03 (2H, t, J=6.9 Hz), 7.05 (2H, d, J=8.7 Hz), 7.70 (2H, d, J=8.7 Hz), 7.79 (2H, d, J=8.3 Hz), 8.00 (2H, d, J=8.3 Hz), 8.06 (2H, d, J=8.6 Hz), 8.10 (2H, d, J=8.6 Hz), 10.60 (1H, s), 10.72 (1H, s)

MASS (m/z): 475 (M$^+$+1)

Preparation 89

1-[4-(4'-n-Heptyloxyphenyl)benzoyl]-2-(4-methoxycarbonylbenzoyl)hydrazine

IR (KBr): 3219, 3091, 3029, 2956, 2931, 2856, 1722, 1679, 1652, 1604 cm$^{-1}$

NMR (DMSO-d$_6$, δ): 0.88 (3H, br), 1.29 (8H, br), 1.75 (2H, br), 3.90 (3H, s), 4.02 (2H, br), 7.03 (2H, d, J=8.4 Hz), 7.70 (2H, d, J=8.4 Hz), 7.80 (2H, d, J=8.8 Hz), 8.00 (2H, d, J=8.8 Hz), 8.45 (2H, br)

MASS (m/z): 489 (M$^+$+1)

Preparation 90

1-[4-[4'-[3-(Piperidin-1-yl)propyloxy]phenyl]-benzoyl]-2-(4-methoxycarbonylbenzoyl)hydrazine IR (KBr): 3061, 3026, 2933, 2852, 2805, 2771, 2391, 1724 cm$^{-1}$ NMR (DMSO-d$_6$, δ): 1.49 (6H, m), 1.88 (2H, tt, J=6.2 and 6.2 Hz), 2.36 (6H, m), 3.90 (3H, s), 4.06 (2H, t, J=6.2 Hz), 7.05 (2H, d, J=8.7 Hz), 7.70 (2H, d, J=8.7 Hz), 7.78 (2H, d, J=8.4 Hz), 8.00 (2H, d, J=8.4 Hz), 8.05 (2H, d, J=8.5 Hz), 8.11 (2H, d, J=8.5 Hz), 10.6 (1H, s)

MASS (m/z): 516 (M$^+$+1)

Preparation 91

N-(4-Methoxycarbonylbenzoyl)-N'-(1-n-decyl-4-pyrazolylcarbonyl)hydrazine

NMR (DMSO-d$_6$, δ): 0.82–0.89 (3H, m), 1.24 (14H, br s), 1.70–1.90 (2H, m), 3.90 (3H, s), 4.14 (2H, t, J=7 Hz), 7.95 (1H, s), 8.02 (2H, d, J=8.5 Hz), 8.10 (2H, d, J=8.5 Hz), 8.28 (1H, s), 10.18 (1H, s), 10.50 (1H, s)

MASS (m/z): 429 (M$^+$)

Preparation 92

N-[4-[4'-(3-Phenoxypropyloxy)phenyl]benzoyl]-N'-(4-methoxycarbonylbenzoyl)hydrazine IR (KBr): 3210.9, 1724.0, 1650.8, 1602.6, 1560.1, 1523.5, 1502.3, 1469.5, 1432.9, 1284.4, 1247.7 cm$^{-1}$ NMR (DMSO-d$_6$, δ): 2.18–2.24 (2H, m), 3.90 (3H, s), 4.13–4.21 (4H, m), 6.95–6.99 (3H, m), 7.09 (2H, d, J=7.9 Hz), 7.25–7.33 (2H, m), 7.69–7.81 (4H, m), 7.98–8.09 (6H, m), 10.61 (1H, s), 10.73 (1H, s)

MASS (m/z): 525 (M$^+$)

Preparation 93

N-[4-(4'-Allyloxyphenyl)benzoyl]-N'-(4-methoxycarbonylbenzoyl)hydrazine

IR (KBr): 3228.3, 3023.8, 1724.0, 1679.7, 1654.6, 1604.5, 1554.3, 1513.8, 1492.6, 1434.8 cm$^{-1}$

NMR (DMSO-d$_6$, δ): 3.90 (3H, s), 4.64 (2H, d, J=5.1 Hz), 5.26–5.47 (2H, m), 5.98–6.17 (1H, m), 7.08 (2H, d, J=8.7 Hz), 7.72 (2H, d, J=8.7 Hz), 7.80 (2H, d, J=8.4 Hz), 8.00 (2H, d, J=8.5 Hz), 8.05 (2H, d, J=8.6 Hz), 8.11 (2H, d, J=8.6 Hz), 10.60 (1H, s), 10.72 (1H, s)

MASS (m/z): 431 (M$^+$)

Preparation 94

N-[4-[4'-(4-Phenoxybutyloxy)phenyl]benzoyl]-N'-(4-methoxycarbonylbenzoyl)hydrazine IR (KBr): 3228.3, 1724.0, 1679.7, 1654.6, 1602.6 cm$^{-1}$ NMR (DMSO-d$_6$, δ): 1.90 (4H, br s), 3.90 (3H, s), 4.05–4.11 (4H, m), 6.88–6.96 (3H, m), 7.05–7.09 (2H, m), 7.25–7.28 (2H, m), 7.69–8.09 (10H, m), 10.60 (1H, s), 10.72 (1H, s)

Preparation 95

N-[4-[4'-[3-(2,6-Dimethylmorpholino)propyloxy]-phenyl]benzoyl]-N'-(4-methoxycarbonylbenzoyl)hydrazine IR (KBr): 1720.2, 1681.6, 1645.0, 1604.5 cm$^{-1}$ NMR (DMSO-d$_6$, δ): 1.05 (6H, d, J=6.3 Hz), 1.53–1.64 (2H, m), 1.87–1.93 (2H, m), 2.41 (2H, t, J=7.1 Hz), 2.76 (2H, d, J=10.4 Hz), 3.52–3.59 (2H, m), 3.90 (3H, s), 4.00–4.10 (2H, m), 7.05 (2H, d, J=8.7 Hz), 7.71 (2H, d, J=8.7 Hz), 7.79 (2H, d, J=8.4 Hz), 8.00 (2H, d, J=8.6 Hz), 8.02–8.13 (4H, m), 10.60 (1H, s), 10.72 (1H, s)

MASS (m/z): 546 (M$^+$)

Preparation 96

N-[6-(1-Piperidyl)nicotinoyl]-N'-(4-methoxycarbonyl-benzoyl)hydrazine

IR (KBr): 3240, 2933, 2852, 1724, 1686, 1643, 1603, 1547, 1497, 1437 cm$^{-1}$

NMR (DMSO-d$_6$, δ): 1.4–1.7 (6H, m), 3.6–3.7 (4H, m), 3.90 (3H, s), 6.92 (1H, d, J=9.0 Hz), 7.9–8.2 (5H, m), 8.65 (1H, s), 10.34 (1H, s), 10.62 (1H, s)

MASS (m/z): 383 (M$^+$+1)

The following compounds [Preparations 97 to 108] were obtained in a manner similar to that of Preparation 11.

Preparation 97

4-[5-[4'-[4''-(8-Methoxy-n-octyloxy)phenyl]phenyl]-1,3,4-oxadiazol-2-yl]benzoic acid NMR (DMSO-d$_6$, δ): 1.20–1.60 (10H, m), 1.60–1.80 (2H, m), 3.21 (3H, s), 3.25–3.50 (3H, m), 3.90–4.10 (2H, m), 6.95–7.10 (2H, m), 7.50–7.80 (4H, m), 7.80–8.00 (2H, m), 8.10–8.30 (4H, m)

MASS (m/z): 501 (M$^+$)

Preparation 98

4-[5-[4'-(4"-Methoxyphenyl)phenyl]-1,3,4-oxadiazol-2-yl]benzoic acid

IR (KBr): 2960, 2904, 2839, 2675, 2543, 1684, 1604 cm$^{-1}$

NMR (DMSO-d$_6$, δ): 3.83 (3H, s), 7.08 (2H, d, J=8.5 Hz), 7.91 (2H, d, J=8.5 Hz), 8.17 (2H, d, J=8.5 Hz), 8.20 (2H, d, J=8.5 Hz), 8.28 (2H, d, J=8.5 Hz)

MASS (m/z): 373 (M$^+$+1)

Preparation 99

4-[5-[4'-(4"-Butyloxyphenyl)phenyl]-1,3,4-oxadiazol-2-yl]benzoic acid

IR (KBr): 2958, 2935, 2871, 1687 cm$^{-1}$

NMR (DMSO-d$_6$, δ): 0.95 (3H, t, J=7.3 Hz), 1.46 (2H, qt, J=7.3 and 7.5 Hz), 1.73 (2H, tt, J=7.5 and 6.3 Hz), 4.04 (2H, t, J=6.3 Hz), 7.07 (2H, d, J=8.9 Hz), 7.75 (2H, d, J=8.9 Hz), 7.91 (2H, d, J=8.4 Hz), 8.16 (2H, d, J=8.3 Hz), 8.20 (2H, d, J=8.3 Hz), 8.28 (2H, d, J=8.4 Hz).

MASS (m/z): 415 (M$^+$+1)

Preparation 100

4-[5[4'-(4"-Pentyloxyphenyl)phenyl]-1,3,4-oxadiazol-2-yl]benzoic acid

IR (KBr): 2958, 2933, 9533, 2866, 2673, 2546, 1685 cm$^{-1}$

NMR (DMSO-d$_6$, δ): 0.91 (3H, t, J=7.0 Hz), 1.40 (4H, m), 1.75 (2H tt, J=6.6 and 6.6 Hz), 4.04 (2H, t, J=6.6 Hz), 7.07 (3H, d, J=8.8 Hz), 7.74 (2H, d J=8.8 Hz), 7.91 (2H, d, J=8.5 Hz), 8.15 (2H, d J=8.4 Hz), 8.20 (2H, d, J=8.1 Hz), 8.27 (2H, d J=6.5 Hz)

MASS (m/z): 429 (M$^+$+1)

Preparation 101

4-[5[4'-(4"-Hexyloxyphenyl)phenyl]-1,3,4-oxadiazol-2-yl]benzoic acid

IR (KBr): 2954, 2933, 2864, 2675, 2546, 1686 cm$^{-1}$

NMR (DMSO-d$_6$, δ): 0.89 (3H, t, J=6.8 Hz), 1.30 (6H, m), 1.74 (2H, tt, J=7.7 and 6.4 Hz), 4.04 (2H, t J=6.4 Hz), 7.07 (2H, d, J=8.8 Hz), 7.74 (2H, d, J=8.8 Hz), 7.91 (2H, d, J=8.0 Hz), 8.16 (2H, d, J=8.6 Hz), 8.20 (2H, d, J=8.0 Hz), 8.27 (2H, d, J=8.6 Hz)

MASS (m/z): 433 (M$^+$+1)

Preparation 102

4-[5[1'-(4"-n-Heptyloxyphenyl)phenyl]-1,3,4-oxadiazol-2-yl]benzoic acid

IR (KBr): 2956, 2931, 9533, 2856, 2671, 2545, 1686 cm$^{-1}$

MASS (m/z): 457 (M$^{+1}$)

Preparation 103

4-[5(1-n-Decylpyrazol-4-yl)-1,3,4-oxadiazol-2-yl]benzoic acid

NMR (DMSO-d$_6$, δ): 0.75–0.95 (3H, m), 1.23 (14H, br s), 1.83 (2H, br s), 3.33 (1H, br s, CO$_2$H), 4.22 (2H, t, J=6.8 Hz), 8.14 (1H, s), 8.17 (4H, s), 8.65 (1H, s)

MASS (m/z): 397 (M$^+$)

Preparation 104

4-[5(1-n-Decylpyrazol-4-yl)-1,3,4-thiadiazol-2-yl]benzoic acid

NMR (DMSO-d$_6$, δ): 0.80–0.90 (3H, m), 1.23 (14H, br s), 1.70–1.90 (2H, m), 3.34 (1H, br s), 4.19 (2H, t, J=6.9 Hz), 8.08 (1H, s), 8.10 (4H, s), 8.58 (1H, s)

Preparation 105

4-[5[4'-(4"-(3-Phenoxypropyloxy)phenyl]phenyl]-1,3,4-oxadiazol-2-yl]benzoic acid IR (KBr): 1685.5, 1602.6, 1548.6, 1490.7, 1469.5, 1429.0, 1400.1, 1290.9, 1249.6 cm$^{-1}$ NMR (DMSO-d$_6$, δ): 2.18–2.24 (2H, m), 4.13–4.25 (4H, m), 6.90–6.99 (3H, m), 7.11 (2H, d, J=8.8 Hz), 7.26–7.33 (2H, m), 7.75 (2H, d, J=8.7 Hz), 7.91 (2H, d, J=8.5 Hz), 8.15–8.30 (6H, m), 13.20–13.60 (1H, br)

MASS (m/z): 493 (M$^+$)

Preparation 106

4-[5[4'-[4"-Allyloxphenyl]phenyl]-1,3,4-oxadiazol-2-yl]benzoic acid

IR (KBr): 1685.5, 1652.7, 1604.5, 1577.5, 1548.6 1488.8, 1429.0, 1288.2, 1253.5, 823.5 cm$^{-1}$

NMR (DMSO-d$_6$, δ): 4.65 (2H, d, J=5 Hz), 5.27–5.48 (2H, m), 5.99–6.15 (1H, m), 7.10 (2H, d, J=8.7 Hz), 7.75 (2H, d, J=8.6 Hz), 7.91 (2H, d, J=8.3 Hz), 8.15–8.30 (6H, m), 12.38 (1H, br s)

MASS (m/z): 399 (M$^+$)

Preparation 107

4-[5[4'-[4"-(4-Phenoxybutyloxy)phenyl]phenyl]-1,3,4-oxadiazol-2-yl]benzoic acid

IR (KBr): 1733.7, 1697.1, 1650.8, 1602.6 cm$^{-1}$

NMR (DMSO-d$_6$, δ): 1.91 (4H, br s), 3.33 (1H, br,s), 4.05–4.12 (4H, m), 6.88–6.96 (2H, m), 7.07–7.11 (2H, m), 7.25–7.28 (2H, m), 7.66–8.00 (5H, m), 8.14–8.36 (6H, m)

Preparation 108

4-[5[4'-[4"[3-(2,6-Dimethylmorpholino)propyloxy]phenyl]phenyl]-1,3,4-oxadiazol-2-yl]benzoic acid MASS (m/z): 514 (M$^+$)

The following compounds [Preparation 109 to 123]were obtained in a manner similar to that of Preparation 13.

Preparation 109

4-[5[4'-(4"-Methoxyphenyl)phenyl]-1,3,4-oxadiazol-2-yl]benzoic acid benzotriazol-1-yl ester IR (KBr): 1782 cm$^{-1}$ NMR (CDCl$_3$, δ): 3.89 (3H, s) 7.03 (2H, d, J=8.7 Hz), 7.53 (3H, m), 7.62 (2H, d, J=8.7 Hz), 7.76 (2H, d, J=8.4 Hz), 8.13 (1H, d, J=8.2 Hz), 8.23 (2H, d, J=8.5 Hz), 8.41 (2H, d, J=8.4 Hz), 8.48 (2H, d, J=8.7 Hz)

MASS (m/z): 490 (M$^+$+1)

Preparation 110

4-[5[4'-(4"-Butyloxyphenyl)phenyl]-1,3,4-oxadiazol-2-yl]benzoic acid benzotriazol-1-yl ester IR (KBr): 2956, 2933, 2872, 1776 cm$^{-1}$ NMR (CDCl₃, δ): 1.00 (3H, t, J=7.3 Hz), 1.52 (2H, qt, J=7.3 and 6.4 Hz), 1.79 (2H, tt, J=6.4 and 6.4 Hz), 4.04 (2H, t, J=6.4 Hz), 7.02 (2H, d), J=8.7 Hz), 7.45–7.57 (3H, m), 7.61 (2H, d, J=8.7 Hz), 7.76 (2H, d, J=8.4 Hz), 8.14 (1H, d, J=8.2 Hz), 8.22 (2H, d, J=8.4 Hz), 8.40 (2H, d, J=8.7 Hz), 8.47 (2H, d, J=8.7 Hz)

MASS (m/z): 532 (M$^+$+1)

Preparation 111

4-[5[4'-(4''-n-Pentyloxyphenyl)phenyl]-1,3,4-oxadiazol-2-yl]benzoic acid benzotriazol-1-yl ester IR (KBr): 2956, 2935, 2868, 1779 cm$^{-1}$ NMR (CDCl₃, δ): 0.95 (3H, t, J=6.9 Hz), 1.44 (4H, m), 1.77 (2H, m), 4.03 (2H, t, J=6.5 Hz), 7.02 (2H, d), J=8.7 Hz), 7,45–7.57 (3H, m), 7.60 (2H, d, J=8.7 Hz), 7.75 (2H, d, J=8.4 Hz), 8.14 (1H, d, J=8.2 Hz), 8.22 (2H, d, J=8.4 Hz), 8.22 (2H, d, J=8.4 Hz), 8.40 (2H, d, J=8.7 Hz), 8.47 (2H, d, J=8.7 Hz)

MASS (m/z): 546 (M$^+$+1)

Preparation 112

4-[5[4'-(4''-n-Hexyloxyphenyl)phenyl]-1,3,4-oxadiazol-2-yl]benzoic acid benzotriazol-1-yl ester IR (KBr): 2953, 2931, 2866, 1776 cm$^{-1}$ NMR (CDCl₃, δ): 0.92 (3H, t, J=6.7 Hz), 1.36–1.49 (6H, m), 1.82 (2H, m) 4.03 (2H, t, J=6.5 Hz), 7.02 (2H, d, J=8.8 Hz), 7.45–7.57 (3H, m), 7.61 (2H, d, J=8.8 Hz), 7.76 (2H, d, J=8.4 Hz), 8.14 (2H, d, J=8.2 Hz), 8.22 (2H, d, J=8.4 Hz), 8.41 (2H, d, J=8.8 Hz), 8.48 (2H, d, J=8.8 Hz)

MASS (m/z): 560 (M$^+$+1)

Preparation 113

4-[5[4'-(4''-n-Heptyloxyphenyl)phenyl]-1,3,4-oxadiazol-2-yl]benzoic acid benzotriazol-1-yl ester IR (KBr): 2954, 2929, 2856, 1776 cm$^{-1}$ NMR (CDCl₃, δ): 0.91 (3H, m), 1.34 (8H, m), 1.75 (2H, m) 4.03 (2H, t, J=6.5 Hz), 7.02 (2H, t, J=8.7 Hz), 7.47–7.57 (3H, m), 7.61 (2H, d, J=8.7 Hz), 7.76 (2H, d, J=8.3 Hz), 8.14 (1H, d, J=8.2 Hz), 8.22 (2H, d, J=8.3 Hz), 8.41 (2H, d, J=8.5 Hz), 8.48 (2H, d, J=8.5 Hz)

MASS (m/z): 574 (M$^+$+1)

Preparation 114

4-[5(1-n-Dexylpyrazol-4-yl)-1,3,4-oxadiazol-2-yl]benzoic acid benzotriazol-1-yl ester IR (KBr): 1783.8, 1623.8, 1234.2, 989.3 cm$^{-1}$ NMR (CDCl₃, δ): 0.84–0.91 (3H, m), 1.26–1.34 (14H, m), 1.80–2.00 (2H, m) 4.23 (2H, t, J=7.1 Hz), 7.44–7.63 (3H, m), 8.11–8.15 (3H, m) 8.35 (2H, d, J=8.7 Hz), 8.45 (2H, d, J=8.7 Hz)

MASS (m/z): 514 (M$^+$)

Preparation 115

4-[5(1-n-Dexylpyrazol-4-yl)-1,3,4-thiadiazol-2-yl]benzoic acid benzotriazol-1-yl ester IR (KBr): 1776.1, 1576.6, 1234.2, 983.5 cm$^{-1}$ NMR (CDCl₃, δ): 0.84–0.91 (3H, m), 1.26–1.34 (14H, m), 1.94 (2H, br, s) 4.21 (2H, t, J=7.1 Hz), 7.43–7.63 (3H, m), 7.99 (1H, s) 8.09 (1H, s), 8.10–8.15 (1H, m) 8.22 (2H, d, J=8.5 Hz), 8.40 (2H, d, J=8.5 Hz)

MASS (m/z): 530 (M$^+$)

Preparation 116

4-[5-[4'-[4''-(3-Phenoxypropyloxy)phenyl]phenyl]-1,3,4-oxadiazol-2-yl]benzoic acid benzotriazol-1-yl ester IR (KBr): 1778.0, 1602.6, 1490.7, 1471.4, 1238.1 cm$^{-1}$ NMR (CDCl₃, δ): 2.27–2.34 (2H, m), 4.16–4.26 (4H, m), 6.91–7.05 (5H, m) 7.26–7.33 (2H, m), 7.44–7.62 (5H, m), 7.74 (2H, d, J=7.9 Hz), 8.13 (1H, d, J=8.5 Hz), 8.21 (2H, d, J=7.9 Hz), 8.37–8.48 (4H, m)

MASS (m/z): 610 (M$^+$)

Preparation 117

4-[5-[4'-[4''-Allyloxyphenyl]phenyl]-1,3,4-oxadiazol-2-yl]benzoic acid benzotriazol-1-yl ester IR (KBr): 1776.1, 1602.6, 1488.9 1232.3 cm$^{-1}$ NMR (CDCl₃, δ): 4.61 (2H, d, J=5.2 Hz), 5.30–5.50 (2H, m), 6.00–6.19 (1H, m) 7.04 (2H, d, J=8.7 Hz), 7.44–7.63 (4H, m), 7.75 (2H, d, J=8.4 Hz), 8.11–8.30 (4H, m), 8.38–8.49 (4H, m)

MASS (m/z): 516 (M$^+$)

Preparation 118

4-[5[4'-[4''(4-Phenoxybutyloxyxy)phenyl]phenyl]-1,3,4-oxadiazol-2-yl]benzoic acid benzotriazol-1-yl ester IR (KBr): 1776.1 cm$^{-1}$ NMR (CDCl₃, δ): 2.02 (4H, br s), 4.06–4.11 (4H, m), 6.83–7.04 (5H, m) 7.26–7.33 (1H, m), 7.48–7.63 (6H, m), 7.76 (2H, d, J=8.4 Hz), 8.14 (1H, d, J=8.2 Hz), 8.38 (2H, d, J=8.3 Hz), 8.41 (2H, d, J=8.7 Hz), 8.48 (2H, d, J=8.7 Hz)

MASS (m/z): 624 (M$^+$)

Preparation 119

4-[5[4'-[4''-(8-Methoxy-n-octyloxy)phenyl]phenyl]-1,3,4-oxadiazol-2-yl]benzoic acid benzotriazol-1-yl ester IR (KBr): 2931.3, 2856.1, 1776.1 cm$^{-1}$ NMR (CDCl₃, δ): 1.30–1.70 (10H, m), 1.70–1.90 (2H, m), 3.34 (3H, s) 3.38 (2H, t, J=6.4 Hz), 4.02 (2H, t, J=6.5 Hz), 7.02 (2H, d, J=8.7 Hz), 7.45–7.63 (5H, m), 7.76 (2H, d, J=8.5 Hz), 8.12–8.31 (3H, m) 8.41 (2H, d, J=8.8 Hz), 8.48 (2H,d, J=8.8 Hz)

MASS (m/z): 618 (M$^+$)

Preparation 120

4-[5[4'-(4-Phenoxybutyloxy)phenyl]-1,3,4-thiadiazol-2-yl]benzoic acid benzotriazol-1-yl ester IR (KBr): 3058.5, 2956.3, 2873.4, 1778.0, 1602.6, 1236.1 cm$^{-1}$ NMR (CDCl₃, δ): 2.0–2.1 (4H, m), 4.0–4.2 (4H, m), 6.9–7.0 (3H, m) 7.03 (2H, d, J=8.8 Hz), 7.3–7.4 (2H, m), 7.4–7.6 (3H, m), 7.99 (2H, d, J=8.8 Hz), 8.13 (1H, d, J=8.2 Hz), 8.25 (2H, d, J=8.6 Hz), 8.42 (2H,d, J=8.6 Hz)

MASS (m/z): 564 (M$^+$+1)

Preparation 121

4-[5[4'-(5-Phenoxy-n-pentyloxy)phenyl]-1,3,4-thiadiazol-2-yl]benzoic acid benzotriazol-1-yl ester IR (KBr): 2946.7, 2871.5, 1785.8, 1600.6, 1255.4, 1234.2 cm$^{-1}$ NMR (CDCl$_3$, δ): 1.5–2.1 (6H, m), 3.9–4.2 (4H, m), 6.8–7.1 (5H, m) 7.2–7.4 (2H, m), 7.4–7.7 (3H, m), 7.98 (2H, d, J=8.8 Hz), 8.13 (1H, d, J=8.2 Hz), 8.25 (2H, d, J=8.6 Hz), 8.41 (2H, d, J=8.6 Hz)

MASS (m/z): 122 (M$^+$+1)

Preparation 122

4-[5[4'-(5-Methoxy-n-pentyloxy)phenyl]-1,3,4-thiadiazol-2-yl]benzoic acid benzotriazol-1-yl ester NMR (CDCl$_3$, δ): 1.5–2.1 (6H, m), 3.54 (3H, s), 3.43 (2H, t, J=6.1 Hz), 4.06 (2H, t, J=6.3 Hz), 7.02 (2H, d, J=8.8 Hz), 7.4–7.7 (3H, m), 7.98 (2H, d, J=8.8 Hz), 8.13 (1H, d, J=8.2 Hz), 8.25 (2H, d, J=8.5 Hz), 8.41 (2H, d, J=8.5 Hz)

MASS (m/z): 516 (M$^+$+1)

Preparation 123

4-Cyclohexyloxybenzoic acid benzotriazol-1-yl ester

IR (KBr): 2939, 2854.1, 1776.1, 1602.6, 1508.1, cm$^{-1}$

NMR (CDCl$_3$, δ): 1.25–1.67 (6H, m), 1.85 (2H, m), 2.01 (2H, m), 4.43 (1H, m), 7.03 (2H, d, J=7.0 Hz), 7.38–7.54 (3H, m), 8.08 (1H, d, J=8.2 Hz), 8.19 (2H, d, J=7.0 Hz)

MASS (m/z): 338 (M$^+$+1)

Preparation 124

To a solution of 4-methoxybenzoic acid benzotriazol-1-yl ester (80 g) in N,N-dimethylformamide (700 ml) was added thiosemicarazide (28 g) and the mixture was stirred for 23 hours at ambient temperature. The reaction mixture was pulverized with diixopropyl ether. The precipitate was collected by filtration to give 1-(4-methoxybenzoyl)-3-thiosemicarbazide (57 g).

Preparation 125

To a slurry of 1-((4-methoxybenzoyl)-3-thisosemicarbazide (57 g) in toluene (300 ml), was added methanesulfonic acid (25 ml) dropwise over 30 minutes at 40° C. The mixture was stirred under refluxing for 24 hours. After cooling to 10° C., the sulfonate salt was filtered and dried. The salt was placed in water, and the solution was adjusted to pH 9 with 1N sodium hydroxide and extracted with ethyl acetate. The organic layer was separated, washed with brine, dried over magnesium sulfate and evaporated under reduced pressure to give 2-amino-5-(4-methoxyphenyl)-1,3,4-thiadiazole (31.1 g).

IR (KBr): 3251, 3114.5, 1610.3, 1525 cm$^{-1}$

NMR (CDCl$_3$, δ): 3.80 (3H, s), 7.00 (2H, d, J=8.5 Hz), 7.28 (2H, s), 7.69 (2H, d, J=8.5 Hz), 7.28 (2H, s), 7.69 (2H, d, J=8.5 Hz)

MASS (m/z): 208 (M+H$^+$)

Preparation 126

A mixture of 4-bromobenzenethiol (6 g), 1,7-dibromoheptane (16.37 g), and potassium carbonate (8.77 g) in dimethylformanide (30 ml) was stirred at room temperature for 5.5 Hours. The reaction mixture was pulverized with water and extracted with ethyl acetate. The organic layer was separated, washed with brine, dried over magnesium sulfate and evaporated under reduced pressure to give 1-bromo-4-(7-bromoheptylthio)benzene (7.62 g).

IR (KBr): 1465.6, 1089.6, 800.3 cm$^{-1}$

NMR (CDCl$_3$, δ): 1.37–1.88 (10H, m), 2.89 (2H, t, J=7.2 Hz), 3.40 (2H, t, J=6.8 Hz), 7.14–7.21 (2H, m), 7.36–7.43 (2H, m)

Preparation 127

To a solution of 1-bromo-4-(7-bromoheptylthio)benzene (5 g) in methanol (25 ml) was added 28% sodium mehtylate in nethanol (7.9 g) and the mixture was stirred under refluxing for 2 hours. The residue was adjusted to pH 2 with dilute HCl aq. and extracted with ethyl acetate. The organic layer was seperated, wahsed with brine, dried over magnesium sulfate and evaporated under reduced pressure. The residue was purified by column chromatography on silica gel eluting with n-hexane/ethyl acetate (50:1) to give 1-bromo-4-(7-methoxyheptylthio)benzene (3.59 g).

IR (KBr): 1471.4, 1118.5, 1093.4 cm$^{-1}$

NMR (CDCl$_3$, δ): 1.30–1.67 (10H, m), 2.88 (2H, t, J=7.3 Hz), 3.33 (3H, s), 3.36 (2H, t, J=6.2 Hz), 7.13–7.20 (2H, m), 7.35–7.42 (2H, m)

MASS (m/z): 317.1

Preparation 128

To a solution of 4-(4-chlorophenyl)-4-hydroxypiperidine (5.0 g) in dichloromethane (50 ml) was added di-tert-butyl dicarbonate (5.7 g). After stirring for 5 hours at room temperature, the solvent was evaporated in vacuo and the residue was poured into a mixture of ethyl acetate and water. The organic layer was successively washed with brine and dried over magnesium sulfate. The solvent was evaporated in vacuo and the residue was purified by column chromatography on silica gel eluting with a mixture of hexane and ethyl acetate (3:1). The eluted fractions containing the desired product were collected and evaporated in vacuo to give 1-tert-butoxycarbonyl-4-(4-chlorophenyl)-4-hydroxypiperidine (7.58 g).

IR (Film): 2976, 2926, 1668 cm$^{-1}$

NMR (CDCl$_3$, δ): 1.47 (9H, s), 1.6–1.8 (3H, m), 1.9–2.1 (2H, m), 3.1–3.3 (2H, m), 3.9–4.1 (2H, m), 7.2–7.5 (4H, m)

(+) APCI MS: 212 (M+H)$^+$-101

Preparation 129

To a solution of 1-tert-butoxycarbonyl-4-(4-chlorophenyl)-4-hydroxypiperidine (1.0 g) in N,N-dimethyl formamide (10 ml) was added sodium hydride (0.14 g) under ice cooling. Then the reaction mixture was stirred for 30 minutes at room temperature and for 2 hours at 60° C. To the reaction mixture was added iodomethane (4.0 ml) at 60° C. After stirring for 6 hours at 60° C., the reaction mixture was poured into a mixture of ethyl acetate and water. The organic layer was successively washed with brine and dried over magnesium sulfate. The solvent was evaporated in vacuo and the residue was purified by column chromatography on silica gel eluting with a mixture of hexane and ethyl acetate (10:1). The eluted fractions containing the desired product were collected and evaporated in vacuo to give 1-tert-butoxycarbonyl-4-(4-chlorophenyl)-4-methoxypiperidine (0.75 g).

IR (Film): 2976, 2935, 1680 cm$^{-1}$

NMR (CDCl$_3$, δ): 1.47 (9H, s), 1.7–2.1 (4H, m), 2.97 (3H, s), 3.0–3.3 (2H, m), 3.9–4.1 (2H, m), 7.2–7.4 (4H, m)

(+) APCI MS: 226 (M+H)$^+$-101

Preparation 130

To a solution of 2-indanol (4 g) and triethylamine (5.8 ml) in dichloromethane (40 ml) was added dropwise with stirring methanesulfonylchloride (2.8 ml) in an ice-bath. The mixture was then stirred for 1.5 hours. The reaction mixture was added to a mixture of water and dichloromethane. The organic layer was taken and dried over magnesium sulfate. The magnesium sulfate was filtered off, and the filtrate was concentrated under reduced pressure to give methanesulfonic acid indan-2-yl ester (6.29 g).

IR (KBr): 3029.6, 1328.7, 1162.9 cm$^{-1}$

NMR (CDCl$_3$, δ): 3.02 (3H, s), 3.19–3.44 (4H, m), 5.48–5.58 (1H, m), 7.18–7.28 (4H, m)

MASS (m/z): 119.2 (M-OMs+1)

Preparation 131

To a solution of 4-(5-amino-1,3,4-thiadiazol-2-yl)benzoic acid methyl ester trifluoroacetic acid salt (8 g) in water was added 1N sodium hydroxide and the mixture was adjusted to pH 8. The precipitate was collected by filtration to give 4-(5-amino-1,3,4-thiadiazol-2-yl)benzoic acid (5.05 g).

Preparation 132

A mixture of 1-(4-nitrophenyl)-1H-pyrazol-4-carboxylic acid methyl ester (19.44 g), Fe powder, NH$_4$Cl, methanol and H$_2$O was heated for 30 minutes at 80° C. for 3 hours at 100° C. The reaction mixture was concentrated by evaporation, added into dichloromethane, and was filtered. The filtrate was extracted with water, dried over magnesium sulfate and concentrated by evaporation to give 1-(4-aminophenyl)-1H-pyrazol-4-carboxylic acid methyl ester (9.84 g).

IR (KBr): 1701, 1521, 1248 cm$^{-1}$

NMR (CDCl$_3$, δ): 3.86 (2H, brs), 3.90 (3H, s), 6.75 (2H, d, J=8.8 Hz), 7.45 (2H, d, J=8.8 Hz), 8.05 (1H, s), 8.26 (1H, s)

MASS (m/z): 218 (M$^+$+1)

Preparation 133

A mixture of 1-(4-formylphenyl)-1H-pyrazol-4-carboxylic acid methyl ester (1.00 g), methanol (10 ml) and tetrahydrofuran (25 ml) was treated with sodium borohydride at 0° C. After 15 minutes, the mixture was diluted with ethyl acetate and washed with water. The organic layer was dried over magnesium sulfate, filtered, and concentrated by evaporation to give 1-(4-hydroxymethylphenyl)-1H-pyrazol-4-carboxylic acid methyl ester (1.04 g).

IR (KBr): 1724, 1558, 1521, 1443, 1392, 1255 cm$^{-1}$

NMR (CDCl$_3$, δ): 3.88 (3H, s), 4.76 (2H, s), 7.48 (2H, d, J=8.7 Hz), 7.69 (2H, d, J=8.7 Hz), 8.10 (1H, s), 8.41 (1H, s)

MASS (m/z): 233 (M$^+$+1)

Preparation 134

A solution of 1-(4-formylphenyl)-1H-pyrazol-4-carboxylic acid methyl ester (5.0 g) in dichloromethane (100 ml) was treated with 3-chloroperbenzoic acid for 5 minutes at room temperature. The solution was heated at 50° C. for 4 hours, during which period additional 3-chloroperbenzoic acid (1.87 g) was added. After concentration, methanol (150 ml) and potassium carbonate (9.00 g) were added to the residue, and the mixture was stirred for 14 hours at ambient temperature. The reaction mixture was poured into water, adjusted to pH 8 with 1N HCl and the resulting precipitate was collected by filtration to give 1-(4-hydroxyphenyl)-1H-pyrazol-4-carboxylic acid methyl ester (0.51 g).

IR (KBr): 1718, 1691, 1554, 1523, 1250 cm$^{-1}$

NMR (CDCl$_3$, δ): 3.87 (3H, s), 6.92 (2H, d, J=9.0 Hz), 7.55 (2H, d, J=9.0 Hz), 8.07 (1H, s), 8.30 (1H, s)

MASS (m/z): 219 (M$^+$+1)

Preparation 135

A solution of 4-(4-hydroxypiperidin-1-yl)benzoic acid ethyl ester (5.4 g), silver oxide (5.31 g) and 3-bromocyclohexene (3.24 ml) in tetrahydrofuran (52 ml) was stirred for 1 day at room temperature. The reaction mixture was filtered off, and the filtrate was concentrated by evaporation under reduced pressure. To the residue was added ethyl acetate, and the resulting precipitate was collected by filtration and dried. The residue was purified by silica gel chromatography (3:2 hexane-ethyl acetate elution) to give 4-[4-(2-cyclohexenyloxy)piperidin-1-yl]benzoic acid ethyl ester (3.84 g).

NMR (CDCl$_3$, δ): 1.36 (3H, t, J=7.1 Hz), 1.40–2.15 (10H, m), 3.00–3.20 (2H, m), 3.50–3.75 (3H, m), 3.90–4.05 (1H, m), 4.32 (2H, q, J=7.1 Hz), 5.60–5.90 (2H, m), 6.86 (2H, d, J=9.1 Hz), 7.90 (2H, d, J=9.1 Hz)

APCI MASS: 330 (M$^+$+1)

Preparation 136

To a solution of 4-[4-(2-cyclohexenyloxy)piperidin-1-yl] benzoic acid ethyl ester (3.82 g) in methanol (80 ml) was added 10% palladium on carbon (1.0 g), and hydrogen gas at atmosphere pressure for 5 hours. The reaction mixture was filtered, and the filtrate was concentrated by evaporation under reduced pressure to give 4-(4-cyclohexyloxypiperidin-1-yl)benzoic acid ethyl ester (2.38 g).

NMR (CDCl$_3$, δ): 1.10–1.32 (4H, m), 1.36 (3H, t, J=7.1 Hz), 1.40–2.00 (9H, m), 2.90–3.15 (2H, m), 3.20–3.45 (1H, m), 3.50–3.75 (3H, m), 4.32 (2H, q, J=7.1 Hz), 6.86 (2H, dd, J=2.2 and 9.1 Hz), 7.85–8.00 (2H, m)

APCI MASS (positive): 332.3 (M$^+$+1)

Preparation 137

To a suspension of 4-[2-(4-methoxyphenyl)imidazo[2,1-b][1,3,4]thiadiazol-6-yl]benzoic acid ethyl ester trifluoroacetic acid salt (1.0 g) in dichloromethane (10 ml) was added borone tribromide (1.0M solution in dichloromethane) (8.0 ml) at 0° C. and the mixture was stirred at ambient temperature for 1 week. The reaction mixture was pulverized with cold water. The precipitate was collected by filtration and dried to give 4-[2-(4-hydroxyphenyl)imidazo[2,1-b][1,3,4]thiadiazol-6-yl]benzoic acid (893 mg).

IR (KBr): 3209, 1689.3, 1604.5, 1484.9 cm$^{-1}$

NMR (DMSO-d$_6$, δ): 6.97 (2H, d, J=8.5 Hz), 7.81 (2H, d, J=8.5 Hz), 8.00 (4H, s), 8.84 (1H, s)

MASS (m/z): 338 (M+H$^+$)

Preparation 138

To a solution of 5-(4-pentyloxyphenyl)-1,3,4-thiadiazol-2-yl-amine (20 g) in pyridine (200 ml) was added 4-methoxycarbonylbenzoylchloride (15 g) and the mixture was stirred at ambient temperature for 2 hours. The reaction mixture was pulverized with water. The precipitate was collected by filtration and dried to give N-[5-(4-pentyloxyphenyl)-1,3,4-thiadiazol-2-yl]terephthalamic acid methyl ester (30.3 g).

IR (KBr): 2946, 2863, 1724, 1670, 1604, 1538, 1521, 1457, 1317, 1276, 1249, 1174, 1106 cm$^{-1}$

NMR (DMSO-d$_6$, δ): 0.91 (3H, t, J=7.0 Hz), 1.2–1.5 (4H, m), 1.6–1.9 (2H, m), 3.90 (3H, s), 4.05 (2H, t, J=6.5 Hz), 7.09 (2H, d, J=8.8 Hz), 7.91 (2H, d, J=8.8 Hz), 8.12 (2H, d, J=8.4 Hz), 8.25 (2H, d, J=8.4 Hz)

MASS (m/z): 426 (M+H$^+$)

Preparation 139

To a solution of N-tert-butoxycarbonyl-4-piperidinone (3.3 g) and 1-(4-cyclohexylphenyl)piperazine (4.0 g) in dichloromethane (20 ml) was added titanium(IV)

isopropoxide (8 ml) and the mixture was stirred at ambient temperature for 2 hours. Then, to the reaction mixture was added ethanol (20 ml) and sodium cyanoborohydride (1 g) in several portions, the reaction mixture was stirred at ambient temperature for 2 hours. The reaction mixture was pulverized with water. The precipitate was filtered off and the filtrate was extracted with dichloromethane. The organic layer was taken and dried over magnesium sulfate. Magnesium sulfate was filtered off, and the filtrate was evaporated under reduced pressure and chromatographed (Silica gel 60 (Trademark: prepared by Merck)) eluting with hexane/ethyl acetate to afford 1-tert-butoxycarbonyl-4-[4-(4-cyclohexylphenyl)piperazin-1-yl]piperidine (1.35 g).

NMR (CDCl$_3$, δ): 1.3–1.6 (6H, m), 1.45 (9H, s), 1.6–2.0 (8H, m), 2.3–2.6 (2H, m), 2.6–3.0 (6H, m), 3.0–3.3 (4H, m), 4.17 (2H, d, J=13 Hz), 6.86 (2H, d, J=8.7 Hz), 7.11 (2H, d, J=8.7 Hz)

MASS (m/z): 428 (M+H$^+$)

Preparation 140

To a solution of 4-[4-[4-(4-cyclohexylphenyl)piperazin-1-yl]piperidin-1-yl]benzonitrile (1.95 g) in acetic acid (10 ml) was added concentrated hydrogen chloride (20 ml) and the mixture was stirred at 120° C. for 10 hours. The reaction mixture was added to water and the resulting precipitate was collected by filtration to give 4-[4-[4-(4-cyclohexylphenyl)piperazin-1-yl]piperidin-1-yl]benzoic acid (959 mg).

IR (KBr): 3400, 2927, 2620, 2514, 1714, 1608, 1513, 1452, 1274, 1226, 1182, 1010 cm$^{-1}$

NMR (DMSO-d$_6$, δ): 1.2–1.5 (5H, m), 1.6–1.9 (7H, m), 2.2 (2H, m), 2.4 (1H, m), 2.84 (2H, t, J=8.5 Hz), 3.20 (4H, d, J=8.5 Hz), 3.4–3.8 (5H, m), 4.08 (2H, d, J=12.5 Hz), 6.93 (2H, d, J=8.8 Hz), 7.03 (2H, d, J=8.8 Hz), 7.12 (2H, d, J=8.8 Hz), 7.78 (2H, d, J=8.8 Hz), 11.13 (1H, s)

MASS (m/z): 448 (M+H$^+$)

Preparation 141

A mixture of 1-(4-formylphenyl)-1H-pyrazol-4-carboxylic acid methyl ester (5.0 g), 1-phenyl piperazine (4.21 g), acetic acid (3.7 ml), sodium cyanoborohydride (1.55 g), methanol (110 ml), tetrahydrofuran (75 ml) and dichloromethane (20 ml) was stirred for 15 minutes at 0° C. and for 14 hours at ambient temperature. The reaction mixture was poured into saturated NaHCO$_3$ aqueous solution and extracted with ethyl acetate. The organic layer was dried over magnesium sulfate, filtered, and evaporated. The residue was purified by silica gel chromatography (1:1 hexane-ethyl acetate elution) and recrystallized from diisopropyl ether and acetone to give 1-[4-(4-phenylpiperazin-1-yl-methyl)phenyl]-1H-pyrazol-4-carboxylic acid methyl ester (3.90 g).

IR (KBr): 1702, 1600, 1560, 1271 cm$^{-1}$

NMR (DMSO-d$_6$, δ): 2.4–2.6 (4H, m), 3.14 (3H, t, J=4.8 Hz), 3.58 (2H, s), 3.81 (3H, s), 6.76 (1H, t, J=7.2 Hz), 6.91 (2H, d, J=7.8 Hz), 7.20 (2H, t, J=7.8 Hz), 7.48 (2H, t, J=8.6 Hz), 7.90 (2H, d, J=8.6 Hz), 8.15 (1H, s), 9.11 (1H, s)

MASS (m/z): 377 (M$^+$+1)

Preparation 142

To an ice-cooled solution of methyl 4-(4-hydroxyphenyl) benzoate (3.00 g) and N-phenyltrifluoromethanesulfonide (4.84 g) in tetrahydrofuran (60 ml) was added triethylamine (1.98 ml), then the solution was stirred at this temperature for 1 hour and at ambient temperature for further 18 hours. Water (200 ml) was added to the reaction mixture and the mixture was extracted with methylene chloride. The organic layer was dried over magnesium sulfate, filtered and evaporated to give a crude oil. This oil was purified on a silica gel column chromatography eluting successively with the following solvents: (1) 2.5% ethyl acetate in n-hexane, (2) 5% ethyl acetate in n-hexane. The fractions containing the object compound were concentrated to give methyl 4-(4-trifluoromethanesulfonyloxyphenyl)benzoate (5.30 g) as a white solid.

IR (KBr): 1713, 1691, 1606, 1522, 1495, 1420 cm$^{-1}$

NMR (CDCl$_3$, δ): 3.95 (3H, s), 7.31–7.46 (2H, m), 7.56–7.75 (4H, m), 8.08–8.20 (2H, m)

MASS (m/z): 361 (M$^+$+1)

Preparation 143

To a suspension of 4-piperazin-1-yl-benzoic acid ethyl ester dihydrochloride (1 g) and potassium bicarbonate (1.57 g) in acetonitrile (10 ml) was added methanesulfonic acid indane-2-yl ester (0.69 g) and the mixture was stirred under refluxing for 8 hours. The reaction mixture was pulverized with water. The precipitate was collected by filtration and dried over under reduced pressure. The powder was purified by column chromatography on silica gel using methanol/dichloromethane (50:1) as the eluent to give 4-(4-indan-2-yl-piperazin-1-yl)benzoic acid ethyl ester (0.38 g).

IR (KBr): 1697.1, 1606.4, 1349.9, 1238.1 cm$^{-1}$

NMR (CDCl$_3$, δ): 1.37 (3H, t, J=7.1 Hz), 2.67–2.72 (4H, m), 2.88–3.40 (9H, m), 4.33 (2H, q, J=7.1 Hz), 6.85–6.90 (2H, m), 7.12–7.23 (4H, m), 7.91–7.96 (2H, m)

MASS (m/z): 351.3 (M+1)

Preparation 144

To a solution of 2-amino-4'-bromoacetophenone hydrochloride (5.0 g), 4-heptyloxybenzoic acid (4.72 g) and 1-hydroxybenzotriazole (2.7 g) in dichloromethane (50 ml) was added 1-ethyl-3-(3'-dimethylaminopropyl)carbodiimide (WSCD) (3.65 ml) and the mixture was stirred for 3 hours at ambient temperature. The reaction mixture was diluted with dichloromethane (200 ml), and washed with water, 1N hydrochloric acid, saturated sodium hydrogen carbonate aqueous solution and brine. The organic layer was dried over magnesium sulfate. Magnesium sulfate was filtered off, and the filtrate was evaporated under reduced pressure. The solids were slurried in ethyl acetate and collected by filtration to give 2-(4-heptyloxybenzoylamino)-4'-bromoacetophenone (6.73 g).

IR (KBr): 3318.9, 2937.1, 2858.0, 1699.0, 1639.2, 1556.3, 1508.1, 1255.4 cm$^{-1}$

NMR (CDCl$_3$, δ): 0.80–1.10 (3H, m), 1.20–1.60 (8H, m), 1.75–1.95 (2H, m), 4.01 (2H, t, J=6.5 Hz), 4.91 (2H, d, J=4.2 Hz), 6.94 (2H, d, J=8.8 Hz), 7.14 (1H, brs), 7.67 (2H, d, J=8.6 Hz), 7.83 (2H, d, J=8.8 Hz), 7.90 (2H, d, J=8.6 Hz)

APCI-MS (m/z): 432, 434

Preparation 145

A solution of 2-(4-heptyloxyphenyl)-5-(4-bromophenyl) thiazole (2.06 g) in dry tetrahydrofuran (60 ml) was cooled to −60° C., and a solution of n-butyllithium (1.56M) in n-hexane, 4.05 ml) was added slowly to maintain the reaction temperature at −60° C. After stirring for 1 hour, dry-ice (4 g) was added. The reaction mixture was allowed to warm to room temperature over 30 minutes. To the reaction mixture was added water (20 ml) and 0.5N hydrochloric acid (80 ml), then extracted with dichloromethane (700 ml). The organic layer was washed with brine, and dried over magnesium sulfate. Magnesium sulfate was filtered off, and the filtrate was evaporated under reduced pressure. The solids were slurried in acetonitrile and collected by filtration to give 4-[5-(4-heptyloxyphenyl)thiazol-2-yl]benzoic acid (1.68 g).

IR (KBr): 2929.3, 2856.1, 2674.8, 2549.4, 1683.6, 1604.5, 1432.9, 1297.9, 1253.5 cm$^{-1}$

NMR (DMSO-d$_6$, δ): 0.70–1.00 (3H, m), 1.10–1.60 (8H, m), 1.60–1.90 (2H, m), 4.04 (2H, t, J=6.4 Hz), 7.07 (2H, d, J=8.7 Hz), 7.83 (2H, d, J=8.2 Hz), 7.91 (2H, d, J=8.7 Hz), 8.00 (2H, d, J=8.2 Hz), 8.39 (1H, s)

APCI-MS (m/z): 396

The following compound was obtained in a manner similar to that of Preparation 19.

Preparation 146

N-[4-[5-(4-Pentyloxyphenyl)-1,3,4-thiadiazol-2-yl]benzoyl]-N'-(4-methoxycarbonylbenzoyl)hydrazine NMR (DMSO-d$_6$, δ): 0.91 (3H, t, J=6.9 Hz), 1.28–1.52 (4H, m), 1.68–1.86 (2H, m), 3.91 (3H, s), 4.08 (2H, t, J=6.5 Hz), 7.14 (2H, d, J=8.8 Hz), 7.98 (2H, d, J=8.8 Hz), 8.01–8.24 (8H, m), 10.82 (2H, s)

MASS (m/z): 545 (M$^+$+1)

Preparation 147

To a solution of 1-tert-butoxycarbonyl-4-(4-chlorophenyl)-4-methoxypiperidine (0.72 g) in ethyl acetate (10 ml) was added 4N HCl in ethyl acetate (5.5 ml). After stirring for 6.7 hours, the reaction mixture was poured into a mixture of ethyl acetate and water, followed by alkalification of the solution to pH 12. The organic layer was successively washed with water and brine and dried over magnesium sulfate. The solvent was evaporated in vacuo to give 4-(4-chlorophenyl)-4-methoxypiperidine (0.39 g).

IR (Film): 2943, 2827, 1541 cm$^{-1}$

NMR (CDCl$_3$, δ): 1.7–2.1 (4H, m), 2.17 (1H, s), 2.9–3.2 (7H, m), 7.33 (4H, s)

The following compound was obtained in a manner similar to that of Preparation 147.

Preparation 148

1-[4-(5-Methoxypentyloxy)biphenyl-4-yl]piperazine Dihydrochloride

IR (KBr): 2940.9, 2508.9, 1498.4, 1249.6 cm$^{-1}$

NMR (CDCl$_3$, δ): 1.51–1.83 (6H, m), 3.34 (3H, s), 3.40 (2H, t, J=6.2 Hz), 3.93 (2H, t, J=6.4 Hz), 4.00–4.40 (8H, m), 6.84–6.89 (2H, m), 7.36–7.40 (2H, m), 7.58–7.62 (2H, m), 7.87–7.92 (2H, m), 9.90–10.15 (1H, m)

MASS (m/z): 355 (M+1)

Preparation 149

To a solution of 4-hydroxyacetophenone (10 g) and pyridinium hydrobromide perbromide (23.5 g) in acetic acid (80 ml) was added hydrogenbromide (30% in acetic acid solution) (40 ml) and the mixture was stirred overnight at ambient temperature. The reaction mixture was added to ice water and extracted with ethyl acetate. The organic layer was taken and dried over magnesium sulfate. Magnesium sulfate was filtered off, and the filtrate was evaporated under reduced pressure to afford 2-bromo-1-(4-hydroxyphenyl)ethanone (1.72 g).

NMR (CDCl$_3$, δ): 4.40 (2H, s), 5.78 (1H, s), 6.92 (2H, d, J=8.8 Hz), 7.94 (2H, d, J=8.8 Hz)

MASS (m/z): 217 (M+H$^+$)

The following compound was obtained in a manner similar to that of Preparation 149.

Preparation 150

2-Bromo-1-(4-pentyloxyphenyl)ethanone

NMR (CDCl$_3$, δ): 0.94 (3H, t, J=6.8 Hz), 1.3–1.5 (4H, m), 1.82 (2H, q, J=6.8 Hz), 4.03 (2H, t, J=6.8 Hz), 4.40 (2H, s), 6.94 (2H, d, J=9.0 Hz), 7.96 (2H, d, J=9.0 Hz)

MASS (m/z): 287 (M+H$^+$)

Preparation 151

A solution of 1-(4-aminophenyl)-1H-pyrazol-4-carboxylic acid methyl ester (3.0 g) in N,N-dimethylformamide (30 ml) was treated with potassium carbonate (5.72 g), sodium iodide (4.14 g) and 1,5-dibromopentane, and the mixture was stirred for 20 hours at room temperature and 6 hours at 80° C., during which period additional N,N-dimethylformamide (20 ml), 1.5-dibromopentane (1.14 g) and potassium carbonate (0.95 g) were added. The reaction mixture was cooled to room temperature and poured into water. The precipitate was collected by filtration, dried over under reduced pressure. The residue was purified by silica gel chromatography (dichloromethane elution) to give 1-(4-piperidylphenyl)-1H-pyrazol-4-carboxylic acid methyl ester (1.34 g).

IR (KBr): 1720, 1521, 1248 cm$^{-1}$

NMR (CDCl$_3$, δ): 1.5–1.8 (6H, m), 3.21 (4H, t, J=5.3 Hz), 3.86 (3H, s), 6.98 (2H, d, J=9.1 Hz), 7.53 (2H, d, J=9.1 Hz), 8.06 (1H, s), 8.29 (1H, s)

MASS (m/z): 286 (M$^+$+1)

The following compound was obtained in a manner similar to that of Preparation 151.

Preparation 152

1-(4-Pyrrolidinylphenyl)-1H-pyrazol-4-carboxylic Acid Methyl Ester

IR (KBr): 1720, 1541, 1525, 1246 cm$^{-1}$

NMR (CDCl$_3$, δ): 2.0–2.1 (4H, m), 3.2–3.4 (4H, m), 3.86 (3H, s), 6.59 (2H, dd, J=6.9 and 2.1 Hz), 7.49 (2H, dd, J=6.9 and 2.1 Hz), 8.05 (1H, s), 8.25 (1H, s)

MASS (m/z): 294 (M$^+$+23)

Preparation 153

To a suspension of cyclohexane-1-4-dicarboxylic acid monomethyl ester (1.57 g) in thionyl chloride (3.14 ml) was added N,N-dimethylformamide (2 drops) and the mixture was stirred under refluxing for 1 hour. The reaction mixture was concentrated by evaporation under reduced pressure to give 4-chlorocarbonylcyclohexane carboxylic acid methyl ester (1.78 g).

NMR (CDCl$_3$, δ): 1.38–1.64 (4H, m), 2.09–2.32 (5H, m), 2.64–2.77 (1H, m), 3.68 (3H, s)

Preparation 154

Thionyl chloride (8.47 ml) was added dropwise to methanol (54 ml) at 10° C. To the solution was added trans-1,4-cyclohexane dicarboxylic acid (4 g) and the mixture was stirred for 24 hours at ambient temperature. The reaction mixture was evaporated under reduced pressure to give cyclohexane-1,4-dicarboxylic acid dimethyl ester (4.68 g).

IR (KBr): 1729.8, 1195.6 cm$^{-1}$

NMR (CDCl$_3$, δ): 1.34–2.15 (8H, m), 2.23–2.34 (2H, m), 3.67 (6H, s)

MASS (m/z): 201 (M+1)

The following compounds [Preparations 155 to 157] were obtained in a manner similar to that of Preparation 154.

Preparation 155

2,5-Dimethyl-terephthalic Acid Dimethyl Ester

IR (KBr): 1722.1, 1261.2, 1101.2 cm$^{-1}$

NMR (CDCl$_3$, δ): 2.57 (6H, s), 3.91 (6H, s), 7.76 (2H, s)

MASS (m/z): 223 (M+1)

Preparation 156

2,4-Hexendioic Acid Dimethyl Ester

IR (KBr): 1702.8, 1612.2, 1249.6 cm$^{-1}$
NMR (CDCl$_3$, δ): 3.71 (6H, s), 6.49 (2H, dd, J=3.1 and 11.5 Hz), 7.40 (2H, dd, J=3.1 and 11.5 Hz)
MASS (m/z): 171 (M+1)

Preparation 157

Naphthalene-1,4-dicarboxylic Acid Dimethyl Ester

NMR (CDCl$_3$, δ): 4.03 (6H, s), 7.65 (2H, q, J=3.3 Hz), 8.09 (2H, s), 8.83 (2H, q, J=3.3 Hz)
MASS (m/z): 245 (M+1)

The following compounds [Preparations 158 to 162] were obtained in a manner similar to that of Preparation 153.

Preparation 158

5-Chlorocarbonylthiophene-2-carboxylic Acid Methyl Ester

IR (KBr): 1724.0, 1666.2, 1251.6 cm$^{-1}$
NMR (CDCl$_3$, δ): 3.86 (3H, s), 7.73–7.87 (2H, m)

Preparation 159

4-Chlorocarbonyl-2,5-dimethylbenzoic Acid Methyl Ester

IR (KBr): 1756.8, 1718.3, 1220.7 cm$^{-1}$
NMR (CDCl$_3$, δ): 2.54 (3H, s), 2.60 (3H, s), 3.93 (3H, s), 7.78 (1H, s), 1H, s)

Preparation 160

5-Chlorocarbonyl-2,4-pentenoic Acid Methyl Ester

IR (KBr): 1745.3, 1714.4, 1243.9 cm$^{-1}$
NMR (CDCl$_3$, δ): 3.70 (3H, s), 6.29–6.64 (2H, m), 7.24–7.64 (2H, m)

Preparation 161

4-Chlorocarbonylnaphtalene-1-carboxylic Acid Methyl Ester

IR (KBr): 1762.6, 1724.0, 1257.4 cm$^{-1}$
NMR (CDCl$_3$, δ): 3.98 (3H, s), 7.68–7.77 (2H, m), 8.14 (2H, s), 8.66–8.82 (2H, m)

Preparation 162

6-Chlorocarbonylnaphtalene-2-carboxylic Acid Methyl Ester

IR (KBr): 1743.3, 1714.4, 1290.1 cm$^{-1}$
NMR (CDCl$_3$, δ): 3.94 (3H, s), 8.04–8.08 (2H, m), 8.21–8.27 (2H, m), 8.68–8.71 (2H, m)

Preparation 163

To a solution of 4-piperidin-1-yl-benzonitrile (3 g) and thiosemicarbazide (1.8 g) in toluene (30 ml) was added trifluoroacetic acid (20 ml) and the mixture was stirred at 60° C. for 6 hours. The reaction mixture was placed in water, the solution was adjusted to pH 9 with 1N sodium hydroxide and the precipitate was collected by filtration to give 5-(4-piperidin-1-yl-phenyl)-[1,3,4]thiadiazol-2-yl-amine (3.58 g).

IR (KBr): 2933, 2838, 1604, 1502, 1463, 1386, 1349, 1245, 1126, 1043, 821 cm$^{-1}$
NMR (DMSO-d$_6$, δ): 1.57 (6H, m), 3.24 (4H, m), 6.96 (2H, d, J=8.8 Hz), 7.19 (2H, s), 7.54 (2H, d, J=8.8 Hz)
MASS (m/z): 261 (M+H$^+$)

The following compounds [Preparations 164 to 169] were obtained in a manner similar to that of Preparation 163.

Preparation 164

5-(4-Morpholinylphenyl)-[1,3,4]thiadiazol-2-yl-amine

IR (KBr): 3274, 3106, 1604, 1508, 1465, 1378, 1324, 1267, 1238, 1122 cm$^{-1}$
NMR (DMSO-d$_6$, δ): 3.19 (4H, t, J=4.8 Hz), 3.74 (4H, t, J=4.8 Hz), 7.00 (2H, d, J=8.8 Hz), 7.22 (2H, s), 7.59 (2H, d, J=8.8 Hz)
MASS (m/z): 263 (M+H$^+$)

Preparation 165

5-[4-(cis-2,6-Dimethylmorpholin-4-yl)phenyl]-[1,3,4]thiadiazol-2-yl-amine

IR (KBr): 3272, 3106, 1608, 1525, 1469, 1376, 1346, 1245, 1176, 1145, 1081 cm$^{-1}$
NMR (DMSO-d$_6$, δ): 1.16 (6H, d, J=6.2 Hz), 2.31 (2H, t, J=11.5 Hz), 3.6–3.8 (4H, m), 7.00 (2H, d, J=8.8 Hz), 7.21 (2H, s), 7.58 (2H, d, J=8.8 Hz)
MASS (m/z): 291 (M+H$^+$)

Preparation 166

5-(4-Thiomorpholinophenyl)-[1,3,4]thiadiazol-2-yl-amine

IR (KBr): 3340, 3270, 3129, 1604, 1506, 1467, 1384, 1295, 1230, 1195 cm$^{-1}$
NMR (DMSO-d$_6$, δ): 2.64 (4H, t, J=5.0 Hz), 3.66 (4H, t, J=5.0 Hz), 6.97 (2H, d, J=8.8 Hz), 7.21 (2H, s), 7.57 (2H, d, J=8.8 Hz)
MASS (m/z): 279 (M+H$^+$)

Preparation 167

5-[4-(4-Ethylpiperazinylphenyl)]-[1,3,4]thiadiazol-2-yl-amine

IR (KBr): 3278, 3120, 2967, 2829, 1685, 1608, 1517, 1467, 1388, 1240, 1203, 1130 cm$^{-1}$
NMR (DMSO-d$_6$, δ): 1.04 (3H, t, J=7.2 Hz), 2.41 (2H, q, J=7.2 Hz), 2.51 (4H, m), 3.23 (4H, m), 6.99 (2H, d, J=8.8 Hz), 7.21 (2H, s), 7.57 (2H, d, J=8.8 Hz)
MASS (m/z): 290 (M+H$^+$)

Preparation 168

5-[4-(4-Cyclohexylpiperazinylphenyl)]-[1,3,4]thiadiazol-2-yl-amine

IR (KBr): 3016, 2950, 2865, 1743, 1672, 1606, 1513, 1456, 1430, 1402, 1201, 1133 cm$^{-1}$
NMR (DMSO-d$_6$, δ): 1.0–1.6 (5H, m), 1.63 (1H, d, J=10 Hz), 1.85 (2H, d, J=10 Hz), 2.09 (2H, d, J=10 Hz), 2.8–3.3 (5H, m), 3.55 (2H, m), 3.99 (2H, d, J=10 Hz), 7.09 (2H, d, J=8.8 Hz), 7.65 (2H, d, J=8.8 Hz)
MASS (m/z): 344 (M+H$^+$)

Preparation 169

4-(5-Amino-[1,3,4]thiadiazol-2-yl)benzoic Acid Methyl Ester Trifluoroacetic Acid Salt IR (KBr): 3004, 2746, 1726, 1675, 1645, 1608, 1436, 1284, 1211, 1186, 1137, 1112 cm$^{-1}$ NMR (DMSO-d$_6$, δ): 3.88 (3H, s), 7.19 (2H, s), 7.90 (2H, d, J=8.5 Hz), 8.04 (2H, d, J=8.5 Hz)

MASS (m/z): 236 (M+H$^+$)

Preparation 170

To a mixture of 4-methoxycarbonylphenylboronic acid (2.01 g) and 1-bromo-4-ethoxymethylbenzene (2.00 g) in a mixed solvent of ethylene glycol dimethyl ether (20 ml) and 2M aqueous sodium carbonate solution (6 ml) was added tetrakis(triphenylphosphine)palladium (0) (0.54 g). The mixture was heated at 80° C. for 5 hours. After cooling to room temperature, water (150 ml) was added to the reaction mixture and the resulting precipitate was collected by filtration, washed thoroughly with water and dried to give a crude solid. This solid was purified by column chromatography on silica gel (60 g) eluting successively with the following solvents: (1) n-hexane:ethyl acetate=50:1, (2) n-hexane:ethyl acetate=10:1. The fractions containing the object compound were concentrated and dried to give methyl 4-(4'-ethoxymethylphenyl)benzoate as a white solid (1.85 g).

NMR (CDCl$_3$, δ): 1.27 (3H, t, J=7.0 Hz), 3.58 (2H, q, J=7.0 Hz), 3.94 (3H, m), 4.56 (2H, s), 7.44 (2H, d, J=8.7 Hz), 7.54–7.61 (4H, m), 8.04–8.15 (2H, m)

The following compound was obtained in a manner similar to that of Preparation 170.

Preparation 171

Methyl 4-[4'-(2-methoxyethoxymethyl)phenyl]benzoate

NMR (CDCl$_3$, δ): 3.41 (3H, m), 3.55–3.70 (4H, m), 3.94 (3H, s), 4.63 (2H, s), 7.45 (2H, d, J=8.3 Hz), 7.56–7.74 (4H, m), 8.07–8.20 (2H, m)

MASS (m/z): 301 (M$^+$+1)

Preparation 172

To an ice-cooled solution of 4-bromobenzyl bromide (3.00 g) and 2-methoxyethanol (1.04 ml) in tetrahydrofuran (30 ml) was added sodium hydride (60%) (0.58 g) in a stream of nitrogen. The mixture was stirred at this temperature for 15 minutes and at room temperature for further 4 hours. To the mixture was added water (1 ml) under ice-cooling. The reaction mixture was diluted with ethyl acetate and washed successively with water and saturated sodium chloride solution. The organic layer was dried over magnesium sulfate, filtered and evaporated to give 1-bromo-4-(2-methoxyethoxymethyl)benzene (3.10 g) as a pale yellow oil.

NMR (DMSO-d$_6$, δ): 3.25 (3H, m), 3.43–3.60 (2H, m), 4.46 (2H, s), 7.28 (2H, d, J=8.5 Hz), 7.49–7.60 (4H, m)

The following compounds [Preparations 173 to 175] were obtained in a manner similar to that of Preparation 172.

Preparation 173

Ethyl 4-(4-propoxypiperidin-1-yl)benzoate

NMR (DMSO-d$_6$, δ): 0.87 (3H, t, J=7.4 Hz), 1.28 (3H, t, J=7.1 Hz), 1.36–1.60 (4H, m), 1.80–1.98 (2H, m), 3.00–3.20 (2H, m), 3.39 (2H, t, J=6.5 Hz), 3.41–3.76 (3H, m), 4.23 (2H, q, J=7.1 Hz), 6.97 (2H, d, J=9.1 Hz), 7.76 (2H, d, J=9.0 Hz)

MASS (m/z): 292 (M$^+$+1)

Preparation 174

Ethyl 4-(4-benzyloxypiperidin-1-yl)benzoate

NMR (DMSO-d$_6$, δ): 1.28 (3H, t, J=7.1 Hz), 1.45–1.66 (2H, m), 1.85–2.02 (2H, m), 3.00–3.21 (2H, m), 3.55–3.78 (3H, m), 4.23 (2H, q, J=7.1 Hz), 4.55 (2H, s), 6.98 (2H, d, J=9.1 Hz), 7.23–7.43 (5H, m), 7.76 (2H, d, J=9.0 Hz)

MASS (m/z): 340 (M$^+$+1)

Preparation 175

1-(4-Heptyloxymethylphenyl)-1H-pyrazol-4-carboxylic Acid Methyl Ester

IR (KBr): 1703, 1558, 1265 cm$^{-1}$

NMR (DMSO-d$_6$, δ): 0.85 (3H, m), 1.1–1.6 (10H, m), 3.44 (2H, t, J=6.4 Hz), 3.81 (3H, s), 4.49 (2H, s), 7.45 (2H, d, J=8.5 Hz), 7.91 (2H, d, J=8.5 Hz), 8.15 (1H, s), 9.11 (1H, s)

MASS (m/z): 331 (M$^+$+1)

Preparation 176

To a solution of methyl 4-(4-hydroxyphenyl)benzoate (3.00 g) and cyclohexanol (1.58 g) in tetrahydrofuran (60 ml) was added dropwise diethyl azodicarboxylate (2.48 ml) at 0–10° C. under nitrogen atmosphere, and the mixture was stirred at ambient temperature for 4 hours. After concentration, to the residue was added ethyl acetate (50 ml) and n-hexane (10 ml), and the resulting precipitate was removed by filtration and discarded. To the filtrate was added silica gel (12 g) and the mixture was evaporated. The residue was purified by column chromatography on silica gel (80 g) eluting with a mixed solvent of 5% ethyl acetate in n-hexane to give methyl 4-(4-cyclohexyloxyphenyl)benzoate (1.79 g) as a white solid.

IR (KBr): 1720, 1603, 1525, 1495, 1437 cm$^{-1}$

NMR (CDCl$_3$, δ): 1.22–1.66 (6H, m), 1.72–1.90 (2H, m), 1.95–2.10 (2H, m), 3.93 (3H, s), 4.22–4.37 (1H, m), 6.89–7.03 (2H, m), 7.47–7.76 (4H, m), 8.00–8.13 (2H, m)

MASS (m/z): 311 (M$^+$+1)

The following compound was obtained in a manner similar to that of Preparation 176.

Preparation 177

4-Cyclohexyloxybenzoic Acid Methyl Ester

NMR (CDCl$_3$, δ): 1.20–2.10 (10H, m), 3.88 (3H, s), 4.20–4.40 (1H, m), 6.85–6.95 (2H, m), 7.90–8.00 (2H, m)

APCI MASS (positive): 235.2 (M$^+$+1)

Preparation 178

To an ice-cooled solution of ethyl 4-(piperazin-1-yl)benzoate (2.00 g) and 4-methylcyclohexanone (1.05 ml) in a mixed solvent of methanol (40 ml) and acetic acid (1.47 ml) was added sodium cyanoborohydride (0.59 g) in a stream of nitrogen. The mixture was stirred at this temperature for 1 hour and at room temperature for 17 hours. The reaction mixture was quenched with saturated aqueous sodium hydrogen carbonate solution and the resulting precipitate was collected by filtration, washed thoroughly with water and dried to give a mixture of cis and trans products. This mixture was separated by column chromatography on silica gel eluting with a mixed solvent of methylene chloride-methanol (from 0% to 2% gradient solution) to give ethyl 4-[4-(cis-4-methylcyclohexyl)piperazin-1-yl]benzoate (0.80 g) as a pale green solid and ethyl 4-[4-(trans-4-methylcyclohexyl)piperazin-1-yl]benzoate (0.64 g) as a pale green solid. Trans-product was confirmed by X-ray crystal analysis.

Ethyl 4-[4-(cis-4-methylcyclohexyl)piperazin-1-yl]benzoate

IR (KBr): 1697, 1608, 1520, 1446 cm$^{-1}$

NMR (DMSO-d$_6$, δ): 0.89 (3H, d, J=6.8 Hz), 1.28 (3H, t, J=7.1 Hz), 1.23–1.52 (6H, m), 1.52–1.76 (3H, m), 2.07–2.25 (1H, m), 2.47–2.63 (4H, m), 3.20–3.40 (4H, m), 4.23 (2H, q, J=7.1 Hz), 6.96 (2H, d, J=9.1 Hz), 7.78 (2H, d, J=8.9 Hz)

MASS (m/z): 331 (M$^+$+1)

Ethyl 4-[4-(trans-4-methylcyclohexyl)piperazin-1-yl]benzoate

IR (KBr): 1709, 1608, 1518, 1444 cm$^{-1}$

NMR (DMSO-d$_6$, δ): 0.85 (3H, d, J=6.8 Hz), 0.80–1.02 (2H, m), 1.28 (3H, t, J=7.1 Hz), 1.09–1.56 (3H, m), 1.56–1.88 (4H, m), 2.08–2.34 (1H, m), 2.50–2.67 (4H, m), 3.18–3.34 (4H, m), 4.23 (2H, q, J=7.1 Hz), 6.95 (2H, d, J=9.1 Hz), 7.77 (2H, d, J=8.9 Hz)

MASS (m/z): 331 (M$^+$+1)

The following compound was obtained in a manner similar to that of Preparation 178.

Preparation 179

Ethyl 4-[4-(4,4-dimethylcyclohexyl)piperazin-1-yl]benzoate

NMR (CDCl$_3$, δ): 0.91 (6H, s), 1.07–1.55 (6H, m), 1.36 (3H, t, J=7.1 Hz), 1.64–1.82 (2H, m), 2.10–2.30 (1H, m), 2.72 (4H, t, J=5.1 Hz), 3.33 (4H, t, J=5.1 Hz), 4.32 (2H, q, J=7.1 Hz), 6.86 (2H, d, J=9.1 Hz), 7.87–7.99 (2H, m)

MASS (m/z): 345 (M$^+$+1)

Preparation 180

To a mixture of cesium carbonate (1.90 g), palladium (II) acetate (46.7 mg) and 2,2'-bis(diphenylphosphino)-1,1'-binaphthyl (194 mg) in toluene (3.3 ml) was successively added a solution of cis-2,6-dimethyl morpholine (0.58 g) in toluene (5 ml) and methyl 4-(4-trifluoromethanesulfonyloxyphenyl)benzoate (1.50 g) in a stream of nitrogen. The mixture was stirred at ambient temperature for 30 minutes and refluxed for further 6 hours. After cooling to room temperature, water was added to the reaction mixture and the mixture was extracted with methylene chloride. The organic layer was washed with saturated aqueous sodium chloride solution, dried over magnesium sulfate, filtered and concentrated in vacuo. The residue was pulverized with acetonitrile and collected by filtration to give methyl 4-[4-(cis-2,6-dimethylmorpholinophenyl)]benzoate (525 mg) as a pale yellow solid.

IR (KBr): 1720, 1603, 1497, 1446 cm$^{-1}$

NMR (CDCl$_3$, δ): 1.28 (6H, d, J=6.3 Hz), 2.46 (1H, d, J=10.6 Hz), 2.49 (1H, d, J=10.6 Hz), 3.46–3.62 (2H, m), 3.72–3.94 (2H, m), 3.93 (3H, s), 6.98 (2H, d, J=8.9 Hz), 7.51–7.70 (4H, m), 8.02–8.14 (2H, m)

MASS (m/z): 326 (M$^+$+1)

The following compound was obtained in a manner similar to that of Preparation 180.

Preparation 181

Methyl 4-[4-(4-cyclohexylpiperazin-1-yl)phenyl]benzoate

IR (KBr): 2929, 2852, 2829, 1714, 1603, 1529, 1498, 1439 cm$^{-1}$

NMR (CDCl$_3$, δ): 1.00–1.41 (5H, m), 1.51–2.05 (5H, m), 2.24–2.43 (1H, m), 2.69–2.84 (4H, m), 3.22–3.36 (4H, m), 3.93 (3H, s), 7.00 (2H, d, J=8.9 Hz), 7.48–7.68 (4H, m), 8.00–8.12 (2H, m)

MASS (m/z): 379 (M$^+$+1)

Preparation 182

To a suspension of 2-amino-5-(4-methoxyphenyl)-1,3,4-thiadiazole (7.2 g) in ethanol (50 ml) was added ethyl 4-bromoacetylbenzoate (11.3 g) and the mixture was stirred under refluxing for 2.5 hours. The reaction mixture was pulverized with ethyl acetate. The precipitate was collected by filtration and dried. To a suspension of the powder in xylene (50 ml) was added trifluoroacetic acid (5 ml) and the mixture was stirred under refluxing for 3.5 hours. The reaction mixture was pulverized with diisopropyl ether. The precipitate was collected by filtration and dried to give 4-[2-(4-methoxyphenyl)imidazo[2,1-b][1,3,4]thiadiazol-6-yl]benzoic acid ethyl ester trifluoroacetic acid salt (13.7 g).

IR (KBr): 2360.4, 1746.3, 1604.5, 1483.0 cm$^{-1}$

MASS (m/z): 380 ((M–TFA)+H$^+$)

The following compounds [Preparations 183 to 190] were obtained in a manner similar to that of Preparation 182.

Preparation 183

4-[2-(4-Piperidin-1-yl-phenyl)imidazo[2,1-b][1,3,4]thiadiazol-6-yl]benzoic acid ethyl ester trifluoroacetic acid salt IR (KBr): 2940, 2584, 2474, 1702, 1608, 1523, 1471, 1409, 1367, 1280 cm$^{-1}$ MASS (m/z): 433 ((M–TFA)+H$^+$)

Preparation 184

4-[2-(4-Morpholin-4-yl-phenyl)imidazo[2,1-b][1,3,4]thiadiazol-6-yl]benzoic acid ethyl ester trifluoroacetic acid salt IR (KBr): 2669, 1706, 1606, 1473, 1274, 1236, 1176, 1118, 1020, 929 cm$^{-1}$ MASS (m/z): 435 ((M–TFA)+H$^+$)

Preparation 185

4-[2-(cis-2,6-Dimethylmorpholin-4-yl-phenyl)imidazo[2,1-b][1,3,4]thiadiazol-6-yl]benzoic acid ethyl ester trifluoroacetic acid salt IR (KBr): 2979, 1710, 1606, 1473, 1371, 1278, 1241, 1176, 1106 cm$^{-1}$ MASS (m/z): 463 ((M–TFA)+H$^+$)

Preparation 186

4-[2-(4-Thiomorpholin-4-yl-phenyl)imidazo[2,1-b][1,3,4]thiadiazol-6-yl]benzoic acid ethyl ester trifluoroacetic acid salt IR (KBr): 2979, 1708, 1604, 1504, 1471, 1274, 1193, 1105 cm$^{-1}$ MASS (m/z): 451 ((M–TFA)+H$^+$)

Preparation 187

4-[2-[4-(4-Ethylpiperazin-1-yl)phenyl]imidazo[2,1-b][1,3,4]thiadiazol-6-yl]benzoic acid ethyl ester trifluoroacetic acid salt IR (KBr): 2983, 2931, 2674, 2605, 1702, 1606, 1471, 1405, 1282, 1241, 1201 cm$^{-1}$ NMR (DMSO-d$_6$, δ): 1.23–1.38 (6H, m), 3.30–3.23 (6H, m), 3.61 (2H, d, J=8.2 Hz), 4.12 (2H, d, J=8.2 Hz), 4.33 (2H, q, J=7.2 Hz), 7.20 (2H, d, J=8.8 Hz), 7.85 (2H, d, J=8.8 Hz), 8.02 (4H, s), 8.86 (1H, s)

MASS (m/z): 462 ((M–TFA)+H$^+$)

Preparation 188

4-[2-[4-(4-Cyclohexylpiperazin-1-yl)phenyl]imidazo[2,1-b][1,3,4]thiadiazol-6-yl]benzoic acid ethyl ester trifluoroacetic acid salt IR (KBr): 2935, 2586, 1708, 1604, 1571, 1488, 1409, 1367, 1278, 1199, 1106 cm$^{-1}$ MASS (m/z): 516 ((M–TFA)+H$^+$)

Preparation 189

4-[6-(4-Hydroxyphenyl)imidazo[2,1-b][1,3,4]thiadiazol-2-yl]benzoic acid methyl ester trifluoroacetic acid salt IR (KBr): 3214, 3027, 1720, 1629, 1610, 1513, 1434, 1284, 1187, 1112 cm$^{-1}$ NMR (DMSO-d$_6$, δ): 2.91 (3H, s), 7.72 (2H, d, J=8.5 Hz), 7.91 (2H, d, J=8.5 Hz), 8.12 (4H, s), 8.61 (1H, s)

MASS (m/z): 352 ((M−TFA)+H$^+$)

Preparation 190

4-[6-(4-Pentyloxyphenyl)imidazo[2,1-b][1,3,4]thiadiazol-2-yl]benzoic acid methyl ester trifluoroacetic acid salt IR (KBr): 2952, 2869, 1720, 1612, 1494, 1471, 1436, 1405, 1280, 1251, 1182, 1110 cm$^{-1}$ MASS (m/z): 422 ((M−TFA)+H$^+$)

Preparation 191

A solution of methyl 4-[4-(4-bromobutoxy)phenyl]benzoate (1.40 g) in methanol (14 ml) was treated with 28% sodium methoxide in methanol (14 ml) and the solution was reluxed for 5 hours. After cooling to room temperature, the reaction mixture was poured into cold 1N-hydrochloric acid (110 ml) and the resulting precipitate was collected by filtration, washed thoroughly with water and dried to give a white solid. To a mixture of this solid in methanol (20 ml) was added concentrated sulfuric acid (0.5 ml) and refluxed for 4 hours. After cooling to room temperature, the reaction mixture was poured into cold water and the resulting precipitate was collected by filtration, washed thoroughly with water and dried to give methyl 4-[4-(4-methoxybutoxy)phenyl]benzoate (1.16 g) as a white solid.

IR (KBr): 2949, 2873, 1720, 1603, 1529, 1498, 1439 cm$^{-1}$

NMR (DMSO-d$_6$, δ): 1.54–1.85 (4H, m), 3.24 (3H, s), 3.38 (2H, t, J=6.2 Hz), 3.87 (3H, s), 4.04 (2H, t, J=6.1 Hz), 7.05 (2H, t, J=8.8 Hz), 7.69 (2H, d, J=8.7 Hz), 7.78 (2H, d, J=8.4 Hz), 8.00 (2H, d, J=8.4 Hz)

MASS (m/z): 315 (M$^+$+1)

The following compounds [Preparations 192 to 194] were obtained in a manner similar to that of Preparation 191.

Preparation 192

Methyl 4-[4'-(3-methoxypropoxy)phenyl]benzoate

IR (KBr): 2953, 2875, 1724, 1603, 1529, 1495, 1435 cm$^{-1}$

NMR (DMSO-d$_6$, δ): 1.96 (2H, m), 3.26 (3H, s), 3.49 (2H, t, J=6.3 Hz), 3.87 (3H, s), 4.08 (2H, t, J=6.4 Hz), 6.98–7.14 (2H, m), 7.64–7.86 (4H, m), 7.96–8.10 (2H, m)

MASS (m/z): 301 (M$^+$+1)

Preparation 193

1-Bromo-4-ethoxymethylbenzene

NMR (DMSO-d$_6$, δ): 1.15 (3H, t, J=7.0 Hz), 3.47 (2H, q, J=7.0 Hz), 4.42 (2H, s), 7.28 (2H, d, J=8.5 Hz), 7.46–7.61 (2H, m)

Preparation 194

Methyl 4-[4-(3-ethoxypropoxy)phenyl]benzoate

NMR (DMSO-d$_6$, δ): 1.11 (3H, t, J=7.0 Hz), 1.96 (2H, m), 3.43 (2H, q, J=7.0 Hz), 3.52 (2H, t, J=6.3 Hz), 3.87 (3H, s), 4.08 (2H, t, J=6.3 Hz), 7.06 (2H, d, J=8.8 Hz), 7.70 (2H, d, J=8.8 Hz), 7.78 (2H, d, J=8.5 Hz), 8.00 (2H, d, J=8.5 Hz)

MASS (m/z): 315 (M$^+$+1)

Preparation 195

To a suspension of 4-[2-(4-hydroxyphenyl)imidazo[2,1-b][1,3,4]thiadiazol-6-yl]benzoic acid ethyl ester (500 mg) and potassium carbonate (2 g) in N,N-dimethylformamide (25 ml) was added 1,4-dibromobutane (1 ml) and the mixture was stirred at room temperature for 22 hours. The reaction mixture was pulverized with ethyl acetate. The precipitate was collected by filtration and dried. To a suspension of the powder in N,N-dimethylformamide (25 ml) was added piperidine (2 ml) and the mixture was stirred at room temperature for 21 hours. The reaction mixture was pulverized with water. The precipitate was collected by filtration, washed with water, acetonitrile and diisopropyl ether and dried to give 4-[2-[4-(4-piperidin-1-yl-butyloxy)phenyl]imidazo[2,1-b][1,3,4]ethiadiazol-6-yl]benzoic acid ethyl ester (479 mg).

IR (KBr): 2933.2, 1708.6, 1608.3, 1471.4, 1274.7, 1176.4, 1101.2 cm$^{-1}$

MASS (m/z): 505 (M+H$^+$)

The following compounds [Preparations 196 to 201] were obtained in a manner similar to that of Preparation 195.

Preparation 196

4-[2-[4-(5-Piperidin-1-yl-pentyloxy)phenyl]imidazo[2,1-b][1,3,4]thiadiazol-6-yl]benzoic acid ethyl ester IR (KBr): 2935, 1708, 1608, 1471, 1274, 1176, 1101 cm$^{-1}$ MASS (m/z): 519 (M+H$^+$)

Preparation 197

4-[2-[4-(6-Piperidin-1-yl-hexyloxy)phenyl]imidazo[2,1-b][1,3,4]thiadiazol-6-yl]benzoic acid ethyl ester IR (KBr): 2933, 1710, 1608, 1471, 1274, 1176, 1103 cm$^{-1}$ MASS (m/z): 533 (M+H$^+$)

Preparation 198

4-[2-[4-(5-Morpholin-4-yl-pentyloxy)phenyl]imidazo[2,1-b][1,3,4]thiadiazol-6-yl]benzoic acid ethyl ester IR (KBr): 2940, 1708, 1608, 1471, 1276, 1176, 1163 cm$^{-1}$ MASS (m/z): 521 (M+H$^+$)

Preparation 199

4-[2-[4-[5-(cis-2,6-Dimethylmorpholin-4-yl)pentyloxy]phenyl]imidazo[2,1-b][1,3,4]thiadiazol-6-yl]benzoic acid ethyl ester IR (KBr): 2937, 1708, 1608, 1471, 1409, 1369, 1307, 1278, 1176 cm$^{-1}$ MASS (m/z): 549 (M+H$^+$)

Preparation 200

4-[2-[4-[6-(cis-2,6-Dimethylmorpholin-4-yl)hexyloxy]phenyl]imidazo[2,1-b][1,3,4]thiadiazol-6-yl]benzoic acid ethyl ester IR (KBr): 2937, 1710, 1606, 1544, 1471, 1403, 1305, 1270, 1257, 1176 cm$^{-1}$ MASS (m/z): 563 (M+H$^+$)

Preparation 201

4-[2-[4-(5-Thiomorpholin-4-yl-pentyloxy)phenyl]imidazo[2,1-b][1,3,4]thiadiazol-6-yl]benzoic acid ethyl ester IR (KBr): 2939, 1706, 1608, 1471, 1274, 1176, 1108 cm$^{-1}$ MASS (m/z): 537 (M+H$^+$)

Preparation 202

To a suspension of 4-[2-(4-hydroxyphenyl)imidazo[2,1-b][1,3,4]thiadiazol-6-yl]benzoic acid ethyl ester (1 g) and potassium carbonate (4 g) in N,N-dimethylformamide (50 ml) was added 1,5-dibromopentane (2 ml) and the mixture was stirred at room temperature for 6 hours. The reaction mixture was pulverized with ethyl acetate. The precipitate was collected by filtration, washed with water and methanol. To a suspension of the powder in methanol (10 ml) was added sodium methylate (28% in methanol) (20 ml) and the mixture was stirred at 80° C. for 19 hours. The reaction mixture was pulverized with water. The precipitate was collected by filtration, washed with water, methanol and diisopropyl ether and dried to give 4-[2-[4-(5-methoxypentyloxy)phenyl]imidazo[2,1-b][1,3,4]thiadiazol-6-yl]benzoic acid methyl ester (479 mg).

MASS (m/z): 452 (M+H$^+$)

The following compounds [Preparations 203 to 205] were obtained in a manner similar to that of Preparation 202.

Preparation 203

4-[2-[4-(6-Methoxyhexyloxy)phenyl]imidazo[2,1-b][1,3,4]thiadiazol-6-yl]benzoic acid methyl ester IR (KBr): 2935, 2861, 1712, 1608, 1591, 1533, 1471, 1417, 1305, 1259, 1178, 1116 cm$^{-1}$ MASS (m/z): 466 (M+H$^+$)

Preparation 204

4-[2-[4-(7-Methoxyheptyloxy)phenyl]imidazo[2,1-b][1,3,4]thiadiazol-6-yl]benzoic acid methyl ester IR (KBr): 2933, 2858, 1714, 1608, 1591, 1533, 1469, 1419, 1305, 1259, 1178, 1112 cm$^{-1}$ MASS (m/z): 480 (M+H$^+$)

Preparation 205

4-[2-[4-(8-Methoxyoctyloxy)phenyl]imidazo[2,1-b][1,3,4]thiadiazol-6-yl]benzoic acid methyl ester IR (KBr): 2931, 2856, 1712, 1610, 1591, 1533, 1471, 1419, 1305, 1259, 1178, 1112 cm$^{-1}$ MASS (m/z): 494 (M+H$^+$)

Preparation 206

A mixture of piperazin-1-carboxylic acid tert-butyl ester (0.64 g), 4-bromo-4'-(5-methoxypentyloxy)biphenyl (1 g), tris(dibenzylideneacetone) (chloroform) dipalladium(0) (59 mg), (S)-(−)-2,2'-bis(diphenylphosphino)-1,1'-binaphthyl (0.12 g) and sodium tert-butoxide (0.55 g) in toluene (10 ml) was stirred for 54 hours at 90° C. The reaction mixture was added to a mixture of water and ethyl acetate. The organic layer was taken and dried over magnesium sulfate. The magnesium sulfate was filtered off, and the filtrate was evaporated under reduced pressure to give 4-[4'-(5-methoxypentyloxy)biphenyl-4-yl]piperazin-1-carboxylic acid tert-butyl ester (1.19 g).

IR (KBr): 1691.3, 1504.2, 1232.3 cm$^{-1}$

NMR (CDCl$_3$, δ): 1.49 (9H, s), 1.49–1.90 (6H, m), 3.14–3.19 (4H, m), 3.34 (3H, s), 3.41 (2H, t, J=6.2 Hz), 3.57–3.62 (4H, m), 3.99 (2H, t, J=6.4 Hz), 6.91–6.99 (4H, m), 7.44–7.49 (4H, m)

MASS (m/z): 455 (M+1)

The following compound was obtained in a manner similar to that of Preparation 206.

Preparation 207

4-[4-[4-(7-Methoxyheptylthio)phenyl]piperazin-1-yl]benzoic acid

IR (KBr): 1681.6, 1585.2, 1423.2, 1230.4 cm$^{-1}$

NMR (DMSO-d$_6$, δ): 1.20–1.55 (10H, m), 2.80 (2H, t, J=6.7 Hz), 3.20 (3H, s), 3.24–3.43 (10H, m), 6.82–6.86 (2H, m), 6.94–6.98 (2H, m), 7.23–7.27 (2H, m), 7.69–7.73 (2H, m)

MASS (m/z): 443.2 (M+1)

Preparation 208

1-tert-Butoxycarbonyl-4-[4-(4-cyclohexylphenyl)piperazin-1-yl]piperidine (3.3 g) and trifluoroacetic acid (10 ml) were mixed and the mixture was stirred at ambient temperature for 1 hour. The solution was placed in water, adjusted to pH 8 with 1N sodium hydroxide and extracted with ethyl acetate. The organic layer was separated, washed with brine, dried over magnesium sulfate and evaporated under reduced pressure to give 1-(4-cyclohexylphenyl)-4-piperidylpiperazine (3.83 g).

Preparation 209

To a suspension of 4-[2-(4-hydroxyphenyl)imidazo[2,1-b][1,3,4]thiadiazol-6-yl]benzoic acid (4.0 g) in ethanol (50 ml) was added sulfuric acid (1.0 ml) and the mixture was stirred at 80° C. for 9 hours. The reaction mixture was pulverized with water. The precipitate was collected by filtration, washed with water, acetonitrile and diisopropyl ether and dried to give 4-[2-(4-hydroxyphenyl)imidazo[2,1-b][1,3,4]thiadiazol-6-yl]benzoic acid ethyl ester (2.09 g).

IR (KBr): 3215, 1679.7, 1608.3, 1473.3, 1288.2 cm$^{-1}$

NMR (DMSO-d$_6$, δ): 1.34 (3H, t, J=7.1 Hz), 4.32 (2H, q, J=7.1 Hz), 6.96 (2H, d, J=8.5 Hz), 7.89 (2H, d, J=8.5 Hz), 8.02 (4H, s), 8.84 (1H, s), 10.40 (1H, s)

MASS (m/z): 366 (M+H$^+$)

The following compound was obtained in a manner similar to that of Preparation 209.

Preparation 210

4-Cyclohexylbenzoic acid methyl ester

NMR (CDCl$_3$, δ): 1.10–1.55 (5H, m), 1.65–1.95 (5H, m), 2.45–2.65 (1H, m), 3.98 (3H, s), 7.26 (2H, d, J=8.2 Hz), 7.95 (2H, d, J=8.2 Hz)

APCI MASS: 219 (M$^+$+1)

The Object Compounds (211) to (457) obtained in the following Preparations 211 to 457 are given in the tables as below.

| Preparation No. | Formula |
|---|---|
| 211 | 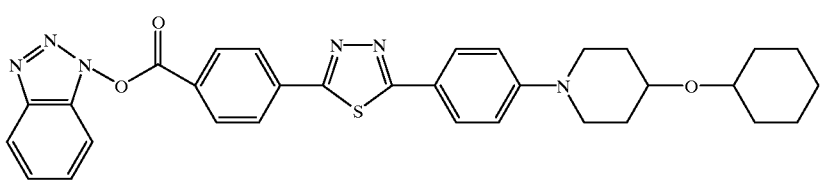 |
| 212 | 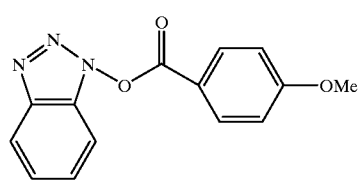 |
| 213 | 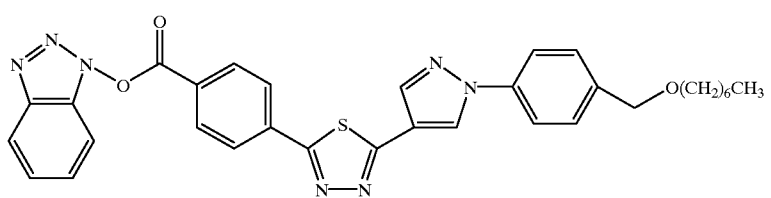 |
| 214 | 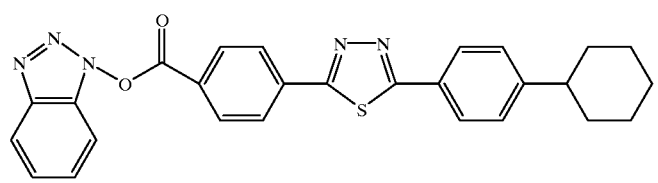 |
| 215 | 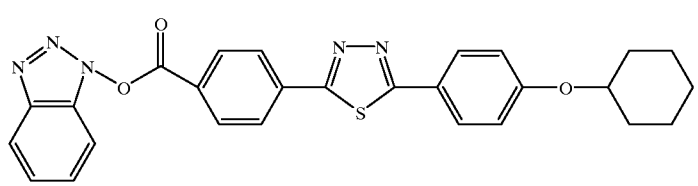 |
| 216 | 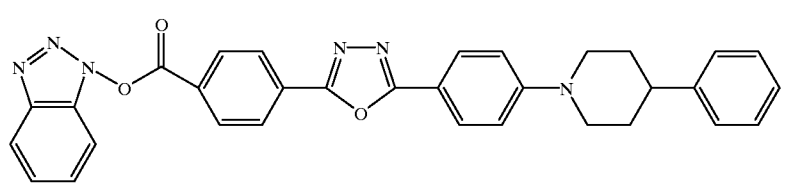 |
| 217 | 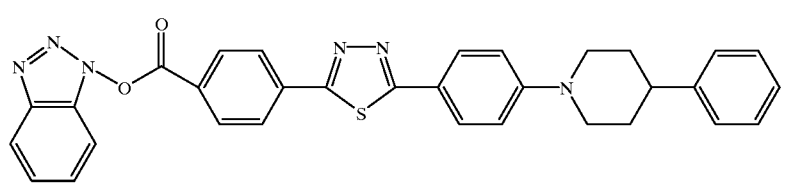 |
| 218 | 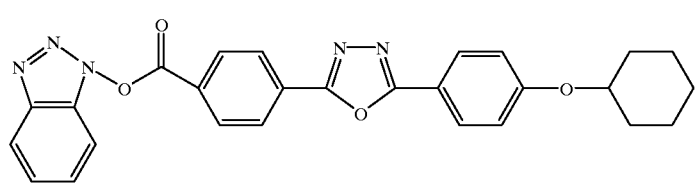 |

| Preparation No. | Formula |
|---|---|
| 219 | 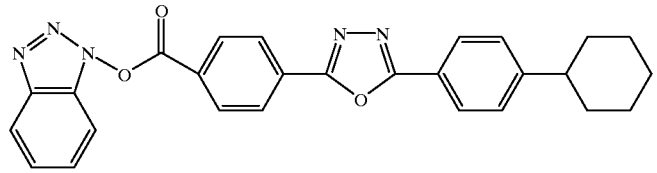 |
| 220 | 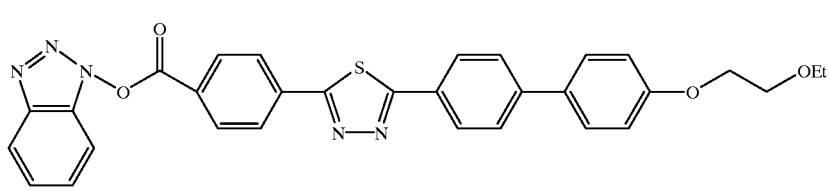 |
| 221 | 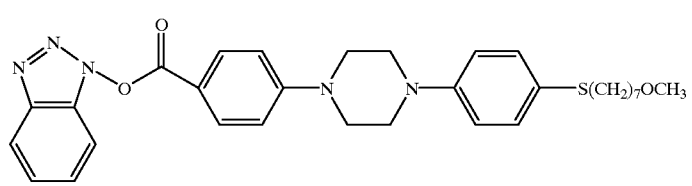 |
| 222 | 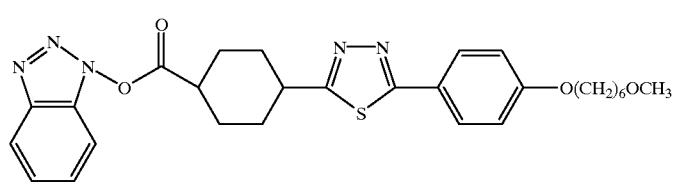 |
| 223 | 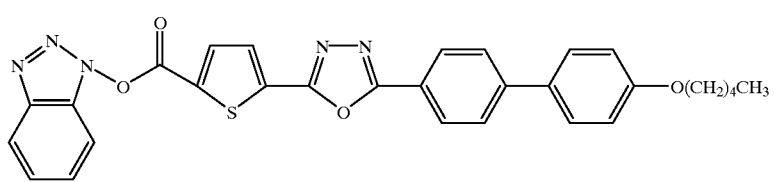 |
| 224 | 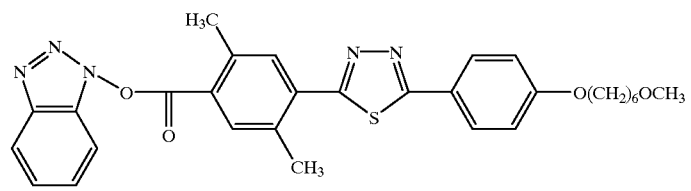 |
| 225 | 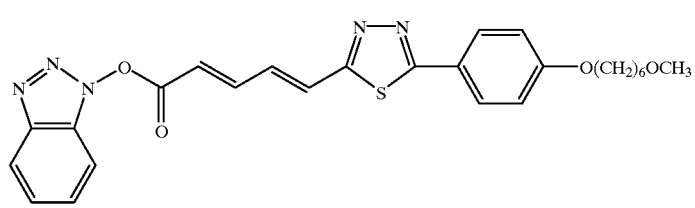 |

| Preparation No. | Formula |
|---|---|
| 226 | [structure: benzotriazole-O-C(=O)-naphthalene-(1,3,4-oxadiazole)-biphenyl-O(CH₂)₂CH₃] |
| 227 | [structure: benzotriazole-O-C(=O)-naphthalene-(1,3,4-thiadiazole)-phenyl-O(CH₂)₆OCH₃] |
| 228 | [structure: benzotriazole-O-C(=O)-phenyl-(1,3,4-thiadiazole)-biphenyl-O-butyl] |
| 229 | [structure: benzotriazole-O-C(=O)-phenyl-(1,3,4-thiadiazole)-biphenyl-O(CH₂)₄OMe] |
| 230 | [structure: benzotriazole-O-C(=O)-phenyl-(1,3,4-thiadiazole)-biphenyl-CH₂OEt] |
| 231 | [structure: benzotriazole-O-C(=O)-phenyl-(1,3,4-thiadiazole)-biphenyl-CH₂OCH₂CH₂OMe] |
| 232 | [structure: benzotriazole-O-C(=O)-phenyl-(1,3,4-thiadiazole)-biphenyl-O-CH₂CH₂-O-CH₂CH₂-OMe] |
| 233 | [structure: benzotriazole-O-C(=O)-phenyl-(1,3,4-thiadiazole)-biphenyl-O(CH₂)₃OEt] |

| Preparation No. | Formula |
|---|---|
| 234 | 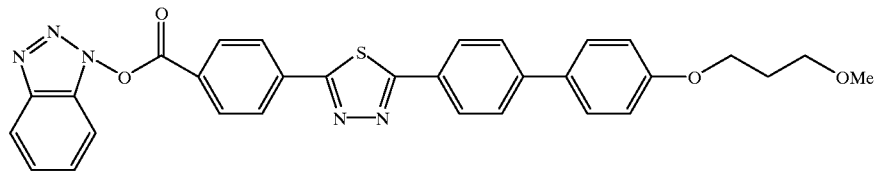 |
| 235 | 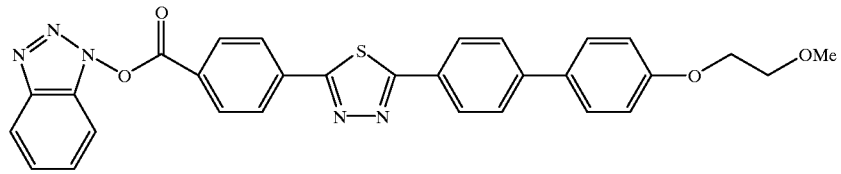 |
| 236 | 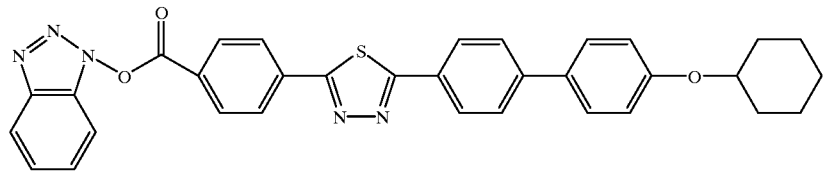 |
| 237 | 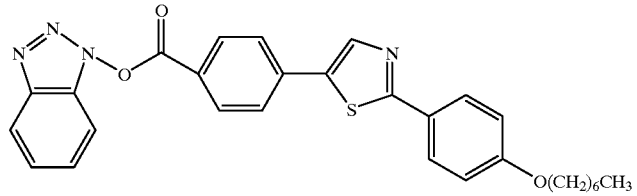 |
| 238 | 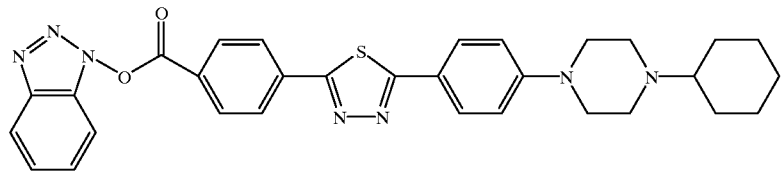 |
| 239 | 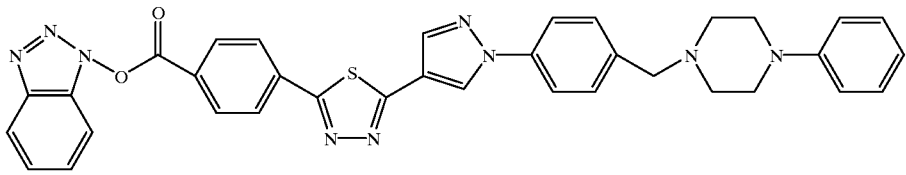 |
| 240 | 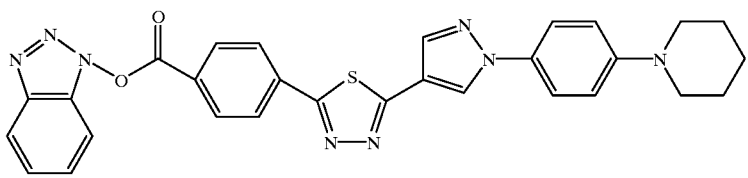 |

| Preparation No. | Formula |
|---|---|
| 241 | 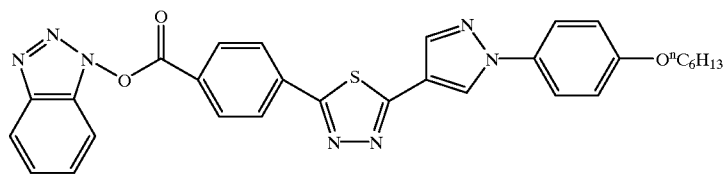 |
| 242 | 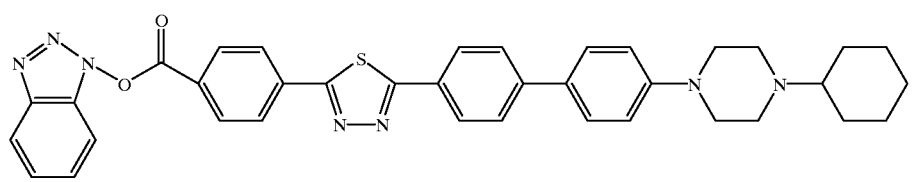 |
| 243 | 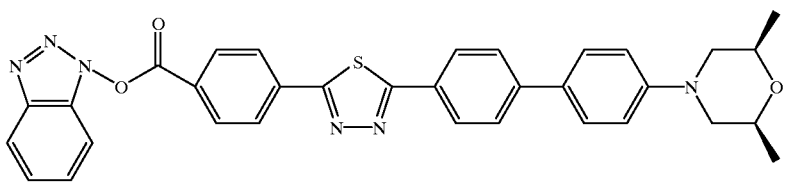 |
| 244 | 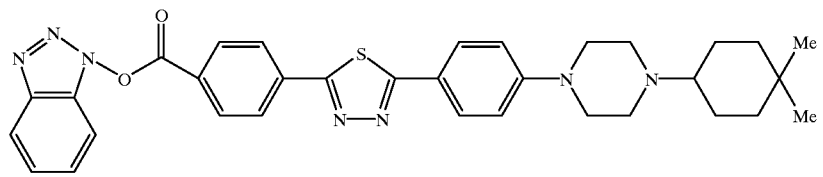 |
| 245 | 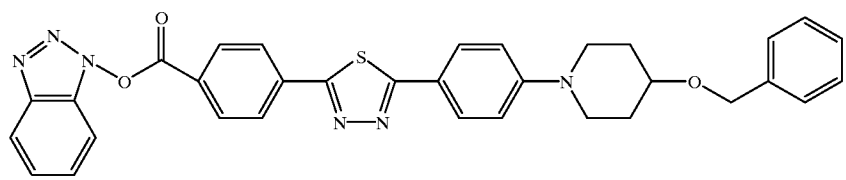 |
| 246 | 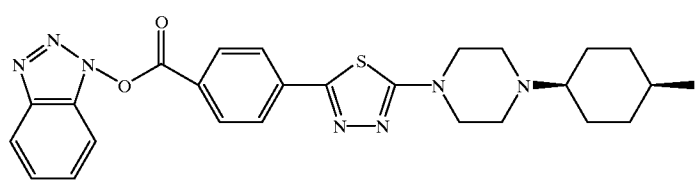 |
| 247 | 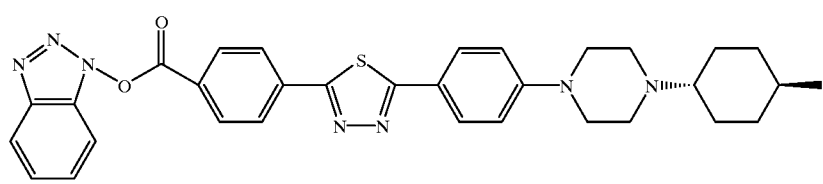 |

-continued

| Preparation No. | Formula |
|---|---|
| 248 | |
| 249 | |
| 250 | |
| 251 | |
| 252 | |
| 253 | |
| 254 | |
| 255 | |

-continued
| Preparation No. | Formula |
|---|---|
| 256 | 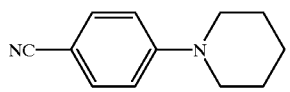 |
| 257 | 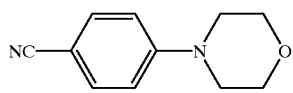 |
| 258 | 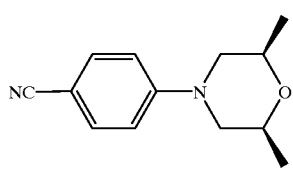 |
| 259 | 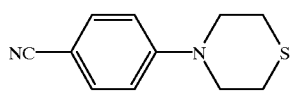 |
| 260 | 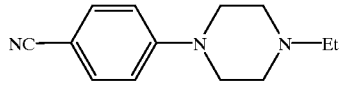 |
| 261 | 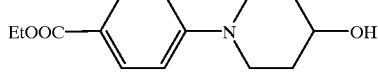 |
| 262 | 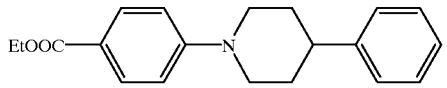 |
| 263 | 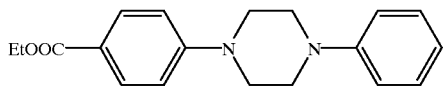 |
| 264 | 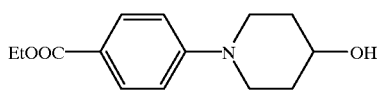 |
| 265 | 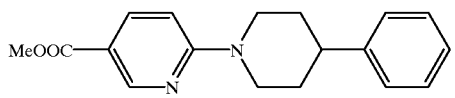 |
| 266 | 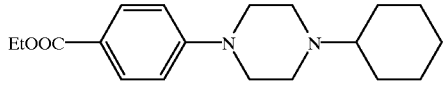 |
| 267 | 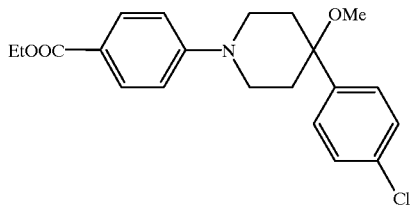 |

| Preparation No. | Formula |
|---|---|
| 268 | 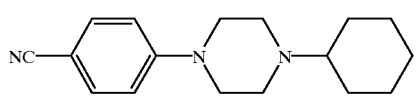 |
| 269 | 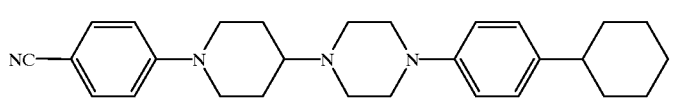 |
| 270 | 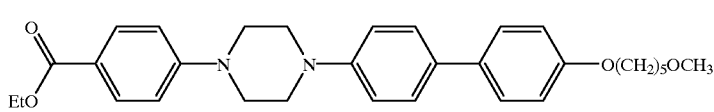 |
| 271 | 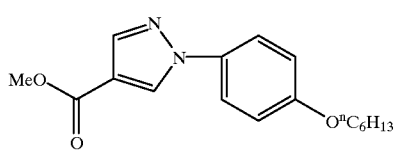 |
| 272 | 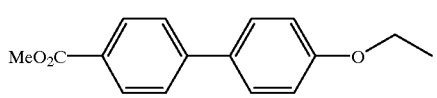 |
| 273 | 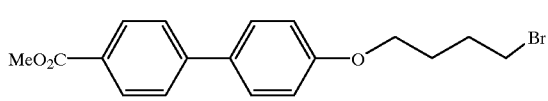 |
| 274 | 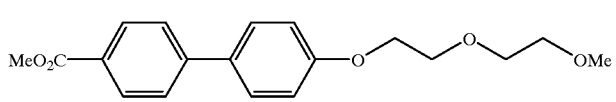 |
| 275 | 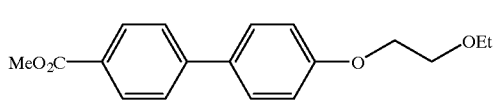 |
| 276 | 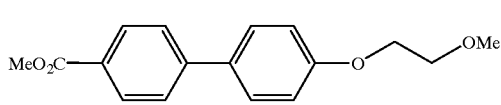 |
| 277 | 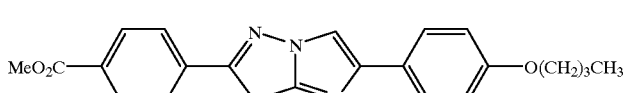 |
| 278 | 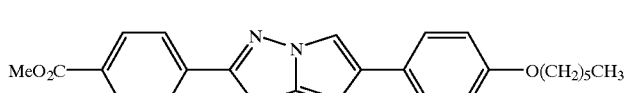 |
| 279 | 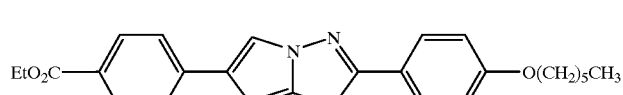 |

| Preparation No. | Formula |
|---|---|
| 280 | 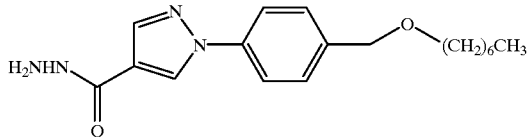 |
| 281 | 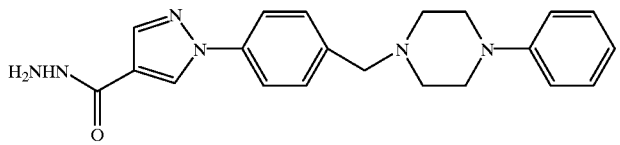 |
| 282 | 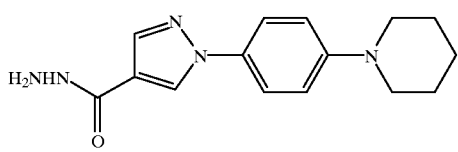 |
| 283 | 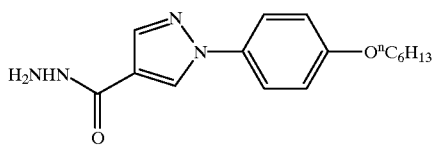 |
| 284 | 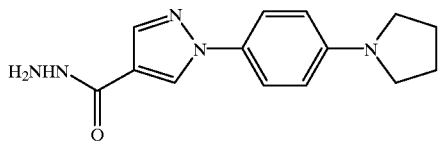 |
| 285 | 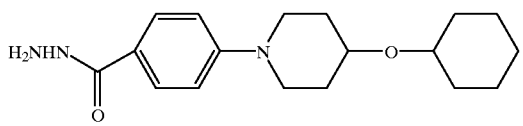 |
| 286 | 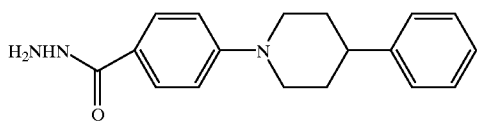 |
| 287 | 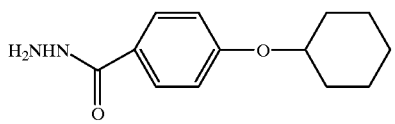 |
| 288 | 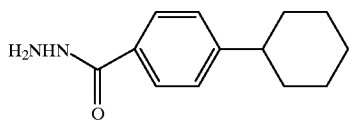 |
| 289 | 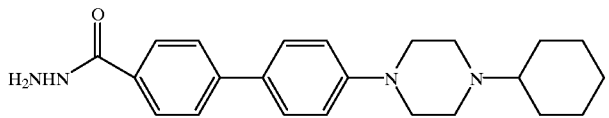 |

-continued

| Preparation No. | Formula |
|---|---|
| 290 | H₂NHN-C(O)-C₆H₄-N(piperazine)N-C₆H₅ |
| 291 | H₂NHN-C(O)-C₆H₄-N(piperidine)-O-propyl |
| 292 | H₂NHN-C(O)-C₆H₄-C₆H₄-N(2,6-dimethylmorpholine) |
| 293 | H₂NHN-C(O)-C₆H₄-N(piperazine)N-(4,4-dimethylcyclohexyl) |
| 294 | H₂NHN-C(O)-C₆H₄-N(piperidine)-O-CH₂-C₆H₅ |
| 295 | H₂NHN-C(O)-C₆H₄-C₆H₄-O-cyclohexyl |
| 296 | H₂NHN-C(O)-(pyridine)-N(piperidine)-C₆H₅ |
| 297 | H₂NHN-C(O)-C₆H₄-C₆H₄-O-ethyl |
| 298 | H₂NHN-C(O)-C₆H₄-C₆H₄-O-(CH₂)₄-OMe |
| 299 | H₂NHN-C(O)-C₆H₄-N(piperazine)N-cyclohexyl |

| Preparation No. | Formula |
|---|---|
| 300 | 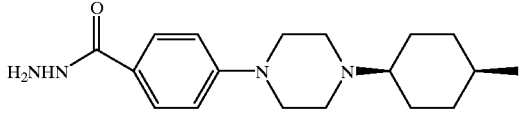 |
| 301 | 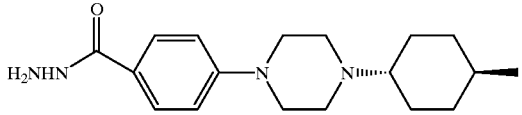 |
| 302 | 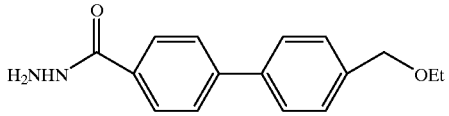 |
| 303 | 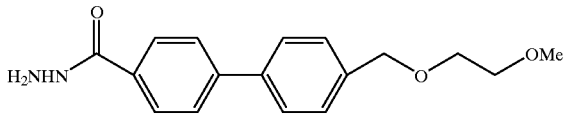 |
| 304 | 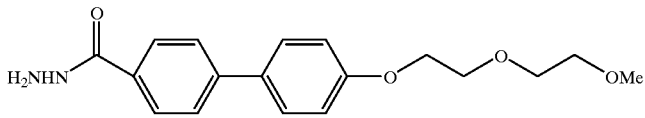 |
| 305 | 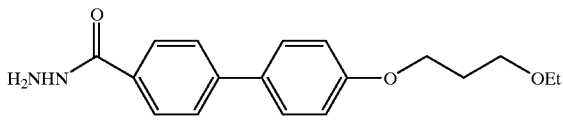 |
| 306 | 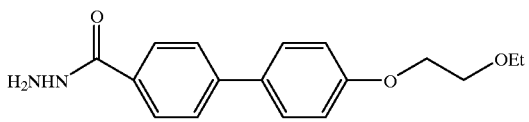 |
| 307 | 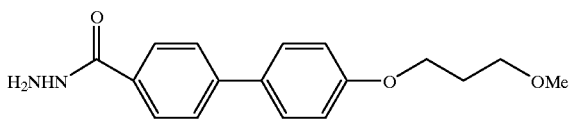 |
| 308 | 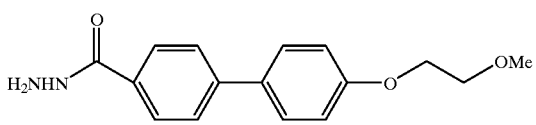 |
| 309 | 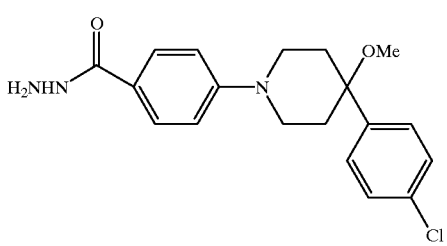 |

-continued
| Preparation No. | Formula |
|---|---|
| 310 | 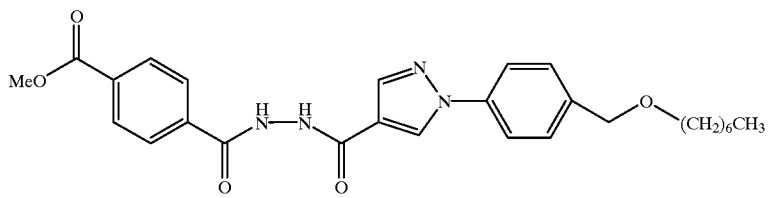 |
| 311 | 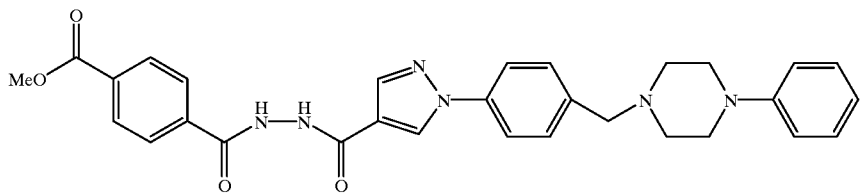 |
| 312 | 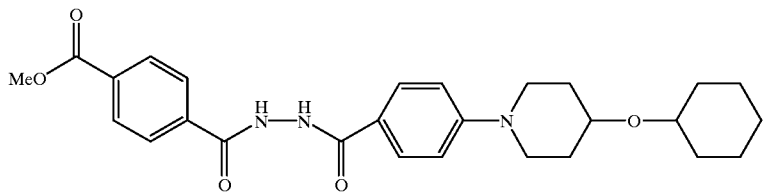 |
| 313 | 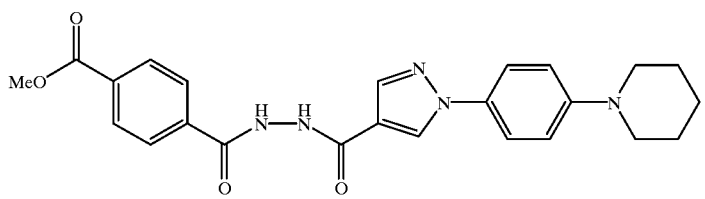 |
| 314 | 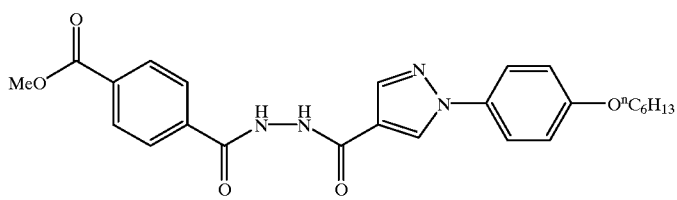 |
| 315 | 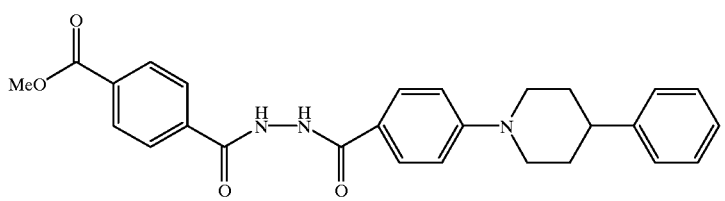 |
| 316 | 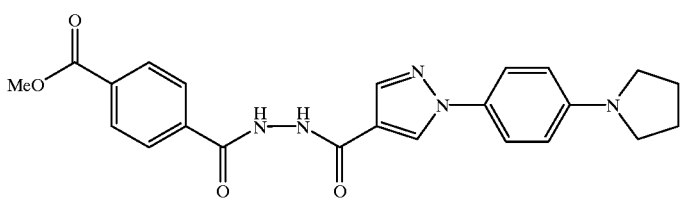 |

| Preparation No. | Formula |
|---|---|
| 317 | 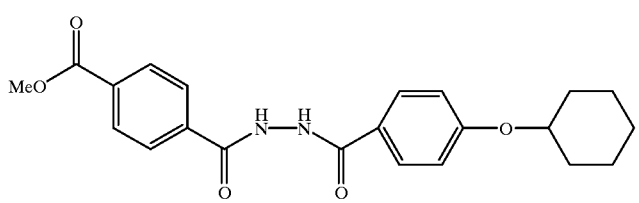 |
| 318 | 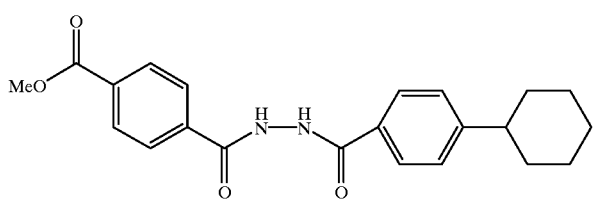 |
| 319 | 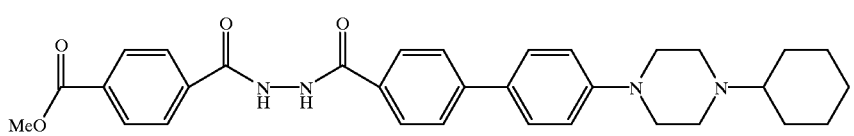 |
| 320 | 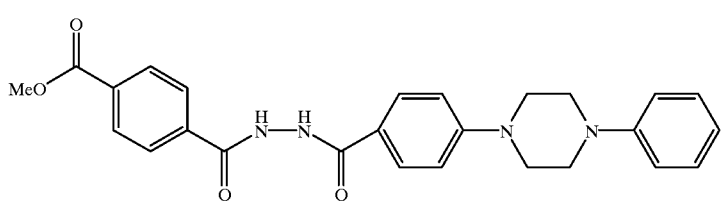 |
| 321 | 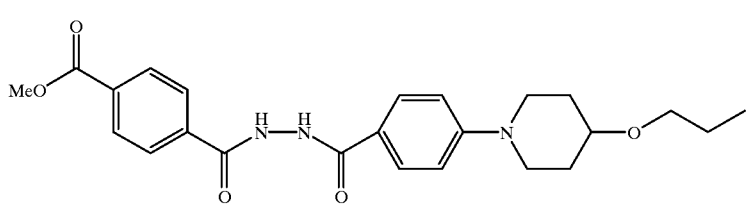 |
| 322 | 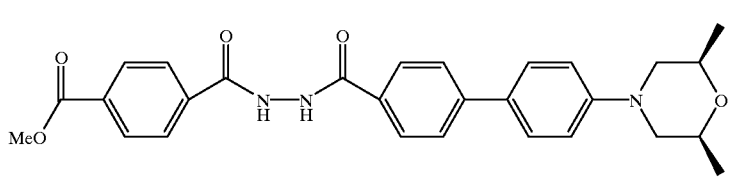 |
| 323 | 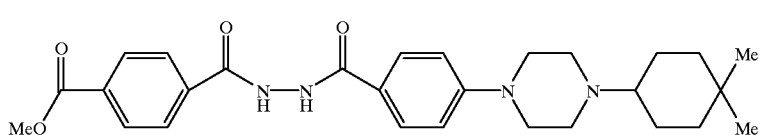 |
| 324 | 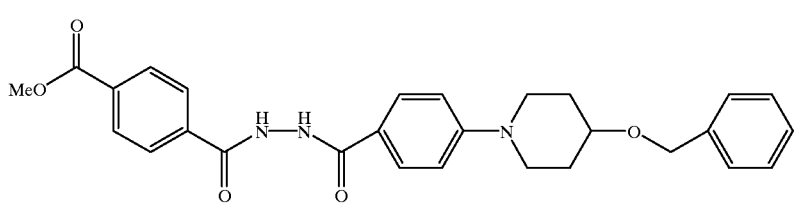 |

-continued
| Preparation No. | Formula |
|---|---|
| 325 | 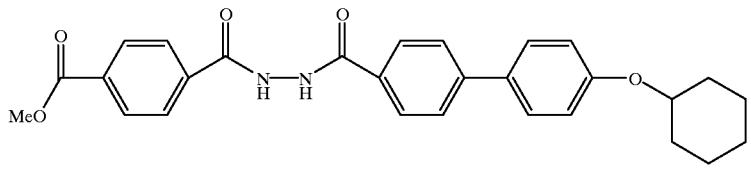 |
| 326 | 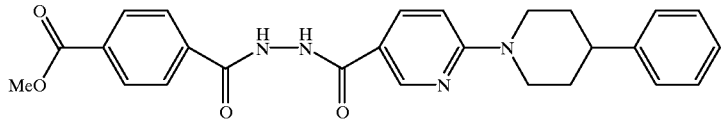 |
| 327 | 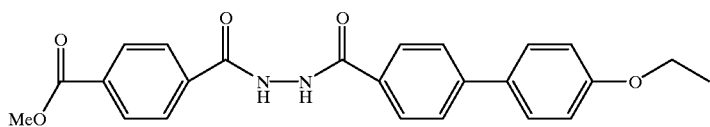 |
| 328 | 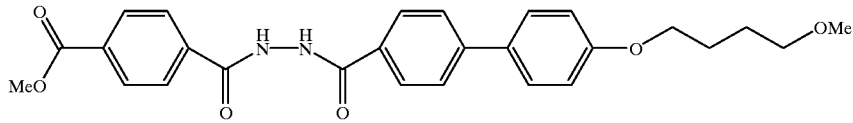 |
| 329 | 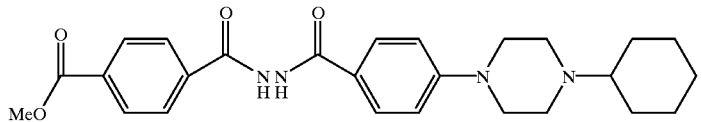 |
| 330 | 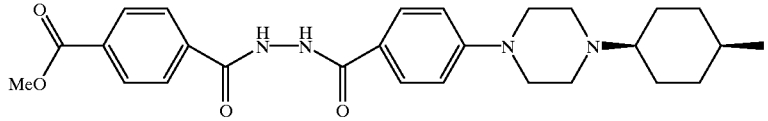 |
| 331 | 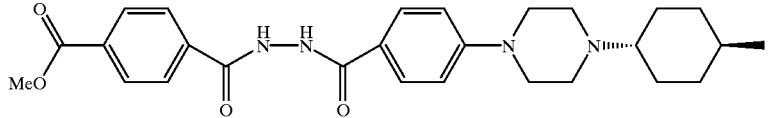 |
| 332 | 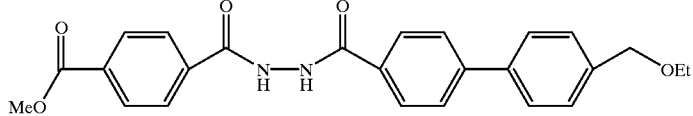 |
| 333 | 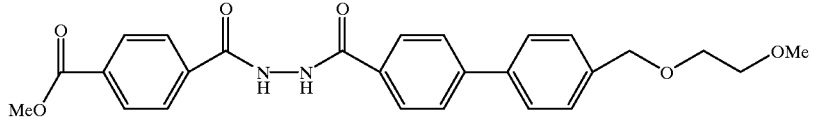 |
| 334 | 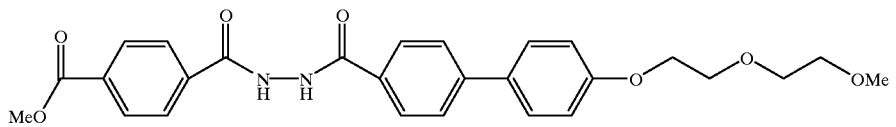 |

-continued
| Preparation No. | Formula |
|---|---|
| 335 | 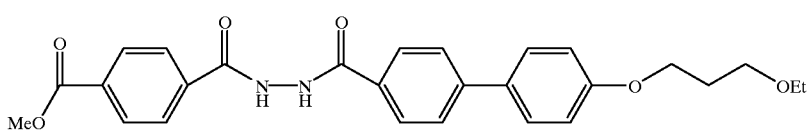 |
| 336 | 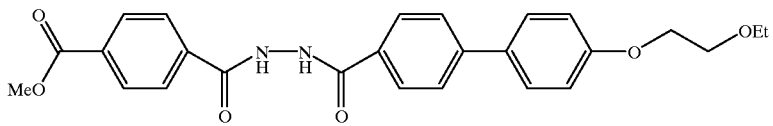 |
| 337 | 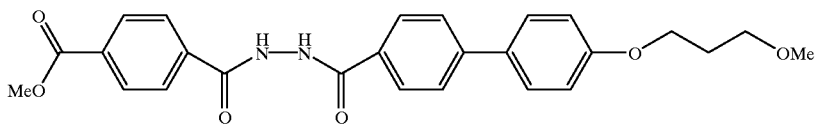 |
| 338 | 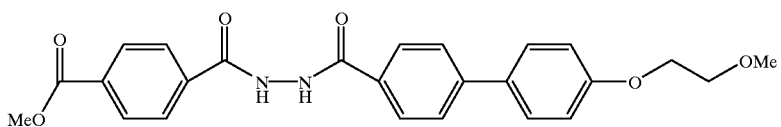 |
| 339 | 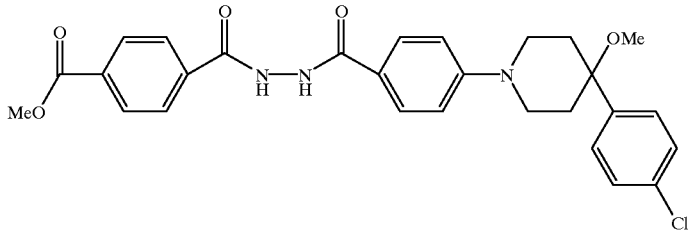 |
| 340 | 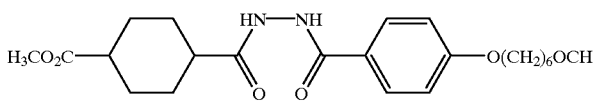 |
| 341 | 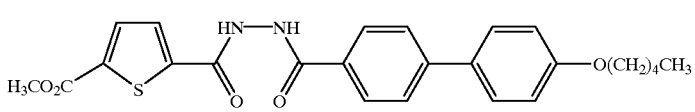 |
| 342 | 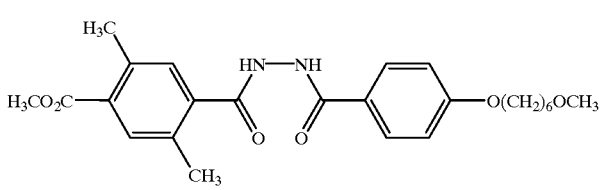 |
| 343 | 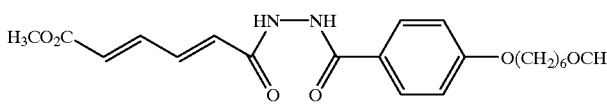 |
| 344 | 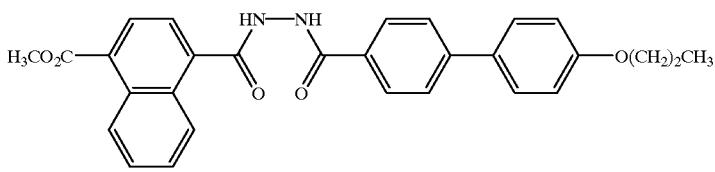 |

| Preparation No. | Formula |
|---|---|
| 345 | 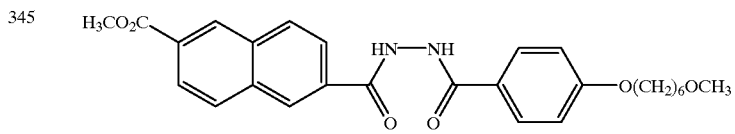 |
| 346 | 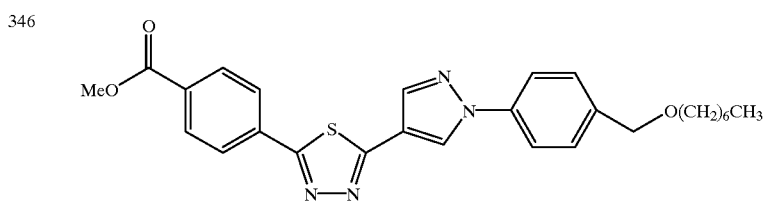 |
| 347 | 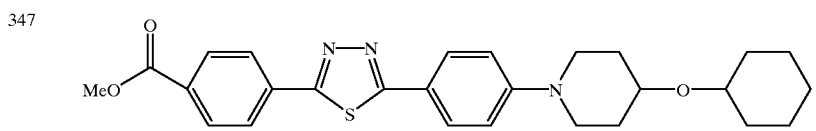 |
| 348 | 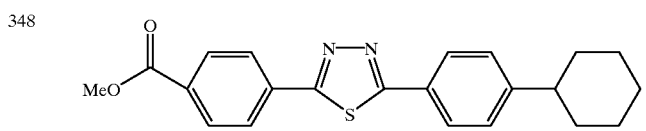 |
| 349 | 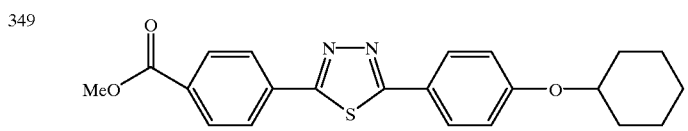 |
| 350 | 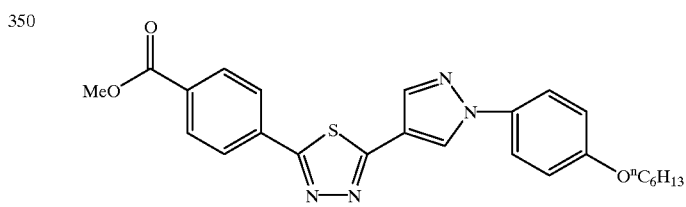 |
| 351 | 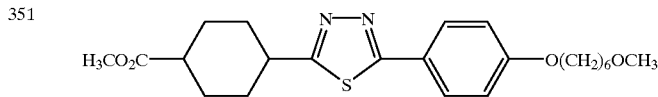 |
| 352 | 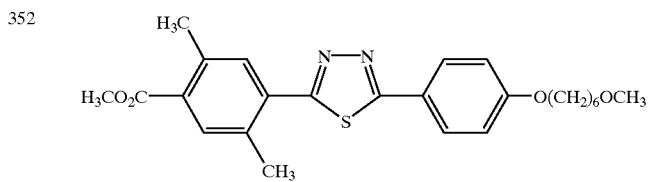 |
| 353 | 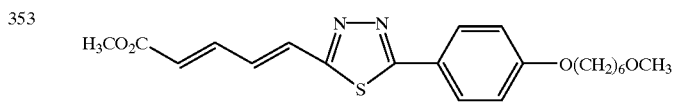 |

| Preparation No. | Formula |
|---|---|
| 354 | 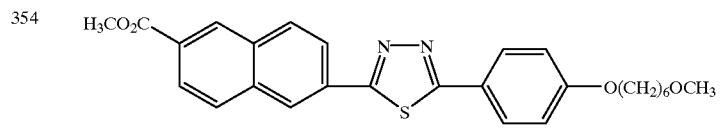 |
| 355 | 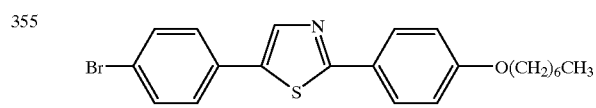 |
| 356 | 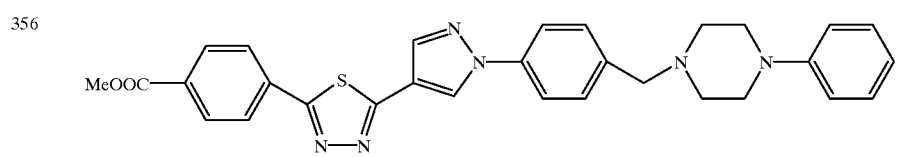 |
| 357 | 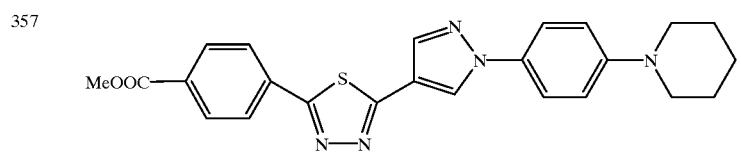 |
| 358 | 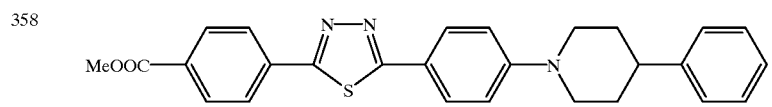 |
| 359 | 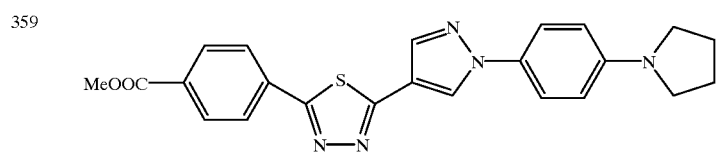 |
| 360 | 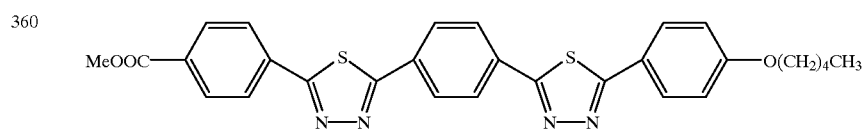 |
| 361 | 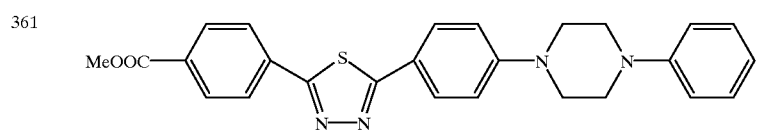 |
| 362 | 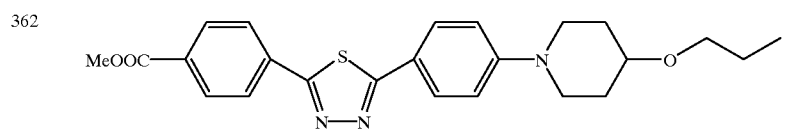 |
| 363 | 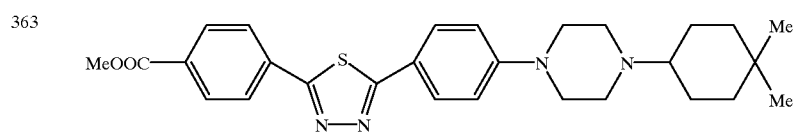 |

-continued
| Preparation No. | Formula |
|---|---|
| 364 | 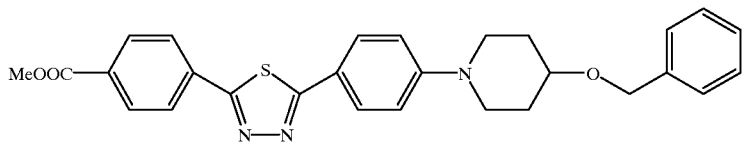 |
| 365 | 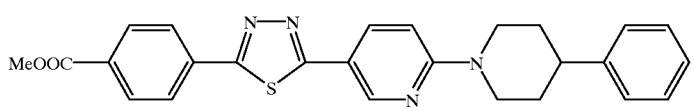 |
| 366 | 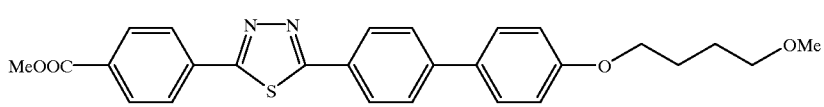 |
| 367 | 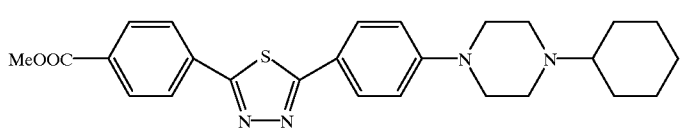 |
| 368 | 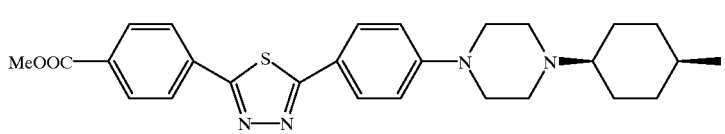 |
| 369 | 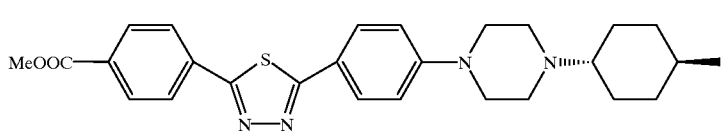 |
| 370 | 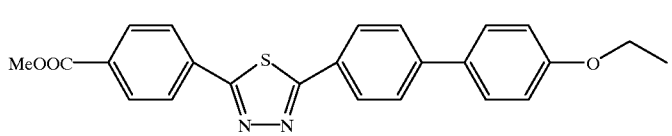 |
| 371 | 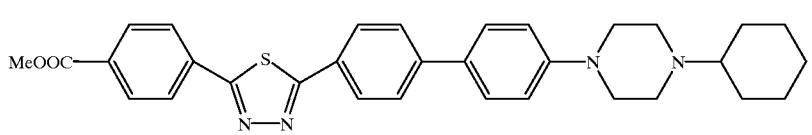 |
| 372 | 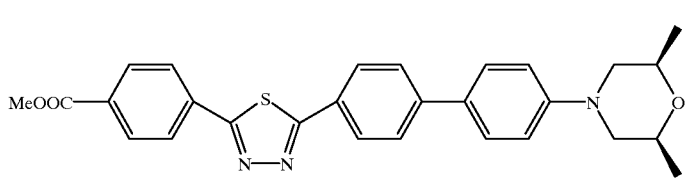 |
| 373 | 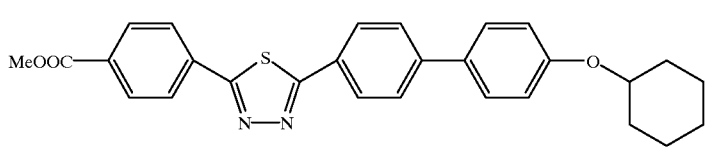 |

-continued
| Preparation No. | Formula |
|---|---|
| 374 | 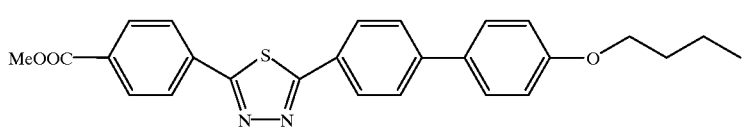 |
| 375 | 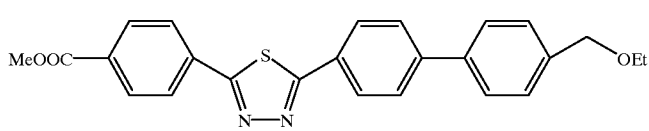 |
| 376 | 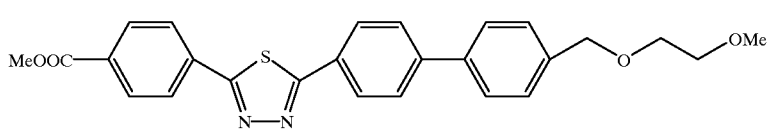 |
| 377 | 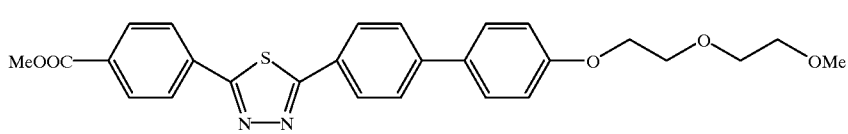 |
| 378 | 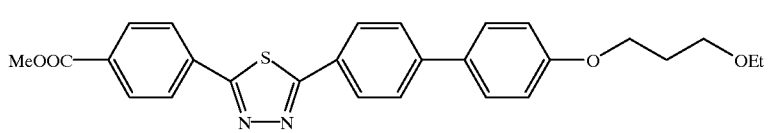 |
| 379 | 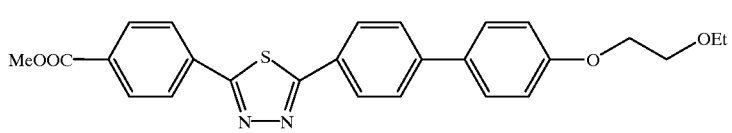 |
| 380 | 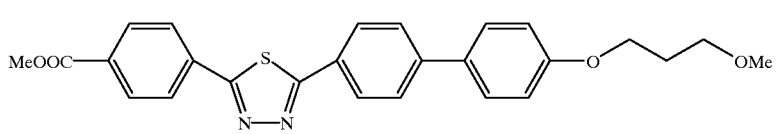 |
| 381 | 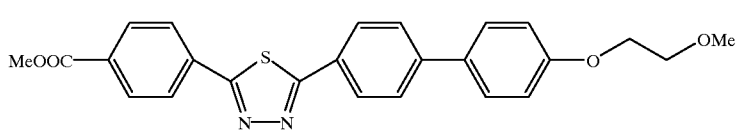 |
| 382 | 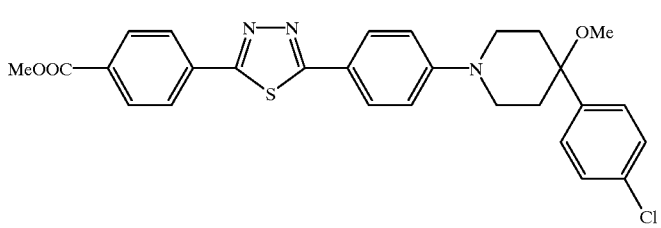 |
| 383 | 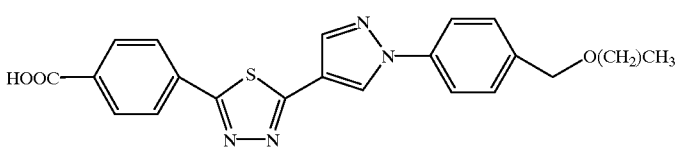 |

| Preparation No. | Formula |
|---|---|
| 384 | 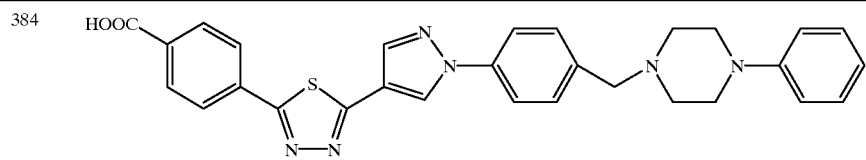 |
| 385 | 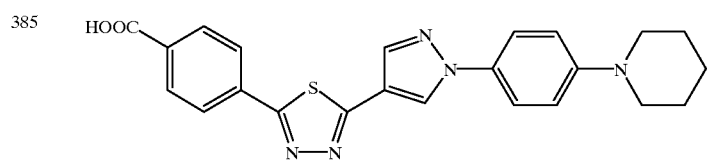 |
| 386 | 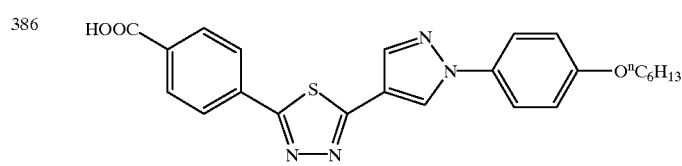 |
| 387 | 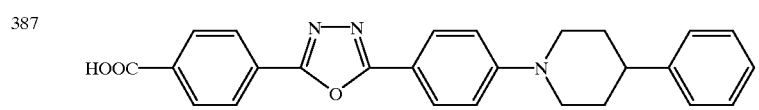 |
| 388 | 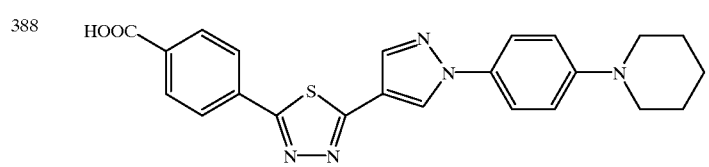 |
| 389 | 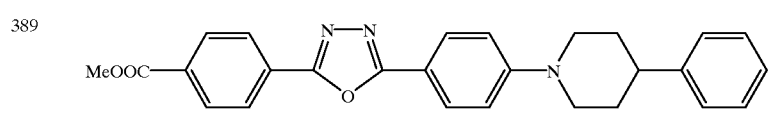 |
| 390 | 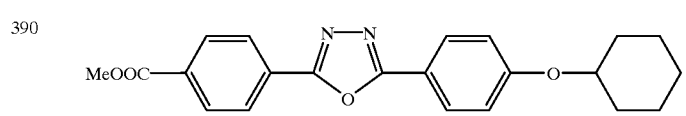 |
| 391 | 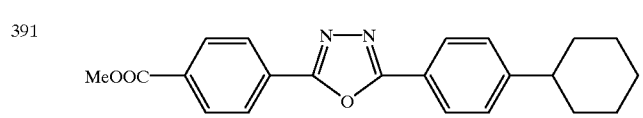 |
| 392 | 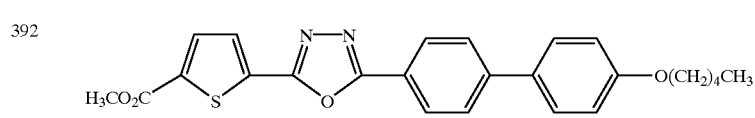 |
| 393 | 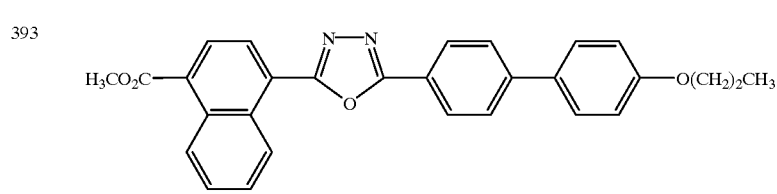 |
| 394 | 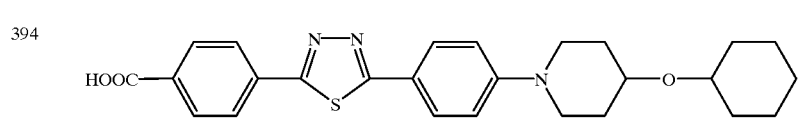 |

-continued
| Preparation No. | Formula |
|---|---|
| 395 | 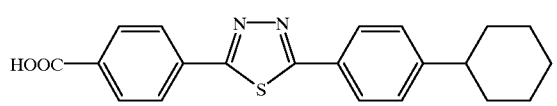 |
| 396 | 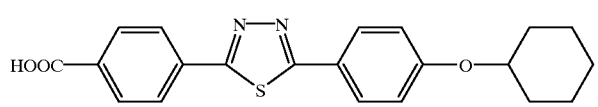 |
| 397 | 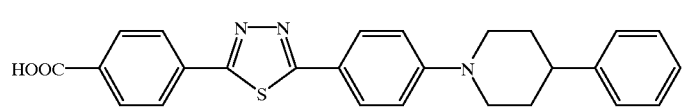 |
| 398 | 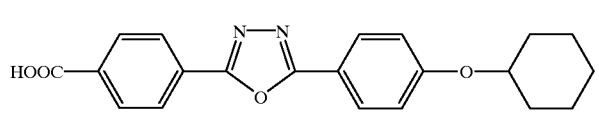 |
| 399 | 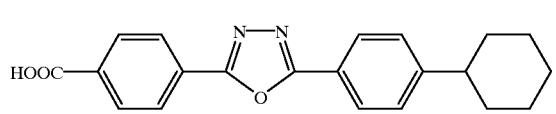 |
| 400 | 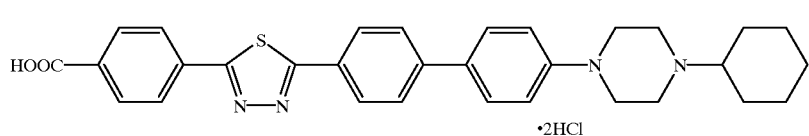 |
| 401 | 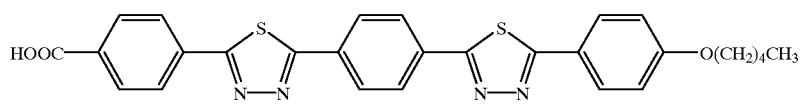 |
| 402 | 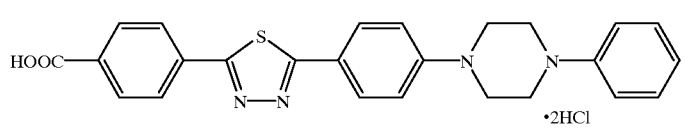 |
| 403 | 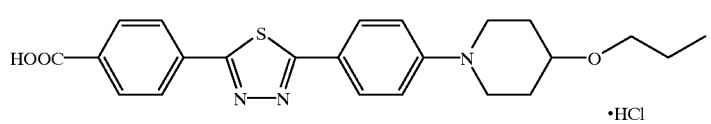 |
| 404 | 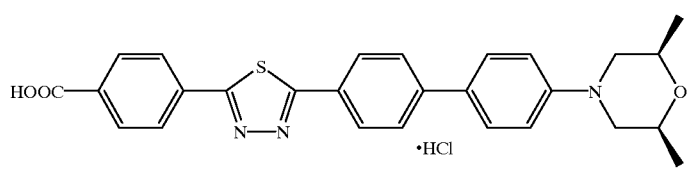 |
| 405 | 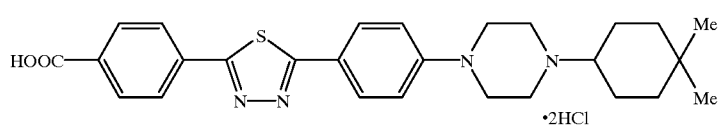 |

-continued
| Preparation No. | Formula |
|---|---|
| 406 | 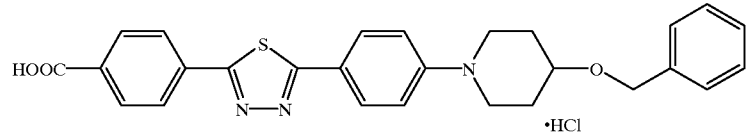 |
| 407 | 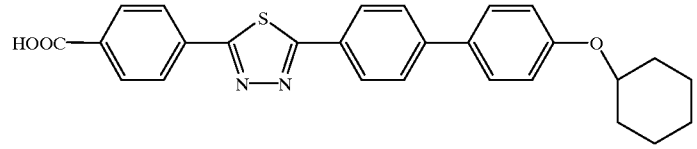 |
| 408 | 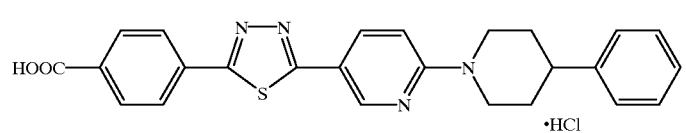 |
| 409 | 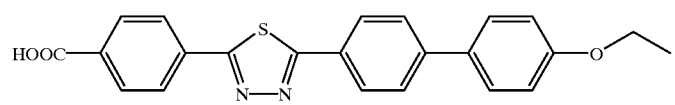 |
| 410 | 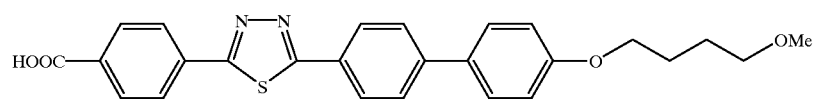 |
| 411 | 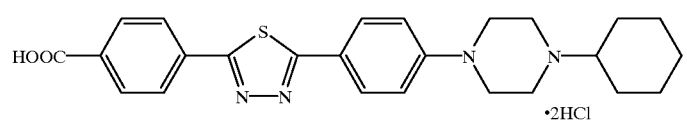 |
| 412 | 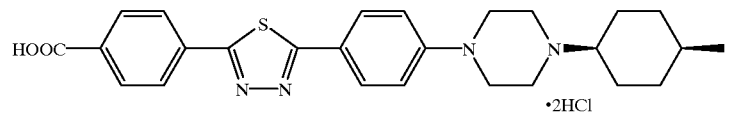 |
| 413 | 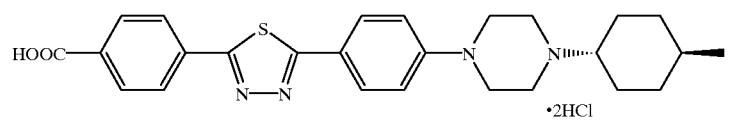 |
| 414 | 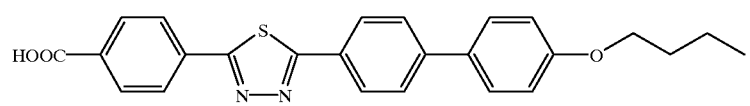 |
| 415 | 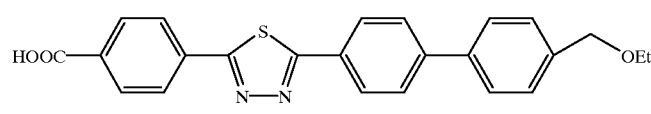 |
| 416 | 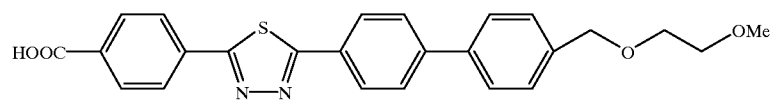 |

-continued

| Preparation No. | Formula |
|---|---|
| 417 | HOOC-C6H4-(thiadiazole)-C6H4-C6H4-O-CH2CH2-O-CH2CH2-OMe |
| 418 | HOOC-C6H4-(thiadiazole)-C6H4-C6H4-O-CH2CH2CH2-OEt |
| 419 | HOOC-C6H4-(thiadiazole)-C6H4-C6H4-O-CH2CH2-OEt |
| 420 | HOOC-C6H4-(thiadiazole)-C6H4-C6H4-O-CH2CH2CH2-OMe |
| 421 | HOOC-C6H4-(thiadiazole)-C6H4-C6H4-O-CH2CH2-OMe |
| 422 | HOOC-C6H4-(thiadiazole)-C6H4-N(piperidine with OMe and 4-chlorophenyl) |
| 423 | HOOC-C6H4-N(piperazine)N-C6H4-C6H4-O(CH2)5OCH3 · HCl |
| 424 | HOOC-C6H4-N(piperazine)N-(indanyl) · HCl |
| 425 | HOOC-(cyclohexyl)-(thiadiazole)-C6H4-O(CH2)6OCH3 |
| 426 | HO2C-(thiophene)-(oxadiazole)-C6H4-C6H4-O(CH2)4CH3 |
| 427 | HO2C-(2,5-dimethylphenyl)-(thiadiazole)-C6H4-O(CH2)6OCH3 |

-continued
| Preparation No. | Formula |
|---|---|
| 428 | 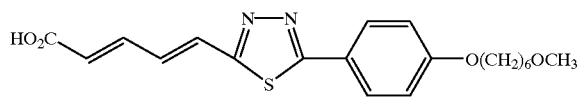 |
| 429 | 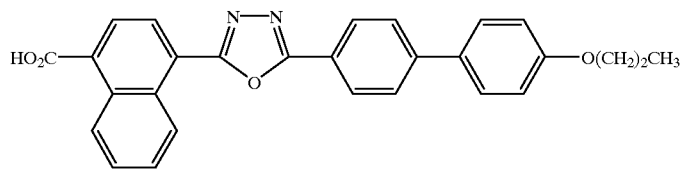 |
| 430 | 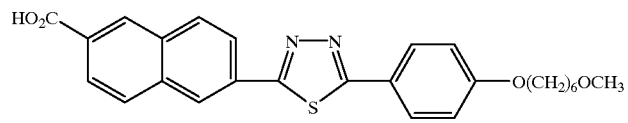 |
| 431 | 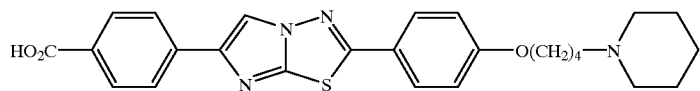 |
| 432 | 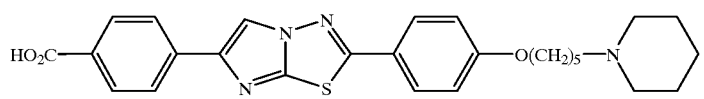 |
| 433 | 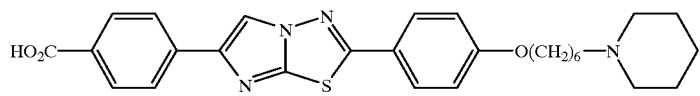 |
| 434 | 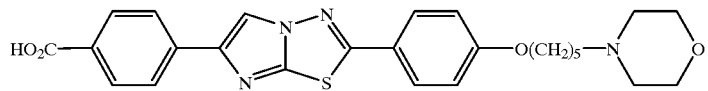 |
| 435 | 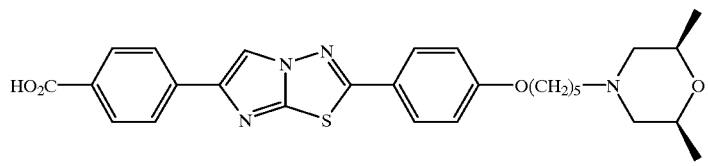 |
| 436 | 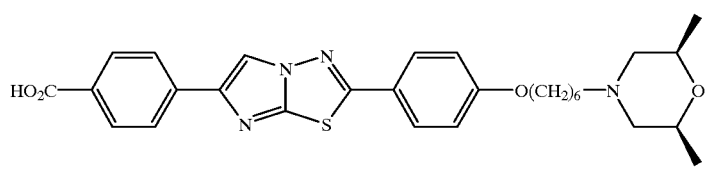 |
| 437 | 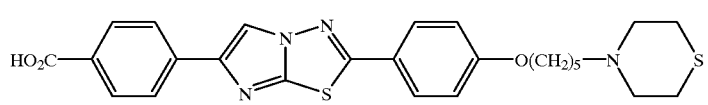 |
| 438 | 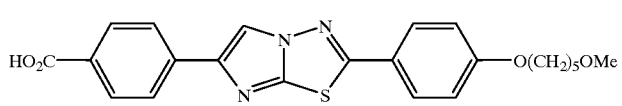 |

| Preparation No. | Formula |
|---|---|
| 439 | 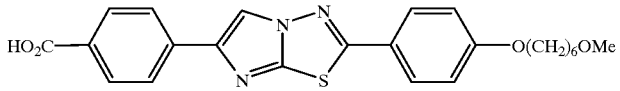 |
| 440 | 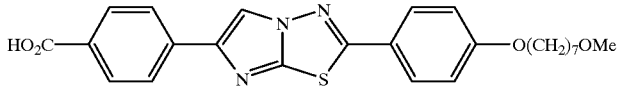 |
| 441 | 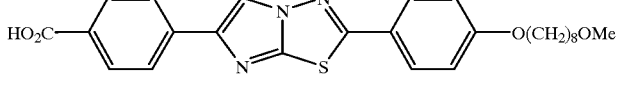 |
| 442 | 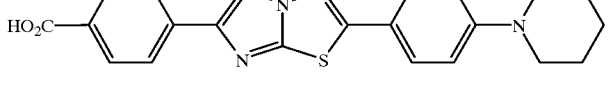 |
| 443 | 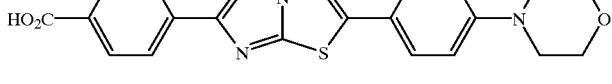 |
| 444 | 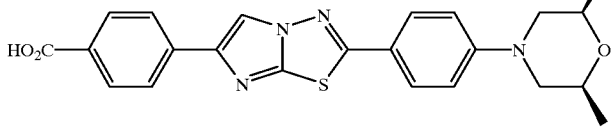 |
| 445 | 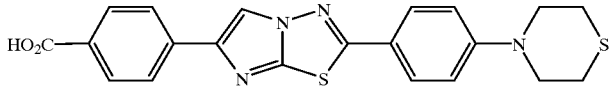 |
| 446 | 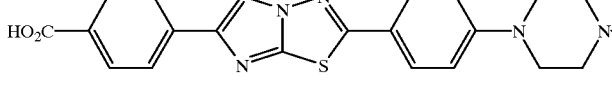 |
| 447 | 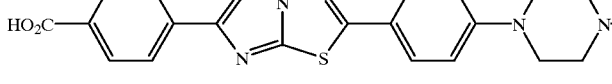 |
| 448 | 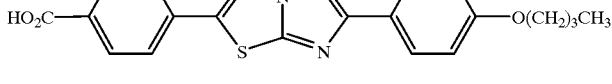 |
| 449 | 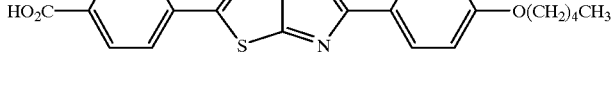 |
| 450 | 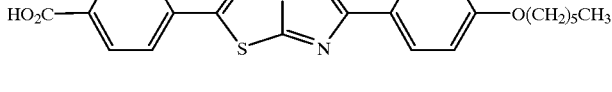 |
| 451 | 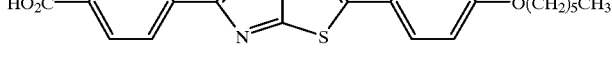 |

| Preparation No. | Formula |
|---|---|
| 452 | 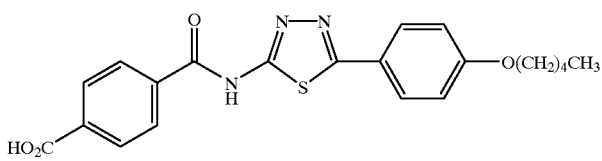 |
| 453 | 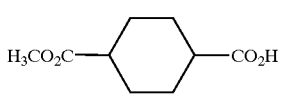 |
| 454 | 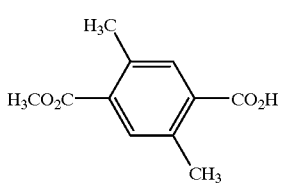 |
| 455 | 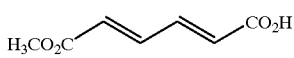 |
| 456 | 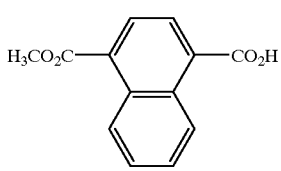 |
| 457 | 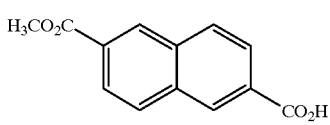 |

The following compounds [Preparations 211 to 253] were obtained in a manner similar to that of Preparation 18.

Preparation 211

NMR (CDCl$_3$, δ): 1.10–1.45 (6H, m), 1.45–2.10 (8H, m), 3.0–3.80 (6H, m), 6.97 (2H, d, J=9.0Hz), 7.40–7.65 (3H, m), 7.90 (2H, d, J=8.9Hz), 8.13 (2H, d, J=8.2Hz), 8.18 (2H, d, J=8.7Hz), 8.39 (2H, d, J=8.6Hz)

APCI MASS: 581 (M$^+$)

Preparation 212

IR (KBr): 3008, 2935, 1792, 1770, 1600 cm$^{-1}$

NMR (CDCl$_3$, δ): 3.97 (3H, s), 7.07 (2H, d, J=8.5Hz), 7.43–7.56 (3H, m), 8.10 (1H, d, J=8.5Hz), 8.23 (2H, d, J=8.5Hz)

MASS (m/z): 270 (M+H$^+$)

Preparation 213

IR (KBr): 1776, 1234, 1095 cm-1

NMR (CDCl$_3$, δ): 0.89 (3H, m), 1.1–2.0 (10H, m), 3.52 (2H, t, J=6.6Hz), 4.57 (2H, s), 7.4–7.6 (4H, m), 7.75 (2H, d, J=8.5Hz), 8.14 (2H, d, J=8.1Hz), 8.22 (1H, s), 8.26 (2H, d, J=8.7Hz), 8.43 (2H, d, J=8.7Hz), 8.59 (1H, s)

MASS (m/z): 594 (M$^+$+1)

Preparation 214

NMR (CDCl$_3$, δ): 1.20–1.60 (5H, m), 1.70–2.05 (5H, m), 2.50–2.75 (1H, m), 7.25–8.50 (12H, m)

ESI MASS (positive): 502.3 (M$^+$+Na)

Preparation 215

NMR (CDCl$_3$, δ): 1.10–2.20 (10H, m), 4.30–4.50 (1H, m), 7.04 (2H, d, J=9.1Hz), 7.40–8.50 (10H, m)

APCI MASS (positive): 518.3 (M$^+$+Na)

Preparation 216

NMR (CDCl$_3$+CD$_3$OD, δ): 1.70–2.15 (4H, m), 2.70–2.90 (1H, m), 2.90–3.20 (2H, m), 4.00–4.15 (2H, m), 7.08 (2H, d, J=9.1Hz), 7.10–7.40 (5H, m), 7.40–7.70 (3H, m), 7.90–8.55 (7H, m)

APCI MASS: 543 (M$^+$1)

Preparation 217

NMR (CDCl$_3$+CD$_3$OD, δ): 1.70–2.10 (4H, m), 2.60–3.15 (3H, m), 3.90–4.15 (2H, m), 6.90–7.15 (2H, m), 7.15–7.40 (6H, m), 7.40–8.45 (9H, m)

Preparation 218

NMR (CDCl$_3$, δ): 1.20–2.15 (10H, m), 4.25–4.50 (1H, m), 7.05 (2H, d, J=6.9Hz), 7.35–7.65 (3H, m), 8.00–8.50 (7H, m)

APCI MASS (positive): 502.2 (M$^+$Na)

Preparation 219

NMR (CDCl$_3$, δ): 1.15–2.00 (10H, m), 2.45–2.75 (1H, m), 7.30–8.50 (12H, m)

APCI MASS (positive): 4.66.2 (M$^+$+1)

Preparation 220

IR (KBr): 2978, 2937, 2873, 1772, 1599, 1498, 1439 cm$^{-1}$

NMR (CDCl$_3$, δ): 1.27 (3H, t, J=7.0Hz), 3.65 (2H, q, J=7.0Hz), 3.84 (2H, t, J=4.8Hz), 4.20 (2H, t, J=4.8Hz), 7.05 (2H, d, J=8.8Hz), 7.40–7.66 (5H, m), 7.60 (2H, d, J=8.8Hz), 7.72 (2H, d, J=8.4Hz), 8.07–8.17 (1H, m), 8.28 (2H, d, J=8.6Hz), 8.43 (2H, d, J=8.7Hz)

MASS (m/z): 564 (M$^+$+1)

Preparation 221

IR (KBr): 1778.0, 1600.6, 1230.4, 1182.2 cm$^{-1}$

NMR (CDCl$_3$, δ): 1.10–1.74 (10H, m), 2.82 (2H, t, J=7.2Hz), 3.33 (3H, s), 3.33–3.65 (10H, m), 6.88–7.02 (4H, m), 7.32–7.58 (5H, m), 8.07–8.18 (3H, m)

Preparation 222

IR (KBr): 1810.8, 1600.6, 1257.4, 1178.3 cm$^{-1}$

NMB (DMSO—d$_6$, δ): 1.30–2.40 (18H, m), 3.21 (3H, s), 3.28–3.35 (2H, m), 4.05 (2H, t, J=6.6Hz), 7.05–7.10 (2H, m), 7.40–8.18 (6H, m)

MASS (m/z): 536 (M+1)

Preparation 223

IR (KBr): 1776.1, 1677.8, 1251.6, 1197.6 cm$^{-1}$

NMR DMSO—d$_6$, δ): 0.91 (3H, t, J=6.9Hz), 1.23–1.55 (4H, m), 1.60–1.90 (2H, m), 4.00–4.10 (2H, m), 7.03–7.09 (2H, m), 7.39–8.17 (12H, m)

MASS (m/z): 552

Preparation 224

IR (KBr): 1795.4, 1606.4, 1442.5, 1259.3, 1220.7 cm$^{-1}$

NMR (DMSO—d$_6$, δ): 1.44–1.95 (8H, m), 2.71 (3H, s), 2.75 (3H, s), 3.35 (3H, s), 3.40 (2H, t, J=6.4Hz), 4.05 (2H, t, J=6.4Hz), 7.02 (2H, d, J=8.8Hz), 7.43–7.64 (3H, m), 7.84 (1H, s), 7.96–8.15 (3H, m), 8.34 (1H, s)

MASS (M+1): 558 (M+1)

Prepration 225

IR (KBr): 1697.1, 1604.5, 1251.6 cm$^{-1}$

NMR (CDCl$_3$, δ): 1.40–2.00 (8H, m), 3.35 (3H, s), 3.40 (2H, t, J=6.4Hz), 4.04 (2H, t, J=6.4Hz), 6.97–7.02 (2H, m), 7.20–8.07 (9H, m), 8.50–8.54 (1H, m)

MASS (M+1): 506 (M+1)

Preparation 226

IR (KBr): 1778.0, 1602.6, 1238.1 cm$^{-1}$

NMR (CDCl$_3$, δ): 1.07 (3H, t, J=7.4Hz), 1.77–1.94 (2H, m), 4.00 (2H, t, J=6.6Hz), 7.00–7.05 (2H, m), 7.46–9.56 (16H, m)

MASS (M+1): 568 (M+1)

Preparation 227

IR (KBr): 1778.0, 1604.5, 1257.4, 1172.5 cm$^{-1}$

NMR (CDCl$_3$, δ): 1.40–1.90 (8H, m), 3.35 (3H, s), 3.41 (2H, t, J=6.3Hz), 4.05 (2H, t, J=6.3Hz), 7.00–7.04 (2H, m), 7.44–9.04 (12H, m)

MASS (m/z: 580 (M+1)

Preparation 228

Ir (KBr): 2956, 2933, 2872, 1776, 1601, 1500, 1438 cm$^{-1}$

NMR (CDCl$_3$, δ): 1.00 (3H, t, J=7.3Hz), 1.40–1.96 (4H, m), 4.04 (2H, t, J=6.5Hz), 7.02 (2H, d, J=8.7Hz), 7.36–7.66 (5H, m), 7.73 (2H, d, J=8.4Hz), 8.00–8.21 (3H, m), 8.28 (2H, d, J=8.6Hz), 8.44 (2H, d, J=8.7Hz)

MASS (m/z): 548 (M$^+$+1)

Preparation 229

IR (KBr): 2870, 1778, 1649, 1601, 1529, 1500, 1471, 1439 cm$^{-1}$

NMR (CDCl$_3$, δ): 1.70–2.00 (4H, m), 3.37 (3H, s), 3.47 (2H, t, J=6.1Hz), 4.06 (2H, t, J=6.1Hz), 7.01 (2H, d, J=8.7Hz), 7.42–7.68 (3H, m), 7.60 (2H, d, J=8.8Hz), 7.72 (2H, d, J=8.5Hz), 8.06–8.20 (1H, m), 8.28 (2H, d, J=8.7Hz), 8.43 (2H, d, J=8.6Hz)

MASS (m/z): 578 (M$^+$+1)

Preparation 230

NMR (CDCl$_3$, δ): 1.29 (3H, t, J=7.0 Hz), 3.60 (2H, q, J=7.0Hz), 4.58 (2H, s), 7.40–7.64 (5H, m), 7.65 (2H, d, J=8.2Hz), 7.76 (2H, d, J=8.4Hz), 8.09–8.20 (3H, m), 8.29 (2H, d, J=8.7Hz), 8.44 (2H, d, J=8.7Hz)

MASS (m/z): 534 (M$^+$+1)

Preparation 231

IR (KBr): 2978, 2937, 2873, 1772, 1599, 1498, 1439 cm$^{-1}$

NMR (CDCl$_3$, δ): 3.42 (3H, m), 3.55–3.74 (4H, m), 4.65 (2H, s), 7.43–7.63 (5H, m), 7.65 (2H, d, J=8.2Hz), 7.76 (2H, d, J=8.5Hz), 8.08–8.17 (3H, m), 8.28 (2H, d, J=8.7Hz), 8.43 (2H, d, J=8.6Hz)

MASS (m/z): 564 (M$^+$+1)

Preparation 232

NMR (CDCl$_3$, δ): 3.41 (3H, s), 3.54–3.68 (2H, m), 3.68–3.80 (2H, m), 3.90 (2H, t, J=4.9Hz), 4.22 (2H, t, J=4.9Hz), 7.04 (2H, d, J=8.8Hz), 7.44–7.68 (3H, m), 7.55 (2H, d, J=9.1Hz), 7.72 (2H, d, J=8.5Hz), 8.05–8.20 (3H, m), 8.27 (2H, d, J=8.6Hz), 8.43 (2H, d, J=8.7Hz)

MASS (m/z): 594 (M$^+$+1)

Preparation 233

IR (KBr): 2976, 2868, 1778, 1601, 1527, 1500, 1471, 1439 cm$^{-1}$

NMR (CDCl$_3$, δ): 1.22 (3H, t, J=7.0Hz), 2.10 (2H, m), 3.52 (2H, q, J=7.0Hz), 3.63 (2H, t, J=6.2Hz), 4.14 (2H, t, J=6.5Hz), 7.03 (2H, d, J=8.8Hz), 7.42–7.66 (5H, m), 7.72 (2H, d, J=8.5Hz), 8.04–8.20 (1H, m), 8.10 (2H, d, J=8.4Hz), 8.28 (2H, d, J=8.6Hz, 8.43 (2H, d, J=8.6Hz)

Preparation 234

IR (KBr): 2926, 2877, 1768, 1601, 1527, 1500, 1439, 1417 cm$^{-1}$

NMR (CDCl$_3$, δ): 2.09 (2H, m), 3.38 (3H, s), 3.59 (2H, t, J=6.1Hz), 4.13 (2H, t, J=6.3Hz), 7.03 (2H, d, J=8.8Hz), 7.44–7.66 (5H, m), 7.72 (2H, d, J=8.5Hz), 8.08–8.18 (3H, m), 8.28 (2H, d, J=8.7Hz), 8.44 (2H, d, J=8.7Hz)

MASS (m/z): 564 (M$^+$1)

Preparation 235

IR (KBr): 1776, 1655, 1601, 1529, 1498, 1439 cm$^{-1}$

NMR (CDCl$_3$, δ): 3.49 (3H, s), 3.80 (2H, m), 4.20 (2H, m), 7.05 (2H, d, J=8.8Hz), 7.40–7.64 (4H, m), 7.72 (2H, d,

J=8.4Hz), 7.98–8.18 (4H, m), 8.28 (2H, d, J=8.6Hz), 8.44 (2H, d, J=8.7Hz)

MASS (m/z): 550 (M$^+$+1)

Preparation 236

IR (KBr): 1776, 1603, 1527, 1497, 1439 cm$^{-1}$

NMR (CDCl$_3$, δ): 1.19–2.14 (10H, m), 4.23–4.40 (1H, m), 7.02 (2H, d, J=8.8Hz), 7.41–7.67 (5H, m), 7.72 (2H, d, J=8.5Hz), 8.02–8.21 (3H, m), 8.28 (2H, d, J=8.7Hz), 8.43 (2H, d, J=8.7Hz)

MASS (m/z): 574 (M$^+$+1)

Preparation 237

IR (KBr): 2929.3, 2856.1, 1774.2, 1602.6, 1253.5 cm$^{-1}$

NMR (CDCl$_3$, δ): 0.80–1.10 (3H, m), 1.10–1.60 (8H, m), 1.60–2.00 (2H, m), 4.03 (2H, t, J=6.5Hz), 6.98 (2H, d, J=8.8Hz), 7.40–7.70 (3H, m), 7.81 (2H, d, J=8.5Hz), 7.93 (2H, d, J=8.8Hz), 8.12 (2H, d, J=8.1Hz), 8.17 (1H, s), 8.31 (2H, d, J=8.5Hz)

APCI MASS (m/z): 513

Preparation 238

IR (KBr): 1776, 1603, 1524, 1441, 1414 cm$^{-1}$

NMR (CDCl$_3$, δ): 1.03–1.43 (5H, m), 1.54–2.14 (5H, m), 2.24–2.50 (1H, m), 2.65–2.86 (4H, m), 3.23–3.47 (4H, m), 6.98 (2H, d, J=8.7Hz), 7.41–7.68 (3H, m), 7.92 (2H, d, J=8.5Hz), 8.13 (1H, d, J=8.2Hz), 8.24 (2H, d, J=8.2Hz), 8.40 (2H, d, J=8.2Hz)

MASS (m/z): 566 (M$^+$+1)

Preparation 239

IR (KBr): 1772, 1574, 1234 cm$^{-1}$

NMR (CDCl$_3$, δ): 2.6–2.75 (4H, m), 3.2–3.3 (4H, m), 3.65 (2H, s), 6.8–7.0 (3H, m), 7.1–7.3 (2H, m), 7.4–7.6 (4H, m), 7.74 (2H, d, J=8.5Hz), 8.14 (2H, d, J=8.1Hz), 8.21 (1H, s), 8.26 (2H, d, J=8.6Hz, 8.43 (2H, d, J=8.6Hz), 8.59 (1H, s)

MASS (m/z): 640 (M$^+$++1)

Preparation 240

IR (KBr): 1780, 1520, 1236, 982 cm$^{-1}$

NMR (CDCl$_3$, δ): 1.5–1.8 (6H, m), 3.42 (4H, t, J=5.6Hz), 7.02 (2H, d, J=9.1Hz), 7.4–7.7 (5H, m), 8.14 (2H, d, J=10.5Hz), 8.25 (2H, d, J=8.6Hz), 8.42 (2H, d, J=8.6Hz), 8.47 (1H, s)

MASS (m/z): 549 (M$^+$+1)

Preparation 241

IR (KBr): 1776, 1571, 1252 cm$^{-1}$

NMR (CDCl$_3$, δ): 0.8–1.0 (3H, m), 1.2–1.8 (8H, m), 4.02 (2H, t, J=6.5Hz), 7.01 (2H, d, J=9.0Hz), 7.4–7.7 (5H, m), 8.1–8.3 (4H, m), 8.43 (2H, d, J=8.6Hz), 8.51 (1H, s)

Preparation 242

IR (KBr): 2927, 2854, 1599, 1531, 1498, 1444 cm$^{-1}$

MASS (m/z): 642 (M$^+$1)

Preparation 243

IR (KBr): 1782, 1597, 1533, 1502, 1444, 1421 cm$^{-1}$

NMR (CDCl$_3$, δ): 1.30 (6H, d, J=6.3Hz), 2.40–2.58 (2H, m), 3.49–3.63 (2H, m), 3.72–3.94 (2H, m), 7.01 (2H, d, J=8.8Hz), 7.42–7.65 (5H, m), 7.73 (2H, d, J=8.5Hz), 8.09 (2H, d, J=8.6Hz), 8.14 (1H, d, J=8.4Hz), 8.28 (2H, d, J=8.6Hz), 8.44 (2H, d, J=8.6Hz)

MASS (m/z): 589 (M$^+$1)

Preparation 244

IR (KBr): 1778, 1603, 1441, 1414 cm$^{-1}$

NMR (CDCl$_3$, δ): 0.92 (6H, s), 1.10–1.84 (8H, m), 2.16–2.35 (1H, m), 2.68–2.87 (4H, m), 3.30–3.46 (4H, m), 6.98 (2H, d, J=9.0Hz), 7.40–7.65 (3H, m), 7.93 (2H, d, J=8.8Hz), 8.13 (1H, d, J=8.1Hz), 8.25 (2H, d, J=8.7Hz), 8.40 (2H, d, J=8.6Hz)

MASS (m/z): 594 (M$^+$1)

Preparation 245

IR (KBr): 1784, 1603, 1520, 1441, 1414 cm$^{-1}$

NMR (CDCl$_3$, δ): 1.66–2.14 (4H, m), 3.07–3.28 (2H, m), 3.56–3.84 (3H, m), 4.60 (2H, s), 6.98 (2H, d, J=9.0Hz), 7.23–7.67 (8H, m), 7.91 (2H, d, J=8.9Hz), 8.13 (1H, d, J=8.2Hz), 8.23 (2H, d, J=8.6Hz), 8.40 (2H, d, J=8.6Hz)

MASS (m/z): 589 (M$^+$1)

Preparation 246

IR (KBr): 1780, 1603, 1522, 1441, 1414 cm$^{-1}$

NMR (CDCl$_3$, δ): 0.95 (3H, d, J=6.9Hz), 1.37–2.15 (9H, m), 2.25–2.44 (1H, m), 2.68–2.92 (4H, m), 3.27–3.50 (4H, m), 6.98 (2H, d, J=9.0Hz), 7.37–7.67 (3H, m), 7.93 (2H, d, J=8.9Hz), 8.08–8.18 (1H, m), 8.24 (2H, d, J=8.6Hz), 8.40 (2H, d, J=8.6Hz)

Preparation 247

IR (KBr): 1778, 1603, 1524, 1441, 1414 cm$^{-1}$

NMR (CDCl$_3$, δ): 0.90 (3H, d, J=6.4Hz), 0.90–1.13 (2H, m), 1.13–2.05 (7H, m), 2.20–2.48 (1H, m), 2.62–2.90 (4H, m), 3.23–3.53 (4H, m), 6.97 (2H, d, J=9.0Hz), 7.38–7.66 (3H, m), 7.92 (2H, d, J=8.8Hz), 8.06–8.17 (1H, m), 8.24 (2H, d, J=8.6Hz), 8.40 (2H, d, J=8.7Hz)

Preparation 248

IR (Nujol): 1782, 1603 cm$^{-1}$

NMR (CDCl$_3$, δ): 1.9–2.3 (4H, m), 3.03 (3H, s), 3.2–3.5 (2H, m), 3.6–3.9 (2H, m), 7.03 (2H, d, J=8.9Hz), 7.36 (4H, s), 7.4–7.7 (3H, m), 7.93 (2H, d, J=8.9Hz), 8.13 (1H, d, J=8.2Hz)

(+)APCI MASS: 623 (M+H)$^+$

Preparation 249

IR (KBr): 2923, 2848, 2823, 1766, 1602, 1515, 1450, 1378, 1259, 1222, 1186, 1153, 1089, 1014, 971 cm$^{-1}$

NMR (CDCl$_3$, δ): 1.2–1.5 (5H, m), 1.6–1.9 (7H, m), 2.07 (2H, m), 2.43 (1H, m), 2.6–2.9 (5H, m), 3.02 (2H, t, J=8.5Hz), 3.26 (4H, m), 4.07 (2H, d, J=13Hz), 6.8–7.1 (4H, m), 7.12 (2H, d, J=8.6Hz), 7.3–7.6 (3H, m), 8.0–8.2 (3H, m)

MASS (m/z): 462 (M+H$^+$)

Preparation 250

IR (KBr): 1780, 1682, 1655, 1601, 1549, 1498, 1429 cm$^{-1}$

NMR (CDCl$_3$, δ): 1.62–1.95 (2H, m), 2.01 (2H, m), 2.70–3.18 (3H, m), 4.64 (2H, s), 6.80 (1H, d, J=9.1Hz), 7.18–7.40 (5H, m), 7.40–7.65 (3H, m), 8.00–8.25 (2H, m), 8.25 (2H, d, J=8.6Hz), 8.41 (2H, d, J=8.6Hz), 8.76 (1H, d, J=2.3Hz)

MASS (m/z): 560 (M$^+$1)

Preparation 251

IR (KBr): 1781.9, 1602.6, 1228.4 cm$^{-1}$

NMR (CDCl$_3$, δ): 1.54–1.87 (6H, m), 3.35 (3H, s), 3.38–3.68 (10H, m), 4.00 (2H, t, J=6.4Hz), 6.93–7.05 (6H, m), 7.39–7.53 (7H, m), 8.08–8.18 (3H, m)

Preparation 252

IR (KBr): 1776.1, 1600.6, 1232.3 cm$^{-1}$

NMR (CDCl3, δ): 2.73–2.78 (4H, m), 2.93–3.73 (9H, m), 6.94–6.98 (2H, m), 7.14–7.58 (7H, m), 8.07–8.15 (3H, m)

MASS (m/z): 440 (M+1)

Preparation 253

IR (KBr): 1778, 1599, 1576, 1527, 1498, 1473, 1439 cm$^{-1}$

NMR (CDCl$_3$, δ): 1.47 (3H, t, J=7.0Hz), 4.11 (2H, q, J=7.0Hz), 7.02 (2H, d, J=8.9Hz), 7.42–7.80 (7H, m), 8.10–8.56 (7H, m)

MASS (m/z): 520 (M$^+$1)

The following compounds [Preparations 254 to 270] were obtained in a manner similar to that of Preparation 46.

Preparation 254

IR (KBr): 1702.2, 1702.8 cm$^{-1}$

NMR (DMSO—d$_6$, δ): 3.83 (3H, s), 8.06 (2H, d, J=8.7Hz), 8.20 (2H, d, J=8.7Hz), 8.24 (1H, s), 9.31 (1H, s), 10.04 (1H, s)

MASS (m/z): 231 (M$^-$+1)

Preparation 255

IR (KBr): 1722, 1562, 1514, 1346, 1279 cm$^{-1}$

NMR (CDCl$_3$, δ): 3.90 (3H, s), 7.92 (2H, d, J=9.2Hz), 8.16 (1H, s), 8.38 (2H, d, J=9.2Hz), 8.86 (1H, s)

MASS (m/z): 246 (M$^+$+1)

Preparation 256

Ir (KBr): 2937, 2856, 2819, 2213, 1608, 1517, 1448, 1384, 1349, 1247, 1224, 1180, 1122 cm$^{-1}$

NMR (CDCl$_3$, δ): 1.66 (6H, m), 3.32 (4H, t, J=5.0Hz), 6.83 (2H, d, J=9.1Hz), 7.46 (2H, d, J=9.1Hz)

MASS (m/z): 187 (M+H$^+$)

Preparation 257

NMR (CDCl$_3$, δ): 3.28 (4H, t, J=4.9Hz), 3.85 (2H, d, J=4.9Hz), 6.87 (2H, d, J=9.0Hz), 7.52 (2H, d, J=9.0Hz)

MASS (m/z): 189 (M+H$^+$)

Preparation 258

NMR (CDCl$_3$, δ): 1.27 (6H, d, J=6.2Hz), 2.52 (2H, t, J=11.5Hz), 3.57 (2H, dd, J=2.2 and J=12.7Hz), 3.6–3.9 (2H, m), 6.85 (2H, d, J=9.0Hz), 7.50 (2H, d, J=9.0Hz)

MASS (m/z): 217 (M+H$^+$)

Preparation 259

NMR (CDCl$_3$, δ): 2.69 (2H, t, J=5.1Hz), 3.77 (2H, t, J=5.1Hz), 6.81 (2H, d, J=9.0Hz), 7.49 (2H, d, J=9.0Hz)

MASS (m/z): 205 (M+H$^+$)

Preparation 260

NMR (CDCl$_3$, δ): 1.13 (3H, t, J=7.2Hz), 2.47 (2H, q, J=7.2Hz), 2.58 (4H, t, J=5.1Hz), 3.35 (4H, t, J=5.1Hz), 7.22 (2H, d, J=8.8Hz), 7.49 (2H, d, J=8.8Hz)

MASS (m/z): 216 (M+H$^+$)

Preparation 261

NMR (CDCl$_3$, δ): 1.36 (3H, t, J=7.1Hz), 1.55–1.75 (2H, m), 1.80–2.10 (4H, m), 3.00–3.15 (2H, m), 3.60–4.00 (3H, m), 4.31 (2H, q, J=7.1Hz), 6.82 (2H, d, J=9.1Hz), 7.90 (2H, d, J=9.1Hz)

APCI MASS (positive): 250.3 (M$^+$+1)

Preparation 262

NMR (CDCl$_3$, δ): 1.37 (3H, t, J=7.1Hz), 1.60–2.10 (4H, m), 2.55–2.80 (1H, m), 2.95 (2H, dt, J=3.1Hz, J=12.3Hz), 3.90–4.05 (2H, m), 4.32 (2H, q, J=7.1Hz), 6.90 (2H, d, J=9.1Hz), 7.10–7.35 (4H, m), 7.93 (2H, d, J=9.1Hz)

APCI MASS: 310.3 (M$^+$+1)

Preparation 263

NMR (DMSO—d$_6$, δ): 1.29 (3H, t, J=7.1Hz), 3.21–3.34 (4H, m), 3.40–3.53 (4H, m), 4.24 (2H, q, J=7.1Hz), 6.81 (1H, t, J=7.2Hz), 7.00 (2H, d, J=7.9Hz), 7.05 (2H, d, J=9.0Hz), 7.25 (2H, t, J=7.9Hz), 7.81 (2H, d, J=8.9Hz)

MASS (m/z): 311 (M$^+$+1)

Preparation 264

NMR (DMSO—d$_6$, δ): 1.28 (3H, t, J=7.1Hz), 1.26–1.54 (2H, m), 1.64–1.90 (2H, m), 2.90–3.16 (2H, m), 3.58–3.84 (3H, m), 4.23 (2H, q, J=7.1Hz), 4.75 (1H, brs), 6.95 (2H, d, J=9.1Hz), 7.76 (2H, d, J=9.0Hz) MASS (m/z): 250 (M$^+$+1)

Preparation 265

IR (KBr): 2939, 2843, 1703, 1601, 1552, 1497, 1439, 1414 cm$^{-1}$

NMR (DMSO—d$_6$, δ): 1.59 (2H, m), 1.87 (2H, m), 2.78–3.15 (3H, m), 3.79 (3H, s), 4.62 (2H, m), 6.92 (1H, d, J=9.1Hz), 7.21 (5H, m), 7.94 (1H, dd, J=9.1 and 2.3Hz), 8.65 (1H, d, J=2.3Hz)

MASS (m/z): 297 (M$^+$1)

Preparation 266

IR (KBr): 1707, 1610, 1516, 1444 cm$^{-1}$

NMR (DMSO—d$_6$, δ): 1.04–1.30 (5H, m), 1.28 (3H, t, J=7.1Hz), 1.47–1.86 (5H, m), 2.16–2.34 (1H, m), 2.52–2.64 (4H, m), 3.19–3.34 (4H, m), 4.23 (2H, q, J=7.1Hz), 6.95 (2H, d, J=9.0Hz), 7.77 (2H, d, J=8.9Hz)

MASS (m/z): 317 (M$^+$+1)

Preparation 267

IR (Nujol): 1699, 1606 cm$^{-1}$

NMR (CDCl$_3$, δ): 1.37 (3H, t, J=7.1Hz), 1.9–2.2 (4H, m), 3.01 (3H, s), 3.2–3.4 (2H, m), 3.6–3.8 (2H, m), 4.33 (2H, q, J=7.1Hz)

(+)APCI MASS: 374 (M+H)$^+$

Preparation 268

IR (KBr): 2927, 2850, 2212, 1602, 1517, 1442, 1394, 1253, 1178, 1143, 927, 823 cm$^{-1}$

NMR (CDCl$_3$, δ): 1.2(5H, m), 1.65 (1H, m), 1.85 (4H, m), 2.30 (1H,m), 2.70 (4H, t, J=5.1Hz), 3.32 (4H, t, J=5.1Hz), 6.85 (2H, d, J=9.0Hz), 7.48 (2H, d, J=9.0Hz)

MASS (m/z): 270 (M+H$^+$)

Preparation 269

Preparation 270

IR (KBr): 1708.6, 1288.2, 1230.4 cm$^{-1}$

NMR (CDCl$_3$, δ): 1.38 (3H, t, J=7.1Hz), 1.50–1.87 (6H, m), 3.34 (3H, s), 3.37–3.53 (10H, m), 4.00 (2H, t, J=6.4Hz), 4.34 (2H, q, J=7.1Hz), 6.90–7.04 (6H, m), 7.45–7.51 (4H, m), 7.94–7.98 (2H, m)

MASS (m/z): 503 (M+1)

The following compounds [Preparations 271 to 279] were obtained in a manner similar to that of Preparation 16.

Preparation 271

IR (KBr): 1724, 1558, 1521, 1257 cm$^{-1}$

NMR (CDCl$_3$, δ): 0.91 (3H, t, J=6.9Hz), 1.3–1.9 (8H, m), 3.87 (3H, s), 3.99 (2H, t, J=6.5Hz), 6.98 (2H, d, J=9.0Hz), 7.58 (2H, d, J=9.0Hz), 8.30 (1H, s), 8.53 (1H, s)

MASS (m/z): 303 (M$^+$+1)

Preparation 272

NMR (CDCl$_3$), δ): 1.44 (3H, t, J=7.0Hz), 4.08 (2H, qt, J=7.0Hz), 6.98 (2H, d, J=8.8Hz), 7.56 (2H, d, J=8.8Hz), 7.62 (2H, d, J=8.6Hz), 8.07 (2H, d, J=8.6Hz)

MASS (m/z): 257 (M$^+$+1)

Preparation 273

IR (KBr): 2947, 2875, 1722, 1603, 1527, 1495, 1435 cm$^{-1}$

NMR (CDCl$_3$, δ): 1.88–2.18 (4H, m), 3.51 (2H, m), 3.93 (3H, s), 4.05 (2H, m), 6.98 (2H, d, J=8.6Hz), 7.50–7.70 (4H, m), 8.08 (2H, d, J=8.2Hz)

MASS (m/z): 363 (M$^+$+1), 365 (M$^+$+3)

Preparation 274

NMR (CDCl$_3$, δ): 3.40 (3H, s), 3.60 (2H, m), 3.73 (2H, m), 3.89 (2H, m), 3.93 (3H, s), 4.20 (2H, m), 7.01 (2H, d, J=8.8Hz), 7.56 (2H, d, J=8.8Hz), 7.62 (2H, d, J=8.6Hz), 8.08 (2H, d, J=8.6Hz)

MASS (m/z): 331 (M$^+$+1)

Preparation 275

NMR (CDCl$_3$, δ): 1.26 (3H, t, J=7.0Hz), 3.62 (2H, q, J=7.0Hz), 3.76–3.87 (2H, m), 3.93 (3H, s), 4.12–4.24 (2H, m), 6.96–7.08 (2H, m), 7.52–7.70 (4H, m), 8.02–8.14 (2H, m)

MASS (m/z): 301 (M$^+$+1)

Preparation 276

IR (KBr): 2949, 2877, 1722, 1695, 1603, 1529, 1497, 1435 cm$^{-1}$

NMR (CDCl$_3$, δ): 3.47 (3H, s), 3.78 (2H, m), 3.93 (3H, s), 4.18 (2H, m), 6.95–7.08 (2H, m), 7.48–7.68 (4H, m), 8.00–8.12 (2H, m)

MASS (m/z): 287 (M$^+$+1)

Preparation 277

IR (KBr): 2954, 2873, 1718, 1610, 1544, 1494, 1471, 1280, 1249, 1110 cm$^{-1}$

MASS (m/z): 408 ((M—TFA)+H$^+$)

Preparation 278

IR (KBr): 2935, 2867, 1720, 1610, 1544, 1494, 1471, 1436, 1405, 1332, 1280, 1249, 1176, 1110 cm$^{-1}$

MASS (m/z): 436 (M+H$^+$)

Preparation 279

IR (KBr): 2950, 2867, 1708, 1608, 1525, 1741, 1409, 1305, 1259, 1274, 1176, 1103 cm$^{-1}$

MASS (m/z): 450 (M+H$^+$)

The following compounds [Preparations 280 to 309] were obtained in a manner similar to that of Preparation 47.

Preparation 280

IR (KBr): 1653, 1626, 1574, 1524 cm$^{-1}$

NMR (DMSO—d$_6$, δ): 0.85 (3H, m), 1.1–1.6 (10H, m), 3.44 (2H, t, J=6.4Hz), 4.42 (2H, brs), 4.48 (2H, s), 7.44 (2H, d, J=8.6Hz), 7.82 (2H, d, J=8.6Hz), 8.12 (1H,s), 8.88 (1H, s), 9.48 (1H, brs)

MASS (m/z): 331 (M$^+$+1)

Preparation 281

IR (KBr): 1657, 1603, 1570, 1516, 1313 cm$^{-1}$

NMR (DMSO—d$_6$, δ): 2.4–2.6 (4H, m), 3.0–3.2 (4H, m), 3.57 (2H, s), 4.41 (2H, d, J=4.3Hz), 6.76 (1H, t, J=7.8Hz), 6.92 (2H, d, J=7.8Hz), 7.20 (2H, t, J=7.8Hz), 7.47 (2H, t, J=8.5Hz), 7.81 (2H, d, J=8.5Hz), 8.12 (1H, s), 8.88 (1H, s), 9.48 (1H, t, J=4.3Hz)

MASS (m/z): 377 (M$^+$+1)

Preparation 282

IR (KBr): 1632, 1562, 1516 cm$^{-1}$

NMR (DMSO—d$_6$, δ): 1.5–1.8 (6H, m), 3.0–3.3 (4H, m), 4.38 (2H, d, J=3.9Hz), 7.03 (2H, d, J=9.1Hz), 8.04 (1H, s), 8.70 (1H, s), 9.41 (1H, brs)

MASS (m/z): 286 (M$^+$1)

Preparation 283

IR (KBr): 1649, 1623, 1522 cm$^{-1}$

NMR (DMSO—d$_6$, δ): 0.8–1.0 (3H, m), 1.2–1.8 (8H, m), 4.00 (2H, t, J=4.0Hz), 4.39 (2H, d, J=4.0Hz), 7.05 (2H, d, J=9.0Hz), 7.72 (2H, d, J=9.0Hz), 8.07 (1H, s), 8.76 (1H, s), 9.44 (1H, t, J=4.0Hz)

MASS (m/z): 303 (M$^+$+1)

Preparation 284

IR (KBr): 1618, 1560, 1525 cm$^{-1}$

NMR (DMSO—d$_6$, δ): 1.9–2.1 (4H, m), 3.1–3.3 (4H, m), 4.38 (2H, brs), 6.62 (2H, d, J=9.0Hz), 7.58 (2H, d, J=9.0Hz), 8.02 (1H, s), 8.64 (1H, s), 9.40 (1H, brs)

MASS (m/z): 294 (M$^+$+23)

Preparation 285

NMR (CDCl$_3$, δ): 1.10–1.40 (5H, m), 1.40–2.10 (10H, m), 2.90–3.15 (2H, m), 3.25–3.50 (1H, m), 3.50–3.75 (3H, m), 4.05 (2H, d, J=3.9Hz), 6.88 (2H, d, J=9.0Hz), 7.63 (2H, dd, J=9.0 and 2.0 Hz)

APCI MASS (positive): 318.3 (M$^+$+1)

Preparation 286

NMR (CDCl$_3$, δ): 1.70–2.10 (4H, m), 2.60–2.85 (1H, m), 2.85–3.05 (2H, m), 3.05–3.50 (2H, m), 3.85–4.10 (2H, m), 6.85–7.00 (2H, m), 7.10–7.40 (5H, m), 7.68 (2H, d, J=8.8Hz)

APCI MASS: 296 (M$^+$+1)

Preparation 287

NMR (CDCl$_3$, δ): 1.20–2.10 (10H, m), 4.10 (2H, brs), 4.20–4.40 (1H, m), 6.91 (2H, d, J=8.9Hz), 7.49 (1H, brs), 7.78 (2H, d, J=8.9Hz)

ESI MASS: 257.3 (M$^+$+Na)

Preparation 288

NMR (CDCl$_3$, δ): 1.10–1.55 (5H, m), 1.60–2.00 (5H, m), 2.40–2.65 (1H, m), 7.25 (2H, d, J=8.2Hz), 7.67 (2H, d, J=8.2Hz)

APCI MASS: 219 (M$^+$+1)

Preparation 289

IR (KBr): 2958, 2929, 2850, 2821, 1651, 1628, 1603, 1529, 1487, 1443 cm$^{-1}$

NMR (DMSO—d$_6$, δ): 1.00–1.36 (5H, m), 1.50–1.92 (5H, m), 2.16–2.38 (1H, m), 2.57–2.64 (4H, m), 3.10–3.28 (4H, m), 4.48 (2H, s), 7.01 (2H, d, J=8.9Hz), 7.59 (2H, d, J=8.8Hz), 7.67 (2H, d, J=8.5Hz), 7.86 (2H, d, J=8.4Hz), 9.76 (1H, s)

MASS (m/z): 379 (M$^+$+1)

Preparation 290

NMR (DMSO—d$_6$, δ): 3.13–3.54 (8H, m), 4.38 (2H, s), 6.81 (1H, t, J=7.2Hz), 7.00 (2H, d, J=6.9Hz), 7.01 (2H, d, J=8.8Hz), 7.24 (2H, t, J=7.9Hz), 7.74 (2H, d, J=8.8Hz), 9.51 (1H, s)

MASS (m/z): 297 (M$^+$+1)

Preparation 291

NMR (DMSO—d$_6$, δ): 0.87 (3H, t, J=7.4Hz), 1.37–1.60 (4H, m), 1.80–1.98 (2H, m), 2.90–3.10 (2H, m), 3.38 (2H, t, J=6.6Hz), 3.38–3.70 (3H, m), 4.34 and 4.35 (2H, s), 6.92 (2H, d, J=9.0Hz), 7.68 (2H, d, J=8.9Hz), 9.45 (1H, brs)

MASS (m/z): 278 (M$^+$+1)

Preparation 292

IR (KBr): 1666, 1605, 1545, 1495, 1448 cm$^{-1}$

NMR (DMSO—d$_6$, δ): 1.17 (6H, d, J=6.1Hz), 2.20–2.38 (2H, m), 3.59–3.78 (4H, m), 4.49 (2H, s), 7.03 (2H, d J=8.9Hz), 7.61 (2H, d, J=8.8Hz), 7.69 (2H, d, J=8.5Hz), 7.87 (2H, d, J=8.4Hz), 9.77 (1H,—s)

MASS (m/z): 326 (M$^+$+1)

Preparation 293

NMR (DMSO—d$_6$, δ): 0.88 (6H, s), 1.05–1.52 (6H, m), 1.52–1.73 (2H, m), 2.08–2.26 (1H, m), 2.52–2.72 (4H, m), 3.10–3.31 (4H, m), 4.36 (2H, s), 6.91 (2H, d, J=8.9Hz), 7.69 (2H, d, J=8.8Hz), 9.46 (1H, s)

MASS (m/z): 331 (M$^+$+1)

Preparation 294

IR (KBr): 1637, 1606, 1554, 1508, 1456 cm$^{-1}$

NMR (DMSO—d$_6$, δ): 1.46–1.70 (2H, m), 1.87–2.06 (2H, m), 2.92–3.12 (2H, m), 3.52–3.73 (3H, m), 4.35 (2H, s), 4.54 (2H, s), 6.94 (2H, d, J=8.9Hz), 7.20–7.42 (5H, m), 7.69 (2H, d, J=8.8Hz), 9.45 (1H, s)

MASS (m/z): 326 (M$^+$+1)

Preparation 295

NMR (DMSO—d$_6$, δ): 1.16–2.04 (10H, m), 4.29–4.51 (1H, m), 4.51 (2H, s), 7.03 (2H, d, J=8.8Hz), 7.64 (2H, d, J=8.8Hz), 7.69 (2H, d, J=8.4Hz), 7.88 (2H, d, J=8.4 Hz), 9.79 (1H, s)

MASS (m/z): 311 (M$^+$+1)

Preparation 296

IR (KBr): 2912, 2870, 2846, 1608, 1597, 1533, 1493, 1423 cm$^{-1}$

NMR (CDCl$_3$, δ): 1.74 (2H, m), 1.97 (2H, m), 2.70–3.12 (3H, m), 3.31 (2H, brs), 4.58 (2H, m), 6.69 (1H, d, J=9.0 Hz), 7.05–7.55 (6H, m), 7.88 (1H, dd, J=9.0 and 2.3 Hz), 8.56 (1H, d, J=2.3 Hz)

MASS (m/z): 297 (M$^+$+1)

Preparation 297

NMR (DMSO-d$_6$, δ): 1.35 (3H, t, J=7.0 Hz), 4.07 (2H, q, J=7.0 Hz), 4.50 (2H, s), 7.02 (2H, d, J=8.8 Hz), 7.66 (2H, d, J=8.7 Hz), 7.70 (2H, d, J=8.4 Hz), 7.89 (2H, d, J=8.4 Hz), 9.79 (1H, s)

MASS (m/z): 257 (M$^+$+1)

Preparation 298

IR (KBr): 2956, 2916, 2870, 1612, 1535, 1514, 1493 cm$^{-1}$

NMR (DMSO-d$_6$, δ): 1.55–1.87 (4H, m), 3.24 (3H, s), 3.38 (2H, t, J=6.2 Hz), 4.03 (2H, t, J=6.1 Hz), 4.57 (2H, brs), 7.03 (2H, d, J=8.7 Hz), 7.58–7.78 (4H, m), 7.89 (2H, d, J=8.3 Hz), 9.79 (1H, s)

MASS (m/z): 315 (M$^+$+1)

Preparation 299

IR (KBr): 1626, 1606, 1566, 1524, 1498, 1454 cm$^{-1}$

NMR (DMSO-d$_6$, δ): 1.00–1.35 (5H, m), 1.35–1.90 (5H, m), 2.16–2.36 (1H, m), 2.54–2.69 (4H, m), 3.12–3.28 (4H, m), 4.35 (2H, s), 6.91 (2H, d, J=8.9 Hz), 7.69 (2H, d, J=8.8 Hz), 9.46 (1H, s)

MASS (m/z): 303 (M$^+$+1)

Preparation 300

IR (KBr): 1659, 1626, 1606, 1531, 1498, 1446 cm$^{-1}$

NMR (DMSO-d$_6$, δ): 0.89 (3H, d, J=6.8 Hz), 1.32–1.80 (9H, m), 2.10–2.26 (1H, m), 2.50–2.65 (4H, m), 3.15–3.30 (4H, m), 4.36 (2H, s), 6.92 (2H, d, J=9.0 Hz), 7.69 (2H, d, J=8.8 Hz), 9.46 (1H, s)

MASS (m/z): 317 (M$^+$+1)

Preparation 301

IR (KBr): 1660, 1606, 1549, 1506, 1446 cm$^{-1}$

NMR (DMSO-d$_6$, δ): 0.86 (3H, d, J=6.4 Hz), 0.84–1.05 (2H, m), 1.05–1.54 (3H, m), 1.60–1.90 (4H, m), 2.12–2.33 (1H, m), 2.54–2.65 (4H, m), 3.11–3.27 (4H, m), 4.36 (2H, s), 6.91 (2H, d, J=8.9 Hz), 7.69 (2H, d, J=8.8 Hz), 9.46 (1H, s)

MASS (m/z): 317 (M$^+$+1)

Preparation 302

NMR (DMSO-d$_6$, δ): 1.17 (3H, t, J=7.0 Hz), 3.51 (2H, q, J=7.0 Hz), 4.50 (2H, m), 4.52 (2H, s), 7.42 (2H, d, J=8.2 Hz), 7.66–7.80 (4H, m), 7.92 (2H, d, J=8.9 Hz), 9.83 (1H, s)

MASS (m/z): 301 (M$^+$+1)

Preparation 303

NMR (DMSO-d$_6$, δ): 3.27 (3H, m), 3.45–3.68 (4H, m), 4.54 (4H, s), 7.43 (2H, d, J=8.2 Hz), 7.66–7.81 (4H, m), 7.92 (2H, d, J=8.4 Hz), 9.83 (1H, s)

MASS (m/z): 301 (M$^+$+1)

Preparation 304

NMR (DMSO-d$_6$, δ): 3.25 (3H, s), 3.44–3.55 (2H, m), 3.55–3.65 (2H, m), 3.73–3.86 (2H, m), 4.08–4.20 (2H, m), 4.52 (2H, s), 7.05 (2H, d, J=8.8 Hz), 7.67 (2H, d, J=8.7 Hz), 7.70 (2H, d, J=8.4 Hz), 7.89 (2H, d, J=8.5 Hz), 9.80 (1H, s)

MASS (m/z): 331 (M$^+$+1)

Preparation 305

NMR (DMSO-d$_6$, δ): 1.11 (3H, t, J=7.0 Hz), 1.96 (2H, m), 3.43 (2H, q, J=7.0 Hz), 3.52 (2H, t, J=6.4 Hz), 4.07 (2H, t, J=6.4 Hz), 4.50 (2H, s), 7.03 (2H, d, J=8.8 Hz), 7.66 (2H, d, J=8.7 Hz), 7.70 (2H, d, J=8.5 Hz), 7.89 (2H, d, J=8.4 Hz), 9.79 (1H, s)

MASS (m/z): 315 (M$^+$+1)

Preparation 306

NMR (DMSO-d$_6$, δ): 1.14 (3H, t, J=7.0 Hz), 3.51 (2H, q, J=7.0 Hz), 3.66–3.80 (2H, m), 4.07–4.20 (2H, m), 4.51 (2H, s), 7.05 (2H, d, J=8.8 Hz), 7.67 (2H, d, J=8.8 Hz), 7.70 (2H, d, J=8.4 Hz), 7.89 (2H, d, J=8.4 Hz), 9.79 (1H, s)

MASS (m/z): 301 (M$^+$+1)

Preparation 307

IR (KBr): 2933, 2873, 1608, 1531, 1491 cm$^{-1}$

NMR (DMSO-d$_6$, δ): 1.97 (2H, m), 3.26 (3H, s), 3.49 (2H, t, J=6.3 Hz), 4.07 (2H, t, J=6.4 Hz), 4.50 (2H, brs), 7.03 (2H, d, J=8.8 Hz), 7.66 (2H, d, J=8.7 Hz), 7.70 (2H, d, J=8.5 Hz), 7.88 (2H, d, J=8.4 Hz), 9.79 (1H, s)

MASS (m/z): 301 (M$^+$+1)

Preparation 308

IR (KBr): 2927, 2881, 1630, 1606, 1533, 1489 cm$^{-1}$

NMR (DMSO-d$_6$, δ): 3.32 (3H, s), 3.67 (2H, m), 4.14 (3H, s), 4.52 (2H, s), 7.05 (2H, d, J=8.8 Hz), 7.67 (2H, d, J=8.8 Hz), 7.70 (2H, d, J=8.6 Hz), 7.89 (2H, d, J=8.4 Hz), 9.79 (1H, s)

MASS (m/z): 287 (M$^+$+b)

Preparation 309

IR (Nujol): 3292, 1603 cm$^{-1}$

NMR (DMSO-d$_6$, δ): 1.8–2.2 (4H, m), 2.92 (3H, s), 3.0–3.2 (2H, m), 3.6–3.8 (2H, m), 4.36 (2H, s), 6.98 (2H, d, J=8.8 Hz), 7.44 (4H, s), 7.71 (2H, d, J=8.8 Hz), 9.46 (1H, s)

(+)APCI MASS: 360 (M+H)$^+$

The following compounds [Preparations 310 to 345] were obtained in a manner similar to that of Preparation 7.

Preparation 310

IR (KBr): 1724, 1282 cm$^{-1}$

NMR (DMSO-d$_6$, δ): 0.86 (3H, t, J=6.9 Hz), 1.1–1.6 (10H, m), 3.45 (2H, t, J=6.4 Hz), 3.90 (3H, s), 4.50 (2H, s), 7.48 (2H, d, J=8.6 Hz), 7.86 (2H, d, J=8.6 Hz), 8.04 (2H, d, J=8.7 Hz), 8.11 (2H, d, J=8.7 Hz), 8.26 (1H, s), 9.02 (1H, s), 10.37 (1H, s), 10.70 (1H, s)

MASS (m/z): 493 (M$^+$+1)

Preparation 311

IR (KBr): 1718, 1614, 1279 cm$^{-1}$

NMR (DMSO-d$_6$, δ): 2.4–2.6 (4H, m), 3.0–3.2 (4H, m), 3.59 (2H, s), 3.90 (3H, s), 6.77 (1H, t, J=7.7 Hz), 6.92 (2H, d, J=7.7 Hz), 7.20 (2H, t, J=7.7 Hz), 7.50 (2H, t, J=8.5 Hz), 7.86 (2H, d, J=8.5 Hz), 8.04 (2H, t, J=8.6 Hz), 8.11 (2H, d, J=8.6 Hz), 8.26 (1H, s), 9.02 (1H, s), 10.37 (1H, s), 10.70 (1H, s)

MASS (m/z): 539 (M$^+$+1)

Preparation 312

NMR (DMSO-d$_6$, δ): 1.10–2.00 (14H, m), 2.95–3.15 (2H, m), 3.40–3.75 (4H, m), 3.90 (3H, s), 7.00 (2H, d, J=8.9 Hz), 7.80 (2H, d, J=8.8 Hz), 8.03 (2H, d, J=8.7 Hz), 8.10 (2H, d, J=8.7 Hz), 10.25 (1H, s), 10.58 (1H, s)

APCI MASS (positive): 480.3 (M$^+$+1)

Preparation 313

IR (KBr): 1724, 1635, 1570, 1520, 1279 cm$^{-1}$

NMR (DMSO-d$_6$, δ): 1.5–1.7 (6H, m), 3.1–3.3 (4H, m), 3.90 (3H, s), 7.05 (2H, d, J=9.1 Hz), 7.66 (2H, d, J=9.1 Hz), 8.04 (2H, d, J=8.7 Hz), 8.11 (2H, d, J=8.7 Hz), 8.85 (1H, s), 10.30 (1H, s), 10.68 (1H, s)

MASS (m/z): 448 (M$^+$+1)

Preparation 314

IR (KBr): 1716, 1603, 1552, 1521, 1470, 1284, 1257 cm$^{-1}$

NMR (DMSO-d$_6$, δ): 0.89 (3H, t, J=6.8 Hz), 1.2–1.8 (8H, m), 3.90 (3H, s), 4.02 (2H, t, J=6.4 Hz), 7.08 (2H, d, J=9.0 Hz), 7.77 (2H, d, J=9.0 Hz), 8.04 (2H, d, J=8.7 Hz), 8.11 (2H, d, J=8.7 Hz), 8.91 (1H, s), 10.33 (1H, s), 10.69 (1H, s)

MASS (m/z): 465 (M$^+$+1)

Preparation 315

NMR (DMSO-d$_6$, δ): 1.60–1.95 (4H, m), 2.65–3.00 (3H, m), 3.90 (3H, s), 4.04 (2H, m), 7.05 (2H, d, J=8.9 Hz), 7.10–7.40 (5H, m), 7.83 (2H, d, J=8.9 Hz), 8.00–8.15 (4H, m), 10.27 (1H, s), 10.59 (1H, s)

APCI MASS: 458 (M$^+$)

Preparation 316

IR (KBr): 1720, 1645, 1560, 1525, 1281 cm$^{-1}$

NMR (DMSO-d$_6$, δ): 1.9–2.1 (4H, m), 3.2–3.4 (4H, m), 3.90 (3H, s), 6.64 (2H, d, J=9.0 Hz), 7.63 (2H, d, J=9.0 Hz), 8.04 (2H, d, J=8.7 Hz), 8.11 (2H, d, J=8.7 Hz), 8.15 (1H, s), 8.78 (1H, s), 10.28 (1H, s), 10.67 (1H, s)

MASS (m/z): 456 (M$^+$+23)

Preparation 317

NMR (DMSO-d$_6$, δ): 1.10–2.10 (10H, m), 3.90 (3H, s), 4.35–4.55 (1H, m), 7.04 (2H, d, J=8.8 Hz), 7.88 (2H, d, J=8.8 Hz), 8.00–8.15 (4H, m), 10.41 (1H, s), 10.64 (1H, s)

APCI MASS (m/z): 397 (M$^+$+1)

Preparation 318

NMR (DMSO-d$_6$, δ): 1.15–1.60 (5H, m), 1.60–1.90 (5H, m), 2.50–2.70 (1H, m), 3.90 (3H, s), 7.37 (2H, d, J=8.3 Hz), 7.85 (2H, d, J=8.2 Hz), 8.00–8.15 (4H, m), 10.48 (1H, s), 10.68 (1H, s)

APCI MASS: 381 (M$^+$+1)

Preparation 319

IR (KBr): 2927, 2852, 1722, 1684, 1645, 1603, 1495, 1446 cm$^{-1}$

NMR (DMSO-d$_6$, δ): 1.00–1.36 (5H, m), 1.51–1.91 (5H, m), 2.20–2.38 (1H, m), 2.56–2.72 (4H, m), 3.12–3.28 (4H, m), 3.90 (3H, s), 7.03 (2H, d, J=8.9 Hz), 7.64 (2H, d, J=8.7 Hz), 7.77 (2H, d, J=8.5 Hz), 7.97 (2H, d, J=8.4 Hz), 8.00–8.16 (4H, m), 10.57 (1H, s), 10.71 (1H, s)

MASS (m/z): 541 (M$^+$+1)

Preparation 320

NMR (DMSO-d$_6$, δ): 3.21–3.54 (8H, m), 3.90 (3H, s), 6.82 (1H, t, J=7.2 Hz), 7.01 (2H, d, J=7.9 Hz), 7.08 (2H, d, J=8.9 Hz), 7.25 (2H, t, J=7.9 Hz), 7.85 (2H, d, J=8.8 Hz), 8.04 (2H, d, J=8.6 Hz), 8.09 (2H, d, J=8.6 Hz), 10.31 (1H, s), 10.60 (1H, s)

MASS (m/z): 459 (M$^+$+1)

Preparation 321

NMR (DMSO-d$_6$, δ): 0.88 (3H, t, J=7.4 Hz), 1.41–1.63 (4H, m), 1.84–2.01 (2H, m), 2.96–3.16 (2H, m), 3.40 (2H, t, J=6.6 Hz), 3.40–3.76 (3H, m), 3.90 (3H, s), 7.00 (2H, d, J=8.9 Hz), 7.80 (2H, d, J=8.8 Hz), 8.00–8.16 (4H, m), 10.25 (1H, s), 10.58 (1H, s)

MASS (m/z): 440 (M$^+$+1)

Preparation 322

NMR (DMSO-d$_6$, δ): 1.18 (6H, d, J=6.1 Hz), 2.18–2.43 (2H, m), 3.51–3.83 (4H, m), 3.90 (3H, s), 7.06 (2H, d, J=8.9 Hz), 7.66 (2H, d, J=8.7 Hz), 7.78 (2H, d, J=8.4 Hz), 7.98 (2H, J=8.4 Hz), 7.98–8.16 (4H, m), 10.58 (1H, s), 10.71 (1H, s)

MASS (m/z): 488 (M$^+$+1)

Preparation 323

NMR (DMSO-$d_6$, δ): 0.89 (6H, s), 1.05–1.72 (8H, m), 2.09–2.30 (1H, m), 2.54–2.73 (4H, m), 3.14–3.37 (4H, m), 3.90 (3H, s), 6.99 (2H, d, J=8.9 Hz), 7.81 (2H, d, J=8.8 Hz), 8.03 (2H, d, J=8.6 Hz), 8.09 (2H, d, J=8.7 Hz), 10.26 (1H, s), 10.58 (1H, s)

MASS (m/z): 493 ($M^+$+1)

Preparation 324

IR (KBr): 1714, 1687, 1653, 1605, 1560, 1522, 1460, 1439 cm$^{-1}$

NMR (DMSO-$d_6$, δ): 1.45–1.70 (2H, m), 1.87–2.10 (2H, m), 2.98–3.20 (2H, m), 3.56–3.78 (3H, m), 3.90 (3H, s), 4.56 (2H, m), 3.56–3.78 (3H, m), 3.90 (3H, s), 4.56 (2H, s), 7.01 (2H, d, J=9.0 Hz), 7.21–7.46 (5H, m), 7.80 (2H, d, J=8.8 Hz), 8.04 (2H, d, J=8.7 Hz), 8.09 (2H, d, J=8.7 Hz), 10.26 (1H, s), 10.58 (1H, s)

MASS (m/z): 488 ($M^+$+1)

Preparation 325

NMR (DMSO-$d_6$, δ): 1.18–2.05 (10H, m), 3.90 (3H, s), 4.34–4.50 (1H, m), 7.05 (2H, d, J=8.8 Hz), 7.69 (2H, d, J=8.7 Hz), 7.78 (2H, d, J=8.4 Hz), 8.00 (2H, d, J=8.4 Hz), 8.06 (2H, d, J=8.6 Hz), 8.11 (2H, d, J=8.6 Hz), 10.60 (1H, s), 10.72 (1H, s)

MASS (m/z): 473 ($M^+$+1)

Preparation 326

IR (KBr): 2945, 2852, 1720, 1693, 1645, 1601, 1524, 1485 cm$^{-1}$

NMR (DMSO-$d_6$, δ): 1.61 (2H, m), 1.87 (2H, m), 2.78–3.14 (3H, m), 3.90 (3H, s), 4.61 (2H, m), 6.96 (1H, d, J=9.2 Hz), 7.27 (5H, m), 7.98–8.10 (1H, m), 8.03 (2H, d, J=8.7 Hz), 8.10 (2H, d, J=8.6 Hz), 8.70 (1H, d, J=2.3 Hz), 10.34 (1H, s), 10.62 (1H, s)

MASS (m/z): 459 ($M^+$+1)

Preparation 327

NMR (DMSO-$d_6$, δ): 1.36 (3H, t, J=7.0 Hz), 3.90 (3H, s), 4.09 (2H, q, J=6.9 Hz), 7.04 (2H, d, J=8.8 Hz), 7.71 (2H, d, J=8.8 Hz), 7.79 (2H, d, J=8.4 Hz), 8.00 (2H, d, J=8.5 Hz), 8.06 (2H, d, J=8.8 Hz), 8.10 (2H, d, J=8.7 Hz), 10.60 (1H, s), 10.72 (1H, s)

MASS (m/z): 419 ($M^+$+1)

Preparation 328

IR (KBr): 2951, 2872, 1724, 1680, 1651, 1605, 1554, 1497, 1439 cm$^{-1}$

NMR (DMSO-$d_6$, δ): 1.57–1.89 (4H, m), 3.25 (3H, s), 3.39 (2H, t, J=6.2 Hz), 3.91 (3H, s), 4.05 (2H, t, J=6.1 Hz), 7.05 (2H, d, J=8.8 Hz), 7.71 (2H, d, J=8.7 Hz), 7.79 (2H, d, J=8.4 Hz), 8.00 (2H, d, J=8.5 Hz), 8.06 (2H, d, J=8.7 Hz), 8.10 (2H, d, J=8.7 Hz), 10.61 (1H, s), 10.73 (1H, s)

MASS (m/z): 477 ($M^+$+1)

Preparation 329

IR (KBr): 1720, 1678, 1643, 1608, 1564, 1525, 1502 cm$^{-1}$

NMR (DMSO-$d_6$, δ): 0.96–1.36 (5H, m), 1.49–1.91 (5H, m), 2.16–2.35 (1H, m), 2.52–2.75 (4H, m), 3.10–3.35 (4H, m), 3.90 (3H, s), 6.99 (2H, d, J=8.9 Hz), 7.81 (2H, d, J=8.8 Hz), 8.04 (2H, d, J=8.6 Hz), 8.09 (2H, d, J=8.7 Hz), 10.27 (1H, s), 10.59 (1H, s)

MASS (m/z): 465 ($M^+$+1)

Preparation 330

IR (KBr): 1722, 1676, 1641, 1608, 1500, 1446 cm$^{-1}$

NMR (DMSO-$d_6$, δ): 0.90 (3H, J=6.8 Hz), 1.30–1.85 (9H, m), 2.11–2.30 (1H, m), 2.63–2.69 (4H, m), 3.18–3.38 (4H, m), 3.90 (3H, s), 6.99 (2H, d, J=9.0 Hz), 7.81 (2H, d, J=8.8 Hz), 8.04 (2H, d, J=9.1 Hz), 8.09 (2H, d, J=8.7 Hz), 10.27 (1H, s), 10.58 (1H, s)

MASS (m/z): 479 ($M^+$+1)

Preparation 331

IR (KBr): 1722, 1678, 1643, 1608, 1500, 1446 cm$^{-1}$

NMR (DMSO-$d_6$, δ): 0.86 (3H, d, J=6.4 Hz), 0.88–1.08 (2H, m), 1.08–1.51 (3H, m), 1.60–1.90 (4H, m), 2.14–2.35 (1H, m), 2.54–2.66 (4H, m), 3.13–3.36 (4H, m), 3.90 (3H, s), 6.98 (2H, J=8.9 Hz), 7.81 (2H, d, J=8.8 Hz), 8.03 (2H, d, J=8.7 Hz), 8.09 (2H, d, J=8.6 Hz), 10.26 (1H, s), 10.58 (1H, s)

MASS (m/z): 479 ($M^+$30 1)

Preparation 332

NMR (DMSO-$d_6$, δ): 1.18 (3H, t, J=7.0 Hz), 3.52 (2H, q, J=7.0 Hz), 3.90 (3H, m), 4.52 (2H, s), 7.45 (2H, d, J=8.2 Hz), 7.75 (2H, d, J=8.2 Hz), 7.84 (2H, d, J=8.4 Hz), 8.03 (2H, d, J=8.4 Hz), 8.00–8.17 (4H, m), 10.64 (1H, s), 10.74 (1H, s)

MASS (m/z): 433 ($M^+$+1)

Preparation 333

NMR (DMSO-$d_6$, δ): 3.28 (3H, m), 3.47–3.66 (4H, m), 3.91 (3H, s), 4.56 (2H, s), 7.46 (2H, d, J=8.3 Hz), 7.76 (2H, d, J=8.2 Hz), 7.85 (2H, d, J=8.4 Hz), 7.98–8.16 (6H, m), 10.65 (1H, s), 10.74 (1H, s)

MASS (m/z): 463 ($M^+$+1)

Preparation 334

NMR (DMSO-$d_6$, δ): 3.26 (3H, s), 3.39–3.55 (2H, m), 3.55–3.66 (2H, m), 3.77 (2H, t, J=4.5 Hz), 3.90 (3H, s), 4.16 (2H, t, J=4.5 Hz), 7.08 (2H, d, J=8.8 Hz), 7.72 (2H, d, J=8.8 Hz), 7.80 (2H, d, J=8.4 Hz), 8.00 (2H, d, J=8.5 Hz), 8.06 (2H, d, J=8.7 Hz), 8.10 (2H, d, J=8.7 Hz), 10.61 (1H, s), 10.73 (1H, s)

MASS (m/z): 493 ($M^+$+1)

Preparation 335

NMR (DMSO-$d_6$, δ): 1.12 (3H, t, J=7.0 Hz), 1.88–2.12 (2H, m), 3.44 (2H, q, J=7.0 Hz), 3.53 (2H, t, J=6.4 Hz), 3.91 (3H, s), 4.09 (2H, t, J=6.4 Hz), 7.06 (2H, d, J=8.8 Hz), 7.71 (2H, d, J=8.8 Hz), 7.79 (2H, d, J=8.5 Hz), 8.00 (2H, d, J=8.5 Hz), 8.06 (2H, d, J=8.7 Hz), 8.10 (2H, d, J=8.7 Hz), 10.61 (1H, s), 10.72 (1H, s)

MASS (m/z): 477 ($M^+$+1)

Preparation 336

NMR (DMSO-$d_6$, δ): 1.14 (3H, t, J=7.0 Hz), 3.52 (2H, q, J=7.0 Hz), 3.68–3.78 (2H, m), 3.90 (3H, s), 4.14–4.22 (2H, m), 7.08 (2H, d, J=8.8 Hz), 7.72 (2H, d, J=8.8 Hz), 7.80 (2H, d, J=8.4 Hz), 8.00 (2H, d, J=8.4 Hz), 8.06 (2H, d, J=8.7 Hz), 8.10 (2H, d, J=8.7 Hz), 10.61 (1H, s), 10.73 (1H, s)

MASS (m/z): 463 ($M^+$+1)

Preparation 337

IR (KBr): 1724, 1680, 1655, 1605, 1495, 1437 cm$^{-1}$

NMR (DMSO-$d_6$, δ): 1.98 (2H, m), 3.26 (3H, s), 3.49 (2H, t, J=6.3 Hz), 3.90 (3H, s), 4.09 (2H, t, J=6.4 Hz), 7.06

(2H, d, J=8.8 Hz), 7.71 (2H, d, J=8.8 Hz), 7.79 (2H, d, J=8.5 Hz), 8.00 (2H, d, J=8.5 Hz), 8.06 (2H, d, J=8.7 Hz), 8.10 (2H, d, J=8.7 Hz), 10.60 (1H, s), 10.72 (1H, s)

MASS (m/z): 463 (M⁺+1)

Preparation 338

IR (KBr): 1724, 1682, 1645, 1605, 1495, 1439, 1404 cm⁻¹

NMR (DMSO-d₆, δ): 3.33 (3H, s), 3.69 (2H, m), 3.90 (3H, s), 4.16 (2H, m), 7.07 (2H, d, J=8.9 Hz), 7.72 (2H, d, J=8.7 Hz), 7.72 (2H, d, J=8.7 Hz), 7.80 (2H, d, J=8.6 Hz), 9.79 (1H, s)

MASS (m/z): 287 (M⁺+1)

Preparation 339

IR (Nujol): 3259, 1724, 1672, 1626, 1605 cm⁻¹

NMR (DMSO-d₆, δ): 1.9–2.2 (4H, m), 2.93 (3H, s), 3.0–3.4 (2H, m), 3.7–3.8 (2H, m), 3.90 (3H, s), 7.06 (2H, d, J=8.9 Hz), 7.45 (4H, s), 7.82 (2H, d, J=8.9 Hz), 8.0–8.2 (4H, m), 10.27 (1H, s), 10.59 (1H, s)

(+)APCI MASS: 522 (M+H)⁺

Preparation 340

IR (KBr): 3247.5, 1727.9, 1687.4, 1255.4 cm⁻¹

NMR (DMSO-d₆, δ): 1.24–1.99 (16H, m), 2.15–2.45 (2H, m), 3.21 (3H, s), 3.27–3.35 (2H, m), 3.60 (3H, s), 4.02 (2H, t, J=6.4 Hz), 7.00 (2H, d, J=8.6 Hz), 7.83 (2H, d, J=8.6 Hz), 9.74 (1H, s), 10.12 (1H, s)

MASS (m/z): 435 (M+1)

Preparation 341

IR (KBr): 3236.0, 1724.0, 1677.8, 1255.4 cm⁻¹

NMR (DMSO-d₆, δ): 0.91 (3H, t, J=7.0 Hz), 1.30–1.50 (4H, m), 1.70–1.80 (2H, m), 3.87 (3H, s), 4.03 (2H, t, J=6.4 Hz), 7.03–7.07 (2H, m), 7.68–8.00 (8H, m), 10.50–11.00 (2H, m)

MASS (m/z): 467 (M+1)

Preparation 342

IR (KBr): 3201.3, 1714.4, 1594.8, 1253.5 cm⁻¹

NMR (DMSO-d₆, δ): 1.30–1.80 (8H, m), 2.42 (3H, s), 3.21 (3H, s), 3.28–3.34 (2H, m), 3.34 (3H, s), 3.85 (3H, s), 4.04 (2H, t, J=6.4 Hz), 7.04 (2H, d, J=8.8 Hz), 7.36 (1H, s), 7.73 (1H, s), 7.95 (2H, d, J=9 Hz), 10.22 (1H, s), 10.39 (1H, s)

MASS (m/z): 457 (M+1)

Preparation 343

IR (KBr): 3199.3, 1716.3, 1608.3, 1253.5 cm⁻¹

NMR (DMSO-d₆, δ): 1.37–1.80 (8H, m), 3.21 (3H, s), 3.28–3.33 (2H, m), 3.71 (3H, s), 4.03 (2H, t, J=6.4 Hz), 6.39–6.59 (2H, m), 7.00–7.04 (2H, m), 7.24–7.47 (2H, m), 7.83–7.88 (2H, m), 10.35 (2H, d, J=6.9 Hz)

MASS (m/z): 405 (M+1)

Preparation 344

IR (KBr): 3193.5, 1718.3, 1606.4, 1249.6 cm⁻¹

NMR (DMSO-d₆, δ): 1.00 (3H, t, J=7.4 Hz), 1.75–1.85 (2H, m), 3.97–4.03 (5H, m), 7.06–8.78 (12H, m), 10.64 (1H, s), 10.72 (1H, s)

MASS (m/z): 483 (M+1)

Preparation 345

IR (KBr): 3220.5, 1720.2, 1685.5, 1290.1, 1251.6 cm⁻¹

NMR (DMSO-d₆, δ): 1.30–1.80 (8H, m), 3.22 (3H, s), 3.28–3.34 (2H, m), 3.94 (3H, s), 4.05 (2H, t, J=6.3 Hz), 7.04–7.08 (2H, m), 7.91–8.71 (8H, m), 10.47 (1H, bs), 10.70 (1H, bs)

MASS (m/z): 479 (M+1)

The following compounds [Preparations 346 to 355] were obtained in a manner similar to that of Preparation 41.

Preparation 346

IR (KBr): 1726, 1284 cm⁻¹

NMR (CDCl₃, δ): 0.89 (3H, t, J=6.8 Hz), 1.2–1.8 (10H, m), 3.51 (2H, t, J=6.6 Hz), 3.97 (3H, s), 4.56 (2H, s), 7.48 (2H, d, J=8.6 Hz), 7.74 (2H, d, J=8.6 Hz), 8.07 (2H, d, J=8.6 Hz), 8.17 (2H, J=8.6 Hz), 8.18 (1H, s), 8.55 (1H, s)

MASS (m/z): 491 (M⁺+1)

Preparation 347

NMR (CDCl₃–CD₃OD, δ): 1.15–1.40 (6H, m), 1.40–2.30 (12H, m), 2.80–3.55 (4H, m), 3.65–3.80 (4H, m), 3.97 (3H, s), 4.00–4.25 (1H, m), 7.20 (2H, d, J=8.6 Hz), 7.93 (2H, d, J=8.6 Hz), 8.06 (2H, d, J=8.6 Hz), 8.16 (2H, d, J=8.6 Hz)

ESI MASS (positive): 478 (M⁺+1)

Preparation 348

NMR (CDCl₃+CD₃OD, δ); 1.20–1.60 (5H, m), 1.65–2.05 (5H, m), 2.50–2.70 (1H, m), 3.97 (3H, s), 7.36 (2H, d, J=8.2 Hz), 7.92 (2H, d, J=8.3 Hz), 8.05–8.20 (4H, m)

APCI MASS (positive): 379.2 (M⁺+1)

Preparation 349

NMR (CDCl₃, δ): 1.20–2.15 (10H, m), 3.97 (3H, s), 4.30–4.50 (1H, m), 7.01 (2H, d, J=8.9 Hz), 7.92 (2H, d, J=8.9 Hz), 8.00–8.30 (4H, m)

APCI MASS (positive): 395.2 (M⁺+1)

Preparation 350

IR (KBr): 1722, 1651, 1574, 1522, 1279 cm⁻¹

NMR (CDCl₃, δ): 0.92 (3H, t, J=6.7 Hz), 1.2–1.9 (8H, m), 3.97 (3H, s), 4.01 (2H, t, J=6.5 Hz), 7.01 (2H, d, J=9.0 Hz), 7.64 (2H, d, J=9.0 Hz), 8.07 (2H, d, J=8.6 Hz), 8.15 (1H, s), 8.17 (2H, d, J=8.6 Hz), 8.46 (1H, s)

MASS (m/z): 465 (M⁺+1)

Preparation 351

IR (KBr): 1727.9, 1249.6, 1180.2 cm⁻¹

NMR (DMSO-d₆, δ): 1.30–2.30 (18H, m), 3.21 (3H, s), 3.28–3.35 (2H, m), 3.62 (3H, s), 4.04 (2H, t, J=6.4 Hz), 7.07 (2H, d, J=8.7 Hz), 7.85 (2H, d, J=8.7 Hz)

MASS (m/z): 433 (M+1)

Preparation 352

IR (KBr): 1724.0, 1604.5, 1261.2, 1182.2 cm⁻¹

NMR (DMSO-d₆, δ): 1.23–1.80 (8H, m), 2.48 (3H, s), 3.22 (3H, s), 3.22–3.33 (2H, m), 3.33 (3H, s), 3.87 (3H, s), 4.07 (2H, t, J=6.4 Hz), 7.13 (2H, d, J=8.9 Hz), 7.76–8.00 (4H, m)

MASS (m/z): 455 (M+1)

Preparation 353

IR (KBr): 1718.3, 1629.6, 1257.4, 1226.5 cm⁻¹

NMR (DMSO-d₆, δ): 1.25–1.75 (8H, m), 3.21 (3H, s), 3.28–3.34 (2H, m), 3.72 (3H, s), 4.06 (2H, t, J=6.4 Hz), 6.33–6.41 (2H, m), 7.09–7.13 (2H, m), 7.27–7.60 (2H, m), 7.90–7.95 (2H, m)

MASS (m/z): 403 (M+1)

Preparation 354

IR (KBr): 1716.3, 1297.9, 1255.4 cm$^{-1}$

NMR (DMSO-d$_6$, δ): 1.20–1.80 (8H, m), 3.22 (3H, s), 3.28–3.33 (2H, m), 3.95 (3H, s), 4.08 (2H, t, J=6.4 Hz), 7.12–7.17 (2H, m), 7.97–8.73 (8H, m)

MASS (m/z): 477 (M+1)

Preparation 355

IR (KBr): 2935.1, 2854.1, 1257.4, 827.3 cm$^{-1}$

NMR (CDCl$_3$, δ): 0.80–1.10 (3H, m), 1.20–1.60 (8H, m), 1.70–2.00 (2H, m), 4.01 (2H, t, J=6.5 Hz), 6.96 (2H, d, J=8.8 Hz), 7.44 (2H, d, J=8.7 Hz), 7.54 (2H, d, J=8.7 Hz), 7.89 (2H, d, J=8.8 Hz), 7.95 (1H, s)

APCI MASS (m/z): 430, 432

The following compounds [Preparations 356 to 382] were obtained in a manner similar to that of Preparation 48.

Preparation 356

IR (KBr): 1714, 1514, 1277 cm$^{-1}$

NMR (CDCl$_3$, δ): 2.66 (4H, brs), 3.23 (4H, brs), 3.64 (2H, s), 3.90 (3H, s), 6.92 (3H, m), 7.26 (2H, m), 7.52 (2H, d, J=8.0 Hz), 7.73 (2H, d, J=8.0 Hz), 8.0–8.3 (5H, m), 8.56 (1H, s)

MASS (m/z): 537 (M$^+$+1)

Preparation 357

IR (KBr): 1718, 1520, 1275, 1242 cm$^{-1}$

NMR (CDCl$_3$, δ): 1.5–1.8 (6H, m), 3.24 (4H, t, J=5.3 Hz), 3.97 (3H, s), 7.02 (2H, d, J=9.1 Hz), 7.59 (2H, d, J=9.1 Hz), 8.07 (2H, d, J=8.7 Hz), 8.14 (1H, s), 8.17 (2H, d, J=8.7 Hz), 8.44 (1H, s)

MASS (m/z): 446 (M$^+$+1)

Preparation 358

NMR (DMSO-d$_6$, δ): 1.50–1.95 (4H, m), 2.60–3.05 (3H, m), 3.90 (3H, s), 3.95–4.10 (2H, m), 6.90–7.35 (7H, m), 7.65–8.15 (6H, m)

APCI MASS (m/z): 456 (M$^+$)

Preparation 359

NMR (CDCl$_3$, δ): 2.0–2.2 (4H, m), 3.2–3.4 (4H, m), 3.97 (3H, s), 6.62 (2H, d, J=8.8 Hz), 7.56 (2H, d, J=8.8 Hz), 8.07 (2H, d, J=8.4 Hz), 8.13 (1H, s), 8.17 (2H, d, J=8.4 Hz), 8.40 (1H, s)

MASS (m/z): 432 (M$^+$+1)

Preparation 360

NMR (CDCl$_3$, δ): 0.95 (3H, t, J=6.6 Hz), 1.33–1.94 (6H, m), 3.99 (3H, s), 4.05 (2H, t, J=6.5 Hz), 7.02 (2H, d, J=8.8 Hz), 7.98 (2H, d, J=8.7 Hz), 8.05–8.33 (8H, m)

MASS (m/z): 543 (M$^+$+1)

Preparation 361

IR (KBr): 1722, 1603, 1500, 1439, 1417 cm$^{-1}$

NMR (CDCl$_3$, δ): 3.30–3.69 (8H, m), 3.93 (3H, s), 6.88–7.17 (3H, m), 7.03 (2H, d, J=9.0 Hz), 7.34 (2H, t, J=7.7 Hz), 7.94 (2H, d, J=8.8 Hz), 8.08 (2H, d, J=8.6 Hz), 8.16 (2H, d, J=8.6 Hz)

MASS (m/z): 457 (M$^+$+1)

Preparation 362

NMR (CDCl$_3$, δ): 0.95 (3H, t, J=7.4 Hz), 1.40–2.16 (6H, m), 3.03–3.30 (2H, m), 3.45 (2H, t, J=6.7 Hz), 3.44–3.95 (3H, m), 3.96 (3H, s), 6.85–7.12 (2H, m), 7.80–7.97 (2H, m), 8.07 (2H, d, J=8.6 Hz), 8.15 (2H, d, J=8.6 Hz)

MASS (m/z): 438 (M$^+$+1)

Preparation 363

IR (KBr): 1722, 1605, 1520, 1439, 1414 cm$^{-1}$

NMR (CDCl$_3$, δ): 0.92 (6H, s), 1.12–1.90 (8H, m), 2.18–2.24 (1H, m), 2.68–2.86 (4H, m), 3.27–3.46 (4H, m), 3.96 (3H, s), 6.97 (2H, d, J=9.0 Hz), 7.90 (2H, d, J=8.9 Hz), 8.07 (2H, d, J=8.2 Hz), 8.15 (2H, d, J=8.6 Hz)

MASS (m/z): 491 (M$^+$+1)

Preparation 364

IR (KBr): 1716, 1606, 1520, 1441, 1417 cm$^{-1}$

NMR (CDCl$_3$, δ) 1.70–2.26 (4H, m), 3.10–3.31 (2H, m), 3.60–3.84 (3H, m), 3.96 (3H, s), 4.60 (2H, s), 6.90–7.20 (2H, m), 7.26–7.46 (5H, m), 7.91 (2H, d, J=8.8 Hz), 8.09 (2H, d, J=8.7 Hz), 8.15 (2H, d, J=8.7 Hz)

MASS (m/z): 486 (M$^+$+1)

Preparation 365

IR (KBr): 2941, 2845, 1713, 1601, 1549, 1504, 1431, 1404 cm$^{-1}$

NMR (CDCl$_3$, δ): 1.79 (2H, m), 2.01 (2H, m), 2.84 (1H, m), 3.08 (2H, m), 3.96 (3H, s), 4.64 (2H, m), 6.80 (1H, d, J=9.1 Hz), 7.18–7.40 (5H, m), 8.03–8.23 (5H, m), 8.73 (1, d, J=2.3 Hz)

MASS (m/z): 457 (M$^+$+1)

Preparation 366

IR (KBr): 2949, 2870, 1722, 1605, 1504, 1437 cm$^{-1}$

NMR (CDCl$_3$, δ): 1.66–2.00 (4H, m), 3.27 (3H, s), 3.47 (2H, t, J=6.0 Hz), 3.97 (3H, s), 4.05 (2H, t, J=6.1 Hz), 7.00 (2H, d, J=8.6 Hz), 7.59 (2H, d, J=8.6 Hz), 7.70 (2H, d, J=8.2 Hz), 8.00–8.14 (4H, m), 8.17 (2H, d, J=8.5 Hz)

MASS (m/z): 475 (M$^+$+1)

Preparation 367

IR (KBr): 1720, 1605, 1522, 1439, 1416 cm$^{-1}$

NMR (CDCl$_3$, δ): 1.00–1.41 (5H, m), 1.56–2.14 (5H, m), 2.24–2.41 (1H, m), 2.66–2.82 (4H, m), 3.27–3.43 (4H, m), 3.96 (3H, s), 6.96 (2H, d, J=9.0 Hz), 7.89 (2H, d, J=8.9 Hz), 8.06 (2H, d, J=8.6 Hz), 8.14 (2H, d, J=8.6 Hz)

MASS (m/z): 463 (M$^+$+1)

Preparation 368

IR (KBr): 1718, 1605, 1520, 1439, 1414 cm$^{-1}$

NMR (CDCl$_3$, δ): 0.95 (3H, d, J=6.9 Hz), 1.38–1.90 (9H, m), 2.24–2.47 (1H, m), 2.66–2.92 (4H, m), 3.28–3.53 (4H, m), 3.96 (3H, s), 6.97 (2H, d, J=9.0 Hz), 7.90 (2H, d, J=8.9 Hz), 8.07 (2H, d, J=8.7 Hz), 8.15 (2H, d, J=8.7 Hz)

MASS (m/z): 477 (M$^+$+1)

Preparation 369

IR (KBr): 1724, 1605, 1520, 1437, 1412 cm$^{-1}$

NMR (CDCl$_3$, δ): 0.89 (3H, d, J=6.4 Hz), 0.89–1.13 (2H, m), 1.13–2.07 (7H, m), 2.24–2.50 (1H, m), 2.68–2.93 (4H, m), 3.30–3.52 (4H, m), 3.96 (3H, s), 6.97 (2H, d, J=8.9 Hz), 7.90 (2H, d, J=8.9 Hz), 8.07 (2H, d, J=8.6 Hz), 8.15 (2H, d, J=8.6 Hz)

MASS (m/z): 477 (M$^+$+1)

Preparation 370

IR (KBr): 2976, 1716, 1601, 1531, 1500, 1479, 1437 cm$^{-1}$

NMR (CDCl$_3$, δ): 1.46 (3H, t, J=7.0 Hz), 3.97 (3H, s), 4.10 (2H, q, J=7.0 Hz), 7.00 (2H, d, J=8.7 Hz), 7.59 (2H, d, J=8.7 Hz), 7.70 (2H, d, J=8.4 Hz), 8.07 (2H, d, J=8.3 Hz), 8.10–8.30 (4H, m)

MASS (m/z): 417 (M$^+$+1)

Preparation 371

IR (KBr): 2926, 2852, 1722, 1599, 1529, 1498, 1437 cm$^{-1}$

NMR (CDCl$_3$, δ): 1.00–1.41 (5H, m), 1.51–2.05 (5H, m), 2.24–2.43 (1H, m), 2.69–2.84 (4H, m), 3.22–3.36 (4H, m), 3.97 (3H, s), 7.02 (2H, d, J=8.8 Hz), 7.59 (2H, d, J=8.7 Hz), 7.70 (2H, d, J=8.4 Hz), 8.06 (2H, d, J=8.5 Hz), 8.09–8.15 (4H, m)

MASS (m/z): 539 (M$^+$+1)

Preparation 372

IR (KBr): 1718, 1601, 1429 cm$^{-1}$

NMR (CDCl$_3$, δ): 1.29 (6H, d, J=6.3 Hz), 2.36–2.56 (2H, m), 3.44–3.63 (2H, m), 3.74–3.93 (2H, m), 3.96 (3H, s), 6.99 (2H, d, J=8.9 Hz), 7.58 (2H, d, J=8.8 Hz), 7.69 (2H, d, J=8.5 Hz), 8.05 (2H, d, J=8.4 Hz), 8.09 (2H, d, J=8.6 Hz), 8.16 (2H, d, J=8.6 Hz)

MASS (m/z): 486 (M$^{30}$+1)

Preparation 373

IR (KBr): 1707, 1603, 1529, 1498, 1433, 1414 cm$^{-1}$

NMR (CDCl$_3$, δ): 1.23–2.12 (10H, m), 3.97 (3H, s), 4.18–4.38 (1H, m), 7.00 (2H, d, J=8.8 Hz), 7.57 (2H, d, J=8.8 Hz), 7.69 (2H, d, J=8.4 Hz), 8.10 (2H, d, J=8.5 Hz), 8.06–8.25 (4H, m)

MASS (m/z): 471 (M$^{30}$+1)

Preparation 374

IR (KBr): 2956, 2933, 2872, 1722, 1605, 1502, 1435 cm$^{-1}$

NMR (CDCl$_3$, δ): 1.00 (3H, t, J=7.2 Hz), 1.52 (2H, m), 1.72 (2H, m), 3.97 (3H, s), 4.03 (2H, m), 7.00 (2H, m), 7.45–7.78 (4H, m), 7.96–8.29 (6H, m)

MASS (m/z): 445 (M$^{30}$+1)

Preparation 375

IR (KBr): 1716, 1435 cm$^{-1}$

NMR (CDCl$_3$, δ): 1.28 (3H, t, J=7.0 Hz), 3.60 (2H, q, J=7.0 Hz), 3.97 (3H, m), 4.58 (2H, s), 7.47 (2H, d, J=8.3 Hz), 7.56–7.78 (4H, m), 8.04–8.29 (6H, m)

MASS (m/z): 431 (M$^{30}$+1)

Preparation 376

IR (KBr): 1720, 1651, 1606, 1560, 1504, 1435 cm$^{-1}$

NMR (CDCl$_3$, δ): 3.42 (3H, m), 3.55–2.71 (4H, m), 3.97 (3H, s), 4.64 (2H, s), 7.47 (2H, d, J=8.2 Hz), 7.64 (2H, d, J=8.2 Hz), 7.68–7.80 (2H, m), 8.04–8.26 (6H, m)

MASS (m/z): 461 (M$^+$+1)

Preparation 377

IR (KBr): 2926, 2877, 1720, 1605, 1504, 1437 cm$^{-1}$

NMR (CDCl$_3$, δ): 3.41 (3H, s), 3.54–3.64 (2H, m), 3.69–3.78 (2H, m), 3.86–3.96 (2H, m), 3.97 (3H, s), 4.14–4.28 (2H, m), 6.95–7.18 (2H, m), 7.51–5.64 (2H, m), 5.64–6.77 (2H, m), 8.00–8.26 (6H, m)

MASS (m/z): 491 (M$^+$+1)

Preparation 378

NMR (CDCl$_3$, δ): 1.22 (3H, t, J=7.0 Hz), 2.09 (2H, m), 3.52 (2H, q, J=7.0 Hz), 3.63 (2H, t, J=6.2 Hz), 3.97 (3H, s), 4.13 (2H, t, J=6.2 Hz), 7.02 (2H, d, J=8,8 Hz), 7.59 (2H, d, J=8.8 Hz), 7.70 (2H, d, J=8.5 Hz), 8.07 (2H, d, J=8.4 Hz), 8.08–8.26 (4H, m)

MASS (m/z): 475 (M$^+$+1)

Preparation 379

NMR (CDCl$_3$, δ): 1.27 (3H, t, J=7.0 Hz), 3.63 (2H, q, J=7.0 Hz), 3.74–3.90 (2H, m), 3.97 (3H, s), 4.14–4.28 (2H, m), 7.04 (2H, d, J=8.7 Hz), 7.59 (2H, d, J=8.2 Hz), 8.10 (2H, d, J=8.5 Hz), 8.16 (2H, d, J=8.5 Hz)

MASS (m/z): 461 (M$^+$+1)

Preparation 380

IR (KBr): 1722, 1605, 1531, 1500, 1435 cm$^{-1}$

NMR (CDCl$_3$, δ): 2.09 (2H, m), 3.38 (3H, s), 3.59 (2H, t, J=6.1 Hz), 3.97 (3H, s), 4.13 (2H, t, J=6.3 Hz), 7.01 (2H, d, J=8.8 Hz), 7.50–7.64 (2H, m), 7.70 (2H, d, J=8.5 Hz), 8.07 (2H, d, J=8.4 Hz), 8.08–8.25 (4H, m)

MASS (m/z): 461 (M$^+$+1)

Preparation 381

IR (KBr): 1720, 1643, 1603, 1531, 1500, 1435 cm$^{-1}$

NMR (CDCl$_3$, δ): 3.48 (3H, s), 3.80 (2H, m), 3.97 (3H, s), 4.18 (2H, m), 7.04 (2H, d, J=8.8 Hz), 7.51–7.77 (4H, m), 8.03–8.23 (6H, m)

MASS (m/z): 447 (M$^+$+1)

Preparation 382

IR (Nujol): 1714, 1601 cm$^{-1}$

NMR (CDCl$_3$, δ): 1.7–2.0 (4H, m), 2.75 (3H, s), 3.0–3.2 (2H, m), 3.4–3.6 (2H, m), 3.69 (3H, s), 6.77 (2H, d, J=8.8 Hz), 7.08 )4H, s), 7.60 (2H, d, J=8.8 Hz), 7.7–8.0 (4H, m)

(+)APCI MASS: 520 (M+H)$^+$

The following compounds [Preparations 383 to 388] were obtained in a manner similar to that of Preparation 33.

Preparation 383

IR (KBr): 1699, 1684 cm$^{-1}$

NMR (DMSO-d$_6$, δ): 0.86 (3H, t, J=6.6 Hz), 1.2–1.7 (10 H, m), 3.46 (2H, t, J=6.6 Hz), 4.51 (2H, s), 7.50 (2H, d, J=8.6 Hz), 7.95 (2H, d, J=8.6 Hz), 8.13 (4H, s), 8.42 (1H, s), 9.36 (1H, s)

MASS (m/z): 477 (M$^+$+1)

Preparation 384

IR (KBr): 1583, 1543, 1516, 1396 cm$^{-1}$

NMR (DMSO-d$_6$, δ): 2.4–2.6 (4H, m), 3.1–3.3 (4H, m), 3.60 (2H, s), 6.77 (1H, t, J=7.4 Hz), 6.93 (2H, d, J=7.4 Hz), 7.20 (2H, t, J=7.4 Hz), 7.9–8.1 (6H, m), 8.39 (1H, s), 9.32 (1H, s)

MASS (m/z): 523 (M$^+$+1)

Preparation 385

IR (KBr): 1716, 1520, 1277, 1109 cm$^{-1}$

MASS (m/z): 432 (M$^+$+1)

Preparation 386

IR (KBr): 1684, 1518, 1252 cm$^{-1}$

Preparation 387

NMR (DMSO-d$_6$, δ): 1.60–2.10 (4H, m), 2.70–3.10 (3H, m), 4.08 (2H, m), 7.10–7.40 (7H, m), 7.95 (2H, d, J=8.5 Hz), 8.18 (4H, AB-q, J=8.3 Hz, J=16.1 Hz)

APCI MASS: 426 (M$^+$+1)

Preparation 388

IR (KBr): 1687, 1610, 1568, 1527 cm$^{-1}$

MASS (m/z): 418 (M$^+$+1)

The following compounds [Preparations 389 to 393] were obtained in a manner similar to that of Preparation 57.

Preparation 389

NMR (CDCl$_3$-CD$_3$OD, δ): 2.10–2.25 (2H, m), 2.65–3.15 (3H, m), 3.45–3.70 (2H, m), 3.99 (3H, s), 7.30–7.40 (5H, m), 7.90–8.40 (8H, m)

APCI MASS: 440 (M$^+$)

Preparation 390

NMR (DMSO-d$_6$, δ): 1.10–2.10 (10H, m), 3.91 (3H, s), 4.40–4.60 (1H, m), 7.17 (2H, d, J=8.9 Hz), 8.00–8.30 (6H, m)

APCI MASS (positive): 379.2 (M$^+$+1)

Preparation 391

NMR (DMSO-d$_6$, δ): 1.20–1.60 (5H, m), 1.60–1.95 (5H, m), 2.50–2.75 (1H, m), 3.92 (3H, s), 7.50 (2H, d, J=8.3 Hz), 8.07 (2H, d, J=8.3 Hz), 8.18 (2H, d, J=8.7 Hz), 8.28 (2H, d, J=8.7 Hz)

APCI MASS (positive): 363.3 (M$^+$+1)

Preparation 392

IR (KBr): 1724.0, 1253.5, 1199.5 cm$^{-1}$

NMR (CDCl$_3$, δ): 0.95 (3H, t, J=7.0 Hz), 1.35–1.60 (4H, m), 1.70–1.95 (2H, m), 3.88–4.05 (5H, m), 6.98–7.03 (2H, m), 7.57–8.17 (8H, m)

MASS (m/z): 449 (M+1)

Preparation 393

IR (KBr): 1718.3, 1602.6, 1249.6 cm$^{-1}$

NMR (CDCl$_3$, δ): 1.01 (3H, t, J=78.4 Hz), 1.50–1.80 (2H, m), 3.97–4.05 (5H, m), 7.06–7.10 (2H, m), 7.70–9.35 (12H, m)

MASS (m/z): 465 (M+1)

The following compounds [Preparations 394 to 457] were obtained in a manner similar to that of Preparation 49.

Preparation 394

NMR (DMSO-d$_6$, δ): 1.10–1.95 (12H, m), 3.55–3.80 (4H, m), 7.08 (2H, d, J=8.9 Hz), 7.83 (2H, d, J=8.8 Hz), 8.07 (4H, s)

APCI MASS: 464 (M$^+$)

Preparation 395

NMR (DMSO-d$_6$, δ): 1.10–1.60 (5H, m), 1.60–1.95 (5H, m), 2.50–2.70 (1H, m), 7.45 (2H, d, J=8.3 Hz), 7.96 (2H, d, J=8.3 Hz), 8.14 (4H, s)

Preparation 396

NMR (DMSO-d$_6$, δ): 1.20–2.10 (10H, m), 4.35–4.60 (1H, m), 7.13 (2H, d, J=8.9 Hz), 7.95 (2H, d, J=8.9 Hz), 8.12 (4H, s)

APCI MASS (negative): 379.2 (M$^+$−1)

Preparation 397

NMR (DMSO-d$_6$, δ): 1.50–2.00 (4H, m), 2.65–3.10 (3H, m), 3.95–4.15 (2H, m), 6.90–7.35 (7H, m), 7.70–8.30 (6H, m)

APCI MASS: 442 (M$^+$)

Preparation 398

NMR (DMSO-d$_6$, δ): 1.20–2.10 (10H, m), 4.40–4.60 (1H, m), 7.17 (2H, d, J=8.9 Hz), 7.95–8.30 (6H, m), 13.0–13.5 (1H, m)

APCI MASS (positive): 365.2 (M$^+$+1)

Preparation 399

NMR (CDCl$_3$, δ): 1.15–1.60 (5H, m), 1.65–2.05 (5H, m), 2.50–2.70 (1H, m), 7.41 (2H, d, J=8.3 Hz), 8.05 (2H, d, J=8.4 Hz), 8.23 (4H, s)

APCI MASS (positive): 349.2 (M$^+$+1)

Preparation 400

IR (KBr): 2935, 2858, 1705, 1649, 1601, 1531, 1500, 1441, 1400 cm$^{-1}$

MASS (m/z): 523 (M$^+$−1)

Preparation 401

MASS (m/z): 527 (M$^+$−1)

Preparation 402

NMR (DMSO-d$_6$, δ): 3.30–3.64 (8H, m), 6.75–7.33 (7H, m), 7.70–8.29 (6H, m)

MASS (m/z): 443 (M$^+$-2HCl+1)

Preparation 403

NMR (DMSO-d$_6$, δ): 0.88 (3H, t, J=7.4 Hz), 1.35–1.63 (4H, m), 1.82–2.03 (2H, m), 2.99–3.20 (2H, m), 3.40 (2H, t, J=6.6 Hz), 3.40–3.80 (3H, m), 7.09 (2H, d, J=9.0 Hz), 7.84 (2H, d, J=8.9 Hz), 8.11 (4H, s), 13.22 (1H, brs)

MASS (m/z): 424 (M$^+$-HCl+1)

Preparation 404

IR (KBr): 1686, 1601, 1531, 1500, 1421 cm$^{-1}$

NMR (DMSO-d$_6$, δ): 1.18 (6H, d, J=6.1 Hz), 2.24–2.45 (2H, m), 3.63–3.82 (4H, m), 7.08 (2H, d, J=8.6 Hz), 7.68 (2H, d, J=8.8 Hz), 7.90 (2H, d, J=8.5 Hz), 8.08 (2H, d, J=8.3 Hz), 8.13 (2H, d, J=8.7 Hz), 8.16 (2H, d, J=8.7 Hz)

MASS (m/z): 472 (M$^+$+1)

Preparation 405

IR (KBr): 1705, 1606, 1524, 1441, 1412 cm$^{-1}$

MASS (m/z): 477 (M$^+$+1)

Preparation 406

IR (KBr): 1686, 1603, 1568, 1520, 1416 cm$^{-1}$

NMR (DMSO-d$_6$, δ): 1.49–1.71 (2H, m), 1.90–2.10 (2H, m), 3.06–3.24 (2H, m), 3.58–3.80 (3H, m), 4.56 (2H, s), 7.10 (2H, d, J=9.0 Hz), 7.23–7.46 (5H, m), 7.85 (2H, d, J=8.9 Hz), 8.10 (4H, m)

MASS (m/z): 472 (M$^+$+1)

Preparation 407

IR (KBr): 1682, 1606, 1572, 1524, 1498, 1427 cm$^{-1}$

NMR (DMSO-d$_6$, δ): 1.25–2.05 (10H, m), 4.35–4.50 (1H, m), 7.07 (2H, d, J=8.8 Hz), 7.64–7.94 (4H, m), 7.99–8.26 (6H, m)

MASS (m/z): 457 (M$^+$+1)

Preparation 408

IR (KBr): 2933, 2846, 1686, 1599, 1552, 1500, 1429 cm$^{-1}$

NMR (DMSO-d$_6$, δ): 1.56–2.00 (4H, m), 2.74–3.18 (3H, m), 4.62 (2H, m), 7.00–7.40 (6H, m), 7.99–8.26 (5H, m), 8.74 (1H, s), 13.20 (1H, brs)

MASS (m/z): 443 (M$^+$+1)

Preparation 409

IR (KBr): 1686, 1603, 1574, 1527, 1500, 1427 cm$^{-1}$

NMR (DMSO-d$_6$, δ): 1.36 (3H, t, J=7.0 Hz), 4.10 (2H, q, J=7.1 Hz), 7.00–7.13 (2H, m), 7.65–8.25 (10H, m)

MASS (m/z): 403 (M$^+$+1)

Preparation 410

IR (KBr): 1693, 1603, 1572, 1527, 1500, 1471, 1425 cm$^{-1}$

NMR (DMSO-d$_6$, δ): 1.60–1.84 (4H, m), 3.25 (3H, s), 3.30–3.50 (2H, m), 4.00–4.16 (2H, m), 7.07 (2H, d, J=8.8 Hz), 7.73 (2H, d, J=8.6 Hz), 7.87 (2H, d, J=8.5 Hz), 8.04–8.20 (6H, m)

MASS (m/z): 461 (M$^+$+1)

Preparation 411

IR (KBr): 1705, 1606, 1524, 1441, 1412 cm$^{-1}$

NMR (DMSO-d$_6$, δ): 1.00–2.20 (10H, m), 3.00–3.35 (9H, m), 7.18 (2H, d, J=9.1 Hz), 7.92 (2H, d, J=8.7 Hz), 8.11 (4H, s)

MASS (m/z): 447 (M$^+$−1)

Preparation 412

IR (KBr): 1703, 1605, 1524, 1441, 1412 cm$^{-1}$

NMR (DMSO-d$_6$, δ): 0.95 (3H, d, J=6.8 Hz), 1.43–2.00 (9H, m), 3.16–3.48 (9H, m), 7.17 (2H, d, J=8.4 Hz), 7.92 (2H, d, J=8.3 Hz), 8.12 (4H, s)

Preparation 413

IR (KBr): 1705, 1605, 1524, 1443, 1414 cm$^{-1}$

NMR (DMSO-d$_6$, δ): 0.88 (3H, d, J=6.4 Hz), 0.86–1.60 (5H, m), 1.74–1.92 (2H, m), 2.00–2.20 (2H, m), 2.97–3.35 (9H, m), 7.18 (2H, d, J=8.9 Hz), 7.92 (2H, d, J=8.8 Hz), 8.12 (4H, s)

Preparation 414

IR (KBr): 2956, 2935, 2872, 1686, 1605, 1500, 1427 cm$^{-1}$

NMR (DMSO-d$_6$, δ): 0.95 (3H, t, J=7.2 Hz), 1.44 (2H, m), 1.74 (2H, m), 4.05 (2H, m), 7.02–7.14 (2H, m), 7.66–8.30 (10H, m)

MASS (m/z): 431 (M$^+$+1)

Preparation 415

IR (KBr): 1686, 1606, 1425 cm$^{-1}$

NMR (DMSO-d$_6$, δ): 1.18 (3H, t, J=7.0 Hz), 3.52 (2H, q, J=6.9 Hz), 4.53 (2H, s), 7.46 (2H, d, J=8.5 Hz), 7.77 (2H, d, J=8.3 Hz), 7.92 (2H, d, J=8.4 Hz), 8.10–8.24 (6H, m)

MASS (m/z): 417 (M$^+$+1)

Preparation 416

IR (KBr): 1682, 1605, 1566, 1425 cm$^{-1}$

NMR (DMSO-d$_6$, δ): 3.28 (3H, m), 3.46–3.64 (4H, m), 4.56 (2H, s), 7.47 (2H, d, J=8.2 Hz), 7.78 (2H, d, J=8.2 Hz), 7.92 (2H, d, J=8.4 Hz), 8.07–8.25 (6H, m)

MASS (m/z): 447 (M$^+$+1)

Preparation 417

IR (KBr): 1684, 1603, 1500, 1423 cm$^{-1}$

NMR (DMSO-d$_6$, δ): 3.26 (3H, s), 3.35–3.54 (2H, m), 3.54–3.68 (2H, m), 3.77 (2H, t, J=4.5 Hz), 4.17 (2H, t, J=4.5 Hz), 7.09 (2 H, d, J=8.8 Hz), 7.74 (2 H, d, J=8.8 Hz), 7.87 (2 H, d, J=8.5 Hz), 8.10 (2 H, d, J=8.4 Hz), 8.09–8.20 (4 H, m)

MASS (m/z): 477 (M$^+$+1)

Preparation 418

NMR (DMSO-d$_6$, δ): 1.12 (3 H, t, J=7.0 Hz), 1.97 (2 H, m), 3.39 (2 H, q, J=7.0 Hz), 3.53 (2 H, t, J=6.6 Hz), 4.09 (2 H, t, J=6.3 Hz), 7.07 (2 H, d, J=8.8 Hz), 7.73 (2 H, d, J=8.7 Hz), 7.87 (2 H, d, J=8.5 Hz), 8.10 (2 H, d, J=8.4 Hz), 8.10–8.25 (4 H, m)

Preparation 419

IR (KBr): 1686, 1603, 1529, 1498, 1470, 1427 cm$^{-1}$

NMR (DMSO-d$_6$, δ): 1.15 (3 H, t, J=7.0 Hz), 3.52 (2 H, q, J=7.0 Hz), 3.68–3.80 (2 H, m) 4.13–4.24 (2 H, m) 7.08 (2 H, m), 7.08 (2 H, d, J=8.8 Hz), 7.73 (2 H, d, J=8.8 Hz), 7.86 (2 H, d, J=8.5 Hz), 8.09 (2 H, d, J=8.4 Hz), 8.10–8.21 (4 H, m)

MASS (m/z): 447 (M$^+$+1)

Preparation 420

IR (KBr): 1986, 1603, 1529, 1498, 1470, 1427 cm$^{-1}$

NMR (DMSO-d$_6$, δ): 1.98 (2 H, m), 3.27 (3 H, s), 3.50 (2 H, t, J=6.2 Hz), 4.09 (2 H, m), 7.07 (2 H, d, J=8.8 Hz), 7.73 (2 H, d, J=8.8 Hz), 7.87 (2 H, d, J=8.5 Hz), 8.10 (2 H, d, J=8.5 Hz), 8.10–8.21 (4 H, m)

MASS (m/z): 447 (M$^+$+1)

Preparation 421

IR (KBr): 1684, 1603, 1525, 1500, 1421 cm$^{-1}$

NMR (DMSO-d$_6$, δ): 3.32 (3 H, s), 3.69 (2 H, m), 4.17 (2 H, m), 7.09 (2 H, d, J=8.9 Hz), 7.73 (2 H, d, J=8.8 Hz), 7.87 (2 H, d, J=8.6 Hz), 8.03–8.20 (6 H, m)

MASS (m/z): 433 (M$^+$+1)

Preparation 422

IR (Nujol): 1684, 1601 cm$^{-1}$

NMR (DMSO-d$_6$, δ): 1.8–2.2 (4 H, m), 2.94 (3 H, s), 3.1–3.3 (2 H, m), 3.7–3.9 (2 H, m), 7.14 (2 H, d, J=8.9 Hz), 7.45 (4 H, s), 7.86 (2 H, d, J=8.9 Hz), 8.0–8.2 (4 H, m)

(+)APCI MASS: 506 (M+H)$^+$

Preparation 423

IR (KBr): 1664.3, 1602.6, 1230.4 cm$^{-1}$

Preparation 424

IR (KBr): 1685.5, 1608.3, 1238.1 cm$^{-1}$

NMR (DMSO-d$_6$, δ): 2.79–4.42 (13 H, m), 6.92–7.14 (2 H, m), 7.21–7.30 (4 H, m), 7.81–7.96 (2 H, m), 11.60 (1 H, bs), 12.55 (1 H, bs)

MASS (m/z): 323 (M+1)

Preparation 425

IR (KBr): 1726.0, 1251.6, 1180.2 cm$^{-1}$

NMR (DMSO-d$_6$, δ): 1.30–4,20 (18 H, m), 3.21 (3 H, s), 3.28–3.35 (2 H, m), 4.04 (2 H, t, J=6.4 Hz), 7.07 (2 H, d, J=8.8 Hz), 7.86 (2 H, d, J=8.8 Hz), 12.14 (1 H, s)

MASS (m/z): 419 (M+1)

Preparation 426

IR (KBr): 1683.6, 1251.6, 825.4 cm$^{-1}$

NMR (DMSO-d$_6$, δ): 0.91 (3 H, t, J=6.9 Hz), 1.24–1.55 (4 H, m), 1.60–1.90 (2 H, m), 4.00–4.10 (2 H, m), 7.02–7.08 (2 H, m), 7.63–8.36 (8 H, m)

MASS (m/z): 435 (M+1)

Preparation 427

IR (KBr): 1693.2, 1305.6, 1259.3, 1178.3 cm$^{-1}$

NMR (DMSO-d$_6$, δ): 1.38–1.80 (8 H, m), 2.56 (3 H, s), 3.22 (3 H, s), 3.28–3.34 (5 H, m), 4.06 (2 H, t, J=6.4 Hz), 7.12 (2 H, d, J=8.9 Hz), 7.72 (1 H, s), 7.86 (1 H, s), 7.97 (2 H, d, J=8.8 Hz), 13.12 (1 H, bs)

MASS (m/z): 441 (M+1)

Preparation 428

IR (KBr): 1675.8, 1606.4, 1259.3 cm$^{-1}$

NMR (DMSO-d$_6$, δ): 1.40–2.00 (8 H, m), 3.35 (3 H, s), 3.40 (2 H, t, J=6.3 Hz), 4.03 (2 H, t, J=6.3 Hz), 6.13–6.20 (2 H, m), 6.96–7.94 (6 H, m)

MASS (m/z): 3.89 (M+1)

Preparation 429

IR (KBr): 1699.0, 1604.5, 1249.6, 1193.7, cm$^{-1}$

NMR (DMSO-d$_6$, δ): 1.00 (3 H, t, J=7.4 Hz), 1.67–1.85 (2 H, m), 3.99 (2 H, t, J=6.5 Hz), 7.04–7.09 (2 H, m), 7.65–9.32 (12 H, m)

MASS (m/z): 451 (M+1)

Preparation 430

IR (KBr): 1685.5, 1253.5, 1174.4 cm$^{-1}$

NMR (DMSO-d$_6$, δ): 1.20–1.80 (8 H, m), 3.22 (3 H, s), 3.29–3.35 (2 H, m), 4.00–4.15 (2 H, m), 7.12–7.17 (2 H, m), 7.97–8.68 (8 H, m)

MASS (m/z): 4.63 (M+1)

Preparation 431

IR (KBr): 2950.6, 1708.6, 1608.3, 1473.3, 1419.4, 1367.3, 1259.3, 1211.1, 1174.4 cm$^{-1}$

MASS (m/z): 477 (M+H$^+$)

Preparation 432

IR (KBr): 2946, 1710, 1608, 1469, 1413, 1369, 1397, 1263, 1218, 1176 cm$^{-1}$

MASS (m/z): 491 (M+H$^+$)

Preparation 433

IR (KBr): 2944, 1706, 1606, 1469, 1417, 1375, 1259, 1176 cm$^{-1}$

MASS (m/z): 505 (M+H$^+$)

Preparation 434

IR (KBr); 3396, 2948, 2871, 1608, 1542, 1471, 1382, 1263, 1180, 1110 cm$^{-1}$

MASS (m/z): 493 (M+H$^+$)

Preparation 435

IR (KBr): 2942, 1687, 1608, 1471, 1309, 1261, 1176 cm$^{-1}$

MASS (m/z): 521 (M+H$^+$)

Preparation 436

IR (KBr): 2937, 1706, 1683, 1606, 1649, 1417, 1307, 1255, 1174, 1110 cm$^{-1}$

MASS (m/z): 535 (M+H$^+$)

Preparation 437

IR (KBr): 2946, 2570, 1706, 1608, 1469, 1415, 1371, 1309, 1259, 1216, 1174, 1108 cm$^{-1}$

MASS (m/z): 509 (M+H$^+$)

Preparation 438

IR (KBr): 2940, 2867, 2665, 2547, 1681, 1606, 1469, 1421, 1311, 1290, 1255, 1176, 1116 cm$^{-1}$

MASS (m/z): 438 (M+H$^+$)

Preparation 439

IR (KBr): 2939, 2861, 1681, 1606, 1469, 1421, 1311, 1253, 1174, 1114, 1016, 833 cm$^{-1}$

MASS (m/z): 452 (M+H$^+$)

Preparation 440

IR (KBr); 2935, 2858, 1681, 1606, 1571, 1467, 1419, 1311, 1253, 1174, 1112 cm$^{-1}$

MASS (m/z): 466 (M+H$^+$)

Preparation 441

IR (KBr): 2931, 2854, 2663, 1679, 1606, 1467, 1421, 1311, 1290, 1253, 1174, 1116 cm$^{-1}$

MASS (m/z): 480 (M+H$^+$)

Preparation 442

IR (KBr): 2935, 2850, 2819, 1608, 1589, 1537, 1473, 1417, 1240 cm$^{-1}$

MASS (m/z): 405 (M+H$^+$)

Preparation 443

IR (KBr): 3361, 2969, 2848, 1606, 1585, 1535, 1475, 1402, 1238, 1180, 1114, 927 cm$^{-1}$

Preparation 444

IR (KBr): 2975, 2873, 2829, 2665, 1681, 1606, 1469, 1423, 1315, 1288, 1240, 1176 cm$^{-1}$

MASS (m/z): 435 (M+H$^+$)

Preparation 445

IR (KBr): 2969, 2530, 1672, 1604, 1467, 1423, 1288, 1267, 1228, 1191 cm$^{-1}$

MASS (m/z): 423 (M+H$^+$)

Preparation 446

IR (KBr): 2937, 1702, 1606, 1473, 1405, 1369, 1268, 1241, 1176 cm$^{-1}$

MASS (m/z): 434 (M+H$^+$)

Preparation 447

MASS (m/z): 488 (M+H$^+$)

Preparation 448

IR (KBr): 2956, 2869, 2665, 2543, 1681, 1608, 1544, 1492, 1469, 1423, 1332, 1292, 1245, 1172 cm$^{-1}$

MASS (m/z): 394 (M+H$^+$)

Preparation 449

IR (KBr): 2954, 2865, 2665, 2545, 1681, 1608, 1544, 1492, 1423, 1332, 1292, 1247, 1172 cm$^{-1}$

NMR (DMSO-d$_6$, δ): 0.91 (3 H, t, J=6.8 Hz), 1.3–1.5 (4 H, m), 1.6–1.8 (2 H, m), 4.00 (2 H, t, J=6.8 Hz), 6.99 (2 H, d, J=8.8 Hz), 7.82 (2 H, d, J=8.8 Hz), 8.11 (4 H, s), 8.69 (1 H, s)

MASS (m/z): 408 (M+H$^+$)

Preparation 450

IR (KBr): 2933, 2865, 2667, 2545, 1681, 1608, 1544, 1492, 1469, 1423, 1332 cm$^{-1}$

MASS (m/z): 422 (M+H$^+$)

Preparation 451

IR (KBr); 2933, 2863, 1677, 1606, 1469, 1421, 1313, 1292, 1255, 1174 cm$^{-1}$

MASS (m/z): 422 (M+H$^+$)

Preparation 452

IR (KBr): 2935, 2871, 2667, 2545, 1683, 1608, 1542, 1525, 1461, 1421, 1319, 1294, 1257, 1176 cm$^{-1}$

NMR (DMSO-d$_6$, δ): 0.91 (3 H, t, J=7.0 Hz), 1.2–1.5 (4 H, m), 1.6–1.9 (2 H, m), 4.05 (2 H, t, J=6.5 Hz), 7.09 (2 H, d, J=8.8 Hz), 7.91 (2 H, d, J=8.8 Hz), 8.09 (2 H, d, J=8.5 Hz), 8.22 (2 H, d, J=8.5 Hz), 13.3 (1 H, s)

MASS (m/z): 412 (M+H$^+$)

Preparation 453

IR (KBr): 1726.0, 1687.4, 1259.3, 1176.4 cm$^{-1}$

NMR (DMSO-d$_6$, δ): 1.23–1.44 (4 H, m), 1.85–1.96 (4 H, m), 2.10–2.40 (2 H, m), 3.58 (3 H, s), 12.08 (1 H, s)

MASS (m/z): 187 (M+1)

Preparation 454

IR (KBr): 1724.0, 1702.8, 1309.4, 1265.1 cm$^{-1}$

NMR (DMSO-d$_6$, δ): 2.49 (6 H, s), 3.84 (3 H, s), 7.70–7.72 (2 H, m), 13.14 (1 H, bs)

Preparation 455

IR (KBr): 1727.9, 1675.8, 1232.3 cm$^{-1}$

NMR (DMSO-d$_6$, δ): 3.70 (3 H, s), 6.24–6.51 (2 H, m), 7.24–7.26 (2 H, m), 12.66 (1 H, bs)

MASS (m/z): 157 (M+1)

Preparation 456

IR (KBr): 1726.0, 1685, 1286.3, 1251.6 cm$^{-1}$

NMR (DMSO-d$_6$, δ): 3.98 (3 H, s), 7.68–7.77 (2 H, m), 8.11 (2 H, s), 8.64–8.82 (2 H, m), 13.58 (1 H, bs)

MASS (m/z): 231 (M+1)

Preparation 457

IR (KBr): 1724.0, 1697.1, 1290.1, cm$^{-1}$

NMR (DMSO-d$_6$, δ): 3.95 (3 H, s), 8.04–8.08 (2 H, m), 8.20–8.27 (2 H, m), 8.68–8.71 (2 H, m)

MASS (m/z): 231 (M+1)

Preparation 458

To a solution of 1-hydroxybenzotriazole (244 mg) and 4-[5-(4-pentyloxyphenyl)isoxazol-3-yl]benzoic acid (528 mg) in dichloromethane (10 ml) was added 1-ethyl-3-(3'-dimethylaminopropyl)carbodiimide hydrochloride (WSCD•HCl) (430 mg) and the mixture was stirred for 4.5 hours at ambient temperature. The reaction mixture was added to water. The organic layer was taken and dried over magnesium sulfate. Magnesium sulfate was filtered off, and the filtrate was evaporated under reduced pressure to give 4-[5-(4-pentyloxyphenyl)isooxazol-3-yl]benzoic acid benzotriazol-1-yl ester (640 mg).

IR (KBr): 1776.1, 1253.5, 1234.2, 1002.8 cm$^{-1}$

NMR (CDCl$_3$, δ): 0.95 (3 H, t, J=7.0 Hz), 1.2–1.6 (4 H, m), 1.6–1.9 (2 H, m), 4.03 (2 H, t, J=6.5 Hz), 6.81 (1 H, s), 7.01 (2 H, d, J=8.3 Hz), 7.3–7.6 (3 H, m), 7.79 (2 H, d, J=8.3 Hz), 8.11 (2 H, d, J=8.0 Hz), 8.12 (1 H, d, J=8.2 Hz), 8.39 (2 H, d, J=8.0 Hz)

The starting compounds (459) to (461) used and the Object Compounds (459) to (461) obtained in the following Preparations 459 to 461 are given in the table as below, in which the formula of the starting compounds are in the upper column and the formula of the object compounds are in the lower column, respectively.

| Preparation No. | Formula |
|---|---|
| 459 | 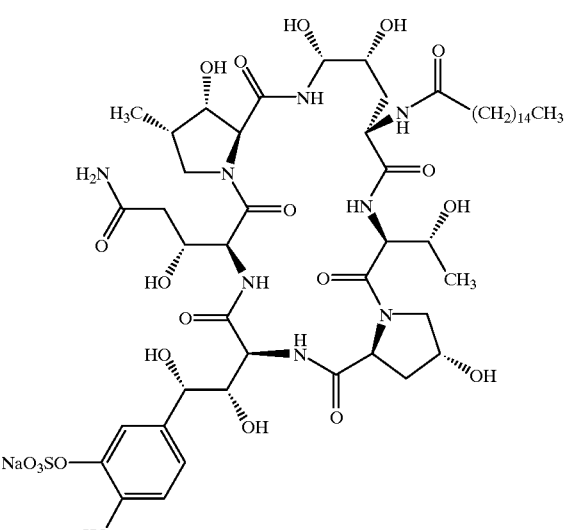 |

| Preparation No. | Formula |
|---|---|
|  | 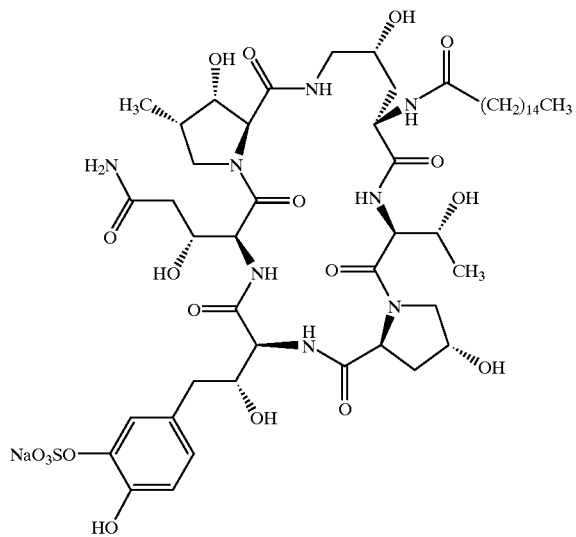 |
| 460 | 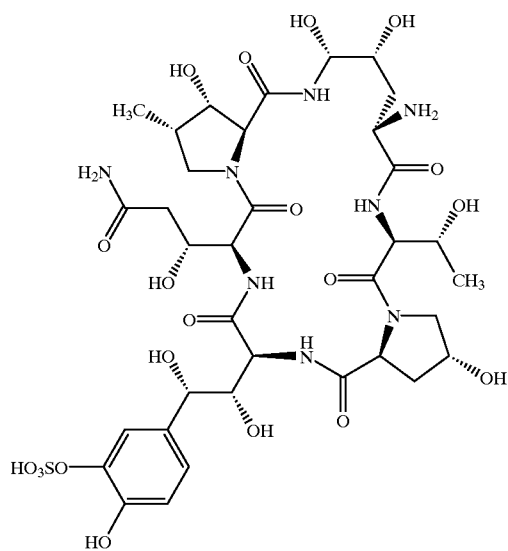 |

-continued
| Preparation No. | Formula |
|---|---|
| | 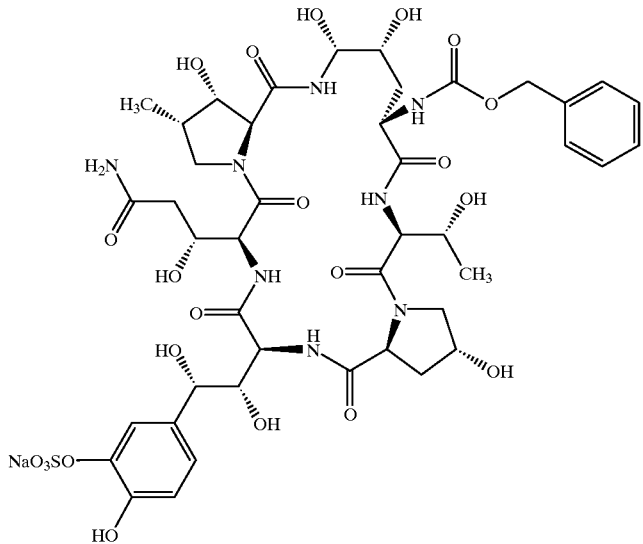 |
| 461 | 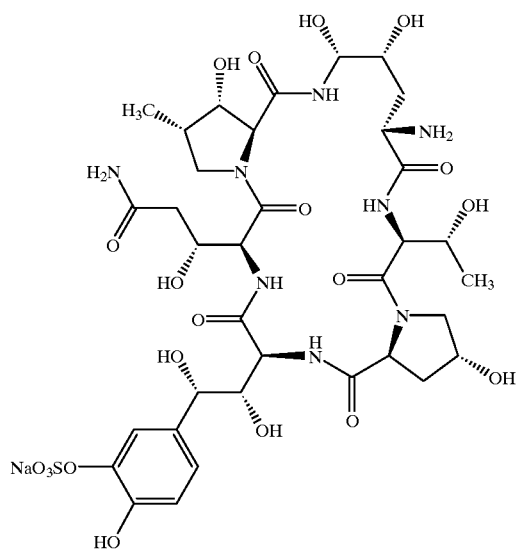 |

| Preparation No. | Formula |
|---|---|
| | 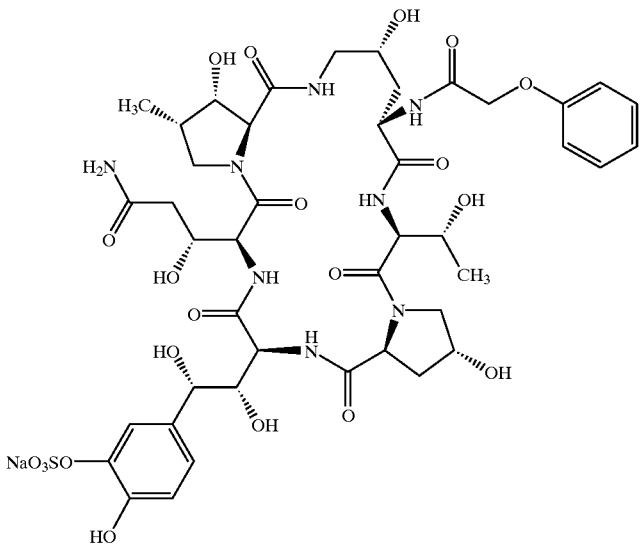 |

Preparation 459

To a suspension of Starting Compound (459) (5.0 g) and triethylsilane (6.67 ml) in dichloromethane (125 ml) was dropwise added trifluoroacetic acid (32.2 ml) with stirring under ice-cooling. The mixture was stirred at ambient temperature for 2 hours. The reaction mixture was slowly poured into pH6.68 standard buffer solution (1.2 L ) with stirring under ice-cooling adjusting pH to 8.5–10 with 1N sodium hydroxide. The mixture was evaporated in vacuo to remove the organic solvent and chromatographed on non-ionic adsorption resin, Diaion SP-205 (Trademark, prepared by Mitsubishi Chemical Industries) (400 ml) eluting in turn with water (2 L), 10% aqueous methanol (2 L), 20% aqueous methanol (2 L), 30% aqueous methanol (2 L), 50% aqueous methanol (2 L), 60% aqueous methanol (2 L) and 90% aqueous methanol (2 L). The fractions containing the desired compound were collected and evaporated in vacuo. The resulting residue was lyophilized to give Object Compound (459) (3.13 g).

NMR (DMSO-$d_6$, δ): 0.85 (3 H, t, J=7.0 Hz), 0.96 (3 H, d, J=6.7 Hz), 1.02 (3 H, d, J=6.1 Hz), 1.24 (26 H, m), 1.35–1.50 (2 H, m), 1.55–2.50 (11 H, m), 2.80–3.30 (2 H, m), 3.60–5.40 (20 H, m), 6.60–6.80 (3 H, m), 6.85–7.75 (5 H, m), 8.00–8.15 (2 H, m), 8.71 (1 H, broad S)

APCI MASS (m/z): 1141.1 ($M^+$–Na)

Preparation 460

A solution of Starting Compound (460) (100 g) in a mixture of tetrahydrofuran (1 L) and pH6.86 standard buffer solution (1 L) was dropwise added benzyloxycarbonyl chloride (16.8 ml) at 5–10° C. adjusting pH to 7.0–8.0 with saturated aqueous sodium hydrogen carbonate. The solution was stirred at the same conditions for 3 hours and adjusted pH to 6.0 with 1N hydrochloride. The mixture was evaporated in vacuo to remove organic solvent. The residue was passed ion exchange resin, DOWEX 50WX4 $Na^+$ type (prepared by Dow Chemical) (1 L) and washed with water (3 L). The eluate was chromatographed on reversed phase silica gel (ODS SP-120, prepared by Daiso Co., Ltd.) (2.5 L) with water (12 L), 10% aqueous methanol (12 L) and 20% aqueous methanol (12 L) successively. The fractions containing the object compound were collected, concentrated by evaporation in vacuo and lyophilized to give Object Compound (460) (76 g, yield 65%)

NMR (DMSO-$d_6$, δ): 0.96 (3 H, d, J=6.7 Hz), 1.05 (3 H, d, J=5.7 Hz), 1.60–2.50 (7 H, m), 3.10–5.20 (29 H, m), 6.73 (1 H, d, J=8.2 Hz), 6.75–6.90 (2 H, m), 6.90–7.10 (2 H, m), 7.20–7.40 (7 H, m), 7.63 (1 H, d, J=7.8 Hz), 8.00–8.15 (2 H, m)

ESI MASS (Negative): 1069.3 ($M^+$–Na)

Preparation 461

To a solution of Starting Compound (461) (30 g) and sodium cyanoborohydride (3.45 g) in dichloromethane (300 ml) was dropwise added trifluoroacetic acid (150 ml) with stirring under in ice-cooling. The mixture was stirred at the same condition for 3 hours. The reaction mixture was slowly poured into pH6.86 standard buffer solution (1.2 L) with stirring on ice-sodium chloride bath adjusting pH to 8.5–10 with 1N sodium hydroxide. An aqueous layer was separated and cooled at refrigerator overnight. The aqueous solution was evaporated in vacuo to remove organic solvent and chromatographed on reversed phase silica gel (ODS SP-120, prepared by Daiso Co., Ltd.) (700 ml) eluting with water (5 L) and 5% aqueous methanol (6 L) successively. The fractions containing the object compound were collected, concentrated by evaporation in vacuo and lyophilized to give Object Compound (461) (17.3 g)

NMR(DMSO-$d_6$, δ): 0.95 (3 H, d, J=6.7 Hz), 1.07 (3 H, d, J=5.7 Hz), 1.40–2.45 (7 H, m), 2.85–3.30 (2 H, m), 3.60–4.50 (13 H, m), 4.60–5.35 (10 H, m), 6.65–7.10 (5 H, m), 7.20–7.75 (8 H, m), 7.92 (1 H, broad d, J=8.4 Hz), 8.84 (1 H, s)

ESI MASS (Negative): 1053.3 ($M^+$–Na)

The Starting Compounds (1) to (169) used and the Object Compounds (1) to (169) obtained in the following Examples 1 to 169 are given in the table as below, in which the formulas of the starting compounds are in the upper column and the formulas of the object compounds are in the lower column, respectively.

| Example No. | Formula |
|---|---|
| 1 | 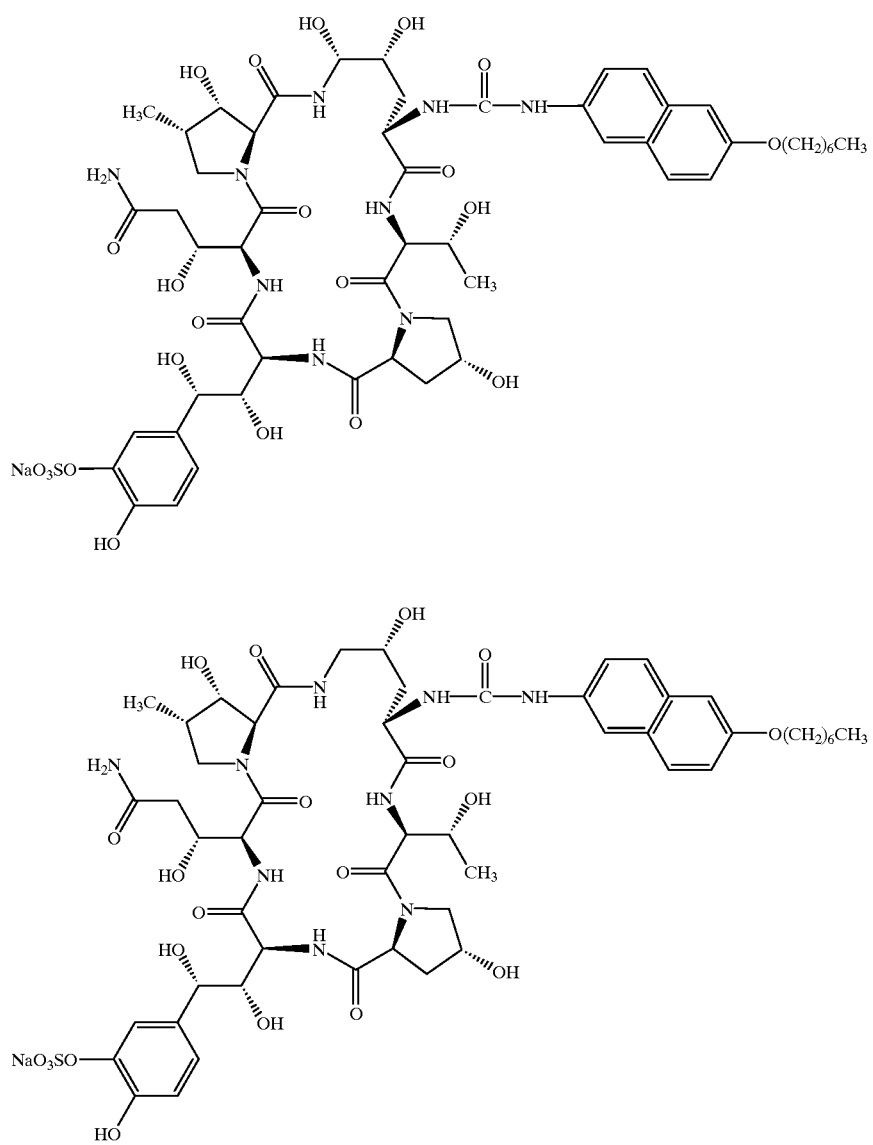 |

-continued
| Example No. | Formula |
|---|---|
| 2 | 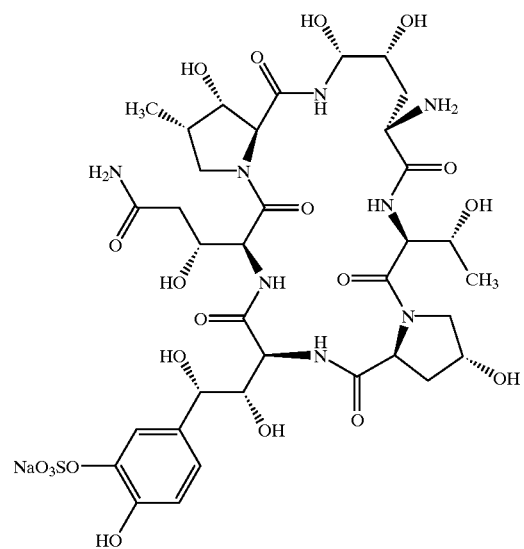 |
| | 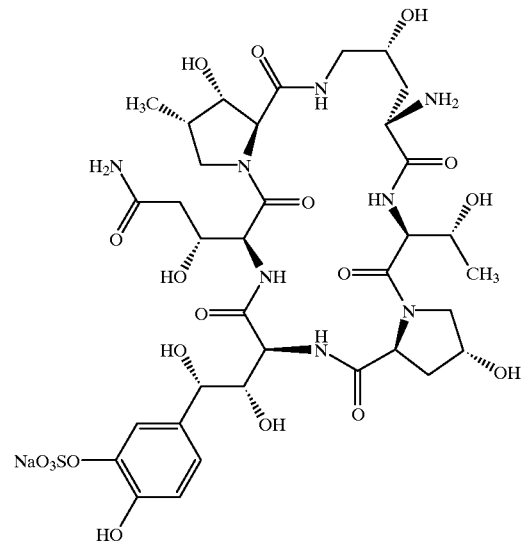 |

-continued
| Example No. | Formula |
|---|---|
| 3 | 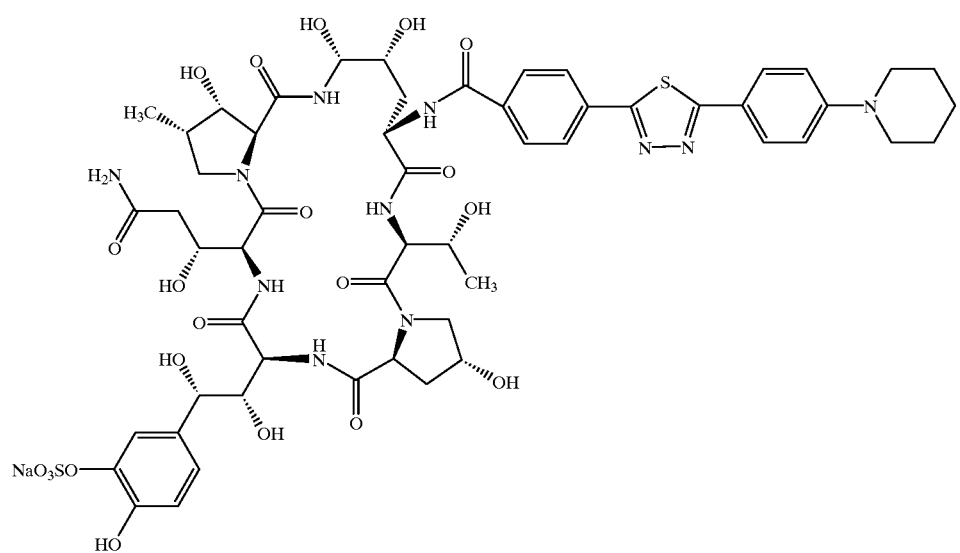 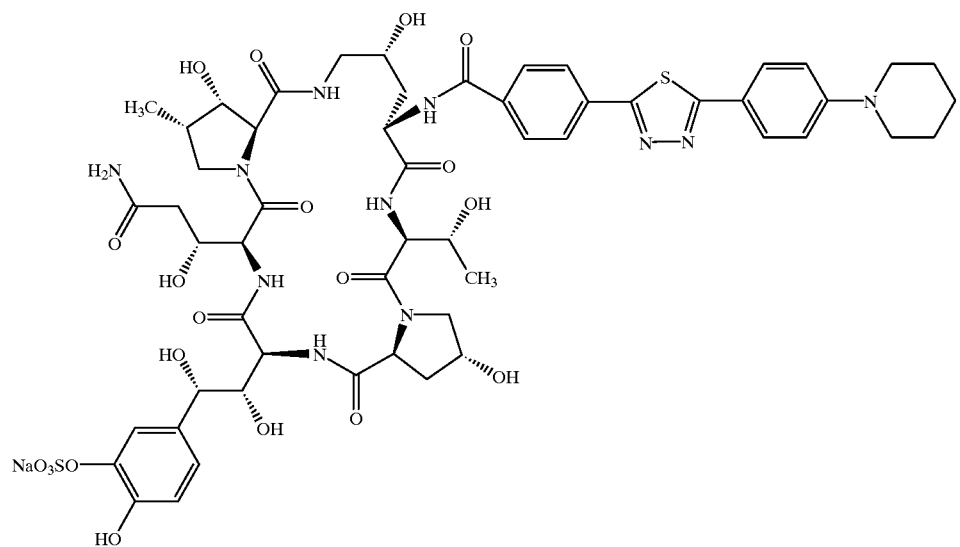 |

-continued
| Example No. | Formula |
|---|---|
| 4 | 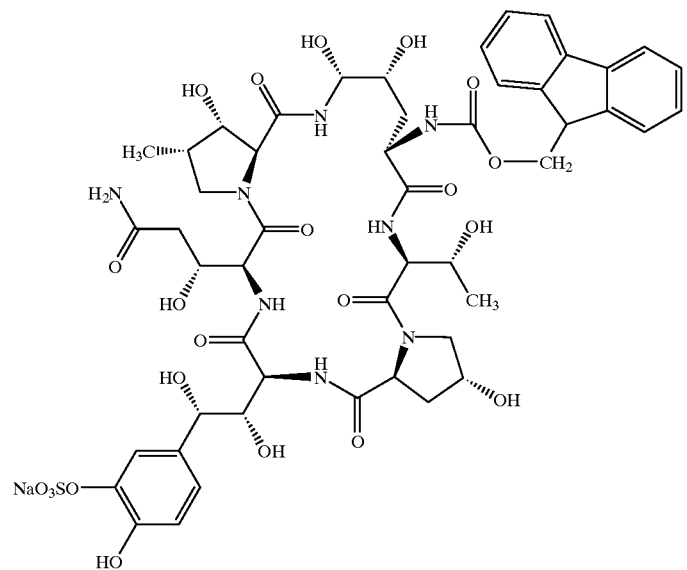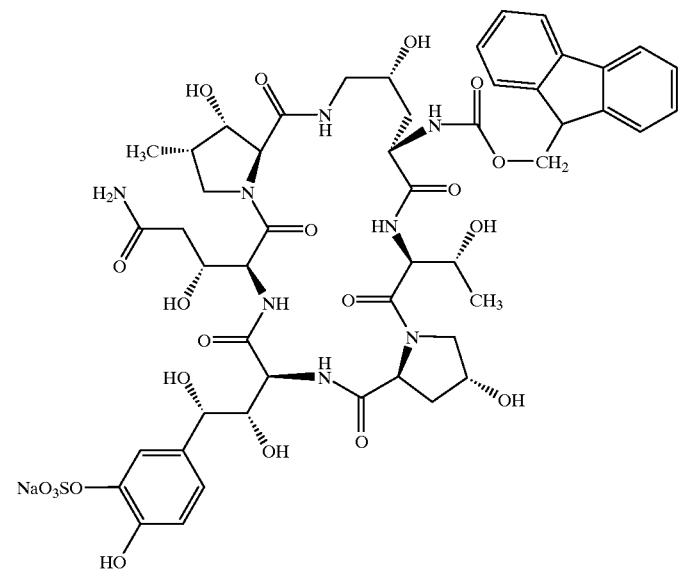 |

-continued
| Example No. | Formula |
|---|---|
| 5 | 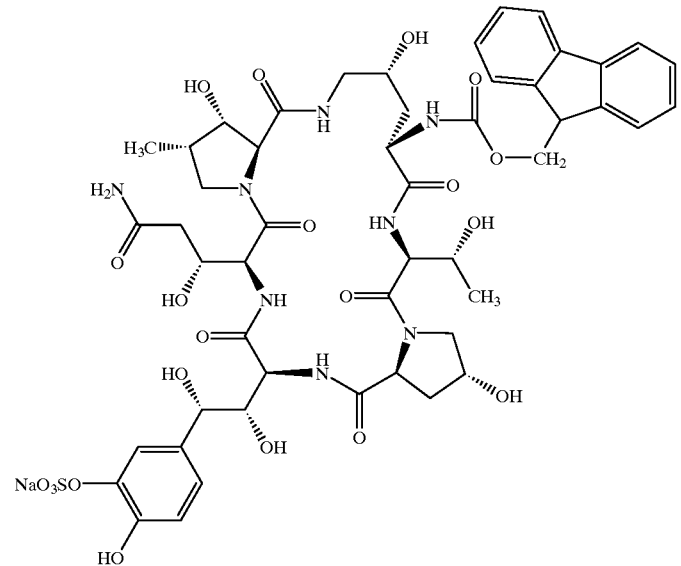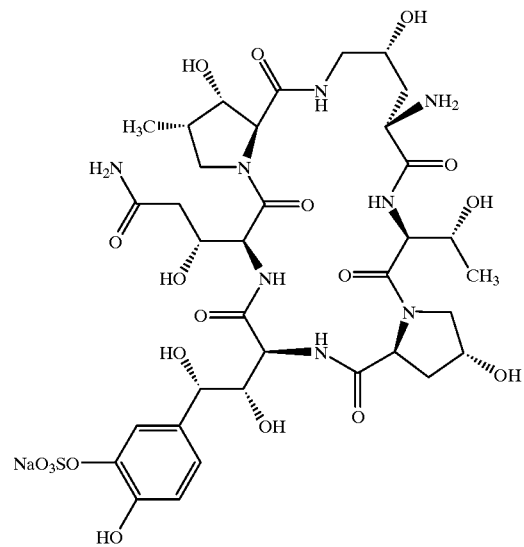 |

-continued
| Example No. | Formula |
|---|---|
| 6 | 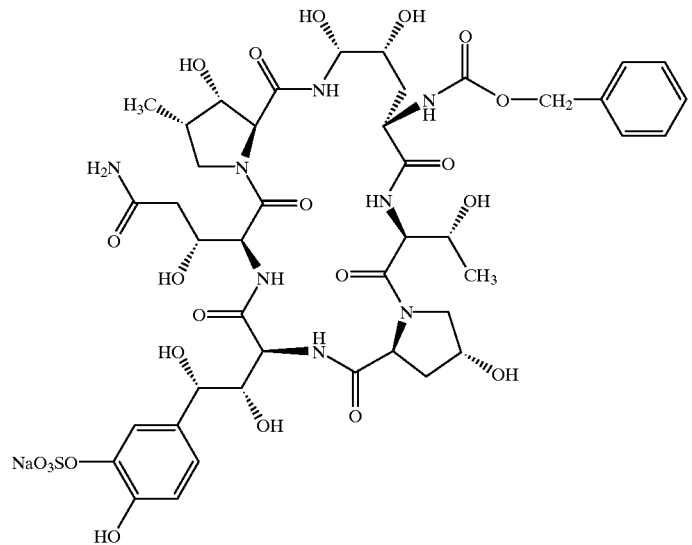 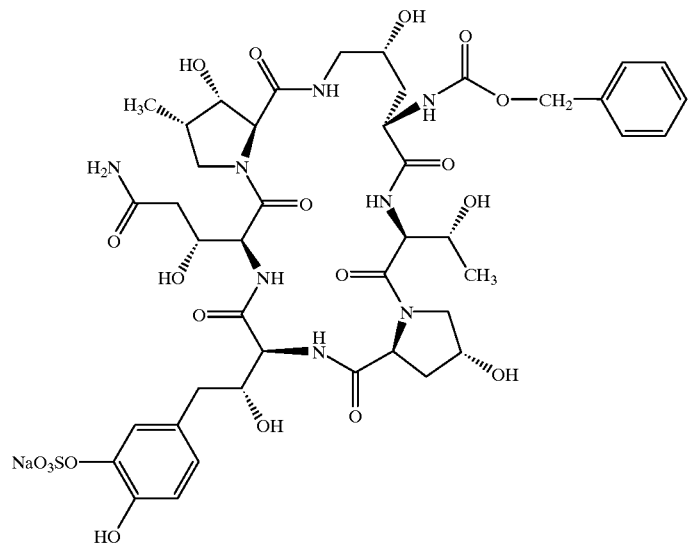 |

-continued
| Example No. | Formula |
|---|---|
| 7 | 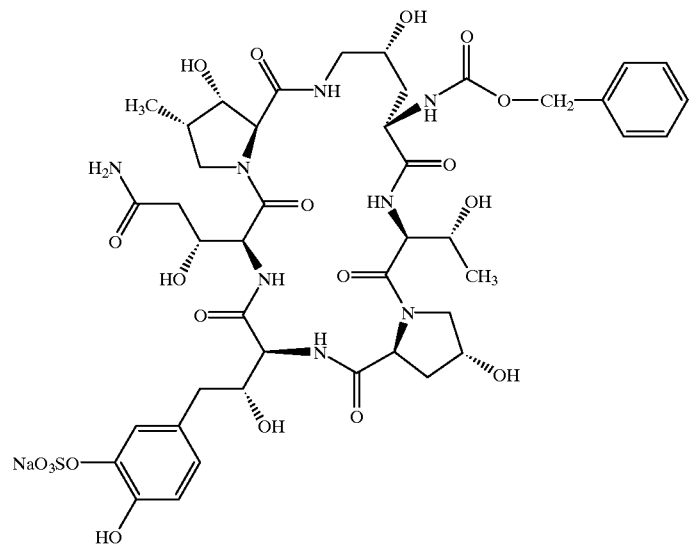 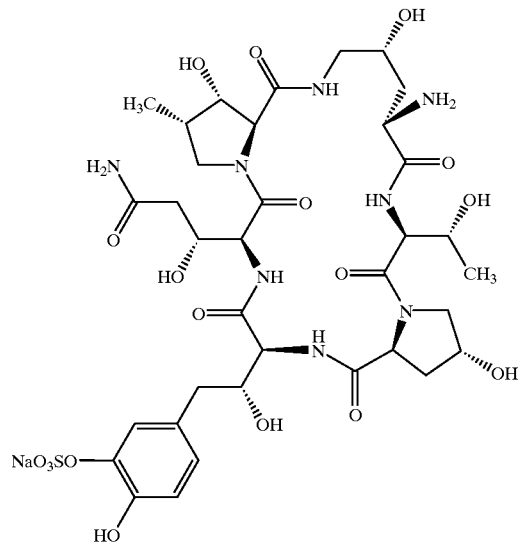 |

-continued
| Example No. | Formula |
|---|---|
| 8 | 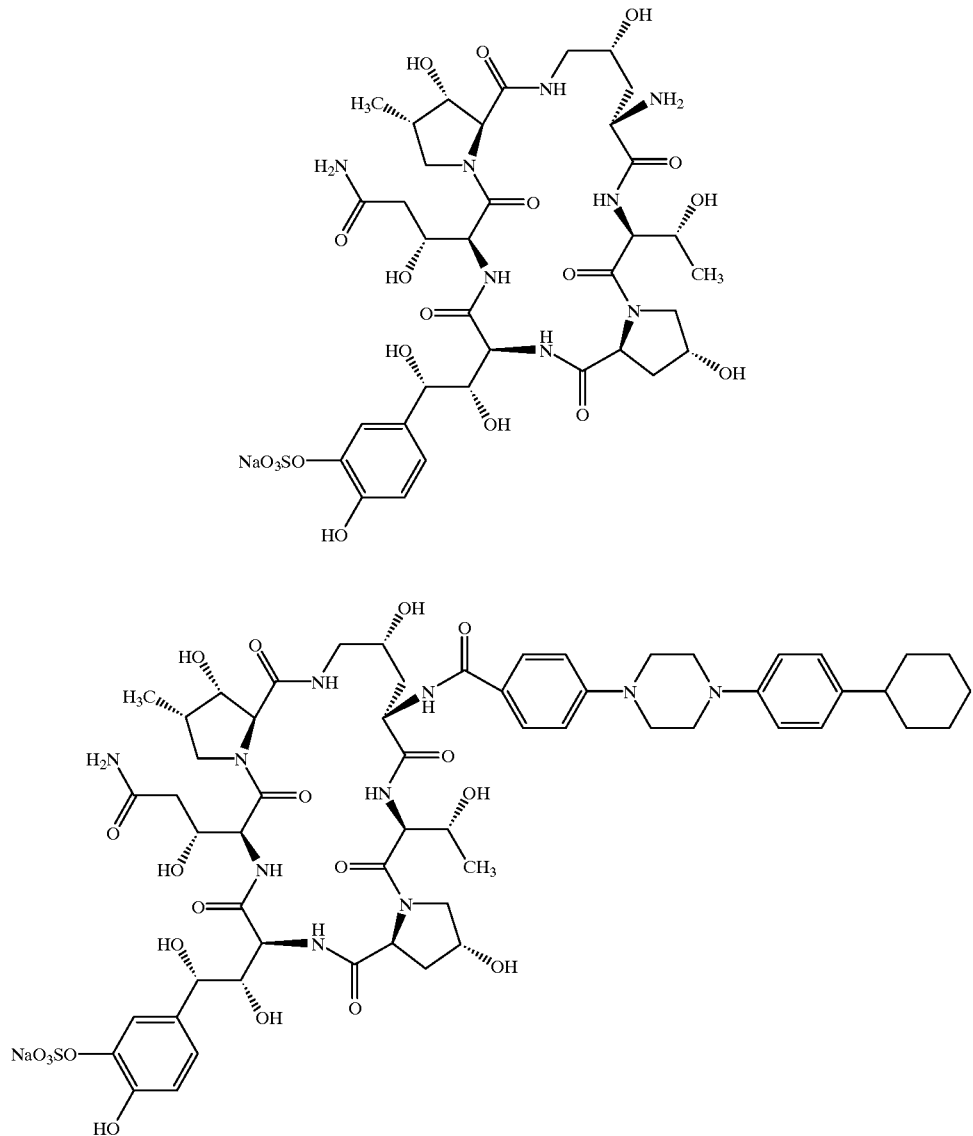 |

| Example No. | Formula |
|---|---|
| 9 | 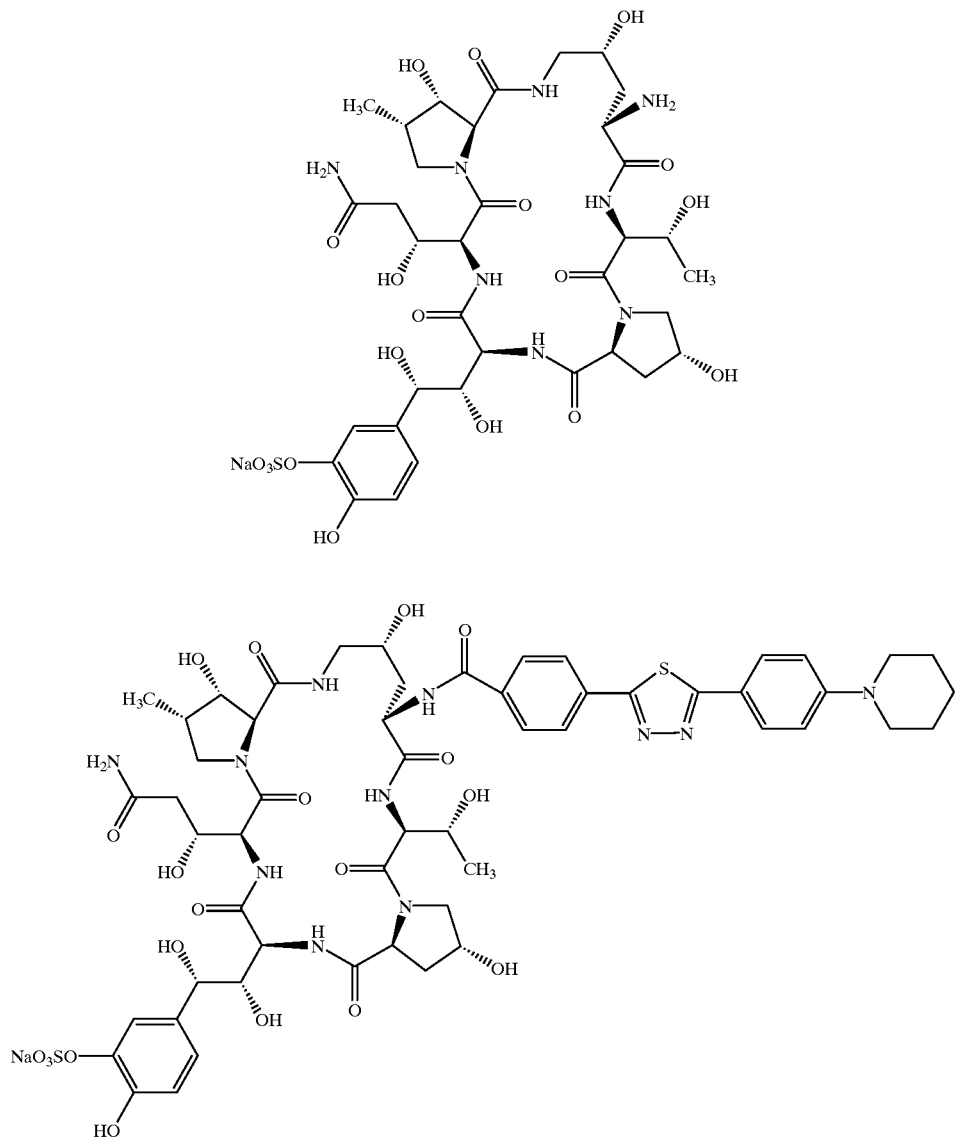 |

-continued
| Example No. | Formula |
|---|---|
| 10 | 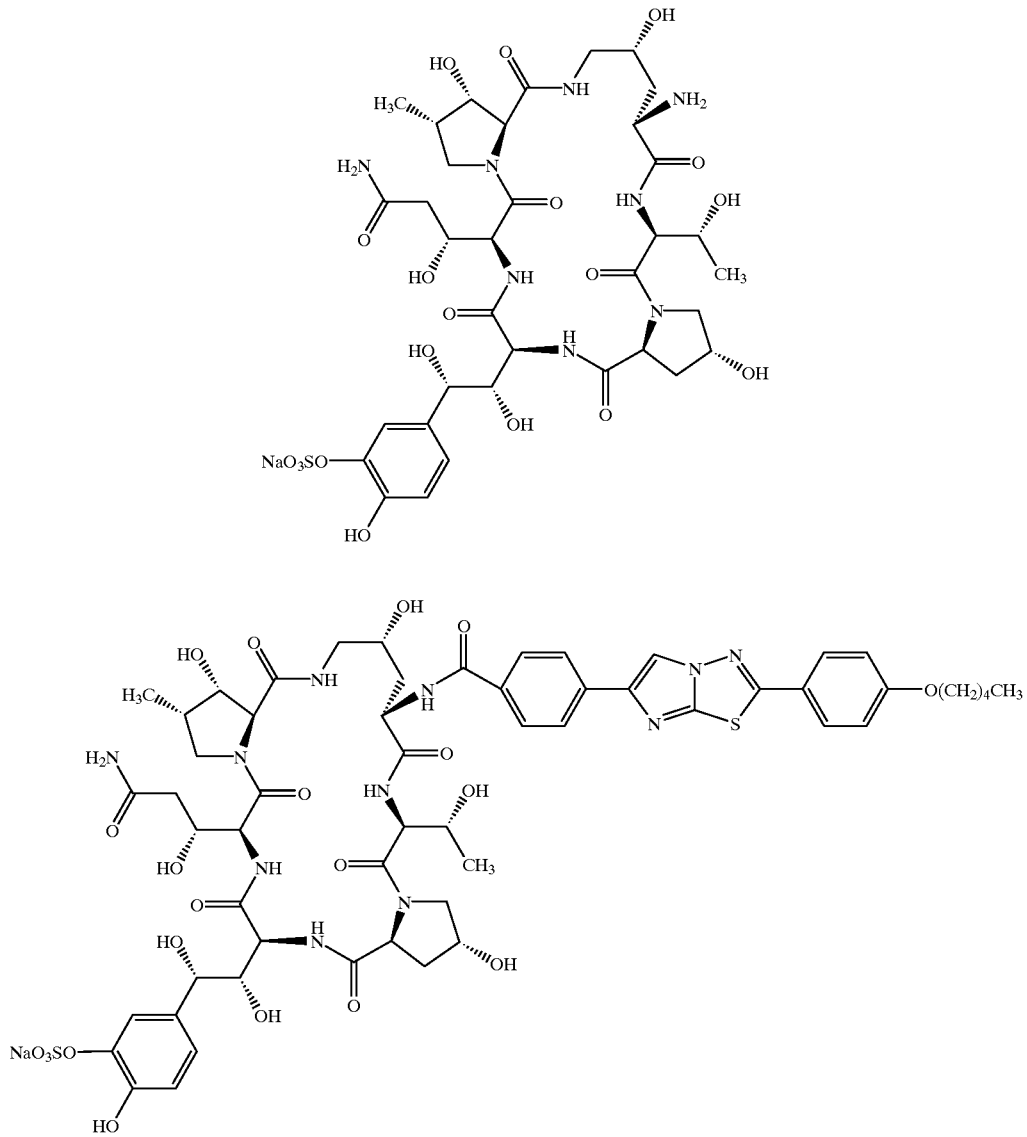 |

-continued
| Example No. | Formula |
|---|---|
| 11 | 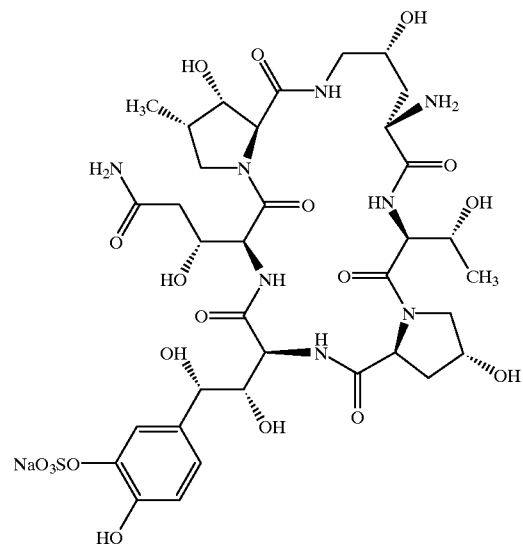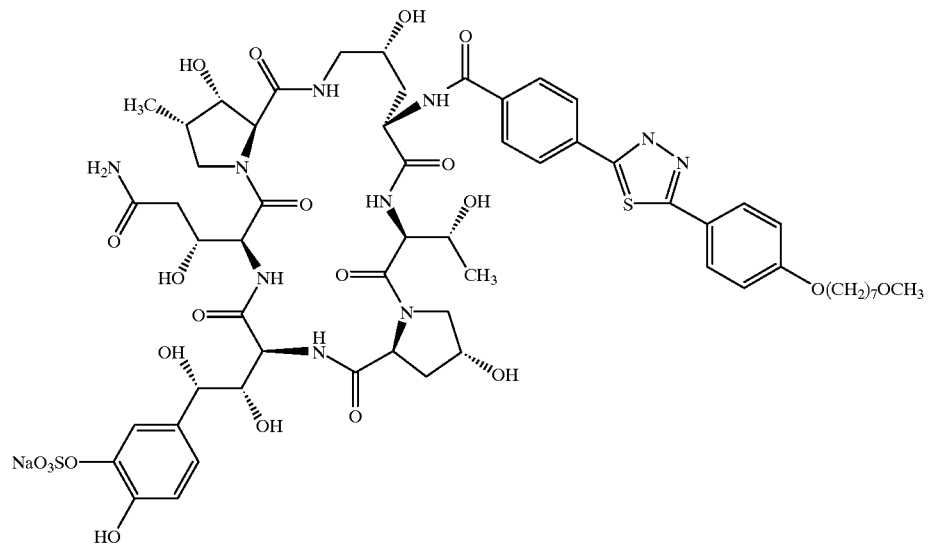 |

-continued
| Example No. | Formula |
|---|---|
| 12 | 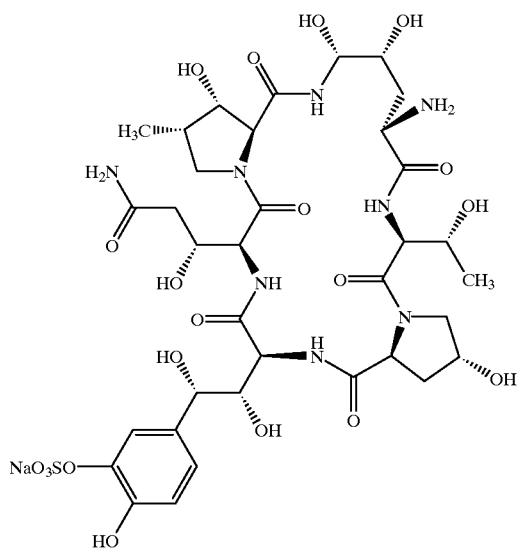 |
| | 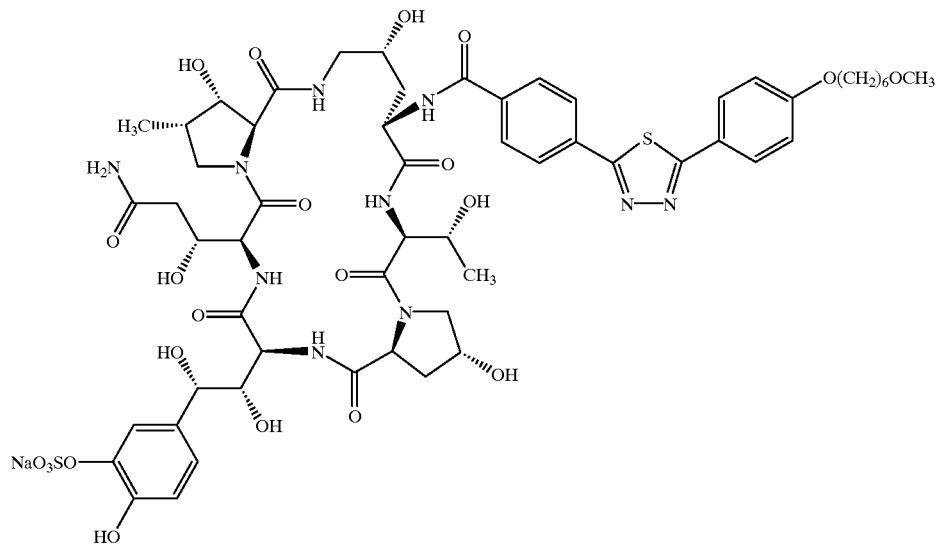 |

-continued
| Example No. | Formula |
|---|---|
| 13 | 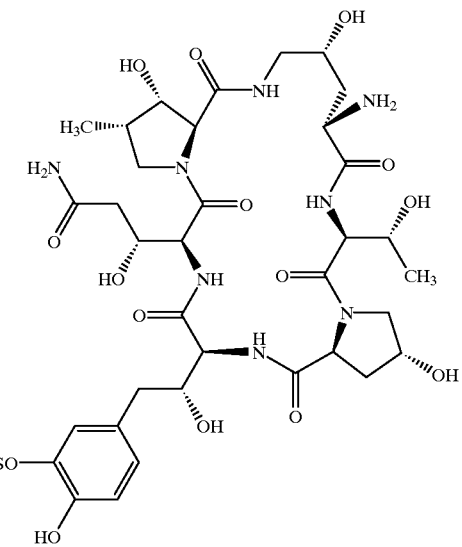 |
| | 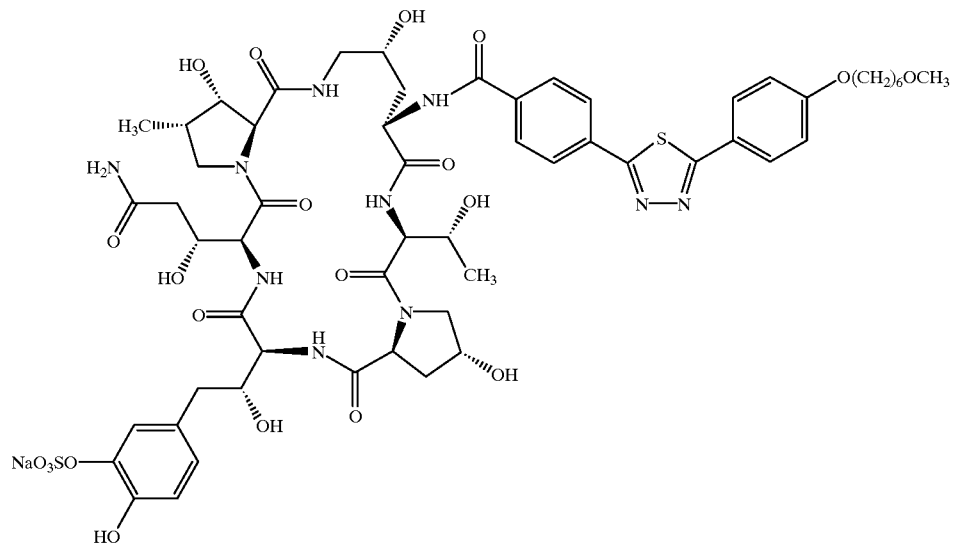 |

| Example No. | Formula |
|---|---|
| 14 | 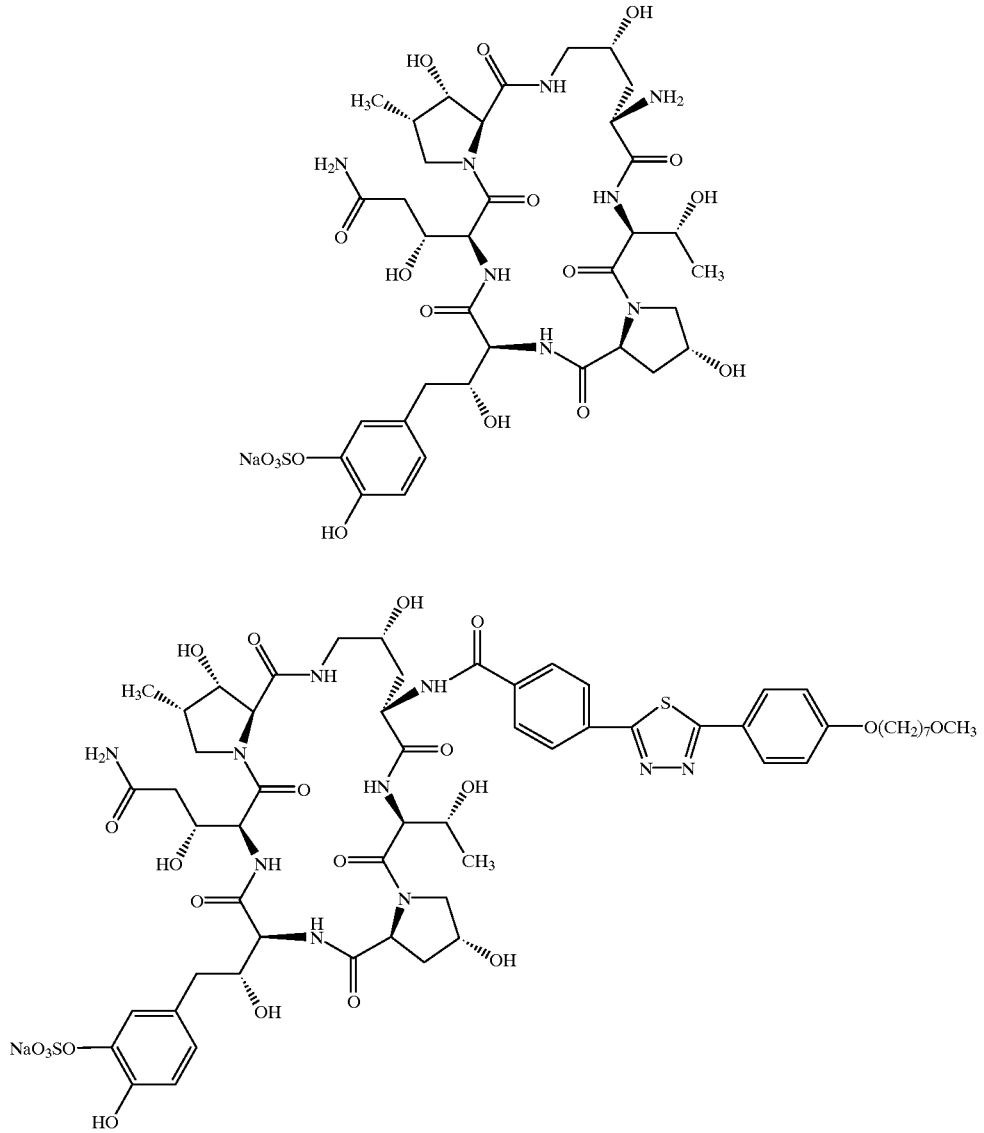 |

-continued
| Example No. | Formula |
|---|---|
| 15 | 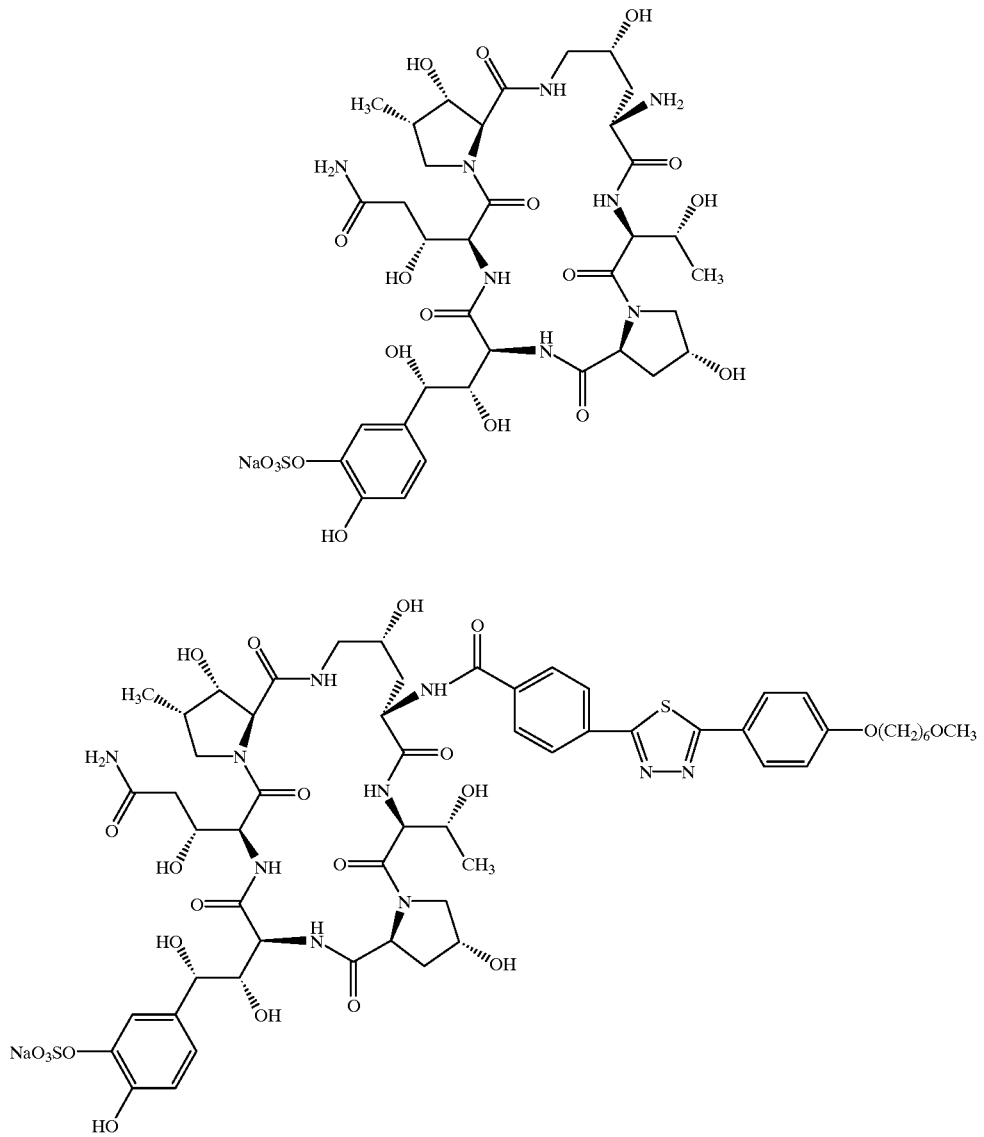 |

-continued
| Example No. | Formula |
|---|---|
| 16 | 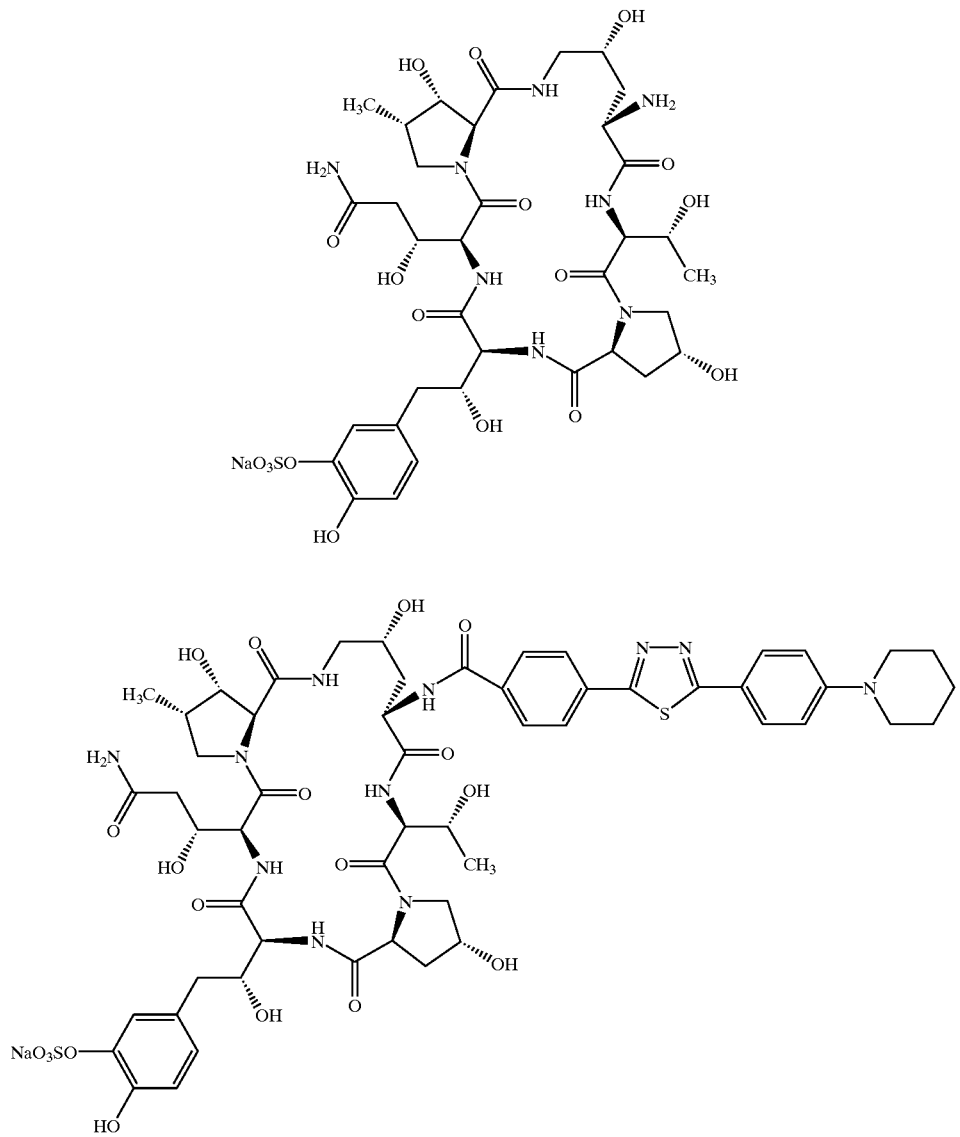 |

| Example No. | Formula |
|---|---|
| 17 | 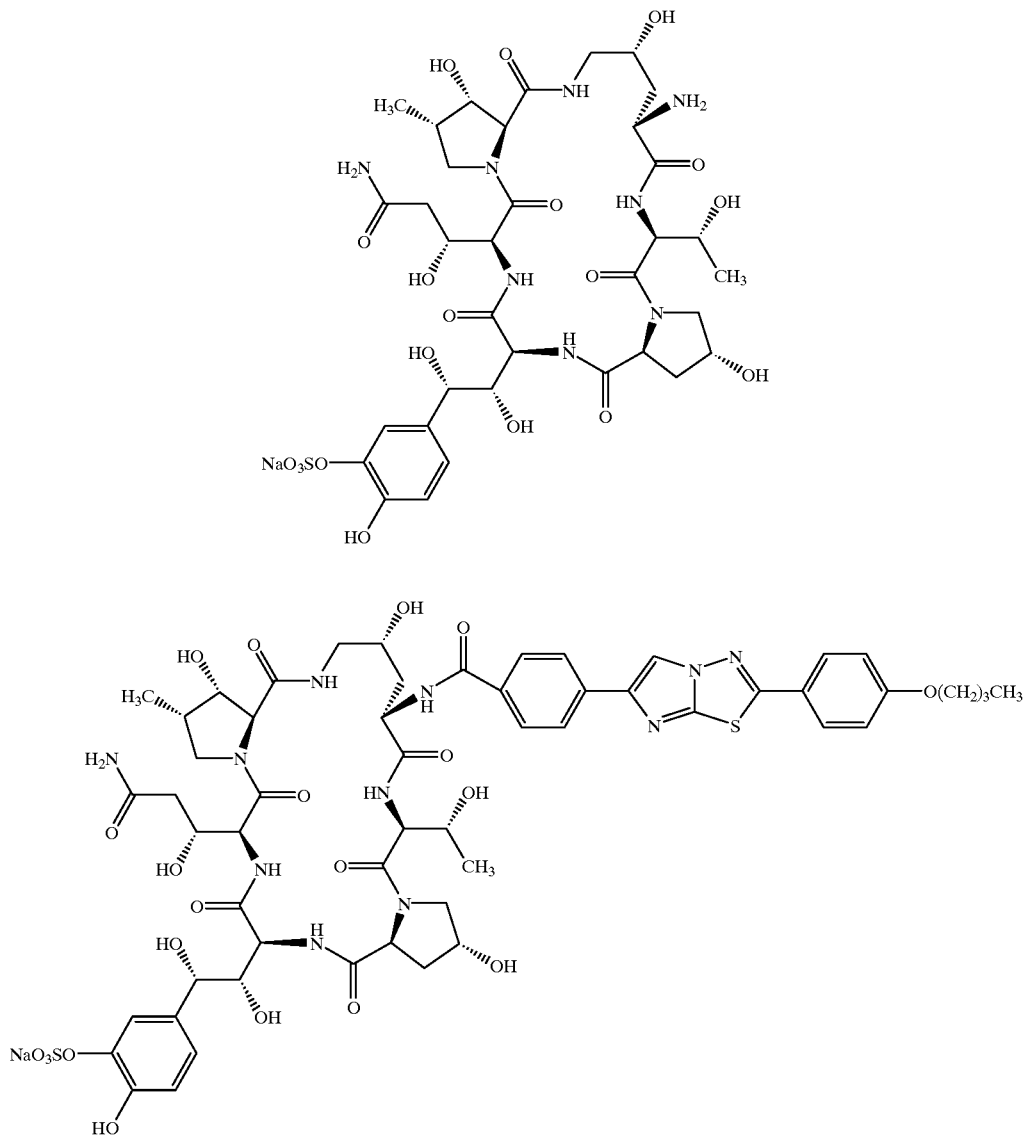 |

| Example No. | Formula |
|---|---|
| 18 | 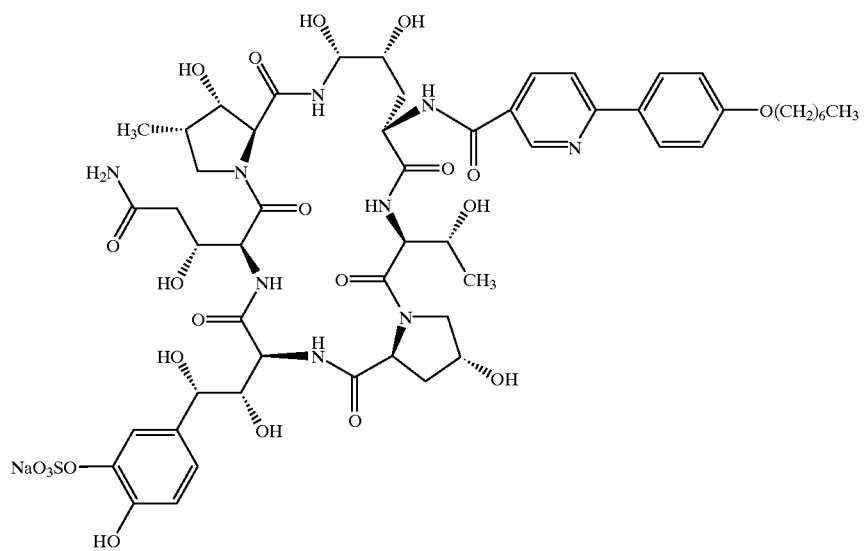 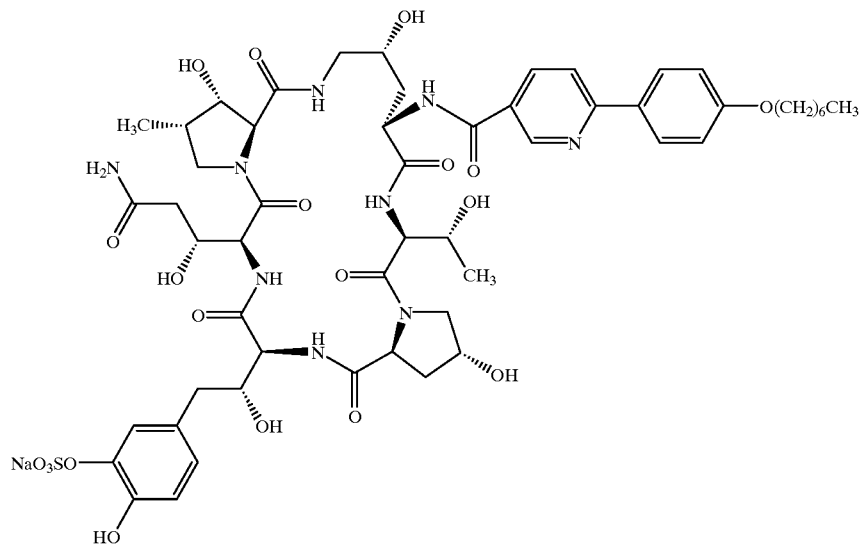 |

-continued
| Example No. | Formula |
|---|---|
| 19 | 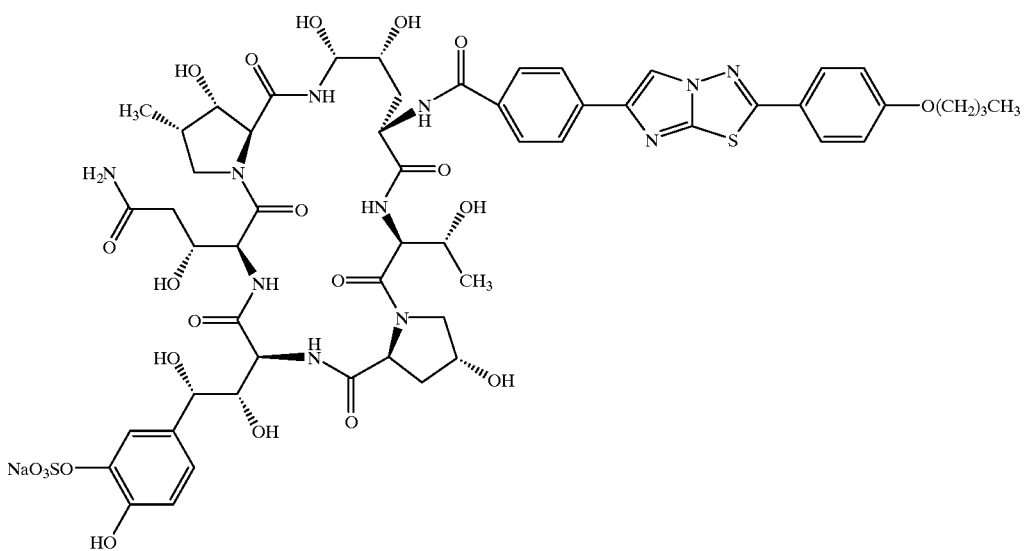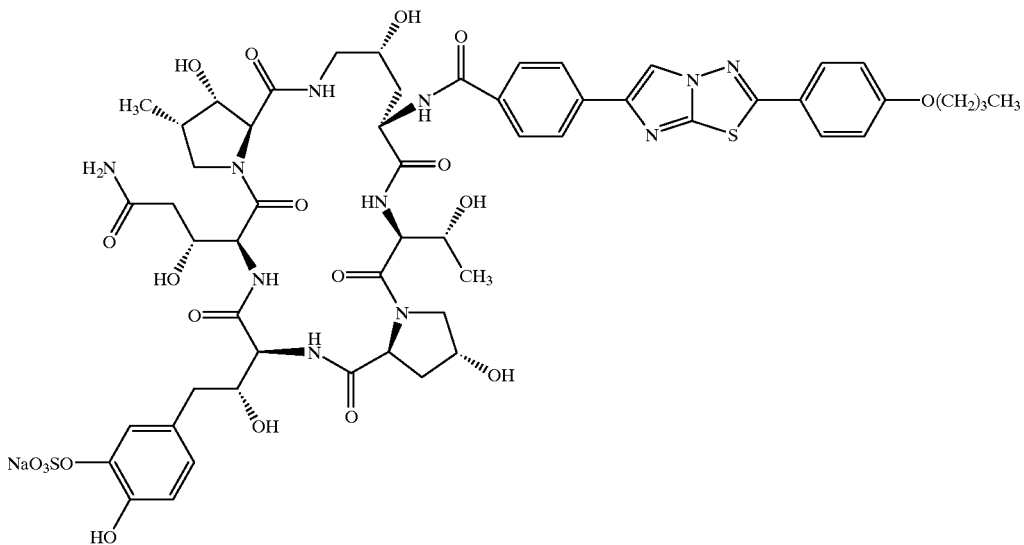 |

-continued

| Example No. | Formula |
|---|---|
| 20 | |

-continued
| Example No. | Formula |
|---|---|
| 21 | 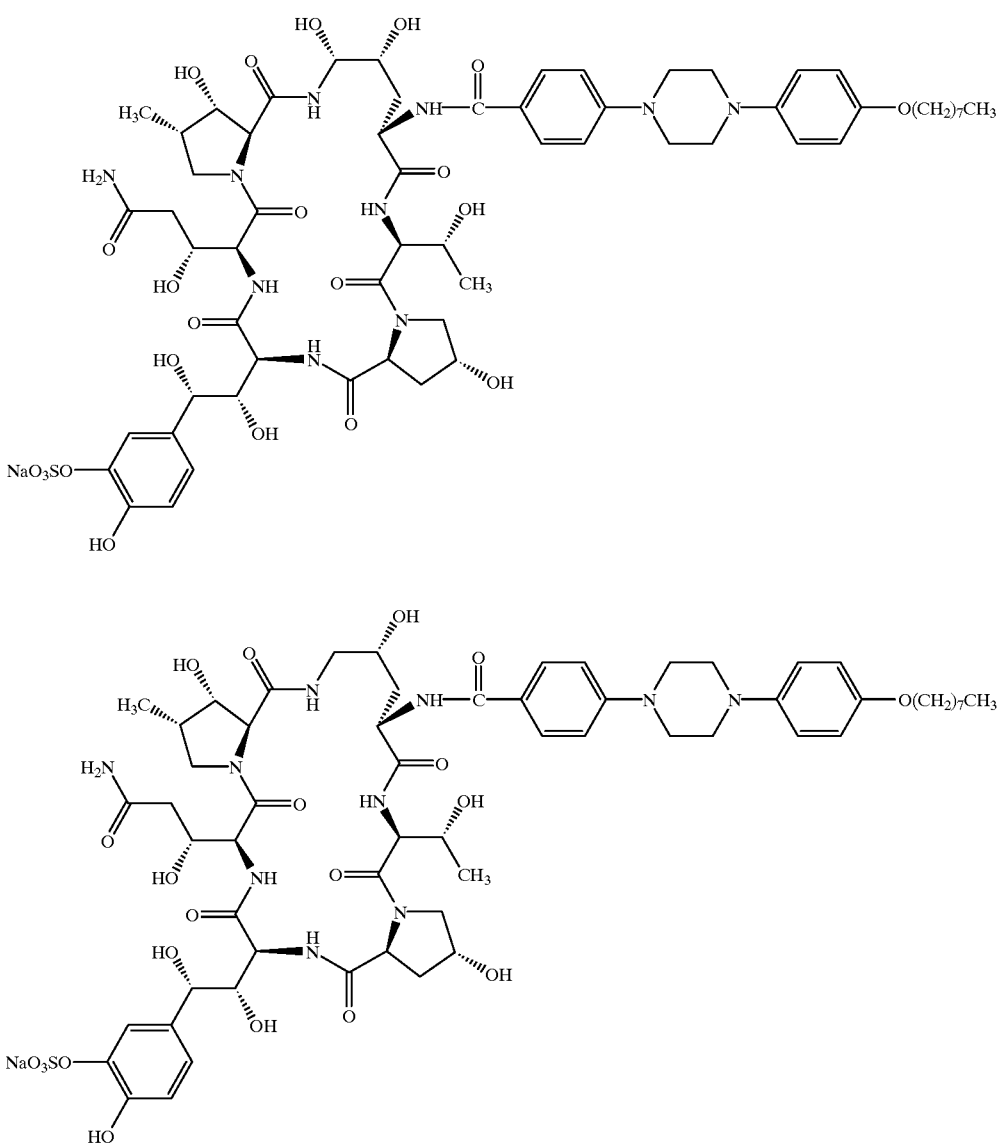 |

-continued
| Example No. | Formula |
|---|---|
| 22 | 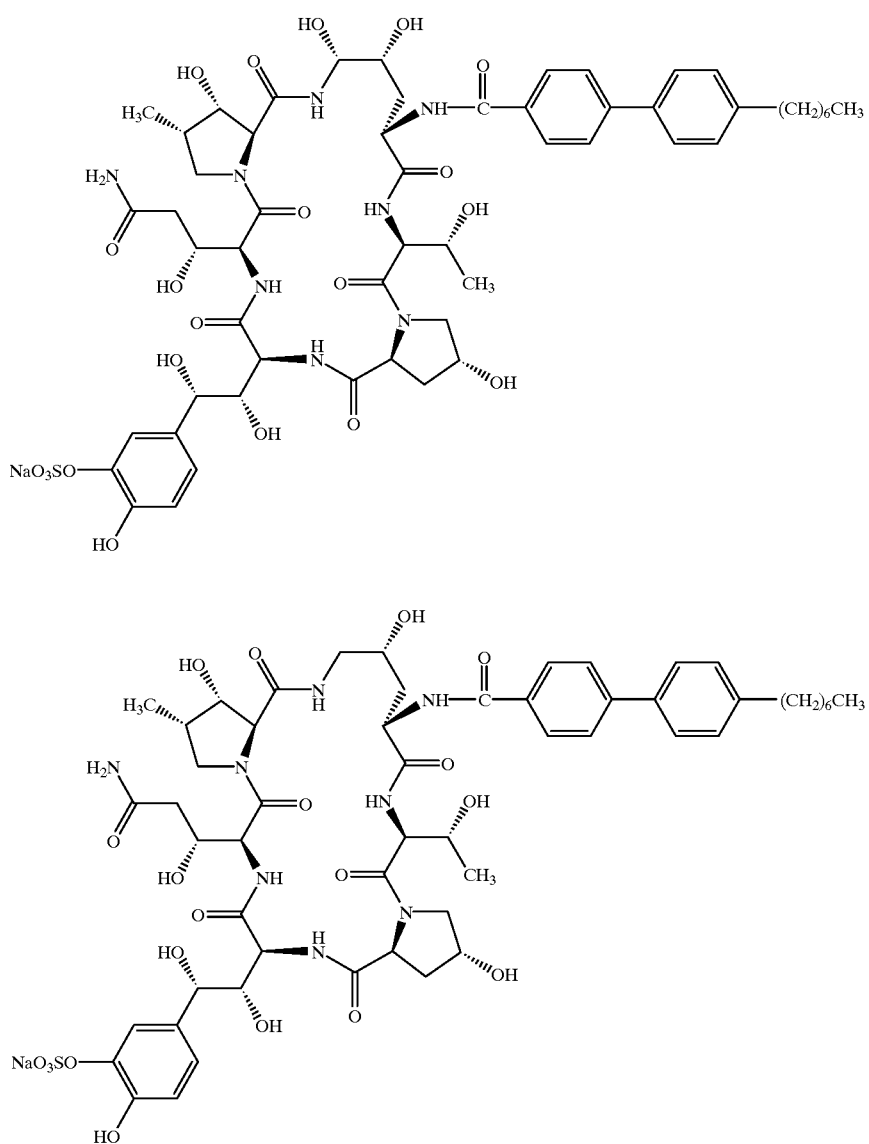 |

| Example No. | Formula |
|---|---|
| 23 | |

| Example No. | Formula |
|---|---|
| 24 | 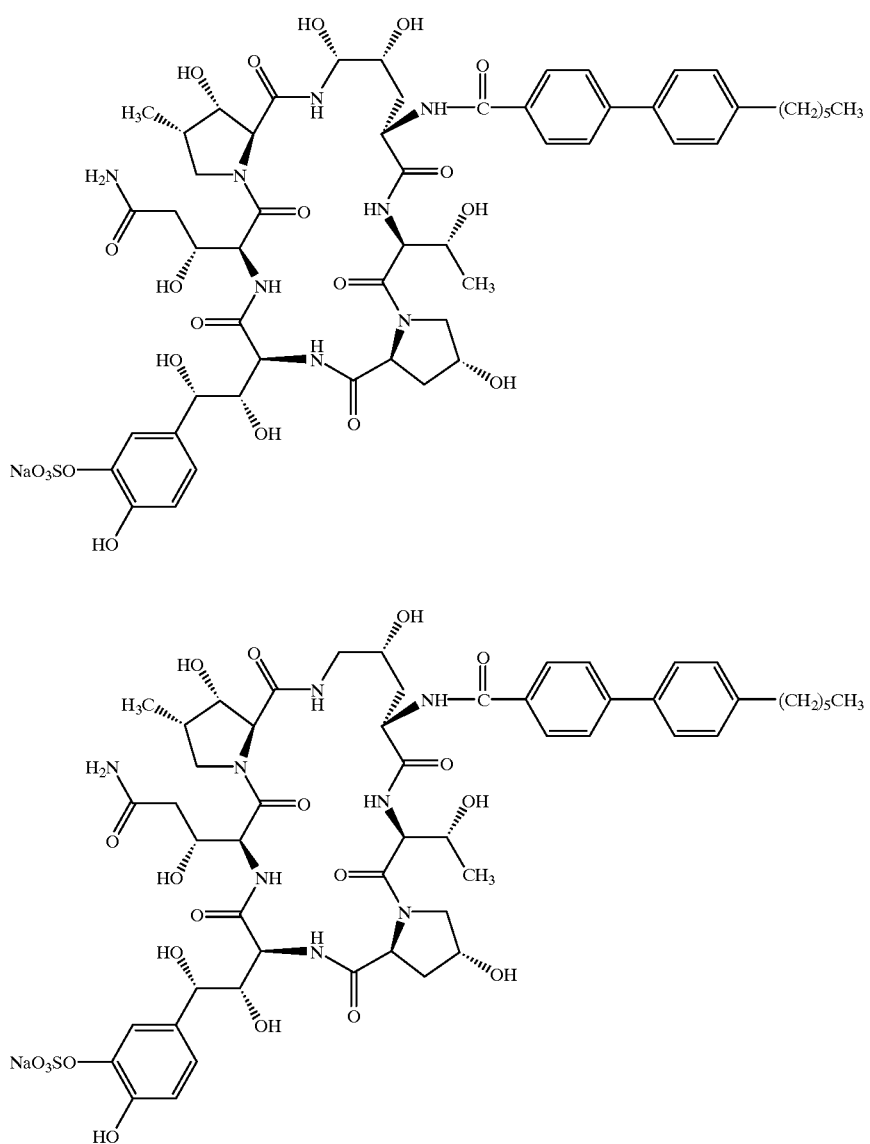 |

-continued
| Example No. | Formula |
|---|---|
| 25 | 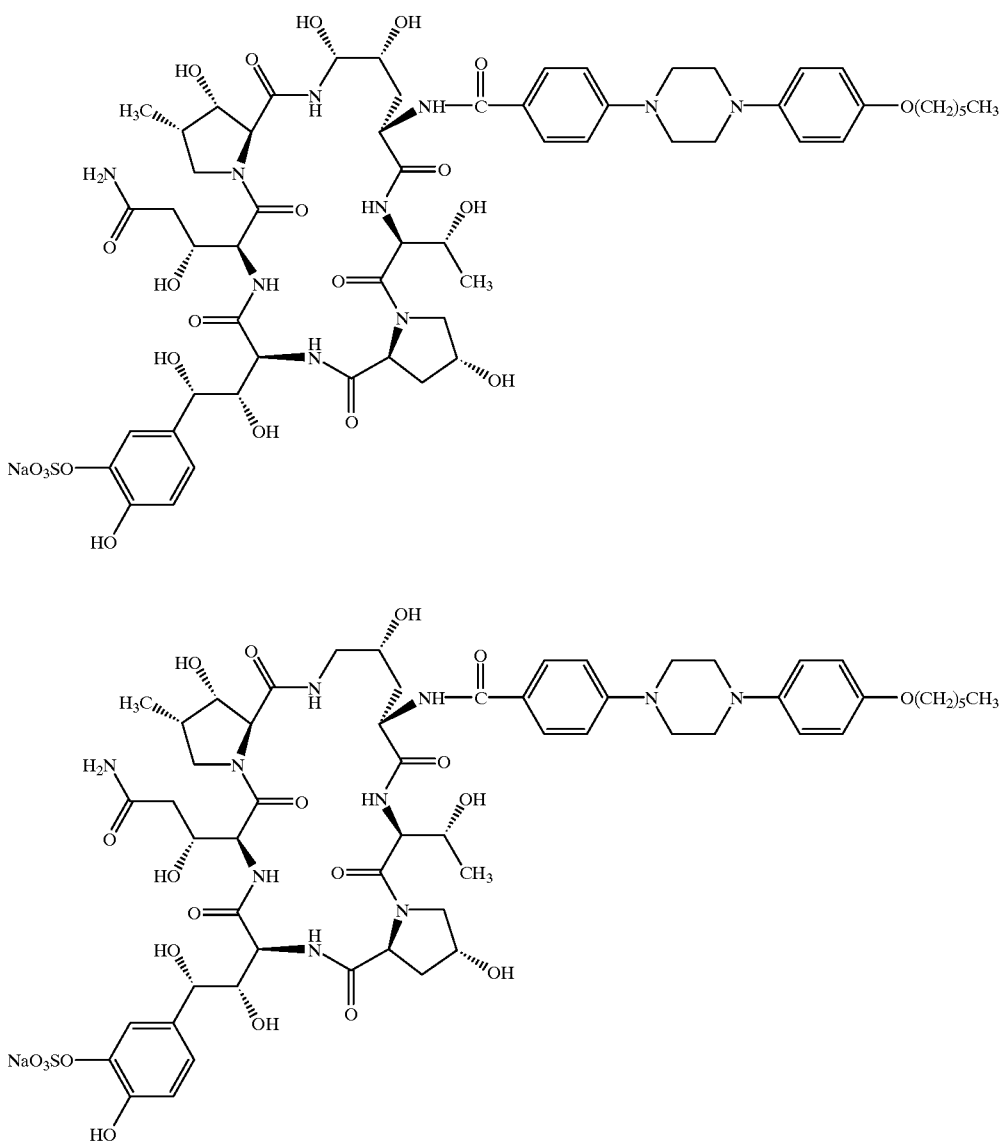 |

-continued

| Example No. | Formula |
|---|---|
| 26 | |

| Example No. | Formula |
|---|---|
| 27 | 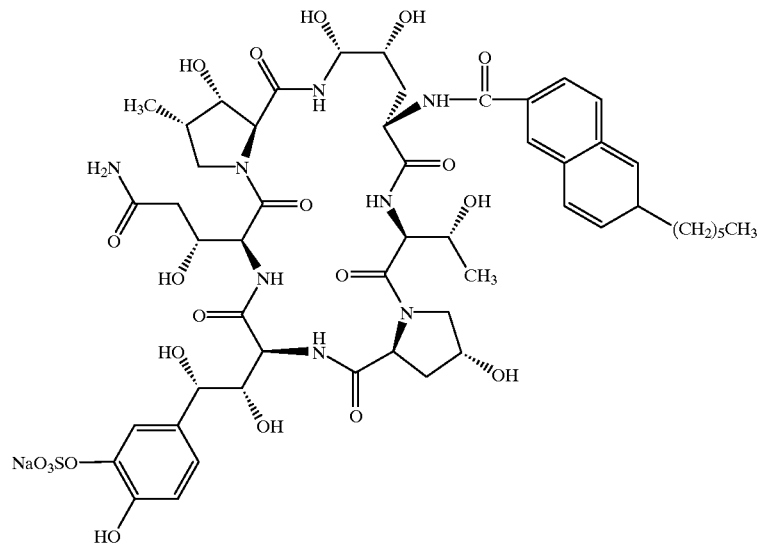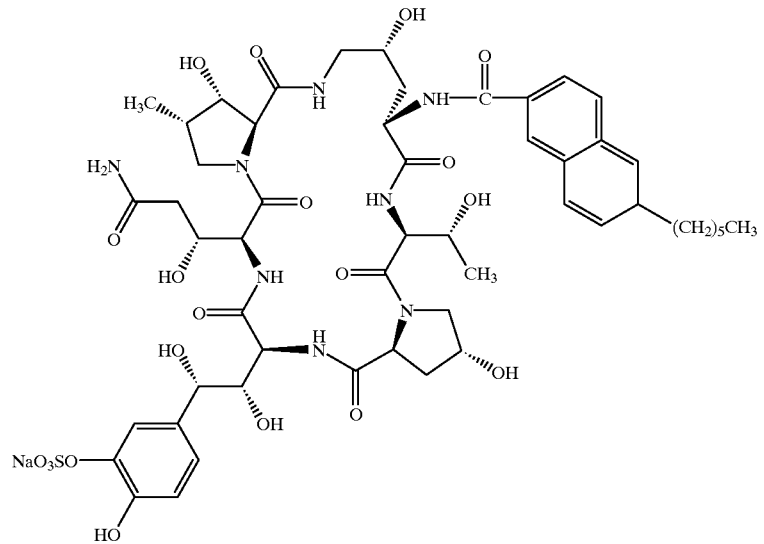 |

-continued
| Example No. | Formula |
|---|---|
| 28 | 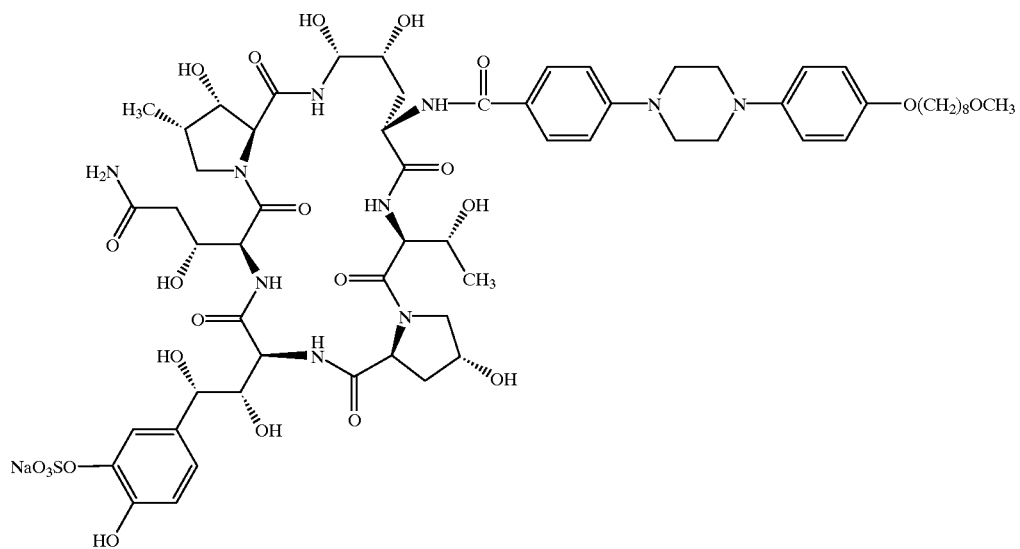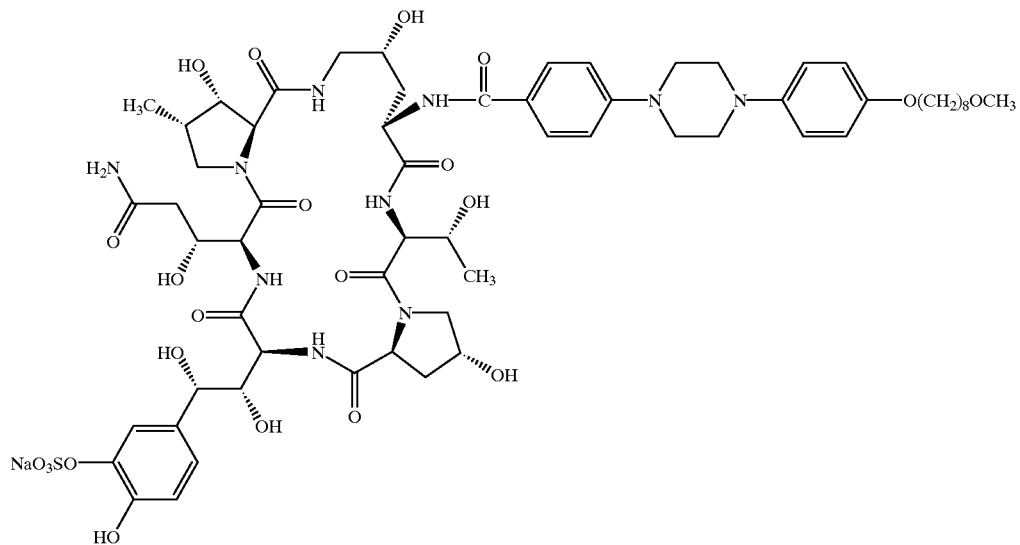 |

| Example No. | Formula |
|---|---|
| 29 | |

-continued
| Example No. | Formula |
|---|---|
| 30 | 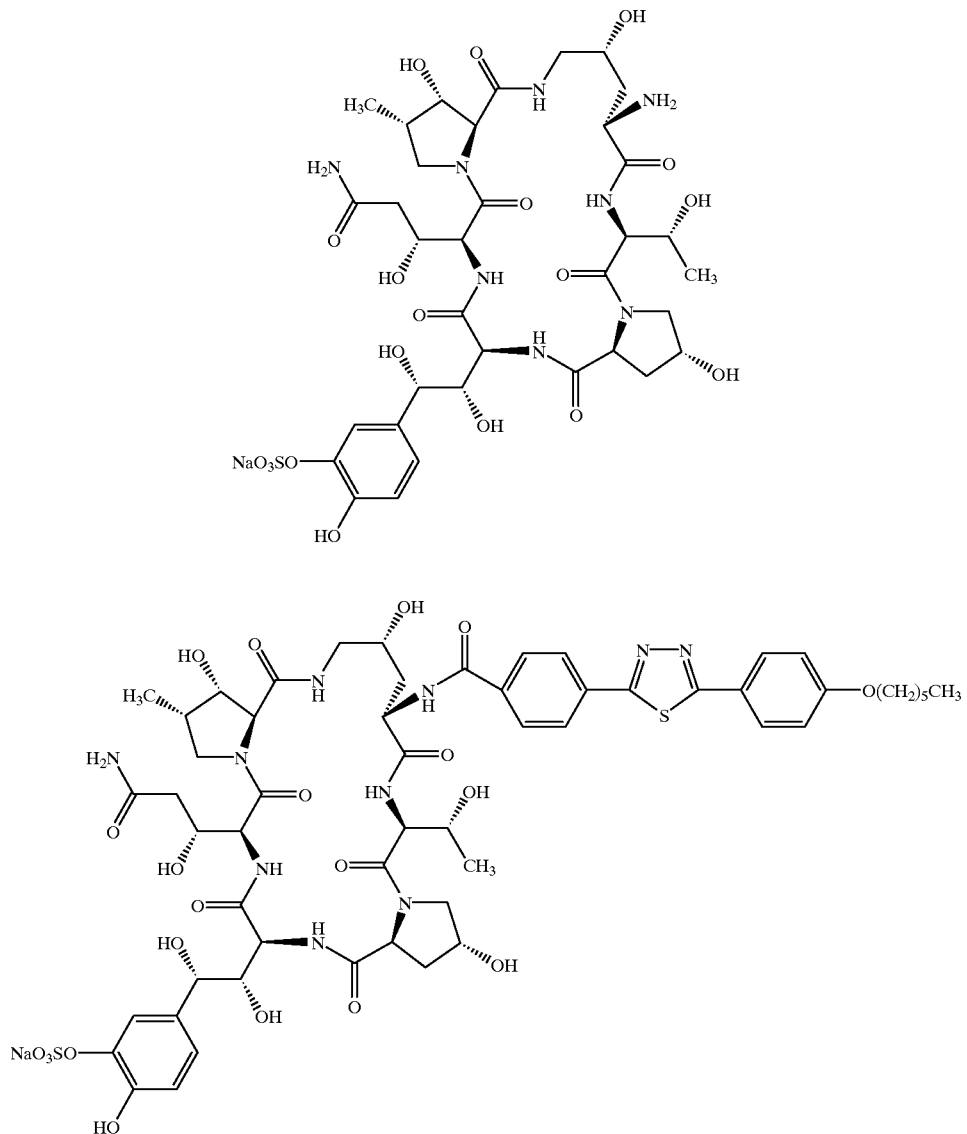 |

| Example No. | Formula |
|---|---|
| 31 | 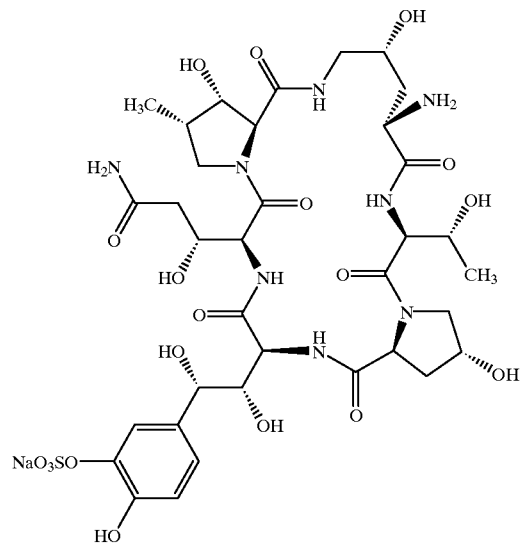 |
| | 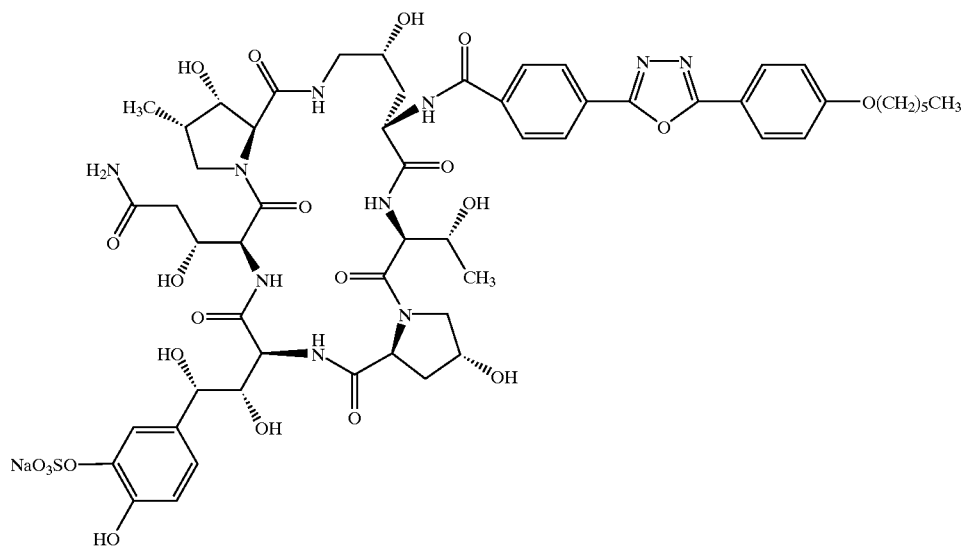 |

| Example No. | Formula |
|---|---|
| 32 | 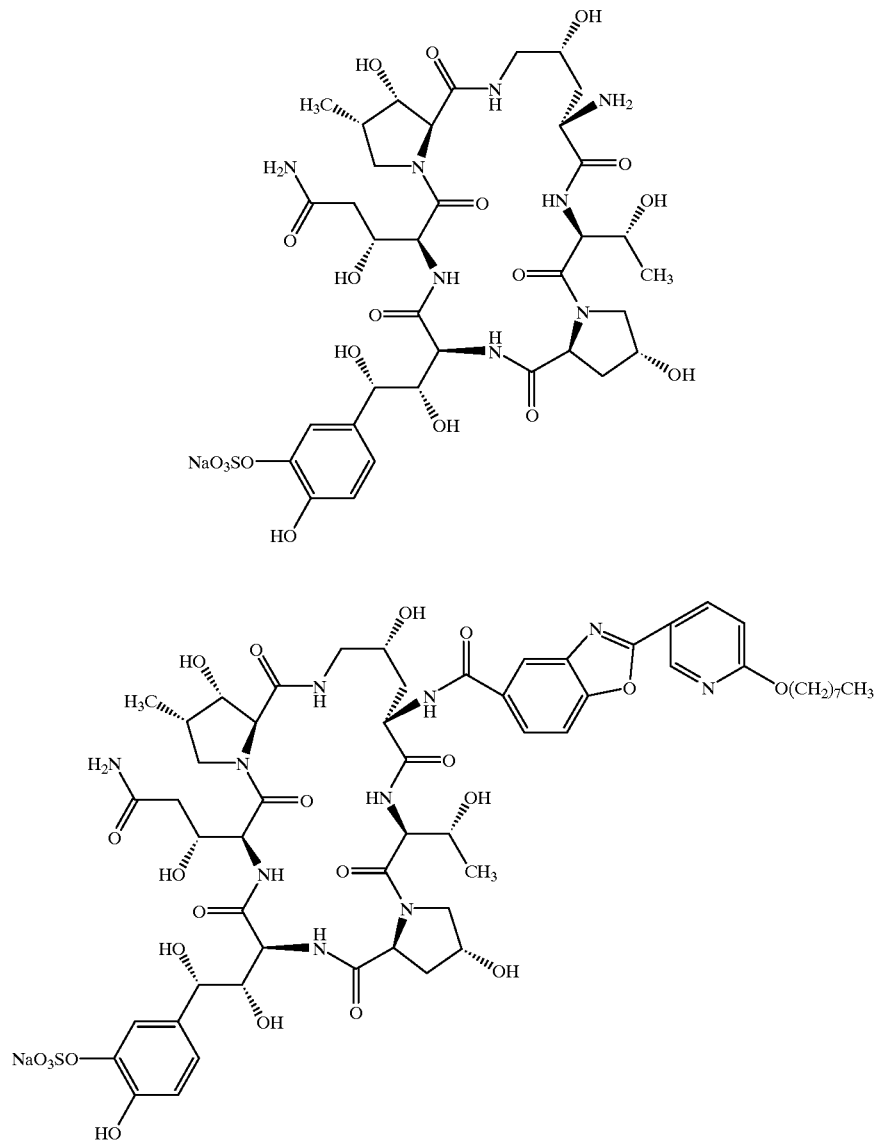 |

-continued
| Example No. | Formula |
|---|---|
| 33 | 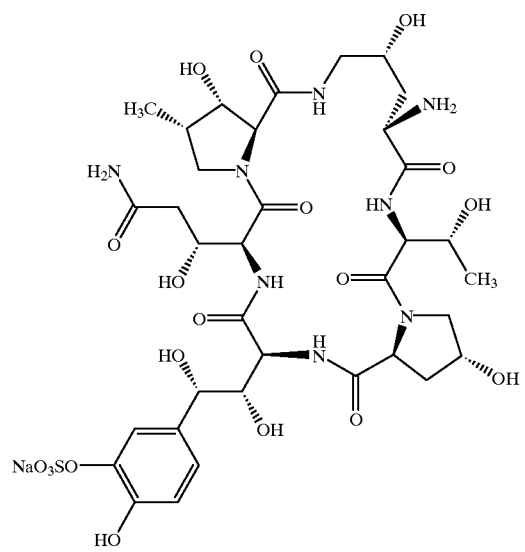 |
| | 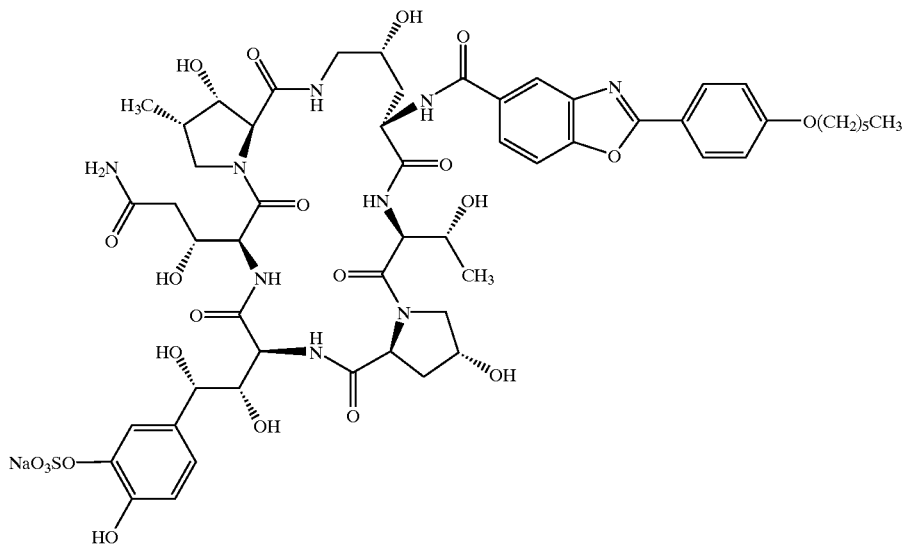 |

| Example No. | Formula |
|---|---|
| 34 | 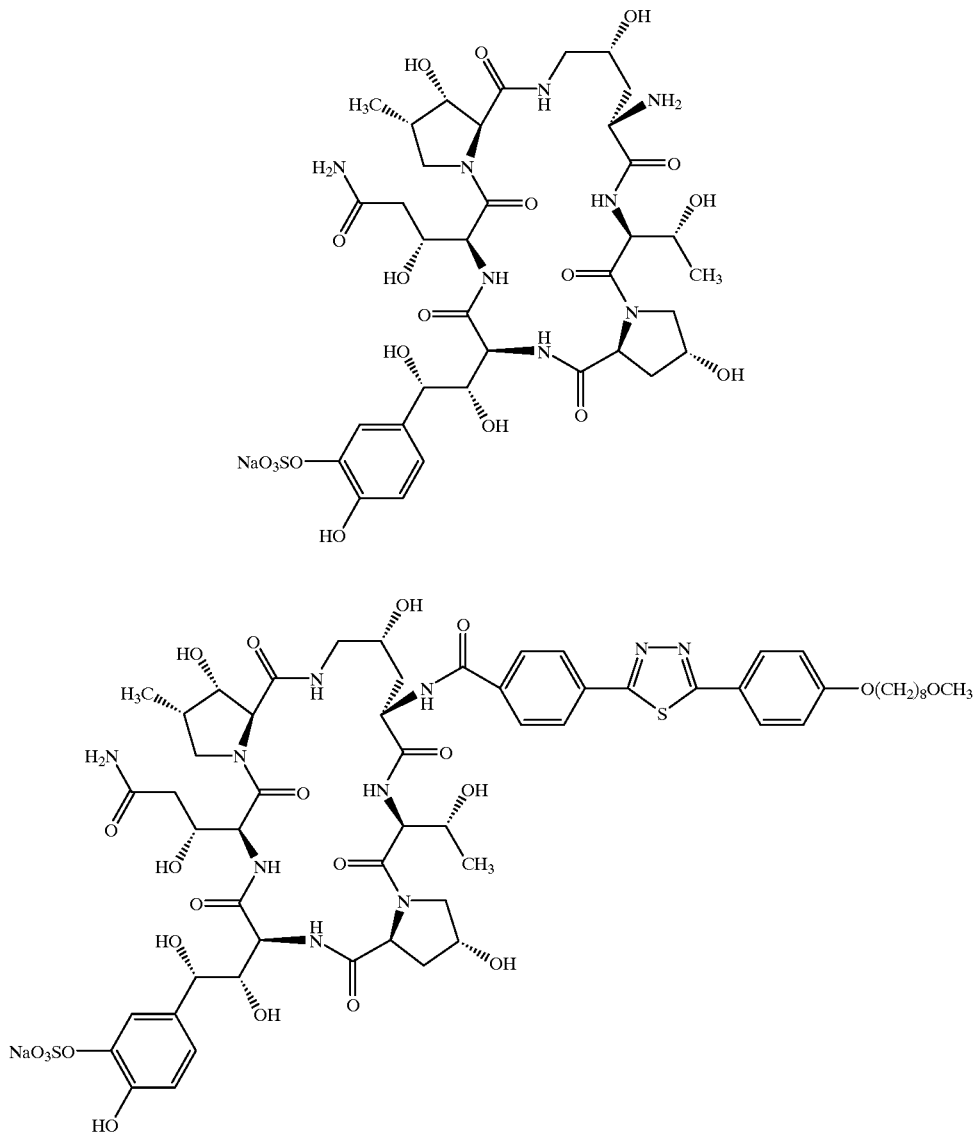 |

-continued
| Example No. | Formula |
|---|---|
| 35 | 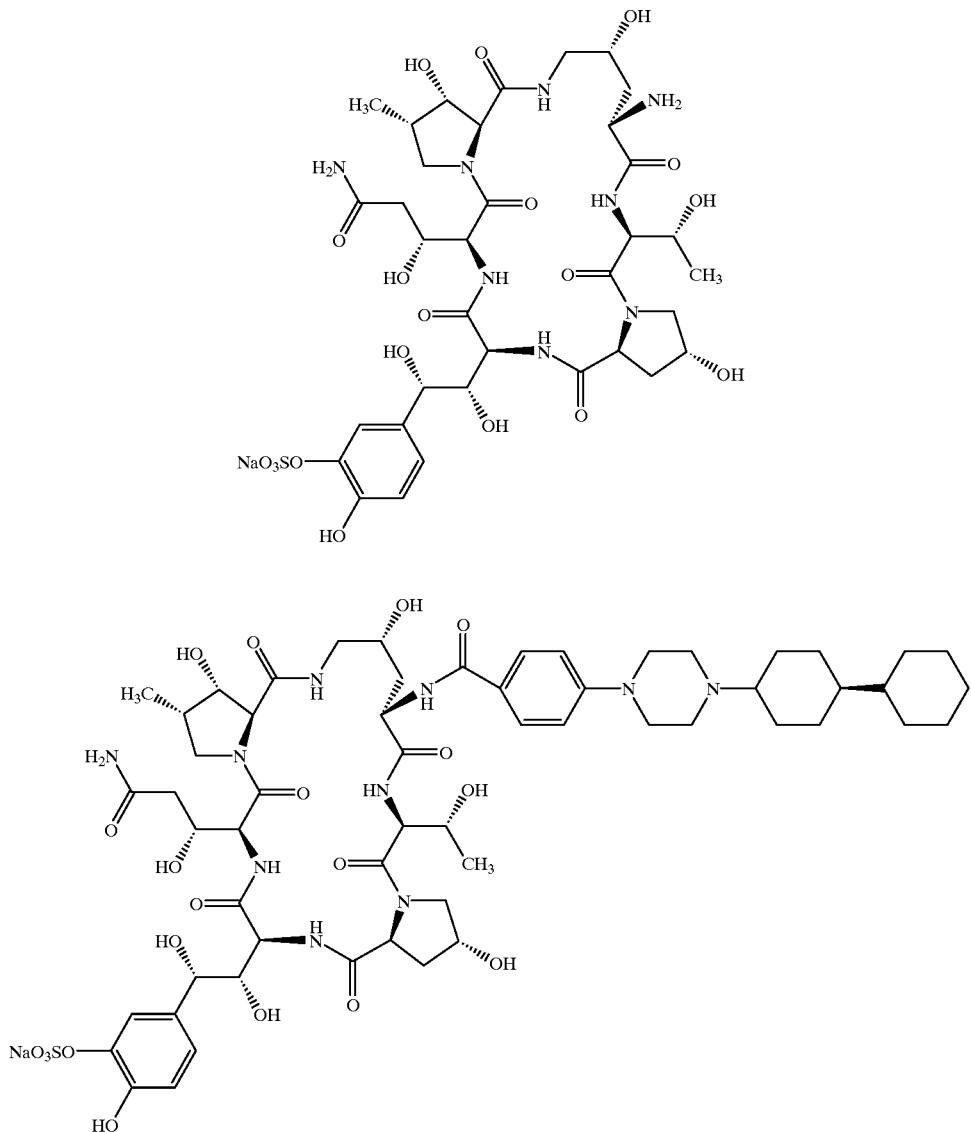 |

-continued
| Example No. | Formula |
|---|---|
| 36 | 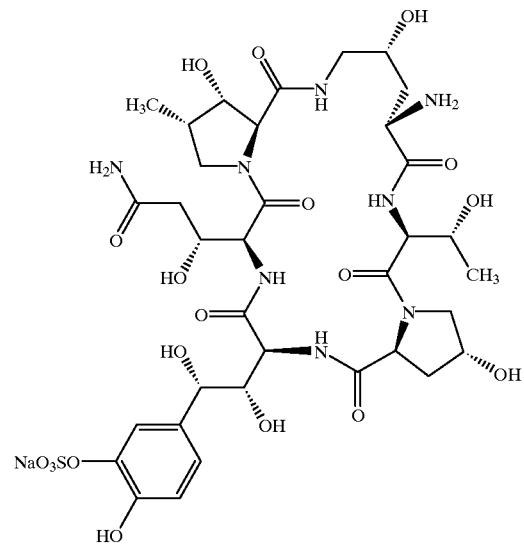 |
| | 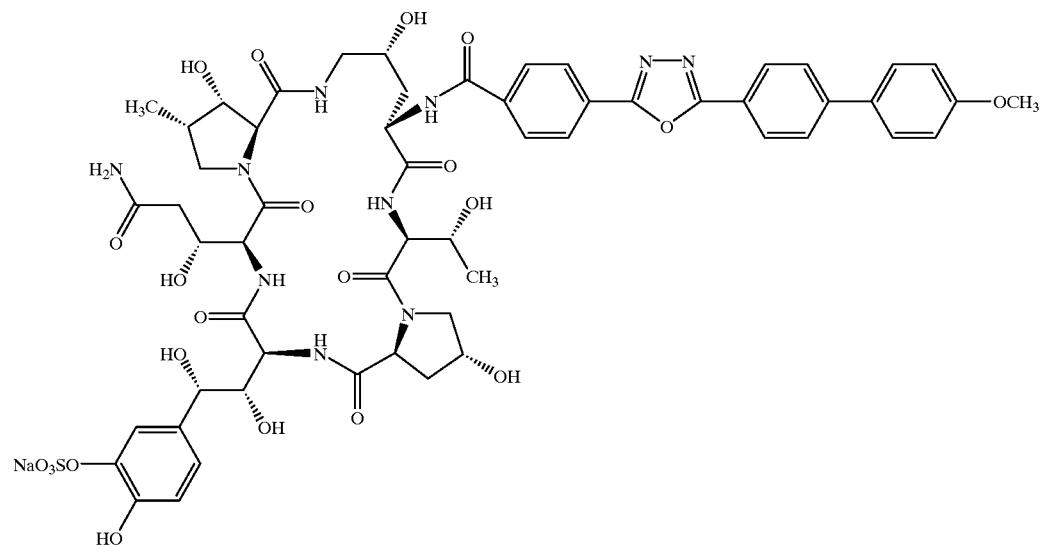 |

-continued
| Example No. | Formula |
|---|---|
| 37 | 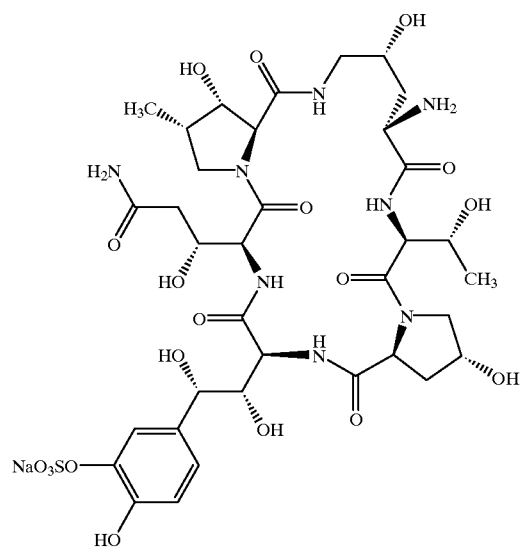 |
| | 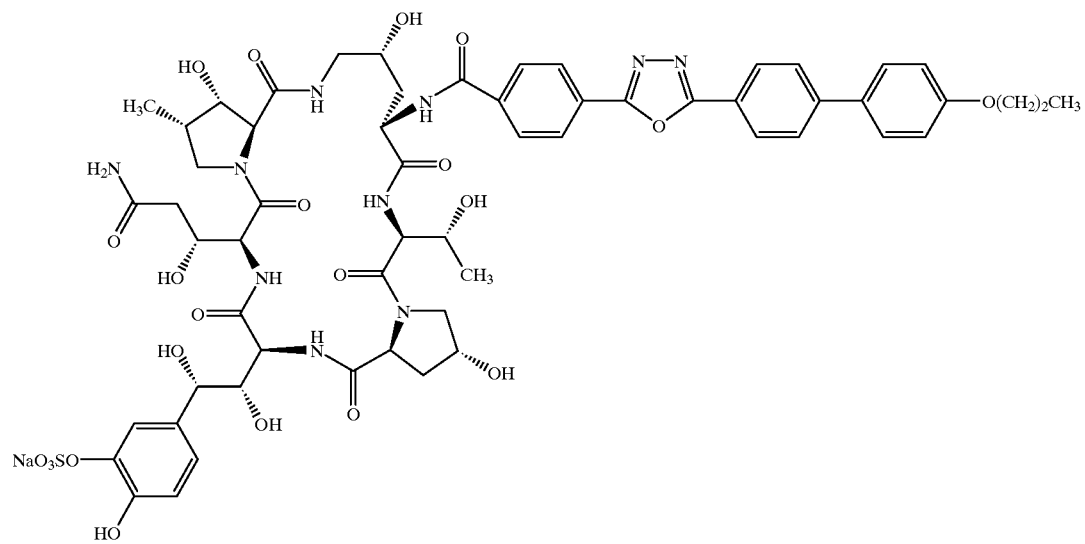 |

| Example No. | Formula |
|---|---|
| 38 | 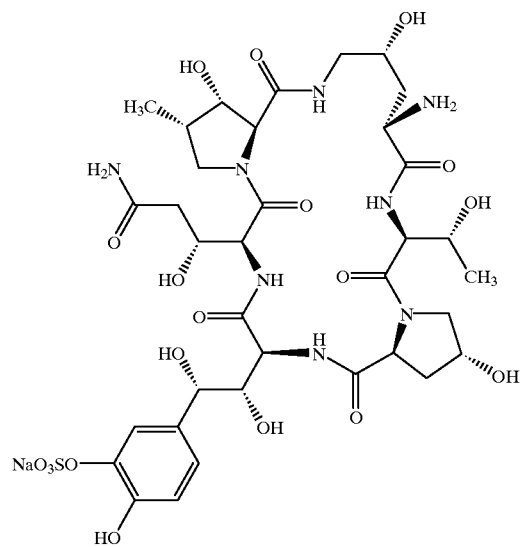 |
| | 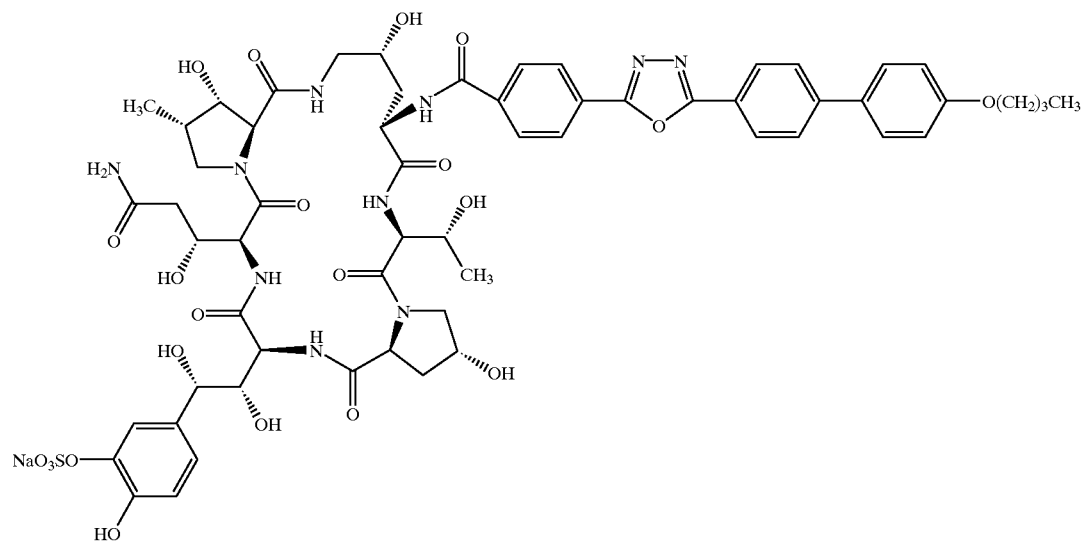 |

-continued
| Example No. | Formula |
|---|---|
| 39 | 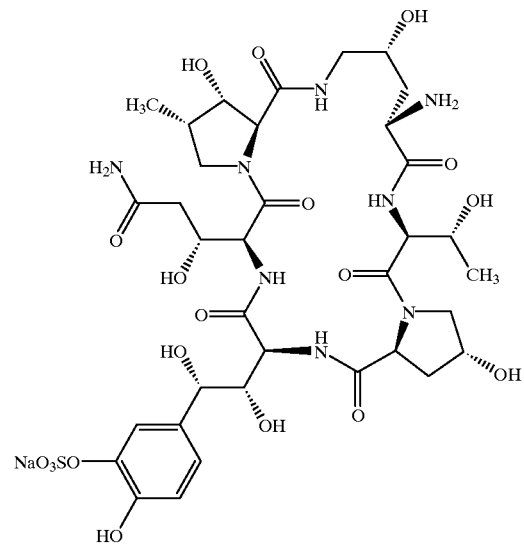 |
| | 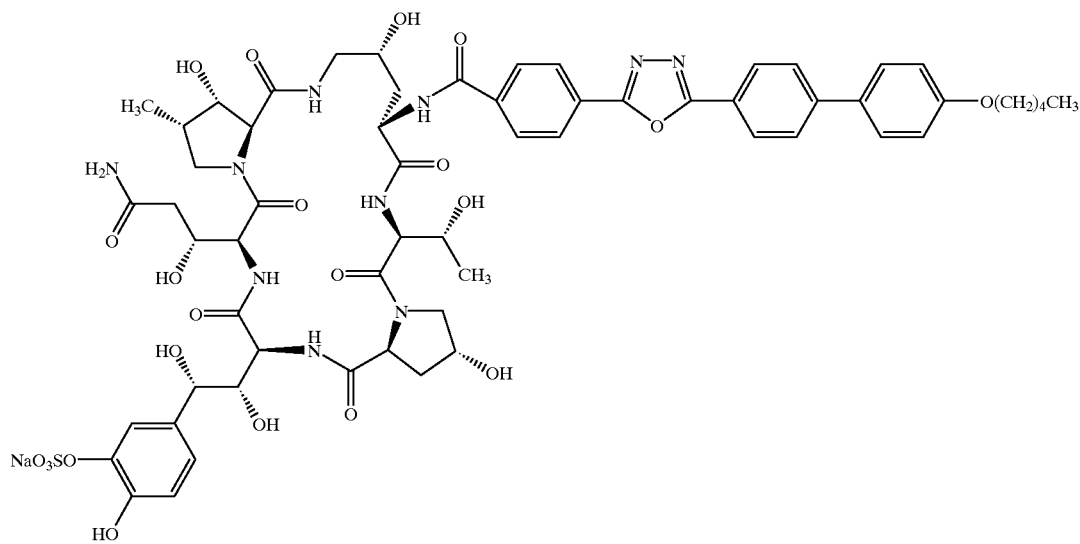 |

| Example No. | Formula |
|---|---|
| 40 | 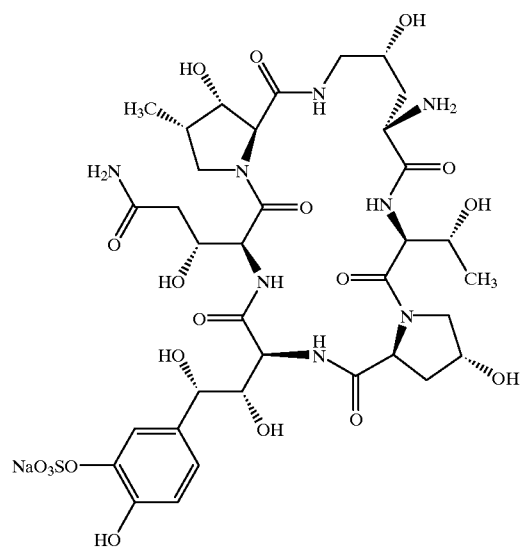 |
| | 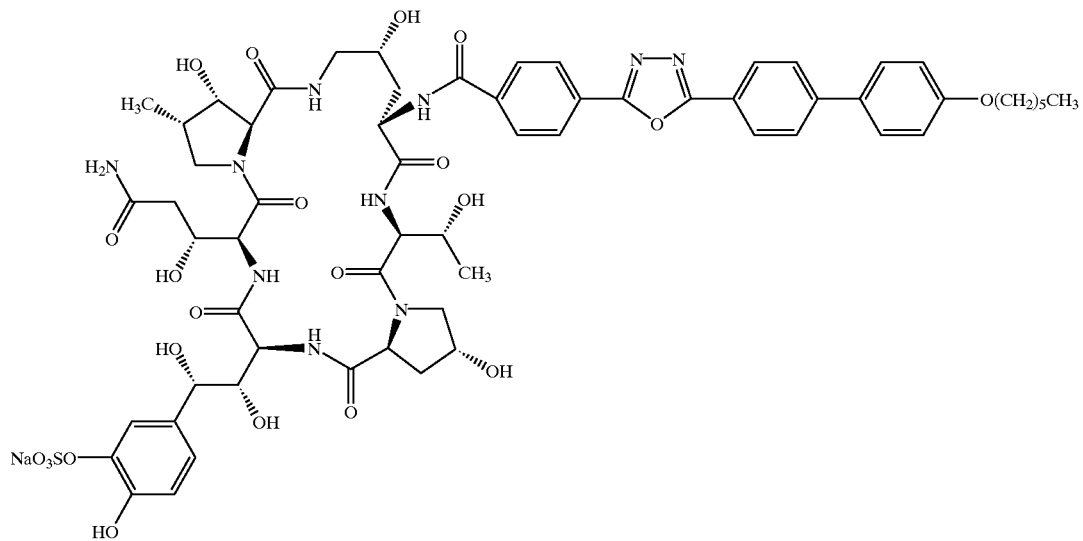 |

| Example No. | Formula |
|---|---|
| 41 | 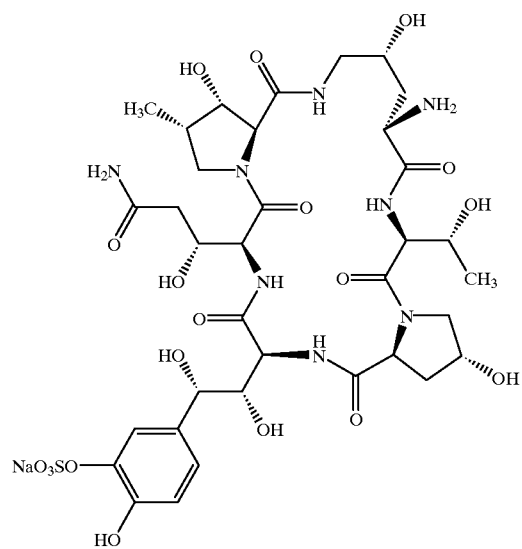 |
| | 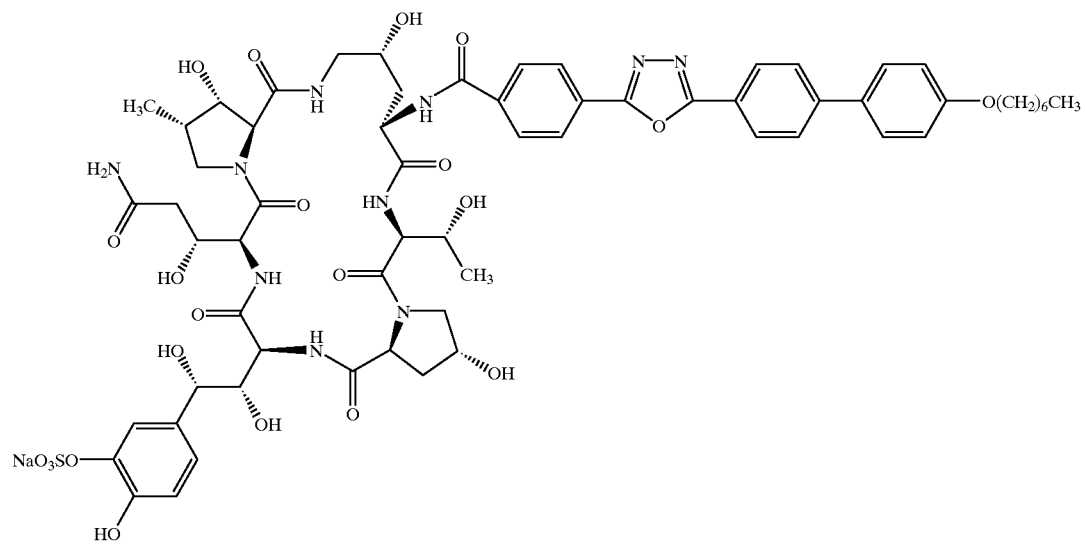 |

-continued
| Example No. | Formula |
|---|---|
| 42 | 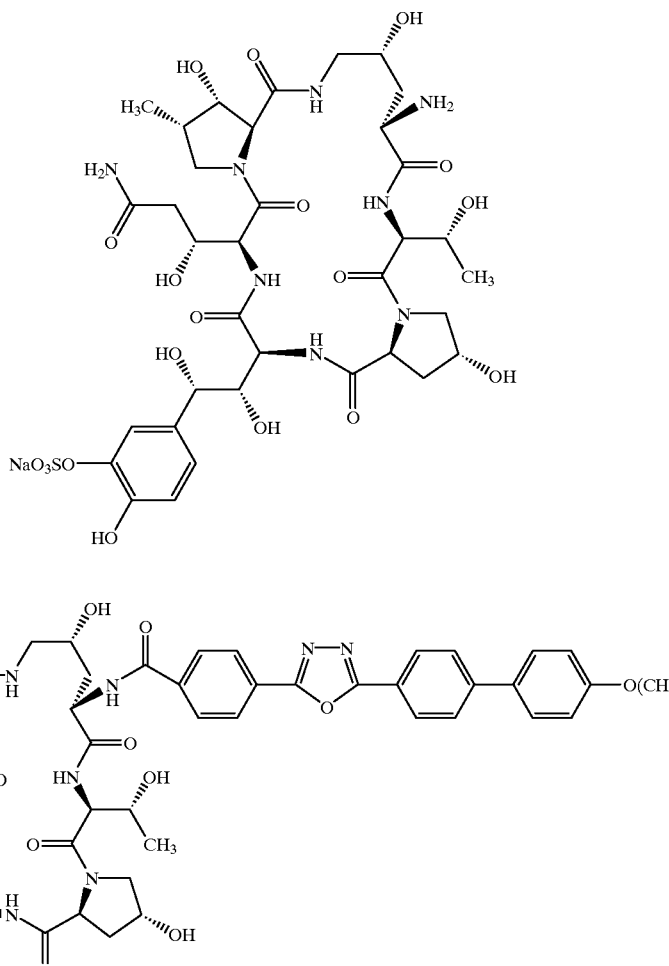 |

-continued
| Example No. | Formula |
|---|---|
| 43 | 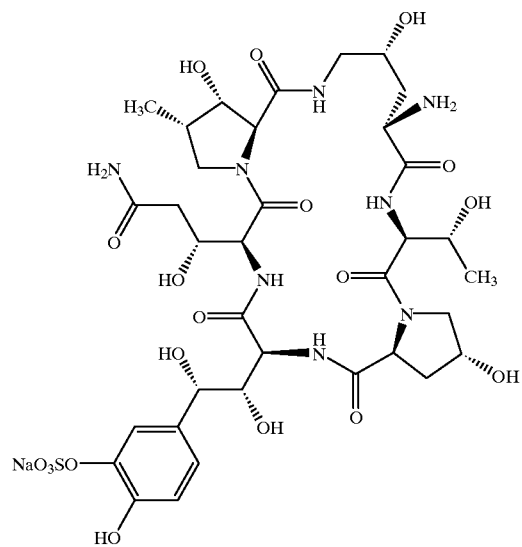 |
| | 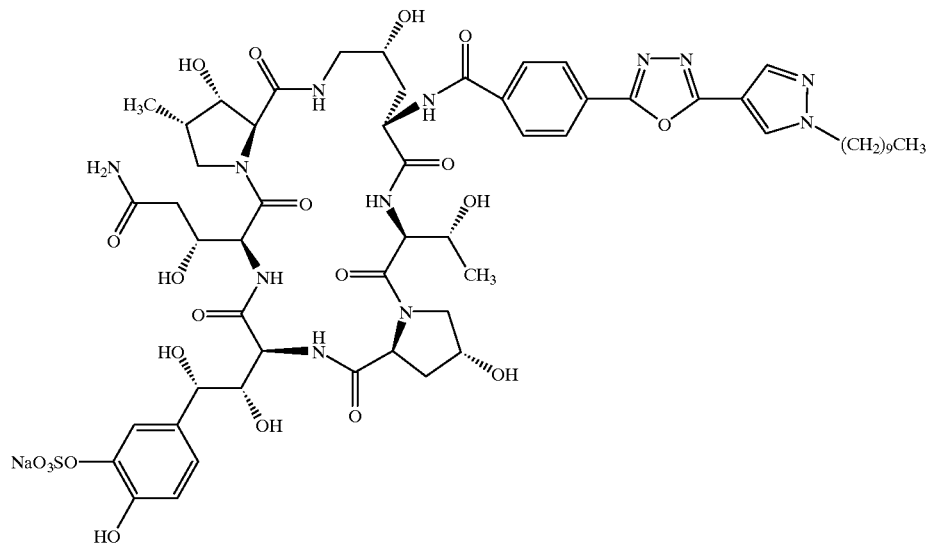 |

-continued
| Example No. | Formula |
|---|---|
| 44 | 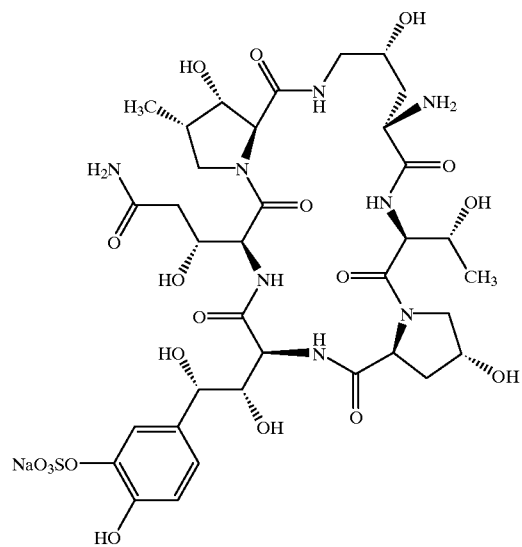 |
| | 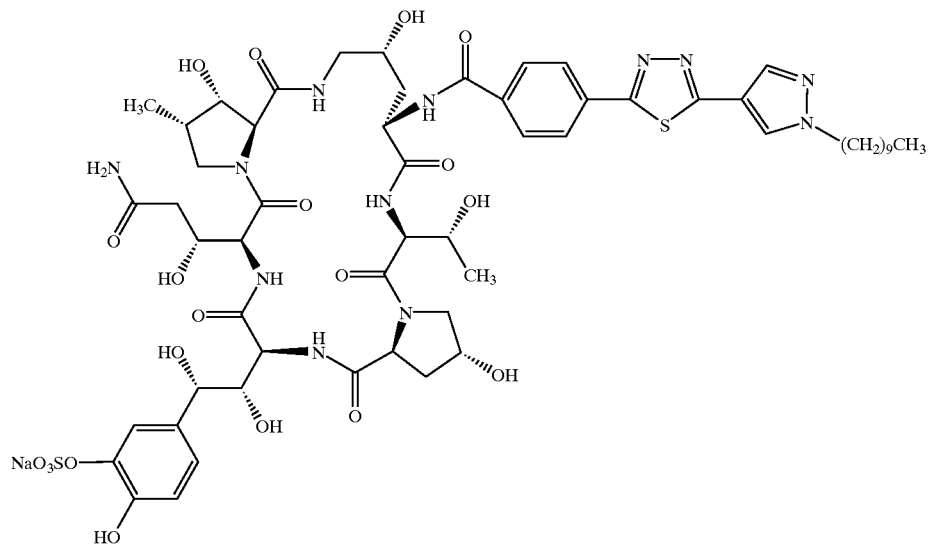 |

-continued
| Example No. | Formula |
|---|---|
| 45 | 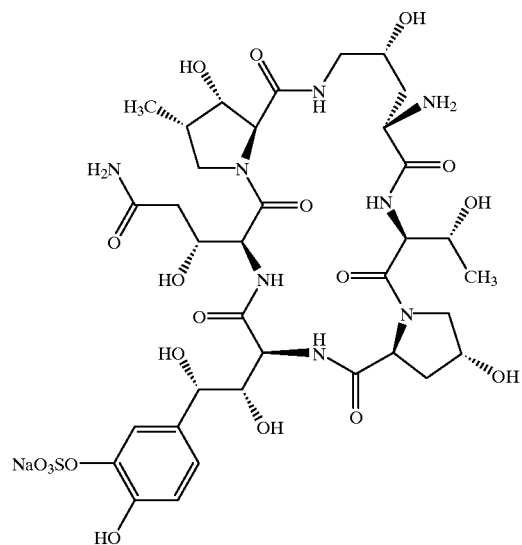 |
| | 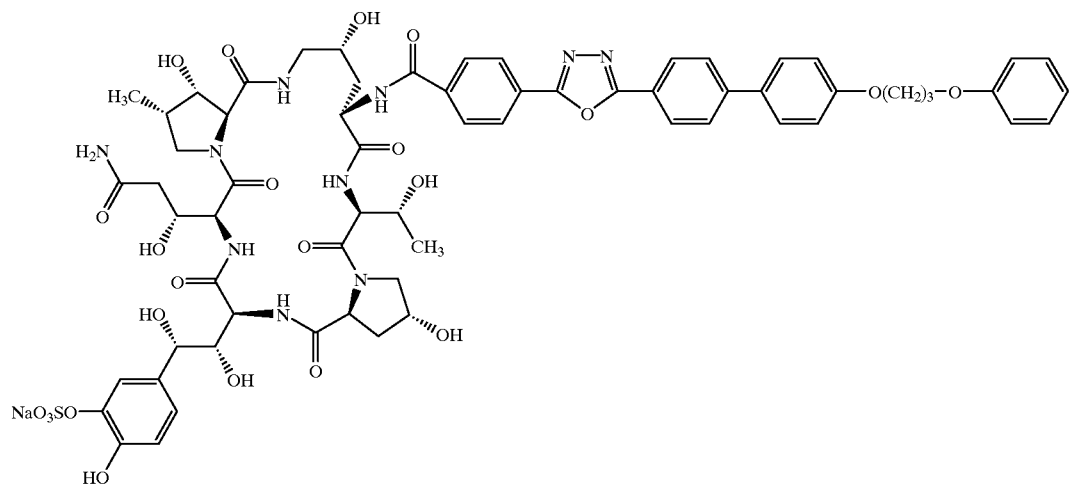 |

| Example No. | Formula |
|---|---|
| 46 | 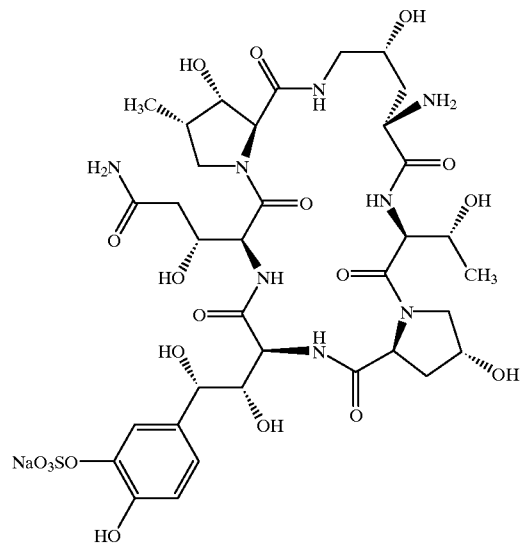 |
| | 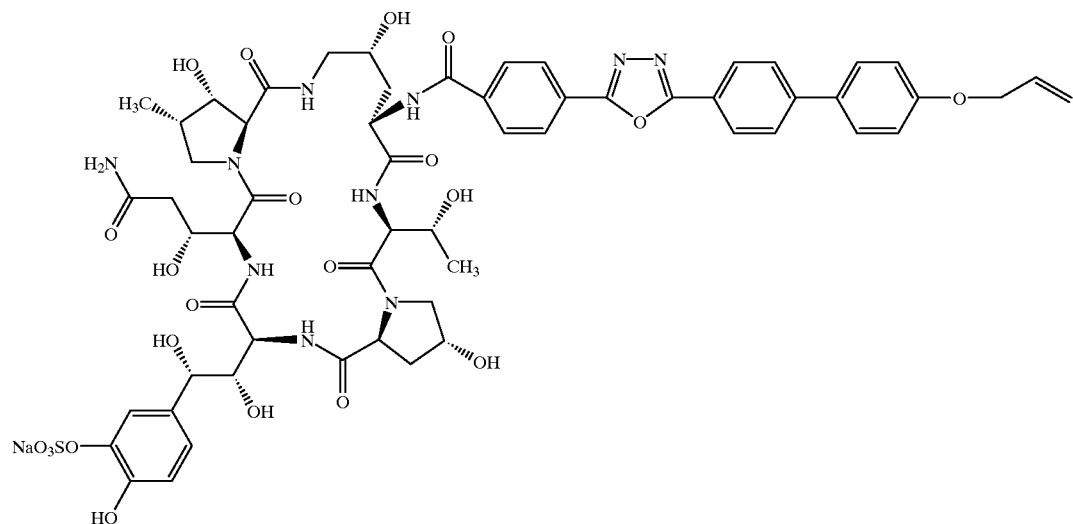 |

| Example No. | Formula |
|---|---|
| 47 | 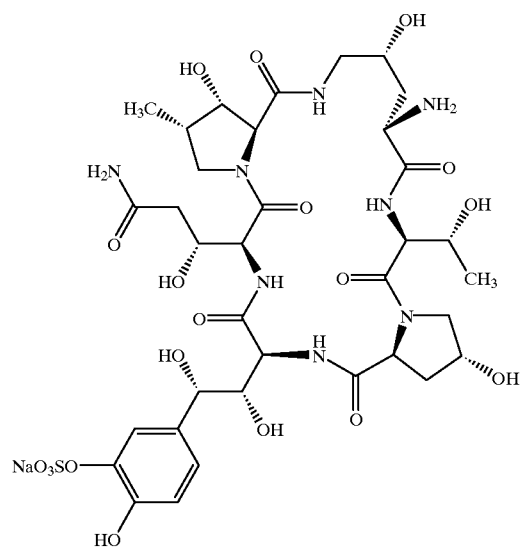 |
| | 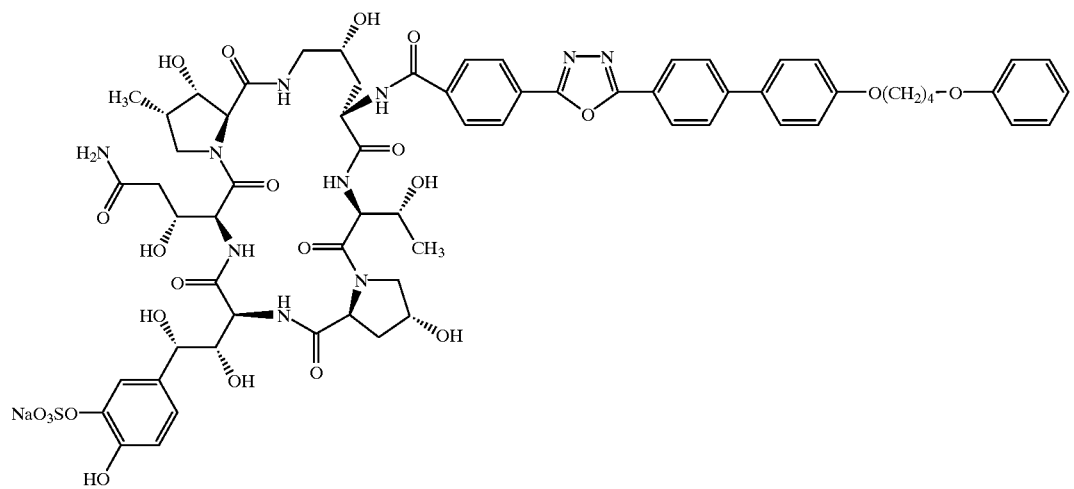 |

| Example No. | Formula |
|---|---|
| 48 | 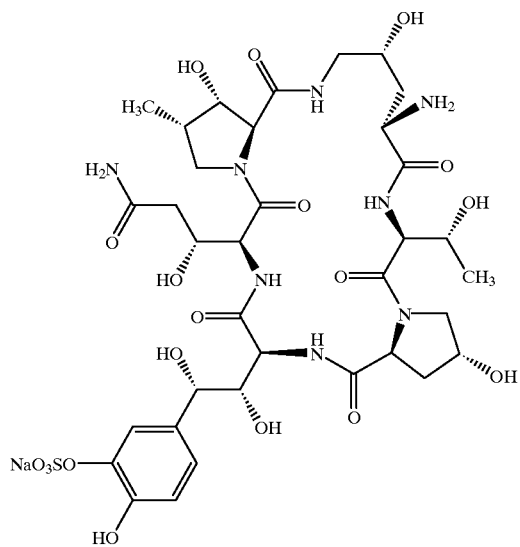 |
| | 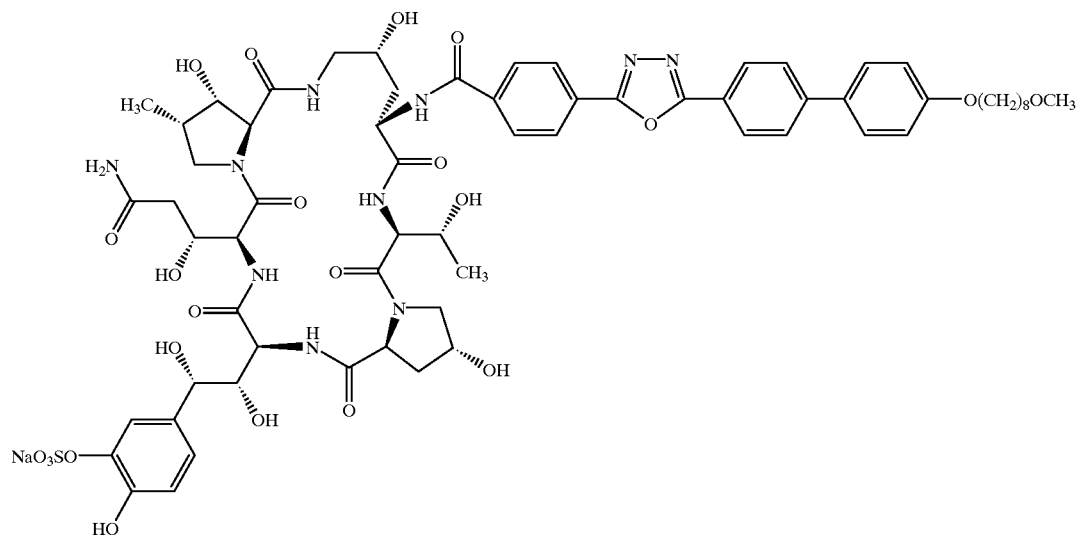 |

-continued
| Example No. | Formula |
|---|---|
| 49 | 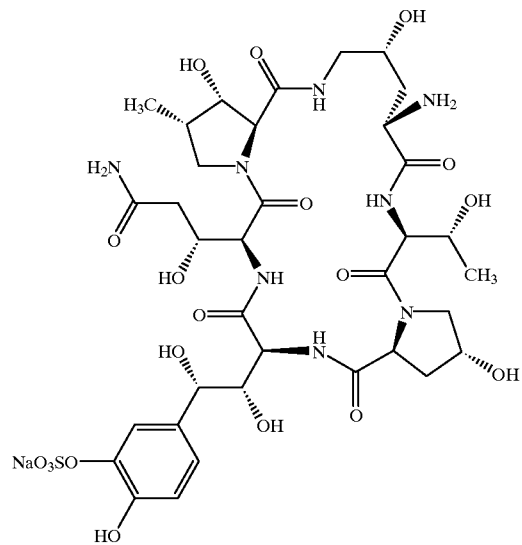 |
| | 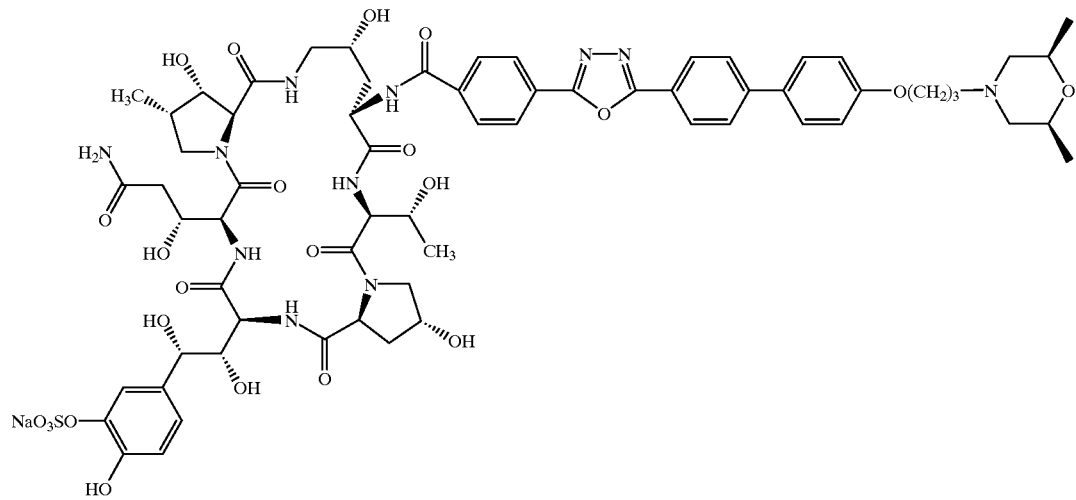 |

| Example No. | Formula |
|---|---|
| 50 | 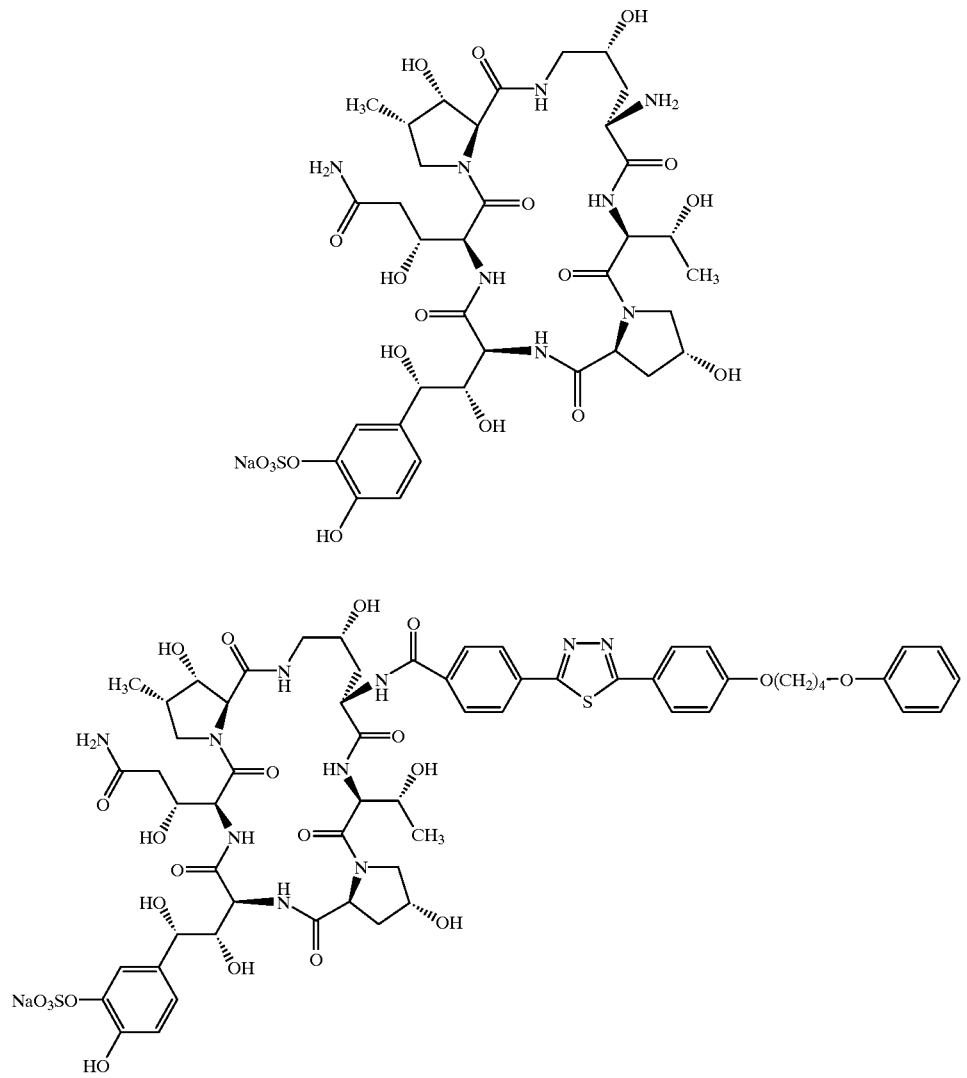 |

-continued
| Example No. | Formula |
|---|---|
| 51 | 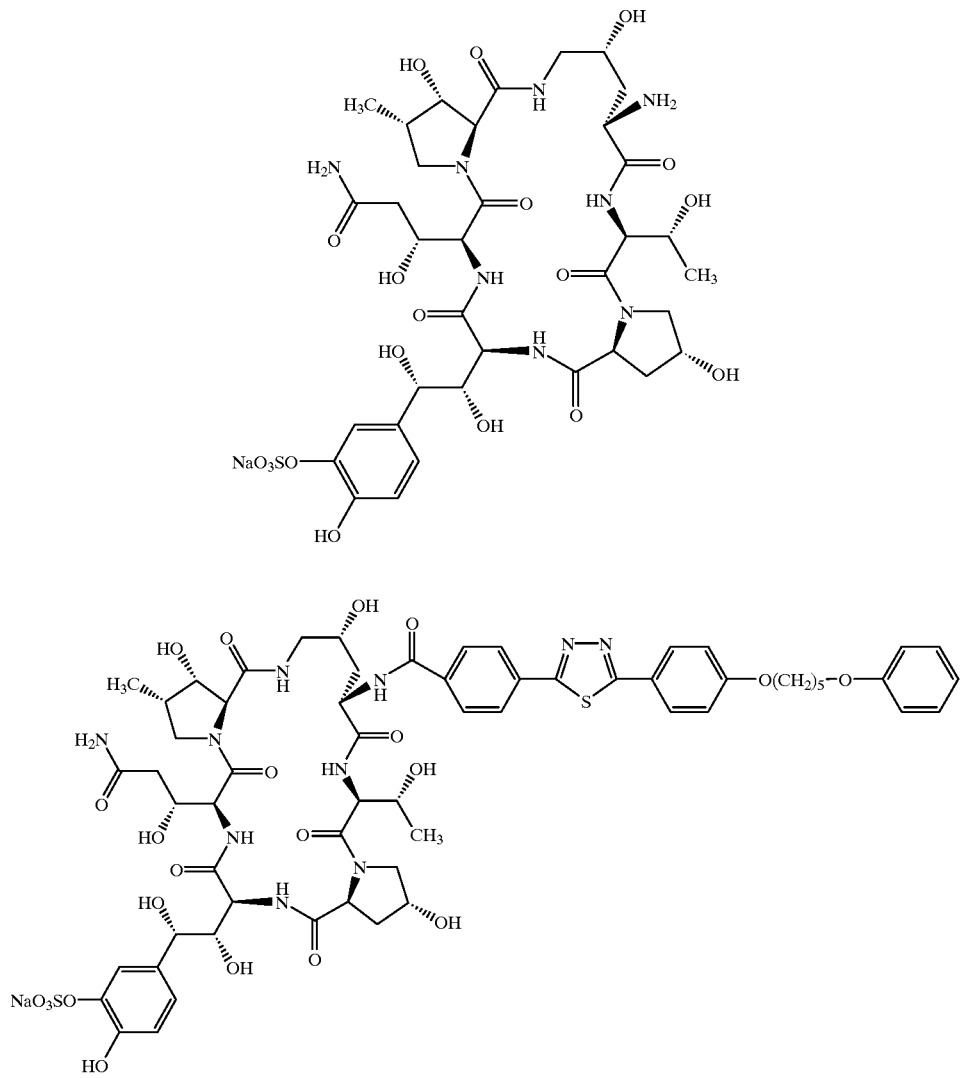 |

-continued
| Example No. | Formula |
|---|---|
| 52 | 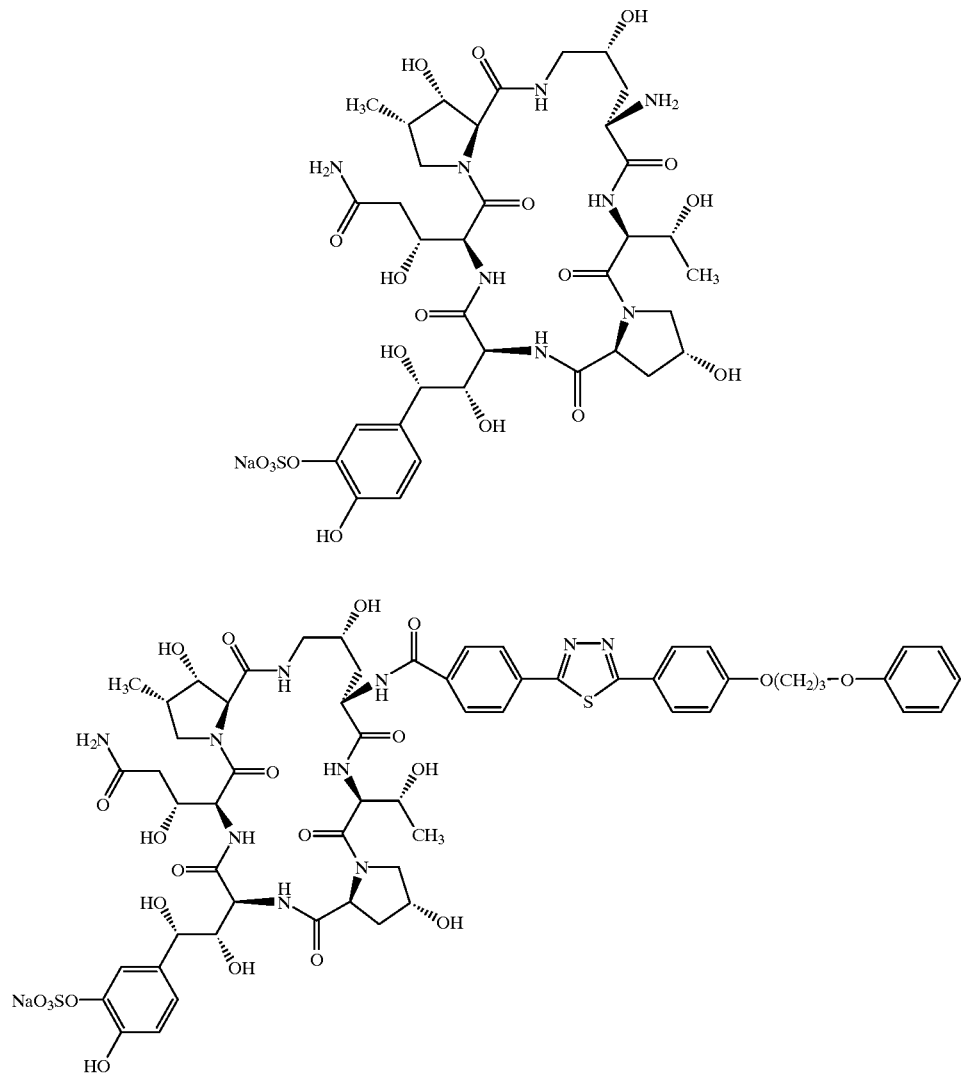 |

| Example No. | Formula |
|---|---|
| 53 | 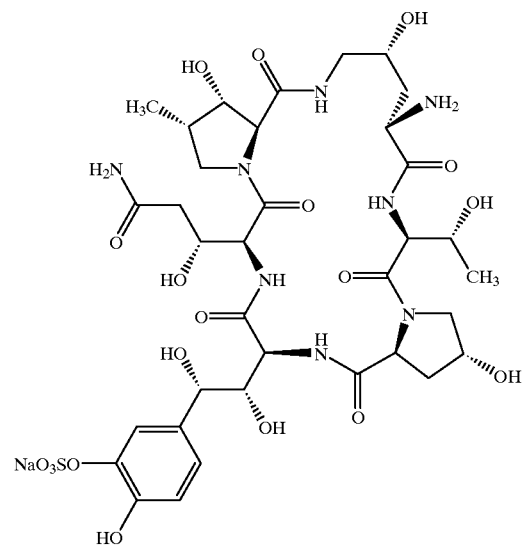 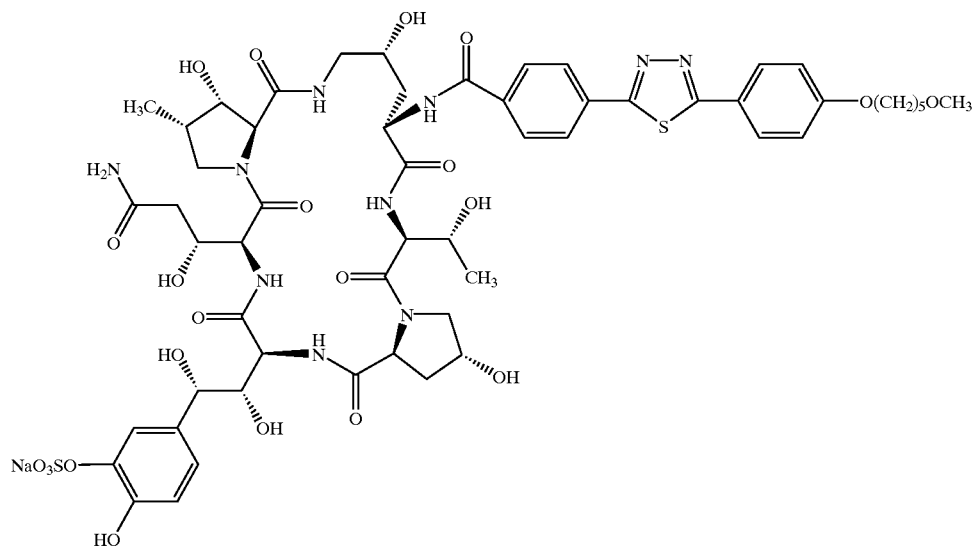 |

| Example No. | Formula |
|---|---|
| 54 | 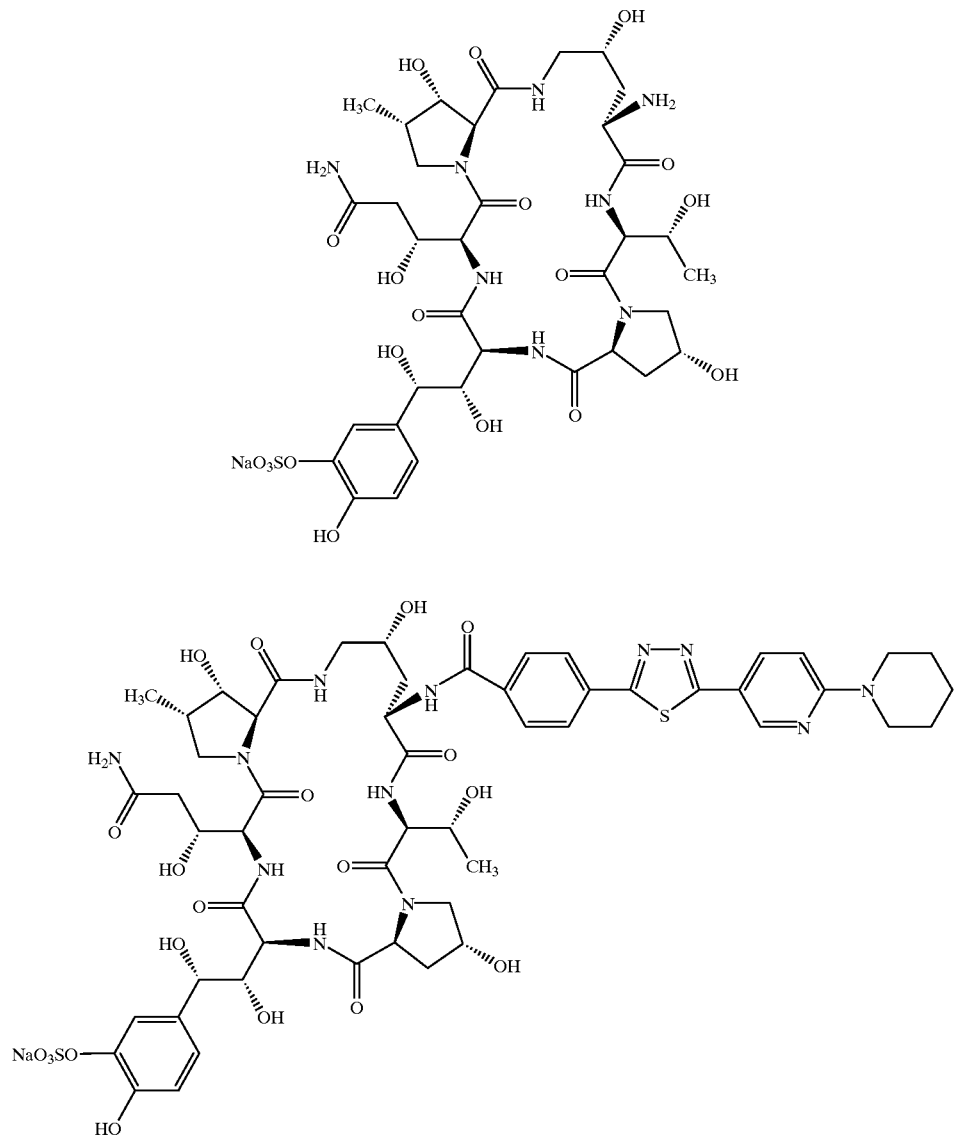 |

-continued
| Example No. | Formula |
|---|---|
| 55 | 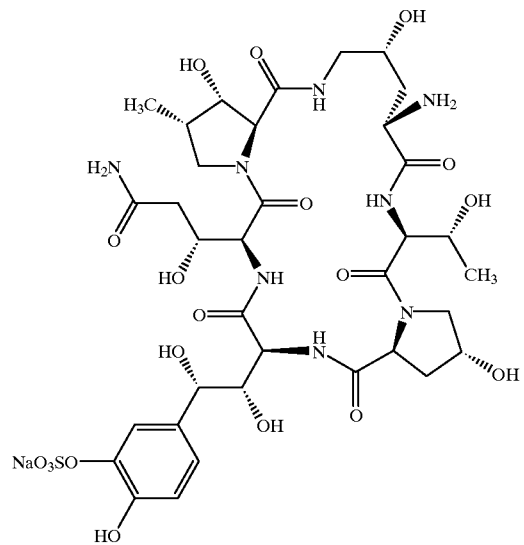 |
| | 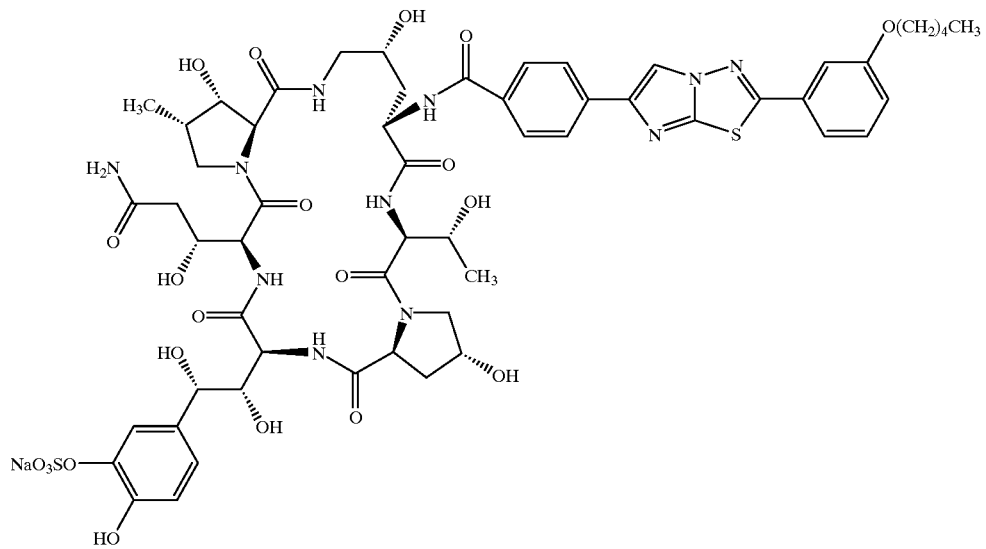 |

-continued
| Example No. | Formula |
|---|---|
| 56 | 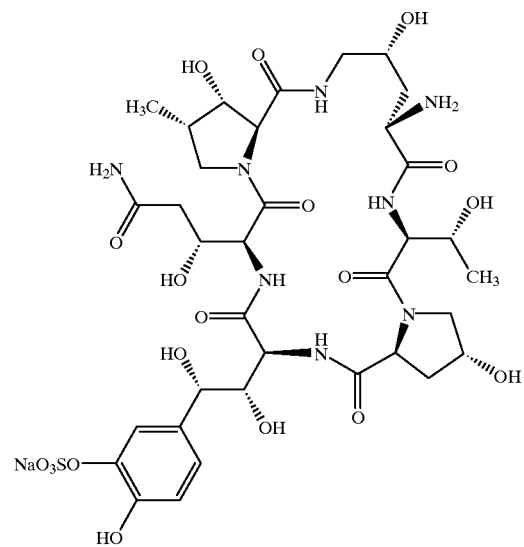<br>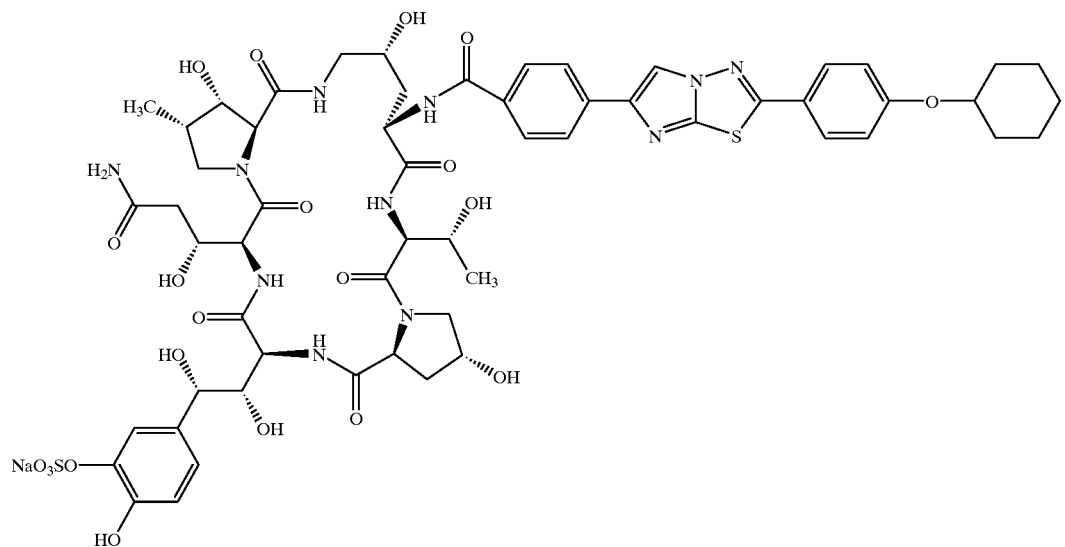 |

| Example No. | Formula |
|---|---|
| 57 | 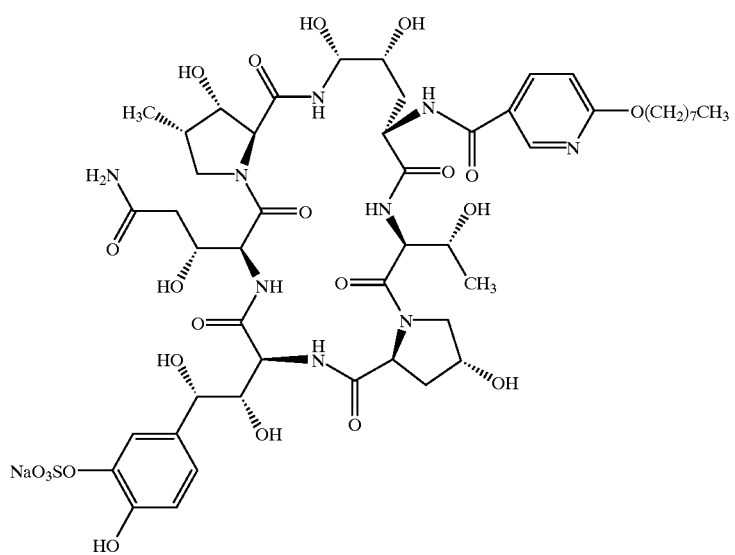 |
| | 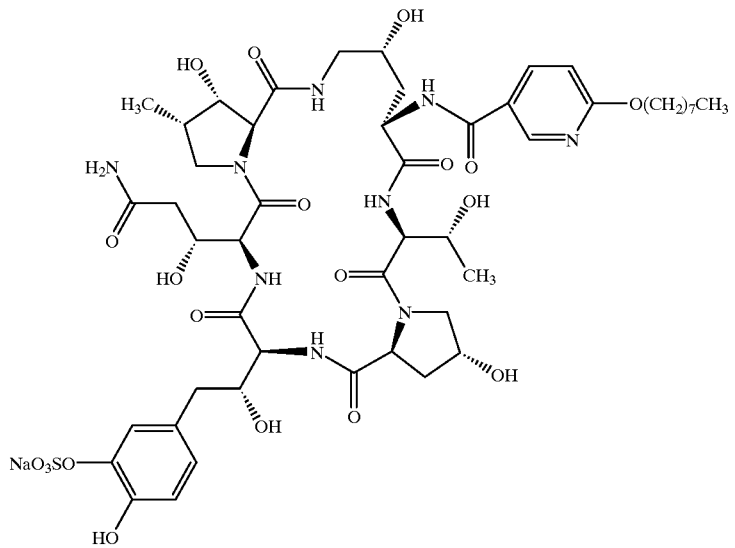 |

-continued
| Example No. | Formula |
|---|---|
| 58 | 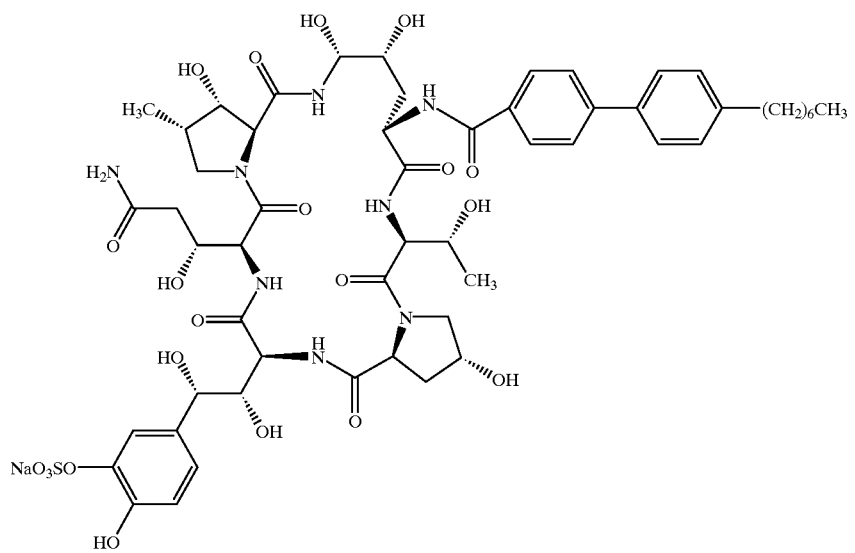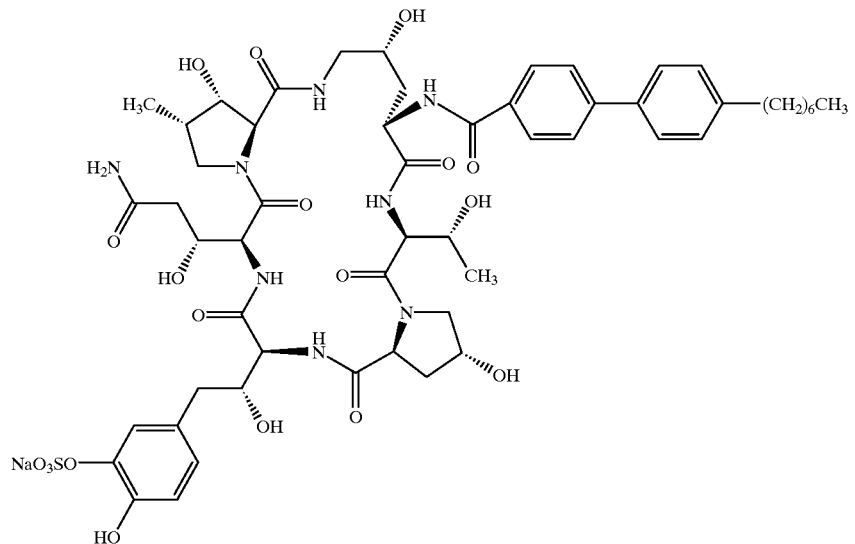 |

-continued
| Example No. | Formula |
|---|---|
| 59 | 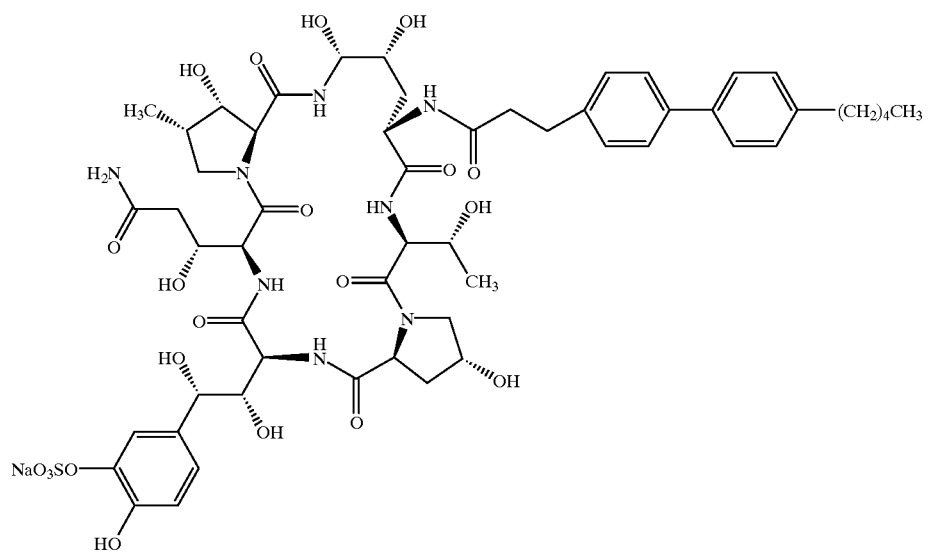 |
| | 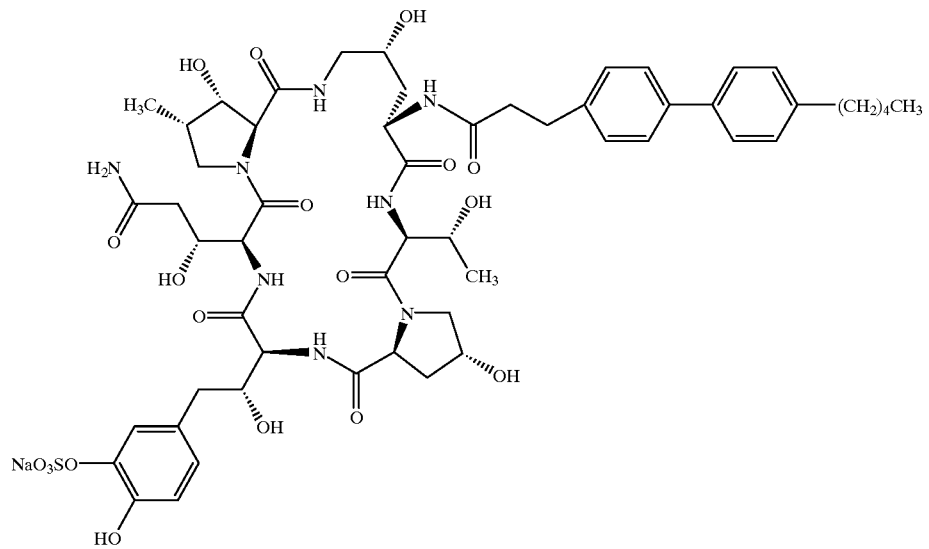 |

-continued
| Example No. | Formula |
|---|---|
| 60 | 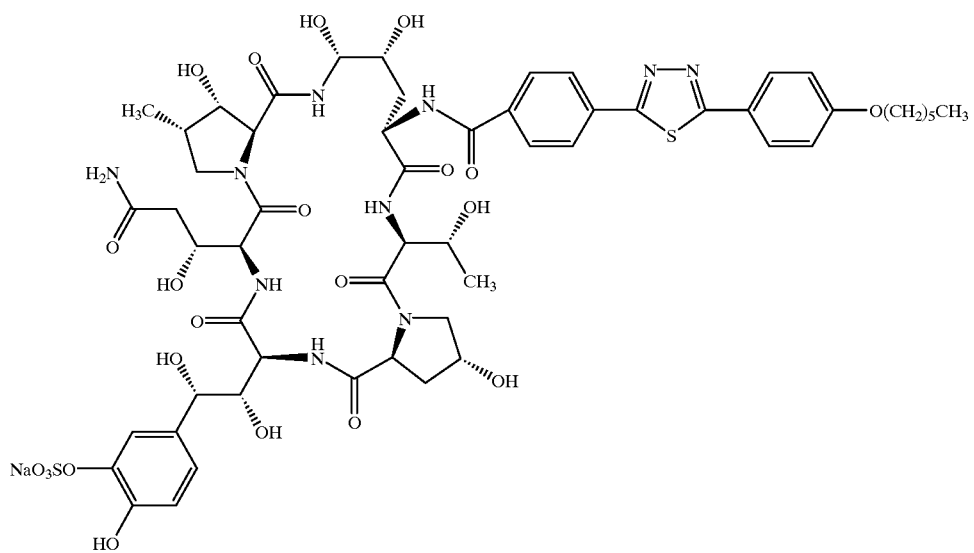 |
| | 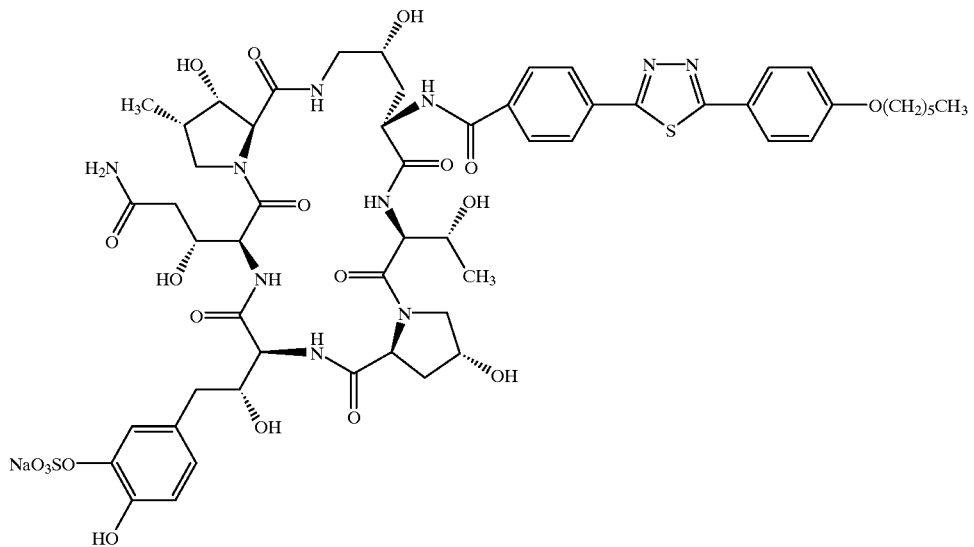 |

| Example No. | Formula |
|---|---|
| 61 | 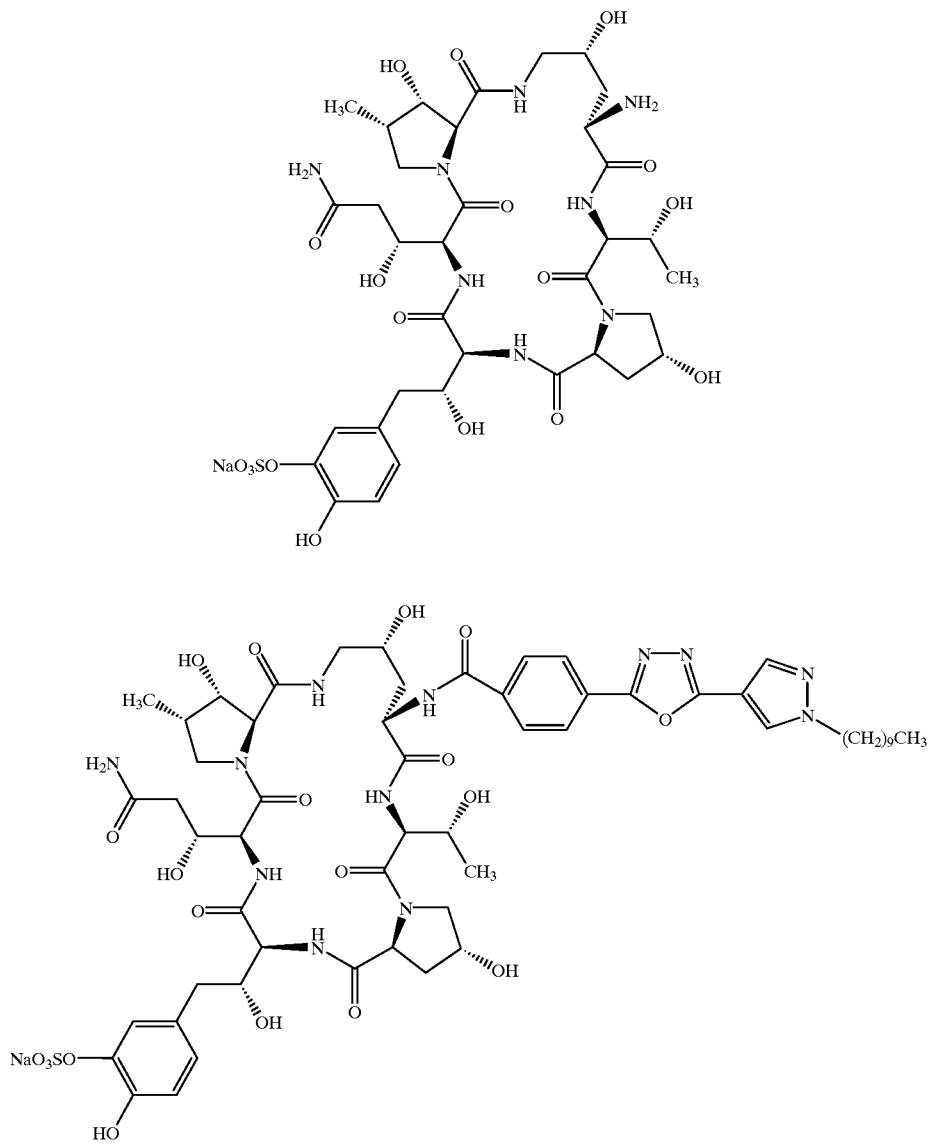 |

| Example No. | Formula |
|---|---|
| 62 | 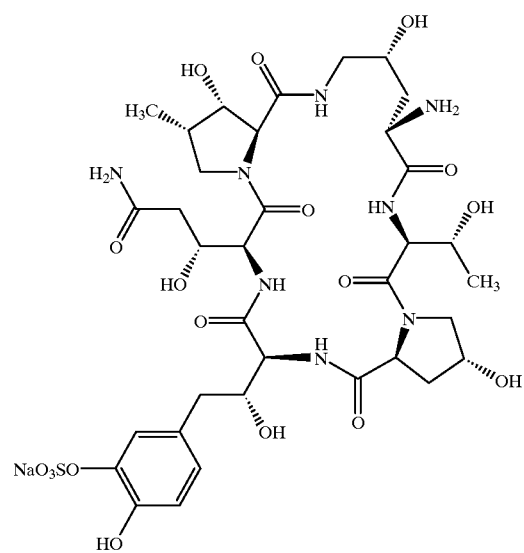 |
| | 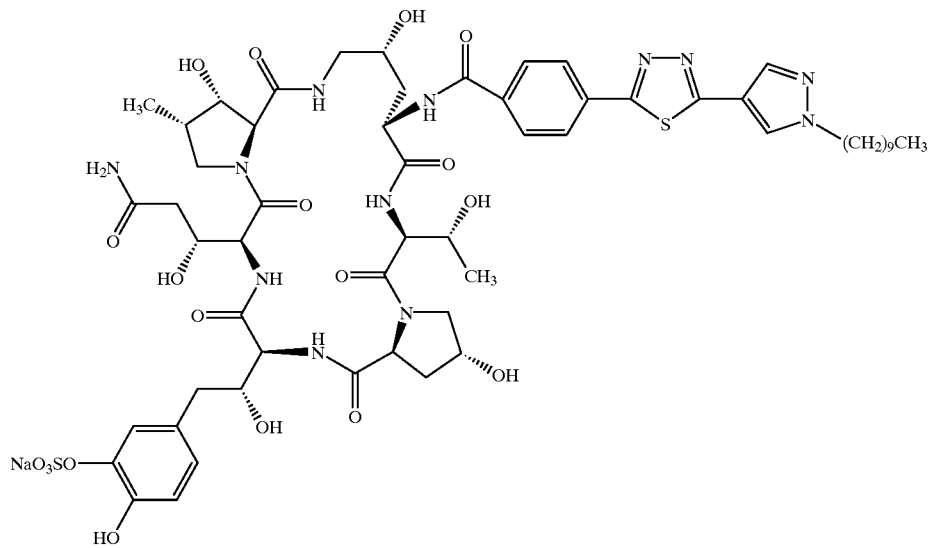 |

-continued
| Example No. | Formula |
|---|---|
| 63 | 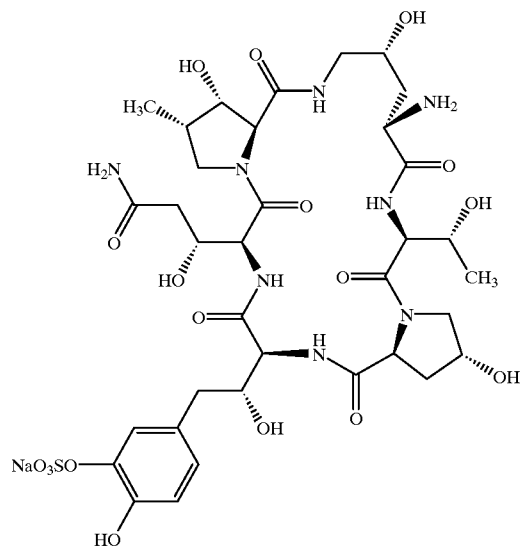 |
| | 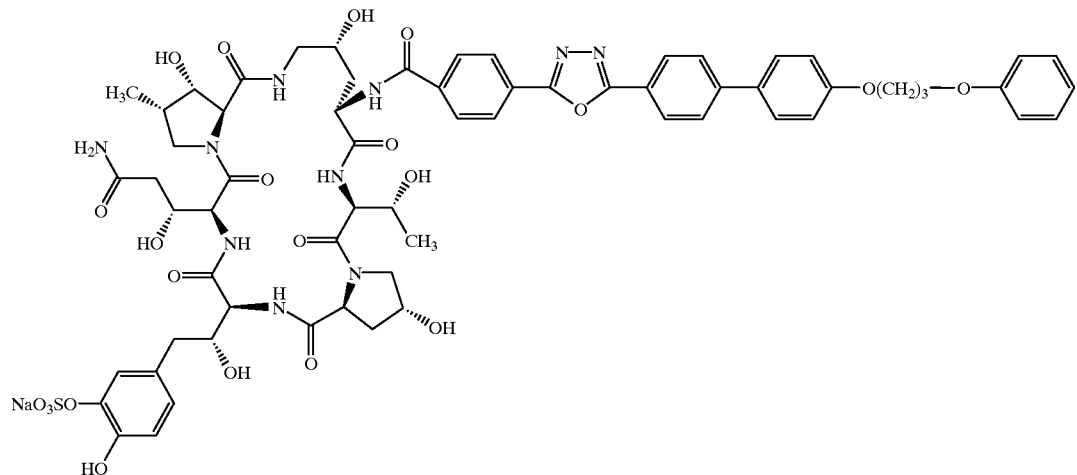 |

| Example No. | Formula |
|---|---|
| 64 | 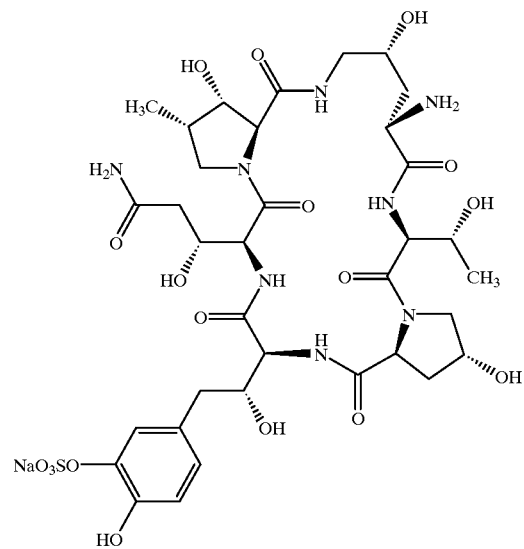 |
| | 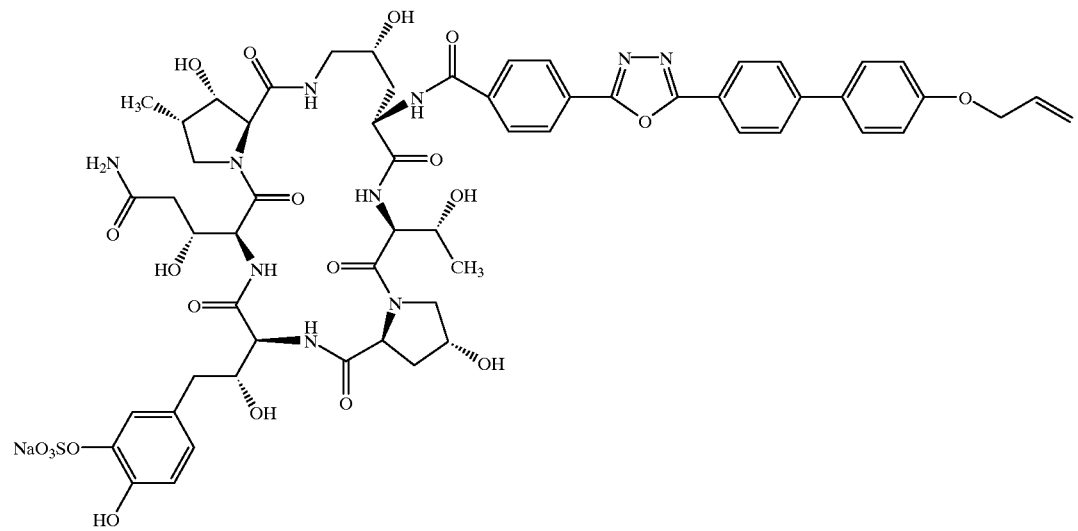 |

-continued
| Example No. | Formula |
|---|---|
| 65 | 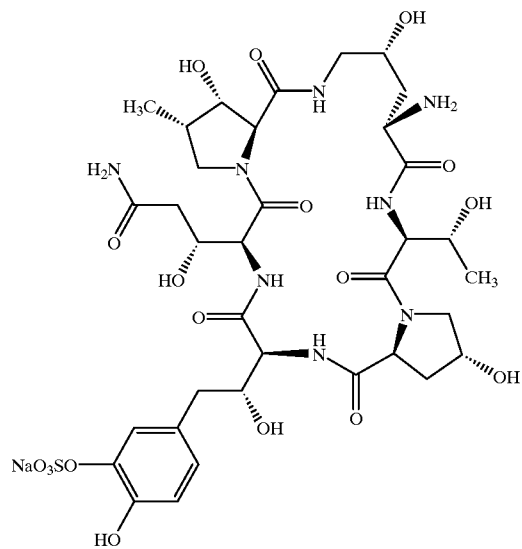 |
| | 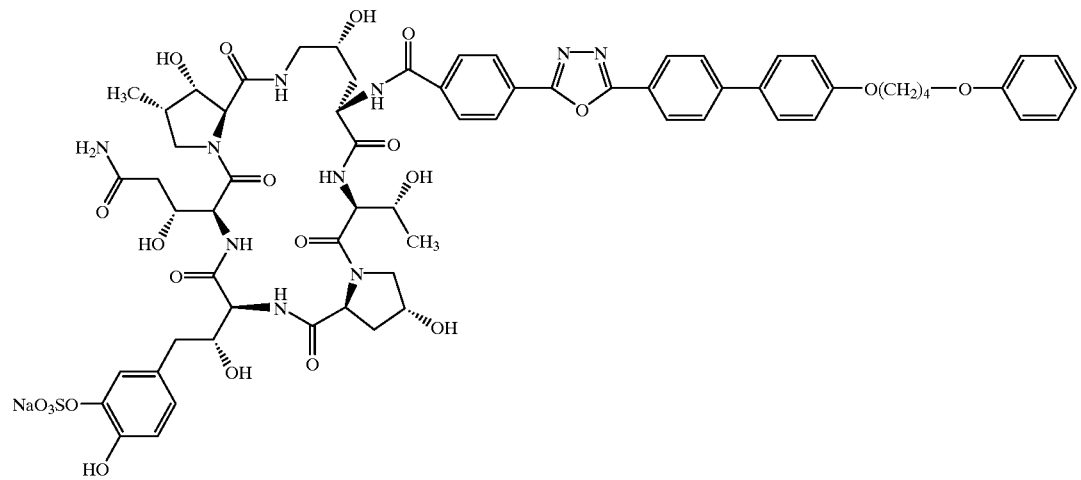 |

| Example No. | Formula |
|---|---|
| 66 | 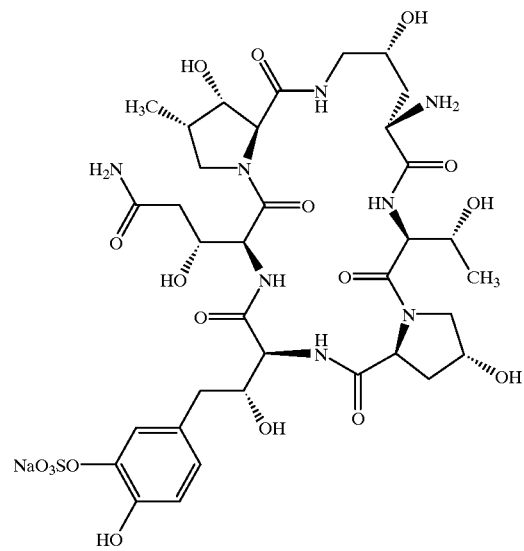 |
| | 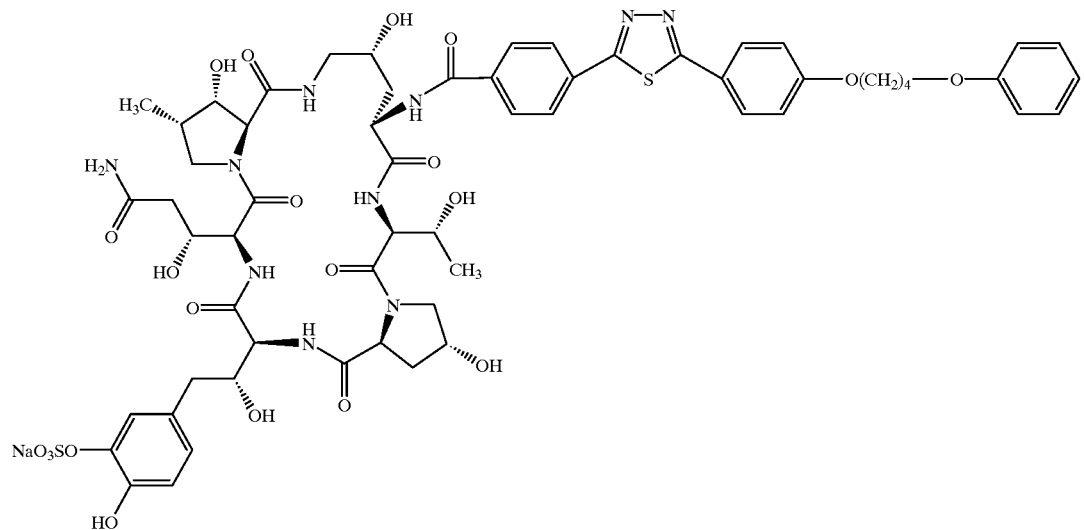 |

| Example No. | Formula |
|---|---|
| 67 | 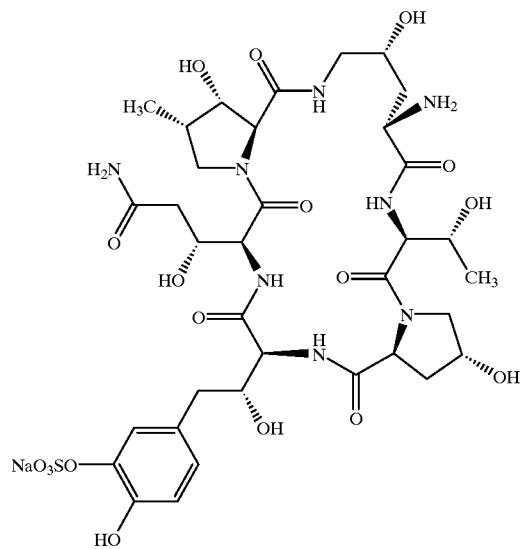 |
| | 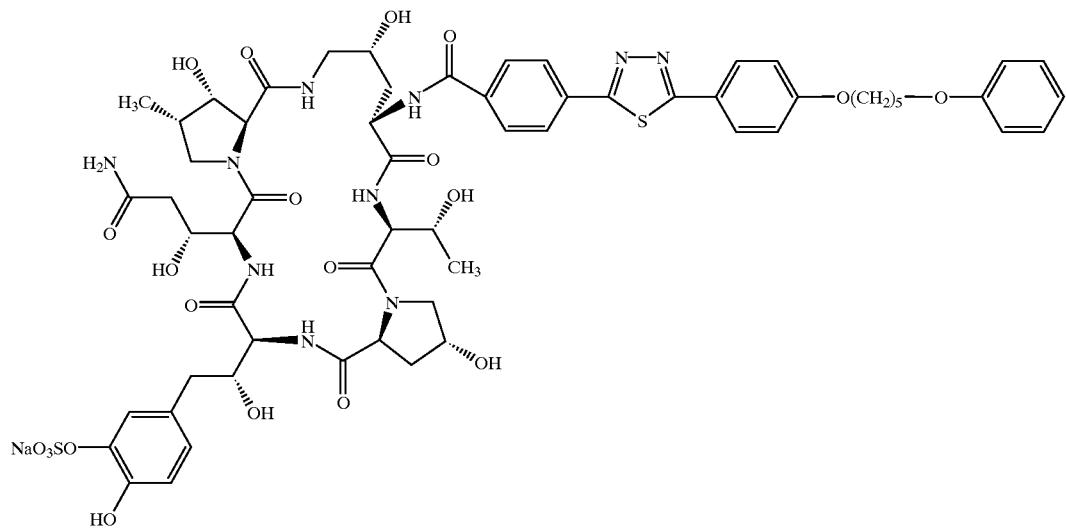 |

| Example No. | Formula |
|---|---|
| 68 | 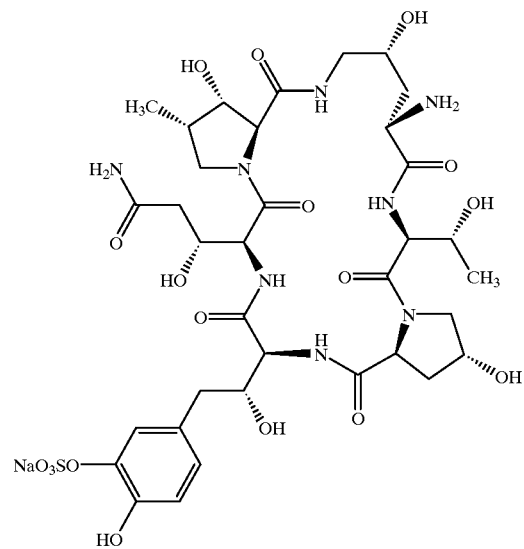 |
| | 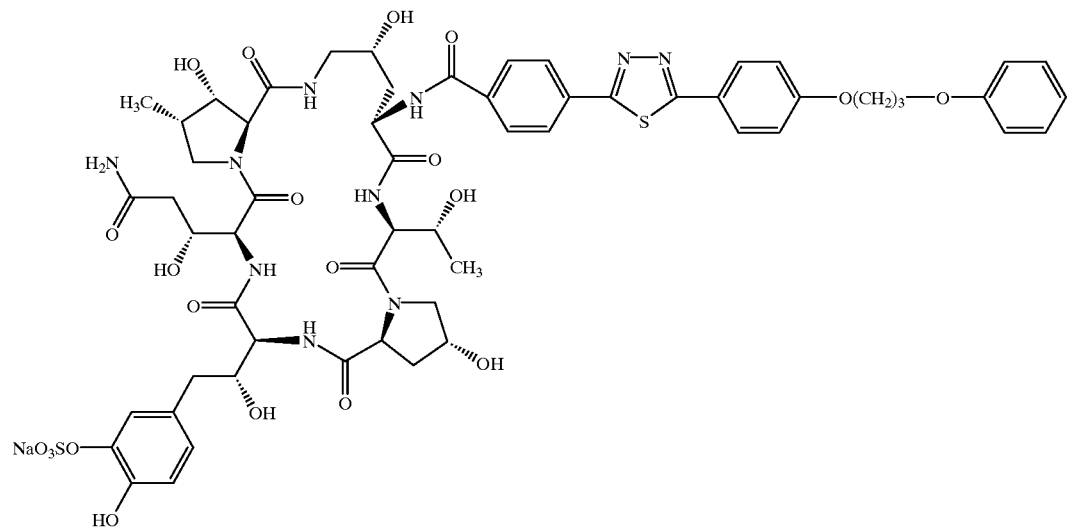 |

-continued
| Example No. | Formula |
|---|---|
| 69 | 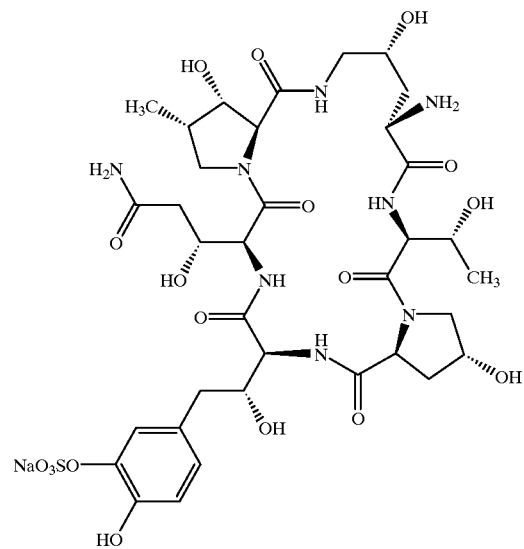 |
| | 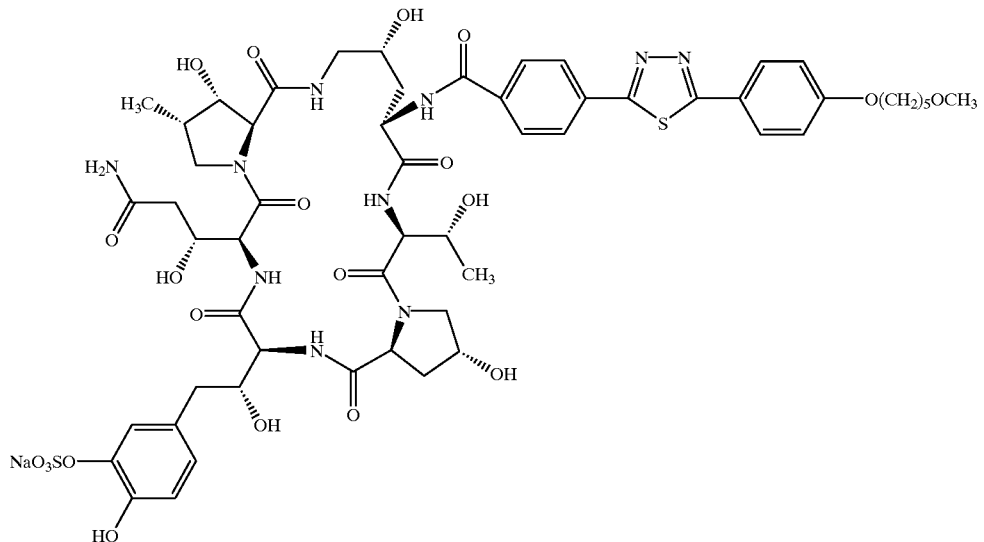 |

| Example No. | Formula |
|---|---|
| 70 | 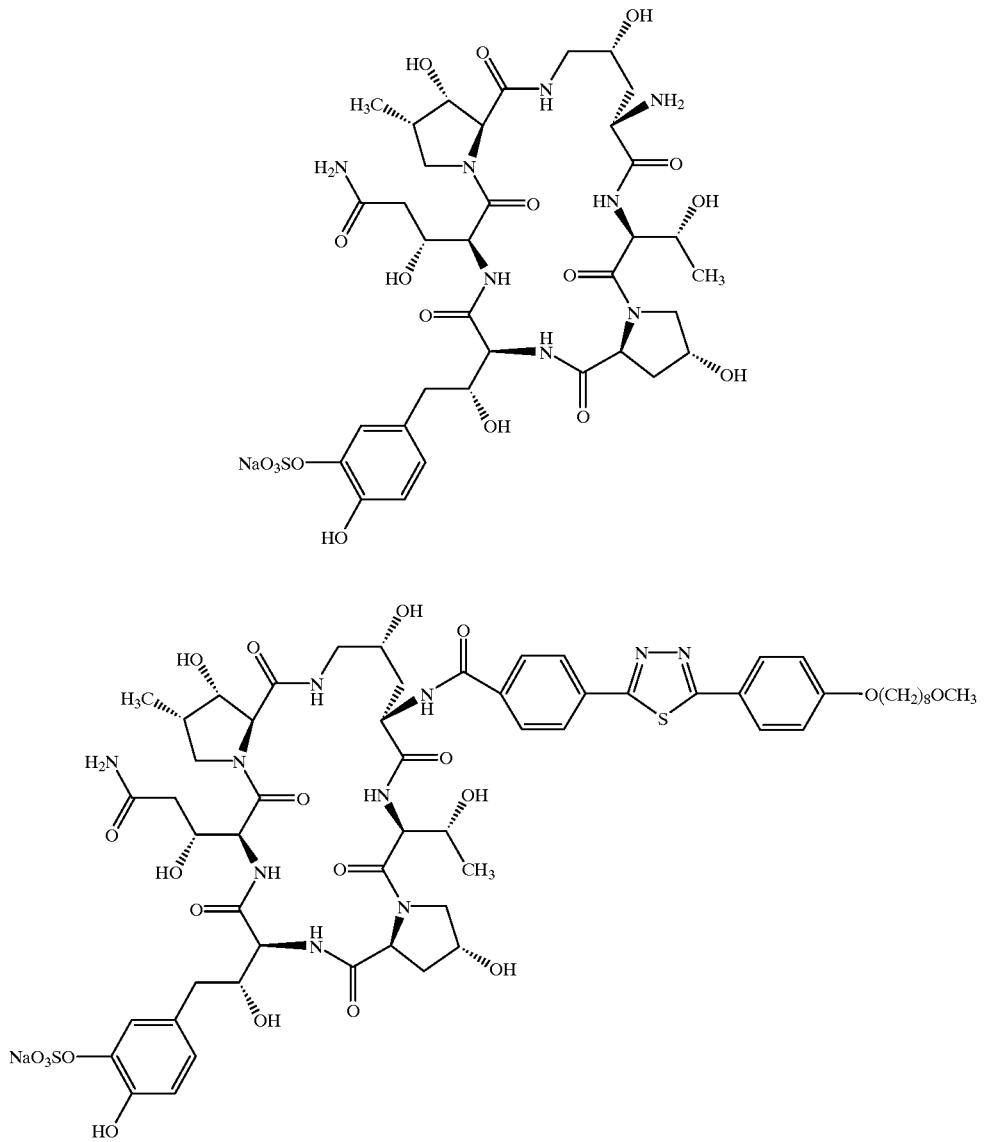 |

-continued
| Example No. | Formula |
|---|---|
| 71 | 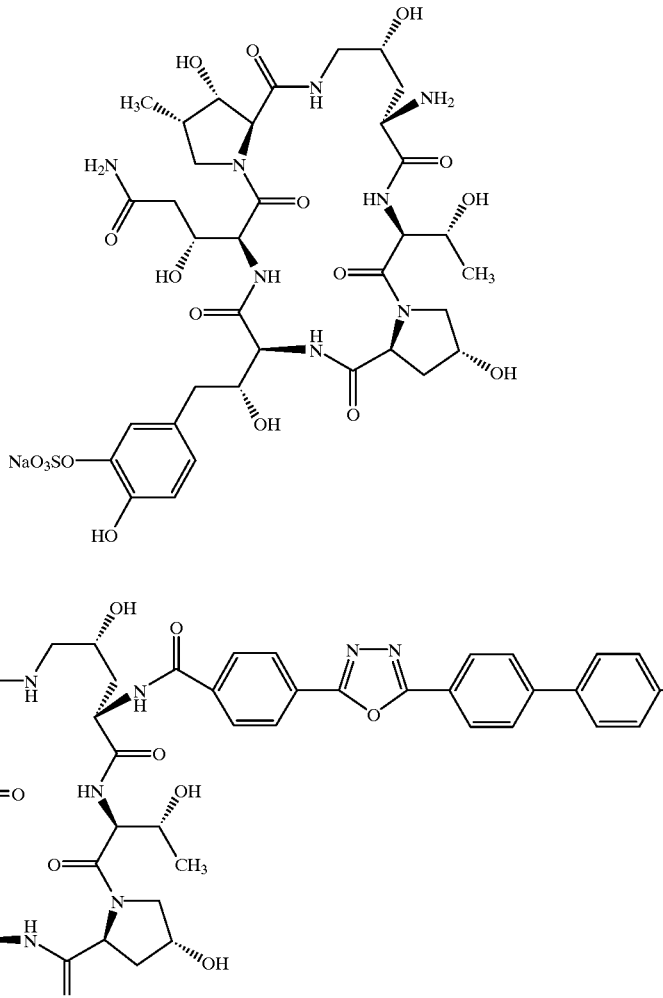 |

-continued
| Example No. | Formula |
|---|---|
| 72 | 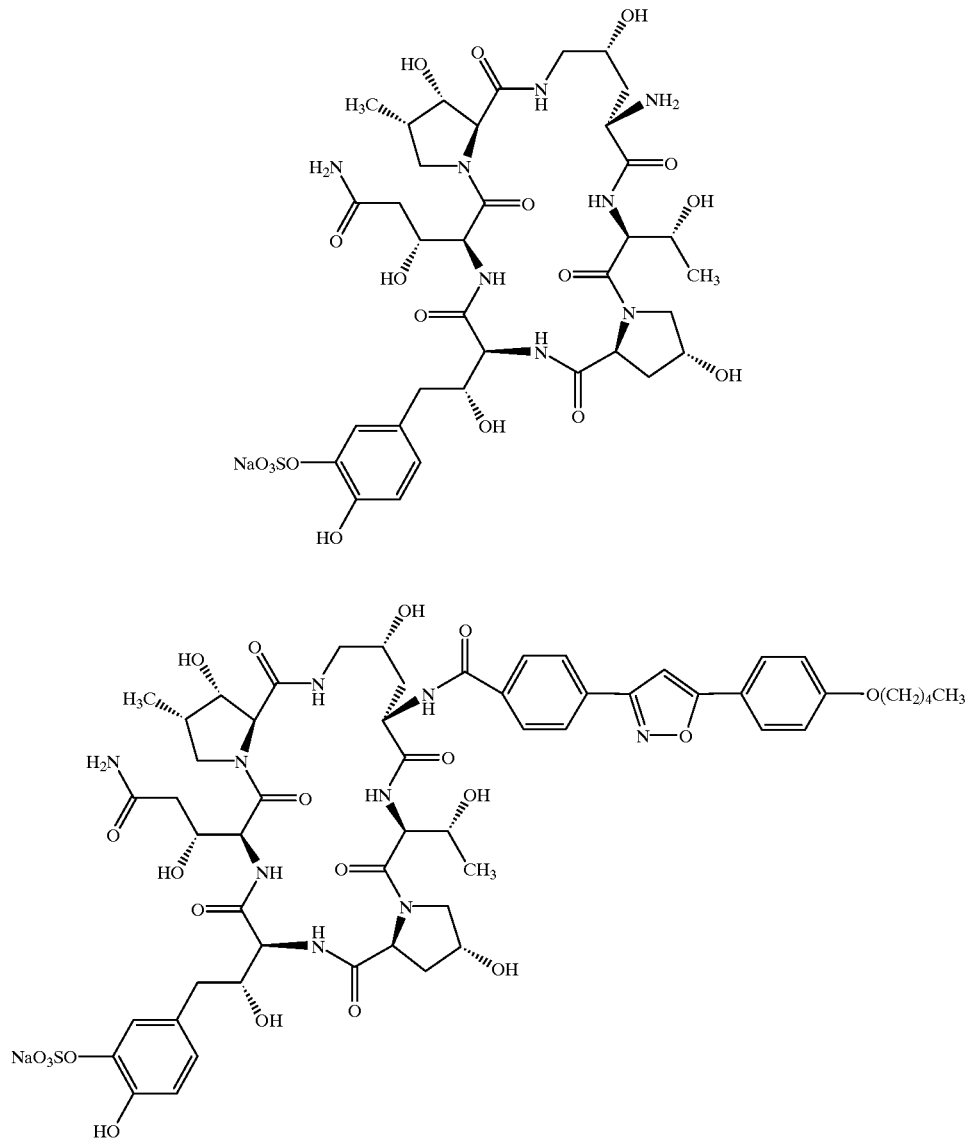 |

-continued
| Example No. | Formula |
|---|---|
| 73 | 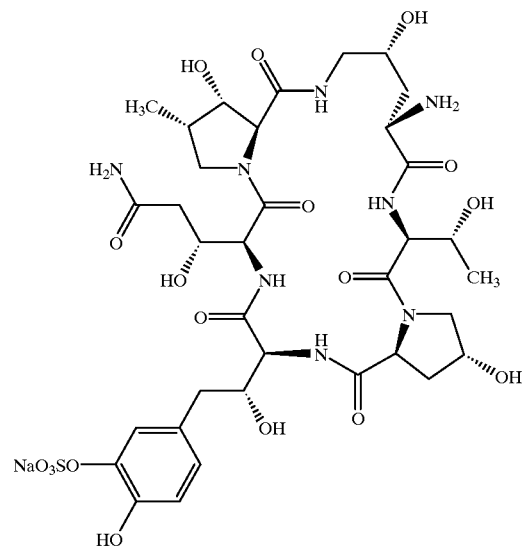 |
| | 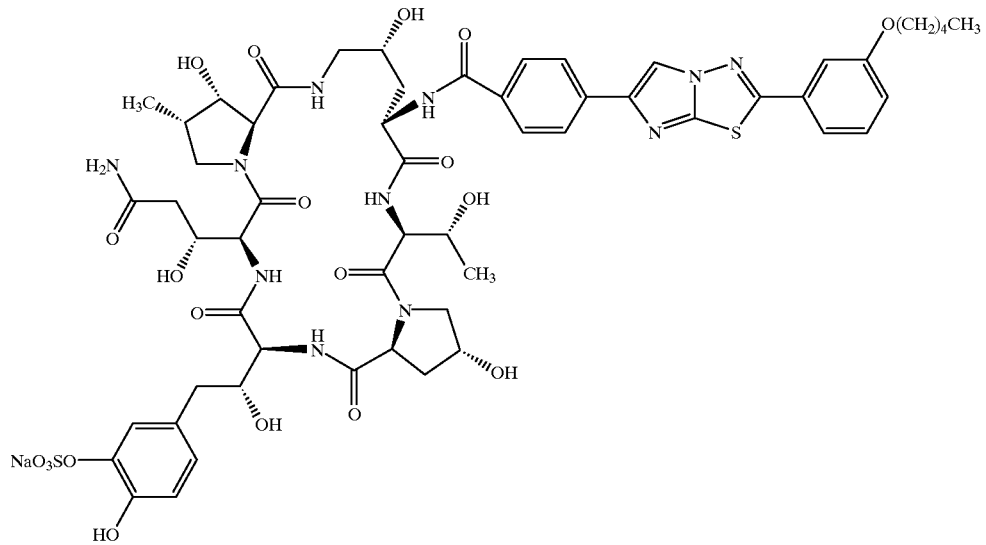 |

| Example No. | Formula |
|---|---|
| 74 | 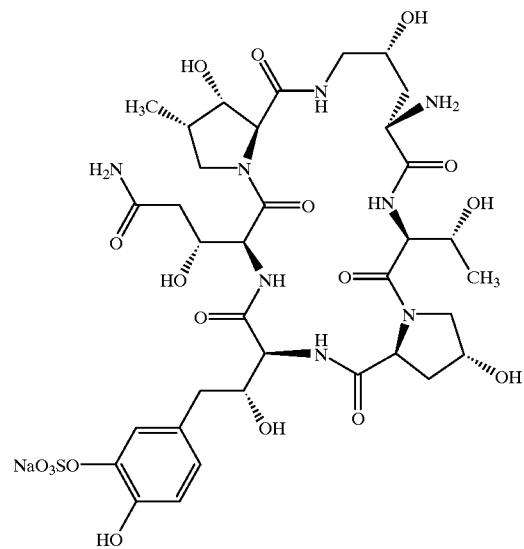<br>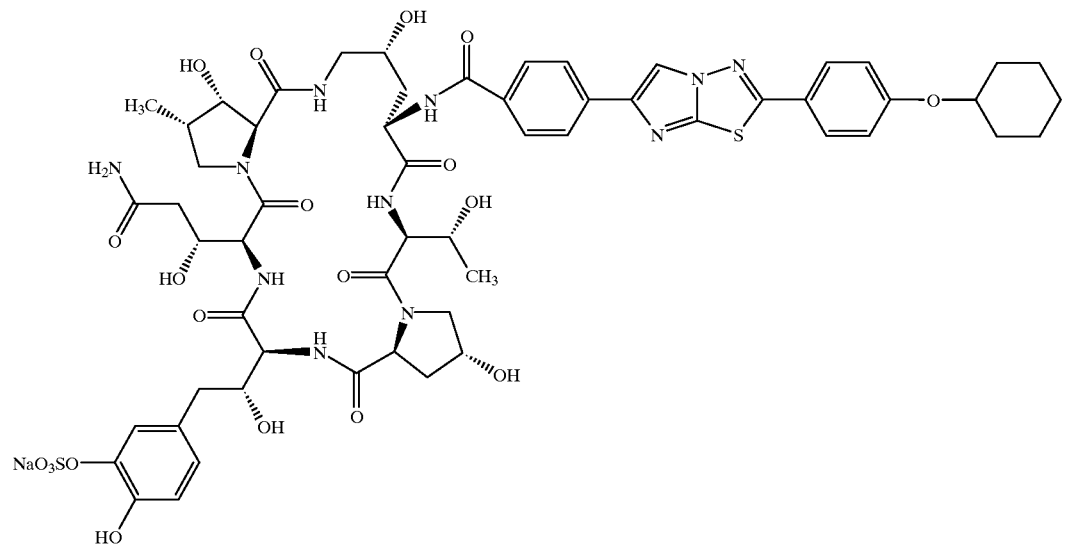 |

-continued
| Example No. | Formula |
|---|---|
| 75 | 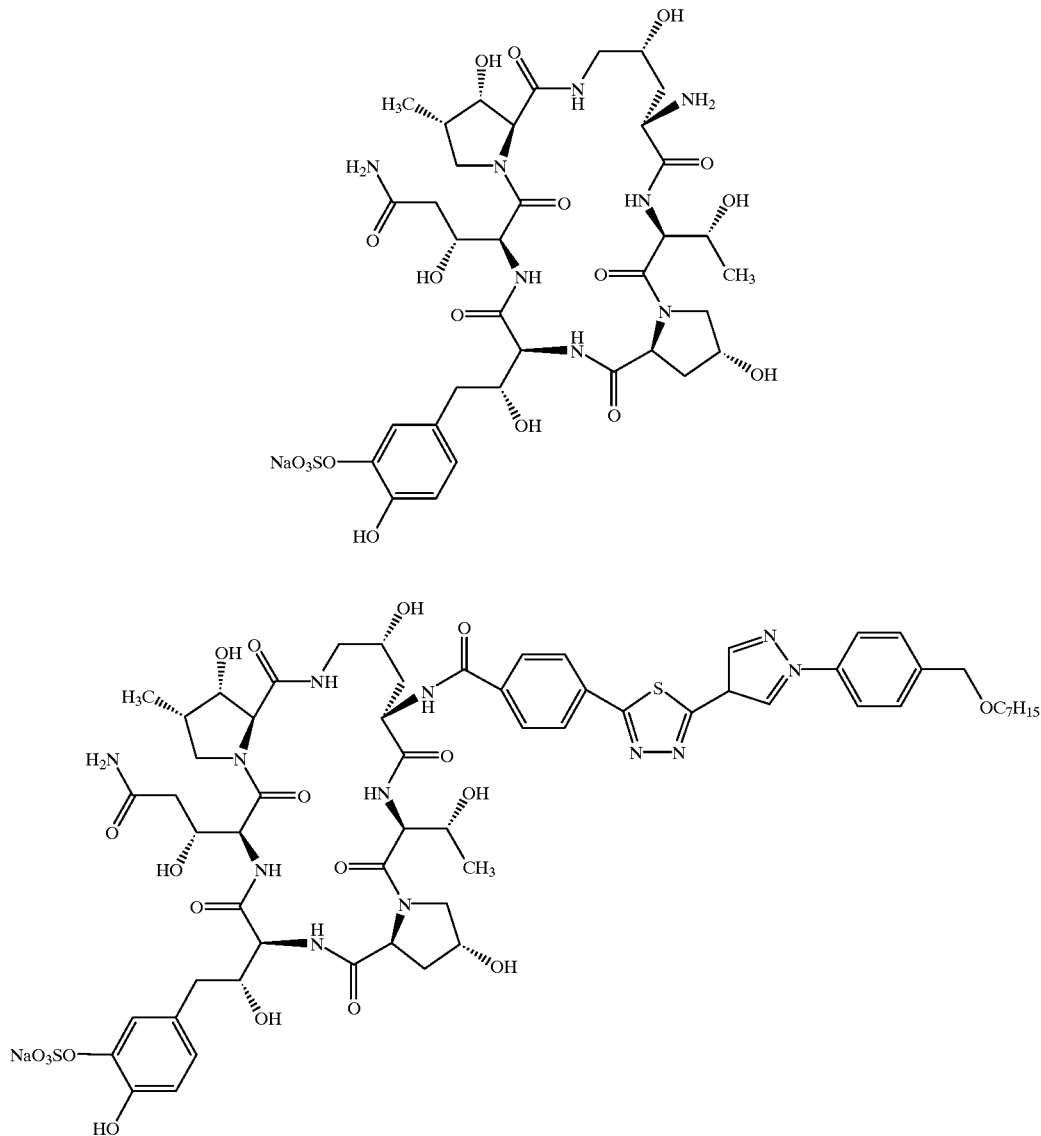 |

-continued
| Example No. | Formula |
|---|---|
| 76 | 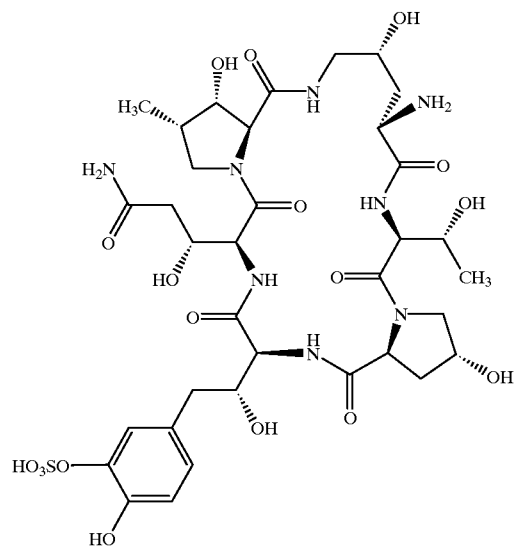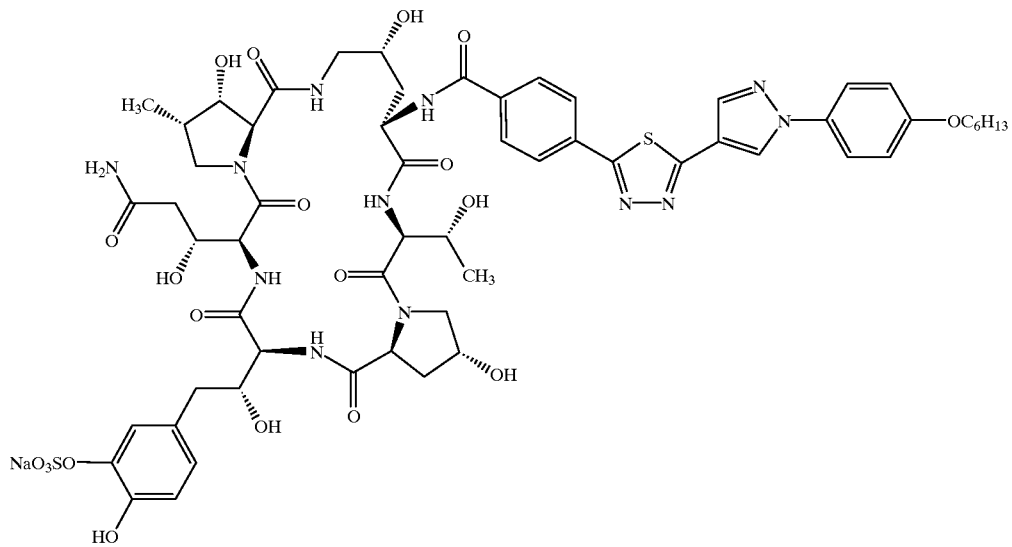 |

| Example No. | Formula |
|---|---|
| 77 | 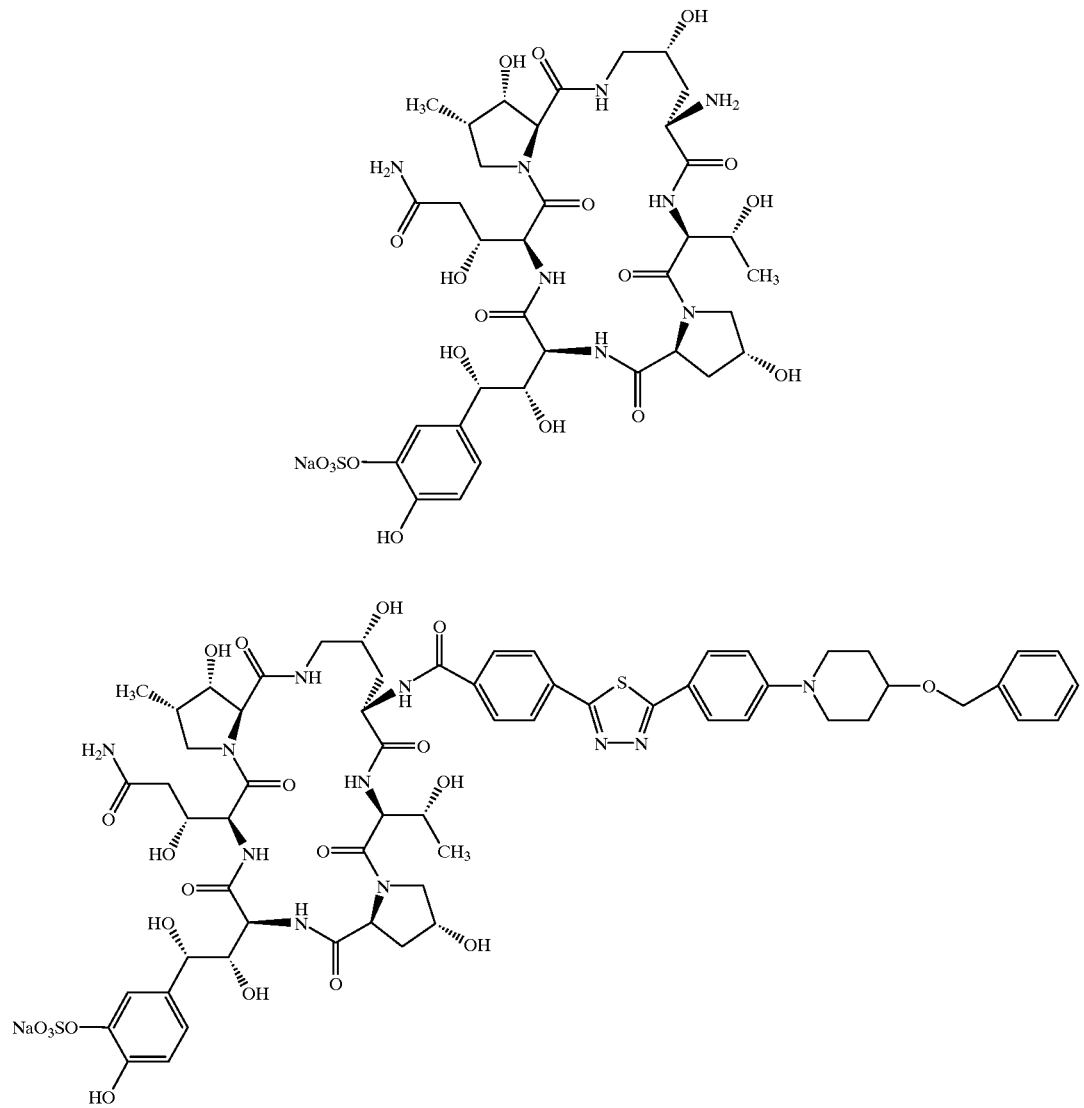 |

-continued
| Example No. | Formula |
|---|---|
| 78 | 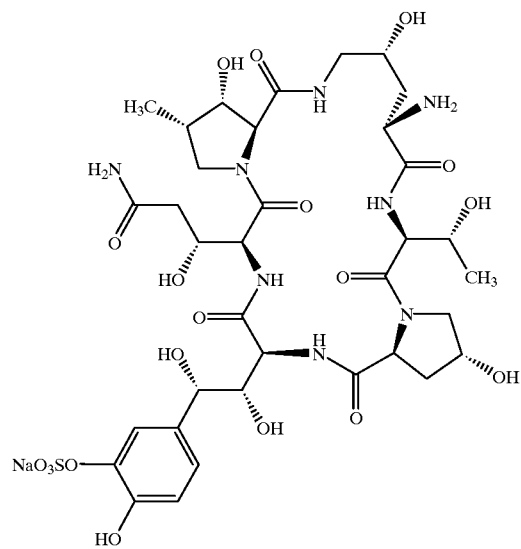 |
| | 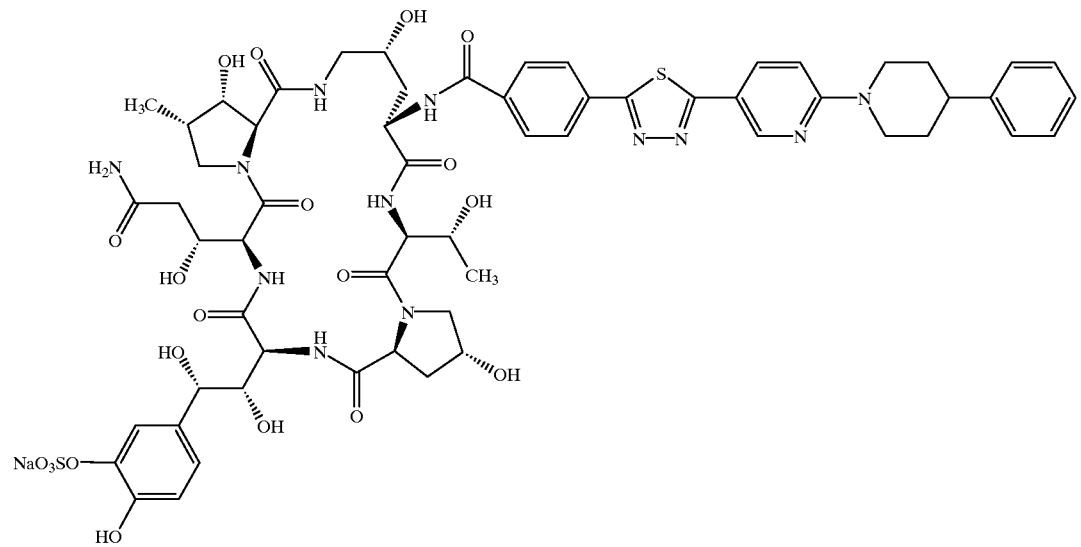 |

-continued
| Example No. | Formula |
|---|---|
| 79 | 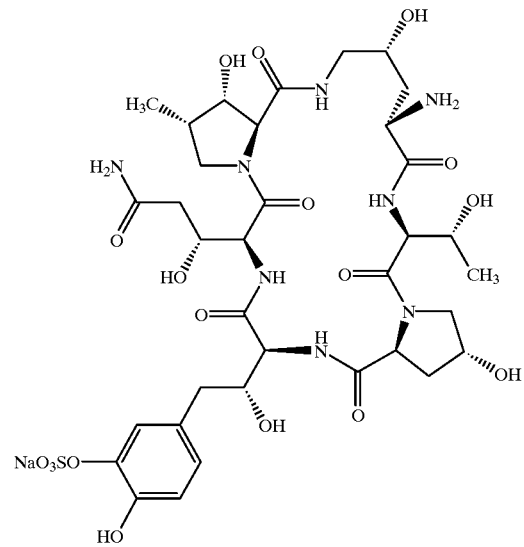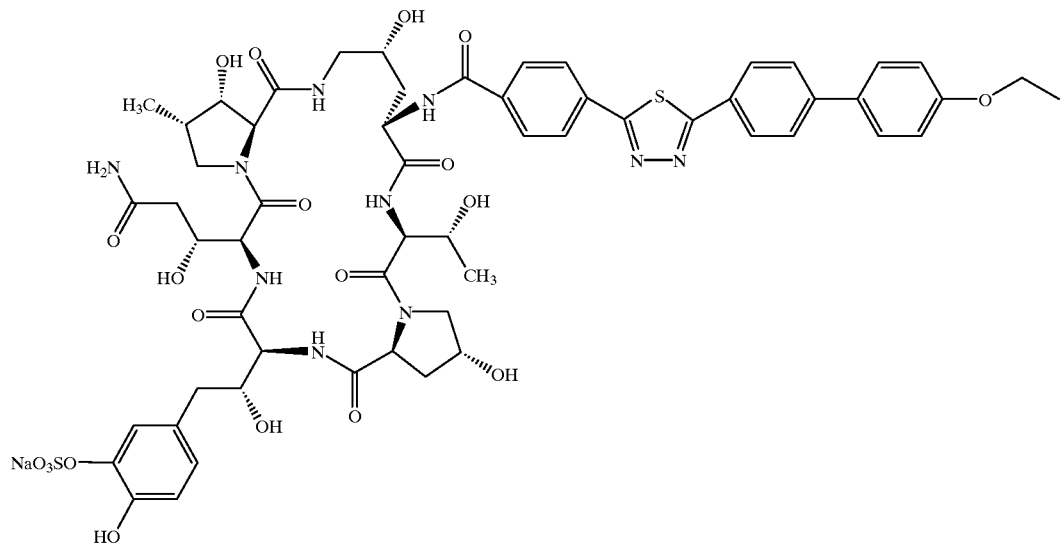 |

| Example No. | Formula |
|---|---|
| 80 | 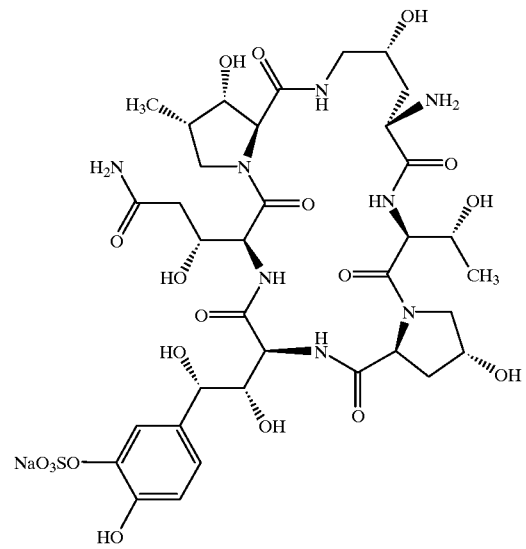 |
| | 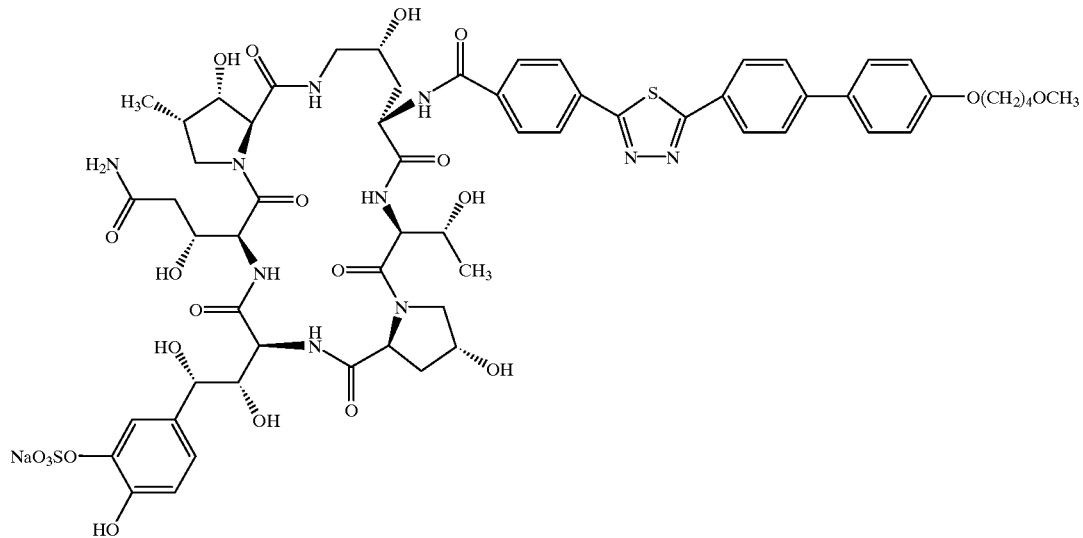 |

-continued
| Example No. | Formula |
|---|---|
| 81 | 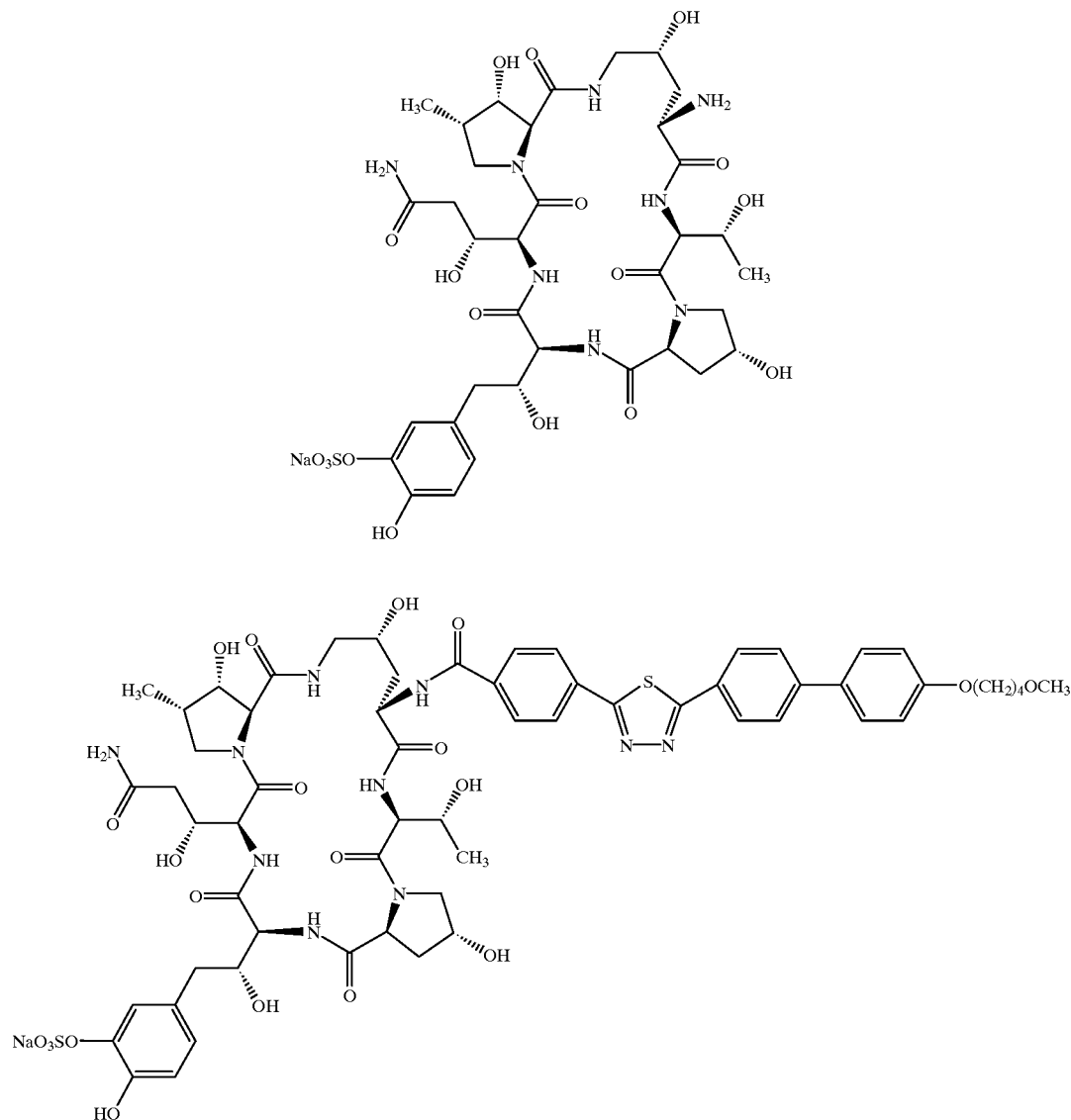 |

-continued
| Example No. | Formula |
|---|---|
| 82 | 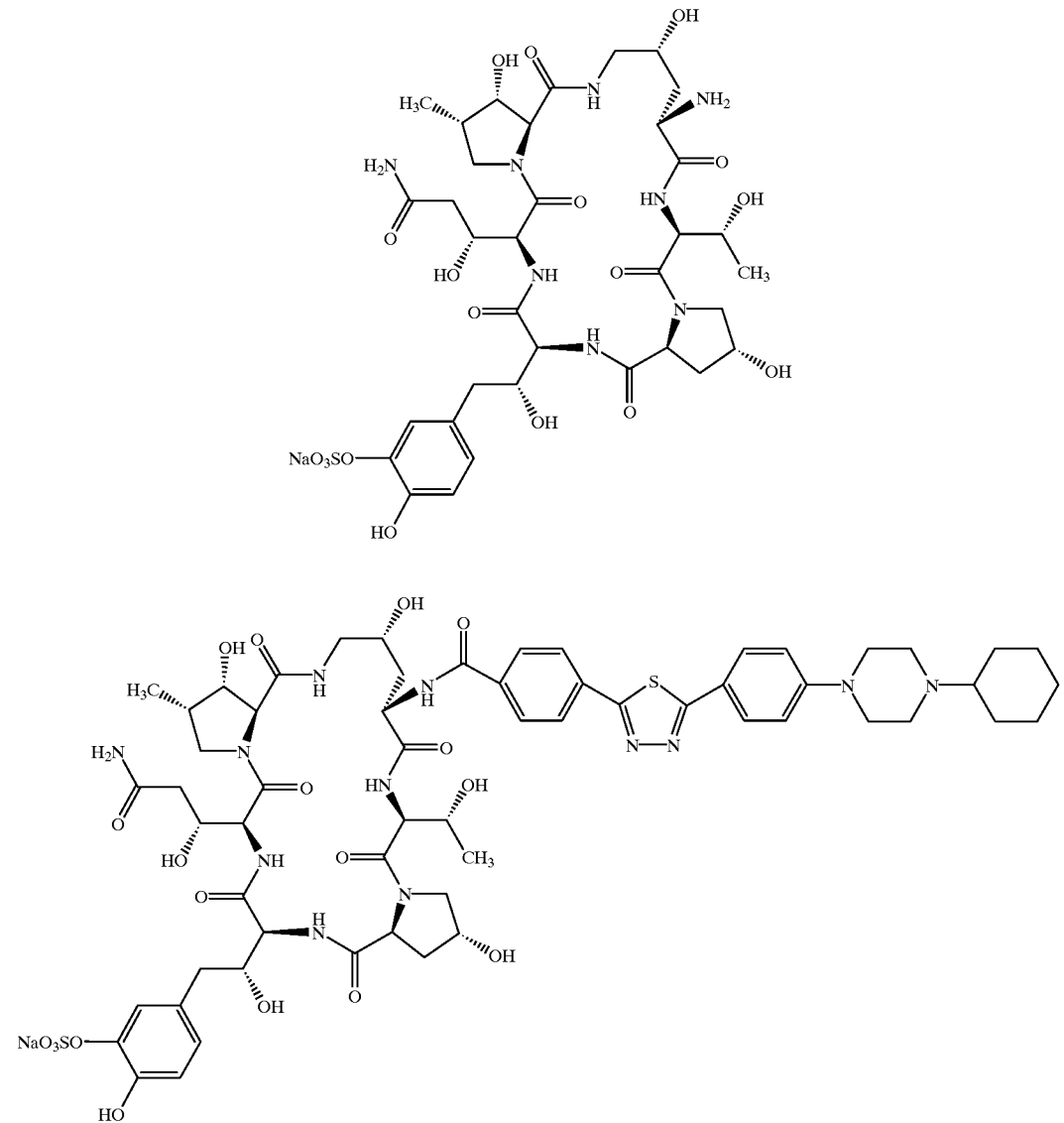 |

-continued
| Example No. | Formula |
|---|---|
| 83 | 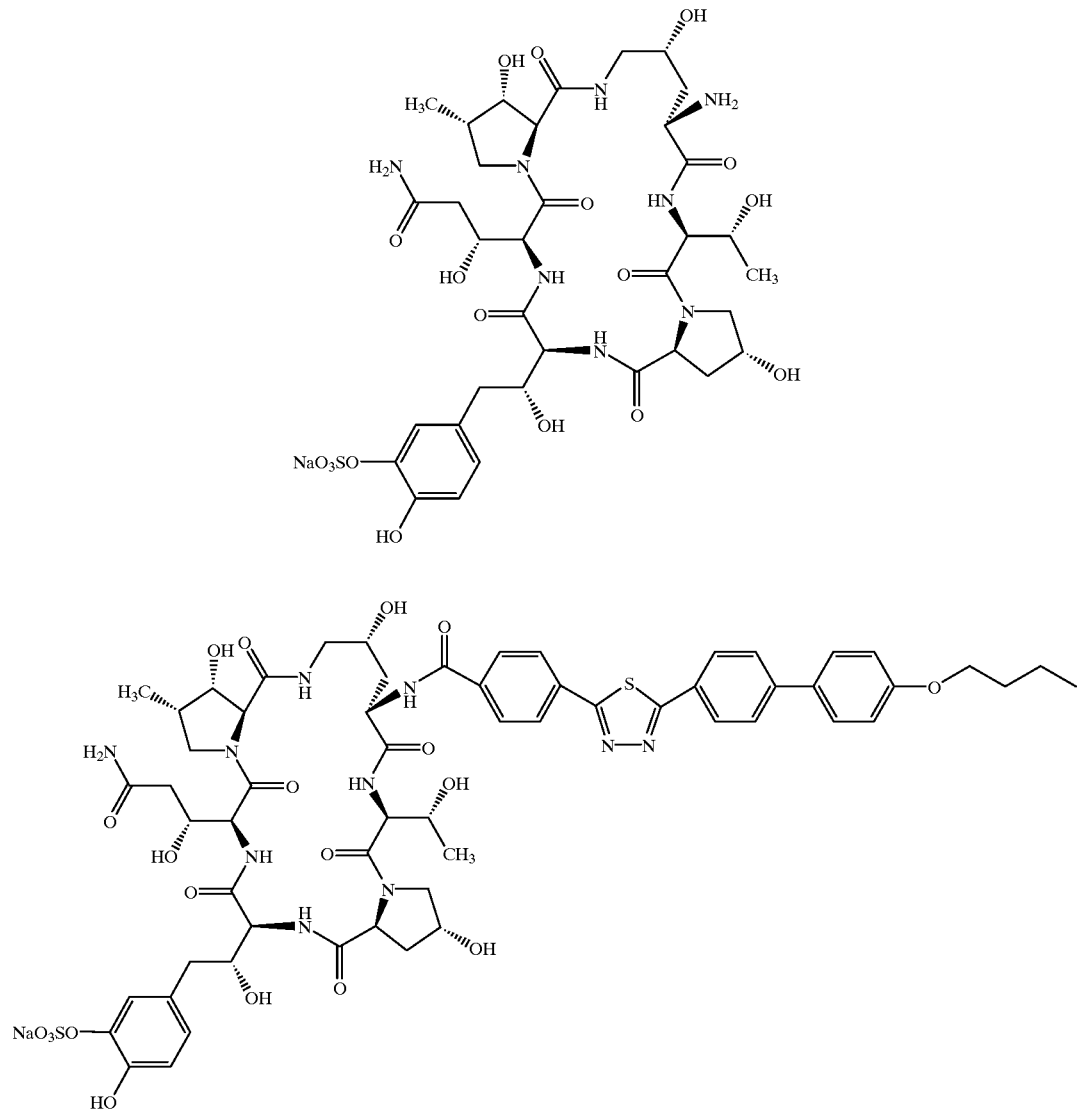 |

-continued
| Example No. | Formula |
|---|---|
| 84 | 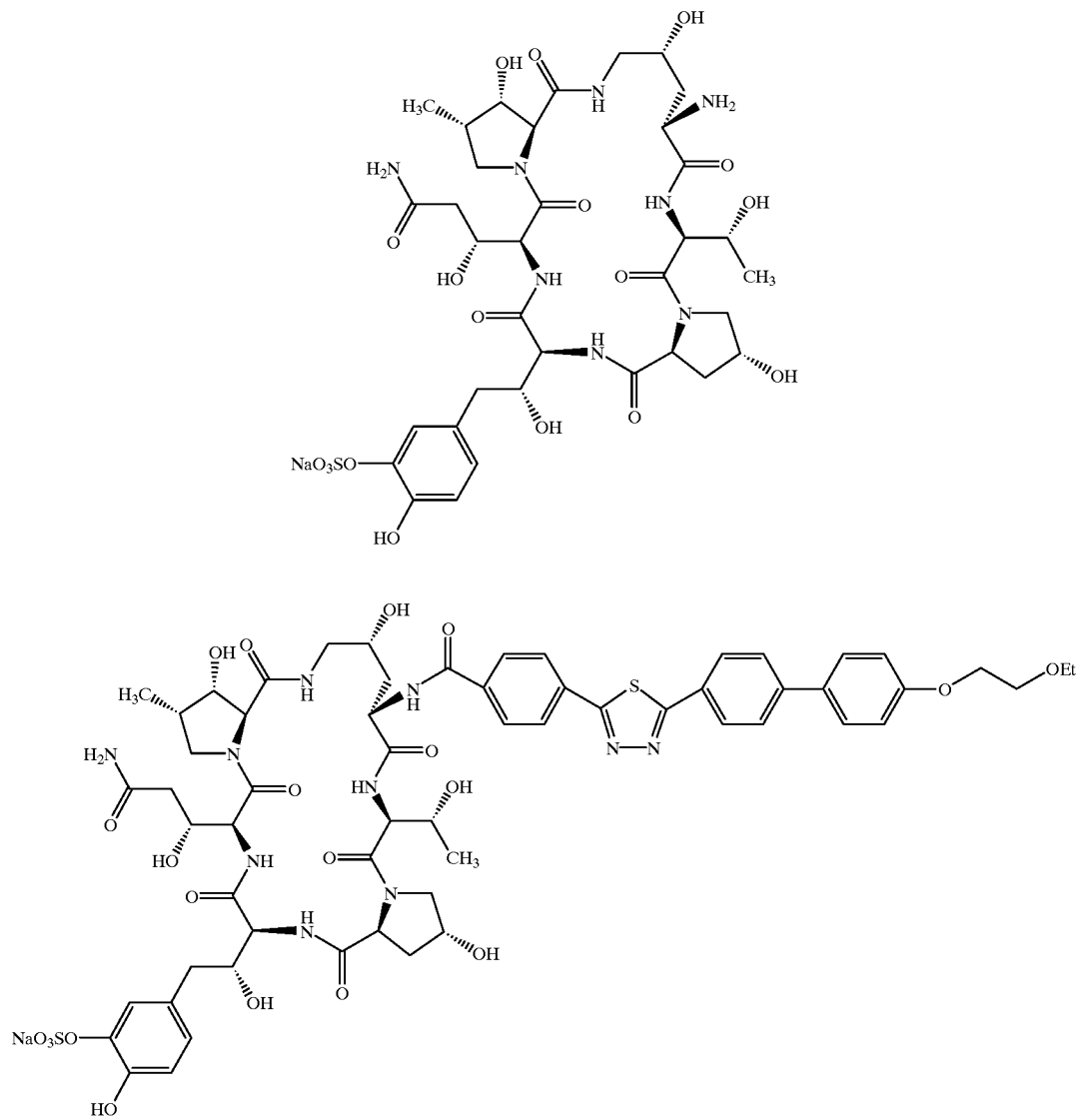 |

| Example No. | Formula |
|---|---|
| 85 | 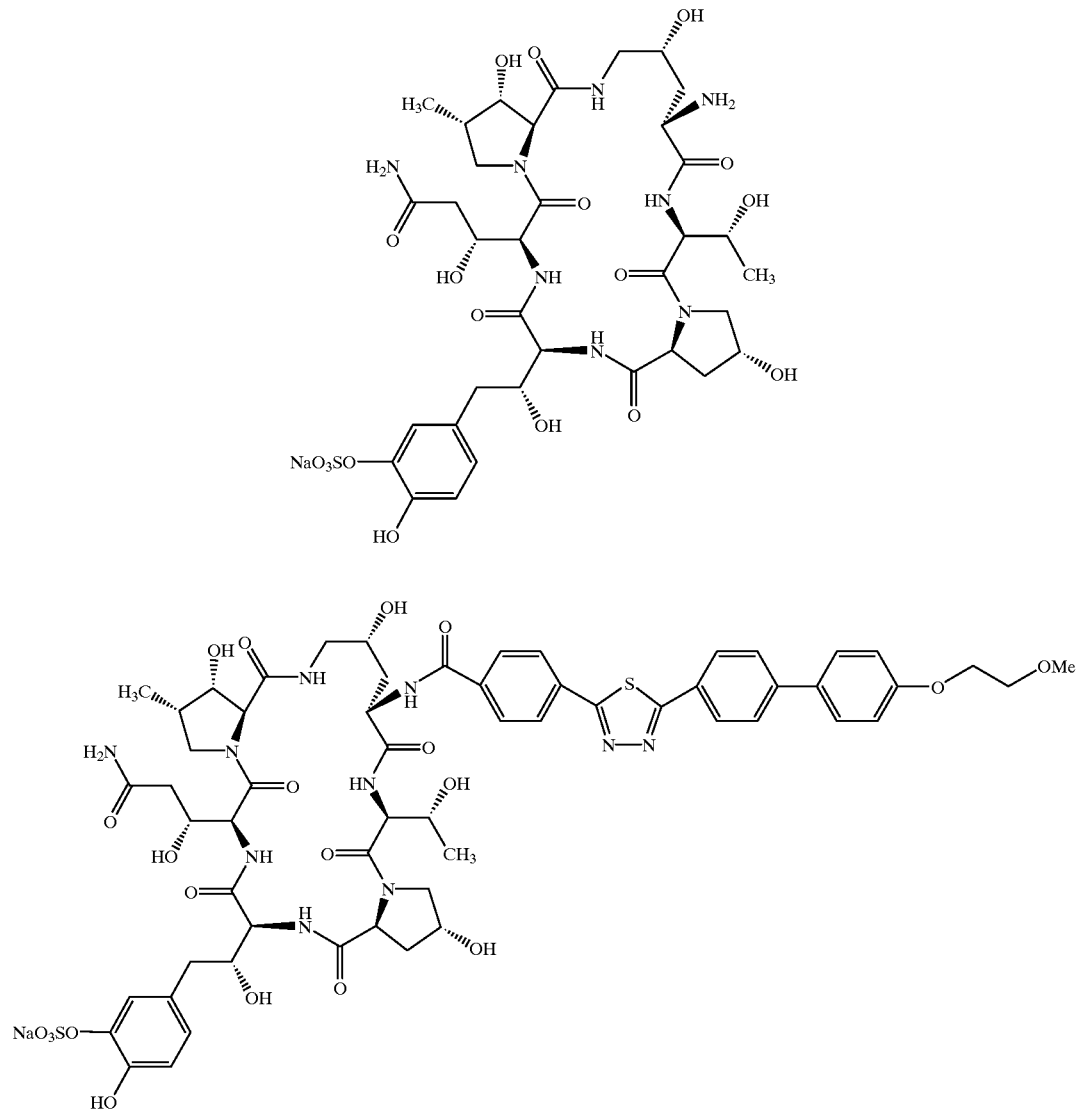 |

-continued
| Example No. | Formula |
|---|---|
| 86 | 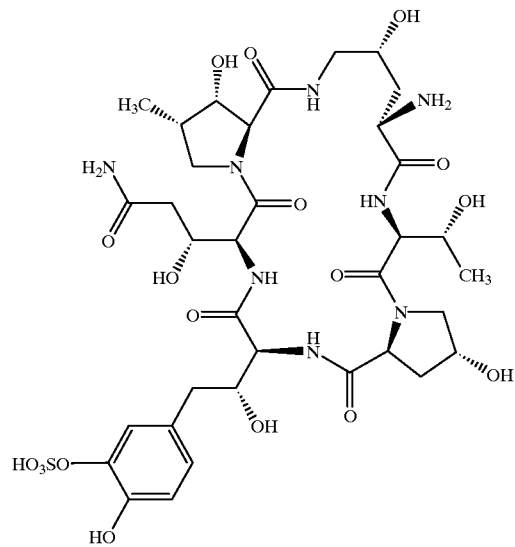 |
| | 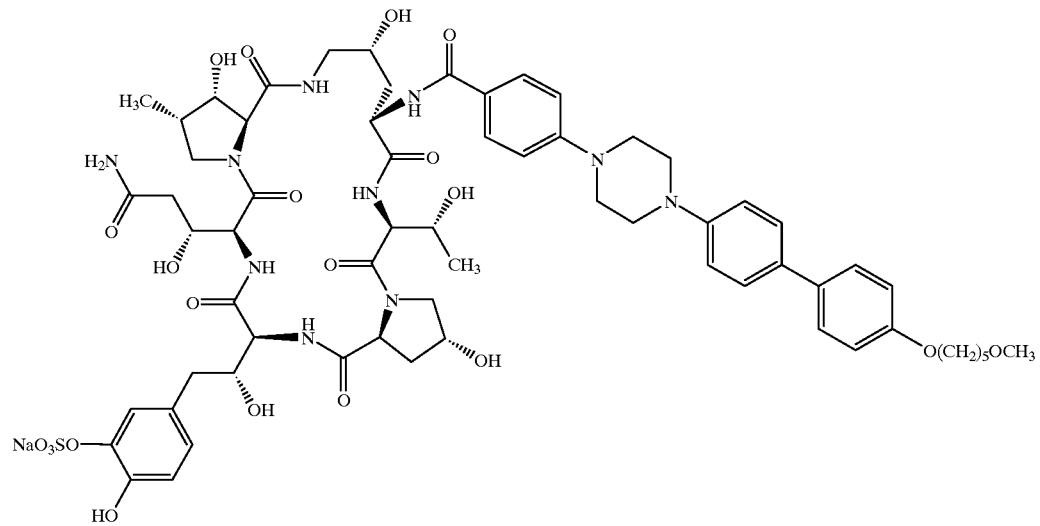 |

-continued
| Example No. | Formula |
|---|---|
| 87 | 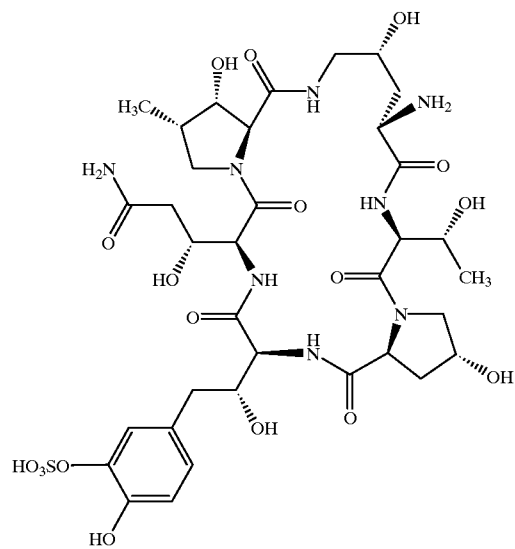 |
|  | 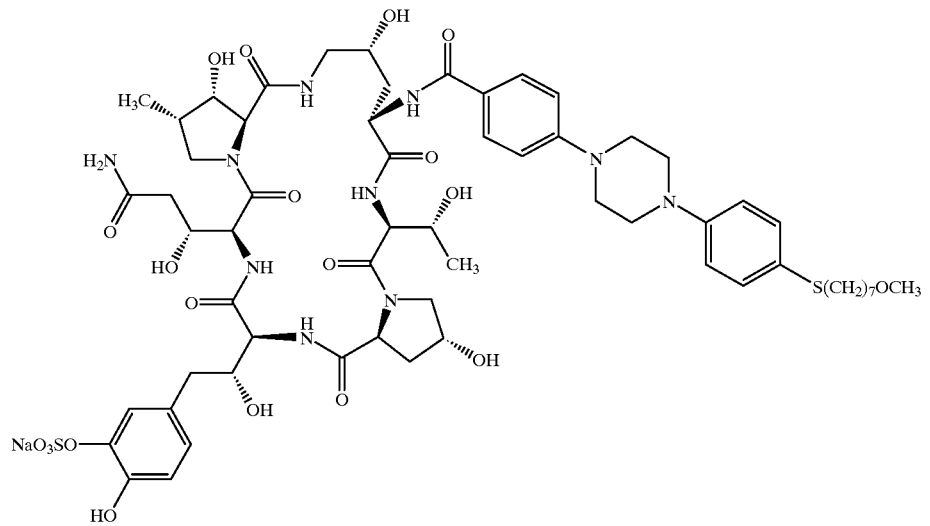 |

-continued
| Example No. | Formula |
|---|---|
| 88 | 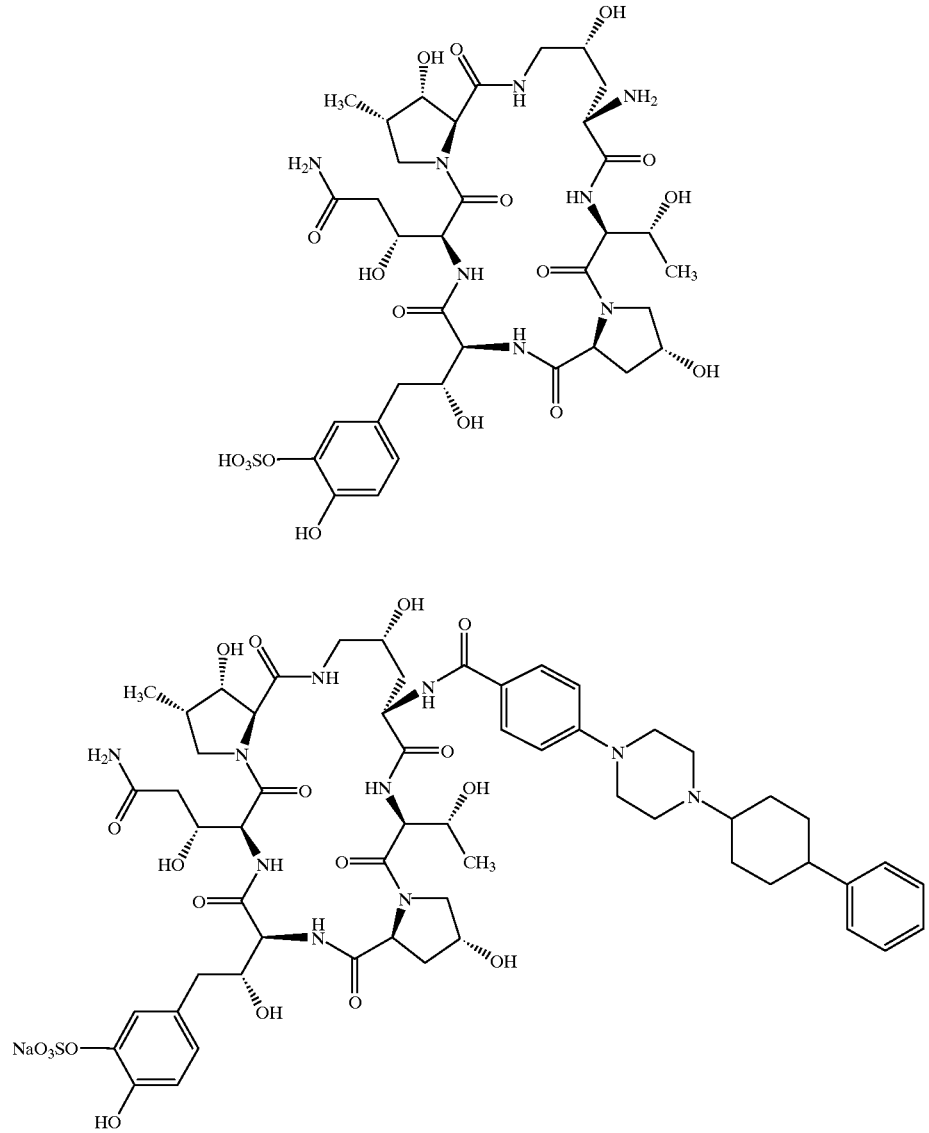 |

| Example No. | Formula |
|---|---|
| 89 | 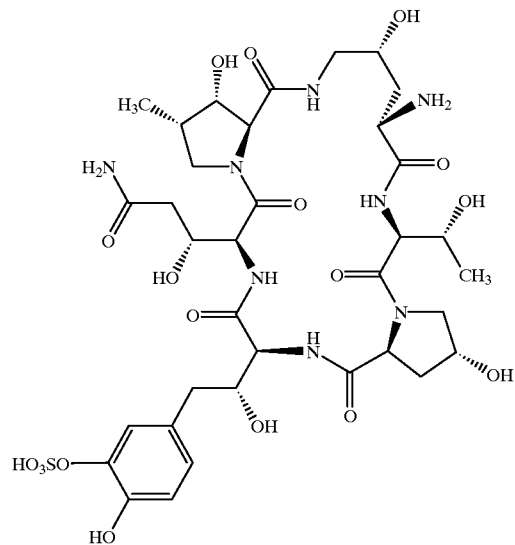 |
| | 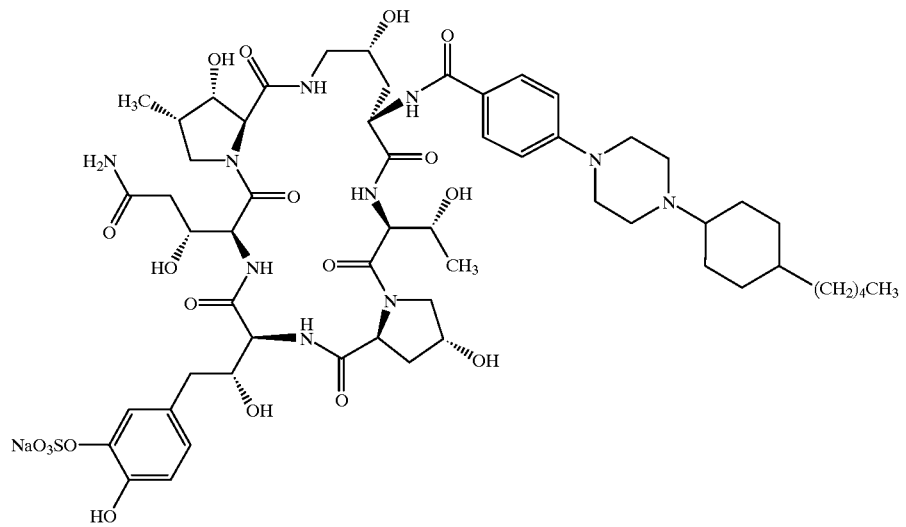 |

-continued
| Example No. | Formula |
|---|---|
| 90 | 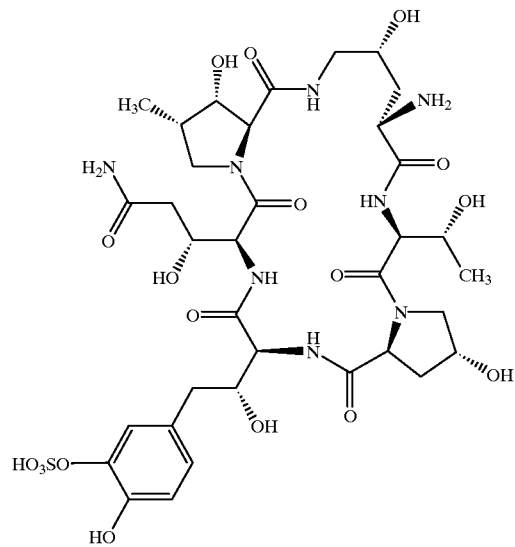 |
| | 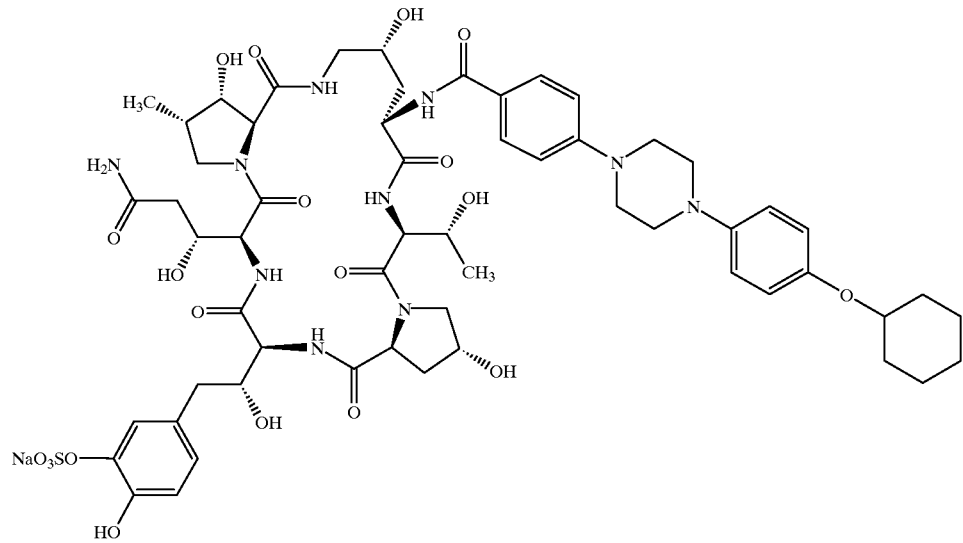 |

| Example No. | Formula |
|---|---|
| 91 | 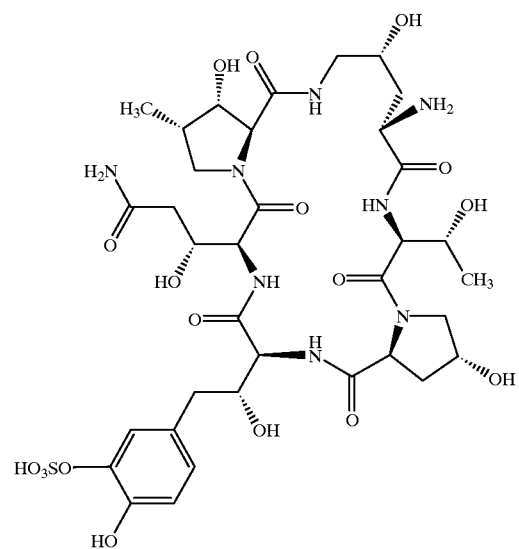 |
| | 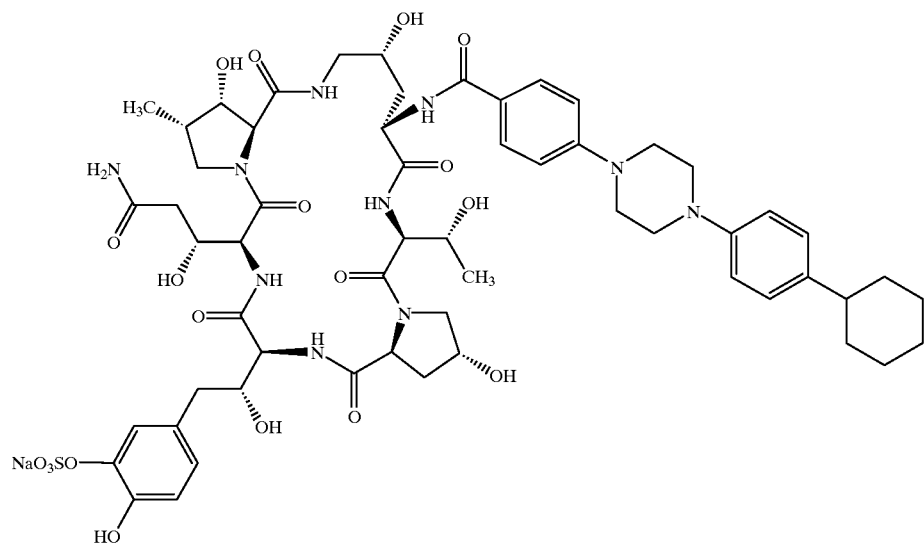 |

| Example No. | Formula |
|---|---|
| 92 | 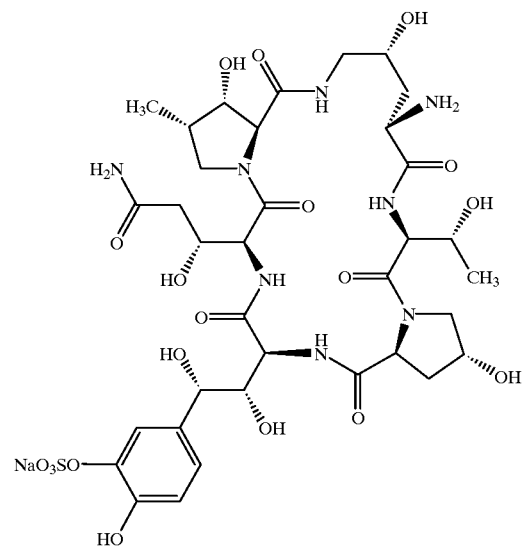 |
| | 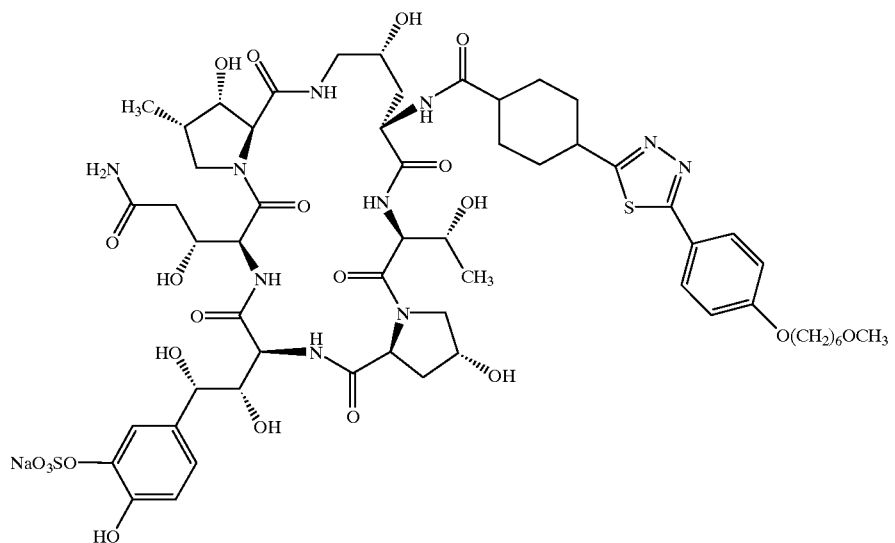 |

-continued
| Example No. | Formula |
|---|---|
| 93 | 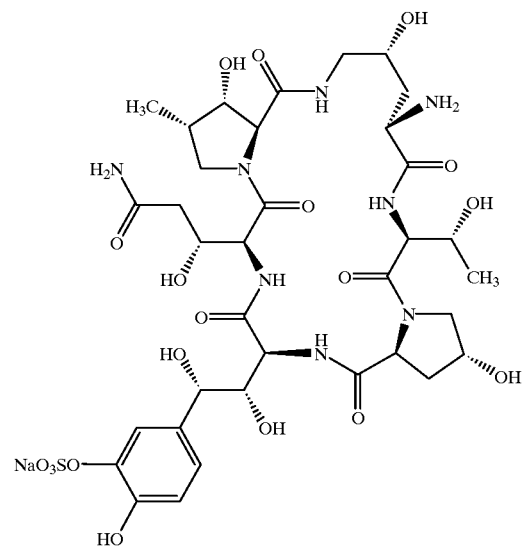 |
| | 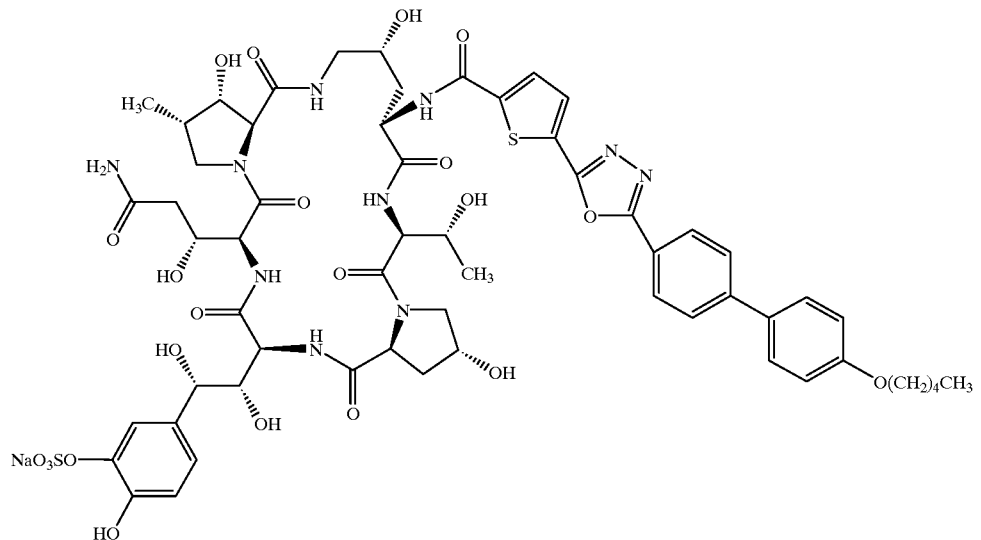 |

| Example No. | Formula |
|---|---|
| 94 | 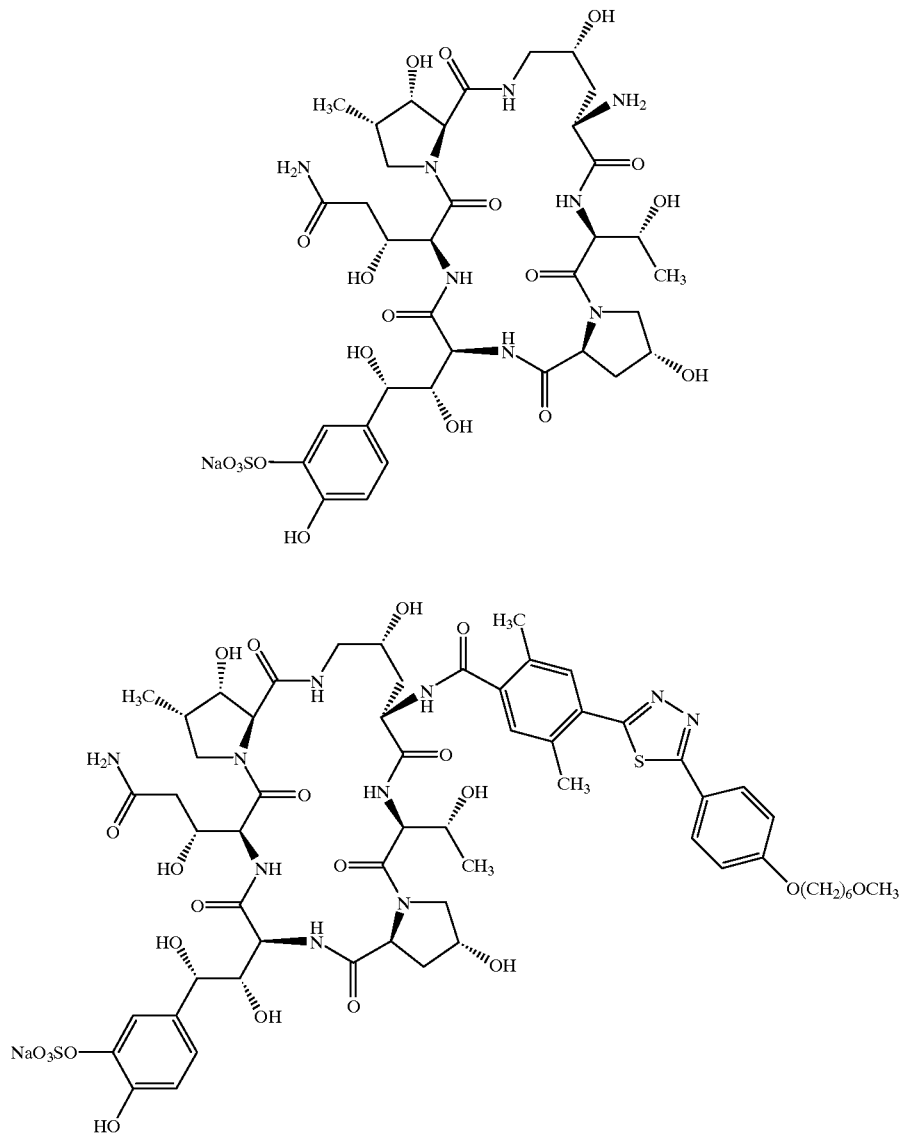 |

| Example No. | Formula |
|---|---|
| 95 | 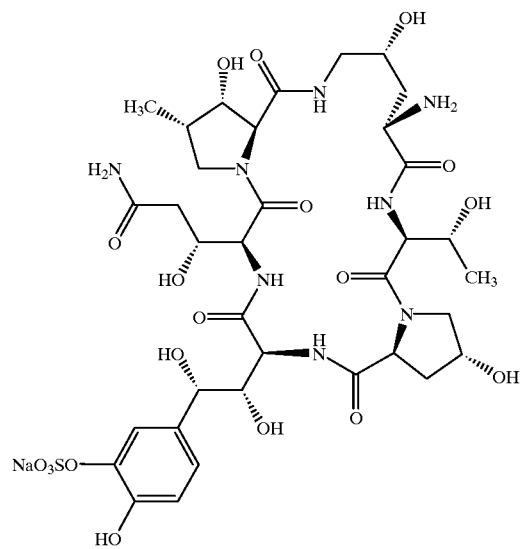 |
| | 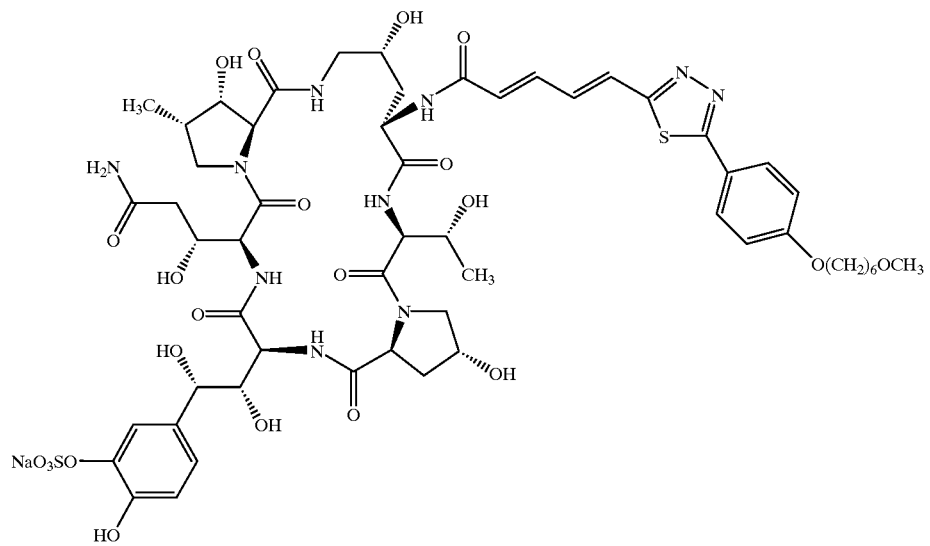 |

-continued
| Example No. | Formula |
|---|---|
| 96 | 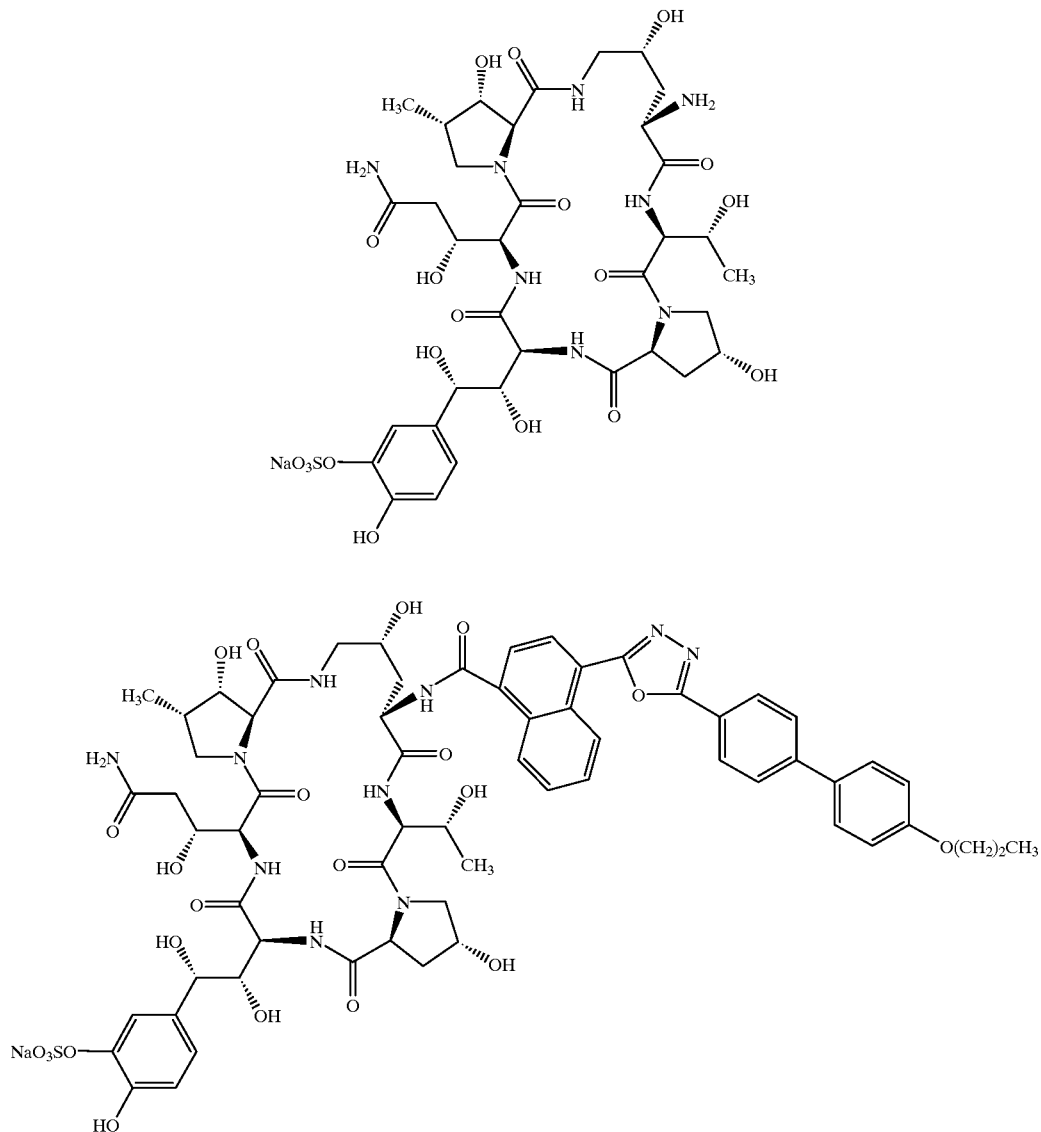 |

-continued
| Example No. | Formula |
|---|---|
| 97 | 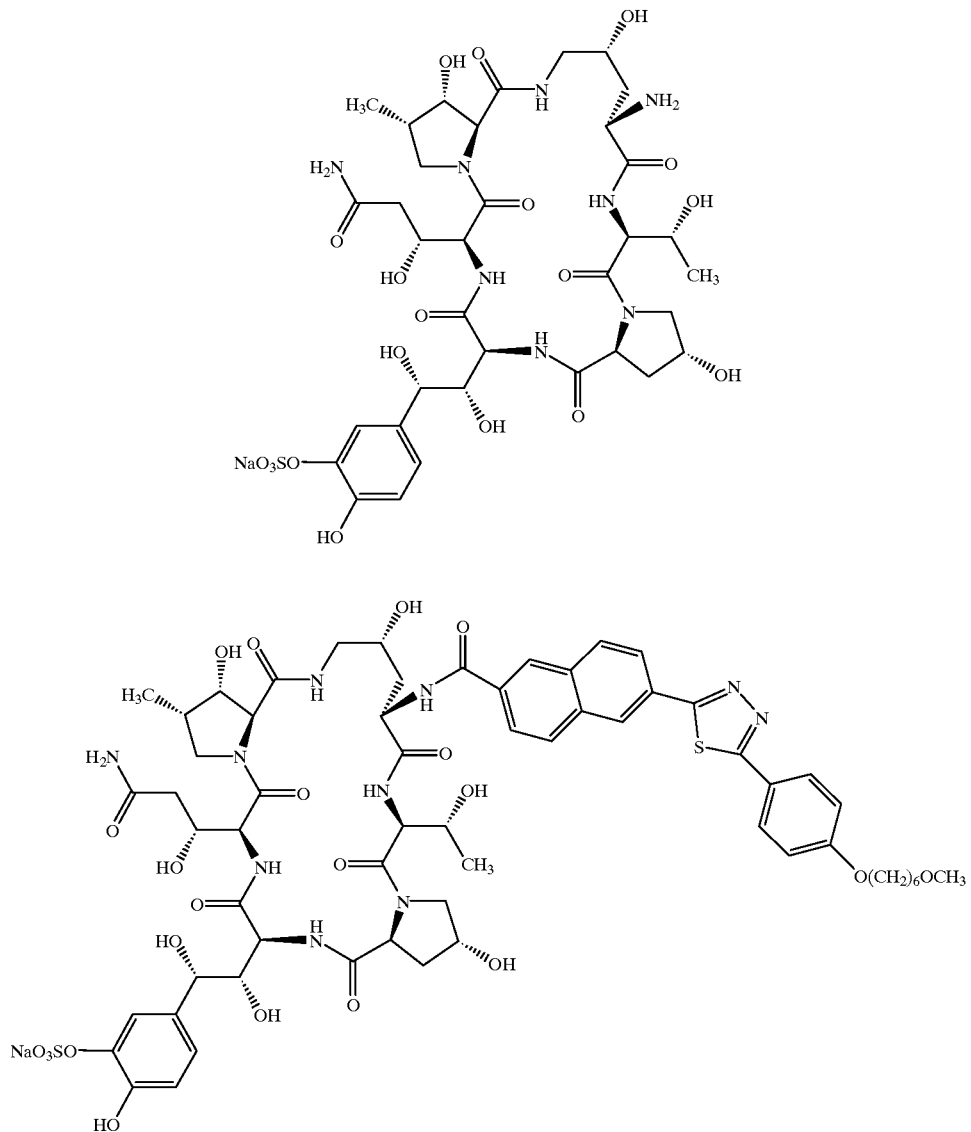 |

-continued
| Example No. | Formula |
|---|---|
| 98 | 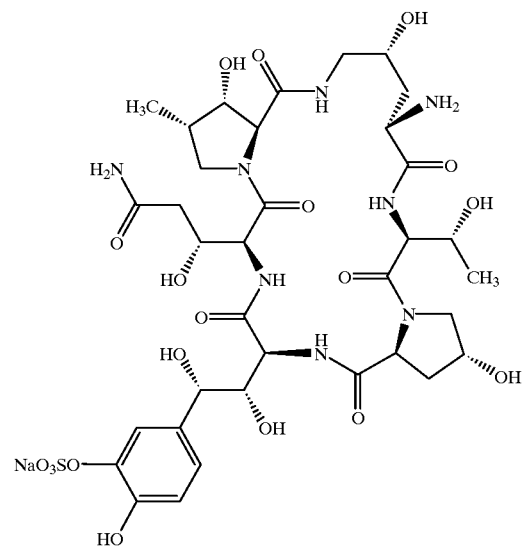 |
| | 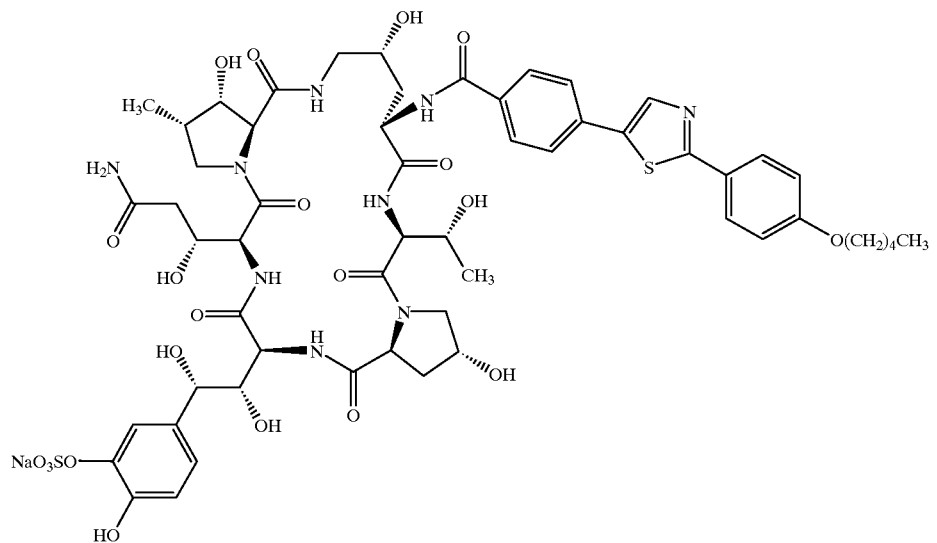 |

-continued
| Example No. | Formula |
|---|---|
| 99 | 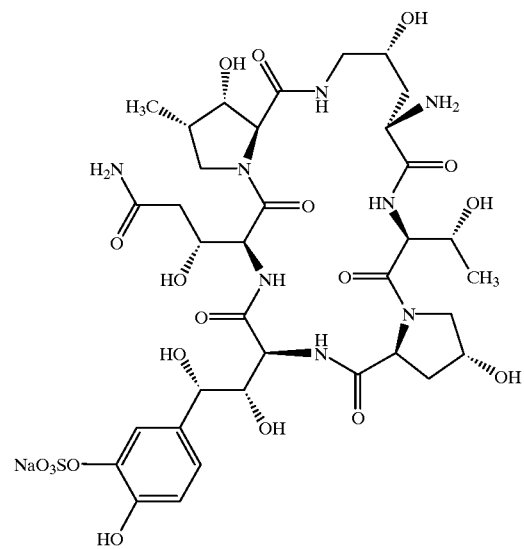 |
| | 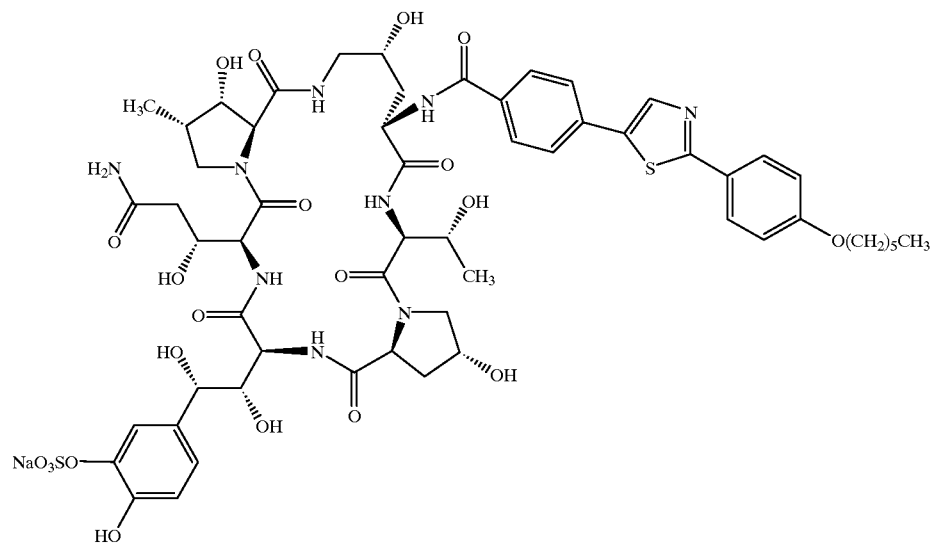 |

-continued
| Example No. | Formula |
|---|---|
| 100 | 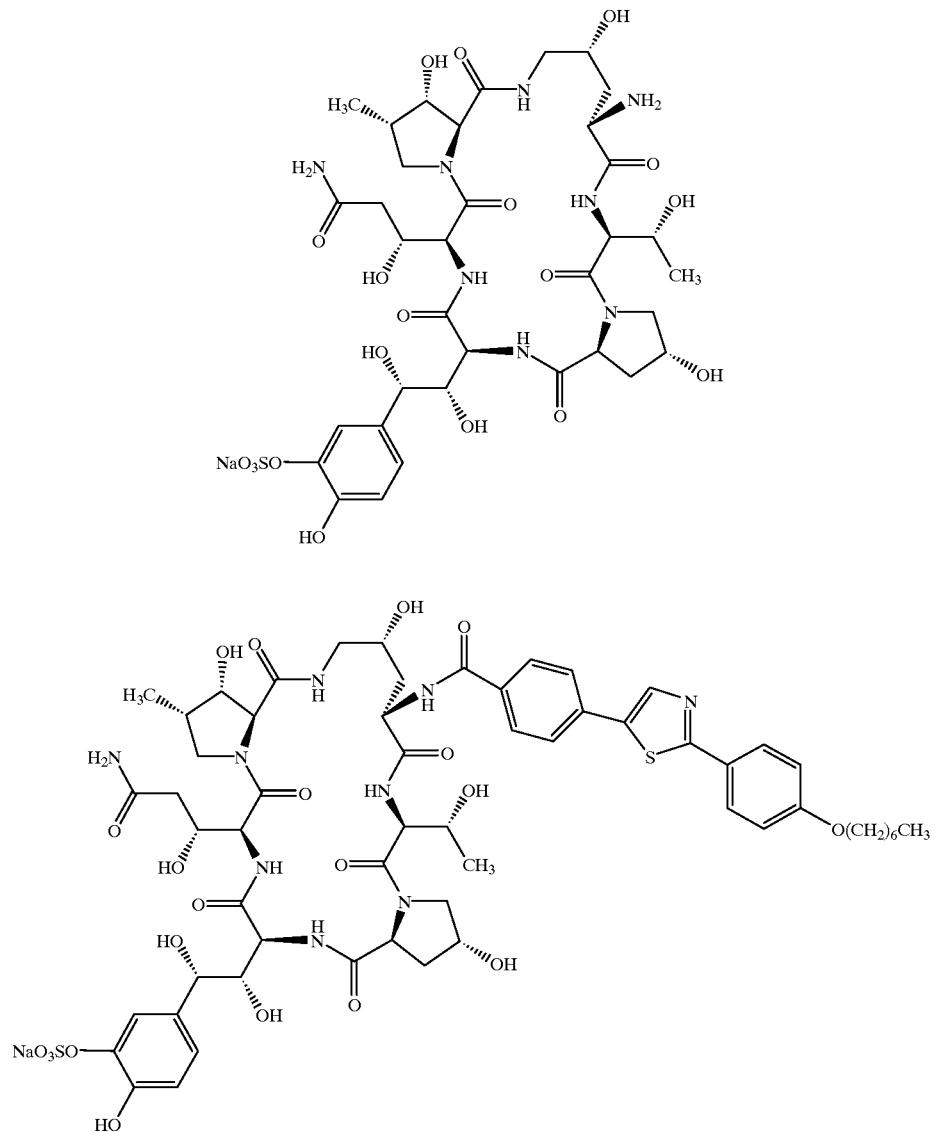 |

-continued
| Example No. | Formula |
|---|---|
| 101 | 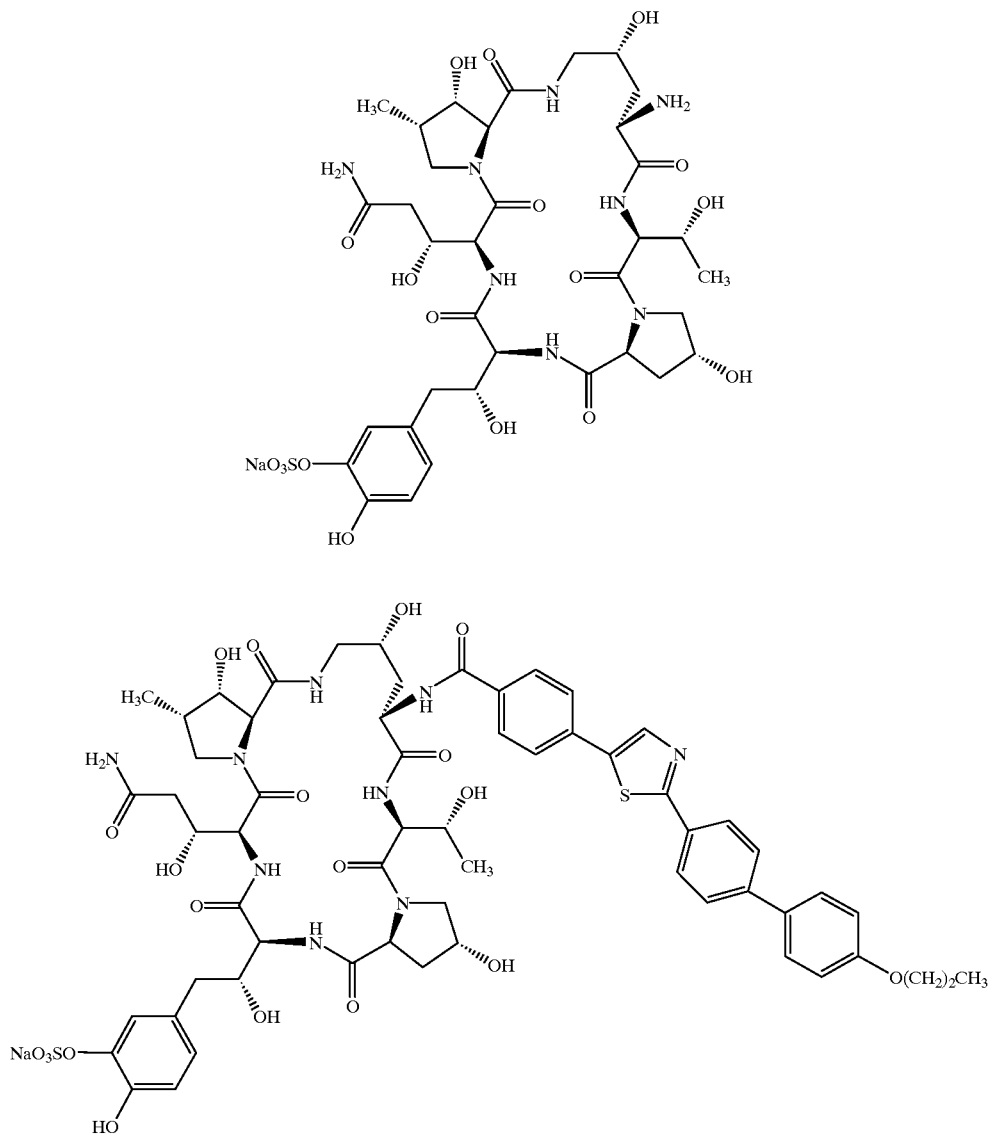 |

-continued
| Example No. | Formula |
|---|---|
| 102 | 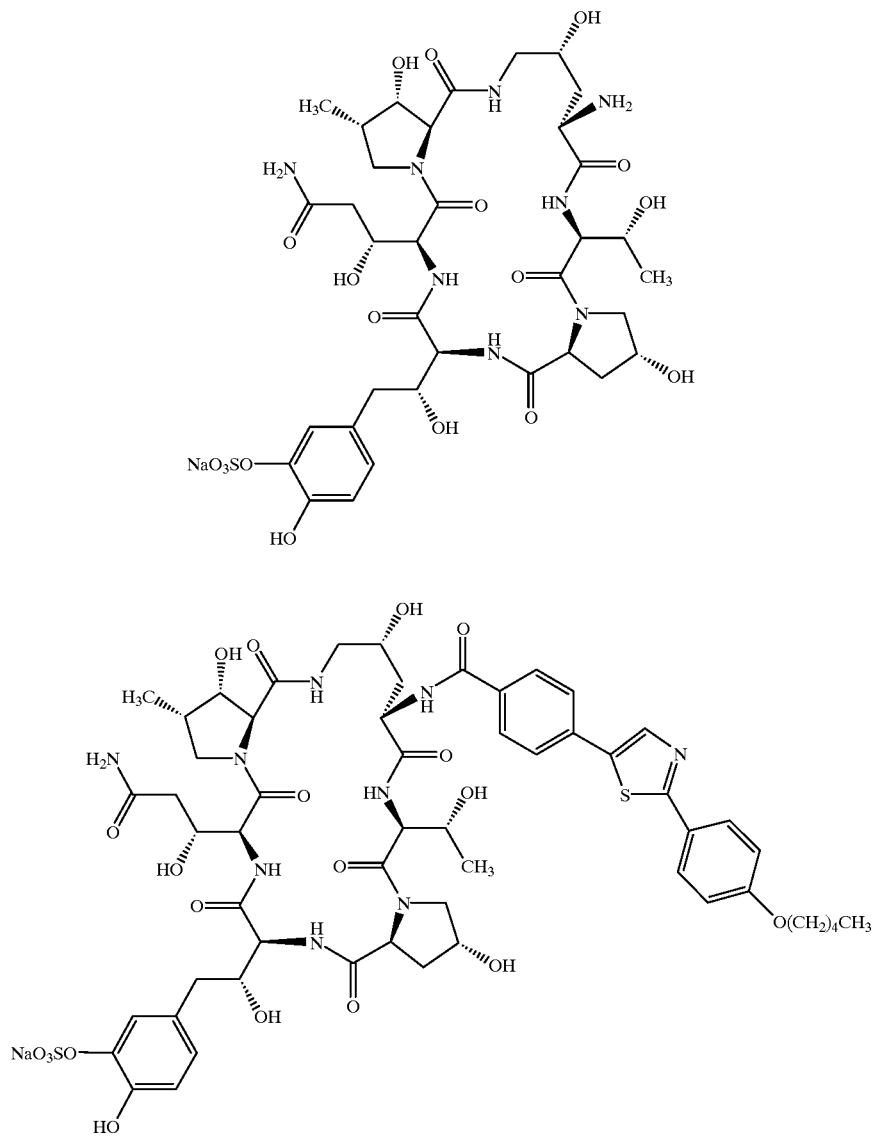 |

-continued
| Example No. | Formula |
|---|---|
| 103 | 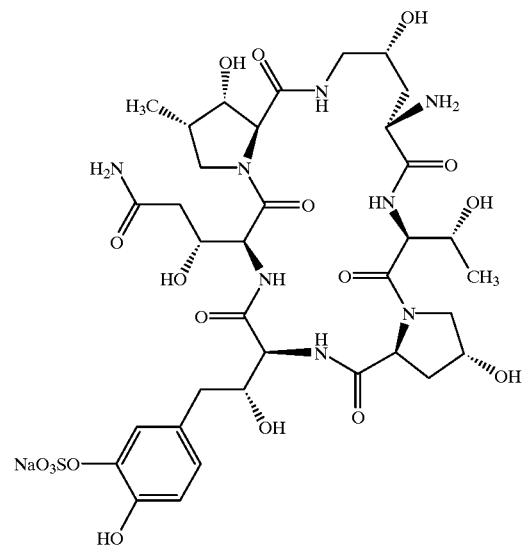 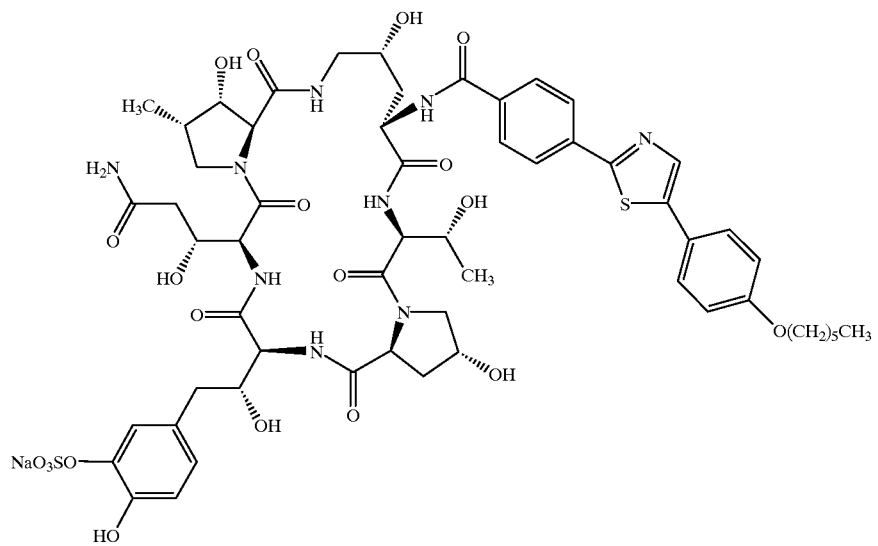 |

-continued
| Example No. | Formula |
|---|---|
| 104 | 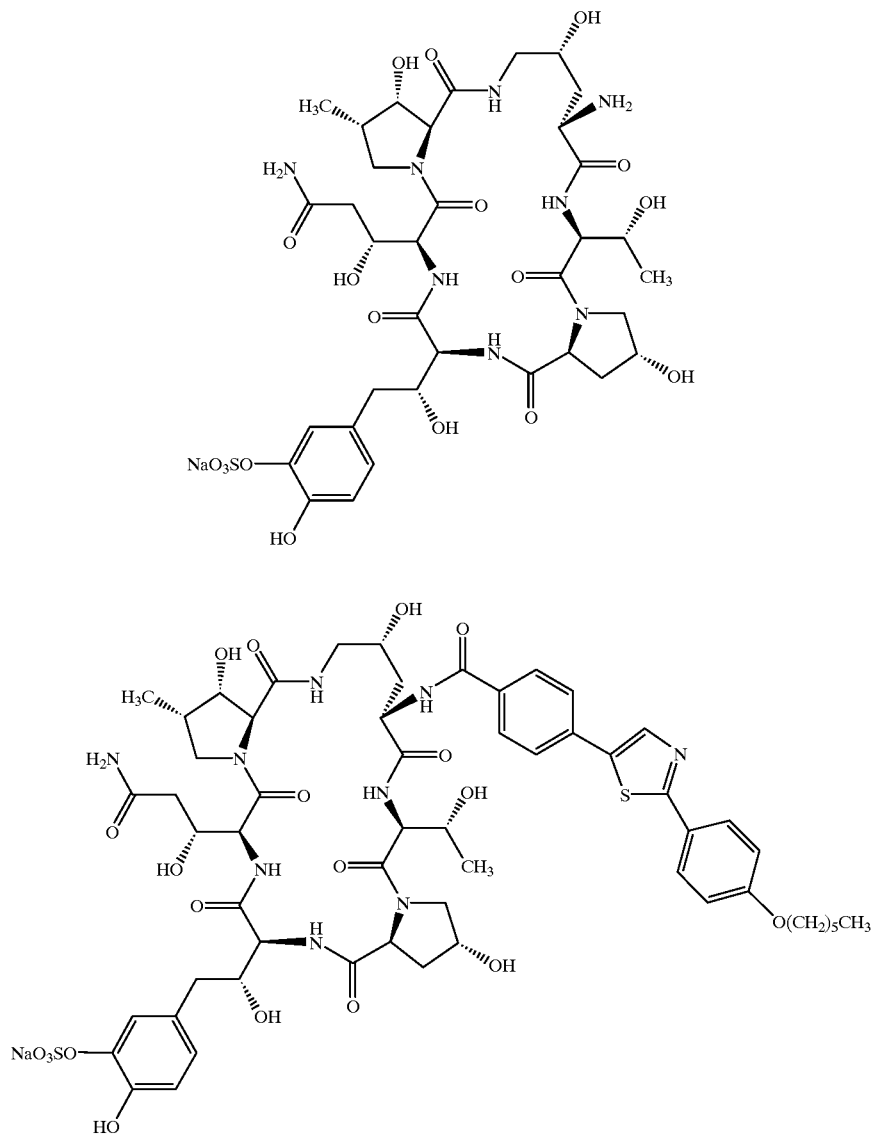 |

-continued
| Example No. | Formula |
|---|---|
| 105 | 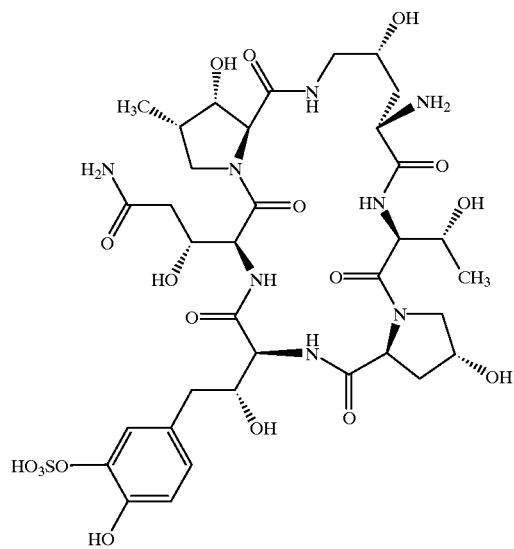 |
| | 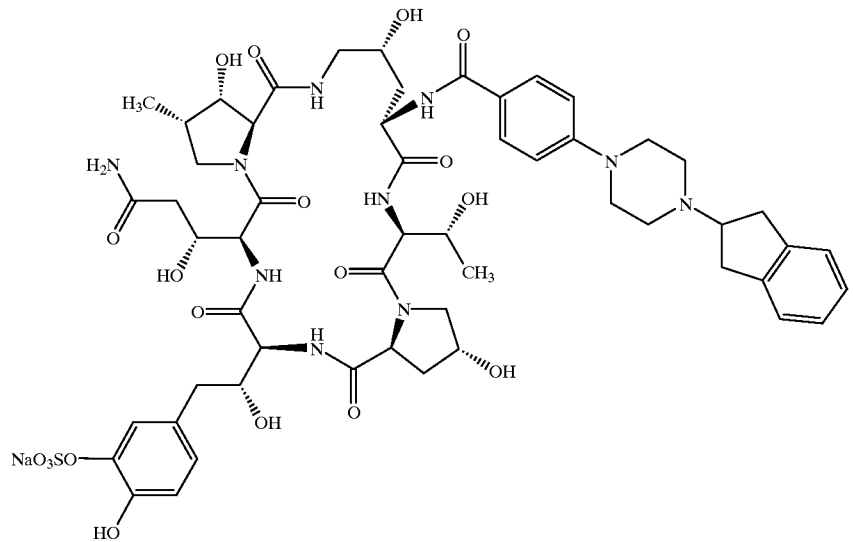 |

| Example No. | Formula |
|---|---|
| 106 | 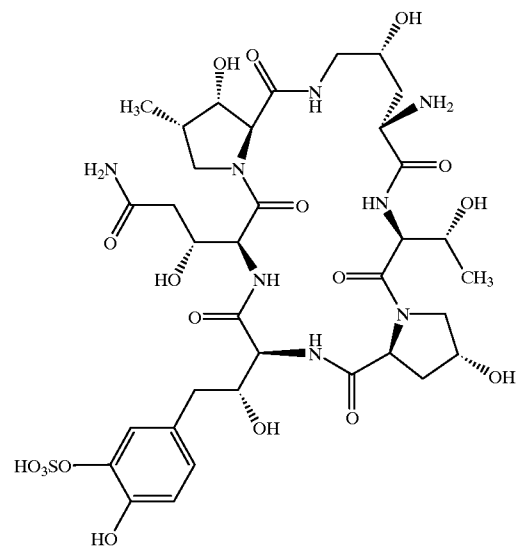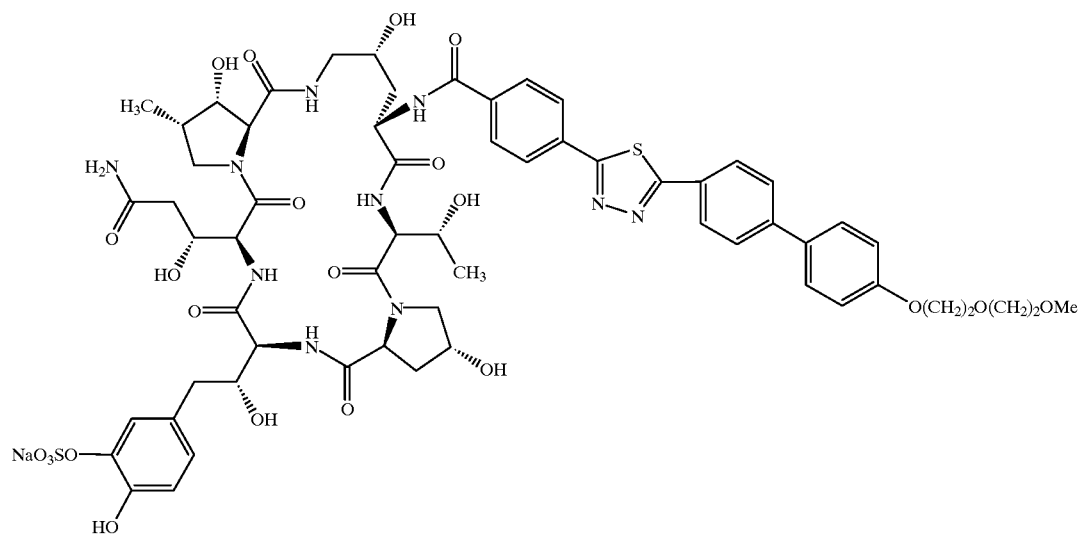 |

-continued
| Example No. | Formula |
|---|---|
| 107 | 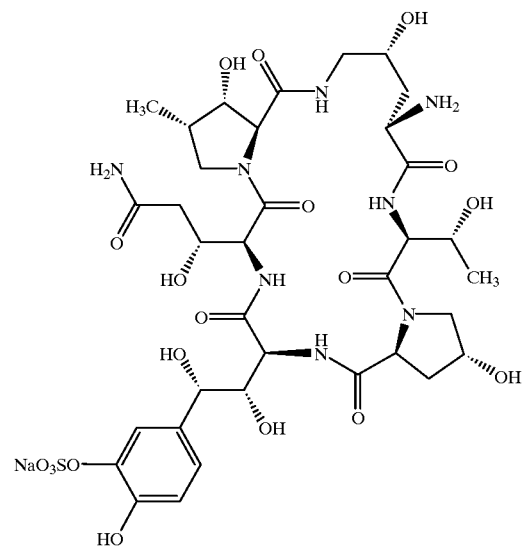 |
| | 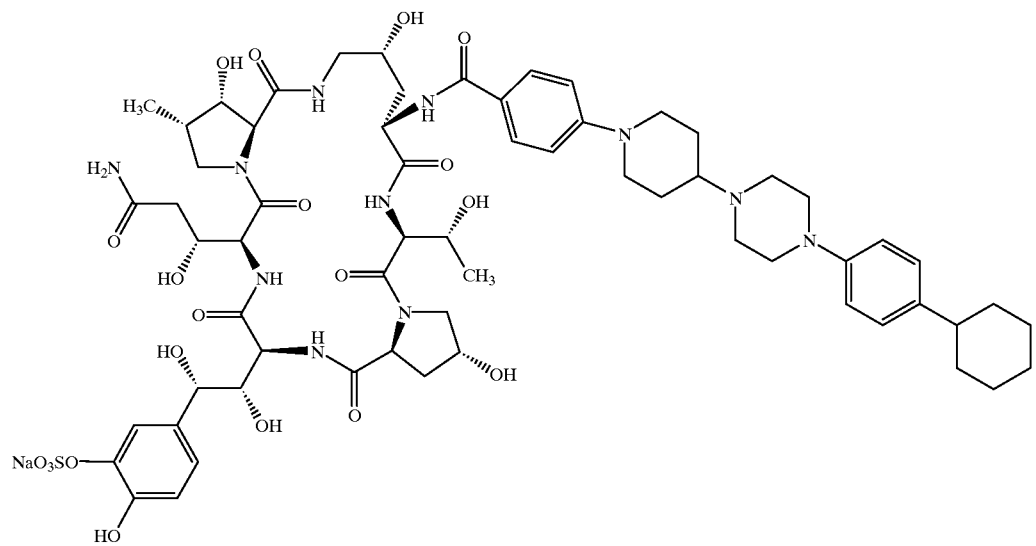 |

| Example No. | Formula |
|---|---|
| 108 | 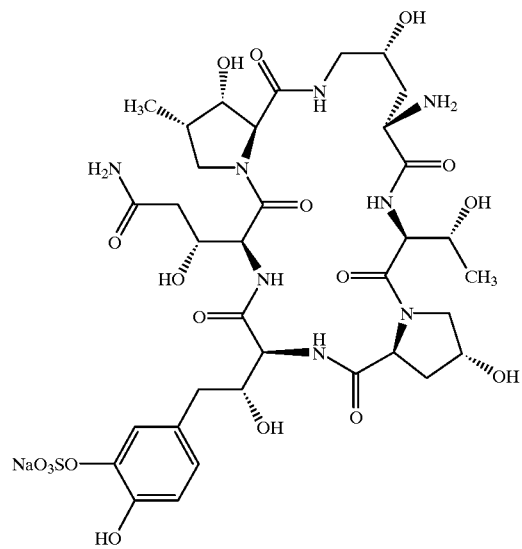 |
|  | 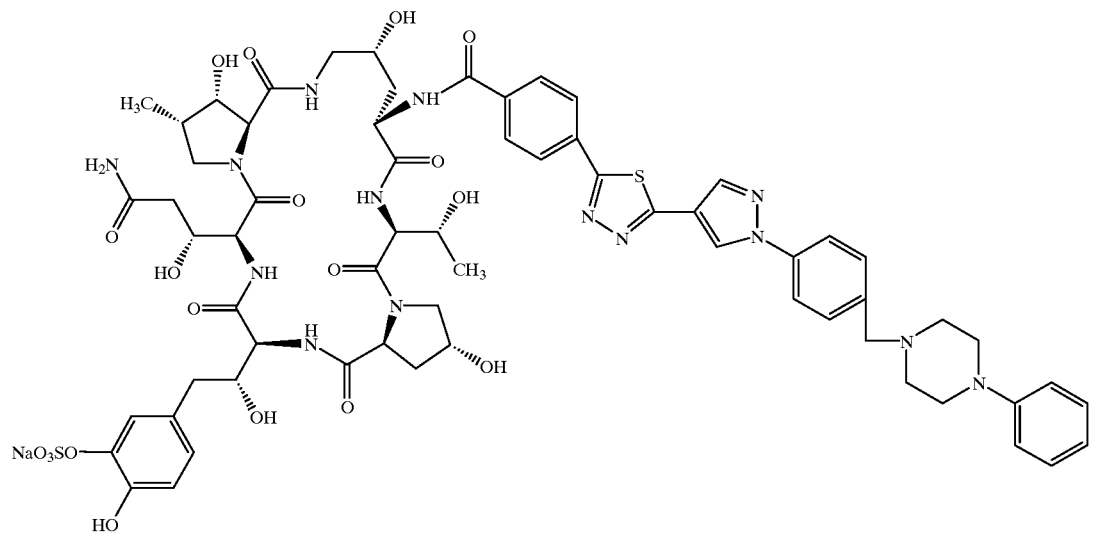 |

-continued
| Example No. | Formula |
|---|---|
| 109 | 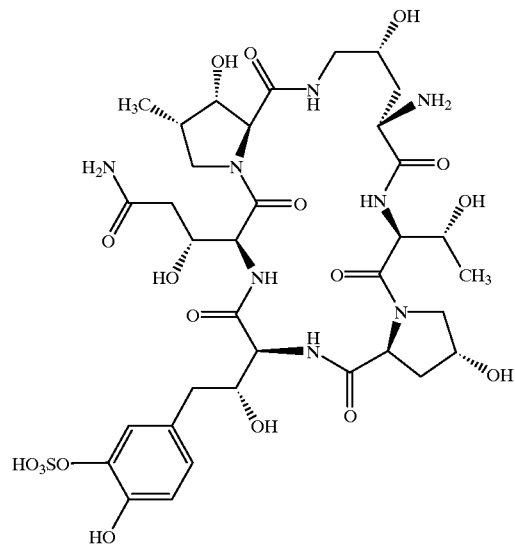 |
| | 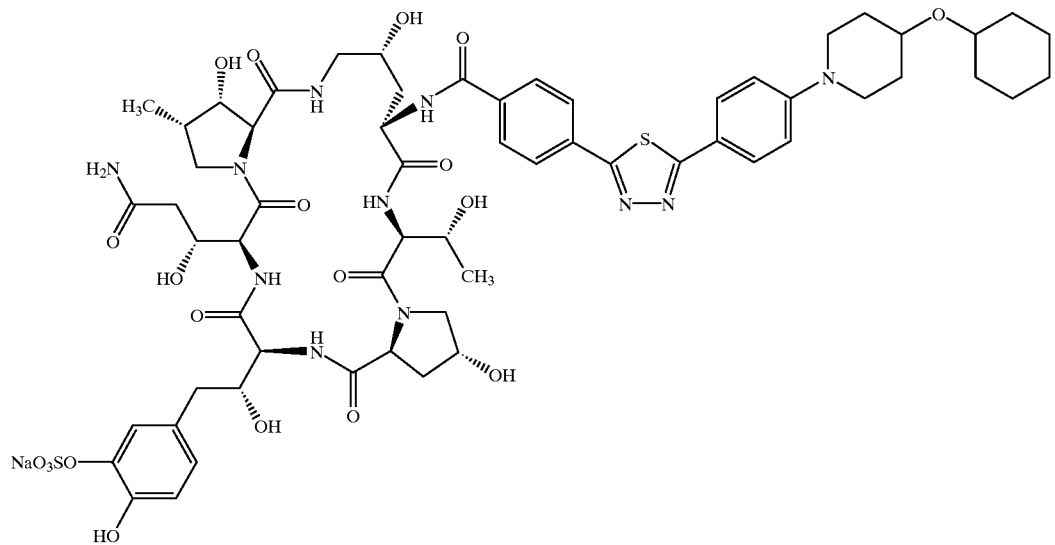 |

-continued
| Example No. | Formula |
|---|---|
| 110 | 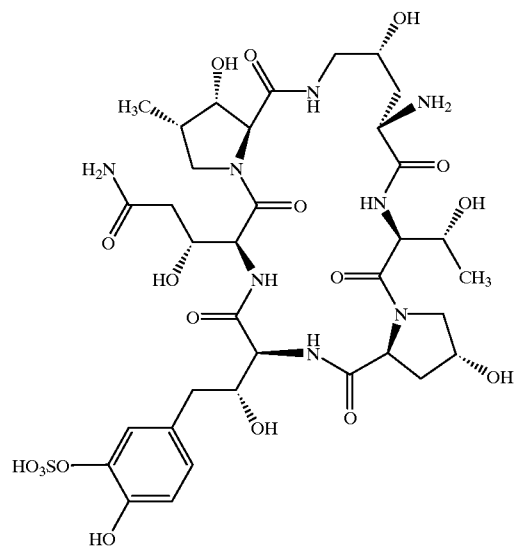 |
| | 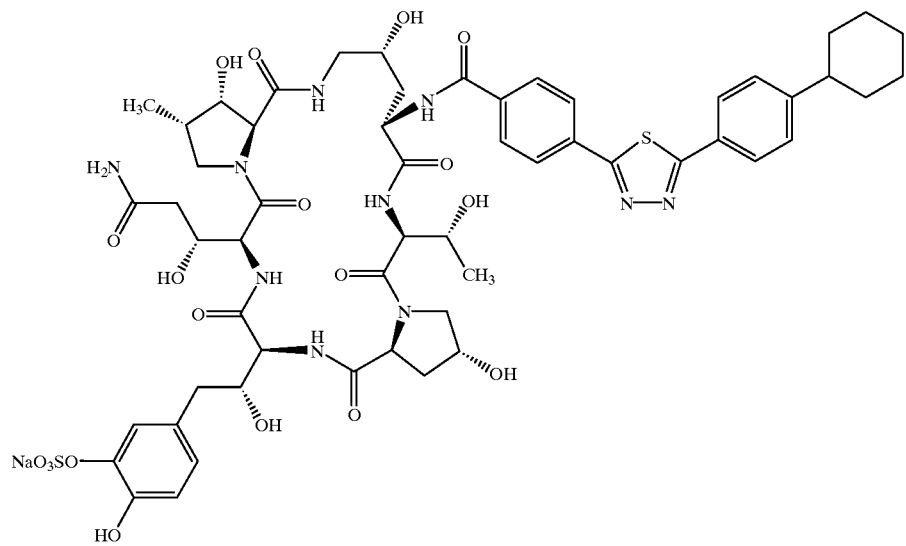 |

| Example No. | Formula |
|---|---|
| 111 | 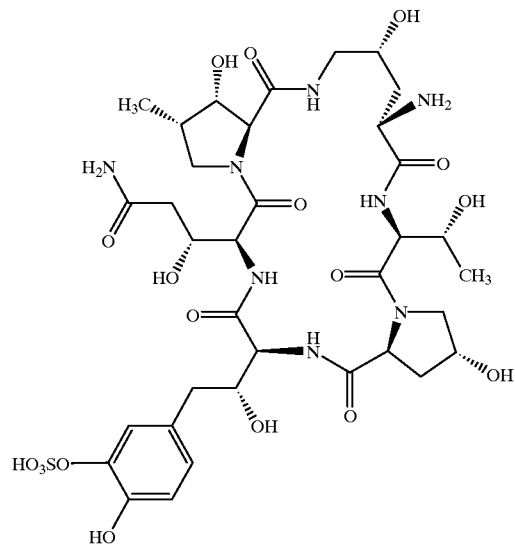<br>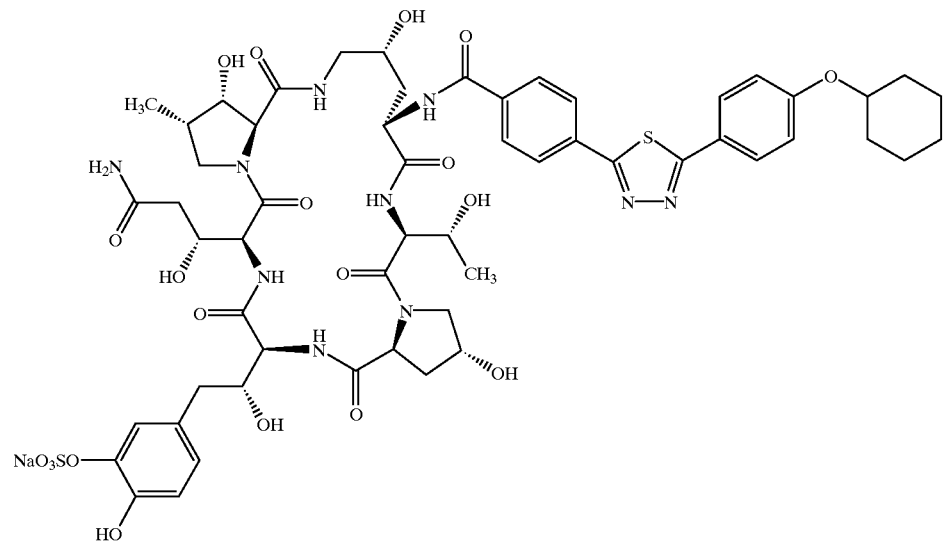 |

| Example No. | Formula |
|---|---|
| 112 | 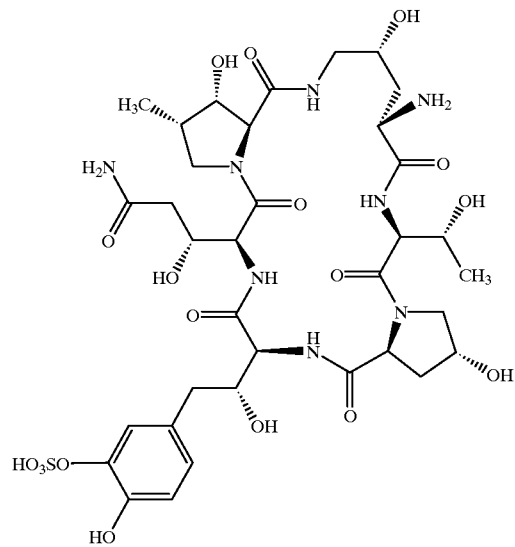 |
| | 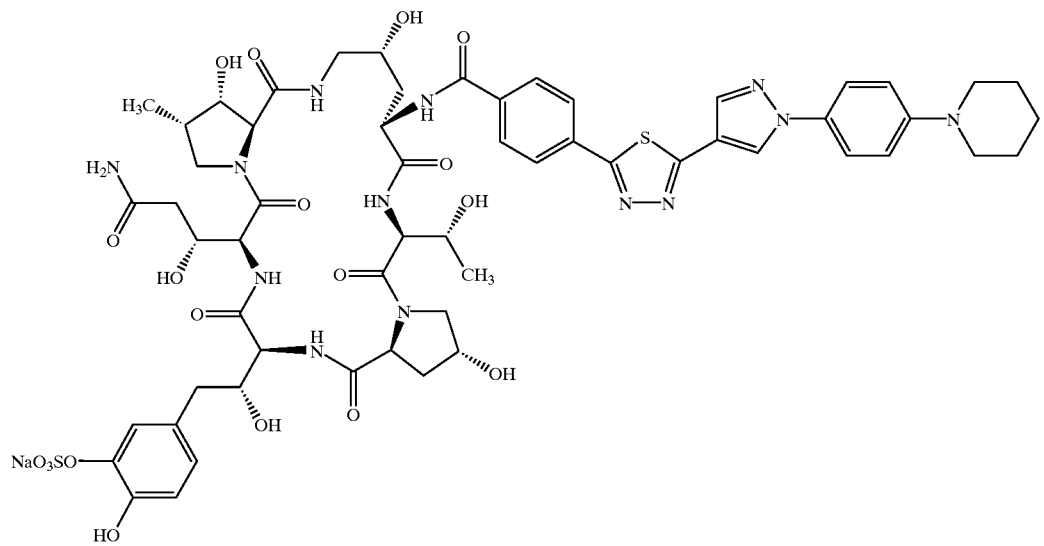 |

-continued
| Example No. | Formula |
|---|---|
| 113 | 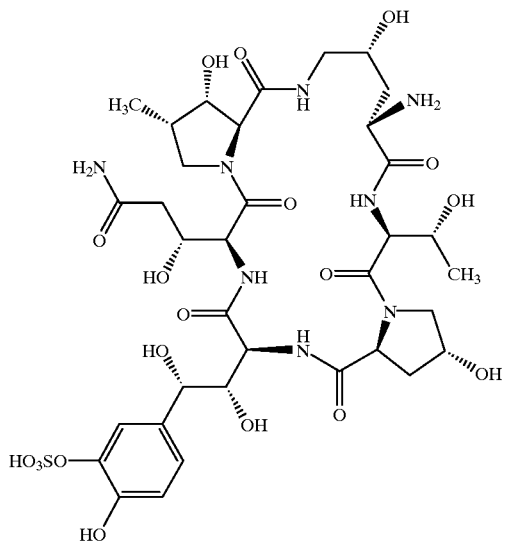 |
| | 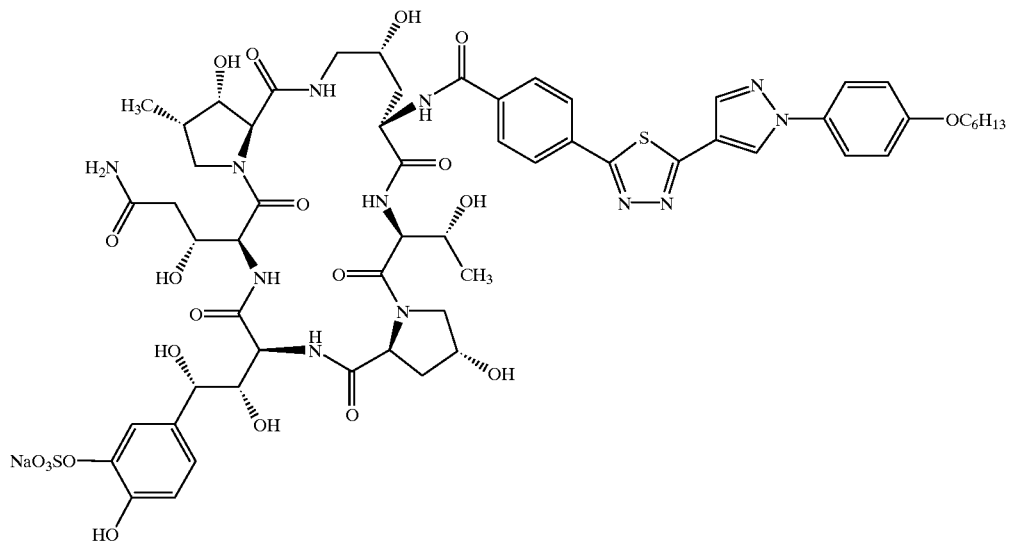 |

| Example No. | Formula |
|---|---|
| 114 | 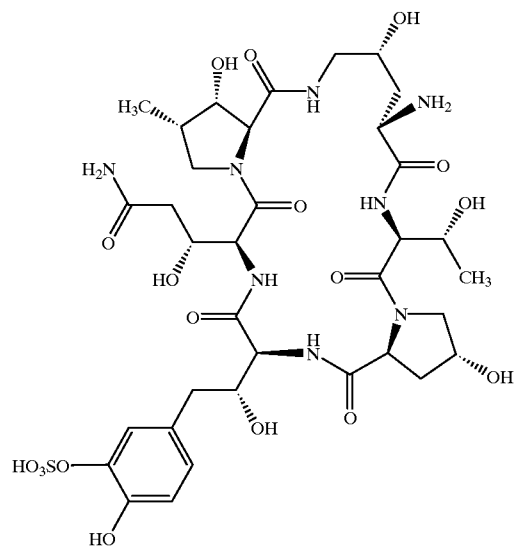 |
| | 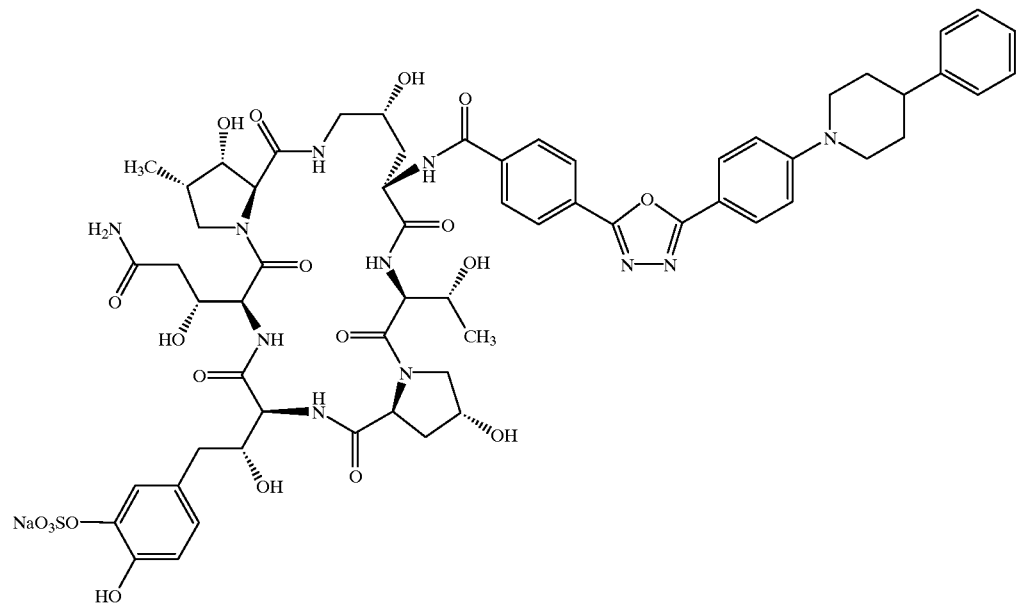 |

| Example No. | Formula |
|---|---|
| 115 | 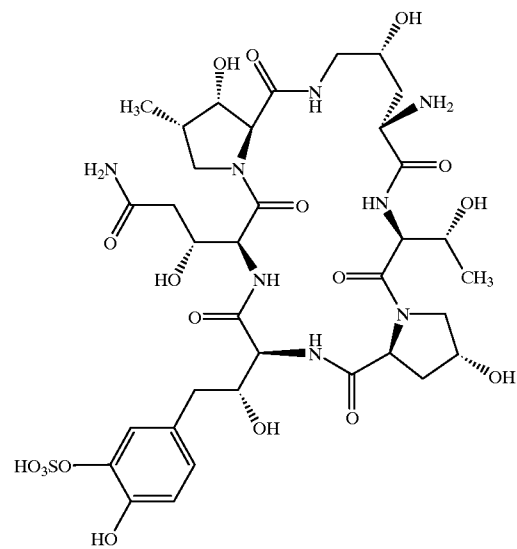 |
| | 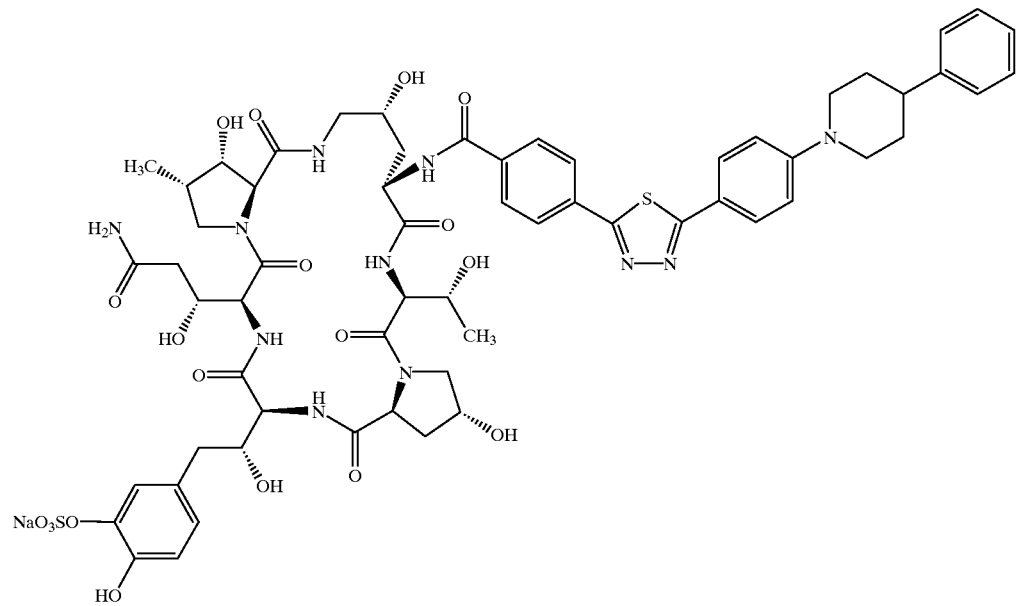 |

-continued
| Example No. | Formula |
|---|---|
| 116 | 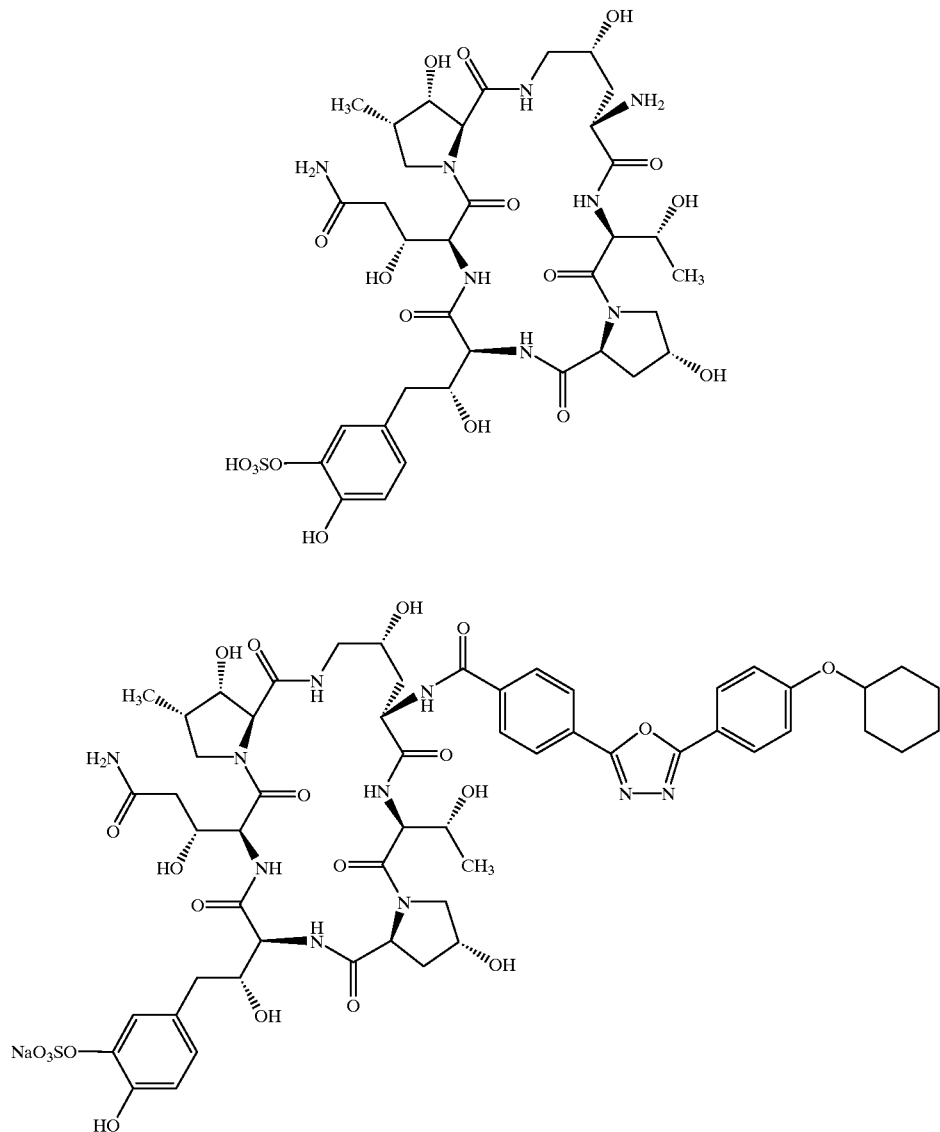 |

-continued
| Example No. | Formula |
|---|---|
| 117 | 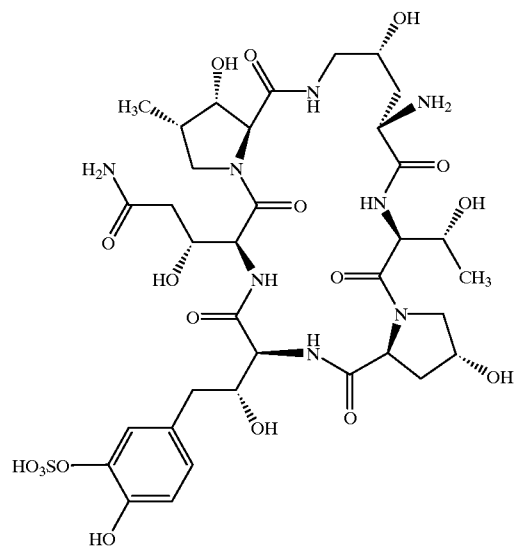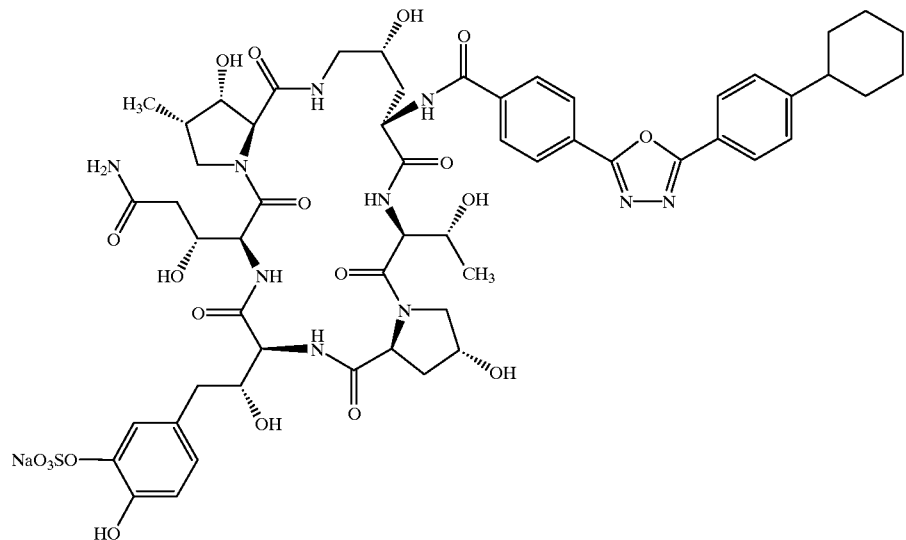 |

| Example No. | Formula |
|---|---|
| 118 | 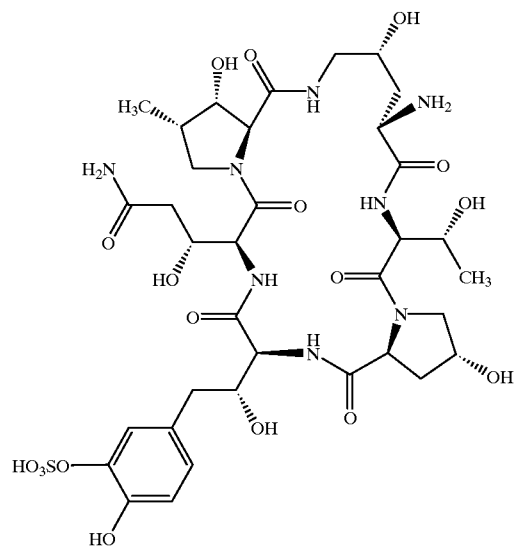 |
| | 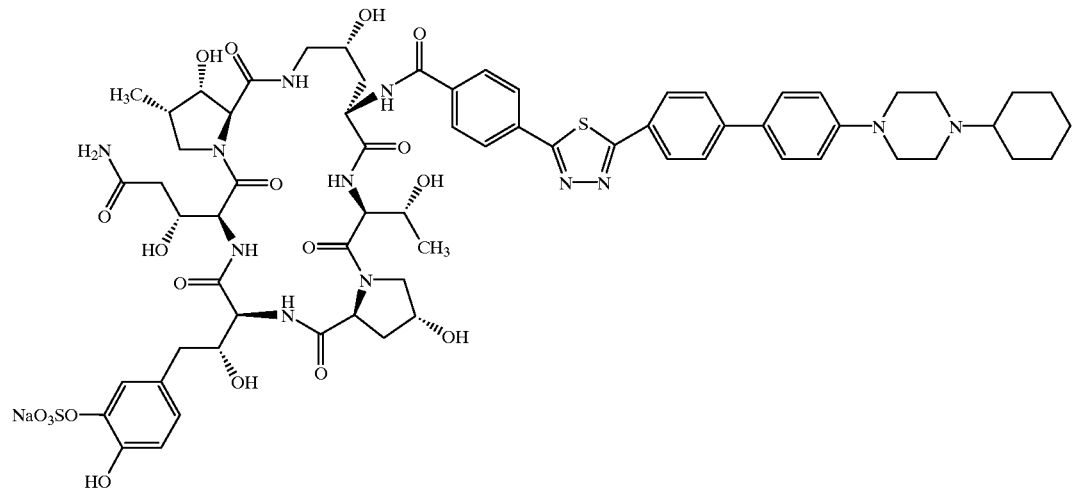 |

| Example No. | Formula |
|---|---|
| 119 | 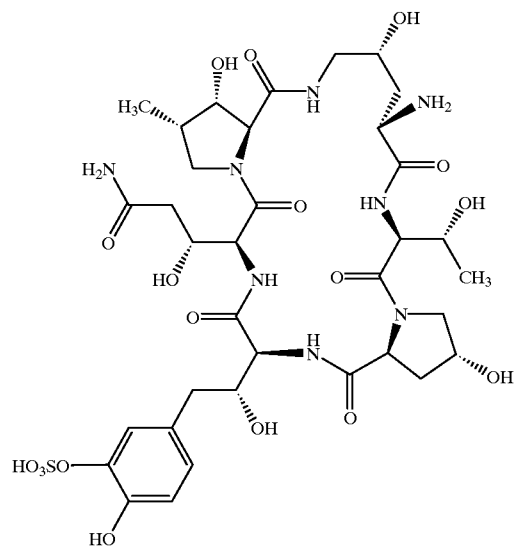 |
| | 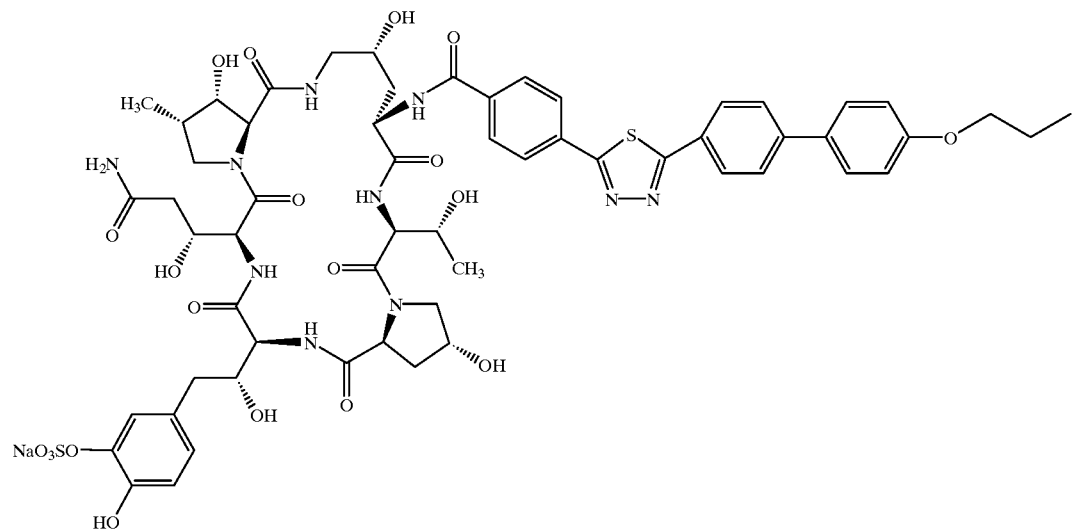 |

-continued
| Example No. | Formula |
|---|---|
| 120 | 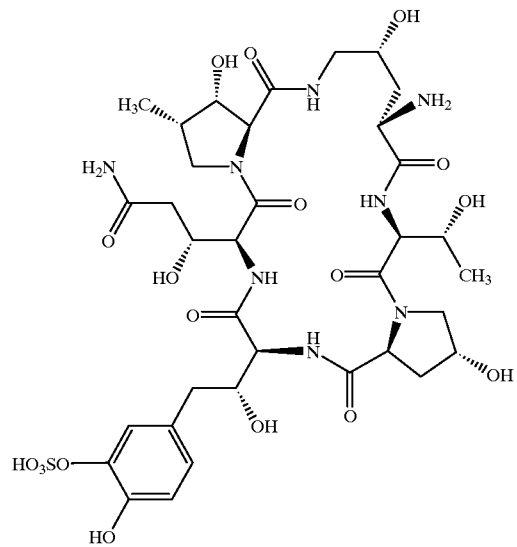 |
| | 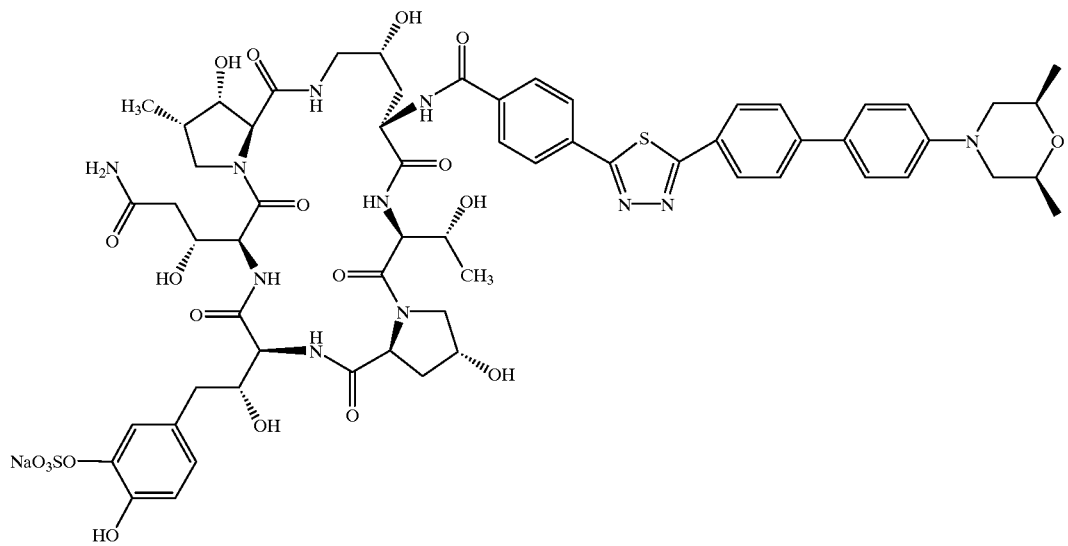 |

-continued
| Example No. | Formula |
|---|---|
| 121 | 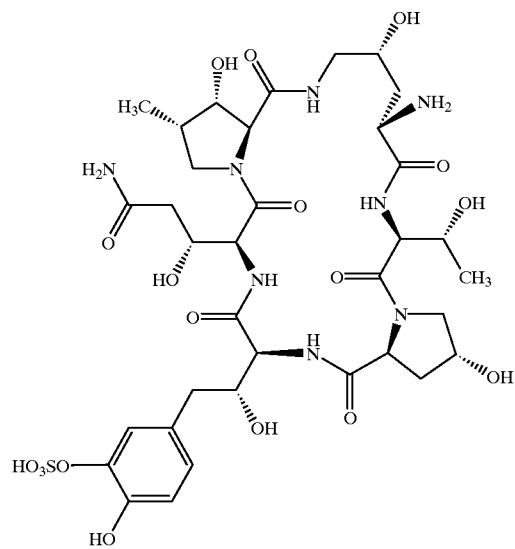 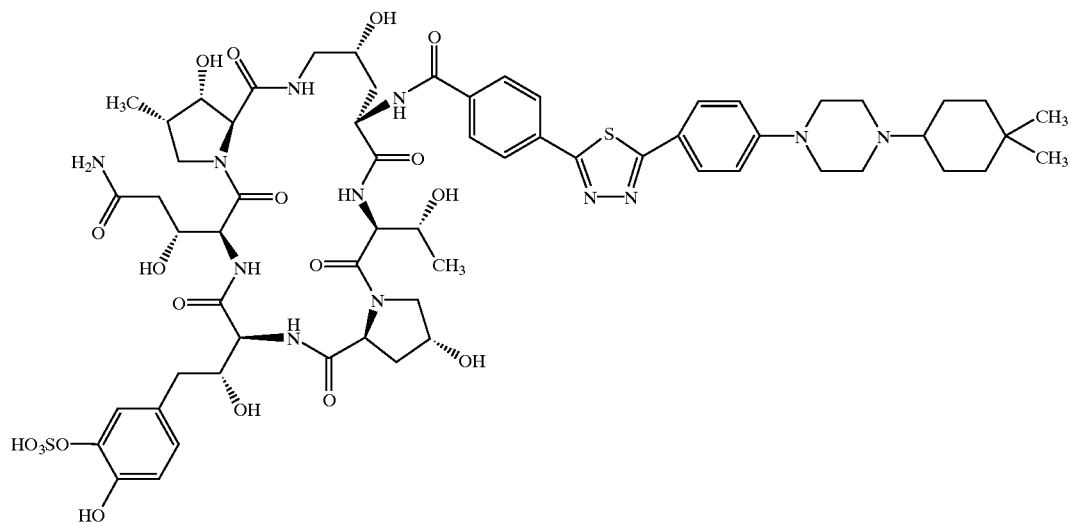 |

-continued
| Example No. | Formula |
|---|---|
| 122 | 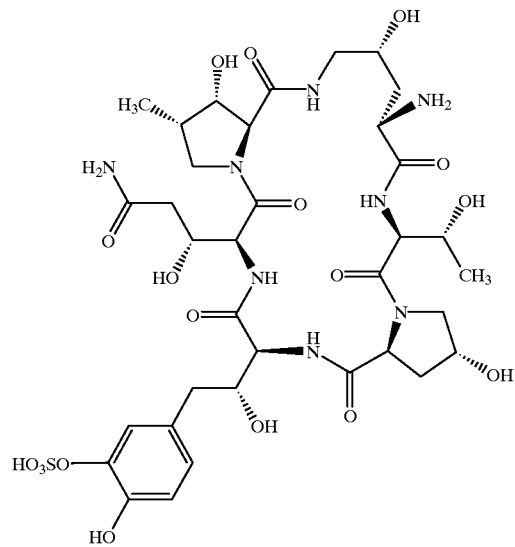 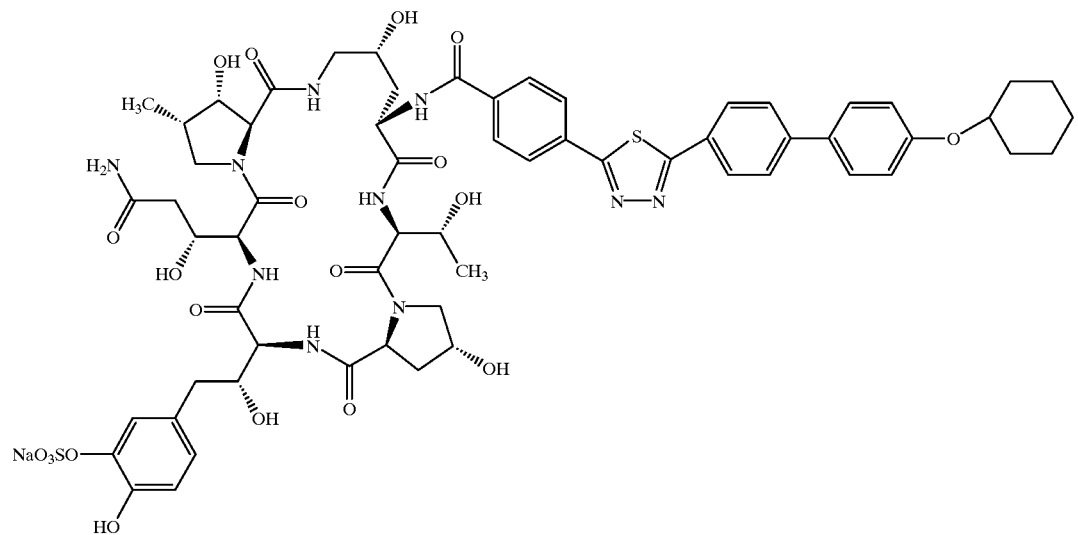 |

-continued
| Example No. | Formula |
|---|---|
| 123 | 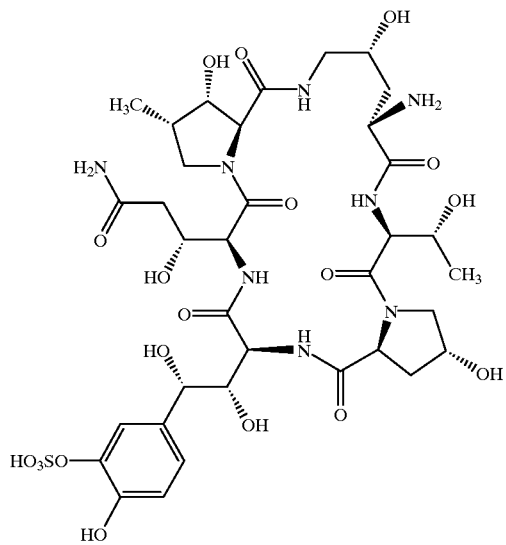 |
| | 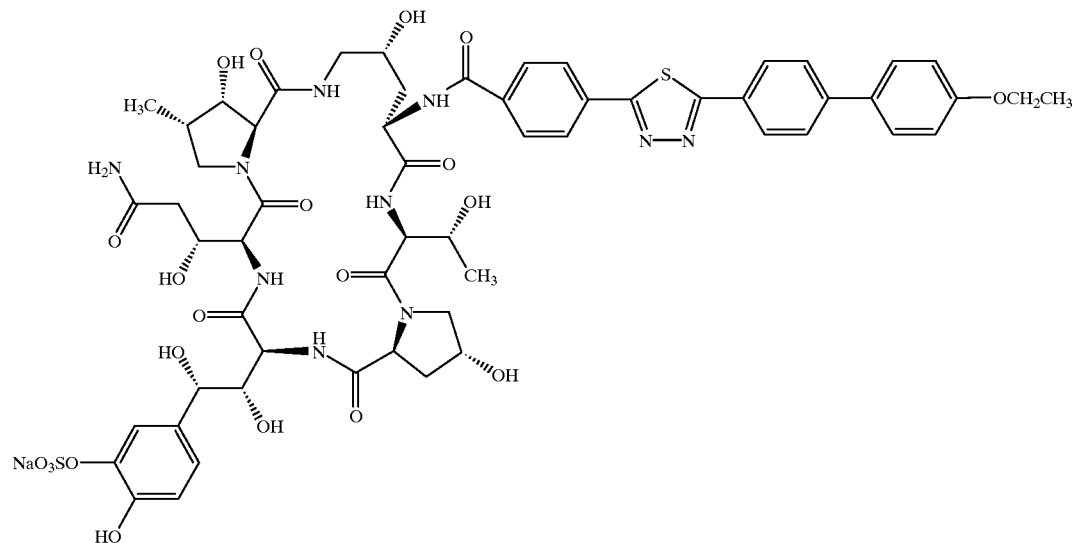 |

| Example No. | Formula |
|---|---|
| 124 | 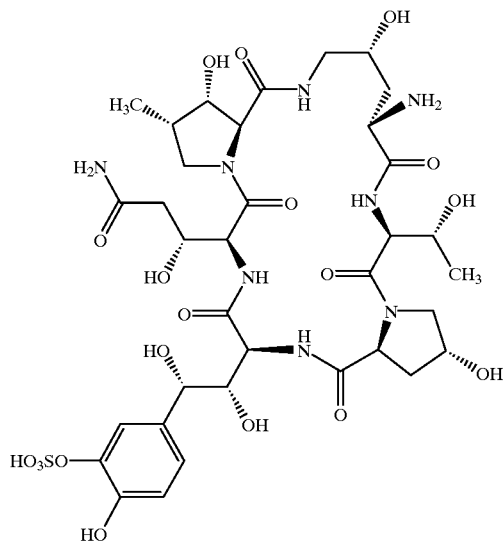 |
| | 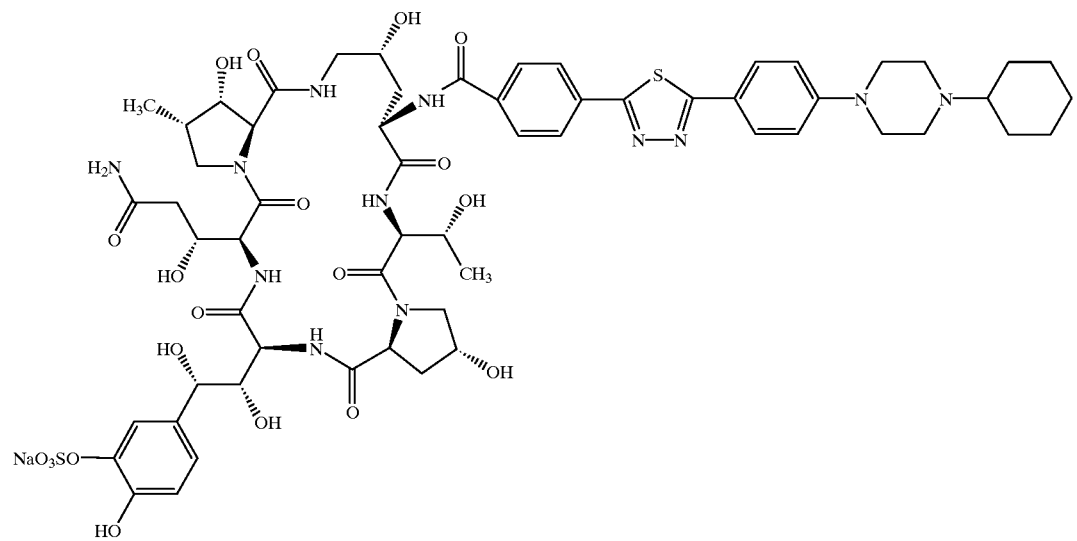 |

-continued
| Example No. | Formula |
|---|---|
| 125 | 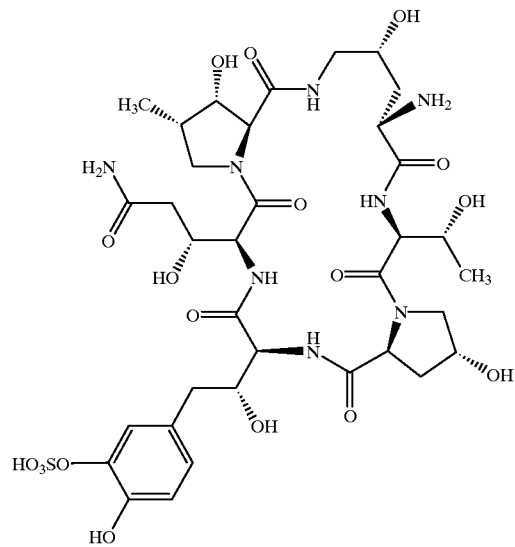 |
| | 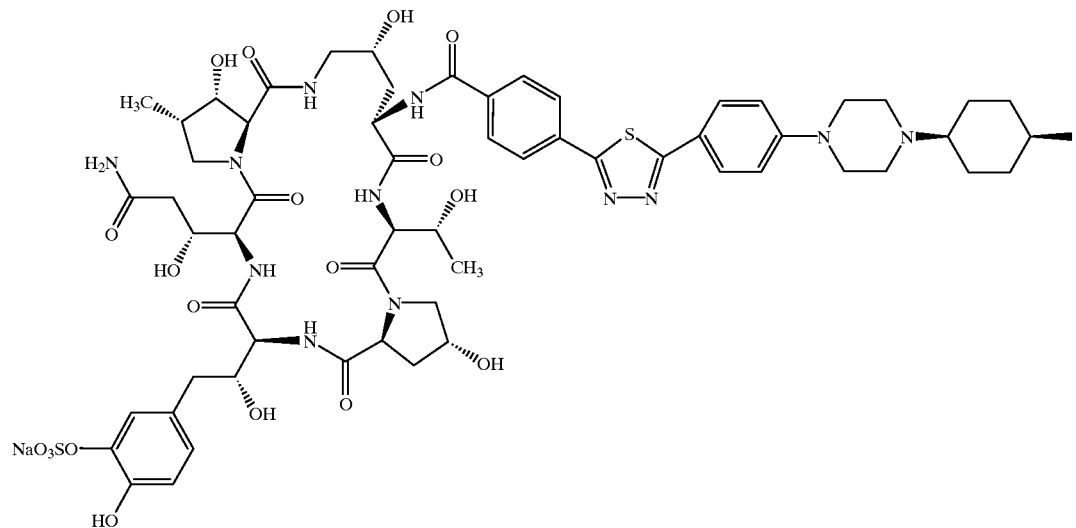 |

-continued
| Example No. | Formula |
|---|---|
| 126 | 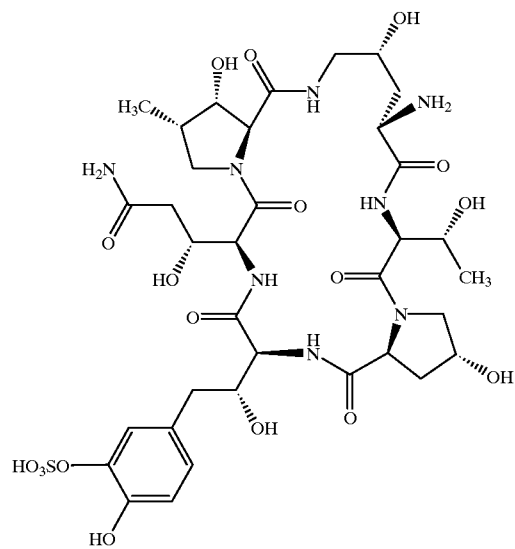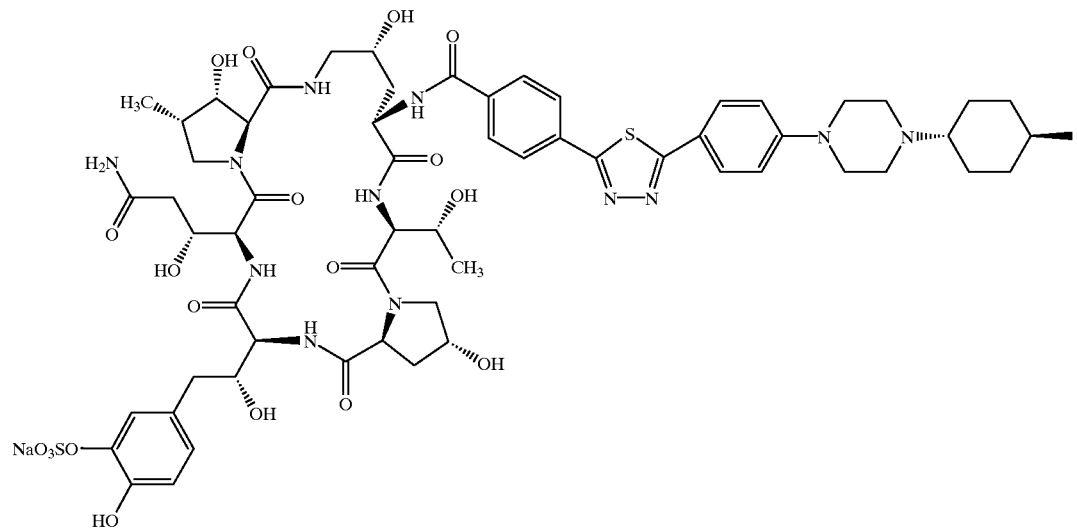 |

-continued
| Example No. | Formula |
|---|---|
| 127 | 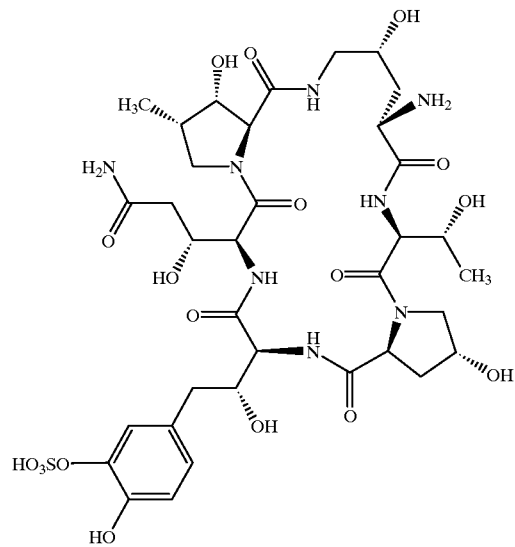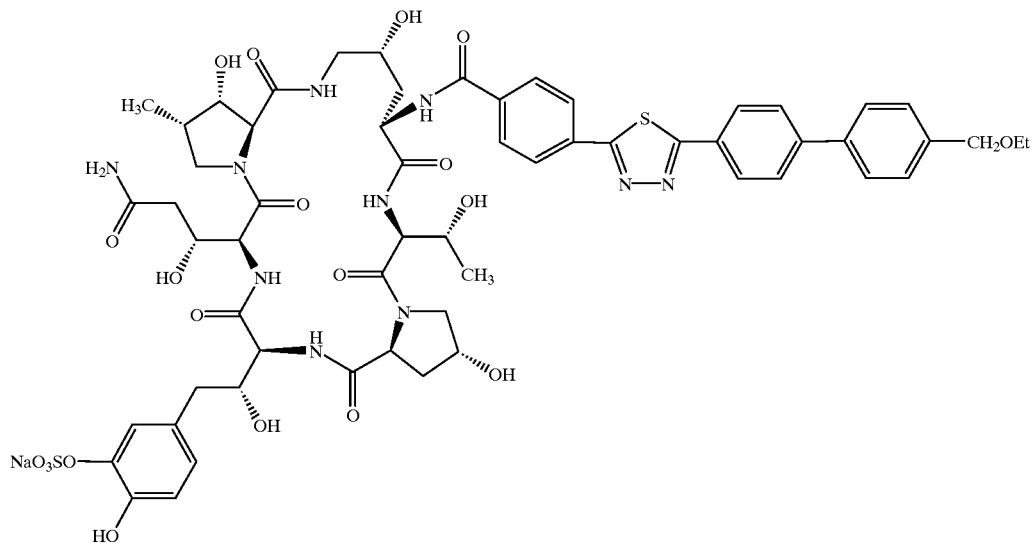 |

-continued
| Example No. | Formula |
|---|---|
| 128 | 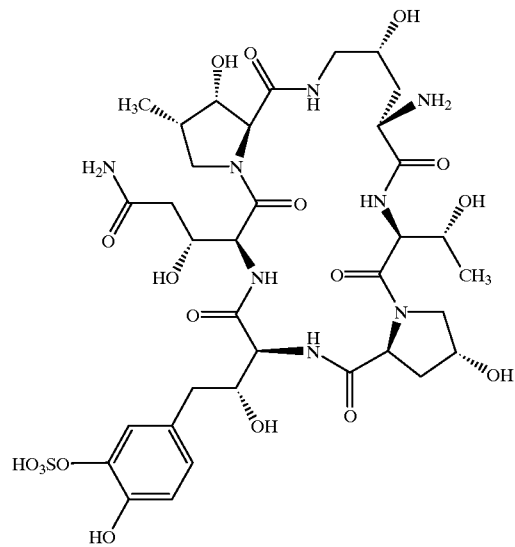 |
| | 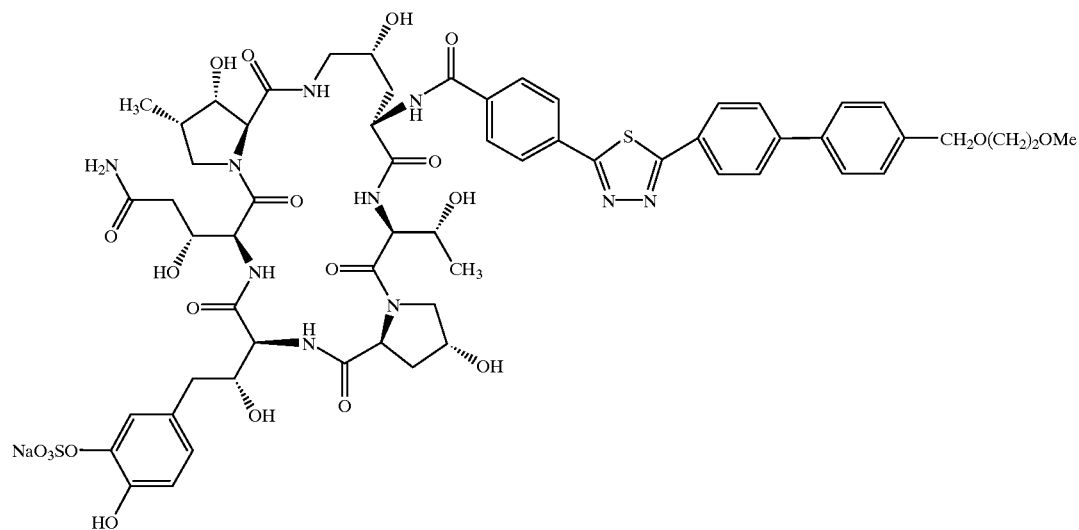 |

-continued
| Example No. | Formula |
|---|---|
| 129 | 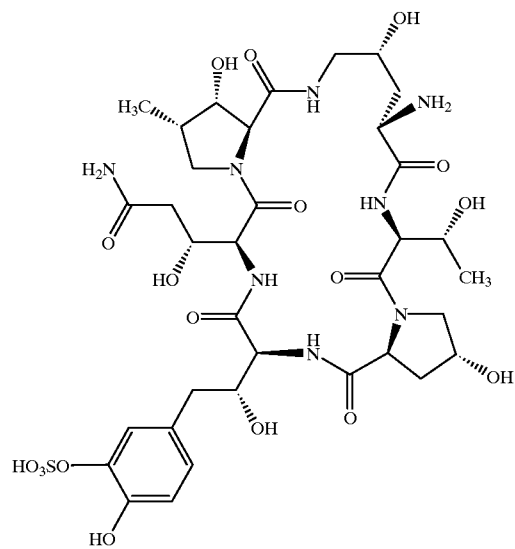 |
| | 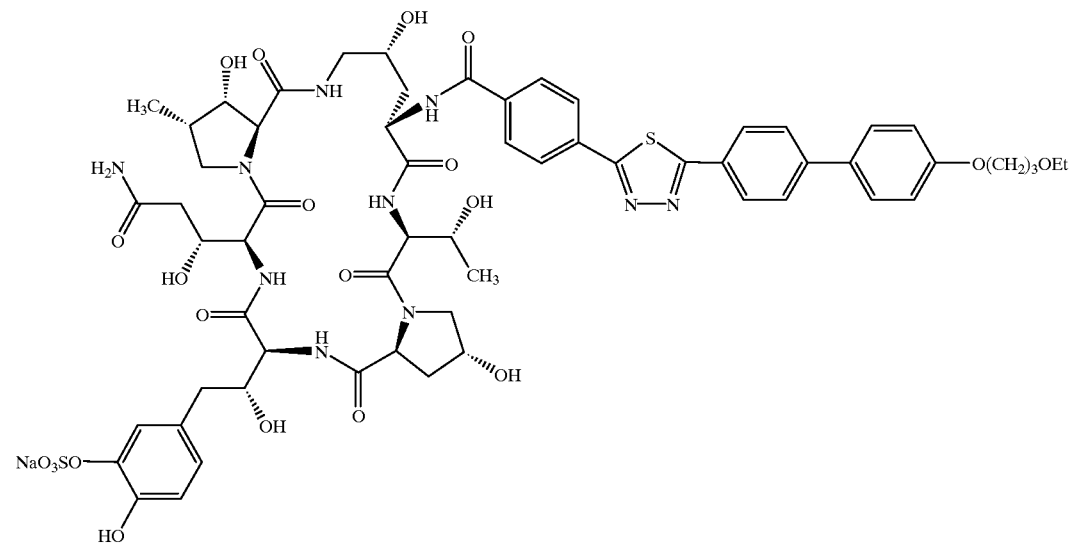 |

| Example No. | Formula |
|---|---|
| 130 | 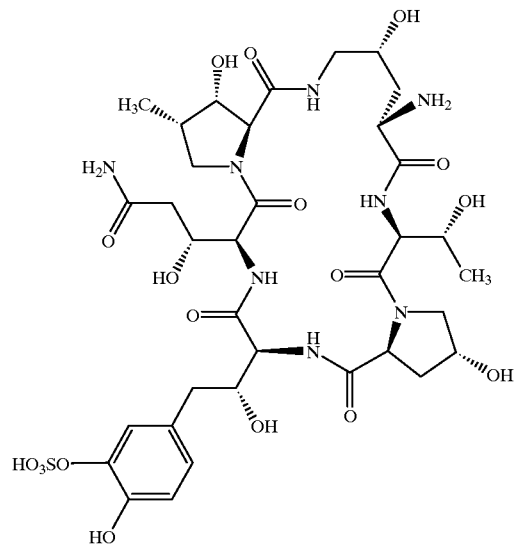 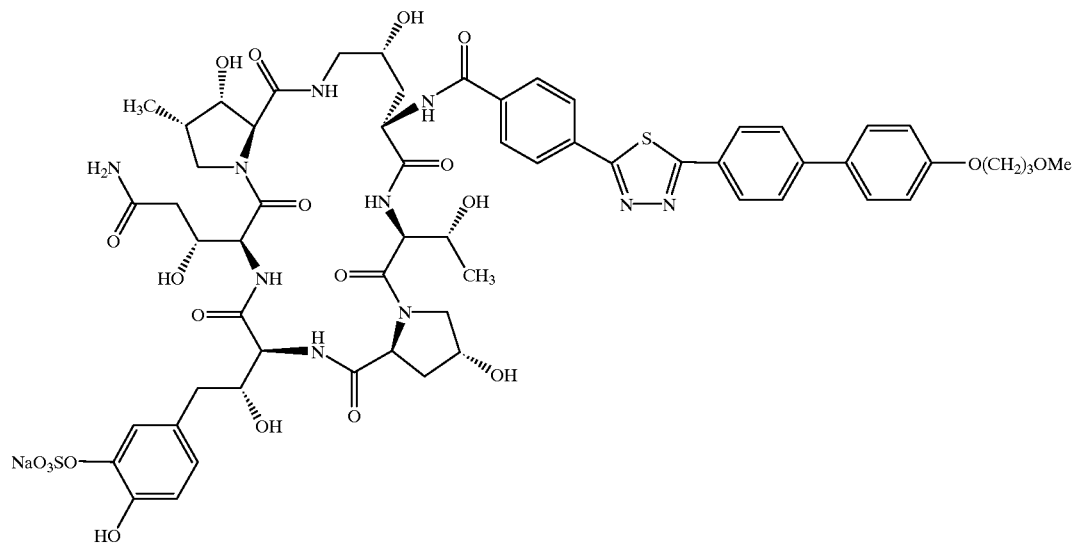 |

-continued
| Example No. | Formula |
|---|---|
| 131 | 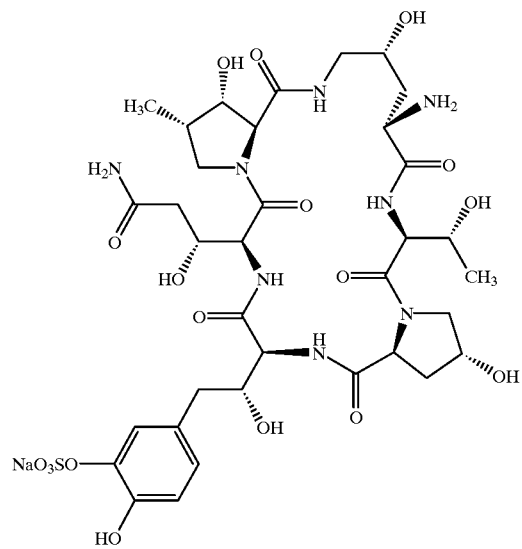 |
| | 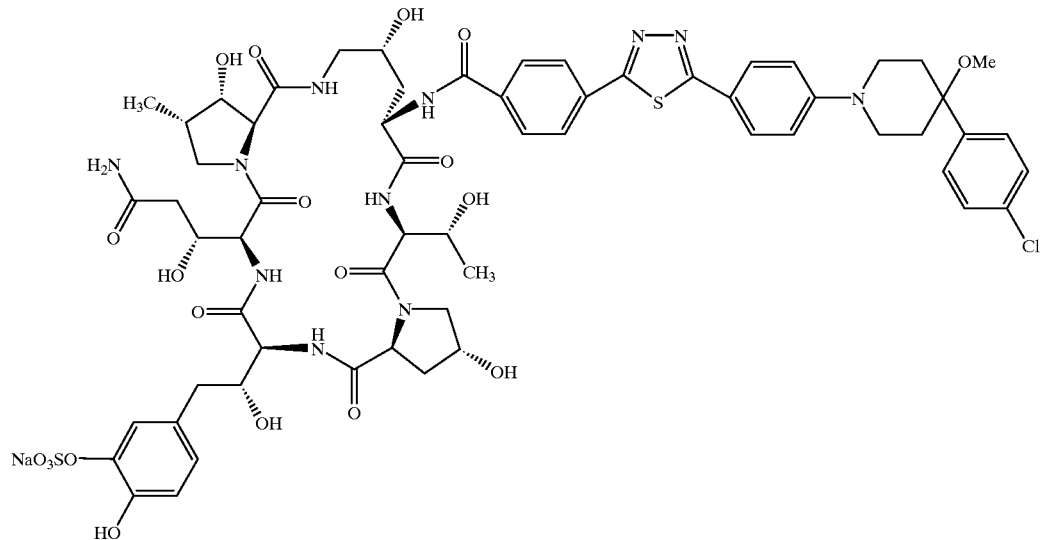 |

| Example No. | Formula |
|---|---|
| 132 | 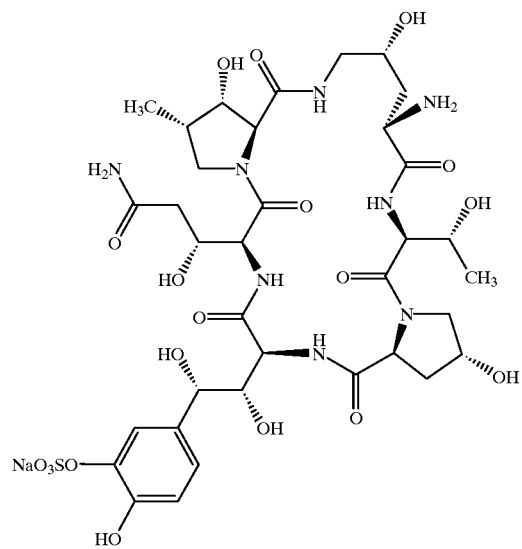 |
| | 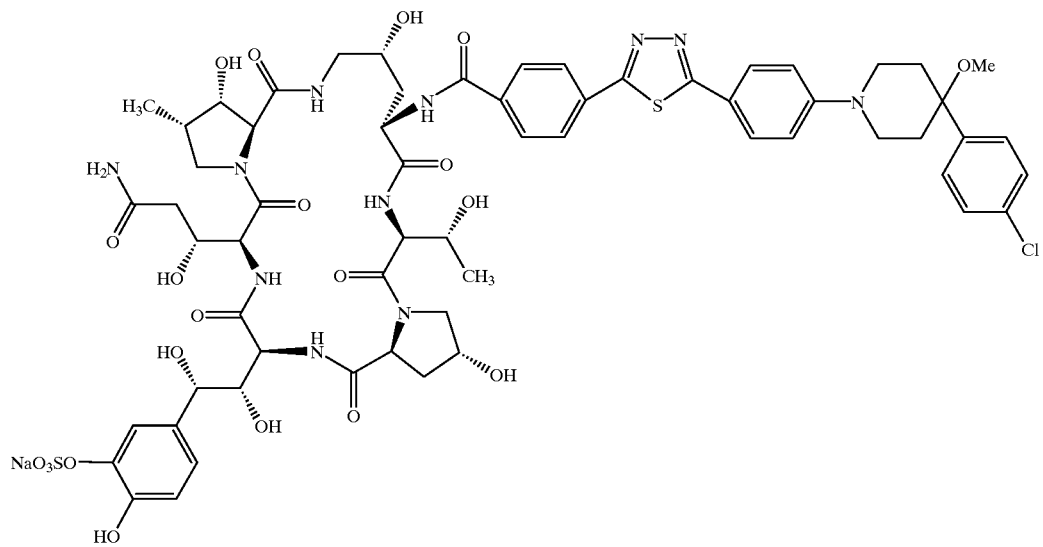 |

| Example No. | Formula |
|---|---|
| 133 | 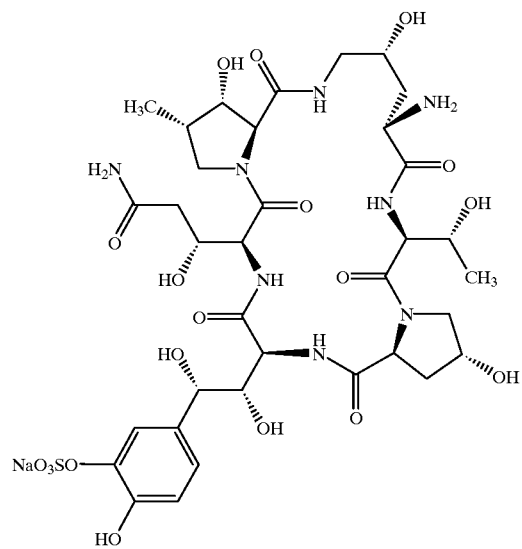 |
| | 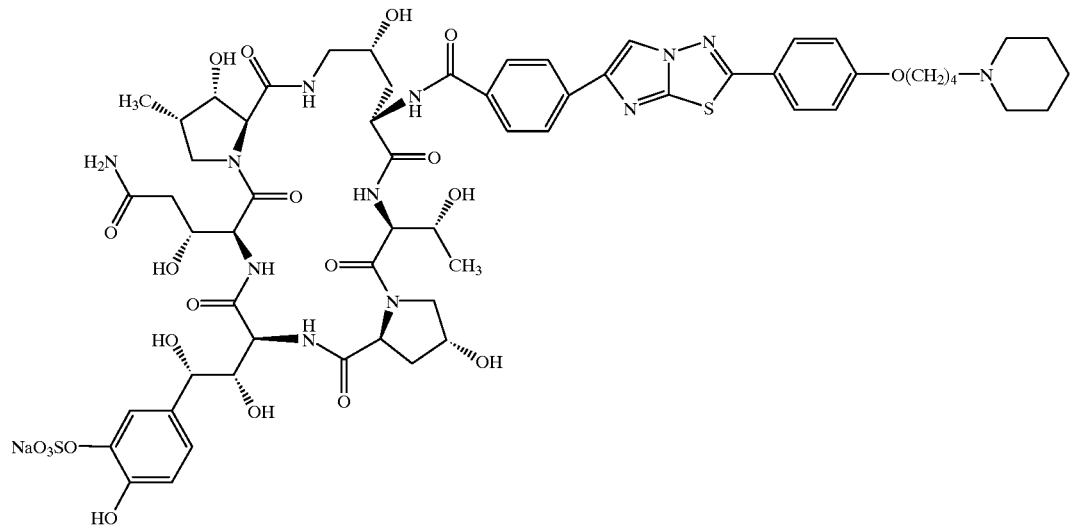 |

-continued
| Example No. | Formula |
|---|---|
| 134 | 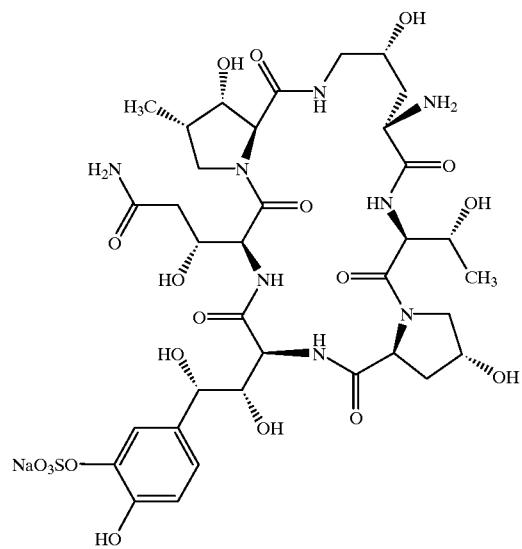 |
| | 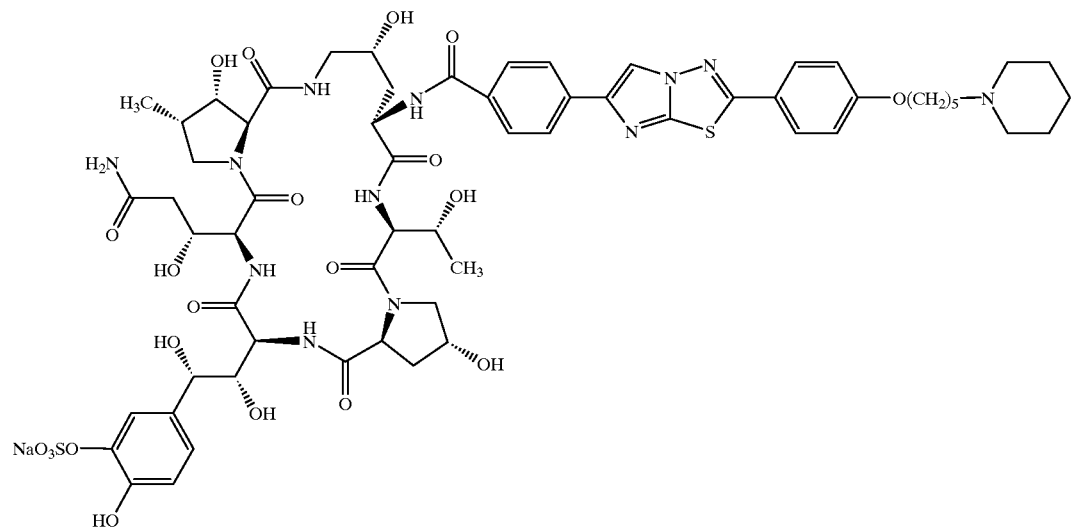 |

| Example No. | Formula |
|---|---|
| 135 | 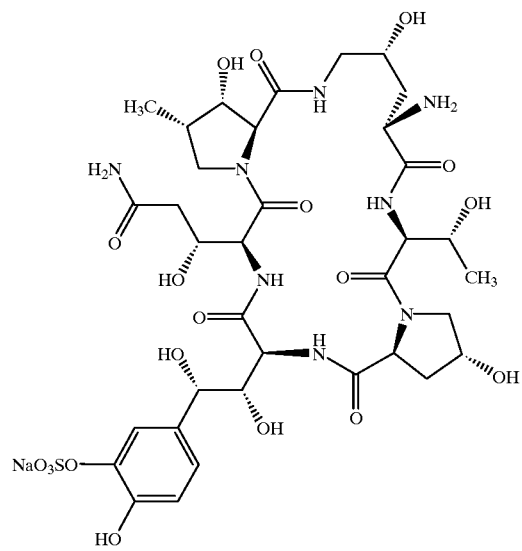 |
| | 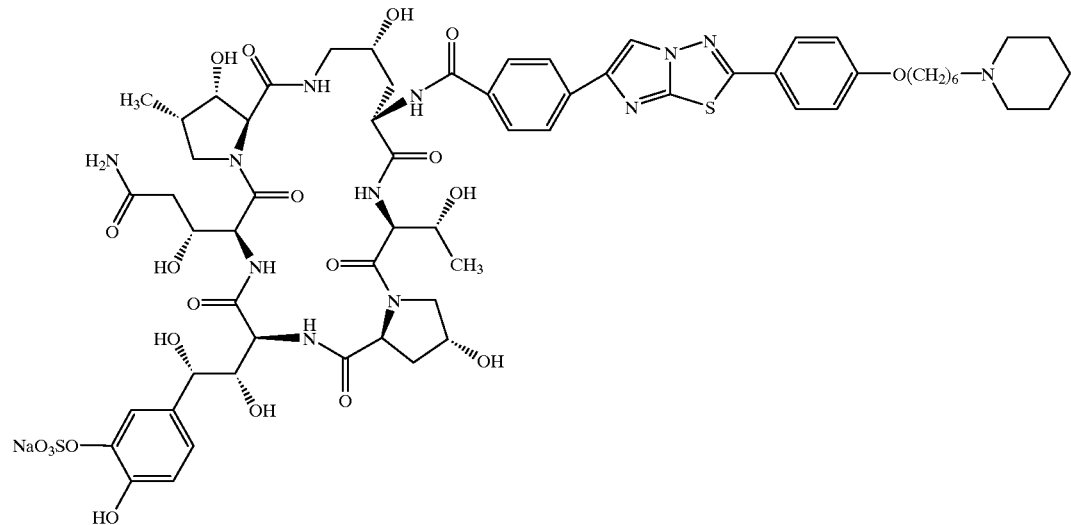 |

-continued
| Example No. | Formula |
|---|---|
| 136 | 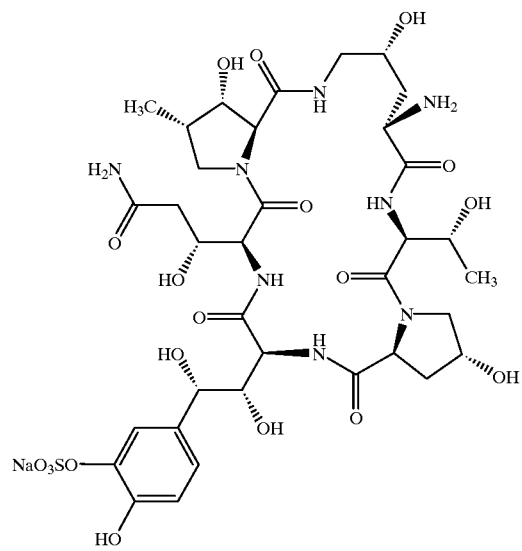 |
| | 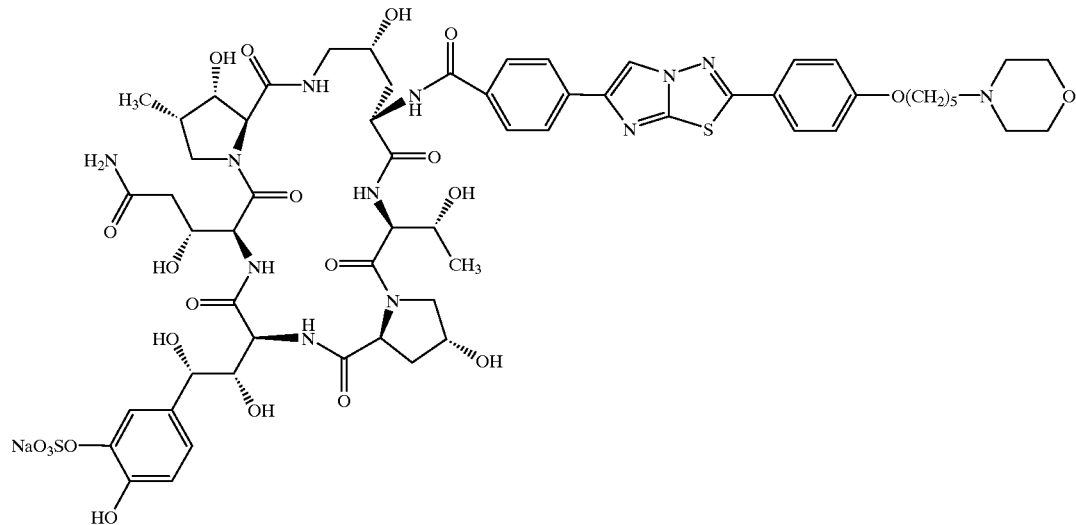 |

-continued
| Example No. | Formula |
|---|---|
| 137 | 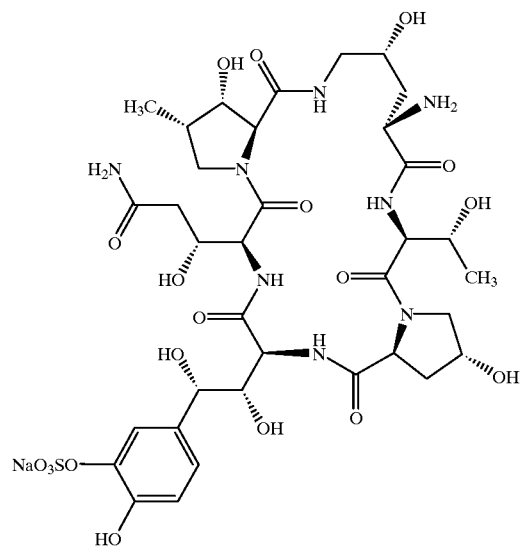 |
| | 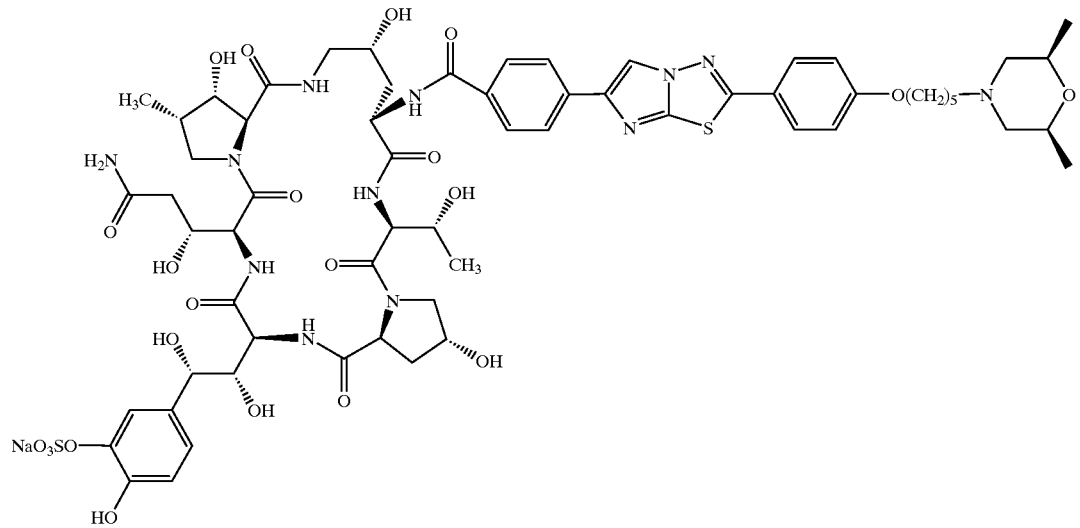 |

| Example No. | Formula |
|---|---|
| 138 | 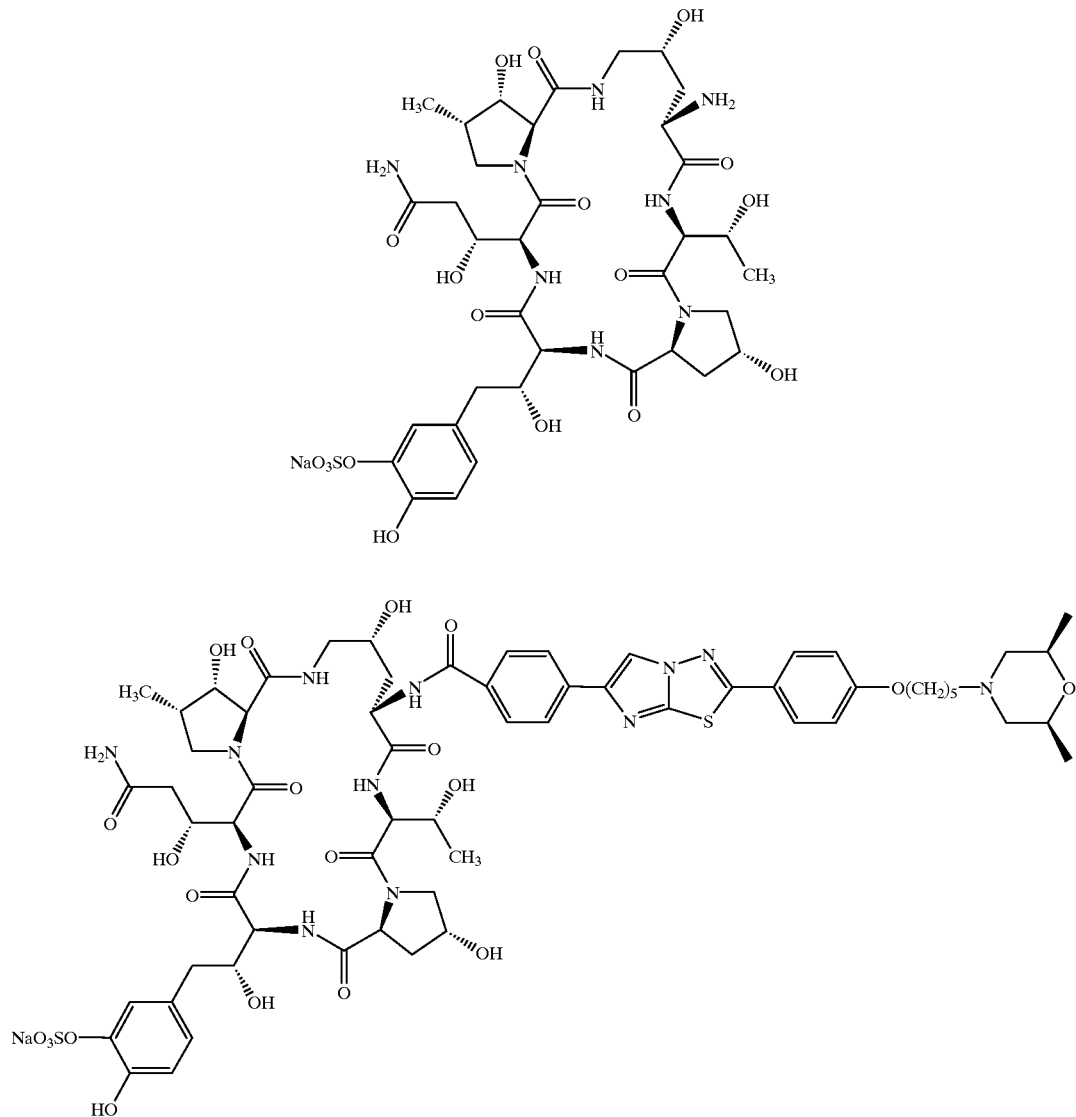 |

-continued
| Example No. | Formula |
|---|---|
| 139 | 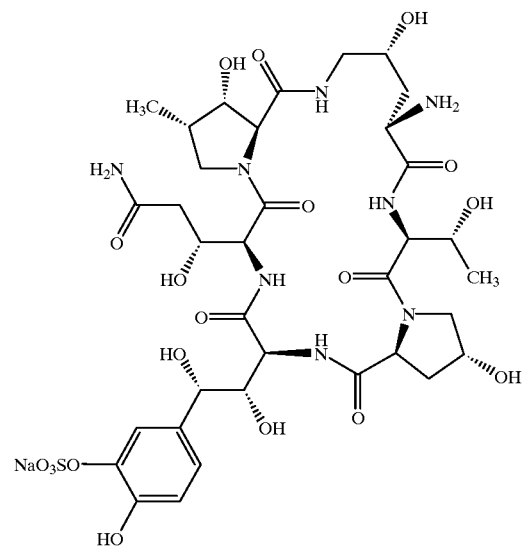 |
| | 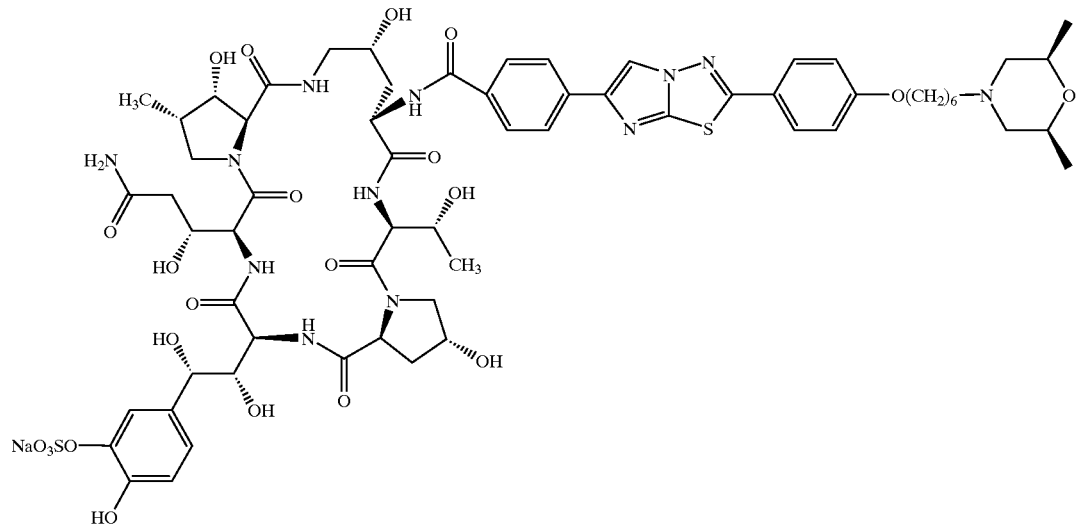 |

| Example No. | Formula |
|---|---|
| 140 | 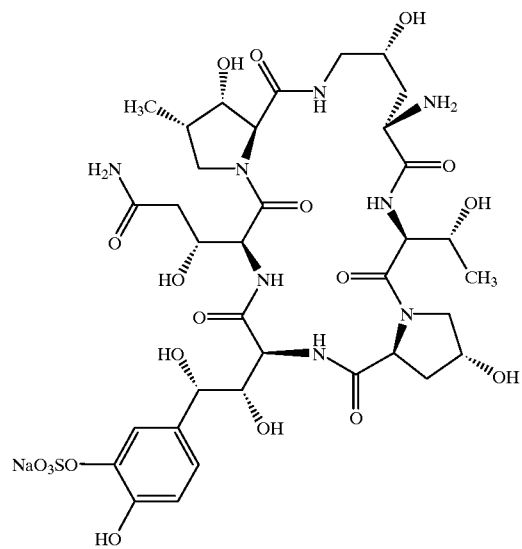 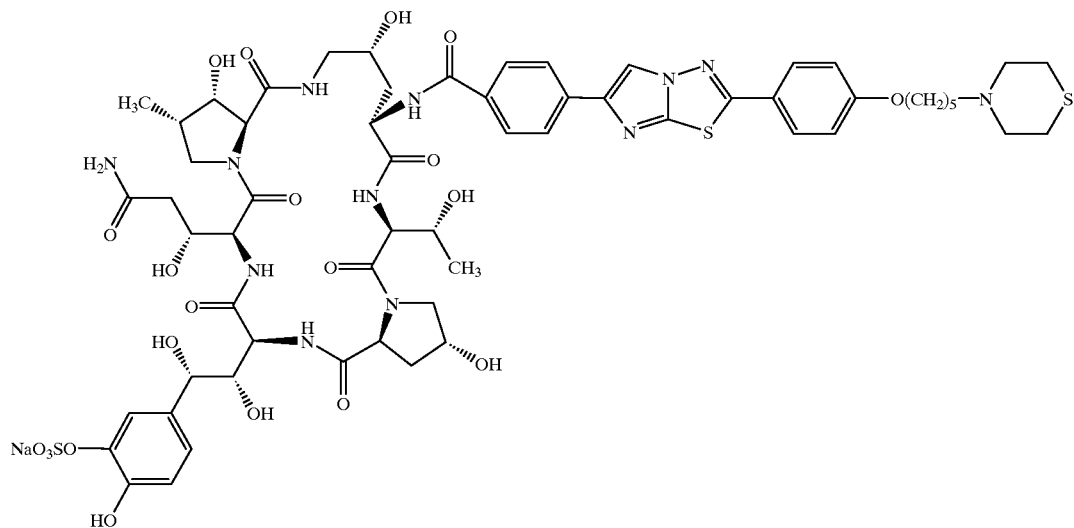 |

-continued
| Example No. | Formula |
|---|---|
| 141 | 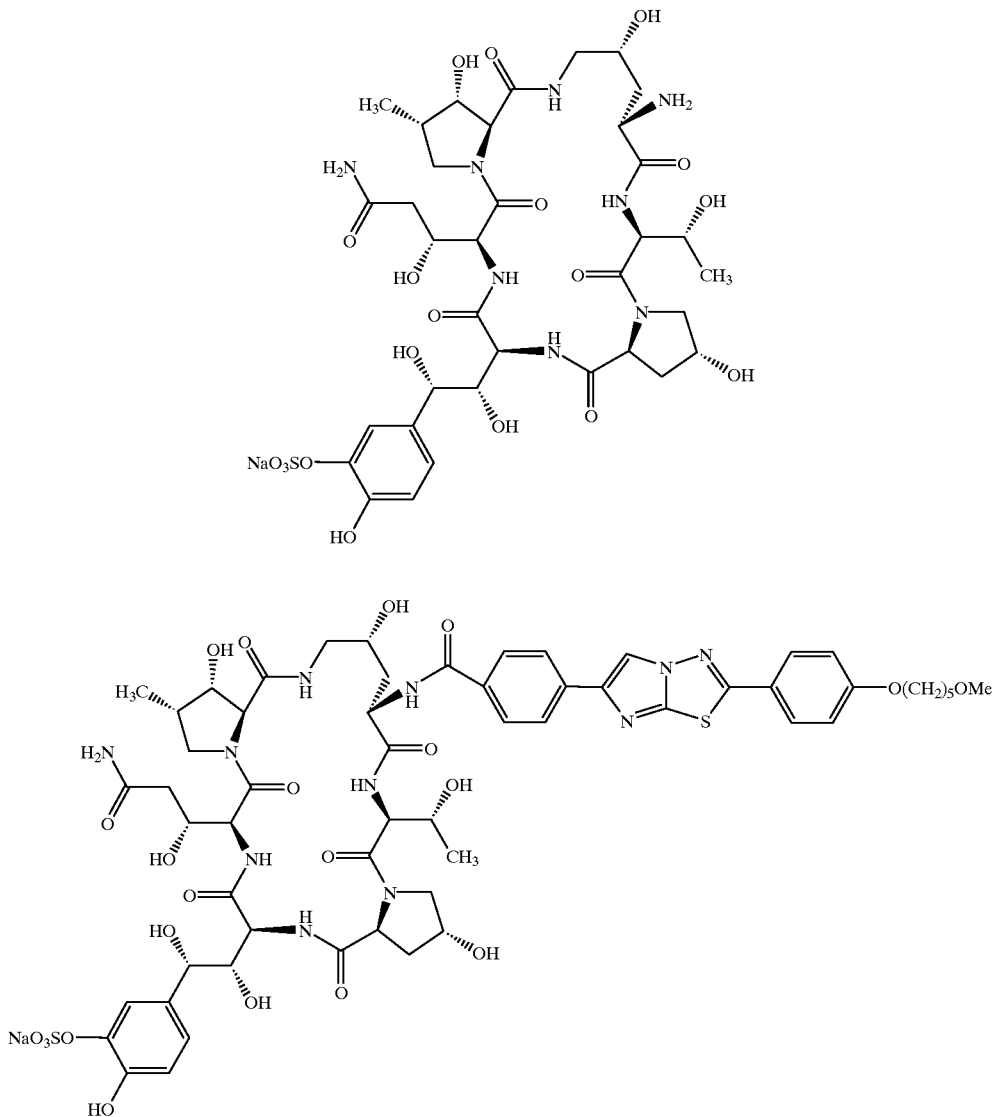 |

-continued
| Example No. | Formula |
|---|---|
| 142 | 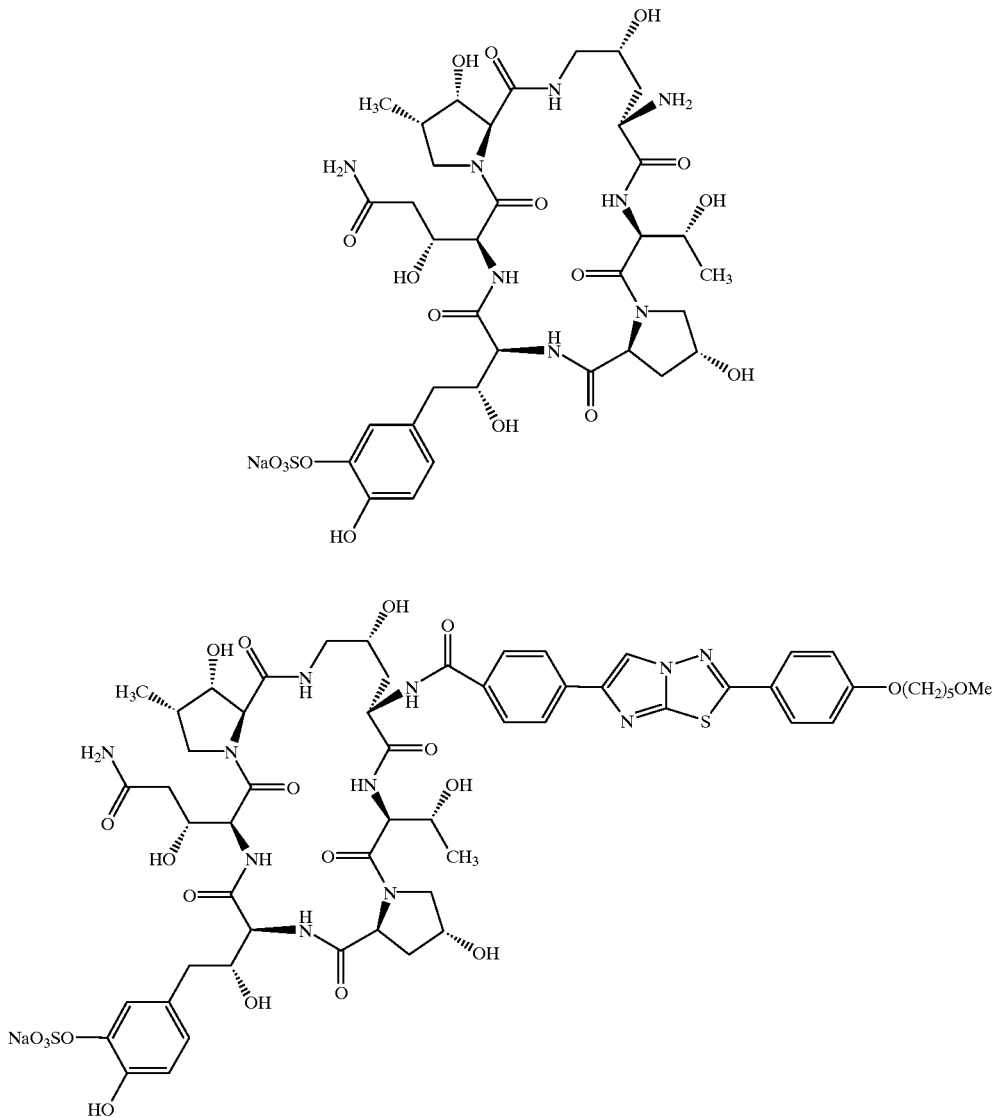 |

-continued
| Example No. | Formula |
|---|---|
| 143 | 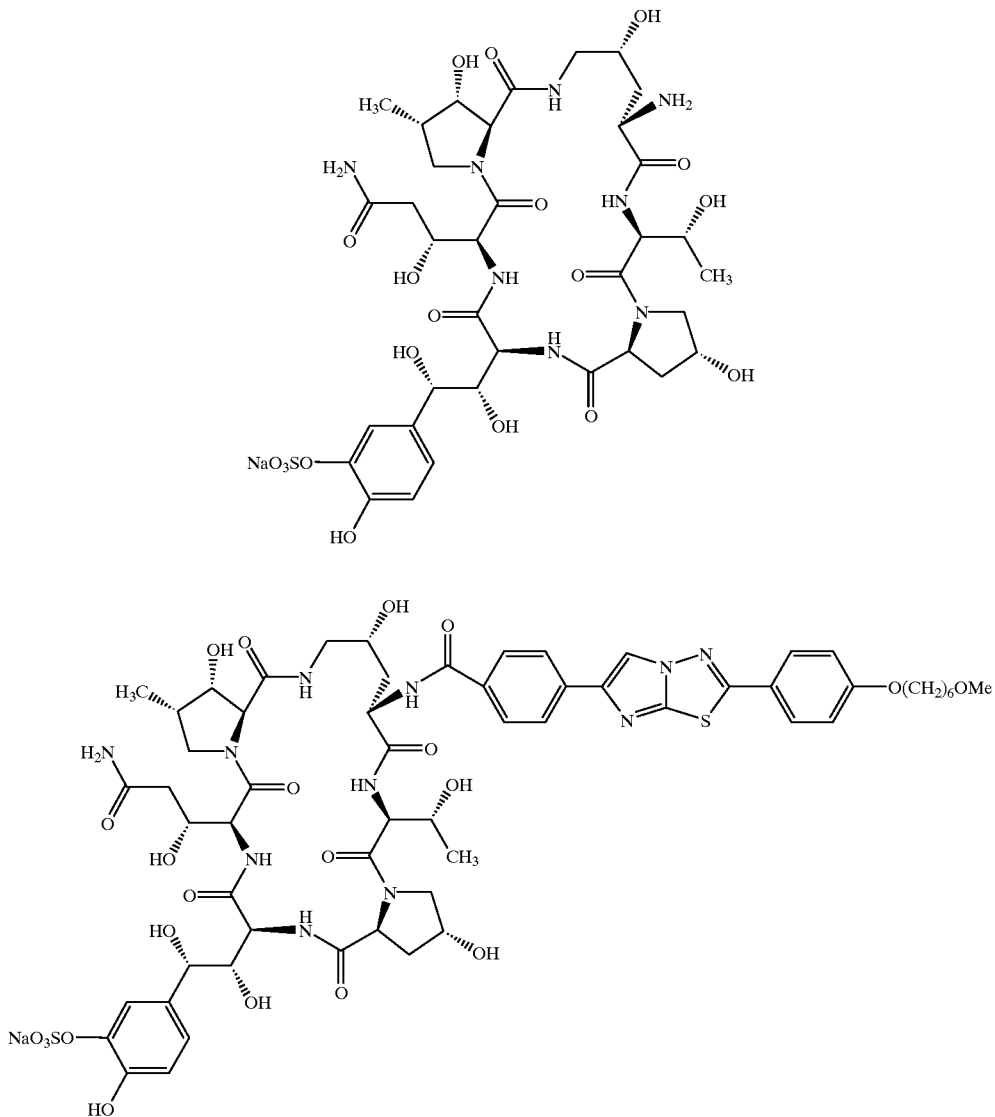 |

-continued
| Example No. | Formula |
|---|---|
| 144 | 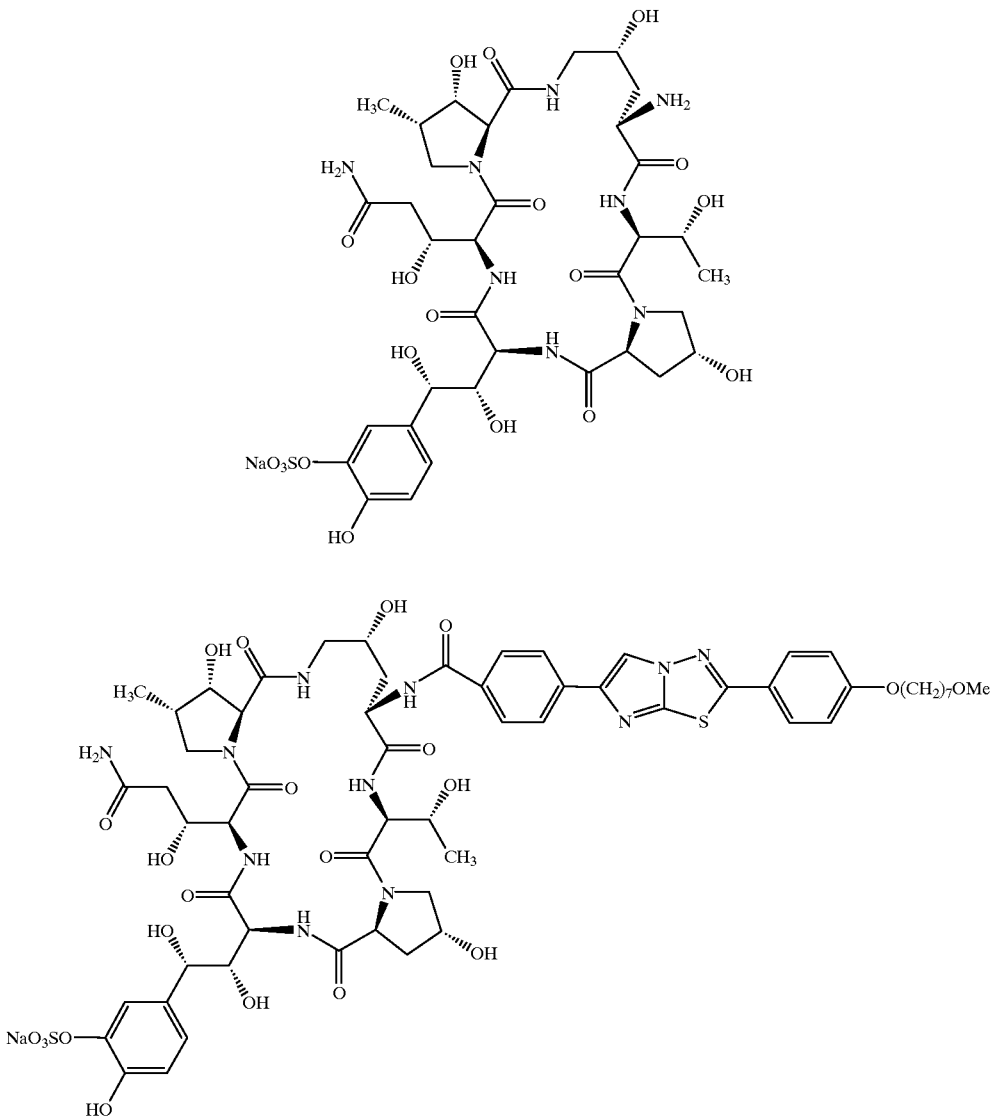 |

-continued
| Example No. | Formula |
|---|---|
| 145 | 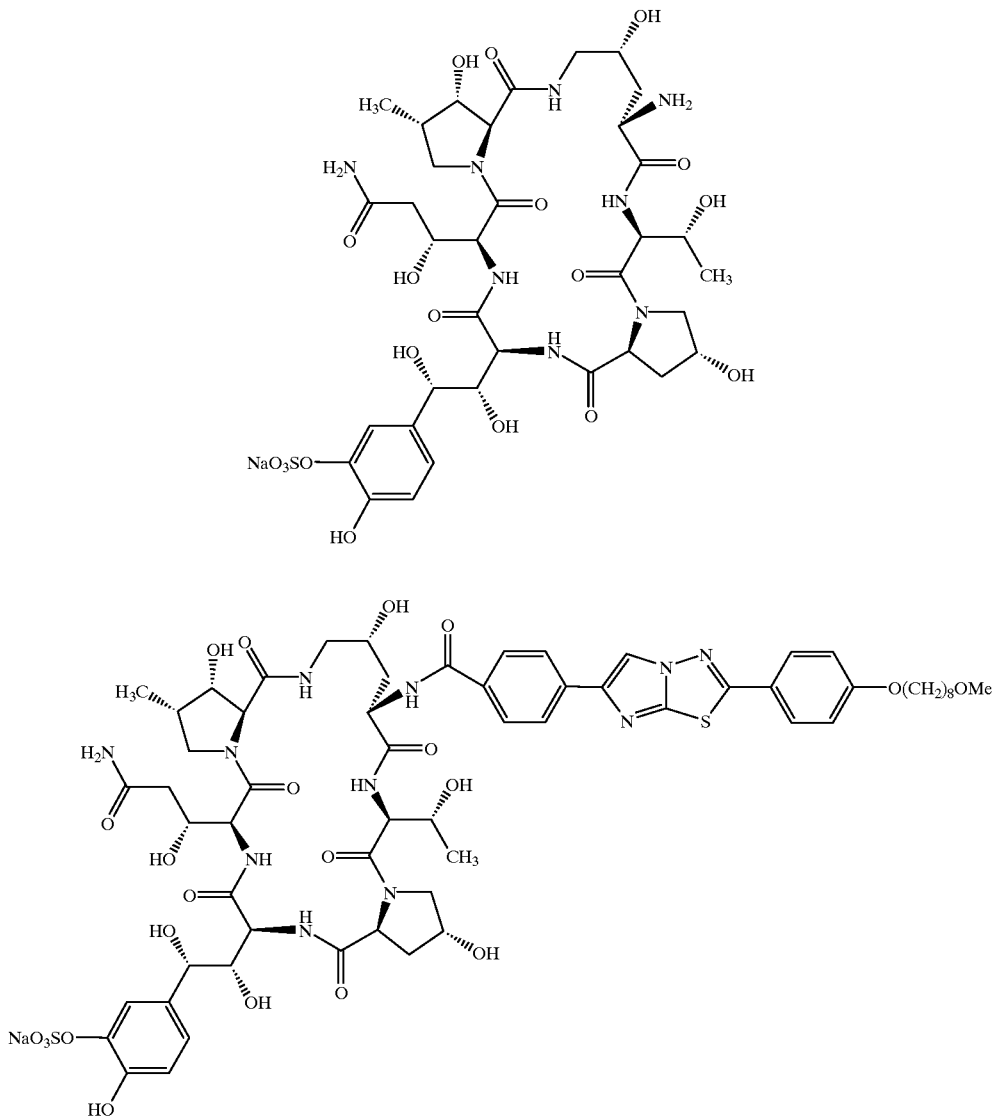 |

-continued
| Example No. | Formula |
|---|---|
| 146 | 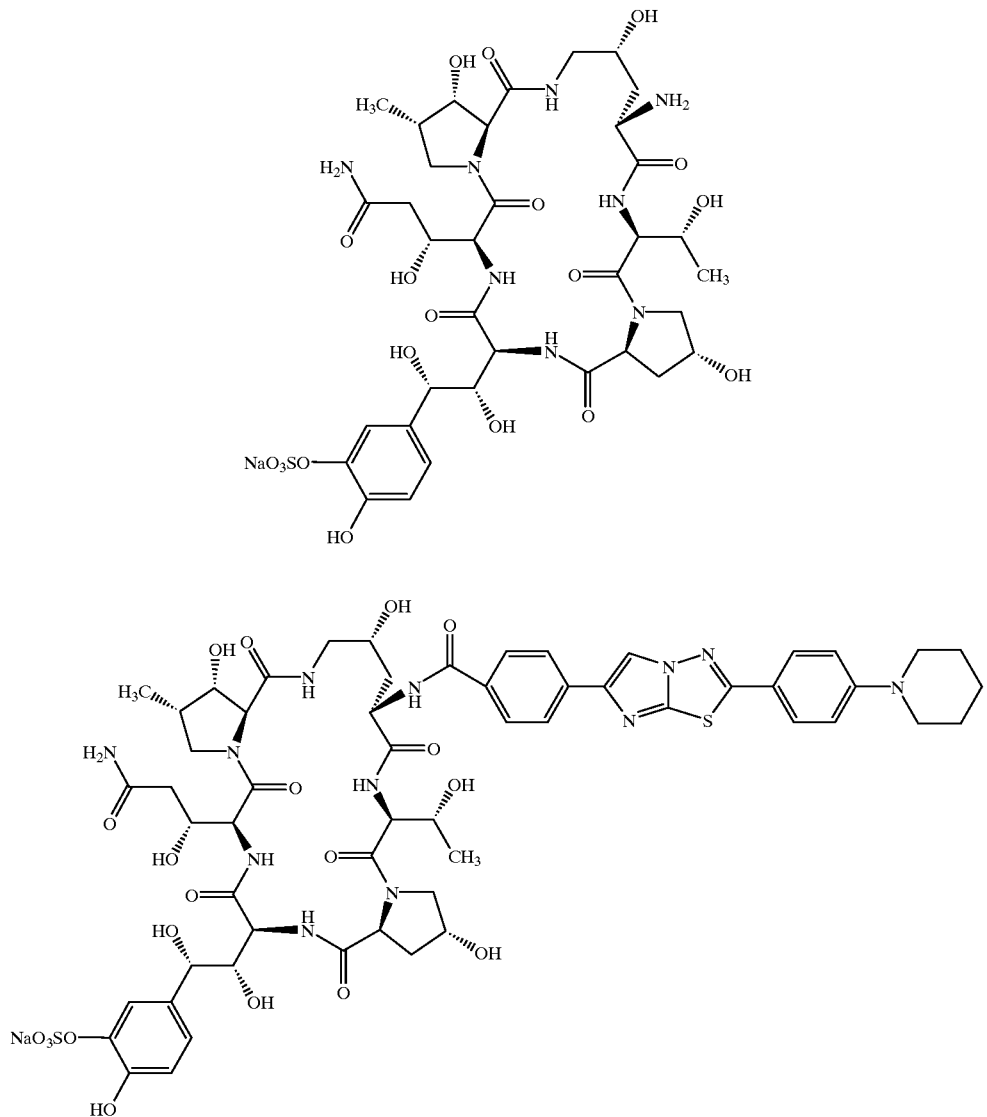 |

| Example No. | Formula |
|---|---|
| 147 | 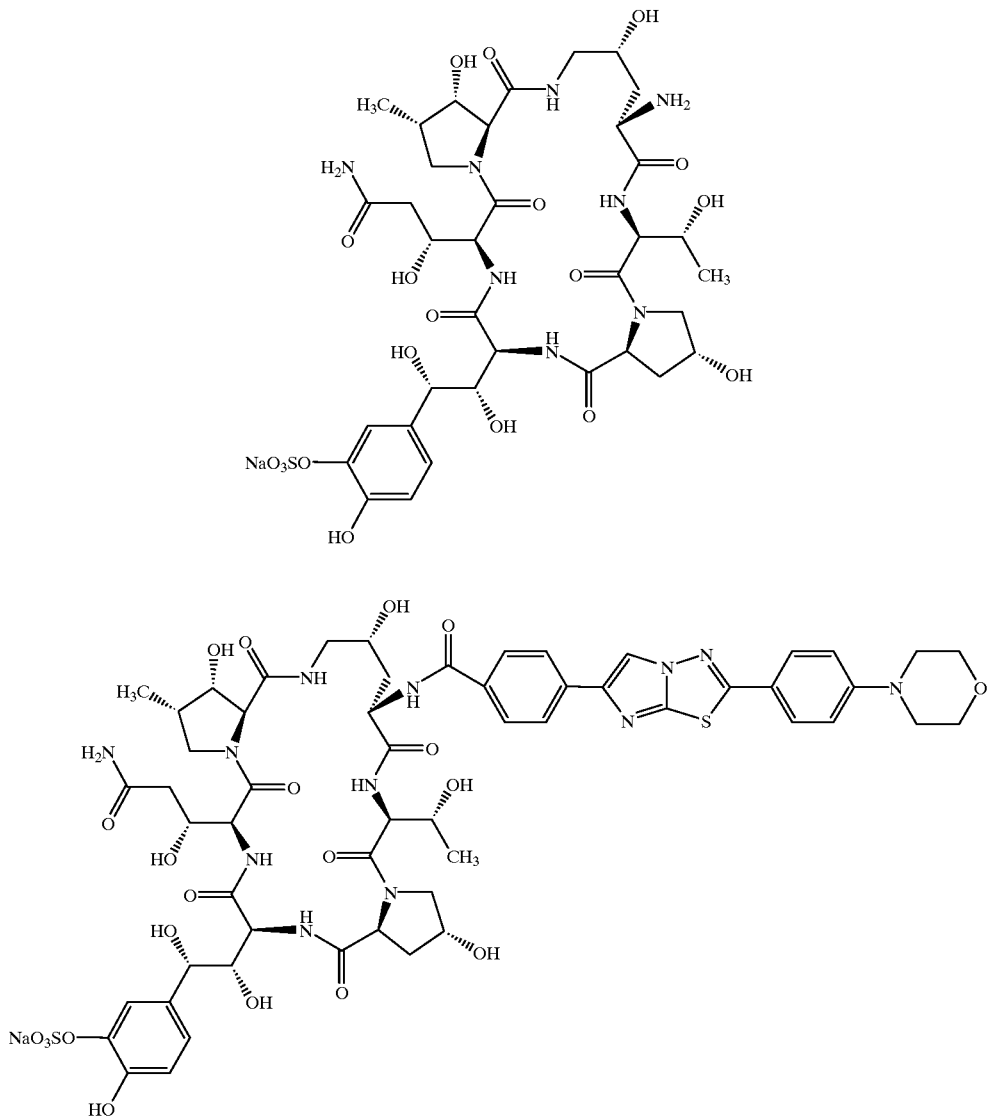 |

| Example No. | Formula |
|---|---|
| 148 | 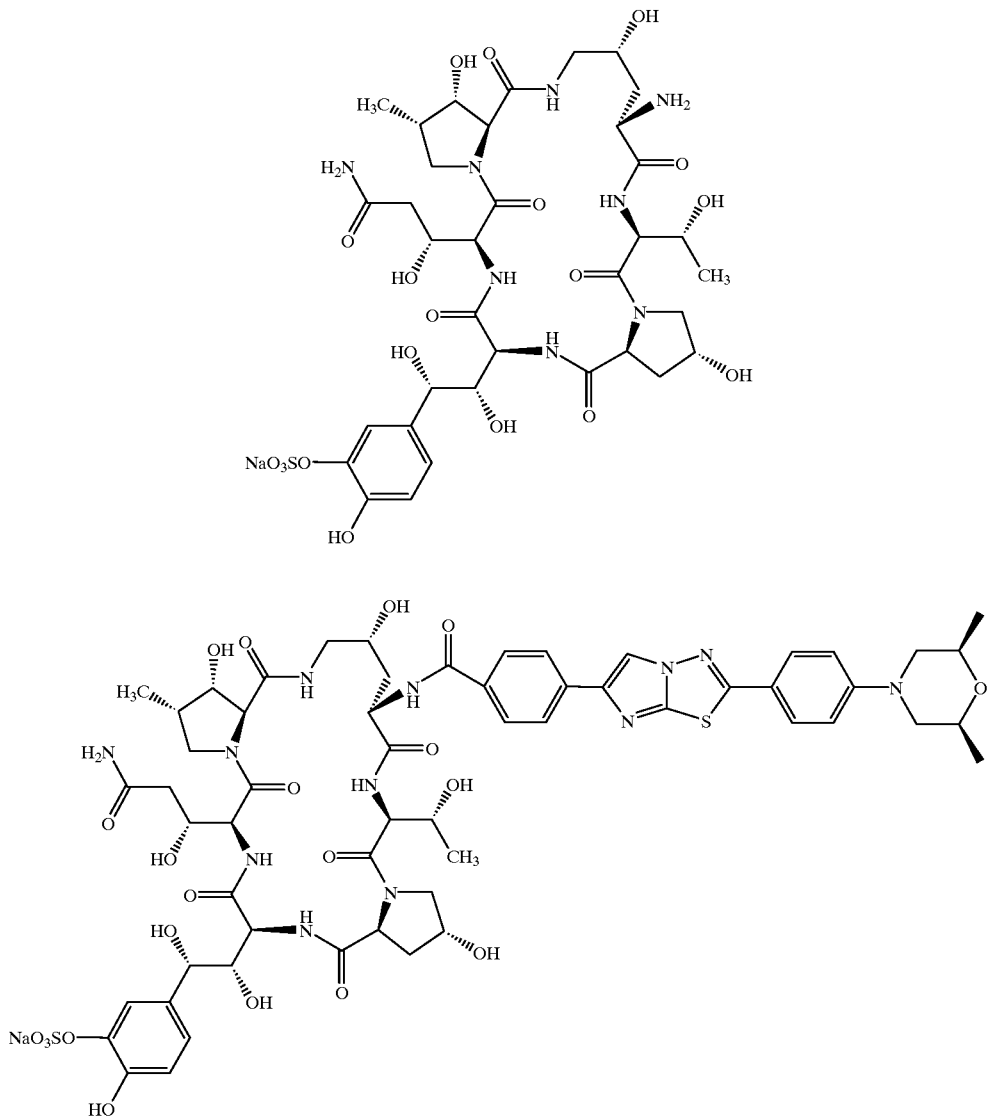 |

| Example No. | Formula |
|---|---|
| 149 | 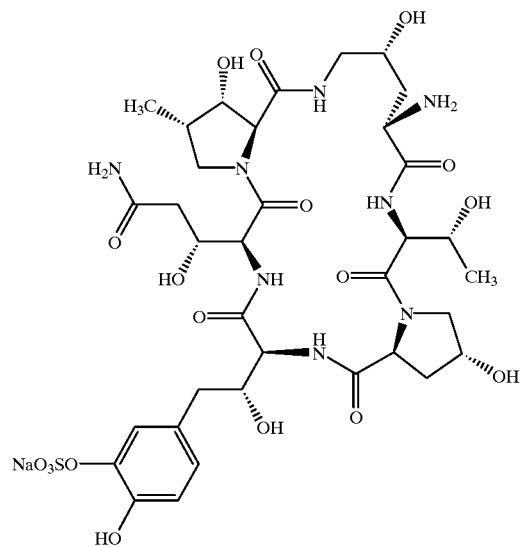 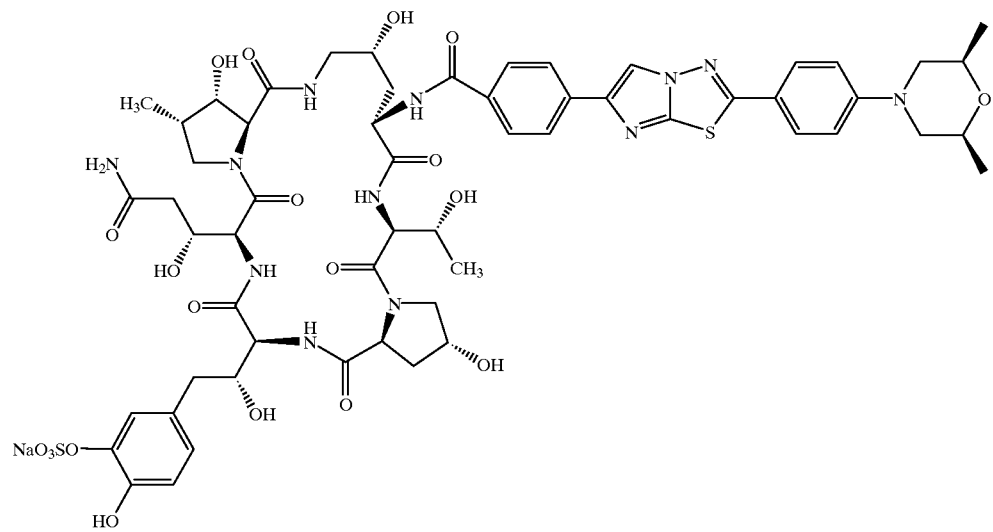 |

| Example No. | Formula |
|---|---|
| 150 | 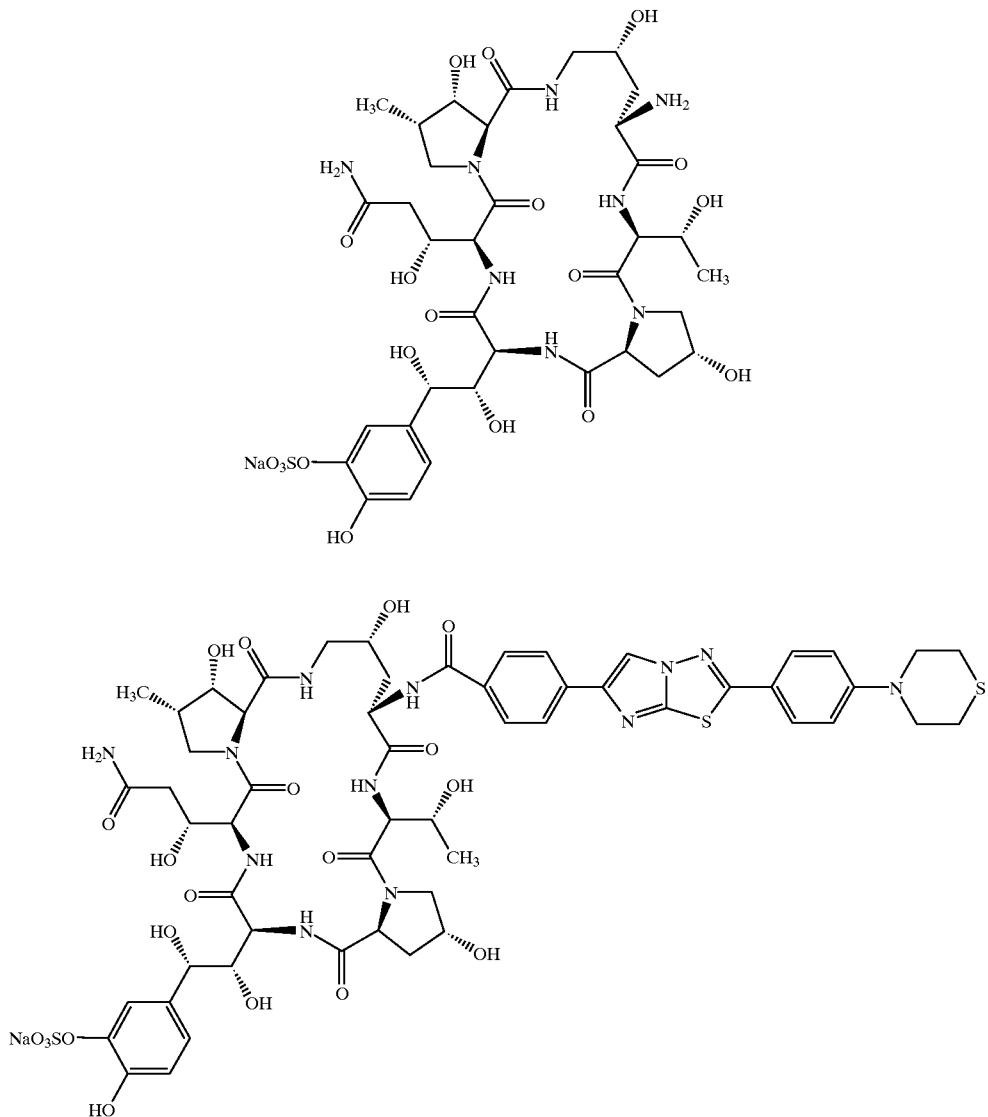 |

-continued
| Example No. | Formula |
|---|---|
| 151 | 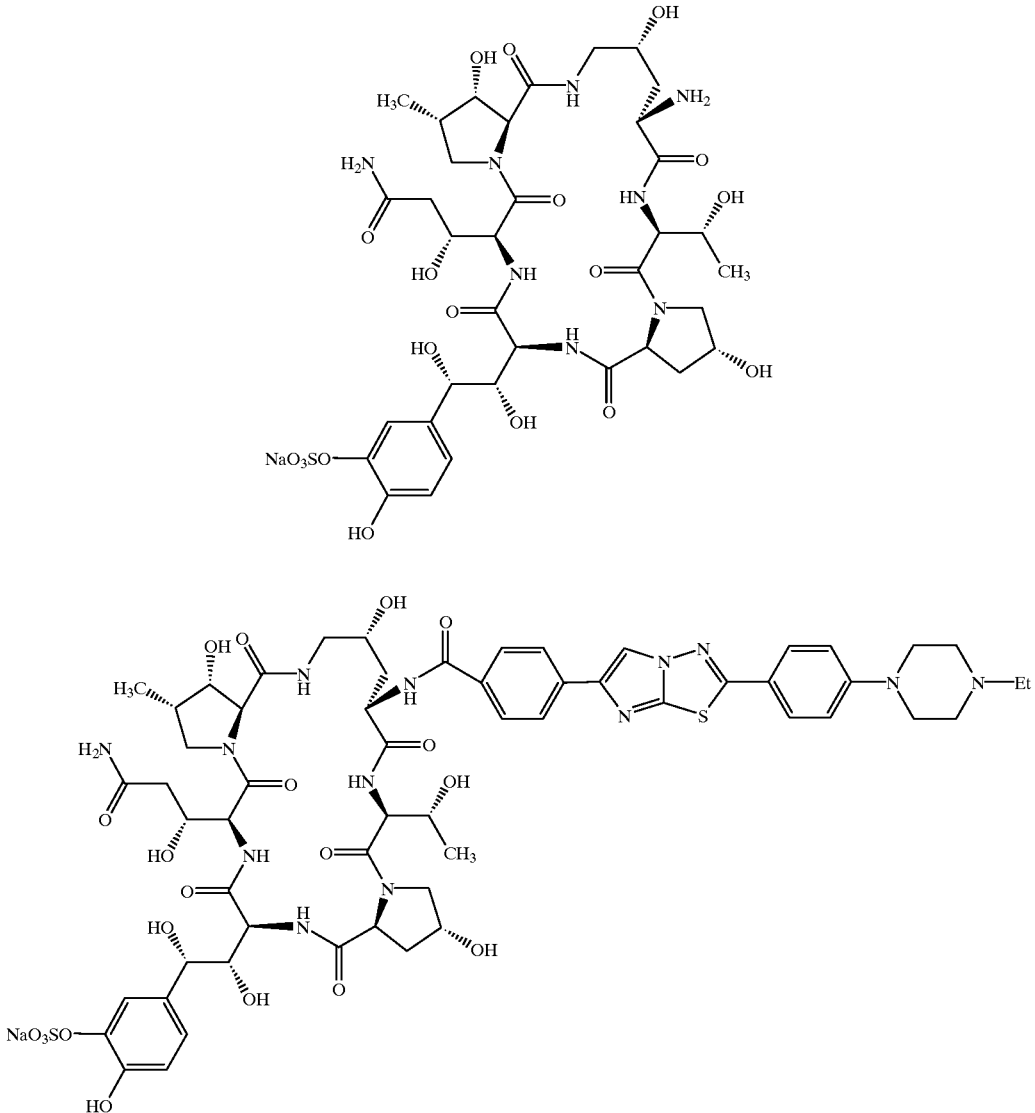 |

-continued
| Example No. | Formula |
|---|---|
| 152 | 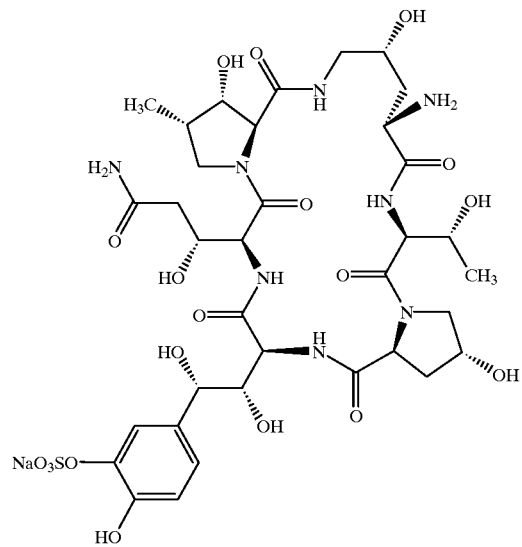 |
| | 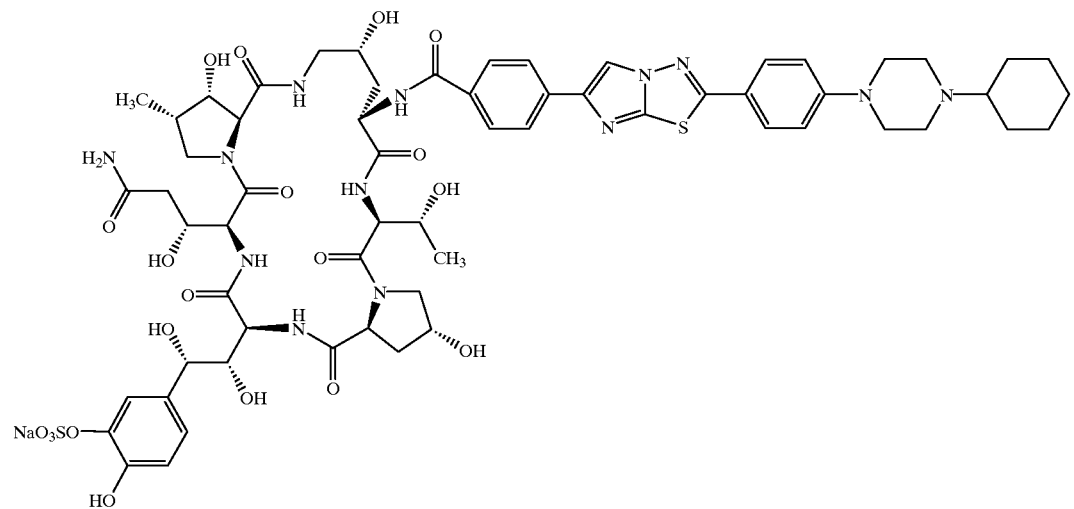 |

| Example No. | Formula |
|---|---|
| 153 | 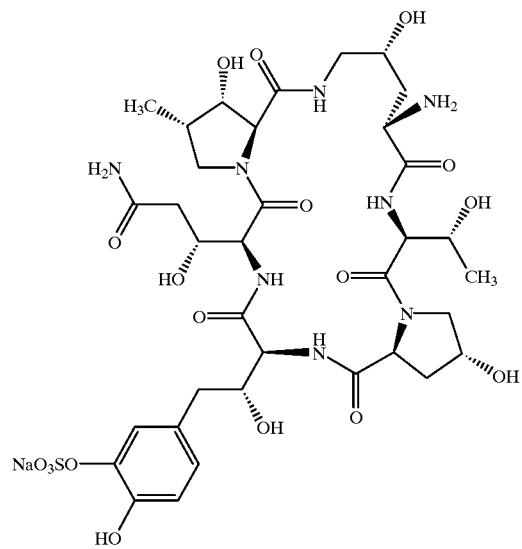 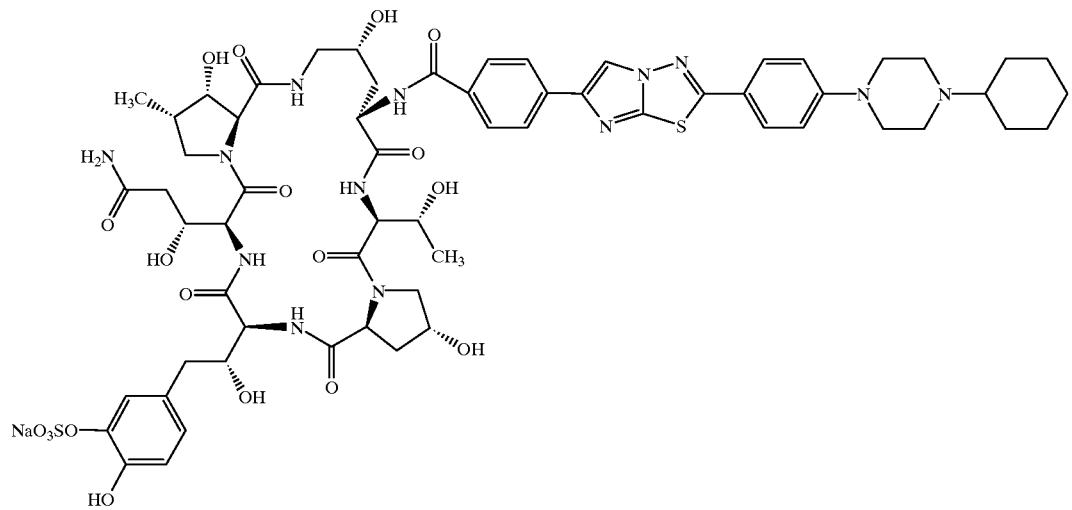 |

| Example No. | Formula |
|---|---|
| 154 | 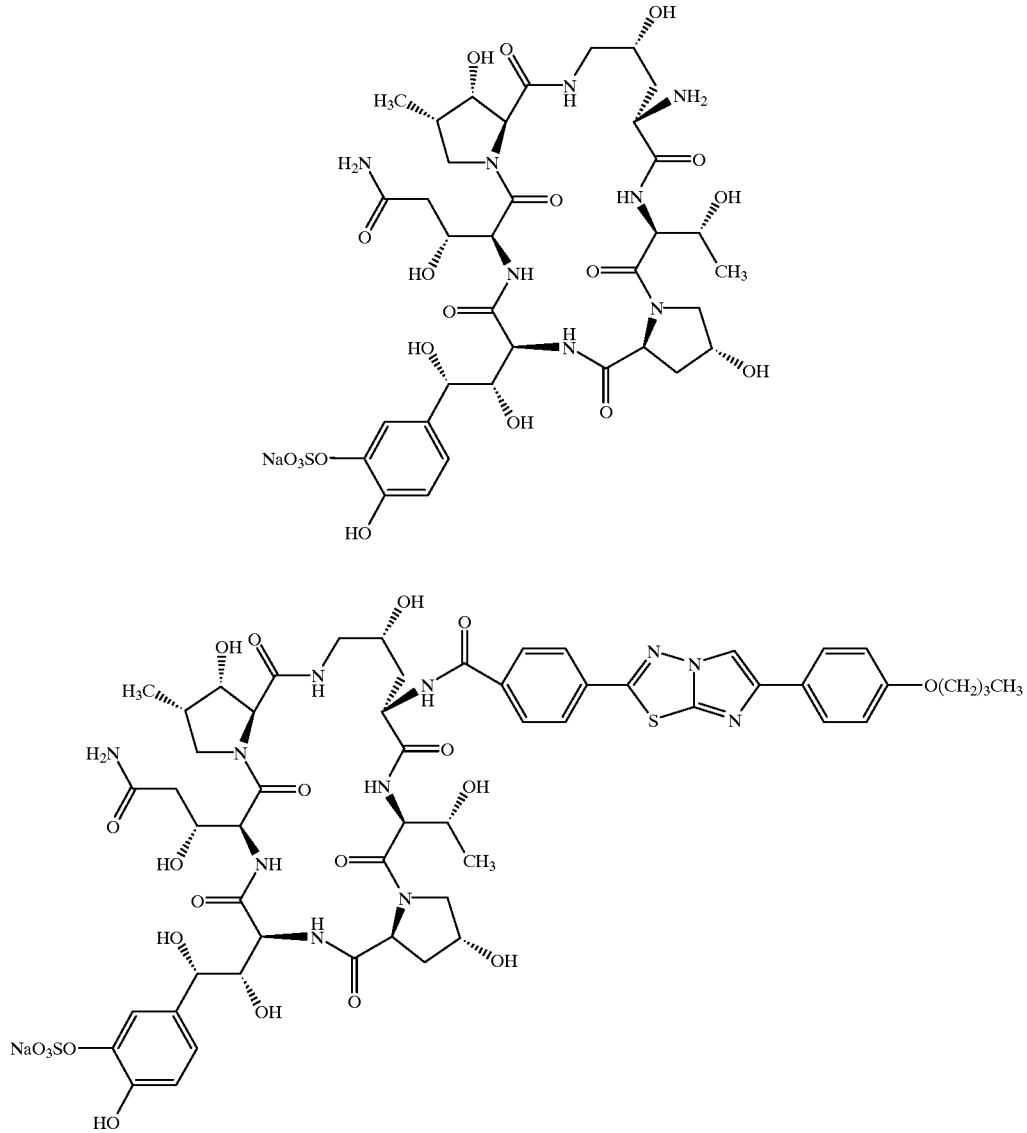 |

-continued
| Example No. | Formula |
|---|---|
| 155 | 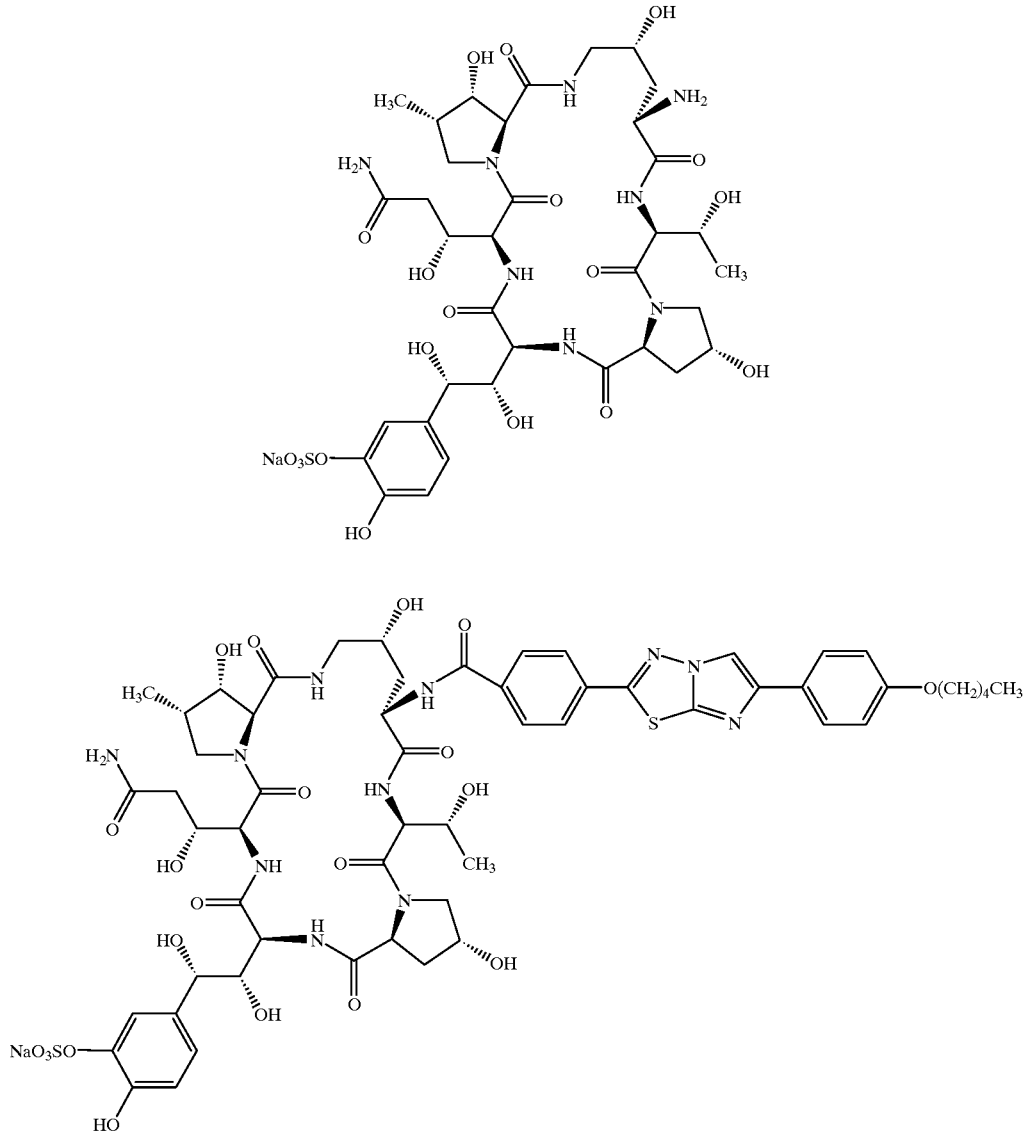 |

| Example No. | Formula |
|---|---|
| 156 | 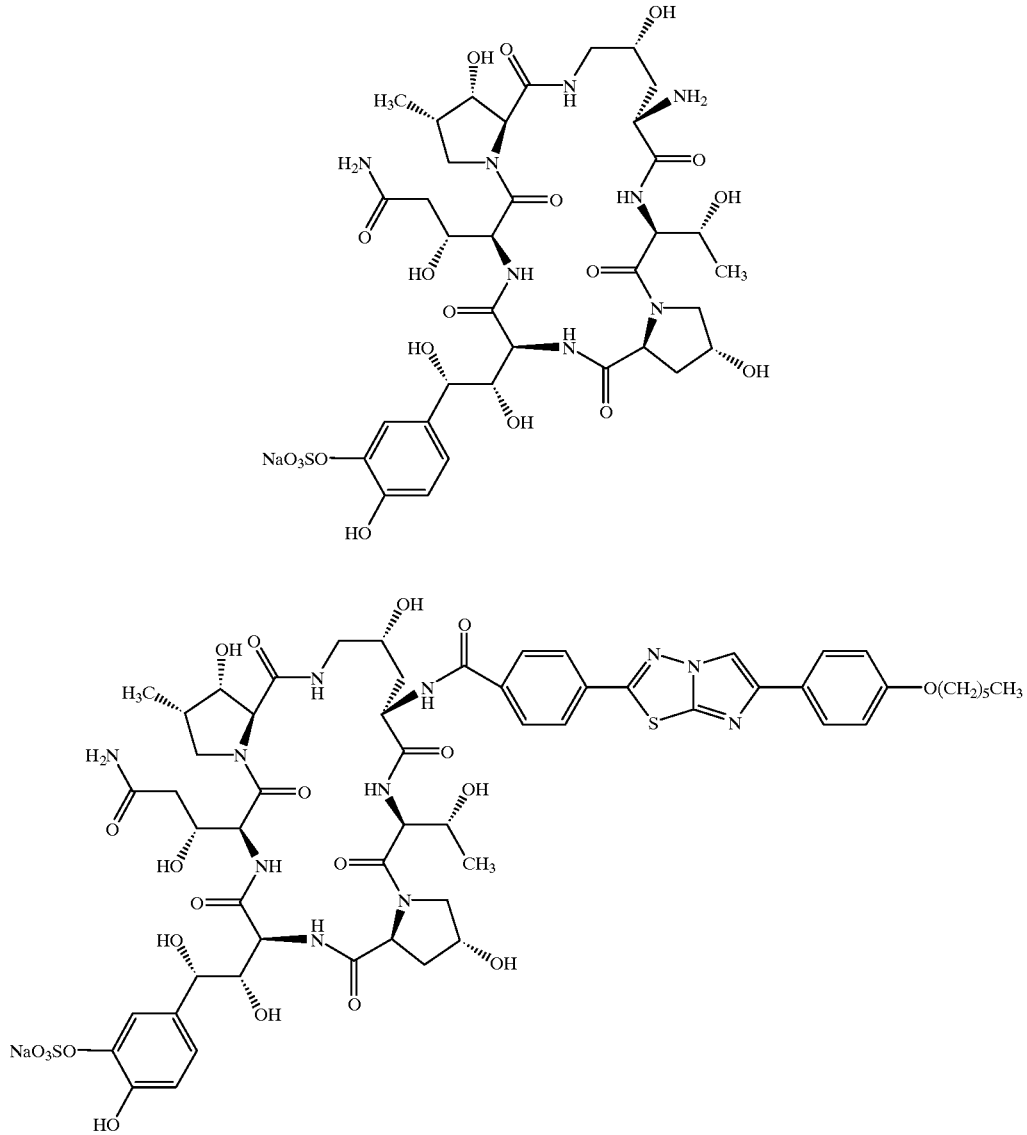 |

| Example No. | Formula |
|---|---|
| 157 | 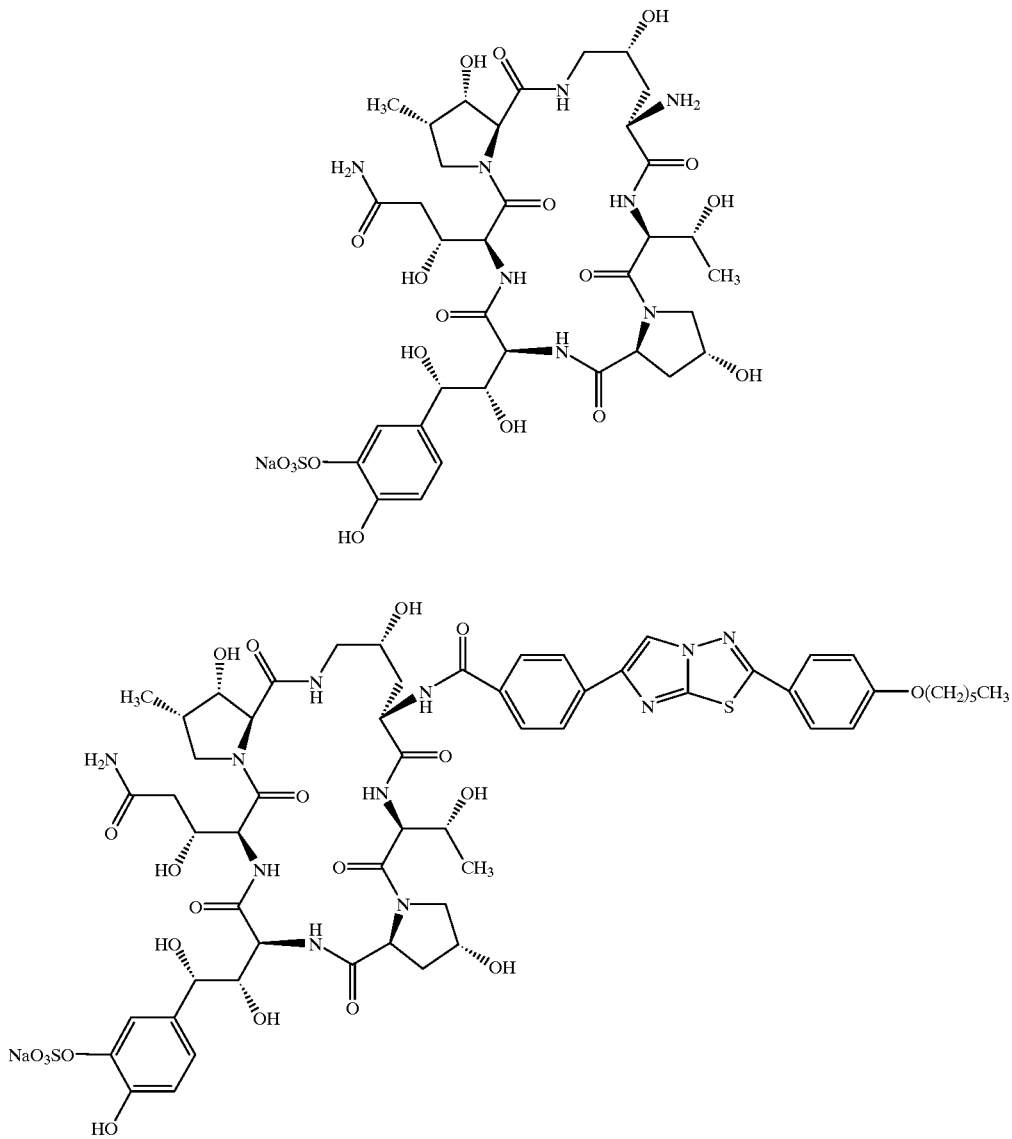 |

-continued
| Example No. | Formula |
|---|---|
| 158 | 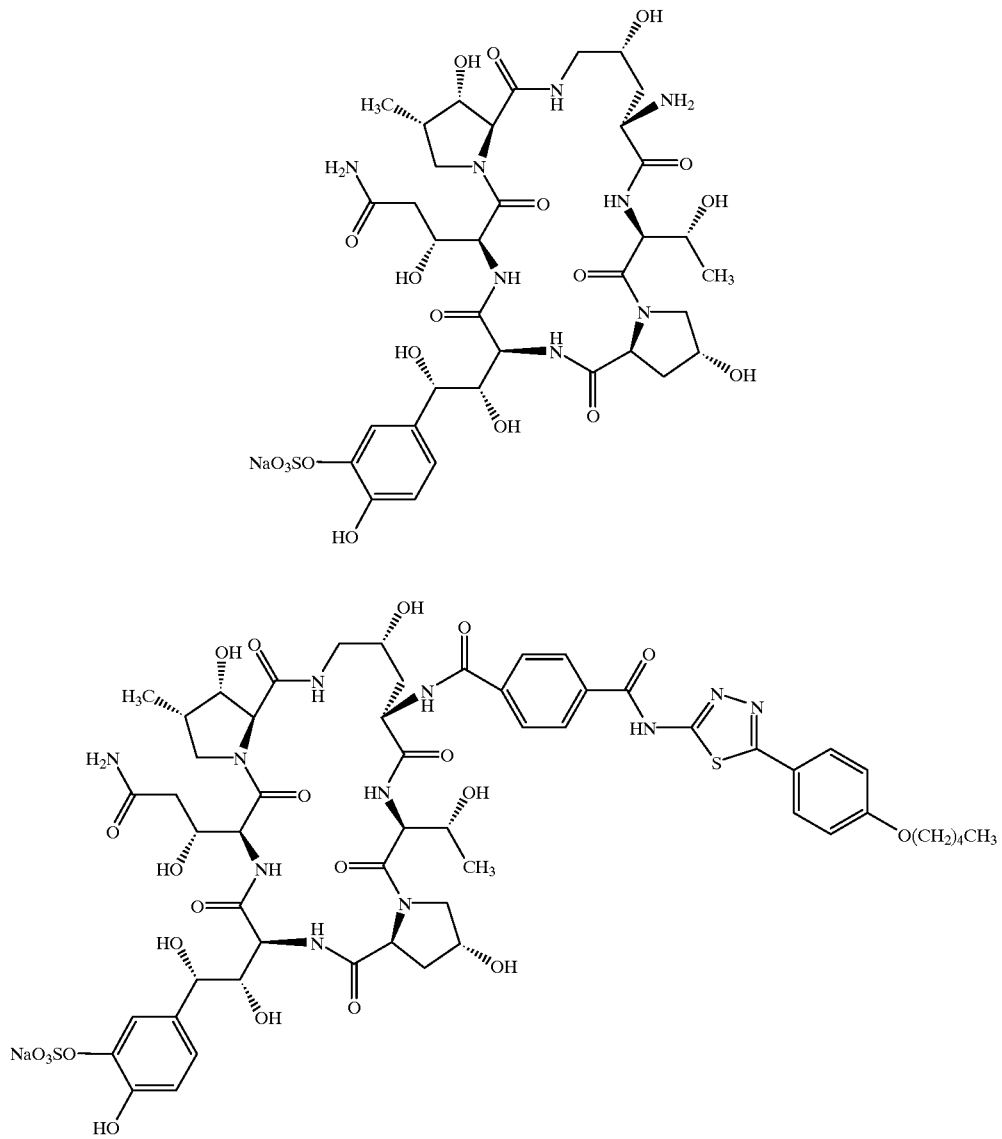 |

-continued
| Example No. | Formula |
|---|---|
| 159 | 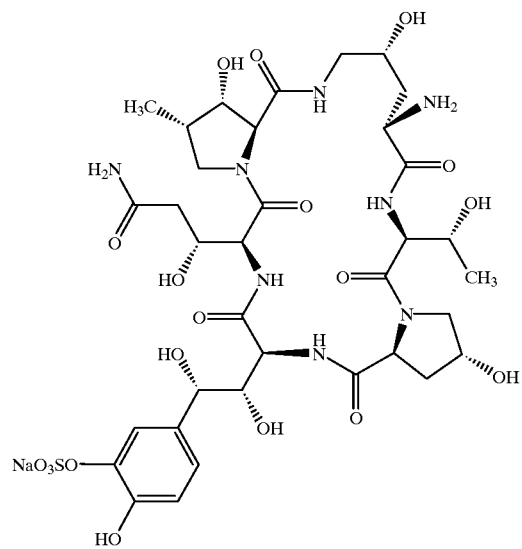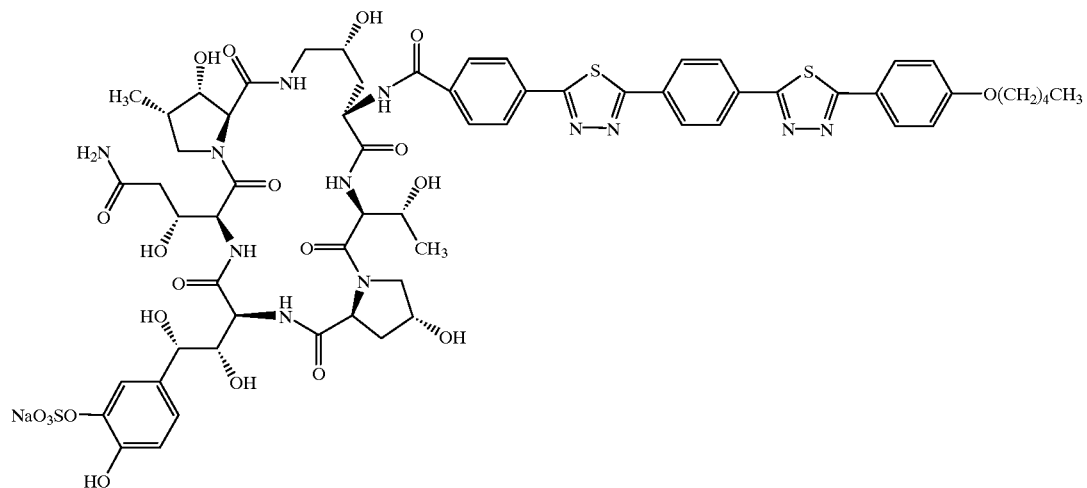 |

| Example No. | Formula |
|---|---|
| 160 | 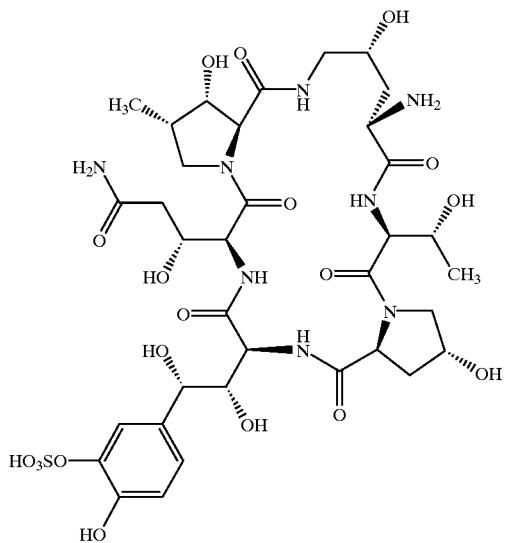 |
| | 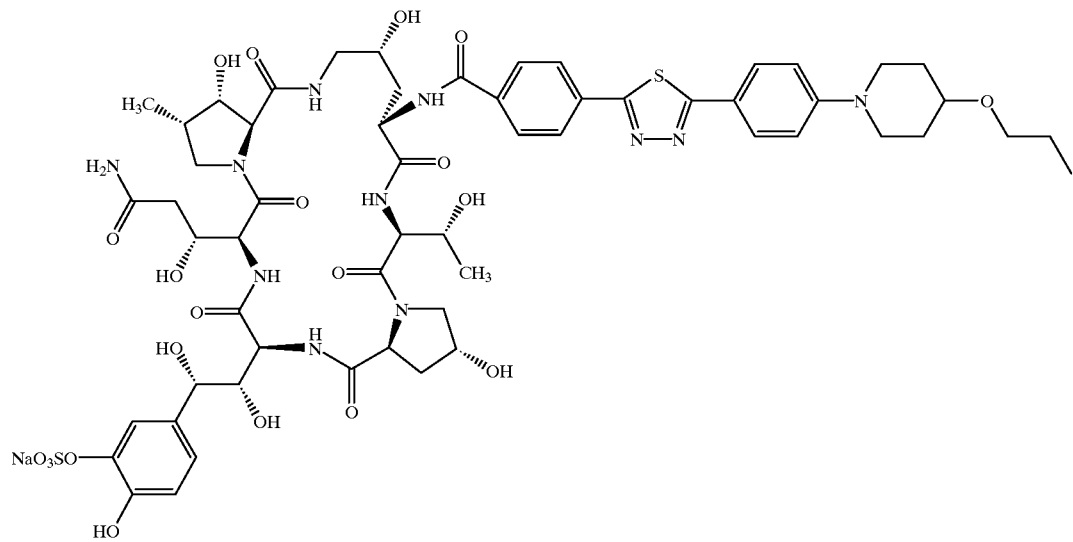 |

| Example No. | Formula |
|---|---|
| 161 | 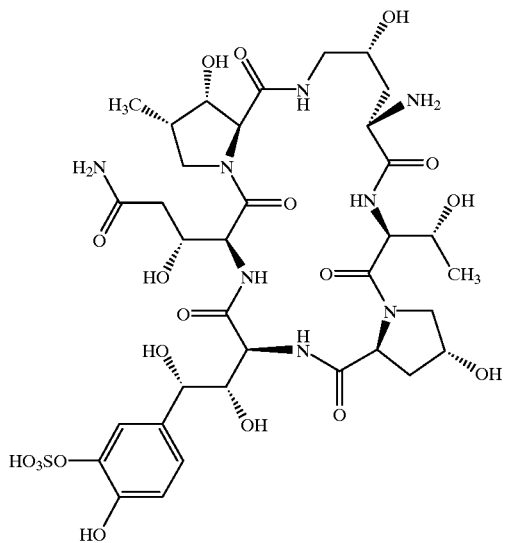 |
| | 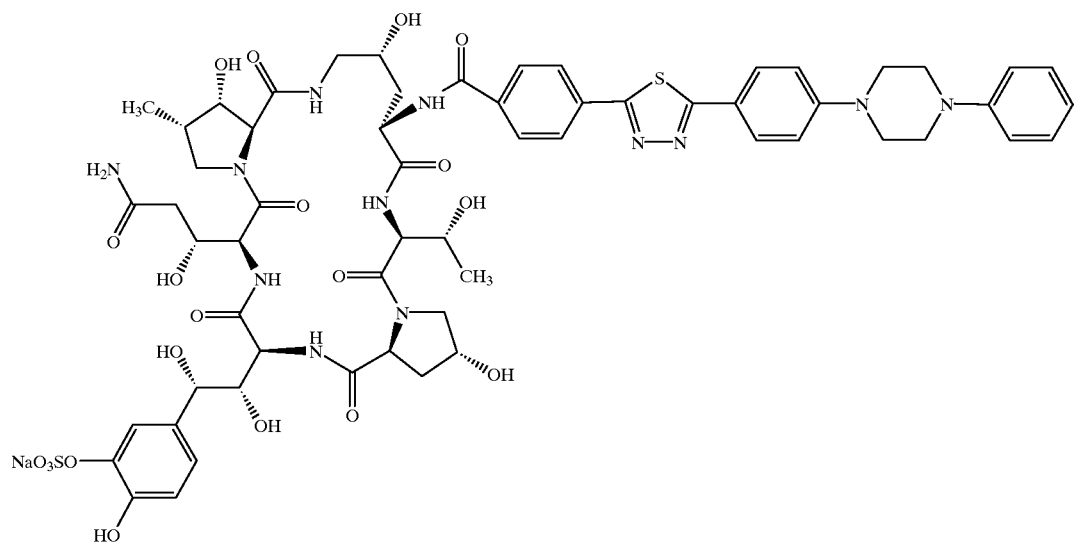 |

-continued
| Example No. | Formula |
|---|---|
| 162 | 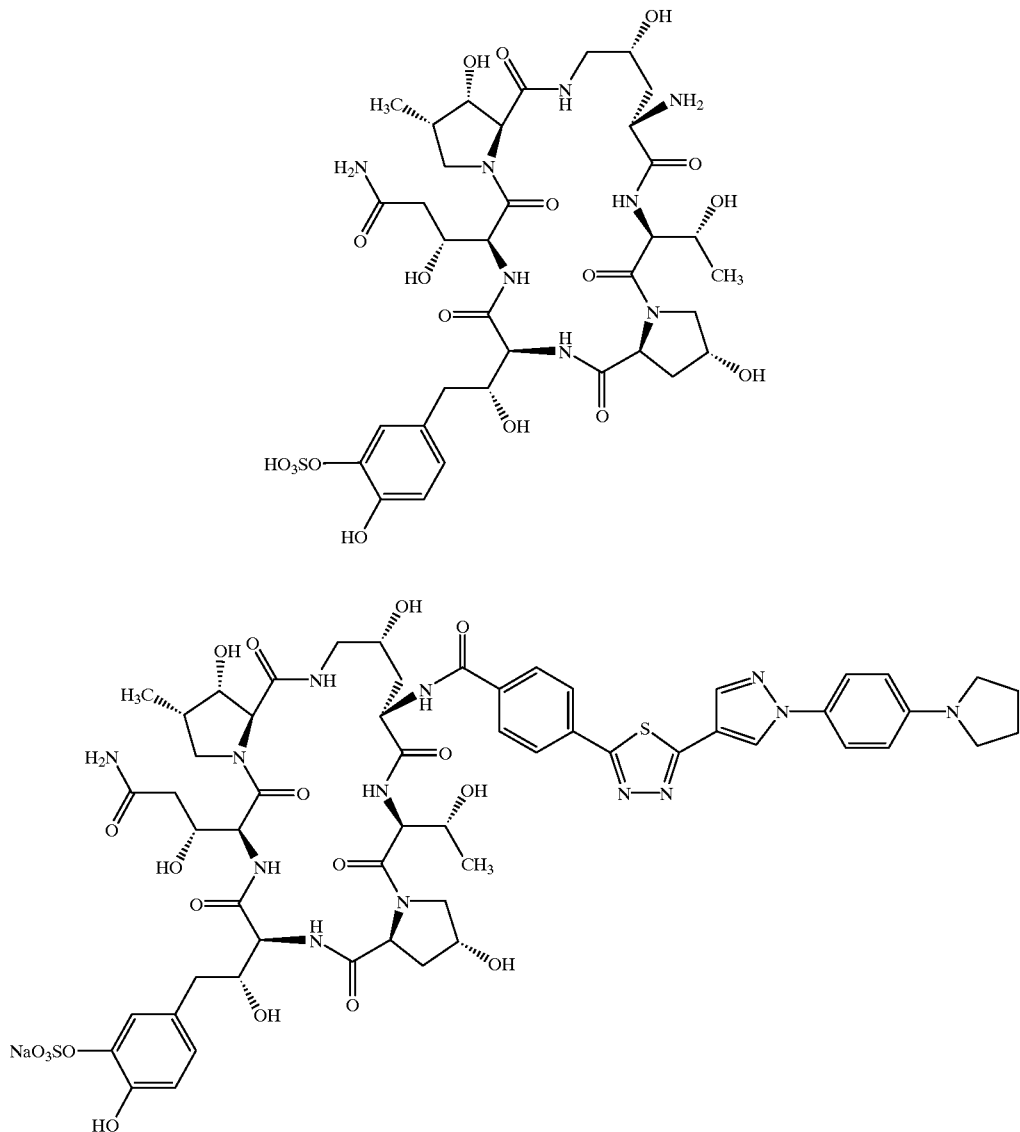 |

| Example No. | Formula |
|---|---|
| 163 | 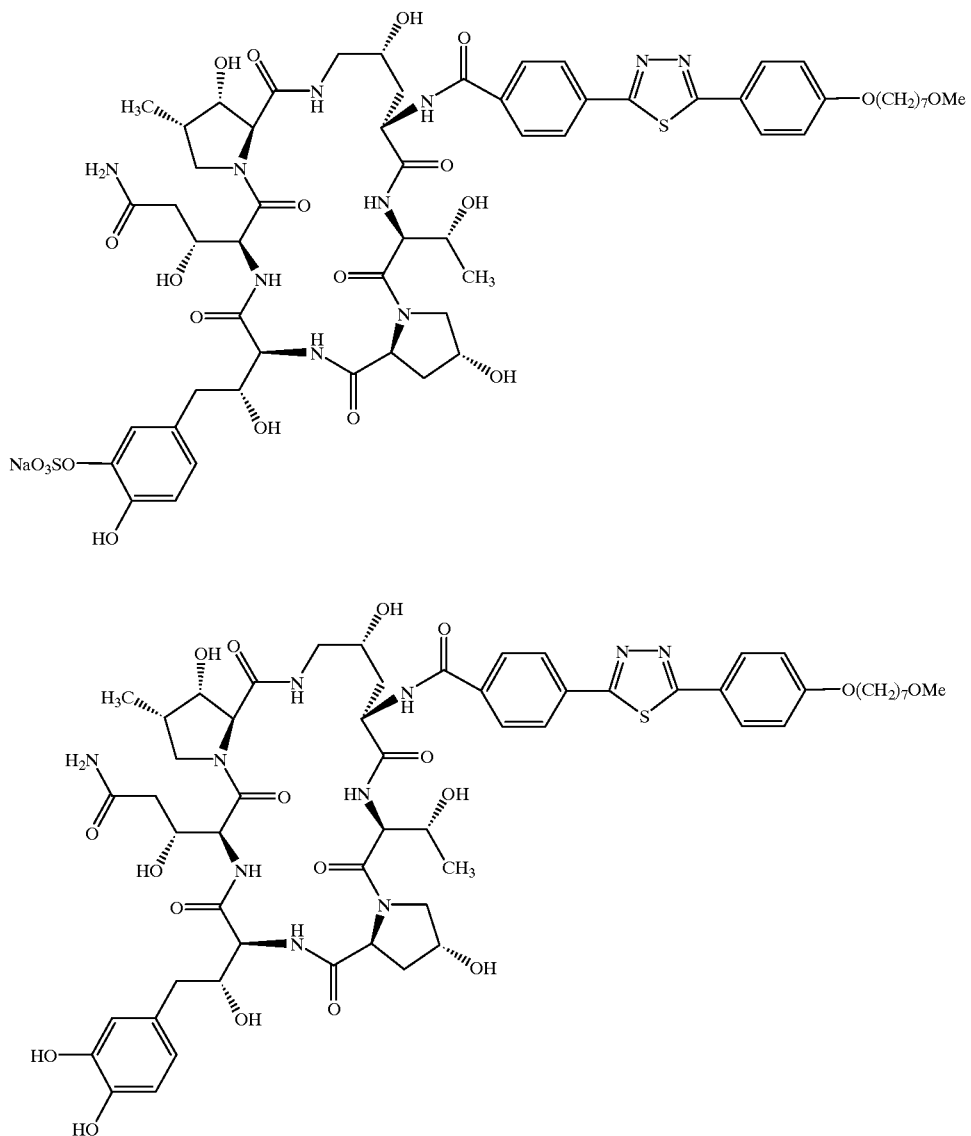 |

| Example No. | Formula |
|---|---|
| 164 | 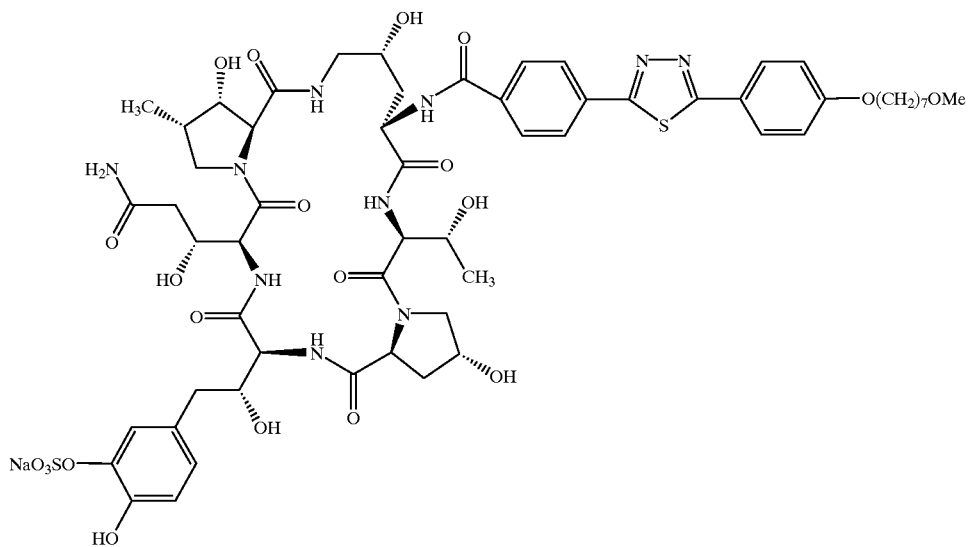<br>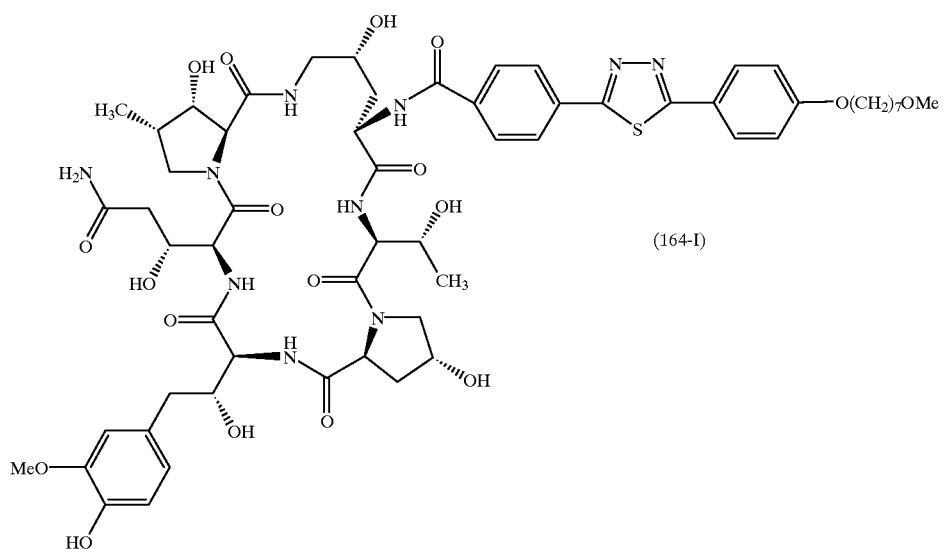(164-I) |

-continued
| Example No. | Formula |
|---|---|
| | 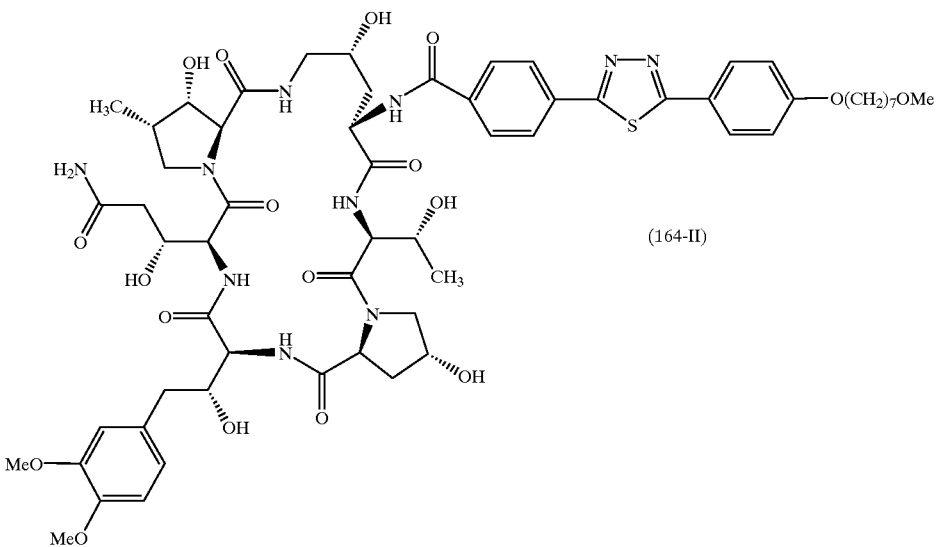 (164-II) |
| 165 | 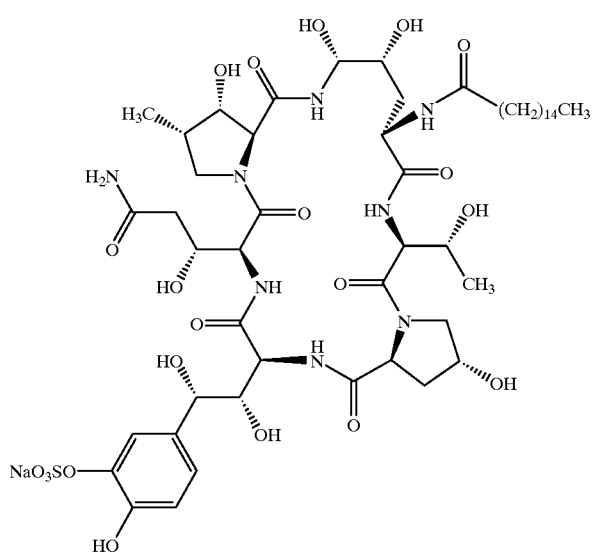 |

-continued
| Example No. | Formula |
|---|---|
| | 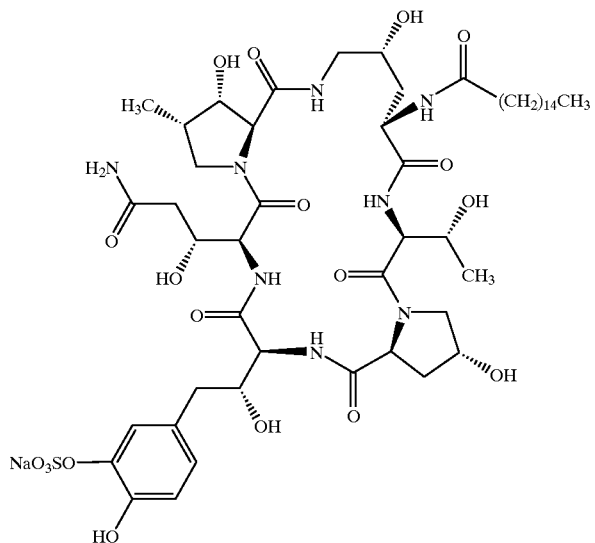 |
| 166 | 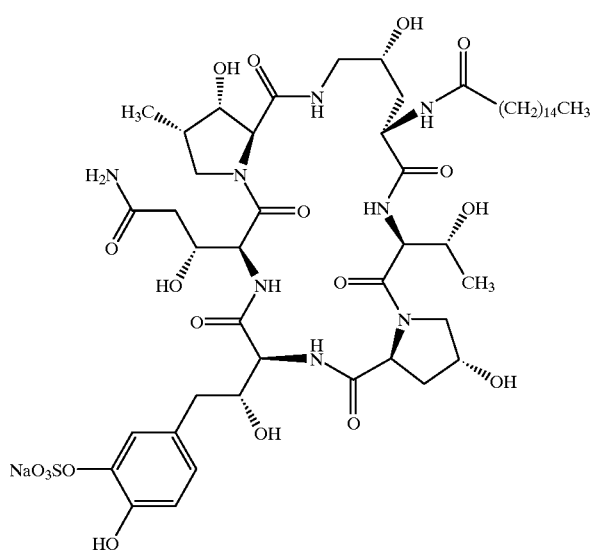 |

| Example No. | Formula |
|---|---|
| | 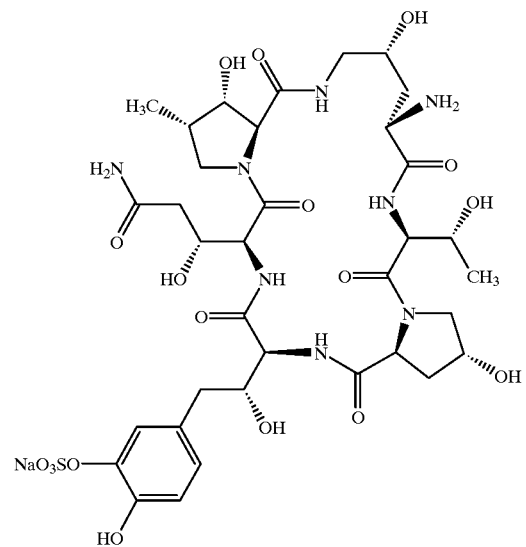 |
| 167 | 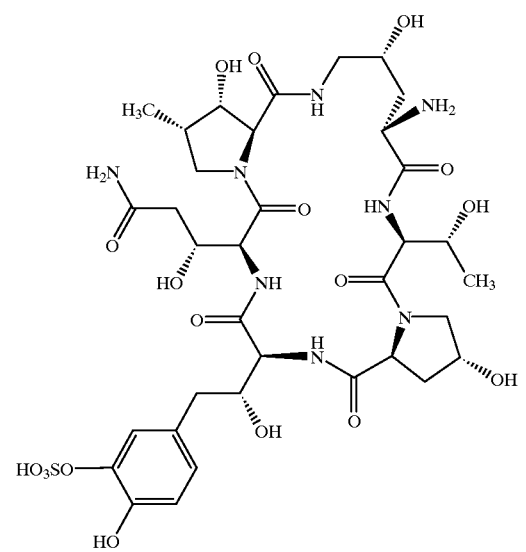 |

-continued
| Example No. | Formula |
|---|---|
| | 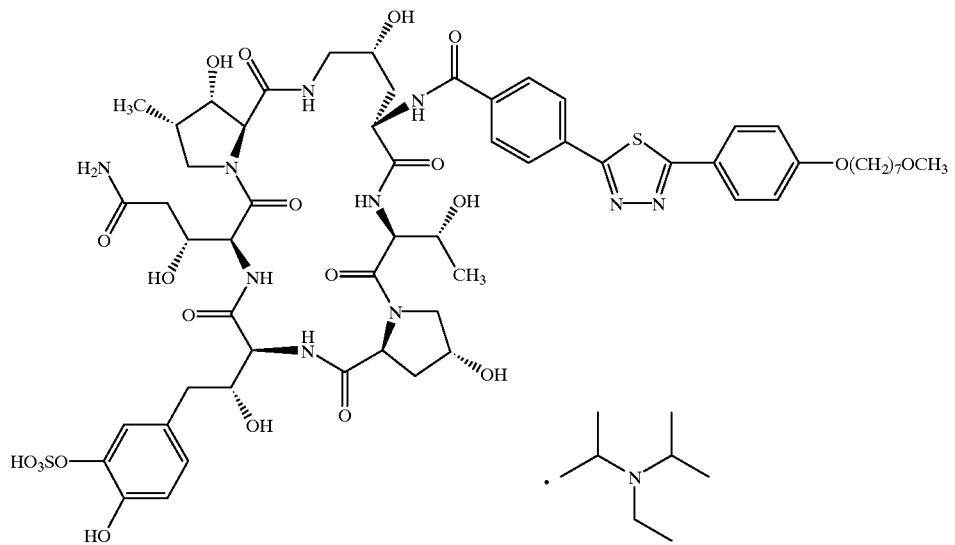 |
| 168 | 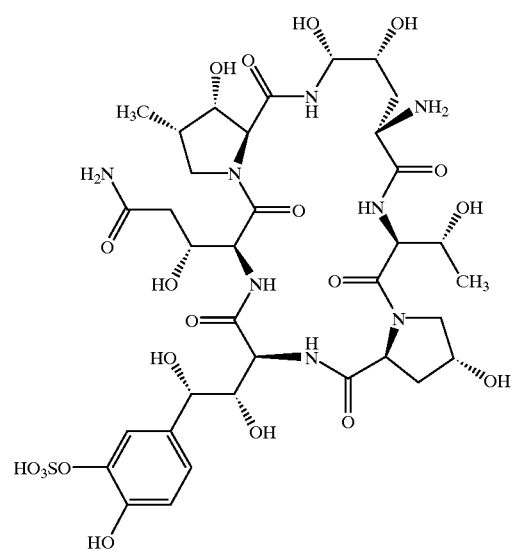 |

| Example No. | Formula |
|---|---|
| | 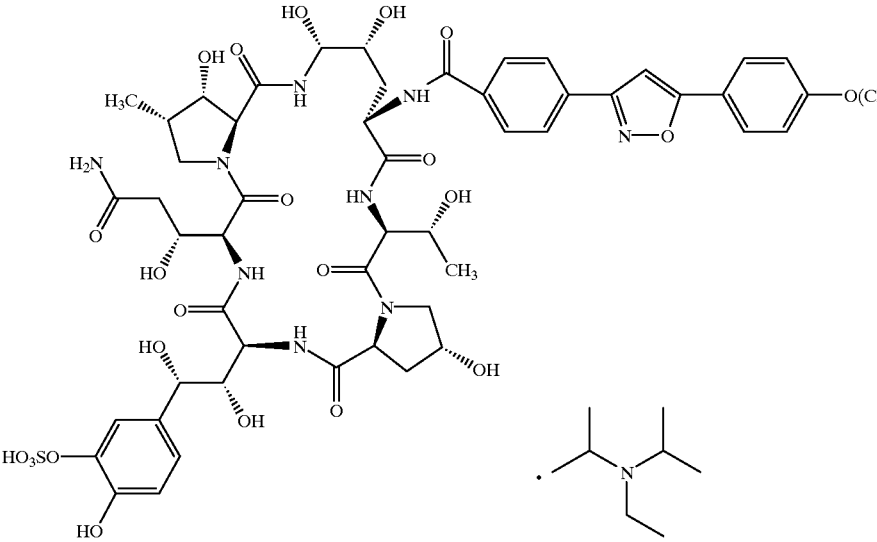 |
| 169 | 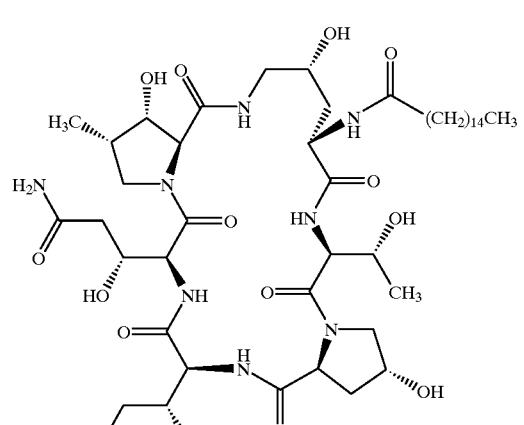 |

-continued

| Example No. | Formula |
|---|---|

EXAMPLE 1

To a suspension of Starting Compound (1) (0.6 g) and sodium cyanoborohydride (0.076 g) in dichloromethane (6 ml) was gradually added trifluoroacetic acid (3 ml) at 4° C. The mixture was stirred for an hour at 4° C. The reaction mixture was evaporated under reduced pressure. The residue was added to water and adjusted to pH 8.5 with 1N NaOH aq. The solution was subjected to column chromatography on ODS (YMC-gel ODS-AM S-50) and eluted with 30% acetonitrile aqueous solution. The fractions containing the object compound were combined and evaporated under reduced pressure to remove acetonitrile. The residue was lyophilized to give Object Compound (1) (0.417 g).

IR (KBr) 3350, 1668.1, 1629.6, 1241.9 cm$^{-1}$

NMR (DMSO-d$_6$, δ): 0.87 (3H, t, J=6.7 Hz), 0.96 (3H, d, J=6.7 Hz), 1.11 (3H, d, J=5.7 Hz), 1.2–1.55 (8H, m), 1.55–2.1 (5H, m), 2.1–2.5 (4H, m), 3.01 (1H, m), 3.19 (1H, m), 3.46 (1H, m), 3.6–3.87 (3H, m), 3.87–4.55 (13H, m), 4.6–5.5 (8H, m), 6.52 (1H, d, J=8.1 Hz), 6.73 (1H, d, J=8.2 Hz), 6.83 (1H, d, J=8.2 Hz), 6.85 (1H, s), 7.0–7.15 (3H, m), 7.19 (1H, s), 7.27–7.55 (3H, m), 7.55–7.78 (3H, m), 7.8–8.0 (2H, m), 8.76 (1H, s), 8.85 (1H, s)

MASS (m/z): 1248 (M+Na$^+$)

Elemental Analysis Calcd. for C$_{53}$H$_{72}$N$_9$NaO$_{21}$S.7H$_2$O: C, 47.07; H, 6.41, N, 9.32; Found: C, 46.82; H, 6.54; N, 9.25.

The following compounds (Examples 2 and 3) were obtained in a manner similar to that of Example 1.

EXAMPLE 2

IR (KBr): 3349.7, 1666.2, 1631. 5, 1267.0 cm$^{-1}$

NMR (DMSO-d$_6$, δ): 0.96 (3H, d, J=6.7 Hz), 1.11 (3H, d, J=5.9 Hz), 1.7–2.0 (2H, m), 2.0–2.6 (4H, m), 2.6–2.8 (1H, m), 3.1–3.3 (1H, m), 3.3–3.5 (1H, m), 3.5–4.5 (16H, m), 4.6–4.9 (2H, m), 5.1–5.5 (5H, m), 6.72 (1H, d, J=8.2 Hz), 6.81 (1H, dd, J=8.2 and 1.9 Hz), 6.9–7.5 (4H, m), 7.05 (1H, d, J=1.9 Hz), 7.4–7.9 (3H, m), 8.84 (1H, s)

MASS (m/z): 965 (M+Na$^+$)

Elemental Analysis Calcd. for C$_{35}$H$_{51}$N$_8$O$_{19}$SNa.5.5H$_2$O: C, 40.35; H, 6.00; N, 10.75; Found: C, 40.33; H, 5.92; N, 10.63.

EXAMPLE 3

IR (KBr): 3350, 1648.8, 1276.6 cm$^{-1}$

MASS (m/z): 1266 (M–Na$^+$)

EXAMPLE 4

To a suspension of Starting Compound (4) (46.1 g) and NaBH$_3$CN (7.7 g) in dichloromethane (600 ml) was added dropwise trifluoroacetic acid (240 ml) for 15 minutes below 5° C. The reaction mixture was stirred for 3 hours at the same temperature. The lower layer (trifluoroacetic acid layer) of the reaction mixture was poured into a large volume of an ice cooled aqueous NaHCO$_3$ solution (pH= 8.5). The upper layer (dichloromethane layer) was also poured into a large volume of an ice cooled aqueous NaHCO$_3$ solution. The aqueous layer was combined together and was purified by column chromatography on ODS to afford Object Compound (4).

NMR (DMSO-d$_6$, δ): 0.95 (3H, d, J=6.7 Hz), 1.04–1.12 (3H, m), 1.48–2.00 (3H, m), 2.07–2.50 (4H, m), 2.90–3.34 (2H, m), 3.60–4.48 (18H, m), 4.60–5.40 (9H, m), 6.72 (1H, d, J=8.2 Hz), 6.81 (1H, dd, J=8.2 and 1.6 Hz), 6.84 (1H, m), 6.98 (1H, m), 7.04 (1H, d, J=1.6 Hz), 7.28–7.50 (6H, m), 7.58 (2H, m), 7.73 (2H, d, J=7.4 Hz), 7.84 (1H, m), 7.88 (2H, d, J=7.6 Hz), 8.84 (1H, s)

MASS (m/z): 1141 (M$^+$)

EXAMPLE 5

To a solution of Starting Compound (5) (38.7 g) in dimethylformamide (250 ml) was added piperidine (17 ml) at room temperature. The solution was stirred for 2.5 hours at the same temperature. Ethyl acetate (25 L) was added to the reaction mixture and the mixture was stirred for 30 minutes. The powder was collected by filtration to give Object Compound (5) (34.6 g).

EXAMPLE 6

To a solution of Starting Compound (6) (0.3 g) and triethylsilane 0.44 ml) in methylene chloride (7 ml) at 10° C., was added dropwise trifloroacetic acid (2 ml). The mixture was stirred at room temperature for 4 hours. The reaction mixture was added in 1N-sodium hydroxide (31 ml) at 10° C. The aqueous layer was subjected to column chromatography on ODS (YMC-gel ODS-AM S-50 (Trademark: prepared by Yamamura Chemical Lab.)) eluting with water. The fractions containing the object compound were combined, and evaporated under reduced pressure. The residue was lyophilized to give Object Compound (6) (0.13 g).

IR (KBr): 3361.3, 1668.1, 1631.5, 1268.9 cm$^{-1}$

NMR (DMSO-d$_6$, δ): 0.96 (3H, d, J=6.7 Hz), 1.06 (3H, d, J=5.5 Hz), 1.60–2.50 (9H, m), 2.90–2.97 (1H, m), 3.16–3.50 (2H, m), 3.69–4.50 (13H, m), 4.74–5.31 (10H, m), 6.72–7.65 (14H, m), 7.93–7.97 (1H, m), 8.71 (1H, s)

EXAMPLE 7

To a solution of Starting Compound (7) (110 mg) in water (5 ml) was added 10% palladium on carbon (11 mg), and hydrogen gas at atmosphere pressure for 7 hours. The reaction mixture was filtered through celite and lyophilized to give Object Compound (7) (70 mg).

IR (KBr): 3394, 3327, 1676, 1633, 1439 cm$^{-1}$

NMR (DMSO-d$_6$, δ): 0.96 (3H, d, J=6.8 Hz), 1.08 (3H, d, J=6.0 Hz), 1.88–5.83 (35H, m), 6.68–8.71 (10H, m)

MASS (m/z): 903.17 (M−Na$^+$)

EXAMPLE 8

To a solution of Starting Compound (8) (350 mg) in N,N-dimethylformamide (6 ml) was added 4-[4-(4-cyclohexylphenyl)-piperazin-1-yl]benzoic acid benzotriazol-1-yl ester (230 mg), and the mixture was stirred for 2 hours at ambient temperature. The reaction mixture was pulverized with ethyl acetate. The precipitate was collected by filtration, and dried under reduced pressure. The powder was dissolved in water, and subjected to column chromatography on ion exchange resin (DOWEX-50WX4 (Trademark: prepared by Dow Chemical)) eluting with water. The fractions containing the object compound were combined, and subjected to column chromatography on ODS (YMC-gel.ODS-AM-S-50 (Trademark: prepared by Yamamura Chemical Lab.)) eluting with 30% acetonitrile in water. The fractions containing the object compound were combined, and evaporated under reduced pressure to remove acetonitrile. The residue was lyophilized to give Object Compound (8) (160 mg).

IR (KBr): 1666.2, 1633.4, 1608.3, 1511.9, 1230.4 cm$^{-1}$

NMR (DMSO-d$_6$, δ): 0.95 (3H, d, J=6.7 Hz), 1.09 (3H, d, J=5.4 Hz), 1.2–1.5 (6H, m), 1.6–2.1 (7H, m), 2.1–2.6 (5H, m), 3.02 (1H, m), 3.1–3.5 (10H, m), 3.6–4.5 (14H, m), 4.6–5.3 (9H, m), 6.73 (1H, d, J=8.2 Hz), 6.77 (1H, d, J=8.2 H), 6.80 (1H, s), 6.91 (2H, d, J=8.7 Hz), 6.9–7.1 (5H, m), 7.26 (1H, s), 7.3–7.5 (2H, m), 7.66 (1H, br s), 7.78 (2H, d, J=8.6 Hz), 8.04 (1H, d, J=7.3 Hz), 8.31 (1H, d, J=7.3 Hz), 8.84 (1H, s)

MASS (m/z): 1311 (M+Na$^+$)

Elemental Analysis Calcd. for $C_{58}H_{77}N_{10}O_{20}S.6H_2O$: C, 49.85; H, 6.42; N, 10.02; Found: C, 50.06; H, 6.36; N, 10.07.

The following compound (Examples 9 to 11) were obtained in a manner similar to that of Example 8.

EXAMPLE 9

IR (KBr): 3350, 1648.8, 1276.6 cm$^{-1}$

NMR (DMSO-d$_6$, δ): 0.95 (3H, d, J=6.8 Hz), 1.11 (3H, d, J=5.2 Hz), 1.5–1.7 (6H, m), 1.7–2.6 (7H, m), 2.94 (1H, m), 3.1–3.5 (6H, m), 3.6–4.6 (14H, m), 4.7–5.3 (9H, m), 6.73 (1H, d, J=8.2 Hz), 6.82 (1H, d, J=8.2 Hz), 6.84 (1H, s), 7.04 (1H, s), 7.06 (2H, d, J=8.7 Hz), 7.18 (1H, s), 7.3–7.5 (2H, m), 7.66 (1H, br s), 7.83 (2H, d, J=8.7 Hz), 8.0–8.2 (5H, m), 8.75 (1H, d, J=7.1 Hz), 8.84 (1H, s)

MASS (m/z): 1266 (M−Na$^+$)

EXAMPLE 10

IR (KBr): 3361.3, 1646.9, 1517.7, 1257.4 cm$^{-1}$

NMR (DMSO-d$_6$, δ): 0.91 (3H, t, J=7.3 Hz), 0.96 (3H, d, J≦6.5 Hz), 1.11 (3H, d, J=5.7 Hz), 1.3–1.6 (4H, m), 1.6–2.6 (9H, m), 2.95 (1H, m), 3.1–3.5 (2H, m), 3.6–4.6 (16H, m), 4.7–5.4 (9H, m), 6.73 (1H, d, J=8.2 Hz), 6.82 (1H, d, J≦8.2 Hz), 6.90 (1H, s), 7.06 (1H, s), 7.14 (2H, d, J=8.9 Hz), 7.23 (1H, s), 7.3–7.5 (2H, m), 7.68 (1H, br s), 7.90 (2H, d, J=8.9 Hz), 7.8–8.2 (5H, m), 8.60 (1H, d, J=6.7 Hz), 8.85 (2H, s)

MASS (m/z): 1308 (M−Na$^+$)

Elemental Analysis Calcd. for $C_{57}H_{70}N_{11}O_{21}S_2Na.10H_2O$: C, 45.26; H, 6.00; N, 10.19; Found: 45.05; H, 5.83; N, 10.19.

EXAMPLE 11

NMR (DMSO-d$_6$, δ): 0.95 (3H, d, J=6.7 Hz), 1.12 (3H, d, J=6.0 Hz), 1.2–1.6 (8H, m), 1.6–2.6 (9H, m), 2.9–3.1 (1H, m), 3.1–3.5 (7H, m), 3.6–4.6 (16H, m), 4.6–5.4 (9H, m) 6.74 (1H, d, J=8.2 Hz), 6.83 (1H, d, J=8.2 Hz), 6.89 (1H, s), 7.05 (1H, s), 7.13 (2H, d, J=8.8 Hz), 7.16 (1H, m), 7.3–7.6 (2H, m), 7.67 (1H, br), 7.97 (2H, d, J=8.8 Hz), 7.9–8.2 (5H, m), 8.7–9.0 (2H, m)

MASS (m/z): 1327.07 (M−Na$^+$)

Elemental Analysis Calcd. for $C_{58}H_{75}N_{10}NaO_{22}S_2.5H_2O$: C, 48.33; H, 5.94; N, 9.72; Found: C, 48.27; H, 6.05; N, 9.69.

EXAMPLE 12

To a solution of Starting Compound (12) (60.0 g) and diethylisopropylamine (16.6 ml) in diethylformamide (340 ml) was added 4-[5-[4-(6-methoxy-n-hexyloxy)phenyl]-1,3,4-thiadiazol-2-yl]benzoic acid benzotriazol-1-yl ester (37.4 g) at room temperature. The solution was stirred for 17 hours at the same temperature. Ethyl acetate (3.4 L) was added to the reaction mixture and the mixture was stirred for 30 minutes. The powder was collected by filtration and washed with ethyl acetate (3.5 L) to give crude N-acylated Starting Compound (12) (93.0 g). This material was used without further purification. To a suspension of crude N-acylated Starting Compound (12) (93.0 g) and NaBH$_3$CN (9.0 g) in dichloromethane (900 ml), was added trifluoroacetic acid (450 ml) at 0° C. over 30 minutes. The solution was stirred for 2 hours at the same temperature. The reaction mixture was slowly poured into an ice cooled aqueous NaOH solution (8<pH<11, Temperature<7° C.) The separated organic layer was extracted with water twice. The combined aqueous solution was subjected to column chromatography on SP20 (7 L), washing with water, and eluting with 60% aqueous CH$_3$CN. The eluent was concentrated to remove CH$_3$CN and chromatographed by reverse-phase (ODS) flash chromatography eluting with 17% CH$_3$CN/water, followed by lyophilization of the appropriate fractions to provide 28.3 g of Object Compound (12).

NMR (DMSO-d$_6$, δ): 0.96 (3H, d, J=6.7 Hz), 1.12 (3H, d, J=5.9 Hz), 1.30–1.60 (6H, m), 1.65–2.60 (9H, m), 2.80–3.50 (5H, m), 3.22 (3H, s), 3.60–4.60 (14H, m), 4.07 (2H, t, J=6.7

Hz), 4.60–5.30 (9H, m), 6.73 (1H, d, J=8.2 Hz), 6.83 (1H, d, J=8.2 Hz), 6.89 (1H, s), 7.05 (1H, s), 7.13 (2H, d, J=8.9 Hz), 7.16 (1H, s), 7.42–7.46 (2H, m), 7.66 (1H, br), 7.97 (2H, d, J=8.8 Hz), 8.07–8.13 (5H, m), 8.77 (1H, d, J=6.8 Hz), 8.84 (1H, s)

MASS (m/z): 1313.25 (M−Na$^+$)

Elemental Analysis Calcd. for $C_{57}H_{73}N_{10}O_{22}S_2Na.7H_2O$: C, 46.78; H, 5.99; N, 9.57; Found: C, 46.56; H, 5.94; N, 9.45.

EXAMPLE 13

A solution of Starting Compound (13) (400 mg) in N,N-dimethylformamide (4 ml) was treated with 4-[5-[4-(6-methoxy-n-hexyloxy)phenyl]-1,3,4-thiadiazol-2-yl] benzoic acid benzotriazol-1-yl ester (343 mg) then stirred 15 hours at room temperature. Ethyl acetate was added to the reaction mixture and the resulting precipitate were collected by filtration, washed thoroughly with ethyl acetate and dried. The powder was dissolved in saturated sodium hydrogen carbonate solution, filtered then purified by ODS column chromatography (YMC-gel ODS-AM S-50) eluting with 19–21% aqueous acetonitrile. Product-containing fractions were pooled, evaporated to remove acetonitrile, and lyophilized to give Object Compound (13) (306.4 mg) as an amorphous white powder.

IR (KBr): 1675.8, 1650.8, 1631.5, 1540.8, 1513.8, 1452.1, 1257.4 cm$^{-1}$

NMR (DMSO-d$_6$, δ): 0.97 (3H, d, J=6.6 Hz), 1.09 (3H, d, J=5.4 Hz), 1.30–1.60 (6H, m), 1.65–2.60 (10H, m), 2.80–4.60 (17H, m), 3.22 (3H, s), 3.32 (2H, t, J=6.3 Hz), 4.07 (2H, t, J=6.5 Hz), 4.68–5.80 (8H, m), 6.68 (1H, d, J=8 Hz), 6.76 (1H, d, J=8 Hz), 6.86 (1H, s), 6.98 (1H, s), 7.13 (2H, d, J=8.8 Hz), 7.16 (1H, s), 7.30–7.50 (3H, m), 7.97 (2H, d, J=8.8 Hz), 8.03–8.13 (4H, m), 8.76–8.79 (2H, m)

MASS (m/z): 1343.13 (M+Na$^+$)

Elemental Analysis Calcd. for $C_{57}H_{73}N_{10}O_{21}S_2Na.8H_2O$: C, 46.72; H, 6.12; N, 9.56; Found: C, 46.66; H, 5.97; N, 9.53.

The following compound was obtained in a manner similar to that of Example 13.

EXAMPLE 14

IR (KBr): 1675.8, 1650.8, 1631.5, 1540.8, 1513.8, 1450.2 cm$^{-1}$

NMR (DMSO-d$_6$, δ): 0.97 (3H, d, J=6.7 Hz), 1.10 (3H, d, J=5.9 Hz), 1.12–1.80 (8H, m), 1.80–2.60 (10H, m), 2.90–3.05 (1H, m), 3.21 (3H, s), 3.27 (2H, t, J=6.3 Hz), 3.30–3.50 (2H, m), 3.68–4.60 (14H, m), 4.07 (2H, t, J=6 Hz), 4.70–5.45 (8H, m), 6.71 (1H, d, J=8.2 Hz), 6.79 (1H, d, J=8.2 Hz), 6.87 (1H, s), 6.97 (1H, s), 7.13 (2H, d, J=8.9 Hz), 7.15 (1H, s), 7.42–7.71 (3H, m), 7.97 (2H, d, J=8.7 Hz), 8.03–8.12 (4H, m), 8.73–8.81 (3H, m)

MASS (m/z): 1311.32 (M−Na$^+$)

Elemental Analysis Calcd. for $C_{58}H_{75}N_{10}O_{21}S_2Na.7H_2O$: C, 47.67; H, 6.14; N, 9.58; Found: C, 47.69; H, 6.09; N, 9.47.

EXAMPLE 15

A solution of Starting Compound (15) (508 mg) in N,N-dimethylformamide (10 ml) was treated with 4-[5-[4-(6-methoxy-n-hexyloxy)phenyl]-1,3,4-thiadiazol-2-yl] benzoic acid benzotriazol-1-yl ester (428 mg) and the mixture was stirred 18 hours at room temperature. Ethyl acetate was added to the reaction mixture and the resulting precipitate was collected by filtration, washed thoroughly with ethyl acetate and dried. The powder was dissolved in saturated sodium hydrogen carbonate solution (100 ml), treated with water (100 ml), then purified by ODS column chromatography (YMC-gel ODS-AM S-50) eluting with 16–17% aqueous acetonitrile. Fractions containing the object compound were combined, evaporated to remove acetonitrile, and lyophilized to give Object Compound (15) (400 mg) as an amorphous white powder.

IR (KBr): 1668.1, 1650.8, 1631.5, 1538.9, 1513.8, 1450.2, 1259.3 cm$^{-1}$

NMR (DMSO-d$_6$, δ): 0.96 (3H, d, J=6.7 Hz), 1.12 (3H, d, J=5.9 Hz), 1.30–1.60 (6H, m), 1.65–2.60 (9H, m), 2.80–3.50 (5H, m), 3.22 (3H, s), 3.60–4.60 (14H, m), 4.07 (2H, t, J=6.7 Hz), 4.60–5.30 (9H, m), 6.73 (1H, d, J=8.2 Hz), 6.83 (1H, d, J=8.2 Hz), 6.89 (1H, s), 7.05 (1H, s), 7.13 (2H, d, J=8.9 Hz), 7.16 (1H, s), 7.42–7.46 (2H, m), 7.66 (1H, br), 7.97 (2H, d, J=8.8 Hz), 8.07–8.13 (5H, m), 8.77 (1H, d, J=6.8 Hz), 8.84 (1H, s)

MASS (m/z): 1313.25 (M−Na$^+$)

Elemental Analysis Calcd. for $C_{57}H_{73}N_{10}O_{22}S_2Na.7H_2O$: C, 46.78; H, 5.99; N, 9.57; Found: C, 46.56; H, 5.94; N, 9.45;

EXAMPLE 16

To a solution of Starting Compound (16) (200 mg) and 4-[5-(4-piperidin-1-yl-phenyl)-1,3,4-thiadiazol-2-yl] benzoic acid benzotriazol-1-yl ester in N,N-dimethylformamide (3 ml) was added dimethylaminopyridine (0.034 g), and the mixture was stirred for 6.5 hours at ambient temperature. The reaction mixture was pulverized with ethyl acetate. The precipitate was collected by filtration, and dried under reduced pressure. The solid was dissolved in water, and subjected to column chromatography on ion exchange resin (DOWEX-50WX4 (Trademark: prepared by Dow Chemical) eluting with water. The fractions containing the object compound were combined, and subjected to column chromatography on ODS (YMC-gel ODS-AM S-50 (Trademark: prepared by Yamamura Chemical Lab.)) eluting with 50% methyl alcohol aqueous solution. The fractions containing the object compound were combined, and evaporated under reduced pressure to remove methanol. The residue was lyophilized to give Object Compound (16) (190 mg).

IR (KBr): 3367, 1651, 1539, 1443 cm$^{-1}$

NMR (DMSO-d$_6$, δ): 0.95–5.30 (49H, m), 6.63–8.72 (19H, m)

MASS (m/z): 1250.22 (M−Na$^+$)

Elemental Analysis Calcd. for $C_{55}H_{68}N_{11}NaO_{19}S_2.12H_2O$: C, 44.05; H, 6.25; N, 10.27; Found: C, 43.94; H, 5.76; N, 10.14;

EXAMPLE 17

To a solution of 1-hydroxybenzotriazole (64 mg) and 4-[2-(4-butyloxyphenyl)imidazo[2,1-b][1,3,4]thiadiazol-6-yl]benzoic acid (125 mg) in N,N-dimethylformamide (4 ml) was added 1-ethyl-3-(3'-dimethylaminopropyl)carbodiimide hydrochloride (73 mg) and the mixture was stirred for 4 hours at ambient temperature. Then to the reaction mixture was added Starting Compound (17) (200 mg) and the mixture was stirred for 4 hours at ambient temperature. The reaction mixture was pulverized with ethyl acetate. The precipitate was collected by filtration and dried over reduced pressure. The powder was added to saturated sodium bicarbonate aqueous solution and subjected to column chromatography on ODS (YMC-gel ODS-AM S-50) and eluted with 30% acetonitrile in water. The fractions containing the object compound were combined and evaporated under reduced pressure to remove acetonitrile. The residue was lyophilized to give Object Compound (17) (123 mg).

NMR (DMSO-d$_6$, δ): 0.91 (3H, t, J=7.3 Hz), 0.96 (3H, d, J=7.2 Hz), 1.11 (3H, d, J=5.5 Hz), 1.3–1.6 (2H, m), 1.6–2.6

(9H, m), 2.95 (1H, m), 3.1–3.5 (2H, m), 3.6–4.6 (16H, m), 4.7–5.5 (9H, m), 6.73 (1H, d, J=8.2 Hz), 6.82 (1H, d, J=8.2 Hz), 6.89 (1H, s), 7.05 (1H, s), 7.14 (2H, d, J=8.9 Hz), 7.24 (1H, s), 7.3–7.5 (2H, m), 7.68 (1H, br s), 7.90 (2H, d, J=8.9 Hz), 7.8–8.1 (5H, m), 8.56 (1H, d, J=6.7 Hz), 8.85 (2H, s)

MASS (m/z): 1341 (M+Na$^+$)

EXAMPLE 18

To a suspension of Starting Compound (18) (1.70 g) and triethylsilane (1.58 g) in dichloromethane (15 ml) was added trifluoroacetic acid (15 ml) dropwise, and the mixture was stirred for 30 minutes under nitrogen atmosphere. The reaction mixture was evaporated under reduced pressure. The residue was dissolved in pH 6.86 phosphate-buffer, and adjusted to pH 9.5 with 1N sodium hydroxide aqueous solution. The solution was subjected to column-chromatography on ODS (YMC-gel ODS-AM S-50) and eluted with 30% acetonitrile aqueous solution (v/v). The fractions containing the object compound were combined and evaporated under reduced pressure to remove acetonitrile. The residue was lyophilized to give Object Compound (18) (136 mg).

IR (KBr): 3350, 2933, 1668, 1635, 1540, 1471, 1249, 1045 cm$^{-1}$

NMR (DMSO-d$_6$, δ): 0.88 (3H, t, J=6.7 Hz), 0.96 (3H, d, J=6.7 Hz), 1.08 (3H, d, J=5.8 Hz), 1.2–1.6 (8H, m), 1.6–2.4 (10H, m), 2.8–4.1 (16H, m), 4.1–5.3 (11H, m), 6.6–7.2 (9H, m), 7.3–7.7 (3H, m), 7.9–8.3 (4H, m), 8.7–8.9 (1H, d, J=6.0 Hz), 9.04 (1H, s)

MASS (m/z): 1244.5 (M+Na$^+$)

Elemental Analysis Calcd. for C$_{54}$H$_{72}$N$_9$O$_{20}$NaS.6H$_2$O: C, 48.75; H, 6.36; N, 9.48; Found: C, 48.53; H, 6.24; N, 9.40;

The following compounds [Examples 19 and 20] were obtained in a manner similar to that of Example 18.

EXAMPLE 19

NMR (DMSO-d$_6$, δ): 0.95 (3H, t, J=7.3 Hz), 0.96 (3H, d, J=7.1 Hz), 1.10 (3H, d, J=5.8 Hz), 1.3–1.6 (2H, m), 1.6–2.6 (10H, m), 2.95 (1H, m), 3.1–3.5 (2H, m), 3.6–4.6 (16H, m), 4.7–5.4 (8H, m), 6.71 (1H, d, J=8.1 Hz), 6.78 (1H, d, J=8.1 Hz), 6.87 (1H, s), 6.97 (1H, s), 7.14 (2H, d, J=8.9 Hz), 7.24 (1H, s), 7.44 (1H, d, J=7.9 Hz), 7.5–7.8 (2H, m), 7.89 (2H, d, J=8.9 Hz), 7.9–8.0 (6H, m), 8.12 (1H, d, J=7.7 Hz), 8.60 (1H, d, J=7.2 Hz), 8.72 (1H, s), 8.85 (1H, s)

MASS (m/z): 1278 (M−Na$^+$)

EXAMPLE 20

NMR (DMSO-d$_6$, δ): 0.91 (3H, t, J=7.3 Hz), 0.96 (3H, d, J=7.1 Hz), 1.09 (3H, d, J=5.8 Hz), 1.3–1.6 (4H, m), 1.6–2.6 (10H, m), 2.95 (1H, m), 3.1–3.5 (2H, m), 3.6–4.6 (16H, m), 4.7–5.4 (8H, m), 6.71 (1H, d, J=8.1 Hz), 6.78 (1H, d, J=8.1 Hz), 6.87 (1H, s), 6.97 (1H, s), 7.14 (2H, d, J=8.9 Hz), 7.24 (1H, s), 7.44 (1H, d, J=7.9 Hz), 7.5–7.8 (2H, m), 7.89 (2H, d, J=8.9 Hz), 7.9–8.0 (6H, m), 8.12 (1H, d, J=7.7 Hz), 8.60 (1H, d, J=7.2 Hz), 8.72 (1H, s), 8.85 (1H, s)

MASS (m/z): 1338 (M+Na$^+$)

The following compounds [Examples 21 to 29] were obtained according to similar manner to that of Example 1.

EXAMPLE 21

IR (KBr): 3353, 1666.2, 1631.5, 1510, 1236 cm$^{-1}$

NMR (DMSO-d$_6$, δ): 0.86 (3H, t, J=6.8 Hz), 0.95 (3H, d, J=6.7 Hz), 1.09 (3H, d, J=5.8 Hz), 1.2–1.5 (10H, m), 1.55–2.6 (9H, m), 2.95 (1H, m), 3.0–3.5 (10H, m), 3.6–4.5 (15H, m), 4.6–5.4 (10H, m), 6.6–7.1 (10H, m), 7.27 (1H, s), 7.35–7.5 (2H, m), 7.65 (1H, br s), 7.78 (2H, d, J=8.8 Hz), 8.03 (1H, d, J=8.7 Hz), 8.30 (1H, d, J=8.7 Hz), 8.83 (1H, s)

MASS (m/z): 1357 (M+Na$^+$)

Elemental Analysis Calcd. for C$_{60}$H$_{83}$N$_{10}$O$_{21}$SNa.5H$_2$O: C, 50.55; H, 6.58; N, 9.83; Found: C, 50.56; H, 6.59; N, 9.76;

EXAMPLE 22

IR (KBr): 3350, 1658.5, 1633, 1278 cm$^{-1}$

NMR (DMSO-d$_6$, δ): 0.86 (3H, t, J=6.7 Hz), 0.96 (3H, d, J=6.7 Hz), 1.11 (3H, d, J=5.7 Hz), 1.2–1.4 (8H, m), 1.45–2.45 (9H, m), 2.62 (2H, t, J=7.4 Hz), 2.98 (1H, m), 3.2 (1H, m), 3.25–3.5 (1H, m), 3.6–5.4 (23H, m), 6.73 (1H, d, J=8.2 Hz), 6.83 (1H, dd, J=1.5 and 8.2 Hz), 6.88 (1H, s), 7.05 (1H, d, J=1.5 Hz), 7.31 (2H, d, J=8.2 Hz), 7.1–7.5 (4H, m), 7.64 (2H, d, J=8.2 Hz), 7.74 (2H, d, J=8.4 Hz), 7.6–7.8 (1H, m), 7.95 (2H, d, J=8.4 Hz), 8.0–8.2 (1H, m), 8.61 (1H, d, J=6.7 Hz), 8.84 (1H, s)

MASS (m/z): 1243 (M+Na$^+$)

Elemental Analysis Calcd. for C$_{55}$H$_{73}$N$_8$NaO$_{20}$S.6H$_2$O: C, 49.69; H, 6.44; N, 8.43; Found: C, 49.99; H, 6.53; N, 8.40;

EXAMPLE 23

IR (Nujol): 1668.1, 1629.6, 1540.8, 1515.8 cm$^{-1}$

NMR (DMSO-d$_6$, δ): 0.87 (3H, t, J=6.7 Hz), 0.95 (3H, d, J=6.7 Hz), 1.07 (3H, d, J=5.9 Hz), 1.25–1.48 (4H, m), 1.49–2.05 (5H, m), 2.05–2.70 (8H, m), 2.70–3.05 (3H, m), 3.08–3.45 (2H, m), 3.55–3.86 (2H, m), 3.88–4.50 (11H, m), 4.65–5.36 (10H, m), 6.67–6.90 (3H, m), 7.04 (1H, d, J=1.0 Hz), 7.10–7.80 (12H, m), 8.00 (1H, d, J=8.4 Hz), 8.13 (1H, d, J=7.7 Hz), 8.84 (1H, s)

MASS (m/z): 1227.5 (M+Na$^+$)

Elemental Analysis Calcd. for C$_{55}$H$_{73}$N$_8$NaO$_{20}$S.5H$_2$O: C, 50.38; H, 6.38; N, 8.54; Found: C, 50.07; H, 6.60; N, 8.58;

EXAMPLE 24

IR (KBr): 3359, 2929, 1664, 1635, 1515, 1440, 1278, 1245, 1085, 1047 cm$^{-1}$

NMR (DMSO-d$_6$, δ): 0.86 (3H, m), 0.96 (3H, d, J=7.7 Hz), 1.11 (3H, d, J=5.7 Hz), 1.30 (6H, m), 1.5–2.4 (9H, m), 2.6–2.8 (2H, t, J=7.2 Hz), 2.9–3.1 (1H, m), 3.1–3.3 (1H, m), 3.4–3.6 (1H, m), 3.7–4.6 (14H, m), 4.6–5.3 (9H, m), 6.7–7.0 (3H, m), 7.04 (1H, s), 7.21 (1H, s), 7.30 (2H, d, J=8.2 Hz), 7.4–7.5 (1H, m), 7.6–7.8 (5H, m), 7.95 (2H, d, J=8.4 Hz), 8.10 (1H, d, J=8.4 Hz), 8.60 (1H, d, J=8.4 Hz), 8.84 (1H, s)

MASS (m/z): 1230 (M+Na$^+$)

Elemental Analysis Calcd. for C$_{54}$H$_{71}$NaO$_{20}$S.4.5H$_2$O: C, 50.34; H, 6.26; N, 8.70; Found: C, 50.43; H, 6.19; N, 8.59;

EXAMPLE 25

IR (KBr): 3350, 1666.2, 1631.5, 1510.0, 1236.1 cm$^{-1}$

NMR (DMSO-d$_6$, δ): 0.88 (3H, t, J=6.6 Hz), 0.95 (3H, d J=6.7 Hz), 1.08 (3H, d, J=5.7 Hz), 1.2–1.5 (6H, m), 1.6–2.1 (5H, m), 2.1–2.5 (4H, m), 2.8–3.0 (1H, m), 3.1–3.3 (5H, m), 3.3–3.4 (4H, m), 3.6–5.4 (23H, m), 6.73 (1H, d, J=8.1 Hz), 6.8–6.9 (4H, m), 6.94 (2H, d, J=9.3 Hz), 7.01 (2H, d, J=8.7 Hz), 7.04 (1H, s), 7.2–7.5 (3H, m), 7.6–7.7 (1H, m), 7.78 (2H, d, J=8.7 Hz), 8.05 (1H, d, J=8 Hz), 8.30 (1H, d, J=6.7 Hz), 8.85 (1H, s)

MASS (m/z): 1329 (M+Na$^+$)

Elemental Analysis Calcd. for C$_{58}$H$_{79}$N$_{10}$O$_{21}$SNa.6H$_2$O: C, 49.22; H, 6.48; N, 9.90; Found: C, 49.46; H, 6.44; N, 9.96;

EXAMPLE 26

IR (KBr): 3347.8, 1670.1, 1652.7, 1635.3 cm$^{-1}$

NMR (DMSO-d$_6$, δ): 0.85 (3H, t, J=6.6 Hz), 0.96 (3H, d, J=6.7 Hz), 1.12 (3H, d, J=5.9 Hz), 1.18–1.40 (8H, m), 1.50–2.10 (5H, m), 2.10–2.60 (4H, m), 2.76 (2H, t, J=7.6 Hz), 2.85–3.50 (3H, m), 3.60–4.60 (14H, m), 4.60–5.33 (9H, m), 6.67–7.00 (3H, m), 7.05 (1H, d, J=0.4 Hz), 7.20–7.50 (4H, m), 7.60–7.80 (2H, m), 7.85–8.00 (3H, m), 8.10 (1H, d, J=8.5 Hz), 8.45 (1H, s), 8.68 (1H, d, J=8.4 Hz), 8.48 (1H, s)

MASS (m/z): 1217.4 (M+Na-1)

Elemental Analysis Calcd. for $C_{53}H_{71}N_8O_{21}SNa.4H_2O$: C, 49.61; H, 6.20; N, 8.73; Found: C, 49.62; H, 6.38; N, 8.68;

EXAMPLE 27

IR (KBr): 3361.3, 1668.1, 1635.3 cm$^{-1}$

NMR (DMSO-d$_6$, δ): 0.89 (3H, t, J=6.8 Hz), 0.95 (3H, d, J=6.7 Hz), 1.10 (3H, d, J=5.9 Hz), 1.20–1.48 (6H, m), 1.55–2.13 (5H, m), 2.13–2.60 (4H, m), 2.76 (2H, t, J=7.6 Hz), 2.89–3.08 (1H, m), 3.10–3.50 (3H, m), 3.60–3.85 (2H, m), 3.85–4.65 (12H, m), 4.65–5.50 (8H, m), 6.62–7.05 (3H, m), 7.06 (1H, d, J=0.4 Hz), 7.15–7.55 (4H, m), 7.55–7.80 (2H, m), 7.80–8.03 (3H, m), 8.03–8.20 (1H, m), 8.45 (1H, s), 8.60–9.05 (2H, m)

MASS (m/z): 1203.4 (M+Na-1)

Elemental Analysis Calcd. for $C_{52}H_{69}N_8NaO_{20}S.6H_2O$: C, 48.44; H, 6.33; N, 8.69; Found: C, 48.55; H, 6.39; N, 8.70;

EXAMPLE 28

IR (KBr): 3359.4, 1664.3, 1631.5, 1510.0, 1230.4, 1045.2 cm$^{-1}$

NMR (DMSO-d$_6$, δ): 0.95 (3H, d, J=6.5 Hz), 1.08 (3H, d, J=5.6 Hz), 1.2–1.6 (10H, m), 1.6–2.1 (5H, m), 2.1–2.5 (4H, m), 2.95 (1H, m), 3.0–3.2 (5H, m), 3.20 ()3H, s), 3.29 (3H, t, J=6.4 Hz), 3.2–3.5 (5H, m), 3.6–4.5 (16H, m), 4.6–5.4 (9H, m), 6.73 (1H, d, J=8.2 Hz), 6.8–7.1 (10H, m), 7.2–7.5 (2H, m), 7.70 (1H, br s), 7.78 (2H, d, J=8.6 Hz), 8.10 (1H, br s), 8.32 (1H, d, J=7.2 Hz), 8.90 (1H, br s)

MASS (m/z): 1387 (M+Na)$^+$

Elemental Analysis Calcd. for $C_{61}H_{84}N_{10}O_{22}SNa.8H_2O$: C, 48.53; H, 6.74; N, 9.28; Found: C, 48.38; H, 7.18; N, 9.18;

EXAMPLE 29

IR (KBr): 3355.5, 1666.2, 1631.5, 1608.3, 1236.1, 1045.2 cm$^{-1}$

NMR (DMSO-d$_6$, δ): 0.93 (3H, d, J=6.6 Hz), 1.07 (3H, d, J=5.7 Hz), 1.2–1.6 (8H, m), 1.6–2.1 (5H, m), 2.1–2.6 (4H, m), 2.96 (1H, m), 3.1–3.3 (5H, m), 3.19 (3H, s), 3.28 (3H, t, J=6.5 Hz), 3.3–3.5 (5H, m), 3.7–4.5 (16H, m), 4.65–5.3 (9H, m), 6.71 (1H, d, J=8.1 Hz), 6.8–7.1 (9H, m), 7.26 (1H, s), 7.3–7.5 (2H, m), 7.66 (1H, br s), 7.76 (2H, d, J=8.6 Hz), 8.07 (1H, d, J=7.7 Hz), 8.31 (1H, d, J=6.8 Hz), 8.83 (1H, s)

MASS (m/z): 1373 (M+Na)$^+$

The following compounds [Examples 30 to 54] were obtained in a manner similar to that of Example 8.

EXAMPLE 30

IR (KBr): 3369, 2935, 1664, 1631, 1444, 1257, 1047 cm$^{-1}$

NMR (DMSO-d$_6$, δ): 0.89 (3H, d, J=6.9 Hz), 0.95 (3H, d, J=6.8 Hz), 1.11 (3H, d, J=5.8 Hz), 1.2–1.5 (6H, m), 1.6–2.4 (9H, m), 2.9–3.4 (2H, m), 3.6–4.5 (16H, m), 4.7–5.4 (9H, m), 6.73 (1H, d, J=8.2 Hz), 6.8–7.0 (2H, m), 7.0–7.2 (4H, m), 7.3–7.7 (3H, m), 7.97 (2H, d, J=8.7 Hz), 8.1–8.3 (5H, m), 8.81 (1H, d, J=7.0 Hz), 8.85 (1H, s)

MASS (m/z): 1329.8 (M+Na)$^+$

Elemental Analysis Calcd. for $C_{56}H_{71}N_{10}O_{21}S_2Na$: C, 46.93; H, 5.98; N, 9.77; Found: C, 46.72; H, 6.11; N, 9.72;

EXAMPLE 31

IR (KBr): 3353, 2935, 2873, 1658, 1635, 1440, 1257, 1047 cm$^{-1}$

NMR (DMSO-d$_6$, δ): 0.89 (3H, t, J=6.9 Hz), 0.96 (3H, d, J=6.8 Hz), 1.12 (3H, d, J=5.8 Hz), 1.2–1.5 (6H, m), 1.6–2.4 (9H, m), 2.9–3.2 (2H, m), 3.3–3.4 (1H, m), 3.8–4.6 (16H, m), 4.6–5.4 (9H, m), 6.7–7.0 (3H, m), 7.0–7.2 (4H, m), 7.3–7.7 (3H, m), 7.9–8.3 (7H, m), 8.7–8.9 (2H, m)

MASS (m/z): 1313.0 (M+Na)$^+$

Elemental Analysis Calcd. for $C_{56}H_{71}N_{10}O_{22}S$: C, 48.07; H, 5.98; N, 10.01; Found: C, 48.23; H, 6.17; N, 10.00;

EXAMPLE 32

IR (KBr): 3350, 2927, 1668, 1627, 1288, 1047 cm$^{-1}$

NMR (DMSO-d$_6$, δ): 0.86 (3H, t, J=6.8 Hz), 0.95 (3H, d, J=6.8 Hz), 1.13 (3H, d, J=6.7 Hz), 1.2–1.5 (10H, m), 1.6–2.4 (8H, m), 2.9–3.2 (2H, m), 3.4–4.6 (16H, m), 4.6–5.3 (9H, m), 6.5–7.5 (8H, m), 7.6–8.2 (4H, m), 8.31 (1H, s), 8.43 (1H, dd, J=8.7 and 2.5 Hz), 8.6–8.8 (1H, d, J=6.3 Hz), 8.85 (1H, s), 8.99 (1H, d, J=2.5 Hz)

MASS (m/z): 1315.3 (M+Na)$^+$

Elemental Analysis Calcd. for $C_{56}H_{73}N_{10}O_{22}NaS.7H_2O$: C, 47.39; H, 6.18; N, 9.87; Found: C, 47.11; H, 6.29; N, 9.72;

EXAMPLE 33

IR (KBr): 3350, 2925, 1670, 1625, 1259, 1047 cm$^{-1}$

NMR (DMSO-d$_6$, δ): 0.7–1.0 (6H, m), 1.1–1.2 (3H, d, J=5.7 Hz), 1.2–2.5 (15H, m), 3.0–3.3 (2H, m), 3.4–3.6 (1H, m), 3.6–3.8 (2H, m), 3.9–4.6 (16H, m), 4.7–5.4 (9H, m), 6.6–7.3 (6H, m), 7.3–8.0 (5H, m), 8.0–8.3 (5H, m), 8.6–9.0 (2H, m)

MASS (m/z): 1286.8 (M+Na)$^+$

Elemental Analysis Calcd. for $C_{55}H_{70}N_9O_{22}NaS.5.5H_2O$: C, 48.46; H, 5.99; N, 9.25; Found: C, 48.47; H, 6.01; N, 9.26;

EXAMPLE 34

MASS (m/z): 1387 (M+Na)$^+$

EXAMPLE 35

IR (KBr): 3363, 1662.3, 1631.5, 1240 cm$^{-1}$

NMR (DMSO-d$_6$, δ): 0.95 (3H, d, J=6.8 Hz), 0.8–1.5 (15H, m), 1.5–2.6 (16H, m), 2.8–3.5 (11H, m), 3.6–4.6 (14H, m), 4.6–5.3 (9H, m), 6.73 (1H, d, J=8.2 Hz), 6.83 (1H, d, J=8.2 Hz), 6.84 (1H, s), 7.00 (2H, d, J=8.8 Hz), 7.04 (1H, s), 7.13 (1H, s), 7.3–7.5 (2H, m), 7.63 (1H, br s), 7.79 (2H, d, J=8.8 Hz), 8.05 (1H, d, J=7.7 Hz), 8.29 (1H, d, J=6.8 Hz), 8.83 (1H, s)

MASS (m/z): 1215 (M–SO$_3$+Na)

Elemental Analysis Calcd. for $C_{58}H_{84}N_{10}O_{20}S.7H_2O$: C 49.78, H 7.06, N 10.01 Found: C 49.93, H 6.92, N 9.98

EXAMPLE 36

IR (KBr): 1648, 1631 cm$^{-1}$

NMR (DMSO-d$_6$, δ): 0.95 (3H, d, J=6.8 Hz), 1.12 (3H, d, J=5.7 Hz), 1.65–2.50 (7H, m), 2.84–3.13 (3H, m), 3.74–5.41 (23H, m), 3.83 (3H, s), 6.74 (1H, d, J=8.2 Hz), 6.77 (1H, d,

J=10.6 Hz), 6.83 (1H, m), 7.08 (3H, m), 7.17 (1H, m), 7.43 (2H, m), 7.65 (1H, m), 7.77 (2H, d, J=8.7 Hz), 7.92 (2H, d, J=8.5 Hz), 8.08 (1H, m), 8.11 (2H, d, J=8.4 Hz), 8.22 (2H, d, J=7.6 Hz), 8.25 (2H, d, J=7.6 Hz), 8.85 (2H, m)

MASS (m/z): 1273

Elemental Analysis Calcd. for $C_{57}H_{65}N_{10}O_{22}SNa.11H_2O$: C 45.78, H 5.86, N 9.37 Found: C 45.75, H 5.95, N 9.27

EXAMPLE 37

IR (KBr): 2968, 2937, 2879, 1651, 1632 cm$^{-1}$

NMR (DMSO-d$_6$, δ): 0.95 (3H, d, J=5.5 Hz), 1.01 (3H, t, J=7.1 Hz), 1.12 (3H, t, J=5.8 Hz), 1.75 (2H, q, J=7.1 Hz), 1.60–2.48 (7H, m), 2.75–3.10 (3H, m), 3.60–5.35 (23H, m), 4.01 (2H, t, J=7.1 Hz), 6.73 (1H, d, J=8.2 Hz), 6.78 (1H, d, J=9.7 Hz), 6.87 (1H, m), 7.07 (3H, m), 7.16 (1H, m), 7.43 (2H, m), 7.64 (1H, m), 7.74 (2H, d, J=8.8 Hz), 7.91 (2H, d, J=8.5 Hz), 8.00 (1H, m), 8.10 (2H, d, J=8.5 Hz), 8.21 (2H, d, J=7.4 Hz) 8.25 (2H, d, J=8.3 Hz), 8.83 (2H, m)

MASS (m/z): 1301

Elemental Analysis Calcd. for $C_{59}H_{69}N_{10}O_{22}SNa.10H_2O$: C 47.07, H 5.96, N 9.30 Found: C 46.88, H 5.70, N 9.14

EXAMPLE 38

IR (KBr): 2395, 2873, 1668, 1651, 1632 cm$^{-1}$

NMR (DMSO-d$_6$, δ): 0.92–0.99 (6H, m), 1.12 (3H, d, J=6.1 Hz), 1.48 (2H, qt, J=5.5 and 5.5 Hz), 1.74 (2H, tt, J=5.5 and 5.5 Hz), 1.60–2.40 (7H, m), 2.80–3.20 (3H, m), 4.05 (2H, t, J=5.5 Hz), 3.74–5.25 (23H, m), 6.74 (1H, d, J=8.2 Hz), 6.78 (1H, d, J=9.5 Hz), 6.87 (1H, m), 7.07 (3H, m), 7.17 (1H, m), 7.43 (2H, m), 7.65 (1H, m), 7.70 (1H, m), 7.74 (2H, d, J=8.7 Hz), 7.91 (2H, d, J=8.5 Hz), 8.00 (1H, m), 8.10 (2H, d, J=8.6 Hz), 8.21 (2H, d, J=7.6 Hz), 8.25 (2H, d, J=8.1 Hz), 8.88 (2H, m)

MASS (m/z): 1315

Elemental Analysis Calcd. for $C_{60}H_{71}N_{10}O_{22}SNa.9H_2O$: C 48.00, H 5.97, N 9.33 Found: C 48.05, H 5.95, N 9.34

EXAMPLE 39

IR (KBr): 2943, 2870, 1668, 1651, 1632 cm$^{-1}$

NMR (DMSO-d$_6$, δ): 0.95 (6H, m), 1.13 (3H, d, J=5.7 Hz), 1.39 (4H, m), 1.60–2.50 (9H, m), 2.80–3.20 (3H, m), 3.74–5.25 (23H, m), 4.04 (2H, t, J=6.3 Hz), 6.74 (1H, d, J=8.2 Hz), 6.78 (1H, d, J=11.2 Hz), 6.88 (1H, m), 7.07 (3H, m), 7.17 (1H, m), 7.45 (2H, m), 7.67 (1H, m), 7.74 (2H, d, J=8.8 Hz), 7.91 (2H, d, J=8.3 Hz), 8.00 (1H, m), 8.10 (2H, d, J=8.4 Hz), 8.21 (2H, d, J=7.9 Hz), 8.25 (2H, d, J=7.9 Hz), 8.25 (2H, d, J=7.9 Hz), 8.80 (1H, m), 8.85 (1H, s)

MASS (m/z): 1330, 1329

Elemental Analysis Calcd. for $C_{61}H_{73}N_{10}O_{22}SNa.10H_2O$: C 47.78, H 6.11, N 9.18 Found: C 47.90, H 6.05, N 9.18

EXAMPLE 40

IR (KBr): 2933, 2871, 1666, 1650, 1632 cm$^{-1}$

NMR (DMSO-d$_6$, δ): 0.89 (3H, t, J=6.9 Hz), 0.96 (3H, d, J=6.8 Hz), 1.12 (3H, d, J=5.7 Hz), 1.32–1.43 (6H, m), 1.60–2.50 (9H, m), 3.02 (3H, m), 4.04 (2H, t, J=6.4 Hz), 3.74–5.25 (23H, m), 6.74 (1H, d, J=8.2 Hz), 6.78 (1H, d, J=11.1 Hz), 6.88 (1H, m), 7.07 (3H, m), 7.17 (1H, m), 7.43 (2H, m), 7.67 (1H, m), 7.75 (2H, d, J=8.8 Hz), 7.91 (2H, d, J=8.5 Hz), 8.00 (1H, m), 8.11 (2H, d, J=8.5 Hz), 8.20 (2H, d, J=7.9 Hz), 8.25 (2H, d, J=8.1 Hz), 8.84 (2H, m)

MASS (m/z): 1343, 1327

Elemental Analysis Calcd. for $C_{62}H_{75}N_{10}O_{22}SNa.7H_2O$: C49.86, H 6.01, N 9.38 Found: C 49.87, H 6.01, N 9.30

EXAMPLE 41

IR (KBr): 2931, 2858, 1651, 1632 cm$^{-1}$

NMR (DMSO-d$_6$, δ): 0.88 (3H, t, J=6.6 Hz), 0.96 (3H, d, J=6.7 Hz); 1.12 (3H, d, J=5.2 Hz), 1.30 (8H, m), 1.60–2.40 (9H, m), 2.80–3.20 (3H, m), 4.03 (2H, t, J=6.3 Hz), 3.74–5.25 (23H, m), 6.72 (1H, d, J=8.2 Hz), 6.78 (1H, d, J=9.7 Hz), 6.87 (1H, m), 7.06 (3H, m), 7.16 (1H, m), 7.44 (2H, m), 7.70 (1H, m), 7.74 (2H, d, J=8.8 Hz), 7.90 (2H, d, J=8.5 Hz), 8.00 (1H, m), 8.10 (2H, d, J=8.6 Hz), 8.20 (2H, d, J=7.8 Hz), 8.25 (2H, d, J=8.2 Hz), 8.84 (2H, m)

MASS (m/z): 1361, 1357, 1341

Elemental Analysis Calcd. for $C_{63}H_{77}N_{10}O_{22}SNa.6H_2O$: C 50.80, H 6.02, N 9.40 Found: C 50.79, H 6.28, N 9.48

EXAMPLE 42

IR (KBr): 2939, 1668, 1651, 1632 cm$^{-1}$

NMR (DMSO-d$_6$, δ): 0.96 (3H, d, J=5.3 Hz), 1.13 (3H, d, J=6.0 Hz), 1.35–2.50 (15H, m), 2.60–3.20 (9H, m), 3.65–5.40 (25H, m), 6.73 (1H, d, J=8.5 Hz), 6.78 (1H, d, J=11.2 Hz), 6.88 (1H, m), 7.09 (3H, m), 7.17 (1H, m), 7.44 (2H, m), 7.70 (1H, m), 7.76 (2H, d, J=7.1 Hz), 7.91 (2H, d, J=6.6 Hz), 8.08 (1H, m), 8.11 (2H, d, J=7.4 Hz), 8.22 (2H, d, J=6.1 Hz), 8.25 (2H, d, J=6.3 Hz), 8.84 (2H, m)

MASS (m/z): 1388, 1384, 1368

Elemental Analysis Calcd. for $C_{64}H_{78}N_{11}O_{22}SNa.7H_2O$: C 50.09, H 6.04, N 10.04 Found: C 50.18, H 6.03, N 9.65

EXAMPLE 43

IR (KBr): 1650.8, 1629.6 cm$^{-1}$

NMR (DMSO-d$_6$, δ): 0.80–0.86 (3H, m), 0.96 (3H, d, J=6.6 Hz), 1.12 (3H, d, J=5.6 Hz), 1.23 (14H, br s), 1.74–2.50 (9H, m), 2.98 (1H, d, J=13.4 Hz), 3.10–3.46 (2H, m), 3.70–4.60 (16H, m), 4.64–5.32 (9H, m), 6.73 (1H, d, J=8.2 Hz), 6.83 (1H, d, J=8.4 Hz), 6.89 (1H, br s), 7.05 (1H, d, J=1.7 Hz), 7.16 (1H, br s), 7.42–7.47 (2H, m), 7.66 (1H, br s), 8.06–8.17 (6H, m), 8.65 (1H, s), 8.80 (1H, d, J=7.5 Hz), 8.84 (1H, s)

MASS (m/z): 1297.03 (M–Na)$^+$

Elemental Analysis Calcd. for $C_{57}H_{77}N_{12}O_{21}SNa.7H_2O$: C 47.30, H 6.34, N 11.61 Found: C 47.33, H 6.16, N 11.54

EXAMPLE 44

IR (KBr): 3361.3, 1650.8, 1631.5 cm$^{-1}$

NMR (DMSO-d$_6$, δ): 0.80–0.90 (3H, m), 0.96 (3H, d, J=6.7 Hz), 1.15 (3H, d, J=6 Hz), 1.23 (14H, br s), 1.70–2.65 (9H, m), 2.90–3.10 (1H, m), 3.20–3.42 (2H, m), 3.65–4.60 (16H, m), 4.66–5.40 (9H, m), 6.73 (1H, d, J=8.3 Hz), 6.83 (1H, d, J=8.8 Hz), 6.89 (1H, s), 7.05 (1H, s), 7.18 (1H, s), 7.42–7.46 (2H, m), 7.66 (1H, br, s), 8.05 (4H, s), 8.08 (1H, s), 8.57 (1H, s), 8.57–8.84 (3H, m)

MASS (m/z): 1313.01 (M–Na)$^+$

Elemental Analysis Calcd. for $C_{57}H_{77}N_{12}O_{20}S_2Na.7H_2O$: C 46.78, H 6.27, N 11.48 Found: C 46.89, H 6.34, N 11.41

EXAMPLE 45

IR (KBr): 1650.8, 1631.5 cm$^{-1}$

NMR (DMSO-d$_6$, δ): 0.96 (3H, d, J=6.7 Hz), 1.10 (3H, d, J=6 Hz), 1.70–2.60 (9H, m), 2.80–3.60 (3H, m), 3.60–4.60 (19H, m), 4.65–5.40 (8H, m), 6.73 (1H, d, J=8.2 Hz), 6.81–6.99 (6H, m), 7.05 (1H, s), 7.11 (2H, d, J=8.8 Hz), 7.34–7.26 (2H, m), 7.34–7.73 (3H, m), 7.76 (2H, d, J=8.8 Hz), 7.91 (2H, d, J=8.4 Hz), 8.11 (2H, d, J=8.4 Hz), 8.19–8.30 (4H, m), 8.70–9.00 (3H, m)

MASS (m/z): 1393.13 (M–Na)$^+$

Elemental Analysis Calcd. for $C_{65}H_{73}N_{10}O_{23}SNa.9H_2O$: C 49.43, H 5.81, N 8.87 Found: C 49.24, H 5.61, N 8.77

EXAMPLE 46

IR (KBr): 3361.3, 1668.1, 1650.8, 1631.5 cm$^{-1}$

NMR (DMSO-d$_6$, δ): 0.96 (3H, d, J=6.6 Hz), 1.12 (3H, d, J=5.6 Hz), 1.70–2.60 (7H, m), 2.80–5.27 (26H, m), 4.65 (2H, d, J=5.2 Hz), 5.27–5.48 (2H, m), 5.99–6.18 (1H, m), 6.72 (1H, d, J=8.1 Hz), 6.82 (1H, d, J=8.1 Hz), 6.89 (1H, s), 7.07 (1H, s), 7.10 (2H, d, J=8.8 Hz), 7.12 (1H, s), 7.46 (2H, br s), 7.68 (1H, br s), 7.75 (2H, d, J=8.7 Hz), 7.91 (2H, d, J=8.4 Hz), 8.11 (2H, d, J=8.5 Hz), 8.19–8.31 (4H, m), 8.80–8.83 (2H, m)

MASS (m/z): 1298.97 (M−Na)$^+$

Elemental Analysis Calcd. for $C_{59}H_{67}N_{10}O_2SNa.9H_2O$: C 47.71, H 5.77, N 9.43 Found: C 47.90, H 5.61, N 9.41

EXAMPLE 47

IR (KBr): 1650.8, 1631.5, 1540.8, 1513.8 cm$^{-1}$

NMR (DMSO-d$_6$, δ) : 0.96 (3H, d, J=6.7 Hz), 1.12 (3H, d, J=5.7 Hz), 1.70–2.60 (11H, m), 2.80–3.60 (3H, m), 3.60–3.60 (18H, m), 4.65–5.40 (9H, m) 6.73 (1H, d, J=8.1 Hz), 6.82 (1H, d, J=9.5 Hz), 6.87–6.97 (5H, m), 7.06 (1H, s), 7.09 (2H, d, J=8.8 Hz), 7.25–7.33 (2H, m), 7.33–7.73 (3H, m), 7.75 (2H, d, J=8.6 Hz), 7.91 (2H, d, J=8.5 Hz), 8.11 (2H, d, J=8.5 Hz), 8.19–8.27 (4H, m), 8.70–8.90 (3H, m)

MASS (m/z): 1407.15 (M−Na)$^+$

Elemental Analysis Calcd. for $C_{66}H_{75}N_{10}O_{23}SNa.7H_2O$: C 50.90, H 5.76, N 8.99 Found: C 50.80, H 5.90, N 8.90

EXAMPLE 48

IR (KBr): 1675.8, 1650.8, 1540.8, 1513.8 cm$^{-1}$

NMR (DMSO-d$_6$, δ): 0.96 (3H, d, J=6.9 Hz), 1.13 (3H, d, J=5.9 Hz), 1.20–1.60 (12H, m), 1.64–2.68 (7H, m), 2.80–3.60 (3H, m), 3.21 (3H, s), 3.60–5.40 (27H, m), 6.73 (1H, d, J=8.4 Hz), 6.83 (1H, d, J=9.3 Hz), 6.89 (1H, s), 7.05 (1H, s), 7.07 (2H, d, J=8.7 Hz), 7.17 (1H, s), 7.30–7.70 (3H, m), 7.74 (2H, d, J=8.7 Hz), 7.91 (2H, d, J=8.4 Hz), 8.11 (2H, d, J=8.5 Hz), 8.19–9.27 (4H, m), 8.74–8.90 (3H, m)

MASS (m/z): 1401.12 (M−Na)$^+$

EXAMPLE 49

IR (KBr): 1675.8, 1650.8, 1540.8 cm$^{-1}$

NMR (DMSO-d$_6$, δ): 0.96 (3H, d, J=6.4 Hz), 1.03–1.10 (9H, m), 1.50–2.50 (11H, m), 2.70–5.50 (34H, m), 6.71 (1H, d, J=7.3 Hz), 6.79–6.90 (2H, m), 7.00–7.10 (4H, m), 7.30–7.80 (3H, m), 7.75 (2H, d, J=8.6 Hz), 7.91 (2H, d, J=8.4 Hz), 8.11 (2H, d, J=7.4 Hz), 8.19–8.27 (4H, m), 8.60–8.90 (3H, m)

MASS (m/z): 1414.08 (M−Na)$^+$

Elemental Analysis Calcd. for $C_{65}H_{80}N_{11}O_{23}SNa.11.6H_2O$: C 47.39, H 6.31, N 9.35 Found: C 47.40, H 6.07, N 9.22

EXAMPLE 50

IR (KBr): 3353.6, 1650.8, 1631.5, 1538.9, 1515.8, 1442.5, 1114.7 cm$^{-1}$

NMR (DMSO-d$_6$, δ): 0.96 (3H, d, J=6.7 Hz), 1.12 (3H, d, J=5.7 Hz), 1.7–2.6 (11H, m), 2.9–3.1 (1H, m), 3.1–3.5 (2H, m), 3.7–4.6 (18H, m), 4.7–5.3 (9H, m), 6.74 (1H, d, J=8.0 Hz), 6.83 (1H, d, J=8.0 Hz), 6.87–7.02 (4H, m), 7.05 (1H, s), 7.15 (2H, d, J=8.7 Hz), 7.17 (1H, m), 7.2–7.4 (2H, m), 7.4–7.6 (2H, m), 7.67 (1H, br), 7.98 (2H, d, J=8.7 Hz), 7.9–8.2 (5H, m), 8.77 (1H, d, J=8.5 Hz), 8.84 (1H, s)

MASS (m/z): 1346.72 (M−Na)$^+$

Elemental Analysis Calcd. for $C_{60}H_{71}N_{10}NaO_{22}S.11H_2O$: C 45.92, H 5.97, N 8.92 Found: C 46.13, H 5.75, N 8.92

EXAMPLE 51

IR (KBr): 3363.2, 1650.8, 1538.9, 1515.8, 1442.5, 1247.7 cm$^{-1}$

NMR (DMSO-d$_6$, δ): 0.96 (3H, d, J=6.7 Hz), 1.12 (3H, d, J=5.9 Hz), 1.5–2.5 (13H, m), 2.9–3.1 (1H, m), 3.1–3.5 (2H, m), 3.6–5.4 (27H, m), 6.73 (1H, d, J=8.2 Hz), 6.82 (1H, d, J=8.2 Hz), 6.87–7.00 (4H, m), 7.05 (1H, s), 7.14 (2H, d, J=8.7 Hz), 7.16 (1H, s), 7.27 (2H, m), 7.42 (2H, m), 7.66 (1H, br), 7.97 (2H, d, J=8.7 Hz), 7.9–8.2 (5H, m), 8.7–8.9 (2H, m)

MASS (m/z): 1360.75 (M−Na)$^+$

Elemental Analysis Calcd. for $C_{61}H_{73}N_{10}NaO_{22}S_2.9H_2O$: C 47.34, H 5.93, N 9.05 Found: C 47.27, H 5.76, N 8.94

EXAMPLE 52

IR (KBr): 3365.2, 1650.8, 1631.5, 1538.9, 1515.8, 1442.5, 1245.8 cm$^{-1}$

NMR (DMSO-d$_6$, δ): 0.96 (3H, d, J=6.7 Hz), 1.12 (3H, d, J=5.6 Hz), 1.7–2.7 (9H, m), 2.9–3.1 (1H, m), 3.1–3.5 (2H, m), 3.6–4.6 (18H, m), 4.6–5.5 (9H, m), 6.73 (1H, d, J=8.3 Hz), 6.83 (1H, d, J=8.3 Hz), 6.84–7.00 (4H, m), 7.05 (1H, s), 7.17 (2H, d, J=8.7 Hz), 7.19 (1H, m), 7.2–7.6 (4H, m), 7.67 (1H, br), 7.98 (2H, d, J=8.7 Hz), 7.8–8.2 (5H, m), 8.6–9.0 (2H, m)

MASS (m/z): 1332.97 (M−Na)$^+$

Elemental Analysis Calcd. for $C_{59}H_{69}N_{10}NaO_{22}S.8H_2O$: C 47.20, H 5.71, N 9.33 Found: C 47.10, H 5.59, N 9.24

EXAMPLE 53

IR (KBr): 3353.6, 1650.8, 1631.5, 1538.9, 1513.8, 1450.2, 1442.5, 1257.4 cm$^{-1}$

NMR (DMSO-d$_6$, δ): 0.96 (3H, d, J=6.6 Hz), 1.12 (3H, d, J=5.7 Hz), 1.3–2.6 (13H, m), 2.9–3.1 (1H, m), 3.1–3.6 (7H, m), 3.6–4.6 (16H, m), 4.6–5.5 (9H, m), 6.73 (1H, d, J=8.2 Hz), 6.83 (1H, d, J=8.2 Hz), 6.89 (1H, s), 7.05 (1H, s), 7.13 (2H, d, J=8.8 Hz), 7.15 (1H, m), 7.3–7.8 (3H, m), 7.97 (2H, d, J=8.8 Hz), 7.8–8.2 (5H, m), 8.6–9.0 (2H, br)

MASS (m/z): 1298.85 (M−Na)$^+$

Elemental Analysis Calcd. for $C_{56}H_{71}N_{10}NaO_{22}S.10H_2O$: C 44.74, H 6.10, N 9.32 Found: C 44.78, H 5.96, N 9.27

EXAMPLE 54

IR (KBr): 3365, 1647, 1541, 1516, 1437, 1248, 1047 cm$^{-1}$

NMR (DMSO-d$_6$, δ): 0.96 (3H, d, J=6.7 Hz), 1.12 (3H, d, J=5.6 Hz), 1.49–1.74 (6H, m), 1.74–2.55 (7H, m), 2.90–3.50 (3H, m), 3.60–3.85 (6H, m), 3.85–4.59 (13H, m), 4.70–5.40 (8H, m), 6.74 (1H, d, J=8.2 Hz), 6.81 (1H, s), 6.87 (1H, d, J=8.2 Hz), 6.99 (1H, d, J=9.1 Hz), 7.06 (1H, s), 7.19 (1H, s), 7.35–7.50 (2H, m), 7.68 (1H, m), 8.05 (1H, m), 8.06 (4H, s), 8.08 (1H, dd, J=9.1 and 2.5 Hz), 8.71 (1H, d, J=2.5 Hz), 8.77 (1H, d, J=7.4 Hz), 8.82 (1H, br s)

MASS (m/z): 1266.93 (M−Na)$^+$

Elemental Analysis Calcd. for $C_{54}H_{67}N_{12}NaO_{20}S_2.10H_2O$: C 44.28, H 5.96, N 11.42 Found: C 44.28, H 5.81, N 11.48

The following compounds [Examples 55 and 56] were obtained in a manner similar to that of Example 17.

EXAMPLE 55

IR (KBr): 3359, 1651, 1539, 1522 cm$^{-1}$

NMR (DMSO-d$_6$, δ): 0.8–1.0 (6H, m), 1.11 (3H, d, J=5.5 Hz), 1.3–1.6 (4H, m), 1.6–2.15 (5H, m), 2.2–2.5 (4H, m), 2.97 (1H, m), 3.20 (1H, m), 3.74 (2H, m), 3.8–4.6 (14H, m), 4.6–5.4 (10H, m), 6.74 (1H, d, J=8.2 Hz), 6.83 (1H, d, J=8.2

Hz), 6.89 (1H, s), 7.05 (1H, s), 7.22 (1H, m), 7.45 (3H, m), 7.52 (2H, d, J=4.9 Hz), 7.66 (1H, m), 7.96 (5H, m), 8.08 (1H, d, J=8.2 Hz), 8.59 (1H, d, J=6.4 Hz), 8.85 (1H, s), 8.89 (1H, s)

MASS (m/z): 1307.69 (M−Na)$^+$

Elemental Analysis Calcd. for $C_{57}H_{70}N_{11}O_{21}S_2Na \cdot 10H_2O$: C 45.26, H 6.00, N 10.19 Found: C 45.11, H 5.84, N 10.28

EXAMPLE 56

IR (KBr): 3359, 1651, 1539, 1524, 1458, 1254 cm$^{-1}$

NMR (DMSO-d$_6$, δ): 0.96 (3H, d, J=6.6 Hz), 1.12 (3H, d, J=5.5 Hz), 1.2–1.6 (6H, m), 1.6–2.1 (7H, m), 2.1–2.4 (4H, m), 2.96 (1H, m), 3.19 (1H, m), 3.42 (1H, m), 3.74 (2H, m), 3.8–4.6 (12H, m), 4.73 (1H, m), 4.8–5.0 (3H, m), 5.06 (1H, d, J=5.8 Hz), 5.1–5.3 (5H, m), 6.74 (1H, d, J=8.2 Hz), 6.83 (1H, d, J=8.2 Hz), 6.89 (1H, s), 7.05 (1H, s), 7.15 (2H, d, J=8.8 Hz), 7.23 (1H, s), 7.3–7.5 (2H, m), 7.66 (1H, s), 7.88 (2H, d, J=8.8 Hz), 7.95 (4H, s), 8.07 (1H, d, J=7.8 Hz), 8.58 (1H, d, J=7.8 Hz), 8.85 (2H, s)

MASS (m/z): 1319.74 (M−Na)$^+$

Elemental Analysis Calcd. for $C_{58}H_{70}N_{11}O_{21}S_2Na \cdot 10H_2O$: C 45.70, H 5.95, N 10.11 Found: C 45.58, H 5.80, N 10.13

The following compounds [Examples 57 to 60] were obtained in a manner similar to that of Example 18.

EXAMPLE 57

IR (KBr): 3350, 2929, 1664, 1629, 1446, 1284, 1047.2 cm$^{-1}$

NMR (DMSO-d$_6$, δ): 0.86 (3H, t, J=6.7 Hz), 0.96 (3H, d, J=6.7 Hz), 1.07 (3H, d, J=5.9 Hz), 1.2–1.5 (10H, m), 1.6–2.5 (9H, m), 2.9–3.5 (4H, m), 3.7–4.5 (16H, m), 4.7–4.8 (1H, m), 4.87 (1H, d, J=5.9 Hz), 5.0–5.4 (5H, m), 6.7–6.9 (4H, m), 6.96 (1H, s), 7.17 (1H, s), 7.40 (1H, d, J=8.4 Hz), 7.5–7.8 (2H, m), 8.0–8.2 (2H, m), 8.61 (1H, d, J=7.7 Hz), 8.68 (1H, d, J=8.9 Hz)

MASS (m/z): 1182.4 (M+Na)$^+$

Elemental Analysis Calcd. for $C_{49}H_{70}N_9NaO_{20}S \cdot 4H_2O$: C 47.76, H 6.38, N 10.23 Found: C 47.81, H 6.73, N 10.12

EXAMPLE 58

IR (KBr): 3349, 2929, 1664, 1633, 1535, 1515, 1440, 1272, 1045 cm$^{-1}$

NMR (DMSO-d$_6$, δ): 0.86 (3H, t, J=6.8 Hz), 0.96 (3H, d, J=6.7 Hz), 1.10 (3H, d, J=5.8 Hz), 1.2–1.4 (8H, m), 1.5–2.5 (10H, m), 2.58 (2H, t, J=7.6 Hz), 2.9–3.1 (1H, m), 3.2–3.6 (3H, m), 3.7–4.2 (5H, m), 4.1–4.6 (8H, m), 4.7–5.2 (7H, m), 5.3–5.4 (1H, m), 6.7–7.8 (14H, m), 7.95 (2H, d, J=8.3 Hz), 8.10 (1H, d, J=8.4 Hz), 8.63 (1H, d, J=7.7 Hz), 8.71 (1H, s)

MASS (m/z): 1227.5 (M+Na)$^+$

Elemental Analysis Calcd. for $C_{55}H_{73}N_8NaO_{19}S \cdot 5H_2O$: C 51.00, H 6.46, N 8.65 Found: C 50.90, H 6.54, N 8.81

EXAMPLE 59

IR (Nujol): 3353.0, 1668.1, 1629.6, 1540.8, 1515.8 cm$^{-1}$

NMR (DMSO-d$_6$, δ): 0.87 (3H, t, J=6.7 Hz), 0.96 (3H, d, J=6.7 Hz), 1.06 (3H, d, J=6.0 Hz), 1.18–1.48 (4H, m), 1.48–2.06 (5H, m), 2.06–2.70 (8H, m), 2.70–3.08 (3H, m), 3.09–3.50 (2H, m), 3.60–4.65 (14H, m), 4.65–5.50 (9H, m), 6.65–6.90 (3H, m), 6.90–7.90 (13H, m), 8.02 (1H, d, J=8.4 Hz), 8.15 (1H, d, J=7.7 Hz), 8.71 (1H, s)

MASS (m/z): 1227.5 (M+Na)$^+$

Elemental Analysis Calcd. for $C_{55}H_{73}N_8NaO_{19}S \cdot 5H_2O$: C 50.99, H 6.46, N 8.65 Found: C 50.84, H 6.62, N 8.81

EXAMPLE 60

IR (KBr): 3353.6, 1635.3, 1257.4 cm$^{-1}$

NMR (DMSO-d$_6$, δ): 0.89 (3H, t, J=6.8 Hz), 0.97 (3H, d, J=6.7 Hz), 1.09 (3H, d, J=5.7 Hz), 1.2–1.5 (6H, m), 1.65–2.6 (10H, m), 2.97 (1H, m), 3.1–3.5 (2H, m), 3.6–4.6 (16H, m), 4.7–5.4 (8H, m), 6.71 (1H, d, J=8.2 Hz), 6.79 (1H, d, J=8.2 Hz), 6.87 (1H, s), 6.97 (1H, s), 7.13 (2H, d, J=8.9 Hz), 7.16 (1H, s), 7.4–7.8 (3H, m), 7.97 (2H, d, J=8.9 Hz), 7.9–8.2 (5H, m), 8.72 (1H, s), 8.78 (1H, d, J=7.1 Hz)

MASS (m/z): 1267 (M−Na)$^+$

The following compounds [Example 61 to 72] were obtained in a manner similar to that of Example 13.

EXAMPLE 61

IR (KBr): 1650.8, 1631.5 cm$^{-1}$

NMR (DMSO-d$_6$, δ): 0.80–0.87 (3H, s), 0.97 (3H, d, J=6.8 Hz), 1.10 (3H, d, J=5.9 Hz), 1.23 (14H, br s), 1.73–2.65 (10H, m), 2.92–3.50 (3H, m), 3.60–4.60 (16H, m), 4.70–5.50 (8H, m), 6.71 (1H, d, J=8.2 Hz), 6.77–6.81 (1H, m), 6.86 (1H, s), 6.97 (1H, s), 7.07–7.86 (4H, m), 8.11 (1H, s), 8.06–8.17 (4H, m), 8.66 (1H, s), 8.66–8.88 (3H, m)

MASS (m/z): 1326.62 (M+Na)$^+$

Elemental Analysis Calcd. for $C_{57}H_{77}N_{12}O_{20}SNa \cdot 7H_2O$: C 47.83, H 6.41, N 11.74 Found: C 47.77, H 6.45, N 11.62

EXAMPLE 62

IR (KBr): 1668.1, 1650.8, 1631.5 cm$^{-1}$

NMR (DMSO-d$_6$, δ): 0.81–0.90 (3H, m), 0.97 (3H, d, J=6.7 Hz), 1.10 (3H, d, J=6 Hz), 1.23 (14H, br s), 1.75–2.70 (10H, m), 2.95–3.02 (1H, m), 3.17–3.30 (2H, m), 3.60–4.60 (16H, m), 4.70–5.46 (8H, m), 6.71 (1H, d, J=8.2 Hz), 6.79 (1H, d, J=8.5 Hz), 6.87 (1H, br s), 6.98 (1H, s), 7.18 (1H, br s), 7.40–7.80 (3H, m), 8.05–8.10 (4H, m), 8.08 (1H, s), 8.57 (1H, s), 8.71–8.80 (3H, m)

MASS (m/z): 1297.14 (M−Na)$^+$

Elemental Analysis Calcd. for $C_{57}H_{77}N_{12}O_{19}S_2Na \cdot 7H_2O$: C 47.30, H 6.34, N 11.61 Found: C 47.07, H 6.23, N 11.42

EXAMPLE 63

IR (KBr): 1675.8, 1650.8 cm$^{-1}$

NMR (DMSO-d$_6$, δ): 0.97 (3H, d, J=6.6 Hz), 1.11 (3H, d, J=6.4 Hz), 1.70–2.60 (10H, m), 2.90–3.60 (3H, m), 3.60–4.60 (18H, m), 4.68–5.60 (8H, m), 6.70 (1H, d, J=8.3 Hz), 6.78 (1H, d, J=9.7 Hz), 6.87 (1H, s), 6.93–6.99 (4H, m), 7.11 (2H, d, J=8.8 Hz), 7.26–7.34 (2H, m), 7.09–7.78 (4H, m), 7.76 (2H, d, J=8.7 Hz), 7.91 (2H, d, J=8.5 Hz), 8.12 (2H, d, J=8.6 Hz), 8.19–8.27 (4H, m), 8,60–9.00 (3H, m)

MASS (m/z): 1377.26 (M−Na)$^+$

Elemental Analysis Calcd. for $C_{65}H_{73}N_{10}O_{22}SNa \cdot 6H_2O$: C 51.72, H 5.68, N 9.28 Found: C 51.54, H 5.73, N 9.25

EXAMPLE 64

IR (KBr): 1675.8, 1650.8, 1631.5 cm$^{-1}$

NMR (DMSO-d$_6$, δ): 0.97 (3H, d, J=6.7 Hz), 1.11 (3H, d, J=5.6 Hz), 1.70–2.60 (8H, m), 2.80–3.60 (3H, m), 3.60–5.26 (22H, m), 4.65 (2H, d, J=5.2 Hz), 5.26–5.48 (2H, m), 5.99–6.18 (1H, m), 6.70 (1H, d, J=8 Hz), 6.78 (1H, d, J=9.9 Hz), 6.87 (1H, s), 6.97 (1H, s), 7.00–7.20 (1H, m), 7.10 (2H, d, J=8.9 Hz), 7.30–7.80 (3H, m), 7.75 (2H, d, J=8.9 Hz), 7.92 (2H, d, J=8.5 Hz), 8.12 (2H, d, J=8.6 Hz), 8.19–8.27 (5H, m), 8.50–9.00 (2H, m)

MASS (m/z): 1282.84 (M−Na)$^+$

Elemental Analysis Calcd. for $C_{59}H_{67}N_{10}O_{21}SNa \cdot 7H_2O$: C 49.44, H 5.70, N 9.77 Found: C 49.33, H 5.64, N 9.74

EXAMPLE 65

IR (KBr): 1650.8, 1631.5, 1540.8, 1513.8, 1245.8 cm$^{-1}$

NMR (DMSO-d$_6$, δ): 0.97 (3H, d, J=6.7 Hz), 1.11 (3H, d, J=5.9 Hz), 1.80–2.60 (11H, m), 2.80–3.60 (3H, m), 3.65–4.60 (19H, m), 4.63–5.50 (8H, m), 6.70 (1H, d, J=8 Hz), 6.77 (1H, d, J=7.9 Hz), 6.87–6.97 (5H, m), 7.02–7.22 (1H, m), 7.09 (2H, d, J=8 Hz), 7.25–7.33 (2H, m), 7.40–7.80 (3H, m), 7.75 (2H, d, J=8.9 Hz), 7.91 (2H, d, J=8.5 Hz), 8.11 (2H, d, J=8.4 Hz), 8.23–8.27 (4H, m), 8.50–9.00 (3H, m)

MASS (m/z): 1391.07 (M–Na)$^+$

Elemental Analysis Calcd. for $C_{66}H_{75}N_{10}O_{22}SNa.7H_2$): C 51.42, H 5.82, N 9.09 Found: C 51.37, H 5.78, N 9.05

EXAMPLE 66

IR (KBr): 3353.6, 2939.0, 1650.8, 1631.5, 1538.9, 1513.8, 1442.5 cm$^{-1}$

NMR (DMSO-d$_6$, δ): 0.97 (3H, d, J=6.6 Hz), 1.10 (3H, d, J=5.7 Hz), 1.7–2.6 (12H, m), 2.9–3.1 (1H, m), 3.1–3.7 (2H, m), 3.7–4.7 (18H, m), 4.7–5.5 (8H, m), 6.71 (1H, d, J=8.0 Hz), 6.78 (1H, d, J=8.0 Hz), 6.83–7.05 (5H, m), 7.15 (2H, d, J'8.7 Hz), 7.17 (1H, m), 7.2–7.35 (2H, m), 7.35–7.9 (3H, m), 7.98 (2H, d, J=8.7 Hz), 7.9–8.2 (5H, m), 8.75 (1H, br), 8.80 (1H, d, J=7.0 Hz)

MASS (m/z): 1331.28 (M–Na)$^+$

Elemental Analysis Calcd. for $C_{60}H_{71}N_{10}NaO_{21}S_2.9H_2O$: C 47.49, H 5.91, N 9.23 Found: C 47.41, H 5.71, N 9.17

EXAMPLE 67

IR (KBr): 3353.6, 1666.2, 1650.8, 1631.5, 1538.9, 1513.8, 1442.5, 1247.7 cm$^{-1}$

NMR (DMSO-d$_6$, δ): 0.97 (3H, d, J=6.7 Hz), 1.10 (3H, d, J=5.7 Hz), 1.4–2.7 (14H, m), 2.9–3.1 (1H, m), 3.1–3.5 (2H, m), 3.6–4.6 (18H, m), 4.7–5.5 (8H, m), 6.71 (1H, d, J=8.1 Hz), 6.79 (1H, d, J=8.1 Hz), 6.84–7.00 (5H, m), 7.14 (2H, d, J=8.7 Hz), 7.16 (1H, m), 7.27 (2H, m), 7.44 (1H, d, J=8.6 Hz), 7.59 (1H, br), 7.71 (1H, br), 7.98 (2H, d, J=8.7 Hz), 7.9–8.2 (5H, m), 8.75 (1H, br), 8.79 (1H, d, J=7.2 Hz)

MASS (m/z): 1345.3 (M–Na)$^+$

Elemental Analysis Calcd. for $C_{61}H_{73}N_{10}NaO_{21}S_2.8H_2O$ C 48.41 H 5.93, N 9.25 Found: C 48.30, H 5.91, N 9.17

EXAMPLE 68

IR (KBr): 3353.6, 2937.1, 1650.8, 1540.8, 1513.8, 1452.1, 1243.9 cm$^{-1}$

NMR (DMSO-d$_6$, δ): 0.97 (3H, d, J=6.7 Hz), 1.11 (3H, d, J=5.7 Hz), 1.7–2.7 (10H, m), 2.9–3.1 (1H, m), 3.1–3.6 (2H, m), 3.6–4.7 (18H, m), 4.7–5.5 (8H, m), 6.71 (1H, d, J=8.1 Hz), 6.79 (1H, d, J=8.1 Hz), 6.84–7.10 (5H, m), 7.17 (2H, d, J=8.7 Hz), 7.19 (1H, m), 7.2–7.4 (2H, m), 7.44 (1H, d, J=9.2 Hz), 7.5–7.9 (2H, m), 7.98 (2H, d, J=8.7 Hz), 7.9–8.2 (5H, m), 8.6–9.0 (2H, m)

MASS (m/z): 1316.8 (M–Na)$^+$

Elemental Analysis Calcd. for $C_{59}H_{69}N_{10}NaO_{21}S_2.9H_2O$: C 47.13, H 5.83, N 9.32 Found: C 47.40, H 5.67, N 9.30

EXAMPLE 69

IR (KBr): 3361.3, 2937.1, 1650.8, 1631.5, 1538.9, 1513.8, 1450.2, 1440.6, 1257.4 cm$^{-1}$

NMR (DMSO-d$_6$, δ): 0.99 (3H, m), 1.11 (3H, m), 1.3–2.7 (14H, m), 2.9–3.1 (1H, m), 3.1–3.6 (7H, m), 3.6–4.7 (16H, m), 4.7–5.6 (8H, m), 6.69 (1H, d, J=8.2 Hz), 6.77 (1H, d, J=8.2 Hz), 6.86 (1H, s), 6.98 (1H, s), 7.13 (2H, d, J=8.7 Hz), 7.15 (1H, m), 7.3–7.9 (3H, m), 7.97 (2H, d, J=8.7 Hz), 7.9–8.2 (5H, m), 8.6–8.9 (2H, m)

MASS (m/z): 1283.2 (M–Na)$^+$

Elemental Analysis Calcd. for $C_{56}H_{71}N_{10}NaO_{21}S_2.10H_2O$: C 45.22, H 6.17, N 9.42 Found: C 45.30, H 5.90, N 9.38

EXAMPLE 70

IR (KBr): 3400, 1651, 1541, 1261 cm$^{-1}$

NMR (DMSO-d$_6$, δ): 0.95–5.40 (58H, m), 6.67–8.77 (19H, m)

MASS (m/z): 1325.29 (M–Na)$^+$

Elemental Analysis Calcd. for $C_{59}H_{77}N_{10}NaO_{21}S_2.37/4H_2O$: C 46.74, H 6.35, N 9.24 Found: C 46.74, H 6.10, N 9.15

EXAMPLE 71

IR (KBr): 3363, 1648, 1619, 1506, 1257 cm$^{-1}$

NMR (DMSO-d$_6$, δ): 0.97 (3H, t, J=3.3 Hz), 1.02 (3H, d, J=7.3 Hz), 1.11 (3H, d, J=5.5 Hz), 1.68–5.40 (38H, m), 6.69–8.86 (22H, m)

MASS (m/z): 1254 (M–Na)$^+$

Elemental Analysis Calcd. for $C_{59}H_{69}N_{10}NaO_{21}S.41/5H_2$): C 48.64, H 5.91, N 9.61 Found: C 48.63, H 5.85, N 9.55

EXAMPLE 72

IR (KBr): 3300, 1651, 1506, 1437 cm$^{-1}$

NMR (DMSO-d$_6$, δ): 0.87–5.30 (50H, m), 6.66–8.73 (20H, m)

MASS (m/z): 1236.29 (M–Na)$^+$

Elemental Analysis Calcd. for $C_{56}H_{70}N_9NaO_{21}S.23/3H_2O$: C 48.10, H 6.15, N 9.01 Found: C 48.14, H 6.03, N 8.97

The following compounds [Examples 73 and 74] were obtained in a manner similar to that of Example 17.

EXAMPLE 73

IR (KBr): 3359, 1676, 1651, 1632, 1514 cm$^{-1}$

NMR (DMSO-d$_6$, δ): 0.87–1.0 (6H, m), 1.09 (3H, d, J=5.4 Hz), 1.2–1.6 (4H, m), 1.6–2.1 (5H, m), 2.1–2.6 (5H, m), 3.00 (1H, m), 3.2 (1H, m), 3.5 (1H, m), 3.6–4.6 (16H, m), 4.6–5.6 (8H, m), 6.70 (1H, d, J=8.2 Hz), 6.77 (1H, d, J=8.2 Hz), 6.87 (1H, s), 6.97 (1H, s), 7.20 (1H, m), 7.3–7.8 (6H, m), 7.8–8.4 (6H, s), 8.4–8.8 (2H, m), 8.89 (1H, s)

MASS (m/z): 1292.51 (M–Na)$^+$

Elemental Analysis Calcd. for $C_{57}H_{70}N_{11}O_{20}S_2Na.12H_2O$: C 44.67, H 6.18, N 10.05 Found: C 44.89, H 6.05, N 10.02

EXAMPLE 74

IR (KBr): 3359, 1668, 1650, 1631 cm$^{-1}$

NMR (DMSO-d$_6$, δ): 0.97 (3H, d, J=6.4 Hz), 1.08 (3H, d, J=5.4 Hz), 1.2–1.6 (6H, m), 1.6–2.0 (7H, m), 2.1–2.4 (4H, m), 3.01 (1H, m), 3.20 (1H, m), 3.67 (1H, m), 3.7–4.6 (16H, m), 4.6–5.6 (8H, m), 6.68 (1H, d, J=8.2 Hz), 6.76 (1H, d, J=8.2 Hz), 6.85 (1H, s), 7.15 (2H, d, J=8.9 Hz), 7.16 (1H, s), 7.2–7.8 (4H, m), 7.88 (2H, d, J=8.9 Hz), 7.96 (4H, s), 8.56 (1H, s), 8.84 (2H, s)

MASS (m/z): 1304.08 (M–Na)$^+$

Elemental Analysis Calcd. for $C_{59}H_{70}N_{11}O_{20}S_2Na.12H_2O$: C 45.10, H 6.13, N 9.98 Found: C 45.33, H 5.89, N 9.94

The following compounds [Examples 75 to 85] were obtained according to a similar manner to that of Example 13.

EXAMPLE 75

IR (KBr): 1668, 1649, 1632, 1541, 1516 cm$^{-1}$

NMR (DMSO-d$_6$, δ): 0.86 (3H, m), 0.97 (3H, d, J=6.7 Hz), 1.0–1.2 (3H, m), 1.2–1.4 (8H, m), 1.45–1.65 (2H, m), 1.7–2.6 (8H, m), 2.8–3.5 (3H, m), 3.46 (2H, t, J=6.4 Hz), 3.6–4.6 (14H, m), 4.51 (2H, s), 4.7–5.4 (8H, m), 6.65–6.85 (2H, m), 6.88 (1H, s), 6.97 (1H, s), 7.18 (1H, s), 7.4–7.8 (3H, m), 7.50 (2H, d, J=8.6 Hz), 8.02 (2H, d, J=8.6 Hz), 8.0–8.2 (5H, m), 8.41 (1H, s), 8.72 (1H, s), 8.7–8.9 (1H, m), 9.35 (1H, s)

MASS (m/z): 1407 (M$^+$+23)

Elemental Analysis Calcd. for C$_{61}$H$_{77}$N$_{12}$NaO$_{20}$O$_2$·7H$_2$O: C 48.47, H 6.07, N 11.12 Found: C 48.51, H 6.01, N 11.17

EXAMPLE 76

IR (KBr): 1632, 1518, 1441, 1250 cm$^{-1}$

NMR (DMSO-d$_6$, δ): 0.89 (3H, t, J=6.6 Hz), 0.97 (3H, d, J=6.7 Hz), 1.10 (3H, d, J=5.3 Hz), 1.1–1.5 (6H, m), 1.6–2.5 (10H, m), 2.9–3.1 (1H, m), 3.1–3.5 (2H, m), 3.6–4.6 (14H, m), 4.03 (2H, t, J=6.4 Hz), 4.7–5.1 (4H, m), 5.15–5.25 (3H, m), 5.3–5.45 (1H, m), 6.7–6.85 (2H, m), 6.87 (1H, s), 6.97 (1H, s), 7.10 (2H, d, J=8.9 Hz), 7.18 (1H, s), 7.4–7.8 (3H, m), 7.85 (2H, d, J=8.9 Hz), 8.0–8.2 (5H, m), 8.06 (1H, s), 8.72 (1H, s), 8.75–8.9 (1H, m), 9.23 (1H, s)

MASS (m/z): 1333 (M$^+$−23)

Elemental Analysis Calcd. for C$_{59}$H$_{73}$N$_{12}$NaO$_{20}$S$_2$·8H$_2$O: C 47.20, H 5.97, N 11.19 Found: C 47.27, H 6.04, N 11.26

EXAMPLE 77

IR (KBr): 1633, 1608, 1531, 1444, 1419 cm$^{-1}$

NMR (DMSO-d$_6$, δ): 0.88–1.25 (6H, m), 1.49–2.50 (11H, m), 2.84–5.48 (33H, m), 6.62–6.98 (3H, m), 7.00–7.16 (2H, m), 7.10 (2H, d, J=8.5 Hz), 7.25–7.80 (7H, m), 7.85 (2H, d, J=8.5 Hz), 7.91–8.14 (6H, m), 8.65–8.89 (2H, m)

MASS (m/z): 1371.69 (M−Na$^+$)

Elemental Analysis Calcd for C$_{62}$H$_{74}$N$_{11}$NaO$_{21}$S$_2$·8H$_2$O: C 48.34, H 5.89, N 10.00 Found: C 48.39, H 5.65, N 9.95

EXAMPLE 78

IR (KBr): 1649, 1605, 1541, 1516, 1448 cm$^{-1}$

NMR (DMSO-d$_6$, δ): 0.96 (3H, d, J=6.7 Hz), 1.12 (3H, d, J=5.9 Hz), 1.40–2.45 (12H, m), 2.78–3.50 (7H, m), 3.64–5.34 (23H, m), 6.47 (1H, d, J=8.2 Hz), 6.83 (1H, d, J=8.2 Hz), 6.89 (1H, s), 7.00–7.50 (10H, m), 7.67 (1H, brs), 7.98–8.20 (6H, m), 8.74 (1H, d, J=2.5 Hz), 8.65–8.92 (2H, m)

MASS (m/z): 1343.11 (M−Na$^+$)

Elemental Analysis Calcd. for C$_{60}$H$_{71}$N$_{12}$NaO$_{20}$S$_2$·7H$_2$O: C 48.25, H 5.74, N 11.25 Found: C 48.32, H 5.62, N 11.74

EXAMPLE 79

IR (KBr): 1637, 1539, 1512, 1443 cm$^{-1}$

NMR (DMSO-d$_6$, δ): 0.97 (3H, d, J=6.7 Hz), 1.11 (3H, d, J=7.1 Hz), 1.36 (3H, t, J=6.9 Hz), 1.73–2.52 (8H, m), 2.79–3.34 (3H, m), 4.10 (2H, q, J=7.0 Hz), 3.66–4.60 (14H, m), 4.70–5.54 (8H, m), 6.71 (1H, d, J=8.1 Hz), 6.79 (1H, dd, J=8.4 and 1.7 Hz), 6.87 (1H, s), 6.98 (1H, d, J=1.7 Hz), 7.06 (2H, d, J=8.9 Hz), 7.19 (1H, s), 7.45 (1H, d, J=8.8 Hz), 7.60 (1H, m), 7.73 (2H, d, J=8.8 Hz), 7.87 (2H, d, J=8.5 Hz), 7.96–8.24 (8H, m), 8.73 (1H, brs), 8.80 (1H, d, J=7.3 Hz)

MASS (m/z): 1287.49 (M−Na$^+$)

Elemental Analysis Calcd. for C$_{58}$H$_{67}$N$_{10}$NaO$_{20}$S$_2$·7H$_2$O: C 48.46, H 5.68, N 9.74 Found: C 48.19, H 5.69, N 9.56

EXAMPLE 80

IR (KBr): 1649, 1635, 1510, 1443 cm$^{-1}$

NMR (DMSO-d$_6$, δ): 0.96 (3H, d, J=6.8 Hz), 1.12 (3H, d, J=5.8 Hz), 1.55–2.51 (11H, m), 2.76–3.64 (3H, m), 3.25 (3H, s), 3.64–4.60 (18H, m), 4.60–5.54 (9H, m), 6.73 (1H, d, J=8.2 Hz), 6.83 (1H, d, J=8.6 Hz), 6.89 (1H, s), 7.02–7.15 (3H, m), 7.36–7.79 (3H, m), 7.73 (2H, d, J=8.8 Hz), 7.87 (2H, d, J=8.4 Hz), 8.00–8.26 (8H, m), 8.70–8.92 (2H, m)

MASS (m/z): 1361.12 (M−Na$^+$)

Elemental Analysis Calcd. for C$_{61}$H$_{73}$N$_{10}$NaO$_{22}$S$_2$·7H$_2$O: C 48.47, H 5.80, N 9.27 Found: C 48.63, H 5.71, N 9.19

EXAMPLE 81

IR (KBr): 1633, 1533, 1512, 1443 cm$^{-1}$

NMR (DMSO-d$_6$, δ): 0.97 (3H, d, J=6.7Hz), 1.10–1.20 (3H, m), 1.56–2.50 (12H, m), 2.88–3.28 (3H, m), 3.25 (3H, s), 3.63–4.56 (18H, m), 4.70–5.50 (8H, m), 6.69 (1H, d, J=8.1Hz), 6.77 (1H, d, J=8.1Hz), 6.87 (1H, s), 6.98 (1H, s), 7.07 (2H, d, J=8.8Hz), 7.28–7.72 (3H, m), 7.73 (2H, d, J=8.7Hz), 7.87 (2H, d, J=8.4Hz), 7.94–8.20 (8H, m), 8.64–8.92 (2H, m)

MASS (m/z): 1345.44 (M−Na$^+$)

Elemental Analysis Calcd. for C$_{61}$H$_{73}$N$_{10}$NaO$_{21}$S$_2$·6H$_2$O: C 49.59, H 5.80, N 9.48

Found: C 49.52, H 5.68, N 9.39

EXAMPLE 82

IR (KBr): 1635, 1608, 1531, 1444, 1419 cm$^{-1}$

NMR (DMSO-d$_6$, δ): 0.97 (3H, d, J=6.8Hz), 1.10 (3H, d, J=5.7Hz), 1.03–1.20 (5H, m), 1.50–2.55 (14H,m), 2.55–2.77 (4H, m), 2.89–3.55 (7H, m), 3.67–4.63 (14H, m), 4.68–5.50 (8H, m), 6.71 (1H, d, J=8.2Hz), 6.78 (1H, d, J=8.2Hz), 6.87 (1H, s), 6.97 (1H, s), 7.08 (2H, d, J=8.7Hz), 7.18 (1H, s), 7.44 (1H, d, J=7.5Hz), 7.58 (1H, m), 7.71 (1H, m), 7.85 (2H, d, J=8.8Hz), 7.94–8.20 (5H, m), 8.72 (1H, s), 8.78 (1H, d, J=7.0Hz),

MASS (m/z): 1332.99 (M−Na$^+$)

Elemental Analysis Calcd for C$_{60}$H$_{77}$N$_{12}$NaO$_{19}$S$_2$·7H$_2$O: C 48.58, H 6.18, N 11.33

Found: C 48.58, H 6.02, N 11.22

EXAMPLE 83

IR (KBr): 1633, 1535, 1512, 1443 cm$^{-1}$

NMR (DMSO-d$_6$, δ): 0.95 (3H, t, J=7.4Hz), 0.97 (3H, d, J=7.1Hz), 1.11 (3H, d, J=5.6Hz), 1.35–1.56 (2H, m), 1.66–2.55 (10H, m), 2.90–3.38 (3H, m), 3.68–4.62 (16H, m), 4.75–5.52 (8H, m), 6.71 (1H, d, J=8.2Hz), 6.79 (1H, d, J=8.2Hz), 6.88 (1H, s), 6.99 (1H, s), 7.07 (2H, d, J=8.8Hz), 7.10–7.68 (3H, m), 7.73 (2H, d, J=8.7Hz), 7.86 (2H, d, J=8.4Hz), 8.05–8.25 (8H, m), 8.50–8.92 (2H, m)

MASS (m/z): 1315.58 (M−Na$^+$)

Elemental Analysis Calcd. for C$_{60}$H$_{71}$N$_{10}$NaO$_{20}$S$_2$·10H$_2$O:

C 47.43, H 6.04, N 9.22

Found: C 47.60, H 5.66, N 9.24

EXAMPLE 84

IR (KBr): 1647, 1539, 1512, 1448 cm$^{-1}$

NMR (DMSO-d$_6$, δ): 0.97 (3H, d, J=6.7Hz), 1.16–1.20 (3H, m), 1.15 (3H, t, J=7.0Hz), 1.73–2.58 (8H, m), 2.84–3.35 (3H, m), 3.49 (2H, q, J=7.0Hz), 3.66–4.62 (18H, m), 4.74–5.50 (8H, m), 6.71 (1H, d, J=8.2Hz), 6.79 (1H, d, J=8.3 and 1.7Hz), 6.88 (1H, brs), 6.98 (1H, d, J=1.7Hz), 7.09

(2H, d, J=8.8Hz), 7.19 (1H, brs), 7.36–7.69 (2H,m), 7.74 (2H, d, J=8.8Hz), 7.87 (2H, d, J=8.5Hz), 8.02–8.24 (8H, m), 8.63–8.90 (2H, m)

MASS (m/z): 1331.2 (M–Na$^+$)

Elemental Analysis Calcd. for $C_{60}H_{71}N_{10}NaO_{21}S_2 \cdot 8H_2O$:

C 48.06, H 5.85, N 9.34

Found: C 47.93, H 5.82, N 9.23

EXAMPLE 85

IR (KBr): 1633, 1537, 1513, 1443 cm$^{-1}$

NMR (DMSO-d$_6$, δ): 0.97 (3H, d, J=6.8Hz), 1.11 (3H, d, J=5.8Hz) 1.74–2.52 (8H, m), 2.90–3.40(3H, m), 3.35 (3H, s), 3.62–4.57 (18H, m), 4.70–5.49 (8H, m), 6.70 (1H, d, J=8.1Hz), 6.78 (1H, d, J=8.1Hz), 6.87 (1H, s), 6.97 (1H, s), 7.09 (2H, d, J=8.8Hz), 7.10–7.51 (3H, m), 7.74 (2H, d, J=8.7Hz), 7.87 (2H, d, J=8.7Hz), 7.94–8.28 (8H, m), 8.56–8.92 (2H, m)

MASS (m/z): 1317.28 (M–Na$^+$)

Elemental Analysis Calcd. for $C_{59}H_{69}N_{10}NaO_{21}S_2 \cdot 9H_2O$:

C 47.13, H 5.83, N 9.32

Found: C 47.24, H 5.55, N 9.35

EXAMPLE 86

To a solution of Starting Compound (86) (0.15 g) and 4-[4-[4-(5-methoxypentyloxy)biphenyl-4-yl]piperazin-1-yl] benzoic acid benzotriazol-1-yl-ester (0.12 g) in N,N-dimethylformamide (3 ml) was added diaminopyridine (0.024 g), and the mixture was stirred for 15 hours at ambient temperature. The reaction mixture was pulverized with ethyl acetate. The precipitate was collected by filtration, and dried under reduced pressure. The solid was dissolved in diluted NaHCO$_3$ aq., and subjected to column chromatography on ODS (YMC-gel ODS-AM S-50 (Trademark: prepared by Yamamura Chemical Lab.)) eluting with 60% methanol aqueous solution. The fractions containing the object compound were combined, and evaporated under reduced pressure to remove methanol. The residue was lyophilized to give Object Compound (86) (0.16 g).

IR (KBr): 1666.2, 1629.6, 1228.4, 1043.3 cm$^{-1}$

NMR (DMSO-d$_6$, δ): 0.96 (3H, d, J=6.4Hz), 1.08 (3H, d, J=5.4Hz), 1.44–5.17 (55H, m), 6.69–8.72 (22H, m)

MASS (m/z): 1405.4 (M+Na)

Elemental Analysis Calcd. for $C_{64}H_{83}N_{10}NaO_{21}S \cdot 7.5H_2O$:

C 50.62, H 6.50, N 9.32

Found: C 50.52, H 6.42, N 9.16

The following compounds [Examples 87 to 105]were obtained in a manner similar to that of Example 86.

EXAMPLE 87

IR (KBr): 1668.1, 1629.6, 1230.4 cm$^{-1}$

NMR (DMSO-d$_6$, δ): 0.96 (3H, d, J=6.6Hz), 1.07 (3H, d, J=5.7Hz), 1.24–5.50 (59H,m), 6.68–8.80 (18H,m)

MASS (m/z): 1327.5 (M–Na)

Elemental Analysis Calcd. for $C_{60}H_{83}N_{10}NaO_{20}S \cdot 6.5H_2O$:

C 49.07, H 6.59, N 9.54

Found: C 49.05, H 6.64, N 9.44

EXAMPLE 88

IR (KBr): 1666.2, 1631.5, 1240.0 cm$^{-1}$

NMR (DMSO-d$_6$, δ): 0.96 (3H, d, J=6.7Hz), 1.07 (3H, d, J=5.9Hz), 1.40–5.40 (52H, m), 6.69–8.71 (19H, m)

MASS (m/z): 1249.3 (M–Na)

Elemental Analysis Calcd. for $C_{58}H_{77}N_{10}NaO_{19}S \cdot 8H_2O$:

C 49.15, H 6.61, N 9.88

Found: C 48.96, H 6.49, N 9.79

EXAMPLE 89

IR (KBr): 1668.1, 1631.5, 1238.1 cm$^{-1}$

NMR (DMSO-d$_6$, δ): 0.82–5.38 (69H, m), 6.69–8.40 (14H, m)

MASS (m/z): 1265.6, 1243.5 (M–Na)

Elemental Analysis Calcd. for $C_{57}H_{83}N_{10}NaO_{19}S \cdot 7H_2O$:

C 49.13, H 7.02, N 10.05

Found: C 49.19, H 7.02, N 10.00

EXAMPLE 90

IR (KBr): 1664.3, 1629.6, 1232.3 cm$^{-1}$

NMR (DMSO-d$_6$, δ): 0.96 (3H, d, J=6.7Hz), 1.07 (3H, d, J=5.6Hz), 1.16–5.20 (53H,m), 6.70–8.30 (18H,m)

MASS (m/z): 1265.4 (M–Na)

Elemental Analysis Calcd. for $C_{58}H_{77}N_{10}NaO_{20}S \cdot 8.5H_2O$:

C 48.29, H 6.57, N 9.71

Found: C 48.04, H 6.21, N 9.60

EXAMPLE 91

IR (KBr): 1666.2, 1631.5, 1232.3, 1045.2 cm$^{-1}$

NMR (DMSO-d$_6$, δ): 0.96 (3H, d, J=6.7Hz), 1.07 (3H, d, J=5.8Hz), 1.30–5.40 (53H, m), 6.69–8.71 (18H,m)

MASS (m/z): 1296.3 (M+Na)

Elemental Analysis Calcd. for $C_{58}H_{77}N_{10}NaO_{19}S \cdot 8H_2O$:

C 49.15, H 6.61, N 9.88

Found: C 49.14, H 6.53, N 9.90

EXAMPLE 92

IR (KBr): 3330.5, 1666.2, 1631.5, 1255.4 cm$^{-1}$

NMR (DMSO-d$_6$, δ): 0.94–5.26 (68H, m), 6.66–8.26 (11H, m)

MASS (m/z): 1319.35 (M–Na)

Elemental Analysis Calcd. for $C_{57}H_{79}N_{10}NaO_{22}S_2 \cdot 4.5H_2O$:

C 48.06, H 6.23, N 9.83

Found: C 48.10, H 6.26, N 9.72

EXAMPLE 93

IR (KBr): 1660.4, 1631.5, 1442.5, 1249.6 cm$^{-1}$

NMR (DMSO-d$_6$, δ): 0.88–1.45 (11H, m), 1.60–3.40 (18H, m), 3.75–5.30 (22H, m), 6.72–9.00 (20H, m)

MASS (m/z): 1334.69 (M–Na)

Elemental Analysis Calcd. for $C_{59}H_{71}N_{10}NaO_{22}S_2 \cdot 6H_2O$:

C 48.29, H 5.70, N 9.54

Found: C 48.40, H 5.62, N 9.44

EXAMPLE 94

IR (KBr): 1666.2, 1631.5, 1515.8, 1257.4, 1178.3 cm$^{-1}$

NMR (DMSO-d$_6$, δ): 0.94–5.25 (51H,m), 6.67–8.84 (16H,m)

MASS (m/z): 1341.55 (M–Na)
Elemental Analysis Calcd. for $C_{59}H_{77}N_{10}NaO_{22}S_2 \cdot 6H_2O$:
C 48.09, H 6.09, N 9.51
Found: C 47.98, H 6.01, N 9.49

EXAMPLE 95

IR (KBr): 1666.2, 1629.6, 1257.4, 1178.3 cm$^{-1}$
NMR (DMSO-d$_6$, δ): 0.94–5.16 (55H, m), 6.41–8.84 (18H, m)
MASS (m/z): 1289.3 (M–Na)
Elemental Analysis Calcd. for $C_{55}H_{73}N_{10}NaO_{22}S_2 \cdot 7H_2O$:
C 45.89, H 6.09, N 9.73
Found: C 45.67, H 5.91, N 9.74

EXAMPLE 96

IR (KBr): 1666.2, 1633.4, 1249.6 cm$^{-1}$
NMR (DMSO-d$_6$, δ): 0.96–5.20 (47H, m), 6.72–9.29 (24H, m)
MASS (m/z): 1351.41 (M–Na)
Elemental Analysis Calcd. for $C_{63}H_{71}N_{10}NaO_{22}S \cdot 8.5H_2O$:
C 49.51, H 5.80, N 9.16
Found: C 49.64, H 5.49, N 9.13

EXAMPLE 97

IR (KBr): 1666.2, 1631.5, 1515.8, 1257.4, 1178.3 cm$^{-1}$
NMR (DMSO-d$_6$, δ): 0.94–5.24 (55H, m), 6.72–8.84 (20H, m)
MASS (m/z): 1363.41 (M–Na)
Elemental Analysis Calcd. for $C_{61}H_{75}N_{10}NaO_{22}S_2 \cdot 7H_2O$:
C 48.41, H 5.93, N 9.25
Found: C 48.45, H 5.80, N 9.14

EXAMPLE 98

IR (KBr): 3355.5, 2935.1, 2873.4, 1633.4, 1521.6, 1438.6, 1255.4 cm$^{-1}$
NMR (DMSO-d$_6$, δ): 0.85–1.05 (m, 6H), 1.10 (d, 3H, J=5.8Hz), 1.25–1.60 (m, 4H), 1.60–2.60 (m, 9H), 2.80–3.10 (m, 1H), 3.10–3.60 (m, 2H), 3.60–4.60 (m, 16H), 4.60–5.60 (m, 9H), 6.71 (d, 1H, J=8.2Hz), 6.81 (d, 1H, J=8.2Hz), 6.89 (s, 1H), 7.05 (s, 1H), 7.08 (d, 2H, J=8.9Hz), 7.15–7.30 (m, 1H), 7.30–7.55 (m, 2H), 7.55–7.70 (m, 1H), 7.80 (d, 2H, J=8.3Hz), 7.91 (d, 2H, J=8.9Hz), 7.96 (d, 2H, J=8.3Hz), 8.00–8.20 (m, 1H), 8.38 (s, 1H), 8.65 (d, 1H, J=6.8Hz), 8.75–9.00 (m, 1H)
MASS (m/z): 1268.40 (M–Na)
Elemental Analysis Calcd. for $C_{56}H_{70}N_9NaO_{21}S_2 \cdot 8H_2O$:
C 46.82, H 6.03, N 8.78
Found: C 47.11, H 5.84, N 8.82

EXAMPLE 99

IR (KBr): 3396.0, 2933.2, 2871.5, 1648.8, 1631.5, 1538.9, 1515.8, 1456.0, 1438.6, 1253.5 cm$^{-1}$
NMR (DMSO-d$_6$, δ): 0.75–0.90 (m, 3H), 0.96 (d, 3H, J=6.7Hz), 1.11 (d, 3H, J=5.8Hz), 1.10–1.60 (m, 6H), 1.60–2.60 (m, 9H), 2.80–3.10 (m, 1H), 3.10–3.60 (m, 2H), 3.60–4.65 (m, 16H), 4.65–5.60 (m, 9H), 6.73 (d, 1H, J=8.2Hz), 6.82 (d, 1H, J=8.2Hz), 6.89 (s, 1H), 7.05 (s, 1H), 7.07 (d, 2H, J=8.9Hz), 7.15–7.30 (m, 1H), 7.30–7.55 (m, 2H), 7.55–7.75 (m, 1H), 7.80 (d, 2H, J=8.3Hz), 7.91 (d, 2H, J=8.9Hz), 7.96 (d, 2H, J=8.3Hz), 8.00–8.20 (m, 1H), 8.38 (s, 1H), 8.65 (d, 1H, J=6.8Hz), 8.75–9.00 (m, 1H)
MASS (m/z): 1282.09 (M–Na)
Elemental Analysis Calcd. for $C_{57}H_{72}N_9NaO_{21}S_2 \cdot 7H_2O$:
C 47.79, H 6.05, N 8.80
Found: C 47.89, H 5.96, N 8.77

EXAMPLE 100

IR (KBr): 3430.7, 2931.3, 2858.0, 1668.1, 1648.0, 1631.5, 1515.8, 1456.0, 1438.6, 1255.4 cm$^{-1}$
NMR (DMSO-d$_6$, δ): 0.75–0.90 (m, 3H), 0.96 (d, 3H, J=6.7Hz), 1.11 (d, 3H, J=5.6Hz), 1.10–1.55 (m, 8H), 1.60–2.60 (m, 9H), 2.80–3.10 (m, 1H), 3.10–3.60 (m, 2H), 3.60–4.65 (m, 16H), 4.65–5.40 (m, 9H), 6.74 (d, 1H, J=8.2Hz), 6.83 (d, 1H, J=8.2Hz), 6.89 (s, 1H), 7.05 (s, 1H), 7.08 (d, 2H, J=8.8Hz), 7.20 (s, 1H), 7.30–7.55 (m, 2H), 7.60–7.75 (m, 1H), 7.80 (d, 2H, J=8.2Hz), 7.92 (d, 2H, J=8.8Hz), 7.96 (d, 2H, J=8.2Hz), 8.07 (d, 1H, J=7.0Hz), 8.38 (s, 1H), 8.66 (d, 1H, J=6.8Hz), 8.85 (s, 1H)
MASS (m/z): 1296.16 (M–Na)
Elemental Analysis Calcd. for $C_{58}H_{74}N_9NaO_{21}S_2 \cdot 6H_2O$:
C 48.77, H 6.07, N 8.82
Found: C 48.61, H 6.06, N 8.78

EXAMPLE 101

IR (KBr): 3425.0, 2969.8, 2937.1, 2881.1, 1633.4, 1517.7, 1438.6, 1247.7 cm$^{-1}$
NMR (DMSO-d$_6$, δ): 0.80–1.10 (m, 6H), 1.10 (d, 3H, J=5.7Hz), 1.60–2.60 (m, 10H), 2.85–3.10 (m, 1H), 3.10–3.60 (m, 2H), 3.60–4.60 (m, 16H), 4.65–5.50 (m, 8H), 6.71 (d, 1H, J=8.1Hz), 6.79 (d, 1H, J=8.1Hz), 6.88 (s, 1H), 6.98 (s, 1H), 7.06 (d, 2H, J=8.8Hz), 7.20 (m, 1H), 7.30–8.20 (m, 12H), 7.70 (d, 2H, J=8.8Hz), 8.48 (s, 1H), 8.60–8.85 (m, 2H)
MASS (m/z): 1300.35 (M–Na)
Elemental Analysis Calcd. for $C_{60}H_{70}N_9NaO_{20}S_2 \cdot 7H_2O$:
C 49.68, H 5.84, N 8.69
Found: C 49.59, H 5.49, N 8.68

EXAMPLE 102

IR (KBr): 3349.7, 2937.1, 2871.5, 1633.4, 1519.6, 1438.6, 1255.4 cm$^{-1}$
NMR (DMSO-d$_6$, δ): 0.70–1.05 (m, 6H), 1.08 (d, 3H, J=5.9Hz), 1.20–1.55 (m, 4H), 1.60–2.60 (m, 10H), 2.80–3.10 (m, 1H), 3.10–3.60 (m, 2H), 3.60–4.60 (m, 16H), 4.60–5.50 (m, 8H), 6.70 (d, 1H, J=8.1Hz), 6.77 (d, 1H, J=8.1Hz), 6.86 (s, 1H), 6.96 (s, 1H), 7.07 (d, 2H, J=8.9Hz), 7.20 (m, 1H), 7.30–7.50 (m, 1H), 7.50–7.80 (m, 2H), 7.79 (d, 2H, J=8.4Hz), 7.90 (d, 2H, J=8.9Hz), 7.96 (d, 2H, J=8.4Hz), 8.00–8.20 (m, 1H), 8.37 (s, 1H), 8.50–8.80 (m, 2H)
MASS (m/z): 1252.57 (M–Na)
Elemental Analysis Calcd. for $C_{56}H_{70}N_9NaO_{20}S_2 \cdot 7H_2O$:
C 47.96, H 6.04, N 8.99
Found: C 47.78, H 5.87, N 8.87

EXAMPLE 103

IR (KBr): 3432.7, 2935.1, 2869.6, 1633.4, 1535.1, 1438.6, 1251.6 cm$^{-1}$
NMR (DMSO-d$_6$, δ): 0.75–0.95 (m, 3H), 0.97 (d, 3H, J=6.8Hz), 1.10 (d, 3H, J=5.9Hz), 1.20–1.55 (m, 6H), 1.60–2.60 (m, 10H), 2.80–3.10 (m, 1H), 3.10–3.60 (m, 2H), 3.60–4.60 (m, 16H), 4.65–5.50 (m, 8H), 6.71 (d, 1H, J=8.2Hz), 6.78 (d, 1H, J=8.2Hz), 6.87 (s, 1H), 6.97 (s, 1H), 7.04 (d, 2H, J=8.7Hz), 7.20 (m, 1H), 7.30–7.90 (m, 3H), 7.67 (d, 2H, J=8.7Hz), 8.01 (s, 4H), 8.05–8.20 (m, 1H), 8.26 (s, 1H), 8.60–8.90 (m, 2H)

MASS (m/z): 1266.27 (M–Na)

Elemental Analysis Calcd. for $C_{57}H_{72}N_9NaO_{20}S_2 \cdot 6H_2O$: C 48.96, H 6.05, N 9.01

Found: C 49.07, H 5.97, N 8.94

EXAMPLE 104

IR (KBr): 3353.6, 2931.3, 2861.8, 1631.5, 1519.6, 1438.6, 1253.5 cm$^{-1}$

NMR (DMSO-d$_6$, δ): 0.70–0.95 (m, 3H), 0.97 (d, 3H, J=6.8Hz), 1.10 (d, 3H, J=6.0Hz), 1.20–1.60 (m, 6H), 1.60–2.60 (m, 10H), 2.80–3.10 (m, 1H), 3.10–3.60 (m, 2H), 3.60–4.65 (m, 16H), 4.70–5.50 (m, 8H), 6.71 (d, 1H, J=8.1Hz), 7.08 (d, 2H, J=8.9Hz), 7.21 (m, 1H), 7.44 (d, 1H, J=7.4Hz), 7.50–7.80 (m, 2H), 7.80 (d, 2H, J=8.4Hz), 7.91 (d, 2H, J=8.9Hz), 7.97 (d, 2H, J=8.4Hz), 8.12 (d, 1H, J=8.1Hz), 8.37 (s, 1H), 8.60–8.80 (m, 1H), 8.72 (s, 1H)

MASS (m/z): 1266.27 (M–Na)

Elemental Analysis Calcd. for $C_{57}H_{72}N_9NaO_{20}S_2 \cdot 6H_2O$: C 48.96, H 6.05, N 9.01

Found: C 48.75, H 5.98, N 8.91

EXAMPLE 105

IR (KBr): 1666.2, 1629.6, 1240.0, 1047.2 cm$^{-1}$

NMR (DMSO-d$_6$, δ): 0.96 (3H, d, J=6.6Hz), 1.07 (3H, d, J=5.8Hz), 1.60–5.40(47H,m), 6.68–8.80(18H,m)

MASS (m/z): 1231.3 (M+1)

Elemental Analysis Calcd. for $C_{55}H_{71}N_{10}NaO_{19}S \cdot 8H_2O$: C 48.03, H 6.38, N 10.18

Found: C 47.84, H 6.46, N 10.12

EXAMPLE 106

A solution of Starting Compound (106) (200 mg) in N,N-dimethylformamide (4 ml) was treated with 4-[5-[4-[4-[2-(2-methoxyethoxy) ethoxy]phenyl]phenyl]-1,3,4-thiadiazol-2-yl]benzoic acid benzotrizol-1-yl ester (144 mg) and diisopropylethylamine (58 μl), and the mixture was stirred for 19 hours at room temperature. Ethyl acetate was added to the reaction mixture and the resulting precipitate was collected by filtration, washed thoroughly with ethyl acetate and diisopropyl ether and dried. The powder was dissolved in saturated aqueous sodium hydrogen carbonate solution, filtered and purified by ODS column chromatography (YMC-gel ODS-AM S-50) eluting with 17–18% aqueous acetonitrile. Product-containing fractions were pooled, evaporated to remove acetonitrile, and lyophilized to give Object Compound (106) (225 mg) as an amorphous pale yellow powder.

IR (KBr): 1659, 1633, 1533, 1510, 1444 cm$^{-1}$

NMR (DMSO-d$_6$, δ): 0.97 (3H, d, J=6.7 Hz), 1.10 (3H, d J=5.6 Hz), 1.76–2.47 (8H, m), 2.83–3.32 (3H, m), 3.26 (3H, s), 3.40–4.60 (22H, m), 4.70–5.54 (8H, m), 6.69 (1H, d, J=8.2 Hz), 6.77 (1H, d, J=8.2 Hz), 6.87 (1H, brs), 6.98 (1H, s), 7.09 (2H, d, J=8.8 Hz), 7.34–7.55 (3H, m), 7.74 (2H, d, J=8.7 Hz), 7.87 (2H, d, J=8.5 Hz), 8.00–8.20 (8H, m), 8.66–8.92 (2H, m)

MASS (m/z): 1361.4 (M—Na$^+$)

Elemental Analysis Calcd. for $C_{61}H_{73}N_{10}NaO_{22}S_2 \cdot 10H_2O$: C 46.80, H 5.99, N 8.95 Found: C 46.93, H 5.80, N 8.89

The following compounds [Examples 107 to 132] were obtained in a manner similar to that of Example 106.

EXAMPLE 107

IR (KBr): 3367, 2935, 1668, 1631, 1538, 1511, 1450, 1265, 1230, 1085, 1047 cm$^{-1}$

NMR (DMSO-d$_6$, δ): 0.95 (3H, d, J=6.7 Hz), 1.07 (3H, d J=5.9 Hz), 1.2–1.6 (5H, m), 1.6–2.1 (10H, m), 2.1–2.5 (8H, m), 2.63 (4H, m), 2.79 (2H, m), 2.98 (2H, m), 3.06 (4H, m), 3.20 (1H, m), 3.71 (2H, m), 3.8–4.6 (14H, m), 4.6–5.6 (9H, m), 6.70 (1H, d, J=8.2 Hz), 6.78 (1H, s), 6.83 (3H, d, J=8.2 Hz), 6.94 (2H, d, J=8.7 Hz), 7.04 (3H, m), 7.2–7.7 (3H, m), 7.74 (2H, d, J=8.7 Hz), 8.07 (1H, m), 8.23 (1H, m), 8.56 (1H, m), 8.84 (1H, s)

MASS (m/z): 1348.35 (M—Na$^+$)

Elemental Analysis Calcd. For $C_{63}H_{86}N_{11}NaO_{20}S_2 \cdot 11H_2O$: C 48.18, H 6.93, N 9.81 Found: C 48.19, H 6.68, N 9.71

EXAMPLE 108

IR (KBr): 1676, 1651, 1622, 1514 cm$^{-1}$

NMR (DMSO-d$_6$, δ): 0.97 (3H, d, J=6.6 Hz), 1.05–1.1 (3H, m), 1.7–2.65 (12H, m), 2.8–3.2 (7H, m), 3.60 (2H, s), 2.65–4.1 (5H, m), 4.1–4.6 (9H, m), 4.7–5.45 (8H, m), 6.65–7.85 (3H, m), 7.85-7.05 (4H, m), 7.15–7.3 (3H, m), 7.4–7.8 (3H, m), 7.52 (2H, d, J=8.6 Hz), 7.94 (2H, d, J=8.6 Hz), 8.0–8.2 (5H, m), 8.41 (1H, s), 8.72 (1H, s), 8.75–8.9 (1H, m), 9.34 (1H, s)

MASS (m/z): 1407 (M$^+$-23)

EXAMPLE 110

IR (KBr): 1651, 1632, 1539, 1514 cm$^{-1}$

NMR (DMSO-D$_6$, δ): 0.97 (3H, d, J=6.8 Hz), 1.10 (3H, d, J=5.8 Hz), 1.2–1.6 (5H, m), 1.6–2.75 (14H, m), 2.85–3.1 (1H, m), 3.1–3.55 (2H, m), 3.6–4.1 (5H, m), 4.1–4.6 (9H, m), 4.6–5.45 (8H, m), 6.71 (1H, d, J=9.0 Hz), 6.78 (1H, d, J=9.0 Hz), 6.85–6.95 (1H, m), 6.95–7.0 (1H, m), 7.1–7.25 (1H, m), 7.4–7.8 (3H, m), 7.46 (2H, d, J=8.3 Hz), 7.96 (2H, d, J=8.3 Hz), 8.0–8.2 (1H, m), 8.06 (2H, d, J=8.8 Hz), 8.12 (2H, d, J=8.8 Hz), 8.72 (1H, s), 8.75–8.85 (1H, m)

MASS (m/z): 1249 (M$^+$-23)

Elemental Analysis Calcd. For $C_{56}H_{69}N_{10}NaO_{19}S_2 \cdot 7H_2O$: C 46.86, H 6.11, N 9.76 Found: C 47.02, H 6.01, N 9.77

EXAMPLE 111

IR (KBr): 1649, 1632, 1541, 1522 cm$^{-1}$

NMR (DMSO-d$_6$, δ): 0.97 (3H, d, J=6.6. Hz), 1.10 (3H, d, J=6.1 Hz), 1.1–1.65 (6H, m), 1.65–2.5 (12H, m), 2.85–3.6 (3H, m), 3.6–4.1 (5H, m), 4.1–4.6 (10H, m), 4.75–5.45 (8H, m), 6.71 (1H, d, J=8.9 Hz), 6.78 (1H, d, J=8.9 Hz), 6.85–6.9 (1H, m), 6.9–7.0 (1H, m), 7.14 (2H, d, J=8.9 Hz), 7.15–7.25 (1H, m), 7.4–7.8 (3H, m), 7.95 (2H, d, J=8.9 Hz), 8.05 (2H, d, J=8.9 Hz), 8.1–8.2 (1H, m), 8.11 (2H, d, J=8.9 Hz), 8.72 (1H, s), 8.75–8.85 (1H, m)

MASS (m/z): 1265 (M$^+$-23)

Elemental Analysis Calcd. For $C_{56}H_{69}N_{10}NaO_{20}S_2 \cdot 9H_2O$: C 46.34, H 6.04, N 9.65 Found: C 46.24, H 5.95, N 9.58

EXAMPLE 112

IR (KBr): 1664, 1628 cm$^{-1}$

NMR (DMSO-d$_6$, δ): 0.97 (3H, d, J=6.5 Hz), 1.05–1.2 (3H, m), 1.5–1.75 (6H, m), 1.75–2.5 (8H, m), 2.8–3.5 (7H, m), 3.6–4.1 (5H, m), 4.1–4.6 (9H, m), 4.7–5.5 (8H, m), 6.65–6.85 (2H, m), 6.87 (1H, s), 6.97 (1H, s), 7.07 (2H, d, J=9.2 Hz), 7.1–7.25 (1H, m), 7.35–7.8 (3H, m), 7.75 (2H, d, J=9.2 Hz), 8.0–8.2 (1H, m), 8.06 (4H, s), 8.32 (1H, s), 8.6–8.9 (2H, m), 9.17 (1H, s)

MASS (m/z): 1316 (M$^+$-23)

Elemental Analysis Calcd. For $C_{58}H_{70}N_{13}NaO_{19}S_2 \cdot 10H_2O$: C 45.82, H 5.97, N 11.98 Found: C45.80, H 5.74, N 11.91

EXAMPLE 113

IR (KBr): 1633, 1518, 1250 cm$^{-1}$

NMR (DMSO-d$_6$, δ): 0.8–1.05 (6H, m), 1.12 (3H, d, J=5.4 Hz), 1.2–1.55 (6H, m), 1.65–2.5 (9H, m), 2.9–3.5 (3H, m), 3.6–4.6 (16H, m), 4.7–5.35 (9H, m), 6.73 (1H, d, J=8.3 Hz), 6.83 (1H, d, J=8.3 Hz), 6.85–6.95 (1H, m), 7.0–7.25 (2H, m), 7.10 (2H, d, J=9.1 Hz), 7.3–7.55 (2H, m), 7.6–7.75 (1H, m), 7.85 (2H, d, J=9.1 Hz), 8.0–8.2 (5H, m), 8.36 (1H, s), 8.7–8.9 (1H, m), 8.84 (1H, s), 9.24 (1H, s)

MASS (m/z): 1349(M$^+$-23)

Elemental Analysis Calcd. For $C_{59}H_{73}N_{12}NaO_{21}S_2$.8 H$_2$O: C 46.70, H 5.91, N 11.08 Found: C 46.64, H 5.88, N 10.90

EXAMPLE 114

IR (KBr): 1612, 1497, 1446 cm$^{-1}$

NMR (DMSO-d$_6$, δ): 0.97 (3H, d, J=6.7 Hz), 1.11 (3H, d, J=6.1 Hz), 1.6–2.5 (12H, m), 2.6–3.1 (4H, m), 3.1–3.5 (2H, m), 3.6–4.6 (16H, m), 4.6–5.45 (8H, m), 6.71 (1H, d, J=8.9 Hz), 6.78 (1H, d, J=8.9 Hz), 6.87 (1H, s), 6.98 (1H, d, J=1.8 Hz), 7.18 (3H, d, J=8.9 Hz), 7.2–7.35 (5H, m), 7.4–7.8 (3H, m), 7.97 (2H, d, J=8.9 Hz), 8.0–8.2 (1H, m), 8.09 (2H, d, J=8.4 Hz), 8.20 (2H, d, J=8.4 Hz), 8.72 (1H, s), 8.75–8.9 (1H, m)

MASS (m/z): 1310 (M$^+$-23)

Elemental Analysis Calcd. For $C_{61}H_{72}N_{11}NaO_{20}S$.9 H$_2$O: C 48.67, H 6.06, N 10.30 Found: C 48.67, H 5.89, N 10.15

EXAMPLE 115

IR (KBr): 1672, 1628, 1605, 1531, 1444 cm$^{-1}$

NMR (DMSO-d$_6$, δ): 0.97 (3H, d, J=6.5 Hz), 1.10 (3H, d, J=5.9 Hz), 1.6–2.5 (12H, m), 2.6–3.1 (4H, m), 3.1–3.5 (2H, m), 3.6–4.6 (16H, m), 4.7–5.45 (8H, m), 6.71 (1H, d, J=8.1 Hz), 6.78 (1H, d, J=8.1 Hz), 6.8–6.9 (1H, m), 6.9–7.0 (1H, m), 7.18 (3H, d, J=9.2 Hz), 7.2–7.35 (5H, m), 7.35–7.8 (3H, m), 7.87 (2H, d, J=9.2 Hz), 8.0–8.2 (5H, m), 8.72 (1H, s), 8.75–8.85 (1H, m)

MASS (m/z): 1326 (M$^+$-23)

Elemental Analysis Calcd. For $C_{61}H_{72}N_{11}NaO_{19}S_2$.9 H$_2$O: C 48.44, H 6.00, N 10.19 Found: C 48.54, H 5.91,N 10.15

EXAMPLE 116

IR (KBr): 1676, 1649, 1541, 1514, 1255 cm$^{-1}$

NMR (DMSO-D$_6$, δ): 0.97 (3H, d, J=6.7 Hz), 1.10 (3H, d, J=5.6 Hz), 1.2–2.5 (18H, m), 2.9–3.1 (1H, m), 2.9–3.6 (2H, m), 3.65–4.1 (5H, m), 4.1–4.6 (10H, m), 4.7–5.45 (8H, m), 6.72 (1H, d, J=9.3 Hz), 6.78 (1H, d, J=9.3 Hz), 6.85–6.95 (1H, m), 6.95–7.0 (1H, m), 7.1–7.25 (1H, m), 7.18 (2H, d, J=8.9 Hz), 7.4–7.8 (3H, m), 8.0–8.15 (5H, m), 8.21 (2H, d, J=8.6 Hz), 8.72 (1H, s), 8.75–8.95 (1H, m)

Mass (m/z): 1249 (M$^+$-23)

Elemental Analysis Calcd. For $C_{56}H_{69}N_{10}NaO_{21}S$.9 H$_2$O: C 46.86, H 6.11, N 9.76 Found: C 47.13, H 5.98, N 9.79

EXAMPLE 117

IR (KBr): 1659, 1628 cm$^{-1}$

NMR (DMSO-d$_6$, δ): 0.95 (3H, d, J=6.8 Hz), 1.09 (3H, d, J=6.9 Hz), 1.2–1.6 (5H, m), 1.6–2.7 (14H, m), 2.8–3.6 (3H, m), 3.6–4.1 (5H, m), 4.1–4.6 (9H, m), 4.6–5.4 (8H, m), 6.7–7.0 (4H, m), 7.1–7.2 (1H, m), 7.4–7.8 (3H, m), 7.49 (2H, d, J=7.2 Hz), 8.05–8.2 (5H, m), 8.21 (2H, d, J=8.4 Hz), 8.70 (1H, s), 8.8–8.9 (1H, m)

MASS (m/z): 1233 (M$^+$-23)

Elemental Analysis Calcd. For $C_{56}H_{69}N_{10}NaO_{20}S$.8 H$_2$O: C 48.00, H 6.11, N 9.99 Found: C 47.81, H 6.04, N 9.93

EXAMPLE 118

IR (KBR): 1664, 1635, 1605, 1531, 1510, 1444 cm$^{-1}$

NMR (DMSO-d$_6$, δ): 0.97 (3H, d, J=6.1 Hz), 1.11 (3H, d, J=6.0 Hz), 1.07–1.37 (5H, m), 1.50–2.44 (14H, m), 2.56–3.50 (11H, m), 3.65–4.60 (14H, m), 4.73–5.44 (8H, m), 6.71 (1H, d, J=8.2 Hz), 6.79 (1H, d, J=8.2 Hz), 6.87 (1H, s), 6.97 (1H, s), 7.05 (2H, d, J=8.9 Hz), 7.18 (1H, s), 7.35–7.77 (2H, m), 7.44 (1H, d, J=9.4 Hz), 7.66 (2H, d, J=8.8 Hz), 7.85 (2H, d, J=8.5 Hz), 7.95–8.21 (7H, m), 8.72 (1H, s), 8.80 (1H, d, J=7.5 Hz)

MASS (m/z): 1409.4 (M—Na$^+$)

Elemental Analysis Calcd. For $C_{66}H_{81}N_{12}NaO_{19}S_2$.7 H$_2$O: C 50.83, H 6.14, N 10.78 Found: C 51.17, H 6.03, N 10.42

EXAMPLE 119

IR (KBr): 1659, 1633, 1531, 1508, 1443 cm$^{-1}$

NMR (DMSO-d$_6$, δ): 0.97 (3H, d, J=6.6 Hz), 1.00 (3H, t, J=7.4 Hz), 1.10 (3H, d, J=5.6 Hz), 1.66–2.56 (10H, m), 2.91–3.36 (3H, m), 3.65–4.60 (14H, m), 4.00 (2H, d, J=6.4 Hz), 4.72–5.52 (8H, m), 6.70 (1H, d, J=8.1 Hz), 6.77 (1H, d, J=8.1 Hz), 6.87 (1H, s), 6.98 (1H, s), 7.07 (2H, d, J=8.9 Hz), 7.34–7.82 (3H, m), 7.73 (2H, d, J=8.8 Hz), 7.86 (2H, d, J=8.5 Hz), 8.04–8.22 (8H, m), 8.74–8.92 (2H, m)

MASS (m/z): 1301.2 (M—Na)$^+$

Elemental Analysis Calcd. For $C_{59}H_{69}N_{10}NaO_{20}S_2$.10 H$_2$O: C 47.07, H 5.96, N 9.30 Found: C 46.90, H 5.72, N 9.22

EXAMPLE 120

IR (KBr): 1659, 1635, 1533, 1510, 1444 cm$^{-1}$

NMR (DMSO-d$_6$, δ): 0.97 (3H, d, J=6.1 Hz), 1.11 (3H, d, J=5.8 Hz), 1.18 (6H, d, J=6.1 Hz), 1.74–2.69 (10H, m), 2.80–3.52 (3H, m), 3.59–4.59 (18H, m), 4.72–5.49 (8H, m), 6.71 (1H, d, J=8.1 Hz), 6.79 (1H, dd, J=8.1 and 1.6 Hz), 6.87 (1H, s), 6.98 (1H, d, J=1.6 Hz) 7.07 (2H, d, J=9.0 Hz), 7.18 (1H, s), 7.33–7.72 (3H, m), 7.68 (2H, d, J=8.8 Hz), 7.85 (2H, d, J=8.5 Hz), 7.96–8.25 (7H, m), 8.72 (1H, s), 8.80 (1H, d, J=7.5 Hz)

MASS (m/z): 1356.3 (M—Na$^+$)

Elemental Analysis Calcd. For $C_{62}h_{74}N_{11}NaO_{20}S_2$9 H$_2$O: C 48.28, H 6.01, N 9.99 Found: C 48.54, H 5.94, n 9.95

EXAMPLE 121

IR (KBr): 1659, 1635, 1606, 1529, 1518, 1444, 1419 cm$^{-1}$

NMR (DMSO-d$_6$, δ): 0.90 (6H, s) 0.97 (3H, d, J=6.7 Hz), 1.10 (3H, d, J=5.8 Hz), 1.03–2.66 (21H, m), 2.66–3.54 (8H, m), 3.65–4.58 (14H, m), 4.68–5.43 (8H, m), 6.71 (1H, d, J=8.1 Hz), 6.79 (1H, dd, J=8.1 and 1.6 Hz), 6.87 (1H, s), 6.98 (1H, d, J=1.6 Hz) 7.11 (2H, d, J=8.6 Hz), 7.18 (1H, s), 7.44 (1H, d, J=9.0 Hz), 7.48–7.77 (2H, m), 7.88 (2H, d, J=8.7 Hz), 7.95–8.20 (5H, m), 8.72 (1H, s), 8.78 (1H, d, J=7.7 Hz)

MASS (m/z): 1361.4 (M$^+$-1)

Elemental Analysis Calcd. For $C_{62}H_{82}N_{12}O_{19}S_2$.10 H$_2$O: C 48.24, H 6.66, N 10.89 Found: C 48.22, H 6.38, N 10.79

EXAMPLE 122

IR (KBr): 1659, 1633, 1531, 1510, 1444 cm$^{-1}$

NMR (DMSO-d$_6$, δ): 0.97 (3H, d, J=6.7 Hz), 1.11 (3H, d, J=5.8 Hz), 1.10–2.68 (18H, m), 2.90–3.55 (3H, m), 3.66–4.62 (15H, m), 4.72–5.52 (8H, m), 6.71 (1H, d, J=8.1 Hz), 6.79 (1H, d, J=8.1 Hz), 6.87 (1H, s), 6.98 (1H, s), 7.07 (2H, d, J=8.9 Hz), 7.19 (1H, s), 7.45 (1H, d, J=8.9 Hz), 7.47–7.77 (1H, m), 7.71 (2H, d, J=8.8 Hz), 7.86 (2H, d, J=8.5 Hz), 7.93–8.28 (8H, m), 8.54–8.92 (1H, m), 8.81 (1H, d, J=7.7 Hz)

MASS (m/z): 1341.3 (M—Na⁺)

Elemental Analysis Calcd. For $C_{62}H_{73}N_{10}NaO_{20}S_2 \cdot 9 H_2O$: C 49.33, H 5.94, N 9.28 Found: C 49.40, H 5.87, N 9.23

EXAMPLE 123

IR (KBr): 1659, 1633, 1531, 1443 cm$^{-1}$

NMR (DMSO-d$_6$, δ): 0.96 (3H, d, J=6.7 Hz), 1.12 (3H, d, J=6.1 Hz), 1.36 (3H, t, J=6.9 Hz), 1.64–2.50 (7H, m), 2.65–3.46 (3H, m), 4.13 (2H, q, J=7.0 Hz), 3.67–4.58 (14H, m), 4.70–5.34 (9H, m), 6.74 (1H, s), 6.97–7.13 (3H, m), 7.19 (1H, s), 7.33 (1H, s), 7.44 (2H, m), 7.70 (1H, brs), 7.73 (2H, d, J=8.8 Hz), 7.87 (2H, d, J=8.5 Hz), 8.00–8.22 (6H, m), 8.80 (1H, d, J=6.9 Hz), 8.84 (1H, s)

MASS (m/z): 1303.3 (M—Na⁺)

Elemental Analysis Calcd. For $C_{58}H_{67}N_{10}NaO_{21}S_2 \cdot 10 H_2O$: C 46.21, H 5.82, N 9.29 Found: C 46.47, H 5.65, n 9.29

EXAMPLE 124

IR (KBr): 1633, 1608, 1531, 1444, 1419 cm$^{-1}$

NMR (DMSO-d$_6$, δ): 0.96 (3H, d, J=6.7 Hz), 1.12 (3H, d, J=5.5 Hz), 1.05–1.36 (5H, m), 1.47–2.50 (13H, m), 2.58–3.46 (11H, m), 3.64–4.60 (14H, m), 4.70–5.34 (9H, m), 6.74 (1H, d, J=8.2 Hz), 6.83 (1H, d, J=8.2 Hz), 6.89 (1H, s), 7.08 (2H, d, J=8.7 Hz), 7.01–7.25 (2H, m), 7.35–7.74 (3H, m), 7.86 (2H, d, J=8.8 Hz), 7.98–8.26 (5H, m), 8.53–8.86 (1H, m), 8.85 (1H, s)

MASS (m/z): 1349.05 (M—Na⁺)

Elementary Analysis Calcd. For $C_{60}H_{77}N_{12}NaO_{20}S_2 \cdot 6 H_2O$: C 48.64, H 6.05, N 11.34 Found: C 48.38, H 6.09, N 11.15

EXAMPLE 125

IR (KBr): 1658, 1633, 1606, 1531, 1444, 1419 cm$^{-1}$

NMR (DMSO-d$_6$, δ): 0.90 (3H, d, J=6.7 Hz), 0.97 (3H, d, J=6.6 Hz), 1.10 (3H, d, J=5.9 Hz), 1.31–2.51 (18H, m), 2.51–2.70 (4H, m), 2.88–3.46 (7H, m), 3.55–4.59 (14H, m), 4.69–5.56 (8H, m), 6.70 (1H, d, J=8.1 Hz), 6.77 (1H, d, J=8.1 Hz), 6.86 (1H, s), 6.97 (1H, s) 7.08 (2H, d, J=8.7 Hz), 7.09–7.78 (3H, m), 7.86 (2H, d, J=8.7 Hz), 7.96–8.18 (6H, m), 8.63–8.92 (1H, s), 8.78 (1H, d, J=6.9 Hz)

MASS (m/z): 1347.3 (M—Na⁺)

Elemental Analysis Calcd. For $C_{61}H_{79}N_{12}NaO_{19}S_2 \cdot 11 H_2O$: C 46.68, H$_{6.49}$, N 10.71 Found: C 46.67, H 6.19, N 10.64

EXAMPLE 126

IR (KBr): 1658, 1633, 1606, 1531, 1518, 1444, 1417 cm$^{-1}$

NMR (DMSO-d$_6$, δ): 0.86 (3H, d, J=6.4 Hz), 0.87–1.44 (2H, m), 0.97 (3H, d, J=6.7 Hz), 1.10 (3H, d, J=5.9 Hz), 1.60–2.55 (16H, m), 2.55–2.73 (4H, m), 2.96–3.54 (7H, m), 3.65–4.60 (14H, m), 4.70–5.28 (8H, m), 6.71 (1H, d, J=8.3 Hz), 6.79 (1H, dd, J=8.3 and 1.7 Hz), 6.87 (1H, s), 6.98 (1H, d, J=1.7 Hz), 7.07 (2H, d, J=9.0 Hz), 7.18 (1H, s), 7.44 (1H, d, J=8.4 Hz), 7.50–7.78 (2H, m), 7.85 (2H, d, J=8.9 Hz), 7.95–8.24 (5H, m), 8.72 (1H, s), 8.79 (1H, d, J=7.1 Hz)

MASS (m/z): 1347.3 (M—Na⁺)

Elementary Analysis Calcd. For $C_{61}H_{79}N_{12}NaO_{19}S_2 \cdot 11 H_2O$: C 46.68, H 6.49, N 10.71 Found: C 46.77, H 6.20, N 10.65

EXAMPLE 127

IR (KBr): 1633, 1533, 1516, 1443, cm$^{-1}$

NMR (DMSO-d$_6$, δ): 0.97 (3H, d, J=6.7 Hz), 1.10 (3H, d, J=5.6 Hz), 1.18 (3H, t, J=7.0 Hz), 173–2.52 (8H, m), 2.86–3.38 (3H, m), 3.52 (2H, q, J=7.0 Hz), 3.63–4.60 (16H, m), 4.53 (2H, s), 4.71–5.53 (6H, m), 6.68 (1H, d, J=8.0 Hz), 6.76 (1H, d, J=7.8 Hz), 6.87 (1H, s), 6.98 (1H, s), 7.28–7.83 (3H, m), 7.47 (2H, d, J=8.5 Hz), 7.77 (2H, d, J=8.2 Hz), 7.92 (2H, d, J=8.5 Hz), 8.00–8.25 (8H, m), 8.70–8.85 (2H, m)

MASS (m/z): 1301.3 (M—Na⁺)

Elementary Analysis Calcd. For $C_{59}H_{69}N_{10}NaO_{20}S_2 \cdot 9 H_2O$: C 47.64, H 5.89, N 9.42 Found: C 47.92, H 5.84, N 9.39

EXAMPLE 128

IR (KBr): 1659, 1633, 1533, 1514, 1443, cm$^{-1}$

NMR (DMSO-d$_6$, δ): 0.97 (3H, d, J=6.7 Hz), 1.10 (3H, d, O=5.9 Hz), 1.75–2.53 (8H, m), 2.81–3.36 (3H, m), 3.28 (3H, s), 3.47–4.64 (20H, m), 4.56 (2H, s), 4.74–5.60 (6H, m), 6.69 (1H, d, J=8.3 Hz), 6.77 (1H, d, J=8.3 Hz), 6.87 (1H, s), 6.98 (1H, s), 7.26–7.84 (3H, m), 7.47 (2H, d, J=8.4 Hz), 7.78 (2H, d, J=8.3 Hz), 7.92 (2H, d, J=8.5 Hz), 8.03–8.28 (8H, m), 8.74–8.90 (2H, m)

MASS (m/z): 1331.3 (M-Na⁺)

Elemental Analysis Calcd. For $C_{60}H_{71}N_{10}NaO_{21}S_2 \cdot 9 H_2O$: C 47.49, H 5.91, N 9.23 Found: C 47.36, H 5.81, N 9.16

EXAMPLE 129

IR (KBr): 1668, 1651, 1632, 1539, 1512 cm$^{-1}$

NMR (DMSO-d$_6$, δ): 0.97 (3H, d, J=6.7 Hz), 1.10–1.12 (3H, m) 1.12 (3H, t, J=7.0 Hz), 1.70–2.50 (10H, m), 2.80–3.30 (3H, m), 3.41 (2H, q, J=7.0 Hz), 3.53 (2H, t, J=6.4 Hz), 3.66–4.60 (14H, m), 4.10 (2H, t, J=6.4 Hz), 4.70–5.52 (8H, m), 6.71 (1H, d, J=8.1 Hz), 6.79 (1H, dd, J=8.1 and 1.6 Hz), 6.87 (1H, s), 6.98 (1H, d, J=1.6 Hz), 7.08 (2H, d, J=8.8 Hz), 7.18 (1H, s), 7.322–7.68 (3H, m), 7.73 (2H, d, J=8.8 Hz), 7.87 (2H, d, J=8.5 Hz), 8.04–8.24 (7H, m), 8.56–8.91 (1H, m), 8.81 (1H, d, J=7.9 Hz)

MASS (m/z): 1345.3 (M—Na⁺)

Elementary Analysis Calcd. For $C_{61}H_{73}N_{10}NaO_{21}S_2 \cdot 10 H_2O$: C 47.28, H 6.05, N 9.04 Found: C 47.44, H 5.91, N 9.02

EXAMPLE 130

IR (KBr): 1649, 1537, 1512 1443 cm$^{-1}$

NMR (DMSO-d$_6$, δ): 0.97 (3H, d, J=6.6. Hz), 1.10 (3H, d, J=5.7 Hz), 1.74–2.22 (10H, m), 2.80–3.30 (3H, m), 3.27 (3H, s), 3.50 (2H, t, J=6.3 Hz), 3.65–4.60 (14H, m), 4.09 (2H, t, J=6.4 Hz), 4.60–5.58 (8H, m), 6.70 (1H, d, J=8.1 Hz), 6.87(1H, s), 6.99 (1H, s), 7.07 (2H, d, J=8.9 Hz), 7.10–7.72 (3H, m), 7.73 (2H, d, J=8.8 Hz), 7.87 (2H, d, J=8.5 Hz), 8.00–8.35 (8H, m), 8.64–8.96 (2H, m)

MASS (m/z): 1331.3 (M—Na⁺)

Elemental Analysis Calcd. For $C_{60}H_{71}N_{10}NaO_{21}S_2 \cdot 9 H_2O$: C 47.49, H 5.91, N 9.23 Found: C 47.39, H, 5.75, N 9.16

EXAMPLE 131

IR (KBr): 3349.7, 1633.4, 1537.0, 1515.8, 1442.5, 1419.4 cm$^{-1}$

NMR (DMSO-d$_6$, δ): 0.97 (3H, d, J=6.8 Hz), 1.10 (3H, d, J=5.3 Hz), 1.7–2.5 (12H, m), 2.94 (3H, s), 2.94–4.6 (21H, m), 4.7–5.4 (8H, m), 6.71 (1H, d, J=8 Hz), 6.79 (1H, dd, J=8.4 and 1.7 Hz), 6.88 (1H, brs), 6.97 (1H, brs), 7.15 (2H, d, J=9 Hz), 7.17 (1H, brs), 7.45 (4H, s), 7.4–7.8 (3H, m), 7.87 (2H, d, J=8.8 Hz), 8.02 (4H, s), 8.02–8.07 (1H, m), 8.72 (1H, s), 8.78 (1H, d, J=7.6 Hz)

MASS (m/z): 1390.23 (M—Na)

Elementary Analysis Calcd. For $C_{62}H_{73}ClN_{11}O_{20}S_2Na \cdot 7 H_2O$: C 48.32, H 5.69, N 10.00 Found: C 48.15, H 5.51, N 9.93

EXAMPLE 132

IR (KBr): 1633.4, 1535.1, 1523.5, 1442.5, 1419.4, 1276.6, 1243.9 cm$^{-1}$

NMR (DMSO-d$_6$, δ): 0.96 (3H, d, J=6.8 Hz), 1.12 (3H, d, J=6 Hz), 1.7–2.5 (10H, m), 2.94 (3H, s), 2.9–5.4 (31H, m), 6.73 (1H, d, J=8.3 Hz), 6.81–6.85 (1H, m), 6.89 (1H, brs), 7.05 (1H, brs), 7.15 (2H, d, J=8.7 Hz), 7.17 (1H, brs), 7.45 (4H, s), 7.3–7.7 (3H, m), 7.87 (2H, d, J=8.7 Hz), 8.06 (4H, s), 8.0–8.15 (1H, m), 8.7–9.0 (2H, m)

MASS (m/z): 1405.8 (M—Na$^+$)

Elemental Analysis Calcd. For C$_{62}$H$_{73}$ClN$_{11}$O$_{21}$S$_2$Na.6H$_2$O: C 48.39, H 5.57, N 10.01 Found: C 48.39, H 5.52, N 9.90

EXAMPLE 133

To a solution of 4-[2-[4-(4-piperidin-1-yl-butyloxy)phenyl]imidazo[2,1-b][1,2,3]thiadiazol-6-yl]benzoic acid (147 mg), 1-ethyl-3-(3'-dimethylaminopropyl)carbodiimide hydrochloride (WSCD.HCl) (74 mg) and 1-hydroxybenzotriazole (66 mg) in N,N-dimethylformamide (4 ml) was added diisopropylethylamine (0.5 ml). After stirring for 24 hours at ambient temperature, the Starting Compound (133) (200 mg) was added to the solution and the mixture was stirred for 8 hours at ambient temperature, The reaction mixture was pulverized with ethyl acetate. The precipitate was collected by filtration, and dried under reduced pressure. The powder was dissolved in water, and subjected to column chromatography on ion exchange resin (DOWEX-50WX4(Trademark: prepared by Dow Chemical)) eluting with water. The fractions containing the object compound were combined, and subjected to column chromatography on ODS (YNS-gel.ODS-AM.S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give Object Compound (133) (30 mg).

IR (KBr): 3326, 2933, 1666, 1631, 1523, 1463, 1367, 1257 cm$^{-1}$

NMR (DMSO-d$_6$, δ): 0.95 (3H, d, J=6.7 Hz), 1.11 (3H, d, J=5.7 Hz), 1.3–1.6 (8H, m), 1.6–2.15 (5H, m), 2.2–2.5 (10H, m), 2.97 (2H, m), 3.20 (1H, m), 3.74 (2H, m), 3.8–4.6 (14H, m), 4.6–5.4 (9H, m), 6.74 (1H, d, J=8.2 Hz), 6.83 (1H, d, J=8.2 Hz), 6.88 (1H, s), 7.04 (1H, s), 7.14 (2H, d, J=8.8 Hz), 7.23 (1H, m), 7.3–7.5 (2H, m), 7.66 (1H, m), 7.88 (2H, d, J=8.8 Hz), 7.95 (4H, s), 8.07 (1H, d, J=7.8 Hz), 8.58 (1H, d, J=7.8 Hz), 8.85 (1H, s), 8.95 (1H, s)

MASS (m/z): 1377.25 (M—Na$^+$)

The following compounds [Examples 134 to 159] were obtained in a manner similar to that of Example 133.

EXAMPLE 131

IR (KBr): 3353, 2940, 1666, 1631, 1523, 1465, 1257 cm$^{-1}$

NMR (DMSO-d$_6$, δ): 0.95 (3H, d, J=6.7 Hz), 1.11 (3H, d, J=5.7 Hz), 1.3–1.6 (10H, m), 1.6–2.15 (5H, m), 2.2–2.5 (10H, m), 2.97 (2H, m), 3.20 (1H, m), 3.74 (2H, m), 3.8–4.6 (14H, m), 4.6–5.4 (9H, m), 6.74 (1H, d, J=8.2 Hz), 6.83 (1H, d, J=8.2 Hz), 6.89 (1H, s), 7.05 (1H, s), 7.14 (2H, d, J=8.8 Hz), 7.23 (1H, m), 7.3–7.5 (2H, m), 7.67 (1H, m), 7.90 (2H, d, J=8.8 Hz), 7.96 (4H, s), 8.07 (1H, d, J=7.8 Hz), 8.57 (1H, d, J=7.8 Hz). 8.85 (1H, s), 8.95 (1H, s)

MASS (m/z): 1391.13 (M—Na$^+$)

EXAMPLE 135

IR (KBr): 3349, 2939, 1666, 1633, 1523, 1440, 1257 cm$^{-1}$

NMR (DMSO-d$_6$, δ): 0.95 (3H, d, J=6.7 Hz), 1.11 (3H, d, J=5.7 Hz), 1.3–1.6 (12H, m), 1.6–2.15 (5H, m), 2.214 2.5 (10H, m), 2.97 (2H, m), 3.20 (1H, m) 3.74 (2H, m), 3.8–4.6 (14H, m), 4.6–5.4 (9H, m), 6.74 (1H, d, J=8.2 Hz), 6.83 (1H, d, J=8.2 Hz), 6.89 (1H, s), 7.05 (1H, s), 7.14 (2H, d, J=8.8 Hz), 7.23 (1H, m), 7.3–7.5 (2H, m), 7.67 (1H, m), 7.90 (2H, d, J=8.8 Hz), 7.96 (4H, s), 8.07 (1H, d, J=7.8 Hz), 8.60 (1H, d, J=7.8 Hz), 8.85 (1H, s), 8.95 (1H, s)

MASS (m/z): 1405.31 (M—Na$^+$)

Elemental Analysis Calcd. For C$_{63}$H$_{81}$N$_{12}$NaO$_{21}$S$_2$.8H$_2$O: C 48.09, H 6.21, N 10.68 Found: C 48.04, H 6.15, N 10.49

EXAMPLE 136

IR (KBr): 3351, 2939, 1658, 1633, 1527, 1465, 1444, 1257 cm$^{-1}$

NMR (DMSO-d$_6$, δ): 0.95 (3H, d, J=6.7 Hz), 1.11 (3H, d, J=5.7 Hz), 1.3–1.6 (4H, m), 1.6–2.15 (5H, m), 2.2–2.5 (10H, m), 2.97 (2H, m), 3.20 (1H, m), 3.56 (4H, t, J=4.6 Hz), 3.71 (2H, m), 3.8–4.6 (14H, m), 4.6–5.4 (9H, m), 6.74 (1H, d, J=8.2 Hz), 6.85 (1H, d, J=8.2 Hz), 6.93 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz), 7.96 (4H, s), 8.07 (1H, d, J=7.8 Hz), 8.57 (1H, d, J=7.8 Hz), 8.85 (1H, s), 8.95 (1H, s)

MASS (m/z): 1392.65 (M-Na$^+$)

Elemental Analysis Calcd. For C$_{61}$H$_{77}$N$_{12}$NaO$_{22}$S$_3$.10H$_2$O: C 45.86, H 6.12, N 10.52 Found: C 45.75, H 5.83, N 10.46

EXAMPLE 137

IR (KBr): 3347, 2935, 1666, 1631, 1523, 1463, 1255, 1078, 1047 cm$^{-1}$

NMR (DMSO-d$_6$, δ): 0.95 (3H, d, J=6.7 Hz), 1.03 (6H, d, J=6.3 Hz), 1.11 (3H, d, J=5.7 Hz), 1.3–1.6 (6H, m), 1.6–2.15 (5H, m), 2.2–2.5 (6H, m), 2.71 (2H, d, J=10.2 Hz), 2.97 (2H, m), 3.20 (1H, m) 3.56 (2H, m) 3.71 (2H, m), 3.8–4.6 (14H, m), 4.6–5.4 (9H, m), 6.74 (1H, d, J=8.2 Hz), 6.85 (1H, d, J=8.2 Hz), 6.93 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz), 7.96 (4H, s), 8.07 (1H, d, J=7.8 Hz), 8.57 (1H, d, J=7.8 Hz), 8.85 (1H, s), 8.95 (1H, s)

MASS (m/z): 1420.94 (M-Na$^+$)

Elemental Analysis Calcd. For C$_{63}$H$_{81}$N$_{12}$NaO$_{22}$S$_2$.8H$_2$O: C 47.60, H 6.15, N 10.57 Found: C 47.84, H 6.06, N 10.50

EXAMPLE 138

IR (KBr): 3347, 2937, 1666, 1631, 1521, 1465, 1257, 1074, 1047 cm$^{-1}$

NMR (DMSO-d$_6$, δ): 0.95 (3H, d, J=6.7 Hz), 1.03 (6H, d, J=6.3 Hz), 1.08 (3H, d, J=5.7 Hz), 1.3–1.6 (6H, m), 1.6–2.15 (5H, m), 2.2–2.5 (6H, m), 2.45 (2H, m), 2.71 (2H, d, J=10.2 Hz), 2.97 (2H, m), 3.20 (1H, m) 3.56 (2H, m), 3.71 (2H, m), 3.8–4.6 (13H, m), 4.6–5.4 (8H, m), 6.68 (1H, d, J=8.2 Hz), 6.76 (1H, d, J=8.2 Hz), 6.86 (1H, s), 6.97 (1H, s), 7.14 (2H, d, J=8.9 Hz), 7.23 (1H, m), 7.3–7.5 (2H, m), 7.67 (1H, m), 7.90 (2H, m), 7.96 (4H, s), 8.07 (1H, m), 8.60 (1H, m), 8.85 (1H, s), 8.95 (1H, s)

MASS (m/z): 1405.74 (M-Na$^+$)

Elemental Analysis Calcd. For C$_{63}$H$_{81}$N$_{12}$NaO$_{21}$S$_2$.9H$_2$O: C 47.54, H 6.27, N 10.56 Found: C 47.68, H 6.21, N 10.50

EXAMPLE 139

MASS (m/z): 1435.29 (M-Na⁺)

EXAMPLE 140

IR (KBr): 3328, 2939, 1664, 1633, 1525, 1465, 1442, 1257, 1047 cm$^{-1}$

NMR (DMSO-d$_6$, δ): 0.95 (3H, d, J=6.7 Hz), 1.10 (3H, d, J=5.7 Hz), 1.3–1.6 (6H, m), 1.6–2.15 (5H, m), 2.2–2.5 (6H, m), 2.5–2.7 (2H, m), 2.59 (4H, s), 2.97 (2H, m), 3.20 (1H, m) 3.73 (2H, m), 3.8–4.6 (14H, m), 4.6–5.4 (9H, m), 6.69 (1H, d, J=8.2 Hz), 6.80 (1H, d, J=8.2 Hz), 6.88 (1H, s), 7.05 (1H, s), 7.14 (2H, d, J=8.8 Hz), 7.23 (1H, m), 7.3–7.5 (2H, m), 7.67 (1H, m), 7.90 (2H, d, J=8.8 Hz), 7.96 (4H, s), 8.07 (1H, d, J=7.8 Hz), 8.57 (1H, d, J=7.8 Hz), 8.85 (1H, s), 8.95 (1H, s)

MASS (m/z): 1408.94 (M-Na⁺)

Elemental Analysis Calcd. For C$_{61}$H$_{77}$N$_{12}$NaO$_{21}$S$_3$.10H$_2$O: C 45.40, H 6.06, N 10.42 Found: C 45.49, H 5.59, N 10.26

EXAMPLE 141

IR (KBr): 3340, 2939, 1631, 1523, 1465, 1442, 1257, 1047 cm$^{-1}$

NMR (DMSO-d$_6$, δ): 0.96 (3H, d, J=6.7 Hz), 1.10 (3H, d, J=5.7 Hz), 1.3–1.6 (4H, m), 1.6–2.15 (5H, m), 2.2–2.5 (4H, m), 2.97 (2H, m), 3.20 (1H, m) 3.23 (3H, s), 3.34 (2H, t J=6.2 Hz), 3.73 (2H, m), 3.8–4.6 (14H, m), 4.6–5.4 (9H, m), 6.69 (1H, d, J=8.2 Hz), 6.76 (1H, d, J=8.2 Hz), 6.88 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz), 7.95 (4H, s), 8.07 (1H, m), 8.57 (1H, m), 8.85 (1H, s), 8.95 (1H, s)

MASS (m/z): 1338.33 (M-Na⁺)

Elemental Analysis Calcd. For C$_{58}$H$_{72}$N$_{11}$NaO$_{22}$S$_2$.10 H$_2$O: C 45.16, H 6.01, N 9.99 Found: C 45.39, H 5.80, N 10.02

EXAMPLE 142

IR (KBr): 3340, 2935, 1648, 1631, 1527, 1515, 1456, 1257, 1047 cm$^{-1}$

NMR (DMSO-d$_6$, δ): 0.96 (3H, d, J=6.7 Hz), 1.10 (3H, d, J=5.7 Hz), 1.3–1.6 (4H, m), 1.6–2.15 (5H, m), 2.2–2.5 (6H, m), 2.97 (2H, m), 3.20 (1H, m) 3.23 (3H, s), 3.34 (2H, t J=6.2 Hz), 3.74 (2H, m), 3.8–4.6 (13H, m), 4.6–5.4 (8H, m), 6.68 (1H, d, J=8.2 Hz), 6.76 (1H, d, J=8.2 Hz), 6.86 (1H, s), 6.97 (1H, s), 7.14 (2H, d, J=8.9 Hz), 7.23 (1H, m), 7.3–7.5 (2H, m), 7.67 (1H, m), 7.90 (2H, m), 7.96 (4H, s), 8.07 (1H, m), 8.60 (1H, m), 8.85 (1H, s), 8.95 (1H, s)

MASS (m/z): 1322.3 (M-Na⁺)

Elemental Analysis Calcd. For C$_{58}$H$_{72}$N$_{11}$NaO$_{21}$S$_2$.9 H$_2$O: C 46.18, H$_{6.01}$, N 10.21 Found: C 45.96, H, 5.86, N 10.12

EXAMPLE 143

IR (KBr): 3349, 2937, 1666, 1631, 1523, 1465, 1257, 1047 cm$^{-1}$

NMR (DMSO-d$_6$, δ): 0.96 (3H, d, J=6.7 Hz), 1.10 (3H, d, J=5.7 Hz), 1.3–1.6 (6H, m), 1.6–2.15 (5H, m), 2.2–2.5 (4H, m), 2.97 (2H, m), 3.20 (1H, m) 3.23 (3H, s), 3.34 (2H, t J=6.2 Hz), 3.73 (2H, m), 3.8–4.6 (14H, m), 4.6–5.4 (9H, m), 6.69 (1H, d, J=8.2 Hz), 6.76 (1H, d, J=8.2 Hz), 6.88 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz), 7.95 (4H, s), 8.07 (1H, m), 8.57 (1H, m), 8.85 (1H, s), 8.95 (1H, s)

MASS (m/z): 1352.48 (M-Na⁺)

Elementary Analysis Calcd. For C$_{59}$H$_{74}$N$_{11}$NaO$_{22}$S$_2$.12 H$_2$O: C 44.50, H 6.20, N 9.67 Found: C 44.74, H 5.71, N 9.70

EXAMPLE 144

IR (KBr): 3330, 29313, 1666, 1631, 1523, 1465, 1257, 1047 cm$^{-1}$

NMR (DMSO-d$_6$, δ): 0.96 (3H, d, J=6.7 Hz), 1.10 (3H, d, J=5.7 Hz), 1.3–1.6 (8H, m), 1.6–2.15 (5H, m), 2.2–2.5 (4H, m), 2.97 (2H, m), 3.20 (1H, m) 3.23 (3H, s), 3.34 (2H, t J=6.2 Hz), 3.73 (2H, m), 3.8–4.6 (14H, m), 4.6–5.4 (9H, m), 6.69 (1H, d, J=8.2 Hz), 6.76 (1H, d, J=8.2 Hz), 6.88 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz),7.95 (4H, s), 8.07 (1H, m), 8.57 (1H, m), 8.85 (1H, s), 8.95 (1H, s)

MASS (m/z): 1366.46 (M-Na⁺)

Elemental Analysis Calcd. For C$_{60}$H$_{76}$N$_{11}$NaO$_{22}$S$_2$.13 H$_2$O: C 44.36, H 6.33, N 9.48 Found: C 44.40, H 5.88, N 9.30

EXAMPLE 145

IR (KBr): 3324, 2933, 1666, 1631, 1523, 1465, 1257, 1047 cm$^{-1}$

NMR (DMSO-d$_6$, δ): 0.96 (3H, d, J=6.7 Hz), 1.10 (3H, d, J=5.7 Hz), 1.3–1.6 (10H, m), 1.6–2.15 (5H, m), 2.2–2.5 (4H, m), 2.97 (2H, m), 3.20 (1H, m) 3.23 (3H, s), 3.34 (2H, t J=6.2 Hz), 3.73 (2H, m), 3.8–4.6 (14H, m), 4.6–5.4 (9H, m), 6.69 (1H, d, J=8.2 Hz),6.76 (1H, d, J=8.2 Hz), 6.88 (1H, s), 7.04 (1H, s), 7.14 (2H, d, J=8.8 Hz), 7.23 (1H, m), 7.3–7.5 (2H, m), 7.67 (1H, m), 7.90 (2H, d, J=8.8 Hz), 7.95 (4H, s), 8.07 (1H, m), 8.57 (1H, m), 8.85 (1H, s), 8.95 (1H, s)

MASS (m/z): 1380.30 (M-Na⁺)

Elemental Analysis Calcd. For C$_{61}$H$_{78}$N$_{11}$NaO$_{22}$S$_2$.10 H$_2$O: C 46.24, H 6.23, N 9.72 Found: C 46.29, H 6.02, N 9.71

EXAMPLE 146

IR (KBr): 3351, 3330, 2935, 1664, 1633, 1606, 1529, 1465, 1446, 1267, 1238 cm$^{-1}$

NMR (DMSO-d$_6$, δ): 0.96 (3H, d, J=6.4 Hz), 1.10 (3H, d, J=5.4 Hz), 1.60 (6H, s), 1.7–2.1 (3H, m), 2.1–2.6 (4H, m), 2.98 (2H, m), 3.20 (1H, m) 3.4 (4H, m), 3.73 (2H, m), 3.8–4.6 (12H, m), 4.6–5.6 (9H, m), 6.70 (1H, d, J=8.2 Hz), 6.81 (1H, d, J=8.2 Hz), 6.89 (1H, s), 7.05 (1H, s), 7.06 (2H, d, J=8.9 Hz), 7.2–7.7 (4H, m), 7.74 (2H, d, J=8.9 Hz), 7.94 (4H, s), 8.07 (1H, m), 8.56 (1H, m), 8.79 (1H, s), 8.95 (1H, s)

MASS (m/z): 1304.84 (M-Na⁺)

Elemental Analysis Calcd. For C$_{57}$H$_{69}$N$_{12}$NaO$_{20}$S$_2$.7 H$_2$O: C 47.04, H 5.75, N 11.55 Found: C 47.32, H 5.75, N 11.67

EXAMPLE 147

IR (KBr): 3351, 3330, 2933, 1668, 1631, 1515, 1454, 1268, 1236 cm$^{-1}$

NMR (DMSO-d$_6$, δ): 0.96 (3H, d, J=6.4 Hz), 1.11 (3H, d, J=5.4 Hz), 1.6–2.1 (3H, m), 2.1–2.6 (4H, m), 2.98 (2H, m), 3.20 (1H, m), 3.4 (4H, m), 3.76 (6H, m), 3.8–4.6 (12H, m), 4.6–5.6 (9H, m), 6.70 (1H, d, J=8.2 Hz), 6.81 (1H, d, J=8.2 Hz), 6.89 (1H, s), 7.05 (1H, s), 7.06 (2H, d, J=8.9 Hz), 7.2–7.7 (4H, m), 7.74 (2H, d, J=8.9 Hz), 7.94 (4H, s), 8.07 (1H, m), 8.56 (1H, m), 8.79 (1H, s), 8.95 (1H, s)

MASS (m/z): 1306.85 (M-Na⁺)

EXAMPLE 148

IR (KBr): 3355, 2975, 2935, 1666, 1631, 1610, 1523, 1465, 1241 cm$^{-1}$

NMR (DMSO-d$_6$, δ): 0.96 (3H, d, J=6.7 Hz), 1.10 (3H, d, J=5.7Hz), 1.18 (6H, d, J=6.2Hz), 1.6–2.1 (3H, m), 2.1–2.6

(6H, m), 2.98 (2H, m), 3.20 (1H, m) 3.4 (2H, m), 3.73 (4H, m), 3.8–4.6 (12H, m), 4.6–5.6 (9H, m), 6.70 (1H, d, J=8.2Hz), 6.81 (1H, d, J=8.2Hz), 6.89 (1H, s), 7.04 (1H, s), 7.11 (2H, d, J=8.9Hz), 7.2–7.7 (4H, m), 7.78 (2H, d, J=8.9Hz), 7.95 (4H, s), 8.07 (1H,m), 8.54 (1H, m), 8.80 (1H, s), 8.95 (1H, s)

MASS (m/z): 1334.95 (M−Na$^+$)

Elemental Analysis Calcd. For $C_{58}H_{71}N_{12}NaO_{21}S_2 \cdot 10H_2O$:

C 45.25, H 5.96, N 10.92

Found: C 45.25, H 5.76, N 10.94

EXAMPLE 149

IR (KBr): 3355, 2971, 2933, 1668, 1648, 1631, 1610, 1535, 1515, 1463, 1241 cm$^{-1}$

NMR (DMSO-d$_6$, δ): 0.96 (3H, d, J=6.7Hz), 1.10 (3H, d, J=5.7Hz), 1.18 (6H, d, J=6.2Hz), 1.6–2.1 (3H, m), 2.1–2.6 (8H, m), 2.98 (2H, m), 3.20 (1H, m) 3.4 (2H, m), 3.73 (4H, m), 3.8–4.6 (11H, m), 4.6–5.6 (8H, m), 6.70 (1H, d, J=8.2Hz), 6.81 (1H, d, J=8.2Hz), 6.89 (1H, s), 6.96 (1H, s), 7.12 (2H, d, J=8.9Hz), 7.2–7.7 (4H, m), 7.78 (2H, d, J=8.9Hz), 7.95 (4H, s), 8.12 (1H,m), 8.56 (1H, m), 8.80 (1H, s), 8.95 (1H, s)

MASS (m/z): 1319.3 (M−Na$^+$)

Elemental Analysis Calcd. For $C_{58}H_{71}N_{12}NaO_{20}S_2 \cdot 9H_2O$:

C 46.27, H 5.96, N 11.16

Found: C 46.03, H 5.85, N 11.02

EXAMPLE 150

IR (KBr): 3353, 2927, 1666, 1631, 1608, 1535, 1465, 1432, 1265, 1193, 1047 cm$^{-1}$

NMR (DMSO-d$_6$, δ): 0.96 (3H, d, J=6.7Hz), 1.10 (3H, d, J=5.7Hz), 1.6–2.1 (3H, m), 2.1–2.6 (4H, m), 2.66 (4H, m), 2.98 (2H, m), 3.20 (1H, m), 3.73 (2H, m), 3.79 (4H, m), 3.8–4.6 (12H, m), 4.6–5.6 (9H, m), 6.72 (1H, d, J=8.2Hz), 6.81 (1H, d, J=8.2Hz), 6.88 (1H, s), 7.04 (1H, s), 7.11 (2H, d, J=8.9Hz), 7.2–7.7 (4H, m), 7.77 (2H, d, J=8.9Hz), 7.94 (4H, s), 8.07 (1H,m), 8.54 (1H, m), 8.80 (1H, s), 8.95 (1H, s)

MASS (m/z): 1322.96 (M−Na$^+$)

EXAMPLE 151

IR (KBr): 3353, 1666, 1629, 1523, 1454, 1378, 1268, 1238 cm$^{-1}$

NMR (DMSO-d$_6$, δ): 0.9–1.4 (9H, m), 1.4–2.1 (3H, m), 2.1–2.6 (10H, m), 2.98 (2H, m), 3.20 (1H, m), 3.4 (4H, m), 3.74 (2H, m), 3.8–4.6 (12H,m), 4.6–5.6 (9H, m), 6.72 (1H, d, J=8.2Hz), 6.81 (1H, d, J=8.2Hz), 6.88 (1H, s), 7.05 (1H, s), 7.09 (2H, d, J=8.9Hz), 7.2–7.7 (4H, m), 7.78 (2H, d, J=8.9Hz), 7.94 (4H, s), 8.07 (1H, m), 8.54 (1H, m), 8.80 (1H, s), 8.95 (1H, s)

MASS (m/z): 1334.63 (M−Na$^+$)

EXAMPLE 152

IR (KBr): 3353, 2927, 1675, 1650, 1538, 1513, 1456, 1396, 1340, 1238, 1047 cm$^{-1}$

NMR (DMSO-d$_6$, δ): 0.95 (3H, d, J=6.7Hz), 1.0–1.4 (8H, m), 1.58 (1H, m), 1.78 (4H, m), 1.8–2.1 (3H, m), 2.1–2.6 (5H, m), 2.63 (4H, m), 2.98 (2H, m), 3.20 (1H, m), 3.4 (4H, m), 3.74 (2H, m), 3.8–4.6 (12H, m), 4.6–5.6 (9H, m), 6.72 (1H, d, J=8.2Hz), 6.81 (1H, d, J=8.2Hz), 6.88 (1H, s), 7.04 (1H, s), 7.08 (2H, d, J=8.9Hz), 7.2–7.7 (4H, m), 7.77 (2H, d, J=8.9Hz), 7.94 (4H, s), 8.10 (1H, m), 8.58 (1H, m), 8.80 (1H, s), 8.95 (1H, s)

MASS (m/z): 1388.3 (M−Na$^+$)

EXAMPLE 153

IR (KBr): 3353, 2931, 1668, 1650, 1631, 1537, 1513, 1456, 1396, 1270, 1238, 1197 cm$^{-1}$

NMR (DMSO-d$_6$, δ): 0.97 (3H, d, J=6.7Hz), 1.0–1.4 (8H, m), 1.58 (1H, m), 1.75 (4H, m), 1.7–2.1 (3H, m), 2.1–2.6 (7H, m), 2.63 (4H, m), 2.98 (2H, m), 3.20 (1H, m), 3.4 (4H, m), 3.74 (2H, m), 3.8–4.6 (11H, m), 4.6–5.6 (8H, m), 6.72 (1H, d, J=8.2Hz), 6.81 (1H, d, J=8.2Hz), 6.88 (1H, s), 7.04 (1H, s), 7.08 (2H, d, J=8.9Hz), 7.2–7.7 (4H, m), 7.77 (2H, d, J=8.9Hz), 7.94 (4H, s), 8.11 (1H, m), 8.58 (1H, m), 8.80 (1H, s), 8.95 (1H, s)

MASS (m/z): 1372.3 (M−Na$^+$)

EXAMPLE 154

IR (KBr): 3353, 2935, 1666, 1633, 1540, 1513, 1461, 1440, 1247 cm$^{-1}$

NMR (DMSO-d$_6$, δ): 0.9–1.1 (6H, m), 1.10 (3H, d, J=5.7Hz), 1.47 (2H, m), 1.6–2.1 (5H, m), 2.1–2.6 (4H, m), 2.98 (2H, m), 3.20 (1H, m), 3.71 (2H, m), 3.8–4.6 (14H, m), 4.6–5.6 (9H, m), 6.67 (1H, d, J=8.2Hz), 6.79 (1H, d, J=8.2Hz), 6.88 (1H, s), 6.99 (2H, d, J=8.8Hz), 7.05 (1H, s), 7.2–7.7 (4H, m), 7.82 (2H, d, J=8.8Hz), 7.97 (4H, s), 8.10 (1H,m), 8.58 (1H, m), 8.66 (1H, s), 8.78 (1H, s)

MASS (m/z): 1294.53 (M−Na$^+$)

Elemental Analysis Calcd. For $C_{56}H_{68}N_{11}NaO_{21}S_2 \cdot 9H_2O$:

C 45.43, H 5.85, N 10.41

Found: C 45.52, H 5.81, N 10.41

EXAMPLE 155

IR (KBr): 3361, 2935, 1650, 1631, 1540, 1515, 1463, 1442, 1247, 1047 cm$^{-1}$

NMR (DMSO-d$_6$, δ): 0.9–1.1 (6H, m), 1.10 (3H, d, J=5.7Hz), 1.2–1.5 (4H, m), 1.6–2.1 (5H, m), 2.1–2.6 (4H, m), 2.98 (2H, m), 3.20 (1H, m), 3.71 (2H, m), 3.8–4.6 (14H, m), 4.6–5.6 (9H, m), 6.69 (2H, d, J=8.2Hz), 6.80 (1H, d, J=8.2Hz), 6.87 (1H, s), 6.99 (2H, d, J=8.8Hz), 7.05 (1H, s), 7.2–7.7 (4H, m), 7.82 (2H, d, J=8.8Hz), 8.06 (4H, s), 8.10 (1H, m), 8.58 (1H, m), 8.67 (1H, s), 8.76 (1H, s)

MASS (m/z): 1308.25 (M−Na$^+$)

Elemental Analysis Calcd. For $C_{57}H_{70}N_{11}NaO_{21}S_2 \cdot 8H_2O$:

C 46.37, H 5.87, N 10.44

Found: C 46.29, H 5.44, N 10.19

EXAMPLE 156

IR (KBr): 3359, 2933, 1666, 1631, 1540, 1513, 1463, 1440, 1295, 1247, 1047 cm$^{-1}$

NMR (DMSO-d$_6$, δ): 0.9–1.1 (6H, m), 1.10 (3H, d, J=5.7Hz), 1.2–1.5 (6H, m), 1.6–2.1 (5H, m), 2.1–2.6 (4H, m), 2.98 (2H, m), 3.20 (1H, m), 3.71 (2H, m), 3.8–4.6 (14H, m), 4.6–5.6 (9H, m), 6.69 (1H, d, J=8.2Hz), 6.79 (1H, d, J=8.2Hz), 6.87 (1H, s), 6.98 (2H, d, J=8.8Hz), 7.04 (1H, s), 7.2–7.7 (4H, m), 7.82 (2H, d, J=8.8Hz), 8.06 (4H, s), 8.10 (1H,m), 8.58 (1H, m), 8.67 (1H, s), 8.77 (1H, s)

MASS (m/z): 1322.61 (M−Na$^+$)

Elemental Analysis Calcd. For $C_{58}H_{72}N_{11}NaO_{21}S_2 \cdot 11H_2O$:

C 45.10, H 6.13, N 9.98

Found: C 45.31, H 5.81, N 9.84

EXAMPLE 157

IR (KBr): 3351, 2933, 1631, 1523, 1465, 1440, 1255, 1178, 1047 cm$^{-1}$

NMR (DMSO-d$_6$, δ): 0.8–1.0 (6H, m), 1.10 (3H, d,J=5.7Hz), 1.2–1.6 (6H, m), 1.6–2.1 (5H, m), 2.1–2.5 (4H, m), 2.98 (2H, m), 3.20 (1H, m), 3.73 (2H, m), 3.8–4.6 (14H, m), 4.6–5.4 (9H, m), 6.69 (1H, d, J=8.2Hz), 6.79 (1H, d, J=8.2Hz), 6.88 (1H, s), 7.05 (1H, s), 7.14 (2H, d, J=8.8Hz), 7.23 (1H, m), 7.3–7.5 (2H, m), 7.67 (1H, m), 7.89 (2H, d, J=8.8Hz), 7.96 (4H, s), 8.07 (1H, m), 8.54 (1H, m), 8.85 (1H, s), 8.95 (1H, s)

MASS (m/z): 1322.12 (M–Na$^+$)

Elemental Analysis Calcd. For C$_{58}$H$_{72}$N$_{11}$NaO$_{21}$S$_2$·8H$_2$O:

C 46.74, H 5.95, N 10.34

Found: C 46.81, H 5.67, N 10.23

EXAMPLE 158

IR (KBr): 3359, 2935, 1652, 1631, 1538, 1523, 1429, 1382, 1299, 1253, 1047 cm$^{-1}$

NMR (DMSO-d$_6$, δ): 0.8–1.0 (6H, m), 1.10 (3H, d,J=5.7Hz), 1.3–1.5 (4H, m), 1.6–2.1 (5H, m), 2.1–2.5 (4H, m), 2.98 (2H, m), 3.20 (1H, m), 3.75 (2H, s), 3.8–4.6 (14H, m), 4.6–5.4 (9H, m), 6.69 (1H, d, J=8.2Hz), 6.77 (1H, d, J=8.2Hz), 6.85 (1H, s), 7.01 (2H, d, J=8.8Hz), 7.05 (1H, s), 7.23 (1H, m), 7.43 (2H, d, J=8.2Hz), 7.69 (1H, m), 7.77 (2H, d, J=8.8Hz), 7.87 (2H, d, J=8.3Hz), 8.05 (1H, d, J=7.9Hz), 8.19 (2H,d, J=8.3Hz), 8.54 (1H, m), 8.61 (1H, d, J=6.7Hz), 8.82 (1H, s)

MASS (m/z): 1312.10 (M–Na$^+$)

Elemental Analysis Calcd. For C$_{56}$H$_{70}$N$_{11}$NaO$_{22}$S$_2$·13H$_2$O:

C 42.83, H 6.16, N 9.81

Found: C 42.83, H 5.39, N 9.75

EXAMPLE 159

MASS (m/z): 1429.04 (M–Na$^+$)

EXAMPLE 160

To a solution of 1-hydroxybenzotriazole (26 mg) and 4-[5-[4-(4-propoxypiperidin-1-yl)phenyl]-1,3,4-thiadiazol-2-yl]benzoic acid hydrochloride (60 mg) in N,N-dimethylformamide (2.4 ml) was added 1-ethyl-3-(3'-dimethylaminopropyl) carbodiimide (48 μl) and the mixture was stirred for 19 hours at ambient temperature. Then to the reaction mixture was added Starting Compound (160) (120 mg) and N,N'-diisopropylethylamine (34 μl) and the mixture was stirred for 24 hours at ambient temperature. The reaction mixture was pulverized with ethyl acetate. The resulting precipitate was collected by filtration, washed with diisopropyl ether and dried under reduced pressure. The solid was added to saturated aqueous sodium hydrogen carbonate solution, subjected to column chromatography on ODS (YMC-gel ODS-AM S-50) and eluted with 20% acetonitrile in water. The fractions containing the object compound were combined and evaporated under reduced pressure to remove acetonitrile. The residue was lyophilized to give Object Compound (160) (48 mg) as a yellow powder.

NMR (DMSO-d$_6$, δ): 0.88 (3H, d, J=7.4Hz), 0.96 (3H, d, J=6.7Hz), 1.10 (3H, d,J=5.6Hz), 1.38–2.47 (16H, m), 2.80–5.50 (30H, m), 6.70 (1H, d, J=8.2Hz), 6.81 (1H, d, J=8.2Hz), 6.87 (1H, s), 7.04 (1H, s), 7.09 (2H, d, J=9.2Hz), 7.26–7.76 (3H, m), 7.84 (2H, d, J=8.8Hz), 7.97–8.14 (6H, m), 8.64–8.95 (2H,m)

MASS (m/z): 1347.44 (M–Na$^+$)

The following compounds [Examples 161 and 162] were obtained in a manner similar to that of Example 160.

EXAMPLE 161

NMR (DMSO-d$_6$, δ): 0.96 (3H, d, J=6.6Hz), 1.10 (3H, d,J=5.6Hz), 1.68–2.50 (7H, m), 2.80–5.50 (34H, m), 6.71 (1H, d, J=8.2Hz), 6.80 (1H, d, J=8.2Hz), 6.86 (1H, s), 6.76–6.94 (1H, m), 6.94–7.09 (3H, m), 7.09–7.34 (4H, m), 7.34–7.78 (3H, m), 7.90 (2H, d, J=8.7Hz), 7.96–8.17 (6H, m), 8.49–8.88 (2H,m)

MASS (m/z): 1343.23 (M–Na$^+$)

EXAMPLE 162

IR (KBr): 1655, 1527 cm$^{-1}$

NMR (DMSO-d$_6$, δ): 0.97 (3H, d, J=6.8Hz), 1.10 (3H, d, J=5.7Hz), 1.8–2.6 (12H, m), 2.8–3.6 (7H, m), 3.7–4.6 (14H, m), 4.7–5.5 (8H, m), 6.6–6.85 (4H, m), 6.85–6.95 (1H, m), 6.97 (1H, s), 7.15–7.25 (1H, m), 7.4–7.8 (3H, m), 7.72 (2H, d, J=8.9Hz), 8.0–8.2 (5H, m), 8.30 (1H, s), 8.71 (1H, s), 8.7–8.9 (1H, m), 9.11 (1H, s)

MASS (m/z): 1302 (M$^+$–23)

Elemental Analysis Calcd. For C$_{57}$H$_{68}$N$_{13}$NaO$_{19}$S$_2$·9H$_2$O:

C 45.99, H 5.82, N 12.23

Found: C 45.92, H 5.73, N 12.09

EXAMPLE 163

To a solution of Starting Compound (163) (2.0 g) in trifluoroacetic acid (48 ml) was added 1N hydrochloric acid (8 ml) with stirring at ambient temperature. The mixture was stirred at the same temperature overnight. The reaction mixture was evaporated to remove trifluoroacetic acid under reduced pressure. To the residue were added standard solution (pH 6.86) (100 ml) and acetonitrile (50 ml), and the solution was adjusted to pH 3 with 1N sodium hydroxide. The solution was chromatographed on reverse phase silica gel, YMC-gel ODS-AM 120-S50 (Trademark, made by YMC) (600 ml) eluting in turn with 20% aqueous acetonitrile (2 L), 30% aqueous acetonitrile (3 L), and 40% aqueous acetonitrile (4 L). The fractions containing the desired compound were collected and evaporated in vacuo to remove organic solvent. The resulting residue was lyophilized to give a white powder. The white powder was washed with ethyl acetate (30 ml) and dried in vacuo at ambient temperature for 3 hours to give Object Compound (163) (1.02 g).

NMR (DMSO-d$_6$+D$_2$O, δ): 0.96 (3H, d, J=6.7Hz), 1.09 (3H, d,J=6.0Hz), 1.25–1.60 (8H, m), 1.60–2.45 (10H, m), 2.80–3.10 (1H, m), 3.21 (3H, s), 3.30 (2H, t, J=6.4Hz), 3.60–4.50 (15H, m), 4.65–4.95 (2H, m), 6.41 (1H, d, J=8.3Hz), 6.50–6.70 (2H, m), 7.11 (1H, s), 7.16 (1H, s), 7.25–7.60 (2H, m), 7.85–8.25 (8H,m)

ESI-MASS (m/z): 1255.08 (M$^+$+Na$^+$)

Elemental Analysis Calcd. For C$_{58}$H$_{76}$N$_{10}$O$_{18}$S·4H$_2$O:

C 53.37, H 6.49, N 10.73

Found: C 53.61, H 6.44, N 10.84

EXAMPLE 164

To a solution of the Starting Compound (164) (6.0 g) in a mixture of tetrahydrofuran (120 ml) and N,N-dimethylamide (30 ml) were added trimethylsilyl chloride (22.8 ml) and triethylamine (37.6 ml) with stirring under ice-cooling and the mixture was stood at ambient temperature overnight. To the reaction mixture was added tetrahydrofuran (50 ml). The resulting precipitates were filtered off. The filtrate was stood at 2–5° C. overnight and evaporated in vacuo. The residue was dissolved in a mixture of hexane (50 ml) and ethyl acetate (50 ml)(1:1, v/v) and the solution was evaporated in vacuo to give a residue. The residue was chromatographed on silica gel (600 ml) eluting in turn with a mixture of hexane and ethyl acetate (3:2, v/v) and a mixture of hexane and ethyl acetate (1:1, v/v). The fractions containing the desired compound were collected and evaporated in vacuo. The resulting residue (5.68 g) was dissolved in a mixture of acetonitrile (30 ml) and methanol (30 ml). To the solution were added in turn diisopropylethylamine (1.68 ml) and trimethylsilyldiazomethane (4.82 ml) with stirring at ambient temperature and the mixture was allowed to stand at the same temperature overnight. To the reaction mixture were added ethyl acetate (150 ml) and saturated aqueous hydrogen carbonate solution (100 ml). The organic layer was separated, washed with saturated aqueous sodium chloride, dried over anhydrous magnesium sulfate and evaporated in vacuo to give a residue. The residue was dissolved in a mixture of tetrahydrofuran (30 ml) and acetic acid (3.68 ml). To the solution was added 1M solution of tetrabutyl ammonium fluoride in water with stirring under ice-cooling and the mixture was stirred at the same temperature for 4 hours. The reaction mixture was evaporated in vacuo and dissolved in 20% aqueous acetonitrile. The solution was chromatographed on reverse phase silica gel, YMC-gel ODS-AM 120-S50 (Trademark, made by YMC) (700 ml) eluting in turn with 20% aqueous acetonitrile (3.5 L), 30% aqueous acetonitrile (3.5 L) and 40% aqueous acetonitrile (3.5 L). The fractions containing the desired compound were collected and evaporated in vacuo to remove organic solvent. The resulting residue was lyophilized to give a white powder. The white powder was purified by liquid chromatography eluting with 38% acetonitrile in pH 6.86 standard buffer solution to give two compounds.

The first compound was chromatographed on reverse phase silica gel, YMC-gel ODS-AM 120-S50 (Trademark, made by YMC) (700 ml) eluting in turn with 20% aqueous acetonitrile (3.5 L) and 50% aqueous acetonitrile (3.5 L). The fractions containing the desired compound were collected and evaporated in vacuo to remove organic solvent. The resulting residue was lyophilized to give Object Compound (164-I) (1.37 g).

The other Object Compound (164-II) was chromatographed on reverse phase silica gel, YMC-gel ODS-AM 120-S50 (Trademark, made by YMC) (700 ml) eluting in turn with 20% aqueous acetonitrile (3.5L) and 50% aqueous acetonitrile (3.5L). The fractions containing the desired compound were collected and evaporated in vacuo to remove organic solvent. The resulting residue was lyophilized to give Object Compound (164-II) (275 mg).

Object Compound (164-I)

NMR (DMSO-$d_6$+$D_2O$, δ): 0.96 (3H, d, J=6.7Hz), 1.09 (3H, d,J=6.1Hz), 1.25–2.50 (19H, m), 2.85–3.00 (1H, m), 3.74 (3H, s), 3.31 (2H, t, J=6.4Hz), 3.75–4.55 (17H, m), 4.70–5.00 (2H, m), 6.40–6.70 (3H, m), 7.14 (2H, d, J=8.9Hz), 7.98 (2H, d, J=8.9Hz), 8.05 (2H, d, J=8.7Hz), 8.12 (2H, d, J=8.7Hz)

ESI-MASS (m/z): 1269.4 ($M^+$+$Na^+$) (positive)

1246.4 ($M^+$−1) (negative)

Elemental Analysis Calcd. For $C_{59}H_{78}N_{10}O_{18}S \cdot 3H_2O$:

C 54.45, H 6.51, N 10.76

Found: C 54.11, H 6.74, N 11.18

Object Compound (164-II)

NMR (DMSO-$d_6$+$D_2O$, δ): 0.96 (3H, d, J=6.7Hz), 1.10 (3H, d, J=6.1Hz), 1.20–2.45 (19H, m), 3.72 (3H, s), 3.73 (3H, s), 3.80–5.00 (15H, m), 6.55–6.90 (3H, m), 7.13 (2H, d, J=8.9Hz), 7.97 (2H, d, J=8.9Hz), 8.00–8.20 (4H, m)

ESI-MASS (m/z): 1283.4 (M+$Na^+$) (positive)

The following compound was obtained according to a similar manner by using tert-butyldimethylsilane instead of tert-butylsilane of Example 6.

EXAMPLE 165

The following compound was obtained in a manner similar to that of Example 2–3 of WO97/32975.

EXAMPLE 166

IR (KBr): 3394, 3327, 1676, 1633, 1439 $cm^{-1}$

NMR (DMSO-$d_6$, δ): 0.96 (3H, d, J=6.8 Hz), 1.08 (3H, d, J=6.0 Hz), 1.88–5.83 (35H, m), 6.68–8.71 (10H, m)

MASS (m/z): 903.17 (M-$Na^+$)

EXAMPLE 167

To a solution of Starting compound (167) (0.1 g) and 4-[5-[4-(7-methoxyheptyloxy)phenyl]-1,3,4-thiadiazol-2-yl]benzoic acid benzotriazol-1-yl ester (66.1 mg) in dimethylformamide (1 ml) was added diisopropylethylamine (0.029 ml) and the mixture was stirred for 5 hours at ambient acetate. The precipitate was collected by filtration and temperature. The reaction mixture was pulverized with ethyl dried under reduced pressure to give Object Compound (167) (159 mg).

IR (KBr): 3344, 1648.8, 1637.3, 1513.8, 1257.4, 1043.3 $cm^{-1}$

NMR (DMSO-$d_6$, δ): 0.97 (3H, d, J=6.6 Hz), 1.10 (3H, d, J=5.6 Hz), 1.2–1.6 (23H, m), 1.6–2.6 (12H, m), 2.9–4.6 (25H, m), 4.7–5.5 (9H, m), 6.71 (1H, d, J=8.2 Hz), 6.78 (1H, d, J=8.2 Hz), 6.88 (1H, s), 6.97 (1H, s), 7.13 (2H, d, J=8.8 Hz), 7.16 (1H, s), 7.44 (1H, d, J=8.0 Hz), 7.59 (1H, br s), 7.70 (1H, brs), 7.97 (2H, d, J=8.8 Hz), 7.9–8.2 (6H, m), 8.72 (1H, s), 8.79 (1H, d, J=7.3 Hz)

MASS (m/z): 1311 (M-diisopropylamine-1)

Elemental Analysis Calcd. For $C_{66}H_{95}N_{11}O_{21}S_2 \cdot 5H_2O$: C51.72, H 6.90, N 10.05 Found: C 51.89, H, 6.57, N 9.98

The following compound was obtained in a manner similar to that of Example 167.

EXAMPLE 168

IR (KBr): 3344, 1664.3, 1633.4, 1506.1, 1436.7, 1257.4 $cm^{-1}$

NMR (DMSO-$d_6$, δ): 0.91 (3H, t, J=7.0 Hz), 0.97 (3H, d, J=6.6 Hz), 1.10 (3H, d, J=5.6 Hz), 1.0–1.5 (19H, m), 1.6–2.7 (10H, m), 3.0–3.3 (3H, m), 3.7–4.6 (15H, m), 4.8–5.3 (11H, m), 5.54 (1H, d, J=5.6 Hz), 6.73 (1H, d, J=8.2 Hz), 6.83 (1H, dd, J=8.2 and 1.5 Hz), 6.85 (1H, s), 7.04 (1H, d, J=1.5 Hz), 7.12 (2H, d, J=8.8 Hz), 7.2–7.5 (3H, m), 7.23 (1H, s), 7.56 (1H, s), 7.58 (1H, m), 7.85 (2H, d, J=8.8 Hz), 7.9–8.1 (5H, m), 8.26 (1H, d, J=8.7 Hz), 8.85 (1H, s), 8.87 (1H, d, J=7.3 Hz)

MASS (m/z): 1268 (M-diisopropylamine-1)

The following compound was obtained in a manner similar to that of Example 2-3 of WO97/32975.

EXAMPLE 169

IR (KBr): 1664, 1627, 1234, 1086, 1043 $cm^{-1}$

NMR (DMSO-$d_6$, δ): 0.96 (3H, d, J=6.7 Hz), 1.14 (3H, d, J=5.9 Hz), 1.3–2.55 (8H, m), 2.6–3.6 (3H, m), 3.65–4.5 (15H, m), 4.7–5.4 (7H, m), 6.65–7.05 (4H, m), 7.07 (1H, s), 7.4–8.25 (7H, m), 8.71 (1H, s)

MASS (m/z): 903 (M-1)

What is claimed is:

1. A polypeptide compound of following the general formula:

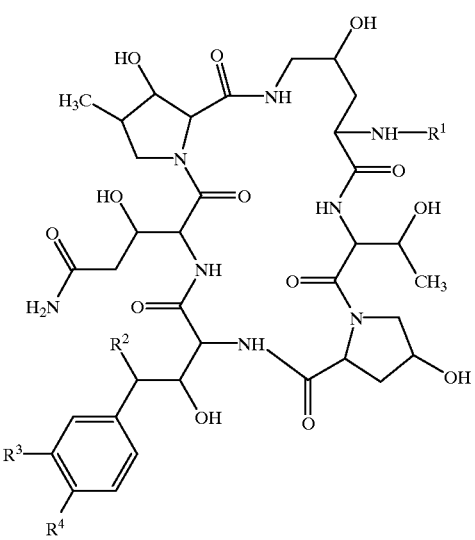

[I]

wherein
R¹ is hydrogen;
arylamino (lower) alkanoyl which may have one or more substituent(s);
aroyl substituted with heterocyclic group which may have one or more substituent(s);
aroyl substituted with aryl having higher alkyl;
aroyl substituted with aryl having lower alkyl;
aryl ($C_2$–$C_6$) alkanoyl substituted with aryl having lower alkyl;
lower alkanoyl substituted with unsaturated condensed heterocyclic group which may have one or more substituent(s);
lower alkanoyl substituted with pyridyl which may have one or more substituent(s);
heptylnaphthoyl;
hexylnaphthoyl;
aroyl substituted with heterocyclic carbamoyl which may have one or more substituent(s);
lower alkanoyl substituted with cyclo (lower) alkyl which may have one or more substituent(s);
lower alkanoyl substituted with thienyl having heterocyclic group which may have one or more substituent(s); or
lower alkanoyl substituted with heterocyclic group which may have one or more substituent(s),
R² is hydrogen or hydroxy,
R³ is hydroxy, hydroxysulfonyloxy or lower alkoxy, and
R⁴ is hydroxy or lower alkoxy, or a salt thereof.

2. A compound of claim 1, wherein
R¹ is aroyl substituted with heterocyclic group which may have one or more substituent(s).

3. A compound of claim 2, wherein
R¹ is benzoyl substituted with unsaturated 3 to 8-membered heteromonocyclic group containing 1 or 2 sulfur atom(s) and 1 to 3 nitrogen atom(s) having phenyl which has a substituent selected from the group consisting of saturated 3 to 8-membered heteromonocyclic group containing 1 to 4 nitrogen atom(s) which may have cyclo (lower) alkyl having di (lower) alkyl, lower alkoxy (lower) alkoxy, lower alkoxy (higher) alkoxy and phenyl substituted with saturated 3 to 8-membered heteromonocyclic group containing 1 or 2 oxygen atom(s) and 1 to 3 nitrogen atom(s) having di(lower) alkyl; or benzoyl substituted with unsaturated condensed heterocyclic group containing 1 or 2 sulfur atom(s) and 1 to 3 nitrogen atom(s) having phenyl which has lower alkoxy.

4. A compound of claim 3, wherein
R¹ is benzoyl substituted with thiadiazolyl which has phenyl having piperidyl,
benzoyl substituted with thiadiazolyl which has phenyl having lower alkoxy (lower) alkoxy,
benzoyl substituted with thiadiazolyl which has phenyl having lower alkoxy (higher) alkoxy,
benzoyl substituted with thiadiazolyl having phenyl which has piperazinyl substituted with cyclohexyl,
benzoyl substituted with thiadiazolyl having phenyl substituted with phenyl which has morpholino having di (lower) alkyl, or
benzoyl substituted with imidazothiadiazolyl having phenyl which has lower alkoxy.

5. A compound of claim 4, wherein
R¹ is benzoyl substituted with thiadiazolyl which has phenyl having piperidyl, or benzoyl substituted with thiadiazolyl which has phenyl having lower alkoxy (higher) alkoxy,
R³ is hydroxysulfonyloxy, and
R⁴ is hydroxy.

6. A process for preparing a polypeptide compound of claim 1 or a salt thereof, which comprises,
i) reacting a compound of the formula:

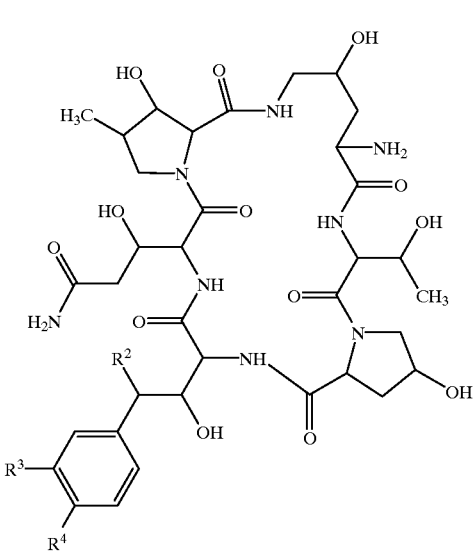

[Ib]

wherein

R², R³ and R⁴ are as defined in claim 1 or its reactive derivative at the amino group or a salt thereof, with a compound of the formula:

$R_a^1$—OH wherein $R_a^1$ is arylamino (lower) alkanoyl which may have one or more substituent(s);

aroyl substituted with heterocyclic group which may have one or more substituent(s);

aroyl substituted with aryl having higher alkyl;

aroyl substituted with aryl having lower alkyl;

aryl ($C_2$–$C_6$) alkanoyl substituted with aryl having lower alkyl;

lower alkanoyl substituted with unsaturated condensed heterocyclic group which may have one or more substituent(s);

lower alkanoyl substituted with pyridyl which may have one or more substituent(s);

heptylnaphthoyl;

hexylnaphthoyl;

aroyl substituted with heterocyclic carbamoyl which may have one or more substituent(s);

lower alkanoyl substituted with cyclo (lower) alkyl which may have one or more substituent(s);

lower alkanoyl substituted with thienyl having heterocyclic group which may have one or more substituent(s); or lower alkenoyl substituted with heterocyclic group which may have one or more substituent(s), or its reactive derivative at the carboxy group or a salt thereof, to give a compound of the formula:

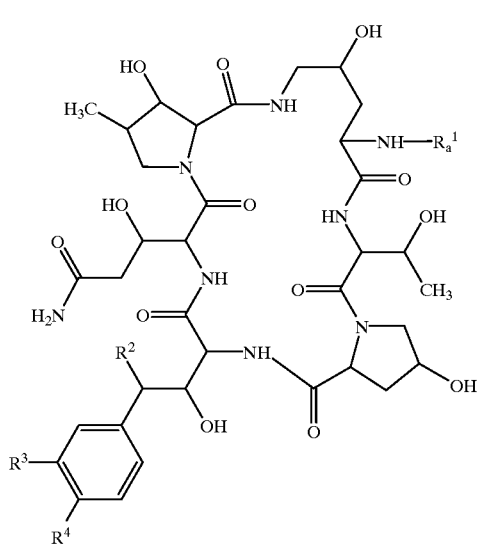

[Ia]

wherein

R², $R_3$ and R⁴ are as defined in claim 1, and $R_a^1$ is as defined above or a salt thereof, or ii) reducing a compound of the formula:

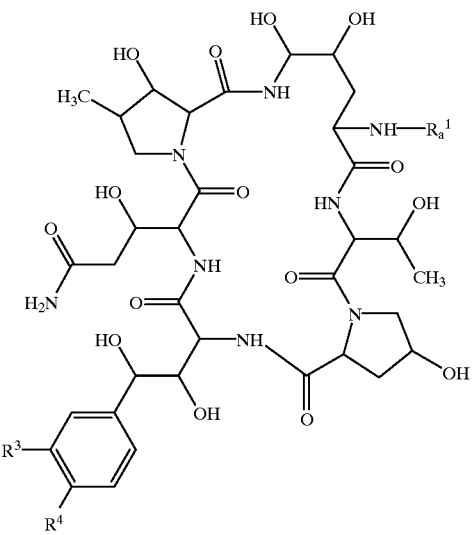

[II]

wherein $R_a^1$, R³ and R⁴ are as defined above, or a salt thereof, to give a compound of the formula:

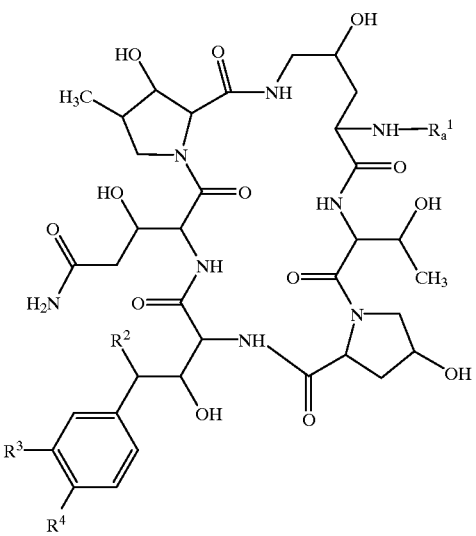

[Ia]

wherein

R², R³ and R⁴ are as defined in claim 1, and R$_a$¹ is as defined above, or a salt thereof, or iii) reducing a compound of the formula:

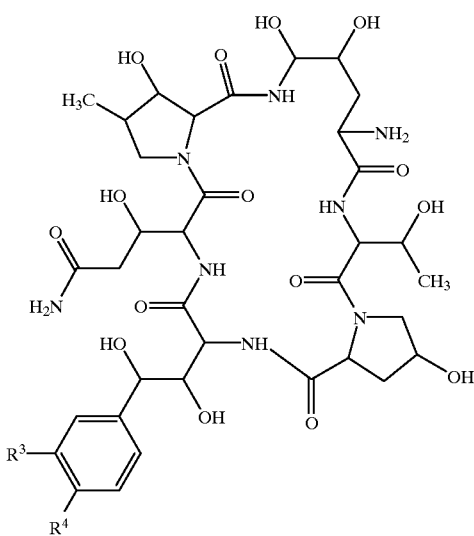

[IV]

wherein

R³ and R⁴ are as defined in claim 1, or a salt thereof, to give a compound of the formula:

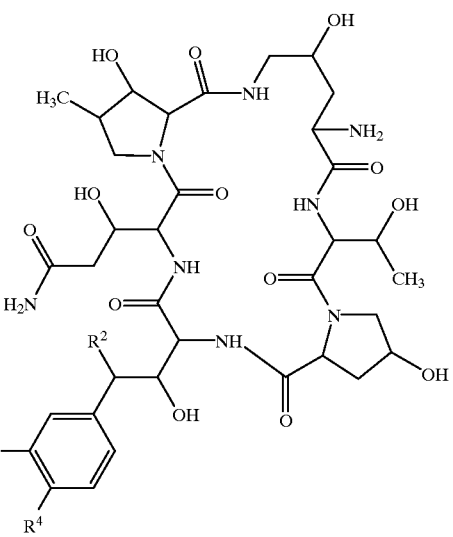

[Ib]

wherein

R₂, R₃ and R₄ are as defined in claim 1, or a salt thereof.

7. A pharmaceutical composition which comprises, as an active ingredient, a compound of claim 1 or a pharmaceutically acceptable salt thereof in admixture with pharmaceutically acceptable carriers or excipients.

8. A compound of claim 1 or a pharmaceutically acceptable salt thereof for use as a medicament.

9. A method for the prophylactic an/or therapeutic treatment of infectious diseases caused by pathogenic microorganisms, which comprises administering a compound of claim 1 or a pharmaceutically acceptable salt thereof to a human being or an animal.

* * * * *